US012622960B2

(12) United States Patent
Ciaramella

(10) Patent No.: US 12,622,960 B2
(45) Date of Patent: *May 12, 2026

(54) VARICELLA ZOSTER VIRUS (VZV) VACCINE

(71) Applicant: ModernaTX, Inc., Cambridge, MA (US)

(72) Inventor: Giuseppe Ciaramella, Sudbury, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/416,835

(22) Filed: Jan. 18, 2024

(65) Prior Publication Data

US 2025/0041407 A1 Feb. 6, 2025

Related U.S. Application Data

(63) Continuation of application No. 17/245,973, filed on Apr. 30, 2021, now Pat. No. 11,918,644, which is a continuation of application No. 16/494,162, filed as application No. PCT/US2018/022643 on Mar. 15, 2018, now Pat. No. 11,045,540.

(60) Provisional application No. 62/490,112, filed on Apr. 26, 2017, provisional application No. 62/471,809, filed on Mar. 15, 2017.

(51) Int. Cl.
| | |
|---|---|
| *A61K 39/25* | (2006.01) |
| *A61K 9/127* | (2025.01) |
| *A61K 9/1271* | (2025.01) |
| *A61K 9/1272* | (2025.01) |
| *A61K 9/51* | (2006.01) |
| *A61K 31/7105* | (2006.01) |
| *A61K 39/00* | (2006.01) |
| *A61K 47/28* | (2006.01) |
| *A61K 47/54* | (2017.01) |
| *A61K 49/00* | (2006.01) |
| *B82Y 5/00* | (2011.01) |
| *C12N 15/86* | (2006.01) |

(52) U.S. Cl.
CPC .............. *A61K 39/25* (2013.01); *A61K 9/127* (2013.01); *A61K 9/51* (2013.01); *A61K 31/7105* (2013.01); *A61K 39/0012* (2013.01); *A61K 49/0091* (2013.01); *B82Y 5/00* (2013.01); *C12N 15/86* (2013.01); *A61K 9/1271* (2013.01); *A61K 9/1272* (2013.01); *A61K 47/28* (2013.01); *A61K 47/543* (2017.08); *A61K 47/544* (2017.08); *C12N 2710/16722* (2013.01); *C12N 2710/16734* (2013.01)

(58) Field of Classification Search
CPC ...... A61K 39/25; A61K 9/51; A61K 49/0091; A61K 39/0012; A61K 9/127; A61K 31/7105; A61K 47/544; A61K 47/543; A61K 47/28; A61K 9/1272; A61K 9/1271; B82Y 5/00; C12N 15/86; C12N 2710/16722; C12N 2710/16734; C07K 14/005; A61P 31/22
See application file for complete search history.

(56) References Cited

U.S. PATENT DOCUMENTS

| | | | |
|---|---|---|---|
| 6,500,419 | B1 | 12/2002 | Hone et al. |
| 6,514,948 | B1 | 2/2003 | Raz et al. |
| 6,610,044 | B2 | 8/2003 | Mathiesen |
| 7,001,890 | B1 | 2/2006 | Wagner et al. |
| 8,058,069 | B2 | 11/2011 | Yaworski et al. |
| 8,569,256 | B2 | 10/2013 | Heyes et al. |
| 8,609,142 | B2 | 12/2013 | Troiano et al. |
| 8,613,954 | B2 | 12/2013 | Zale et al. |
| 8,617,608 | B2 | 12/2013 | Zale et al. |
| 8,710,200 | B2 | 4/2014 | Schrum et al. |
| 8,734,832 | B2 | 5/2014 | O'Hagan et al. |
| 8,734,853 | B2 | 5/2014 | Sood et al. |
| 8,754,062 | B2 | 6/2014 | De Fougerolles et al. |
| 8,822,663 | B2 | 9/2014 | Schrum et al. |
| 8,980,864 | B2 | 3/2015 | Hoge et al. |
| 8,999,351 | B2 | 4/2015 | Manoharan et al. |
| 8,999,380 | B2 | 4/2015 | Bancel et al. |
| 9,012,219 | B2 | 4/2015 | Kariko et al. |
| 9,221,891 | B2 | 12/2015 | Bancel et al. |
| 9,283,287 | B2 | 3/2016 | Bancel et al. |

(Continued)

FOREIGN PATENT DOCUMENTS

| | | |
|---|---|---|
| AU | 652831 B2 | 9/1994 |
| CA | 2473135 A1 | 6/2003 |

(Continued)

OTHER PUBLICATIONS

Reshetnikov V, Terenin I, Shepelkova G, Yeremeev V, Kolmykov S, Nagornykh M, Kolosova E, Sokolova T, Zaborova O, Kukushkin I, Kazakova A, Kunyk D, Kirshina A, et al. Untranslated Region Sequences and the Efficacy of mRNA Vaccines against Tuberculosis. Int J Mol Sci. Jan. 10, 2024;25(2):888. (Year: 2024).*

(Continued)

*Primary Examiner* — Rachel B Gill

(74) *Attorney, Agent, or Firm* — Wolf, Greenfield & Sacks, P.C.

(57) ABSTRACT

Aspects of the disclosure relate to nucleic acid vaccines. The vaccines include at least one RNA polynucleotides having a open reading frame encoding at least varicella zoster virus (VZV) antigen. Methods for preparing and using such vaccines are also described.

15 Claims, 21 Drawing Sheets

Specification includes a Sequence Listing.

(56)  References Cited

U.S. PATENT DOCUMENTS

| | | | |
|---|---|---|---|
| 9,303,079 B2 | 4/2016 | Bancel et al. |
| 9,464,124 B2 | 10/2016 | Bancel et al. |
| 9,512,456 B2 | 12/2016 | Wang et al. |
| 9,533,047 B2 | 1/2017 | de Fougerolles et al. |
| 9,572,896 B2 | 2/2017 | Bancel et al. |
| 9,597,380 B2 | 3/2017 | Chakraborty et al. |
| 9,675,668 B2 | 6/2017 | Bancel et al. |
| 9,737,619 B2 | 8/2017 | Ansell et al. |
| 9,868,691 B2 | 1/2018 | Benenato et al. |
| 9,872,900 B2 | 1/2018 | Ciaramella et al. |
| 10,023,626 B2 | 7/2018 | Bolen et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |
| 10,232,055 B2 | 3/2019 | Kariko et al. |
| 10,273,269 B2 | 4/2019 | Ciaramella |
| 10,286,086 B2 | 5/2019 | Roy et al. |
| 10,323,076 B2 | 6/2019 | Ellsworth et al. |
| 10,385,088 B2 | 8/2019 | Fraley et al. |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,925,958 B2 | 2/2021 | Ciaramella |
| 11,027,025 B2 | 6/2021 | Hoge et al. |
| 11,045,540 B2 | 6/2021 | Ciaramella |
| 11,103,578 B2 | 8/2021 | Ciaramella et al. |
| 11,351,242 B1 | 6/2022 | Lori et al. |
| 11,384,352 B2 | 7/2022 | Miracco |
| 11,406,703 B2 | 8/2022 | Kramarczyk et al. |
| 11,464,848 B2 | 10/2022 | Ciaramella et al. |
| 11,485,960 B2 | 11/2022 | Dousis et al. |
| 11,497,807 B2 | 11/2022 | Ciaramella et al. |
| 11,564,893 B2 | 1/2023 | Smith |
| 11,576,961 B2 | 2/2023 | Ciaramella et al. |
| 11,638,693 B2 | 5/2023 | Geall |
| 11,638,694 B2 | 5/2023 | Geall |
| 11,643,441 B1 | 5/2023 | Ciaramella et al. |
| 11,666,534 B2 | 6/2023 | Geall |
| 11,696,946 B2 | 7/2023 | Ciaramella |
| 11,752,206 B2 | 9/2023 | Ciaramella et al. |
| 11,766,401 B2 | 9/2023 | Geall |
| 11,786,467 B2 | 10/2023 | Geall |
| 11,786,607 B2 | 10/2023 | Hoge et al. |
| 11,851,694 B1 | 12/2023 | Mauger et al. |
| 11,866,696 B2 | 1/2024 | Issa et al. |
| 11,872,278 B2 | 1/2024 | Ciaramella et al. |
| 11,905,525 B2 | 2/2024 | Brito et al. |
| 11,911,453 B2 | 2/2024 | Ciaramella et al. |
| 11,912,982 B2 | 2/2024 | Issa et al. |
| 12,070,495 B2 | 8/2024 | Lusso et al. |
| 2001/0001066 A1 | 5/2001 | Cezayirli et al. |
| 2003/0032615 A1 | 2/2003 | Felgner et al. |
| 2005/0032730 A1 | 2/2005 | Von Der Mulbe et al. |
| 2005/0059624 A1 | 3/2005 | Hoerr et al. |
| 2005/0250723 A1 | 11/2005 | Hoerr et al. |
| 2005/0287539 A1 | 12/2005 | Labourier et al. |
| 2006/0172003 A1 | 8/2006 | Meers et al. |
| 2006/0172966 A1 | 8/2006 | Lipford et al. |
| 2007/0280929 A1 | 12/2007 | Hoerr et al. |
| 2010/0130588 A1 | 5/2010 | Yaworski et al. |
| 2010/0189729 A1 | 7/2010 | Hoerr et al. |
| 2010/0203076 A1 | 8/2010 | Fotin-Mleczek et al. |
| 2010/0239608 A1 | 9/2010 | Von Der Mulbe et al. |
| 2010/0303851 A1 | 12/2010 | Hoerr et al. |
| 2011/0117125 A1 | 5/2011 | Hope et al. |
| 2011/0250225 A1 | 10/2011 | Fotin-Mleczek et al. |
| 2011/0269950 A1 | 11/2011 | Von Der Mulbe et al. |
| 2011/0311472 A1 | 12/2011 | Hoerr et al. |
| 2012/0101148 A1 | 4/2012 | Aking et al. |
| 2012/0189700 A1 | 7/2012 | Aguilar et al. |
| 2012/0258046 A1 | 10/2012 | Mutske |
| 2013/0102034 A1 | 4/2013 | Schrum et al. |
| 2013/0121988 A1 | 5/2013 | Hoerr et al. |
| 2013/0142818 A1 | 6/2013 | Baumhof et al. |
| 2013/0171241 A1 | 7/2013 | Geall |
| 2013/0183355 A1 | 7/2013 | Jain et al. |
| 2013/0189351 A1 | 7/2013 | Geall |
| 2013/0195867 A1 | 8/2013 | Hoerr et al. |
| 2013/0195968 A1 | 8/2013 | Geall et al. |
| 2013/0195969 A1 | 8/2013 | Geall et al. |
| 2013/0202684 A1 | 8/2013 | Geall et al. |
| 2013/0236533 A1 | 9/2013 | Von Andrian et al. |
| 2013/0236974 A1 | 9/2013 | De Fougerolles |
| 2013/0245103 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | De Fougerolles et al. |
| 2013/0295043 A1 | 11/2013 | Kallen et al. |
| 2013/0336998 A1 | 12/2013 | Kallen et al. |
| 2014/0065228 A1 | 3/2014 | Yarowoski et al. |
| 2014/0134201 A1 | 5/2014 | Tureci et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0220083 A1 | 8/2014 | Brito et al. |
| 2014/0271829 A1 | 9/2014 | Lilja et al. |
| 2014/0378538 A1 | 12/2014 | Bancel |
| 2015/0051268 A1 | 2/2015 | Bancel et al. |
| 2015/0056253 A1 | 2/2015 | Bancel et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2016/0024140 A1 | 1/2016 | Issa et al. |
| 2016/0024141 A1 | 1/2016 | Issa et al. |
| 2016/0032273 A1 | 2/2016 | Shahrokh et al. |
| 2016/0032316 A1 | 2/2016 | Weissman et al. |
| 2016/0038612 A1 | 2/2016 | Hoge et al. |
| 2016/0194368 A1 | 7/2016 | Hoge et al. |
| 2016/0194625 A1 | 7/2016 | Hoge et al. |
| 2016/0243221 A1 | 8/2016 | Hoge et al. |
| 2016/0317647 A1 | 11/2016 | Ciaramella et al. |
| 2017/0009244 A1 | 1/2017 | Sahin et al. |
| 2017/0043037 A1 | 2/2017 | Kariko et al. |
| 2017/0130255 A1 | 5/2017 | Wang et al. |
| 2017/0202979 A1 | 7/2017 | Chakraborty et al. |
| 2017/0204152 A1 | 7/2017 | Nelson et al. |
| 2017/0340724 A1 | 11/2017 | Ciaramella et al. |
| 2017/0340725 A1 | 11/2017 | Ciaramella et al. |
| 2018/0000953 A1 | 1/2018 | Almarsson et al. |
| 2018/0002393 A1 | 1/2018 | Bancel et al. |
| 2018/0006700 A1 | 1/2018 | Heineman et al. |
| 2018/0028645 A1 | 2/2018 | Ciaramella et al. |
| 2018/0028664 A1 | 2/2018 | Besin et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0280496 A1 | 10/2018 | Ciaramella et al. |
| 2018/0289792 A1 | 10/2018 | Ciaramella et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0312549 A1 | 11/2018 | Ciaramella |
| 2018/0318409 A1 | 11/2018 | Valiante et al. |
| 2018/0363019 A1 | 12/2018 | Hoge |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0085368 A1 | 3/2019 | Bancel et al. |
| 2019/0099481 A1 | 4/2019 | Ciaramella et al. |
| 2019/0125839 A1 | 5/2019 | Frederick et al. |
| 2019/0175517 A1 | 6/2019 | Martini et al. |

(56) References Cited

U.S. PATENT DOCUMENTS

| | | |
|---|---|---|
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0241633 A1 | 8/2019 | Fotin-Mleczek et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0314493 A1 | 10/2019 | Ciaramella et al. |
| 2019/0315807 A1 | 10/2019 | Molina et al. |
| 2019/0336452 A1 | 11/2019 | Brader |
| 2019/0336595 A1 | 11/2019 | Ciaramella |
| 2019/0351040 A1 | 11/2019 | Valiante et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129445 A1 | 4/2020 | Patel et al. |
| 2020/0129608 A1 | 4/2020 | Ciaramella et al. |
| 2020/0129615 A1 | 4/2020 | Ciaramella et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2020/0306191 A1 | 10/2020 | Schariter et al. |
| 2020/0338004 A1 | 10/2020 | Hansson et al. |
| 2020/0368162 A1 | 11/2020 | Martini |
| 2020/0399322 A1 | 12/2020 | Baumhof et al. |
| 2021/0046173 A1 | 2/2021 | Ciaramella et al. |
| 2021/0087135 A1 | 3/2021 | Benenato et al. |
| 2021/0163919 A1 | 6/2021 | Issa et al. |
| 2021/0187097 A1 | 6/2021 | Ciaramella et al. |
| 2021/0187124 A1 | 6/2021 | Schlake et al. |
| 2021/0206818 A1 | 7/2021 | Huang et al. |
| 2021/0217484 A1 | 7/2021 | Giessel et al. |
| 2021/0228707 A1 | 7/2021 | Mektar et al. |
| 2021/0268086 A1 | 9/2021 | Zhong et al. |
| 2021/0378980 A1 | 12/2021 | Horhota et al. |
| 2022/0031631 A1 | 2/2022 | Almarsson et al. |
| 2022/0047518 A1 | 2/2022 | Hennessy et al. |
| 2022/0054653 A1 | 2/2022 | Martini et al. |
| 2022/0062175 A1 | 3/2022 | Smith et al. |
| 2022/0125899 A1 | 4/2022 | Ashburn et al. |
| 2022/0145381 A1 | 5/2022 | Elich et al. |
| 2022/0236253 A1 | 7/2022 | Hopson |
| 2022/0241399 A1 | 8/2022 | Lusso et al. |
| 2022/0347292 A1 | 11/2022 | Panther et al. |
| 2022/0348900 A1 | 11/2022 | Shamashkin et al. |
| 2022/0349006 A1 | 11/2022 | Amato et al. |
| 2023/0000970 A1 | 1/2023 | Nachbagauer et al. |
| 2023/0142529 A1 | 5/2023 | White et al. |
| 2023/0181481 A1 | 6/2023 | White et al. |
| 2023/0190761 A1 | 6/2023 | Brader et al. |
| 2023/0212645 A1 | 7/2023 | Marquardt et al. |
| 2023/0287437 A1 | 9/2023 | Smith et al. |
| 2023/0338506 A1 | 10/2023 | Shaw et al. |
| 2023/0346914 A1 | 11/2023 | Stewart-Jones et al. |
| 2023/0355743 A1 | 11/2023 | Stewart-Jones et al. |
| 2024/0100145 A1 | 3/2024 | Bollman et al. |
| 2024/0100151 A1 | 3/2024 | Carfi et al. |
| 2024/0139309 A1 | 5/2024 | Carfi et al. |
| 2024/0173400 A1 | 5/2024 | Ciaramella et al. |
| 2024/0181030 A1 | 6/2024 | Himansu et al. |
| 2024/0207392 A1 | 6/2024 | Chandramouli et al. |
| 2024/0209068 A1 | 6/2024 | Deal et al. |
| 2024/0226028 A1 | 7/2024 | Goldman et al. |
| 2024/0226277 A1 | 7/2024 | Nachbagauer et al. |
| 2024/0229109 A1 | 7/2024 | Rabideau et al. |
| 2024/0238211 A1 | 7/2024 | Brader et al. |
| 2024/0263226 A1 | 8/2024 | Schmitt |
| 2024/0285754 A1 | 8/2024 | Stewart-Jones |
| 2024/0293534 A1 | 9/2024 | Stewart-Jones |
| 2024/0299531 A1 | 9/2024 | Stewart-Jones |

FOREIGN PATENT DOCUMENTS

| | | | |
|---|---|---|---|
| CN | 102076847 A | 5/2011 | |
| CN | 102177236 A | 9/2011 | |
| CN | 102548578 A | 7/2012 | |
| CN | 105051213 A | 11/2015 | |
| CN | 106244608 A | 12/2016 | |
| CN | 108366604 A | 8/2018 | |
| CN | 111032863 A | 4/2020 | |
| CN | 114081943 A | 2/2022 | |
| CN | 118240844 A | 6/2024 | |
| CN | 118340875 A | 7/2024 | |
| EP | 1083232 B1 | 2/2005 | |
| EP | 1301614 B1 | 11/2006 | |
| EP | 1383556 B1 | 10/2007 | |
| EP | 1905844 A2 | 2/2008 | |
| EP | 1026253 B2 | 12/2012 | |
| EP | 2188379 B1 | 1/2013 | |
| WO | WO 1990/011092 A1 | 10/1990 | |
| WO | WO 1991/007425 A1 | 5/1991 | |
| WO | WO 1995/008626 A1 | 3/1995 | |
| WO | WO 1995/027069 A1 | 3/1995 | |
| WO | WO 1999/052503 A2 | 10/1999 | |
| WO | WO 2001/021810 A1 | 3/2001 | |
| WO | WO 2004/058166 A2 | 7/2004 | |
| WO | WO 2005/007689 A1 | 1/2005 | |
| WO | WO 2008/014979 A3 | 2/2008 | |
| WO | WO 2008/052770 A2 | 5/2008 | |
| WO | WO 2008/083949 A2 | 7/2008 | |
| WO | WO 2010/037408 A1 | 4/2010 | |
| WO | WO 2010/042877 A1 | 4/2010 | |
| WO | WO 2010/054406 A1 | 5/2010 | |
| WO | WO 2010/088927 A1 | 8/2010 | |
| WO | WO 2010/115046 A2 | 10/2010 | |
| WO | WO 2010/141069 A2 | 12/2010 | |
| WO | WO 2011/005799 A2 | 1/2011 | |
| WO | WO 2011/069529 A1 | 6/2011 | |
| WO | WO 2011/069586 A1 | 6/2011 | |
| WO | WO 2011/144358 A1 | 11/2011 | |
| WO | WO 2012/006369 A2 | 1/2012 | |
| WO | WO 2012/006380 A2 | 1/2012 | |
| WO | WO 2012/019630 A1 | 2/2012 | |
| WO | WO 2012/019780 A1 | 2/2012 | |
| WO | WO 2012/051211 A1 | 4/2012 | |
| WO | WO 2012/075040 A2 | 6/2012 | |
| WO | WO 2012/089225 A1 | 7/2012 | |
| WO | WO 2012/106377 A3 | 8/2012 | |
| WO | WO 2012/113513 A1 | 8/2012 | |
| WO | WO 2012/116714 A1 | 9/2012 | |
| WO | WO 2012/116715 A1 | 9/2012 | |
| WO | WO 2012/116810 A1 | 9/2012 | |
| WO | WO 2012/116811 A1 | 9/2012 | |
| WO | WO 2013/006837 A1 | 1/2013 | |
| WO | WO 2013/006838 A1 | 1/2013 | |
| WO | WO 2013/006842 A2 | 1/2013 | |
| WO | WO 2013/030778 A2 | 3/2013 | |
| WO | WO 2013/052167 A2 | 4/2013 | |
| WO | WO 2013/055905 A1 | 4/2013 | |
| WO | WO 2013/056132 A2 | 4/2013 | |
| WO | WO 2013/059496 A1 | 4/2013 | |
| WO | WO 2013/086373 A1 | 6/2013 | |
| WO | WO 2013/090648 A1 | 6/2013 | |
| WO | WO 2013/113502 A1 | 8/2013 | |
| WO | WO 2013/174409 A1 | 11/2013 | |
| WO | WO 2014/071963 A1 | 5/2014 | |
| WO | WO 2014/072061 A1 | 5/2014 | |
| WO | WO 2014/093924 A1 | 6/2014 | |
| WO | WO 2014/127917 A1 | 8/2014 | |
| WO | WO 2014/144711 A1 | 9/2014 | |
| WO | WO 2014/152027 A1 | 9/2014 | |
| WO | WO 2014/152030 A1 | 9/2014 | |
| WO | WO 2014/159813 A1 | 10/2014 | |

(56)                 References Cited

FOREIGN PATENT DOCUMENTS

| | | |
|---|---|---|
| WO | WO 2014/160243 A1 | 10/2014 |
| WO | WO 2015/013551 A1 | 1/2015 |
| WO | WO 2015/024667 A1 | 2/2015 |
| WO | WO 2015/024668 A2 | 2/2015 |
| WO | WO 2015/062738 A1 | 5/2015 |
| WO | WO 2015/085318 A2 | 6/2015 |
| WO | WO 2015/164674 A1 | 10/2015 |
| WO | WO 2015/189425 A1 | 12/2015 |
| WO | WO 2015/199952 A1 | 12/2015 |
| WO | WO 2016/164762 A1 | 10/2016 |
| WO | WO 2016/176330 A1 | 11/2016 |
| WO | WO 2016/201377 A1 | 12/2016 |
| WO | WO 2016/203025 A1 | 12/2016 |
| WO | WO 2017/011773 A2 | 1/2017 |
| WO | WO 2017/015457 A1 | 1/2017 |
| WO | WO 2017/015463 A1 | 1/2017 |
| WO | WO 2017/019935 A1 | 2/2017 |
| WO | WO 2017/020026 A1 | 2/2017 |
| WO | WO 2017/031232 A1 | 2/2017 |
| WO | WO 2017/031241 A1 | 2/2017 |
| WO | WO 2017/049245 A2 | 3/2017 |
| WO | WO 2017/062513 A1 | 4/2017 |
| WO | WO 2017/066789 A1 | 4/2017 |
| WO | WO 2017/070601 A1 | 4/2017 |
| WO | WO 2017/070616 A1 | 4/2017 |
| WO | WO 2017/070618 A1 | 4/2017 |
| WO | WO 2017/070620 A1 | 4/2017 |
| WO | WO 2017/070622 A1 | 4/2017 |
| WO | WO 2017/070623 A1 | 4/2017 |
| WO | WO 2017/070624 A1 | 4/2017 |
| WO | WO 2017/070626 A2 | 4/2017 |
| WO | WO 2017/112865 A1 | 6/2017 |
| WO | WO 2017/127750 A1 | 7/2017 |
| WO | WO 2017/201333 A1 | 11/2017 |
| WO | WO 2017/201340 A1 | 11/2017 |
| WO | WO 2017/201342 A1 | 11/2017 |
| WO | WO 2017/201347 A1 | 11/2017 |
| WO | WO 2017/201349 A1 | 11/2017 |
| WO | WO 2018/053209 A1 | 3/2018 |
| WO | WO 2018/075980 A1 | 4/2018 |
| WO | WO 2018/078053 A1 | 5/2018 |
| WO | WO 2018/081459 A1 | 5/2018 |
| WO | WO 2018/081462 A1 | 5/2018 |
| WO | WO 2018/089851 A1 | 5/2018 |
| WO | WO 2018/107088 A1 | 6/2018 |
| WO | WO 2018/111967 A1 | 6/2018 |
| WO | WO 2018/144082 A1 | 8/2018 |
| WO | WO 2018/144778 A1 | 8/2018 |
| WO | WO 2018/157009 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/170270 A1 | 9/2018 |
| WO | WO 2018/170347 A1 | 9/2018 |
| WO | WO 2018/175783 A1 | 9/2018 |
| WO | WO 2018/187590 A2 | 10/2018 |
| WO | WO 2018/200737 A1 | 11/2018 |
| WO | WO 2018/232355 A1 | 12/2018 |
| WO | WO 2018/232357 A1 | 12/2018 |
| WO | WO 2019/018765 A1 | 1/2019 |
| WO | WO 2019/036670 A1 | 2/2019 |
| WO | WO 2019/036682 A1 | 2/2019 |
| WO | WO 2019/036683 A1 | 2/2019 |
| WO | WO 2019/036685 A1 | 2/2019 |
| WO | WO 2019/103993 A1 | 5/2019 |
| WO | WO 2019/148101 A1 | 8/2019 |
| WO | WO 2020/006242 A1 | 1/2020 |
| WO | WO 2020/056370 A1 | 3/2020 |
| WO | WO 2020/061284 A1 | 3/2020 |
| WO | WO 2020/061295 A1 | 3/2020 |
| WO | WO 2020/061367 A1 | 3/2020 |
| WO | WO 2020/097291 A1 | 5/2020 |
| WO | WO 2020/172239 A1 | 8/2020 |
| WO | WO 2020/185811 A1 | 9/2020 |
| WO | WO 2020/190750 A1 | 9/2020 |
| WO | WO 2020/243561 A1 | 12/2020 |
| WO | WO 2021/030533 A1 | 2/2021 |
| WO | WO 2021/050864 A1 | 3/2021 |
| WO | WO 2021/055811 A1 | 3/2021 |
| WO | WO 2021/155243 A1 | 8/2021 |
| WO | WO 2021/155274 A1 | 8/2021 |
| WO | WO 2021/159040 A2 | 8/2021 |
| WO | WO 2021/159130 A2 | 8/2021 |
| WO | WO 2021/211343 A1 | 10/2021 |
| WO | WO 2021/222304 A1 | 11/2021 |
| WO | WO 2021/231963 A1 | 11/2021 |
| WO | WO 2021/237084 A1 | 11/2021 |
| WO | WO 2022/032154 A2 | 2/2022 |
| WO | WO 2022/155524 A1 | 7/2022 |
| WO | WO 2022/155530 A1 | 8/2022 |
| WO | WO 2022/187698 A1 | 9/2022 |
| WO | WO 2022/197624 A1 | 9/2022 |
| WO | WO 2022/204491 A1 | 9/2022 |
| WO | WO 2022/212191 A1 | 10/2022 |
| WO | WO 2022/212442 A1 | 10/2022 |
| WO | WO 2022/212711 A1 | 10/2022 |
| WO | WO 2022/221335 A1 | 10/2022 |
| WO | WO 2022/221336 A1 | 10/2022 |
| WO | WO 2022/221359 A1 | 10/2022 |
| WO | WO 2022/221440 A1 | 10/2022 |
| WO | WO 2022/226277 A1 | 10/2022 |
| WO | WO 2022/226318 A1 | 10/2022 |
| WO | WO 2022/232585 A1 | 11/2022 |
| WO | WO 2022/241103 A1 | 11/2022 |
| WO | WO 2022/245888 A1 | 11/2022 |
| WO | WO 2022/266010 A1 | 12/2022 |
| WO | WO 2022/266012 A1 | 12/2022 |
| WO | WO 2022/266389 A1 | 12/2022 |
| WO | WO 2023/283642 A1 | 1/2023 |
| WO | WO 2023/283645 A1 | 1/2023 |
| WO | WO 2023/283651 A1 | 1/2023 |
| WO | WO 2023/014649 A1 | 2/2023 |
| WO | WO 2023/018773 A1 | 2/2023 |
| WO | WO 2023/018923 A1 | 2/2023 |
| WO | WO 2023/019181 A1 | 2/2023 |
| WO | WO 2023/056401 A1 | 4/2023 |
| WO | WO 2023/069625 A1 | 4/2023 |
| WO | WO 2023/069895 A1 | 4/2023 |
| WO | WO 2023/069900 A1 | 4/2023 |
| WO | WO 2023/076358 A1 | 5/2023 |
| WO | WO 2023/076658 A1 | 5/2023 |
| WO | WO 2023/081311 A1 | 5/2023 |
| WO | WO 2023/092069 A1 | 5/2023 |
| WO | WO 2023/107999 A2 | 6/2023 |
| WO | WO 2023/114307 A1 | 6/2023 |
| WO | WO 2023/132885 A1 | 7/2023 |
| WO | WO 2023/137149 A1 | 7/2023 |
| WO | WO 2023/150256 A1 | 8/2023 |
| WO | WO 2023/154818 A1 | 8/2023 |
| WO | WO 2023/196914 A1 | 10/2023 |
| WO | WO 2023/201204 A1 | 10/2023 |
| WO | WO 2023/201294 A1 | 10/2023 |
| WO | WO 2023/201296 A1 | 10/2023 |
| WO | WO 2023/212696 A1 | 11/2023 |
| WO | WO 2023/225524 A1 | 11/2023 |
| WO | WO 2023/250119 A1 | 12/2023 |
| WO | WO 2024/010993 A1 | 1/2024 |
| WO | WO 2024/015890 A1 | 1/2024 |
| WO | WO 2024/026005 A1 | 2/2024 |
| WO | WO 2024/030369 A1 | 2/2024 |
| WO | WO 2024/050483 A1 | 3/2024 |
| WO | WO 2024/097874 A1 | 5/2024 |
| WO | WO 2024/102813 A1 | 5/2024 |
| WO | WO 2024/123978 A1 | 6/2024 |
| WO | WO 2024/151811 A1 | 7/2024 |
| WO | WO 2024/163465 A1 | 8/2024 |

OTHER PUBLICATIONS

Kim SH, Samal SK. Role of untranslated regions in regulation of gene expression, replication, and pathogenicity of Newcastle disease virus expressing green fluorescent protein. J Virol. Mar. 2010;84(5):2629-34. Epub Dec. 16, 2009. (Year: 2009).*

(56)                References Cited

OTHER PUBLICATIONS

Schlake T, Thess A, Fotin-Mleczek M, Kallen KJ. Developing mRNA-vaccine technologies. RNA Biol. Nov. 2012;9(11):1319-30. Epub Oct. 12, 2012. (Year: 2012).*

International Search Report and Written Opinion for Application No. PCT/US2018/022643, mailed Jun. 26, 2018.

Alconada et al., A tyrosine-based motif and a casein kinase II phosphorylation site regulate the intracellular trafficking of the varicella-zoster virus glycoprotein I, a protein localized in the trans-Golgi network. EMBO J. Nov. 15, 1996;15(22):6096-110.

Anderson et al., Stability of mRNA/cationic lipid lipoplexes in human and rat cerebrospinal fluid: methods and evidence for nonviral mRNA gene delivery to the central nervous system. Hum Gene Ther. Feb. 10, 2003;14(3):191-202.

Azarkh et al. Synthesis and decay of varicella zoster virus transcripts. J Neurovirol. Jun. 2011;17(3):281-7. doi: 10.1007/s13365-011-0029-2. Epub Apr. 12, 2011.

Bahl et al., Preclinical and Clinical Demonstration of Immunogenicity by mRNA Vaccines against H10N8 and H7N9 Influenza Viruses. Mol Ther. Jun. 7, 2017;25(6):1316-1327. doi: 10.1016/j.ymthe.2017.03.035. Epub Apr. 27, 2017.

Bose et al., Influence of cationic lipid concentration on properties of lipid-polymer hybrid nanospheres for gene delivery. Int J Nanomedicine. Sep. 2, 2015;10:5367-82. doi: 10.2147/IJN.S87120. eCollection 2015.

Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.

Chen et al., Influence of Particle Size on the in Vivo Potency of Lipid Nanoparticle Formulations of siRNA. J Control Release. Aug. 10, 2016;235:236-244. doi: 10.1016/j.jconrel.2016.05.059. Epub May 26, 2016.

Cheng et al., Multifunctional triblock copolymers for intracellular messenger RNA delivery. Biomaterials. Oct. 2012; 33(28): 6868-6876.

Cu et al., Enhanced Delivery and Potency of Self-Amplifying mRNA Vaccines by Electroporation in Situ, Vaccines, 2013, 1, 367-383. Abstract Only.

Cunnigham, The herpes zoster subunit vaccine. Expert Opin Biol Ther. 2016;16(2):265-71. doi: 10.1517/14712598.2016.1134481. PMID: 26865048.

De Jong et al., Drug delivery and nanoparticles:applications and hazards. Int J Nanomedicine. 2008;3(2):133-49.

Deering et al., Nucleic acid vaccines: prospects for non-viral delivery of mRNA vaccines.Expert Opin Drug Deliv. Jun. 2014;11(6):885-99. doi: 10.1517/17425247.2014.901308. Epub Mar. 26, 2014.

Dicaro et al., In Vivo Delivery of Nucleic Acid-Formulated Microparticles as a Potential Tolerogenic Vaccine for Type 1 Diabetes. Rev Diabet Stud. 2012 Winter;9(4):348-56.

Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.

Ernsting et al., Factors controlling the pharmacokinetics, biodistribution and intratumoral penetration of nanoparticles. J Control Release. Dec. 28, 2013;172(3):782-94. doi: 10.1016/j.jconrel.2013.09.013. Epub Sep. 25, 2013.

Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.

Freer et al., Varicella-zoster virus infection: natural history, clinical manifestations, immunity and current and future vaccination strategies. New Microbiol. Apr. 2018;41(2):95-105. Epub Mar. 2, 2018.

Geall et al., Nonviral delivery of self-amplifying RNA vaccines. Proc Natl Acad Sci U S A. Sep. 4, 2012;109(36):14604-9. doi: 10.1073/pnas.1209367109. Epub Aug. 20, 2012.

Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.

Hassett et al., Optimization of Lipid Nanoparticles for Intramuscular Administration of mRNA Vaccines. Mol Ther Nucleic Acids. Apr. 15, 2019;15:1-11. Epub Feb. 7, 2019.

Hecker, Nonviral, cationic lipid-mediated delivery of mRNA. Methods Mol Biol. 2013;969:73-88. doi: 10.1007/978-1-62703-260-5_5.

Hess et al., Vaccination with mRNAs encoding tumor-associated antigens and granulocyte-macrophage colony-stimulating factor efficiently primes CTL responses, but is insufficient to overcome tolerance to a model tumor/self antigen. Cancer Immunol Immunother. Jun. 2006;55(6):672-83. Epub Aug. 20, 2005.

Holtkamp et al., Modification of antigen-encoding RNA increases stability, translational efficacy, and T-cell stimulatory capacity of dendritic cells. Blood. Dec. 15, 2006;108(13):4009-17.

Hsu et al., Cationic lipid nanoparticles for therapeutic delivery of siRNA and miRNA to murine liver tumor. Nanomedicine. Nov. 2013;9(8):1169-80. doi: 10.1016/j.nano.2013.05.007. Epub May 30, 2013.

John et al., Multi-antigenic human cytomegalovirus mRNA vaccines that elicit potent humoral and cell-mediated immunity. Vaccine. Mar. 14, 2018;36(12):1689-1699. doi:10.1016/j.vaccine.2018.01.029. Epub Feb. 15, 2018.

Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.

Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.

Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.

Kuhn et al., mRNA as a versatile tool for exogenous protein expression. Current Gene Therapy. Oct. 2012; 12 (5): 347-361.

Leitner et al., DNA and RNA-based vaccines: principles, progress and prospects. Vaccine. Dec. 10, 1999;18 (9-10):765-77.

Leroueil et al., Wide varieties of cationic nanoparticles induce defects in supported lipid bilayers. Nano Lett. Feb. 2008;8(2):420-4. doi: 10.1021/n10722929. Epub Jan. 25, 2008.

Li et al., Developing lipid nanoparticle-based siRNA therapeutics for hepatocellular carcinoma using an integrated approach. Mol Cancer Ther. Nov. 2013;12(11):2308-18. doi: 10.1158/1535-7163.MCT-12-0983-T. Epub Aug. 13, 2013.

Lian et al., Trends and developments in liposome drug delivery systems. J Pharm Sci. Jun. 2001;90(6):667-80.

Liang et al., Efficient Targeting and Activation of Antigen-Presenting Cells In Vivo after Modified mRNA Vaccine Administration in Rhesus Macaques. Mol Ther. Dec. 6, 2017;25(12):2635-2647. doi: 10.1016/j.ymthe.2017.08.006. Epub Aug. 12, 2017.

Lin et al., Lipid-based nanoparticles in the systemic delivery of siRNA. Nanomedicine (Lond). Jan. 2014;9(1):105-20. doi: 10.2217/nnm.13.192.

Lindgren et al., Induction of Robust B Cell Responses after Influenza mRNA Vaccination is Accompanied by Circulating Hemagglutinin-Specific ICOS+ PD-1+ CXCR3+ T Follicular Helper Cells. Front Immunol. Nov. 13, 2017;8:1539. doi: 10.3389/fimmu.2017.01539. eCollection 2017.

Lorenzi et al., Intranasal vaccination with messenger RNA as a new approach in gene therapy: Use against tuberculosis. BMC Biotechnol. Oct. 2010; 10(77): 1-11.

Maclachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016.

Madden et al., Systemic delivery of mRNA therapeutics using lipid nanoparticles (LNP): improved potency for novel LNP and influ-

(56)             References Cited

OTHER PUBLICATIONS ence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.

Martinon et al., Induction of virus-specific cytotoxic T lymphocytes in vivo by liposome-entrapped mRNA. EurJ Immunol. Jul. 1993;23(7):1719-22.

Mckay et al., Self-amplifying Rna SARS-CoV-2 lipid nanoparticle vaccine candidate induces high neutralizing antibody titers in mice. Nat Commun. Jul. 9, 2020;11(1):3523. doi: 10.1038/s41467-020-17409-9.

Mckenzie et al., Nucleic acid vaccines: tasks and tactics. Immunol Res. 2001 ;24(3):225-44.

Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review .

Mitchell et al., RNA transfected dendritic cells as cancer vaccines. Curr Opin Mol Ther. Apr. 2000;2(2):176-81.

Mockey et al., mRNA-based cancer vaccine: prevention of B16 melanoma progression and metastasis by systemic injection of MART1 mRNA histidylated lipopolyplexes. Cancer Gene Ther. Sep. 2007;14(9):802-14. Epub Jun. 22, 2007.

Moffat et al., Functions of the C-terminal domain of varicella-zoster virus glycoprotein E in viral replication in vitro and skin and T-cell tropism in vivo. J Virol. Nov. 2004;78(22):12406-15.

Monslow et al., Immunogenicity generated by mRNA vaccine encoding VZV gE antigen is comparable to adjuvanted subunit vaccine and better than live attenuated vaccine in nonhuman primates. Vaccine. Aug. 10, 2020;38(36):5793-5802. doi: 10.1016/j.vaccine.2020.06.062. Epub Jul. 20, 2020.

Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.

Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.

Pollard et al., Type I IFN counteracts the induction of antigen-specific immune responses by lipid-based delivery of mRNA vaccines. Mol Ther. Jan. 2013; 21 (1): 251-259.

Reichmuth et al., mRNA Vaccine Delivery Using Lipid Nanoparticles. Ther Deliv. 2016;7(5):319-34. doi: 10.4155/tde-2016-0006.

Richner et al., Modified mRNA Vaccines Protect against Zika Virus Infection. Cell. Mar. 23, 2017;169(1):176. doi: 10.1016/j.cell.2017.03.016.

Sabnis et al., A Novel Amino Lipid Series for mRNA Delivery: Improved Endosomal Escape and Sustained Pharmacology and Safety in Non-human Primates. Mol Ther. Jun. 6, 2018;26(6):1509-1519. doi: 10.1016/j.ymthe.2018.03.010. Epub Mar. 14, 2018.

Schirrmacher et al., Intra-pinna anti-tumor vaccination with self-replicating infectious RNA or with DNA encoding a model tumor antigen and a cytokine. Gene Ther. Jul. 2000;7(13):1137-47.

Schott et al., Viral and non-viral approaches for transient delivery of mRNA and proteins. Current Gene Ther. 2011; 11 (5): 382-398.

Shah et al., Shingrix for Herpes Zoster: A Review. Skin Therapy Lett. Jul. 2019;24(4):5-7.

Szebeni et al., Activation of complement by therapeutic liposomes and other lipid excipient-based therapeutic products: prediction and prevention. Adv Drug Deliv Rev. Sep. 16, 2011;63(12):1020-30. doi: 10.1016/j.addr.2011.06.017. Epub Jul. 14, 2011.

Szebeni et al., Complement activation as a bioequivalence issue relevant to the development of generic liposomes and other nanoparticulate drugs. Biochem Biophys Res Commun. Dec. 18, 2015;468(3):490-7. doi: 10.1016/j.bbrc.2015.06.177. Epub Jul. 14, 2015.

Szebeni, Complement activation-related pseudoallergy: a stress reaction in blood triggered by nanomedicines and biologicals. Mol Immunol. Oct. 2014;61(2):163-73. doi: 10.1016/j.molimm.2014.06.038. Epub Aug. 12, 2014.

Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.

Vassilev et al., Microparticle-mediated RNA immunization against bovine viral diarrhea virus. Vaccine. Feb. 28, 2001;19(15-16):2012-9.

Wang et al., Essential role played by the C-terminal domain of glycoprotein I in envelopment of varicella-zoster virus in the trans-Golgi network: interactions of glycoproteins with tegument. J Virol. Jan. 2001;75(1):323-40.

Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.

Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.

Wong et al., An mRNA vaccine for influenza. Nat Biotechnol. Dec. 2012;30(12):1202-4. doi: 10.1038/nbt.2439.

Woodward et al., Varicella Virus Vaccine Live: A 22-Year Review of Postmarketing Safety Data. Open Forum Infect Dis. Aug. 1, 2019 ;6(8):ofz295.

Xue et al., Lipid-Based Nanocarriers for RNA Delivery. Curr Pharm Des. 2015;21(22):3140-7.

Yamamoto et al., Current prospects for mRNA gene delivery. Eur J Pharm Biopharm. Mar. 2009;71(3):484-9. doi: 10.1016/j.ejpb.2008.09.016. Epub Oct. 10, 2008.

Ying et al., Cancer therapy using a self-replicating RNA vaccine. Nat Med. Jul. 1999;5(7):823-7.

Zhu et al., Targeting of glycoprotein I (gE) of varicella-zoster virus to the trans-Golgi network by an AYRV sequence and an acidic amino acid-rich patch in the cytosolic domain of the molecule. J Virol. Oct. 1996;70(10):6563-75.

Zou et al., Lipid-mediated delivery of RNA is more efficient than delivery of DNA in non-dividing cells. Int J Pharm. Apr. 15, 2010;389(1-2):232-43. doi: 10.1016/j.ijpharm.2010.01.019. Epub Jan. 18, 2010.

Delmas et al., Preparation and characterization of highly stable lipid nanoparticles with amorphous core of tuneable viscosity. J Colloid Interface Sci. Aug. 15, 2011;360(2):471-81. doi: 10.1016/j.jcis.2011.04.080. Epub Apr. 28, 2011.

Fang et al., Development of lipid-shell and polymer core nanoparticles with water-soluble salidroside for anti-cancer therapy. Int J Mol Sci. Feb. 25, 2014;15(3):3373-88. doi: 10.3390/ijms15033373.

Feng et al., Current status of research on various tumor antigen-related tumor vaccines. West China Med J. Jul. 25, 2008;23(4):928-930.

Govind et al., Primer-independent initiation of RNA synthesis by SeMV recombinant RNA-dependent RNA polymerase. Virology. Jun. 5, 2010;401(2):280-92. doi: 10.1016/j.virol.2010.02.025. Epub Mar. 23, 2010.

Inoue et al., Sequence-dependent hydrolysis of RNA using modified oligonucleotide splints and RNase H. FEBS Lett. May 11, 1987;215(2):327-30. doi: 10.1016/0014-5793(87)80171-0.

Kaukinen et al., The reactivity of phosphodiester bonds within linear single-stranded oligoribonucleotides is strongly dependent on the base sequence. Nucleic Acids Res. Jan. 15, 2002;30(2):468-74. doi: 10.1093/nar/30.2.468.

Lutz et al., Unmodified mRNA in LNPs constitutes a competitive technology for prophylactic vaccines. NPJ Vaccines. Oct. 19, 2017:2:29. doi: 10.1038/s41541-017-0032-6. eCollection 2017.

Perrin, S., Preclinical research: Make mouse studies work. Nature. Mar. 27, 2014;507(7493):423-5. doi: 10.1038/507423a.

Triana-Alonso et al., Self-coded 3'-extension of run-off transcripts produces aberrant products during in vitro transcription with T7 RNA polymerase. J Biol Chem. Mar. 17, 1995;270(11):6298-307. doi: 10.1074/jbc.270.11.6298.

(56) References Cited

OTHER PUBLICATIONS

Wenjie et al., The current situation of epitope peptide in cancer therapy. Modern Oncol. Dec. 2016;24(23):3837-3840. doi: 10.3969/j.issn.1672-4992.2016.23.043.

Zerboni et al., Varicella-zoster virus glycoprotein E is a critical determinant of virulence in the SCID mouse-human model of neuropathogenesis. J Virol. Jan. 2011;85(1):98-111. doi: 10.1128/JVI.01902-10. Epub Oct. 20, 2010.

Allen et al., Liposomal drug delivery systems: from concept to clinical applications. Adv Drug Deliv Rev. Jan. 2013;65(1):36-48. doi: 10.1016/j.addr.2012.09.037. Epub Oct. 1, 2012.

Center et al., mRNA Analytical Development and CMC Support. BioProcess International eBook Series. Messenger RNA Drugs. Dec. 2018. 10 pages.

Cheng et al., The role of helper lipids in lipid nanoparticles (LNPs) designed for oligonucleotide delivery. Adv Drug Deliv Rev. Apr. 1, 2016;99(Pt A):129-137. doi: 10.1016/j.addr.2016.01.022. Epub Feb. 18, 2016.

Decision IPR2023-01358—Inter Partes Review of U.S. Pat. No. 10,702,600. *BioNTech SE and Pfizer Inc.* (Petitioners) v. *ModernaTX, Inc.* (Patent Owner). Mailed Mar. 19, 2024. 97 pages.

Guan et al., Nanotechnologies in delivery of mRNA therapeutics using nonviral vector-based delivery systems. Gene Ther. Mar. 2017;24(3):133-143. doi: 10.1038/gt.2017.5. Epub Jan. 17, 2017.

Karikó, Modified uridines are the key to a successful message. Nat Rev Immunol. Oct. 2021;21(10):619. doi: 10.1038/s41577-021-00608-w.

Li et al., Peptide Vaccine: Progress and Challenges. Vaccines (Basel). Jul. 2, 2014;2(3):515-36. doi: 10.3390/vaccines2030515.

Pardi et al., Nucleoside-modified mRNA immunization elicits influenza virus hemagglutinin stalk-specific antibodies. Nat Commun. Aug. 22, 2018;9(1):3361. doi: 10.1038/s41467-018-05482-0.

Paunovska et al., A Direct Comparison of in Vitro and in Vivo Nucleic Acid Delivery Mediated by Hundreds of Nanoparticles Reveals a Weak Correlation. Nano Lett. Mar. 14, 2018;18(3):2148-2157. doi: 10.1021/acs.nanolett.8b00432. Epub Mar. 5, 2018.

Phua et al., Transfection efficiency and transgene expression kinetics of mRNA delivered in naked and nanoparticle format. J Control Release. Mar. 28, 2013;166(3):227-33. doi: 10.1016/j.jconrel.2012.12.029. Epub Jan. 7, 2013.

Whitehead et al., In vitro-in vivo translation of lipid nanoparticles for hepatocellular siRNA delivery. ACS Nano. Aug. 28, 2012;6(8):6922-9. doi: 10.1021/nn301922x. Epub Jul. 6, 2012.

* cited by examiner

PROPOSED VARICELLAR ZOSTER VIRUS PATHWAY

Single immunization with or without booster on

Dosing     Day 0        Day 28

Bleeding   Day -2   (Day 0 +6h)   Day 14   Day 27   (Day 28 +6h)   Day 42   Day 56

| G# | Antigen | Route | N= | Dosage (ug) | Dose Vol (ul) | 1st dose | 2nd dose | LNP | mRNA Conc. (mg/ml) | Volume +Overage |
|---|---|---|---|---|---|---|---|---|---|---|
| 1 | VZV-gE-oka-hIgkappa (G5; cap1) | IM | 8 | 10 | 50 | Day 0 | | MC3 | 0.2 | 1x600 ul |
| 2 | VZV-gE-oka-hIgkappa (G5; cap1) | IM | 8 | 10 | 50 | Day 0 | Day 28 | MC3 | 0.2 | 2x600 ul |
| 3 | VZV-gE-oka-hIgkappa (G5; cap1) | ID | 8 | 10 | 50 | Day 0 | | MC3 | 0.2 | 1x600 ul |
| 4 | VZV-gE-oka-hIgkappa (G5; cap1) | ID | 8 | 10 | 50 | Day 0 | Day 28 | MC3 | 0.2 | 2x600 ul |
| 5 | VZV-gE-oka (G0; cap1) | IM | 8 | 10 | 50 | Day 0 | | MC3 | 0.2 | 1x600 ul |
| 6 | VZV-gE-oka (G0; cap1) | IM | 8 | 10 | 50 | Day 0 | Day 28 | MC3 | 0.2 | 2x600 ul |
| 7 | VZV-gE-oka (G0; cap1) | ID | 8 | 10 | 50 | Day 0 | | MC3 | 0.2 | 1x600 ul |
| 8 | VZV-gE-oka (G0; cap1) | ID | 8 | 10 | 50 | Day 0 | Day 28 | MC3 | 0.2 | 2x600 ul |
| 9 | VZV-gE-oka (G5; cap1) | IM | 8 | 10 | 50 | Day 0 | | MC3 | 0.2 | 1x600 ul |
| 10 | VZV-gE-oka (G5; cap1) | IM | 8 | 10 | 50 | Day 0 | Day 28 | MC3 | 0.2 | 2x600 ul |
| 11 | VZV-gE-oka (G5; cap1) | ID | 8 | 10 | 50 | Day 0 | | MC3 | 0.2 | 1x600 ul |
| 12 | VZV-gE-oka (G5; cap1) | ID | 8 | 10 | 50 | Day 0 | Day 28 | MC3 | 0.2 | 2x600 ul |
| 13 | Negative control (PBS) | IM | 6 | / | 50 | Day 0 | | PBS | / | 1x600 ul |
| 14 | Negative control (PBS) | IM | 6 | / | 50 | Day 0 | Day 28 | PBS | / | 2x600 ul |
| 15 | Positive control (Varivax) | SC | 6 | 54 (pfu) | 50 | Day 0 | | | / | 1x1250 ul |
| 16 | Positive control (Varivax) | SC | 6 | 54 (pfu) | 50 | Day 0 | Day 28 | | / | |
| 17 | Positive control (Varivax) | SC | 4 | 675 (pfu) | 100 | Day 0 | | | / | 4x220 ul |
| 18 | Positive control (Varivax) | SC | 4 | 675 (pfu) | 100 | Day 0 | Day 28 | | / | |

Fig. 3

Anti GM130 (CST D6B1) - green

Anti Golgin-97 (CST D8P2K) - green

Anti GE Abcam 52549 - green

Untransfected Control

SE-VZV-GE-delete-S62

SE-VZV-GE-full_with_AEAADA

⟶  Perinuclear (Golgi ?) localization

----→  Cell membrane localization

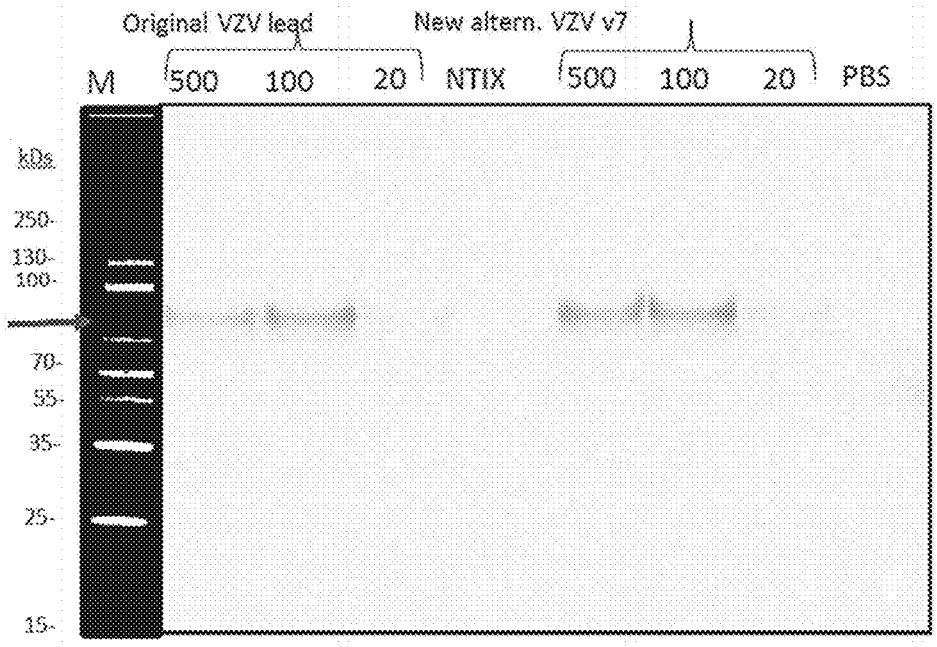
Fig. 19B
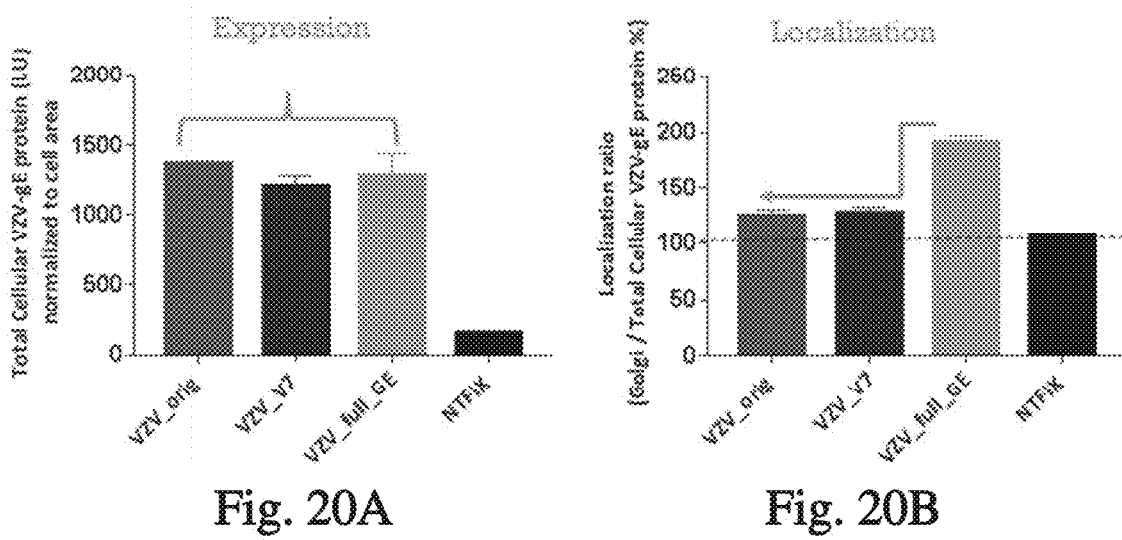
Fig. 20A                    Fig. 20B

VARICELLA ZOSTER VIRUS (VZV) VACCINE

RELATED APPLICATIONS

This application is a continuation of U.S. application Ser. No. 17/245,973, filed Apr. 30, 2021, which is a continuation of U.S. application Ser. No. 16/494,162, filed Sep. 13, 2019, which is a national stage filing under 35 U.S.C. § 371 of international application number PCT/US2018/022643, filed Mar. 15, 2018, which was published under PCT Article 21(2) in English and claims the benefit under 35 U.S.C. § 119(e) of U.S. provisional application No. 62/471,809, filed Mar. 15, 2017, and U.S. provisional application No. 62/490, 112, filed Apr. 26, 2017, each of which is incorporated by reference herein in their entirety.

REFERENCE TO AN ELECTRONIC SEQUENCE LISTING

The contents of the electronic sequence listing (M137870077US04-SUBSEQ-VLJ.xml; Size: 394,171 bytes; and Date of Creation: Sep. 16, 2024) is herein incorporated by reference in its entirety.

BACKGROUND

Varicella is an acute infectious disease caused by varicella zoster virus (VZV). Varicella zoster virus is one of eight herpesviruses known to infect humans and vertebrates. VZV is also known as chickenpox virus, varicella virus, zoster virus, and human herpesvirus type 3 (HHV-3). VZV only affects humans, and commonly causes chickenpox in children, teens and young adults and herpes zoster (shingles) in adults (rarely in children). The primary VZV infection, which results in chickenpox (varicella), may result in complications, including viral or secondary bacterial pneumonia. Even when the clinical symptoms of chickenpox have resolved, VZV remains dormant in the nervous system of the infected person (virus latency) in the trigeminal and dorsal root ganglia. In about 10-20% of cases, VZV reactivates later in life, travelling from the sensory ganglia back to the skin where it produces a disease (rash) known as shingles or herpes zoster. VZV can also cause a number of neurologic conditions ranging from aseptic meningitis to encephalitis. Other serious complications of VZV infection include postherpetic neuralgia, Mollaret's meningitis, zoster multiplex, thrombocytopenia, myocarditis, arthritis, and inflammation of arteries in the brain leading to stroke, myelitis, herpes ophthalmicus, or zoster sine herpete. In rare instances, VZV affects the geniculate ganglion, giving lesions that follow specific branches of the facial nerve. Symptoms may include painful blisters on the tongue and ear along with one sided facial weakness and hearing loss.

Varicella cases have declined 97% since 1995, mostly due to vaccination. However, an estimated 500,000 to 1 million episodes of herpes zoster (shingles) occur annually in just the United States. The lifetime risk of herpes zoster is estimated to be at least 32%, with increasing age and cellular immunosuppression being the most important risk factors. In fact, it is estimated that 50% of persons living until the age of 85 will develop herpes zoster.

A live attenuated VZV Oka strain vaccine is available and is marketed in the United States under the trade name VARIVAX® (Merck). A similar, but not identical, VZV vaccine is marketed globally as VARILRIX® (GlaxoSmithKline). Since its approval in 1995, it has been added to the recommended vaccination schedules for children in Australia, the United States, and several other countries. In 2007, the Advisory Committee on Immunization Practices (ACIP) recommended a second dose of vaccine before school entry to ensure the maintenance of high levels of varicella immunity. In 2001-2005, outbreaks were reported in schools with high varicella vaccination coverage, indicating that even in settings where most children were vaccinated and the vaccine performed as expected, varicella outbreaks could not be prevented with the one-dose vaccination policy. As a result, two-dose vaccination is the adopted protocol; however, even with two doses of vaccine, there are reported incidences of breakthrough varicella. Furthermore, varicella vaccination has raised concerns that the immunity induced by the vaccine may not be lifelong, possibly leaving adults vulnerable to more severe disease as the immunity from their childhood immunization wanes.

In 2005, the FDA approved the combined live attenuated combination measles-mumps-rubella-varicella (MMRV) vaccine PROQUAD™ (Merck) for use in persons 12 months to 12 years in age. While the attenuated measles, mumps, and rubella vaccine viruses in MMRV are identical and of equal titer to those in the MMR vaccine, the titer of Oka/Merck VZV is higher in MMRV vaccine than in single-antigen varicella vaccine.

In 2006, the United States Food and Drug Administration approved ZOSTAVAX® (Merck) for the prevention of shingles (herpes zoster) in persons 60 years or older (currently 50-59 years of age is approved). ZOSTAVAX® contains the same Oka/Merck varicella zoster virus used in the varicella and MMRV vaccines, but at a much higher titer (>10-fold higher viral dose) than that present in both of these vaccines, as the concentrated formulation is designed to elicit an immune response in older adults whose immunity to VZV wanes with advancing age.

Although the varicella vaccine has been shown to be safe in healthy individuals, there is evidence that immunity to VZV infection conferred by the vaccine wanes over time, rendering the vaccinated individuals susceptible to shingles, a more serious condition. In addition, there have been reports that individuals have developed chicken pox or shingles from the varicella vaccination. The vaccine may establish a latent infection in neural ganglia, which can then reactivate to cause herpes zoster.

Moreover, live attenuated virus is not suitable for all subjects, including pregnant women and persons with moderate or severe acute illnesses. Also, varicella is not suitable or approved for immunocompromised patients, including persons with immunosuppression due to leukemia, lymphoma, generalized malignancy, immune deficiency disease or immunosuppressive therapy. Likewise, persons with moderate or severe cellular immunodeficiency resulting from infection with human immunodeficiency virus (HIV) including those diagnosed with acquired immunodeficiency syndrome (AIDS) should not receive the varicella vaccine. Thus, despite the high risk of morbidity and mortality associated with herpes zoster in immunocompromised individuals, this population is not eligible for vaccination with a live attenuated vaccine, such as ZOSTAVAX®.

There are one million cases of herpes zoster in the U.S. each year. An estimated $1 billion is spent annually on direct medical costs for herpes zoster in the US and treatment for herpes zoster is not always effective or available.

Deoxyribonucleic acid (DNA) vaccination is one technique used to stimulate humoral and cellular immune responses to foreign antigens, such as VZV antigens. The direct injection of genetically engineered DNA (e.g., naked plasmid DNA) into a living host results in a small number of host cells directly producing an antigen, resulting in a protective immunological response. With this technique, however, comes potential problems, including the possibility of insertional mutagenesis, which could lead to the activation of oncogenes or the inhibition of tumor suppressor genes.

SUMMARY

Provided herein is a ribonucleic acid (RNA) vaccine that builds on the knowledge that RNA (e.g., messenger RNA (mRNA)) can safely direct the body's cellular machinery to produce nearly any protein of interest, from native proteins to antibodies and other entirely novel protein constructs that can have therapeutic activity inside and outside of cells. The varicella zoster virus (VZV) RNA vaccines of the present disclosure may be used to induce a balanced immune response against VZV comprising both cellular and humoral immunity, without many of the risks associated with attenuated virus vaccination.

The RNA (e.g., mRNA) vaccines may be utilized in various settings depending on the prevalence of the infection or the degree or level of unmet medical need. The RNA (e.g., mRNA) vaccines may be utilized to treat and/or prevent a VZV of various genotypes, strains, and isolates. The RNA (e.g., mRNA) vaccines have superior properties in that they produce much larger antibody titers and produce responses earlier than commercially available anti-viral therapeutic treatments. While not wishing to be bound by theory, it is believed that the RNA vaccines, as mRNA polynucleotides, are better designed to produce the appropriate protein conformation upon translation as the RNA vaccines co-opt natural cellular machinery. Unlike traditional vaccines, which are manufactured ex vivo and may trigger unwanted cellular responses, RNA (e.g., mRNA) vaccines are presented to the cellular system in a more native fashion.

Various VZV amino acid sequences encompasses by the present disclosure are provided in Tables 1-9. RNA (e.g., mRNA) vaccines as provided herein may include at least one RNA polynucleotide encoding at least one of the VZV glycoproteins provided in Table 1, or a fragment, homolog (e.g., having at least 80%, 85%, 90%, 95%, 98% or 99% identity) or variant or derivative thereof.

Some embodiments of the present disclosure provide VZV vaccines that include at least one ribonucleic acid (RNA) polynucleotide having an open reading frame encoding at least one VZV antigenic polypeptide. Some embodiments of the present disclosure provide VZV vaccines that include at least one RNA polynucleotide having an open reading frame encoding two or more VZV antigenic polypeptides. Some embodiments of the present disclosure provide VZV vaccines that include two or more RNA polynucleotides having an open reading frame encoding two or more VZV antigenic polypeptides.

In some embodiments, an antigenic polypeptide is a VZV glycoprotein. For example, a VZV glycoprotein may be VZV gE, gI, gB, gH, gK, gL, gC, gN, or gM. In some embodiments, the antigenic polypeptide is a VZV gE polypeptide. In some embodiments, the antigenic polypeptide is a VZV gI polypeptide. In some embodiments, the antigenic polypeptide is a VZV gB polypeptide. In some embodiments, the antigenic polypeptide is a VZV gH polypeptide. In some embodiments, the antigenic polypeptide is a VZV gK polypeptide. In some embodiments, the antigenic polypeptide is a VZV gL polypeptide. In some embodiments, the antigenic polypeptide is a VZV gC polypeptide. In some embodiments, the antigenic polypeptide is a VZV gN polypeptide. In some embodiments, the antigenic polypeptide is a VZV gM polypeptide. In some embodiments, the VZV glycoprotein is encoded by a nucleic acid sequence of SEQ ID NO: 1 or SEQ ID NO: 2.

In some embodiments, the VZV glycoprotein is a variant gE polypeptide. In some embodiments, the variant VZV gE polypeptide is a truncated polypeptide lacking the anchor domain (ER retention domain). In some embodiments, the truncated VZV gE polypeptide comprises (or consists of, or consists essentially of) amino acids 1-561 of VZV gE polypeptide. In some embodiments, the truncated VZV gE polypeptide comprises (or consists of, or consists essentially of) amino acids 1-561 of SEQ ID NO: 10. In some embodiments, the truncated VZV gE polypeptide comprises (or consists of, or consists essentially of) amino acids 1-573 of SEQ ID NO: 18. In some embodiments, the truncated VZV gE polypeptide comprises (or consists of, or consists essentially of) amino acids 1-573 of SEQ ID NO: 10. In some embodiments, the variant VZV gE polypeptide is a truncated polypeptide lacking the carboxy terminal tail domain. In some embodiments, the truncated VZV gE polypeptide comprises (or consists of, or consists essentially of) amino acids 1-573 of VZV gE polypeptide. In some embodiments, the truncated VZV gE polypeptide comprises (or consists of, or consists essentially of) amino acids 1-573 of SEQ ID NO: 34.

In some embodiments, the variant VZV gE polypeptide has at least one mutation in one or more motif(s) associated with ER retention, wherein the mutation(s) in one or more motif(s) results in decreased retention of the VZV gE polypeptide in the ER and/or golgi. In some embodiments, the variant VZV gE polypeptide has at least one mutation in one or more motif(s) associated with targeting gE to the golgi or trans-golgi network (TGN), wherein the mutation(s) in one or more motif(s) results in decreased targeting or localization of the VZV gE polypeptide to the golgi or TGN. In some embodiments, the variant VZV gE polypeptide has at least one mutation in one or more motif(s) associated with the internalization of VZV gE or the endocytosis of gE, wherein the mutation(s) in one or more motif(s) results in decreased endocytosis of the VZV gE polypeptide. In some embodiments, the variant VZV gE polypeptide has at least one mutation in one or more phosphorylated acidic motif(s), such as SSTT (SEQ ID NO: 122). In some embodiments, the variant VZV gE polypeptide is a full-length VZV gE polypeptide having a Y582G mutation. In some embodiments, the variant VZV gE polypeptide is a full-length VZV gE polypeptide having a Y569A mutation. In some embodiments, the variant VZV gE polypeptide is a full-length VZV gE polypeptide having a Y582G mutation and a Y569A mutation. In some embodiments, the variant VZV gE polypeptide is an antigenic fragment comprising amino acids 1-573 of VZV gE and having a Y569A mutation. In some embodiments, the variant VZV gE polypeptide is an antigenic fragment comprising SEQ ID NO: 38.

In some embodiments, the variant VZV gE polypeptide is a full-length VZV gE polypeptide having an IgK sequence. In some embodiments, the variant VZV gE polypeptide is SEQ ID NO: 14. In some embodiments, the variant VZV gE polypeptide is a full-length VZV gE polypeptide having an A-E-A-A-D-A sequence (SEQ ID NO: 58) that replaces SESTDT (SEQ ID NO: 59). This is a replacement of the Ser/Thr—rich "SSTT" (SEQ ID NO: 122) acidic cluster with an Ala-rich sequence. In some embodiments, the variant VZV gE polypeptide is SEQ ID NO: 26. In some embodiments in which the VZV gE polypeptide has an A-E-A-A-D-A sequence (SEQ ID NO: 58), the variant VZV gE polypeptide also has at least one mutation in one or more motif(s) associated with ER/golgi retention, TGN localization, or endocytosis (e.g., has a Y582G mutation, a Y569A mutation, or both a Y582G mutation and a Y569A mutation) and/or has at least one mutation in one or more phosphorylated acidic motif(s), such as a SSTT (SEQ ID NO: 122) motif. In some embodiments, the variant VZV gE polypeptide is or comprises the amino acid sequence of SEQ ID NO: 30.

In some embodiments, the variant VZV gE polypeptide is a full-length VZV gE polypeptide having an additional sequence at the C-terminus that aids in secretion of the polypeptide or its localization to the cell membrane. In some embodiments, the variant VZV gE polypeptide is a full-length VZV gE polypeptide having an IgKappa sequence at the C-terminus. In some embodiments, the VZV gE polypeptide has additional sequence at the C-terminus that aids in secretion (e.g., has an IgKappa sequence at the C-terminus) and has at least one mutation in one or more motif(s) associated with ER retention, TGN localization, or endocytosis (e.g., has a Y582G mutation, a Y569A mutation, or both a Y582G mutation and a Y569A mutation) and/or has at least one mutation in one or more phosphorylated acidic motif(s), such as the SSTT (SEQ ID NO: 122) motif. In some embodiments, the variant VZV gE polypeptide is a truncated polypeptide lacking the anchor domain (ER retention domain) and having an additional sequence at the C-terminus that aids in secretion of the polypeptide (e.g., an IgKappa sequence at the C-terminus). In some embodiments, the truncated VZV gE polypeptide comprises amino acids 1-561 and has an IgKappa sequence at the C-terminus. In some embodiments, the variant polypeptide is SEQ ID NO: 22. In some embodiments, the variant VZV gE polypeptide is a truncated polypeptide lacking the carboxy terminal tail domain and having an additional sequence at the C-terminus that aids in secretion of the polypeptide, for example, having an IgKappa sequence at the C-terminus. In some embodiments, the truncated VZV gE polypeptide comprises amino acids 1-573 and has an IgKappa sequence at the C-terminus.

In some embodiments, the antigenic polypeptide comprises two or more glycoproteins. In some embodiments, the two or more glycoproteins are encoded by a single RNA polynucleotide. In some embodiments, the two or more glycoproteins are encoded by two or more RNA polynucleotides, for example, each glycoprotein is encoded by a separate RNA polynucleotide. In some embodiments, the two or more glycoproteins can be any combination of VZV gE, gI, gB, gH, gK, gL, gC, gN, and gM polypeptides. In some embodiments, the two or more glycoproteins can be any combination of VZV gE and at least one of gI, gB, gH, gK, gL, gC, gN, and gM polypeptides. In some embodiments, the two or more glycoproteins can be any combination of VZV gI and at least one of gE, gB, gH, gK, gL, gC, gN, and gM polypeptides. In some embodiments, the two or more glycoproteins can be any combination of VZV gE, gI, and at least one of gB, gH, gK, gL, gC, gN, and gM polypeptides.

In some embodiments, the two or more VZV glycoproteins are gE and gI. In some embodiments, the two or more VZV glycoproteins are gE and gB. In some embodiments, the two or more VZV glycoproteins are gI and gB. In some embodiments, the two or more VZV glycoproteins are gE, gI, and gB. In some embodiments, the two or more VZV glycoproteins are gE and gH. In some embodiments, the two or more VZV glycoproteins are gI and gH. In some embodiments, the two or more VZV glycoproteins are gE, gI, and gH. In some embodiments, the two or more VZV glycoproteins are gE and gK. In some embodiments, the two or more VZV glycoproteins are gI and gK. In some embodiments, the two or more VZV glycoproteins are gE, gI, and gK. In some embodiments, the two or more VZV glycoproteins are gE and gL. In some embodiments, the two or more VZV glycoproteins are gI and gL. In some embodiments, the two or more VZV glycoproteins are gE, gI, and gL. In some embodiments, the two or more VZV glycoproteins are gE and gC. In some embodiments, the two or more VZV glycoproteins are gI and gC. In some embodiments, the two or more VZV glycoproteins are gE, gI, and gC. In some embodiments, the two or more VZV glycoproteins are gE and gN. In some embodiments, the two or more VZV glycoproteins are gI and gN. In some embodiments, the two or more VZV glycoproteins are gE, gI, and gN. In some embodiments, the two or more VZV glycoproteins are gE and gM. In some embodiments, the two or more VZV glycoproteins are gI and gM. In some embodiments, the two or more VZV glycoproteins are gE, gI, and gM.

In some embodiments, the vaccine comprises any two or more VZV glycoproteins (e.g., any of the variant VZV gE disclosed in the preceding paragraphs and in the Examples and Figures), and the VZV gE is a variant gE, such as any of the variant VZV gE glycoproteins disclosed herein, for example, any of the variant VZV gE disclosed in the preceding paragraphs and in the Examples and Figures.

In some embodiments, the VZV vaccine includes two or more RNA polynucleotides having an open reading frame encoding two or more VZV antigenic polypeptides (either encoded by a single RNA polynucleotide or encoded by two or more RNA polynucleotides, for example, each glycoprotein encoded by a separate RNA polynucleotide), and the two or more VZV glycoproteins are a variant gE (e.g., any of the variant gE polypeptides disclosed herein in the preceding paragraphs) and a VZV glycoprotein selected from gI, gB, gH, gK, gL, gC, gN, and gM polypeptides. In some embodiments, the two or more VZV glycoproteins are a variant gE (e.g., any of the variant gE polypeptides disclosed herein in the preceding paragraphs) and gI. In some embodiments, the glycoproteins are VZV gI and variant VZV gE, and the variant VZV gE polypeptide is a truncated polypeptide lacking the anchor domain (ER retention domain) (e.g., a truncated VZV gE polypeptide comprising amino acids 1-561 of SEQ ID NO: 10). In some embodiments, the glycoproteins are VZV gI and variant VZV gE, and the variant VZV gE polypeptide is a truncated polypeptide lacking the carboxy terminal tail domain (e.g., a truncated VZV gE polypeptide comprising amino acids 1-573 of SEQ ID NO: 18). In some embodiments, the glycoproteins are VZV gI and variant VZV gE, and the variant VZV gE polypeptide has at least one mutation in one or more motif(s) associated with ER retention, TGN localization, and/or endocytosis (e.g., the variant VZV gE has a Y582G mutation, a Y569A mutation, or both a Y582G mutation and a Y569A mutation) and/or has at least one mutation in one or more phosphorylated acidic motif(s), such as SSTT (SEQ ID NO: 122) motif. In some embodiments, the glycoproteins are VZV gI and variant VZV gE, and the variant VZV gE polypeptide is an antigenic fragment comprising amino acids 1-573 of VZV gE and having a Y569A mutation. In some embodiments, the glycoproteins are VZV gI and variant VZV gE, and the variant VZV gE polypeptide is a full-length VZV gE polypeptide having an A-E-A-A-D-A (SEQ ID NO: 58) sequence. In some embodiments, the glycoproteins are VZV gI and variant VZV gE, and the VZV gE polypeptide has an A-E-A-A-D-A (SEQ ID NO: 58) sequence and a Y582G mutation, a Y569A mutation, or both a Y582G mutation and a Y569A mutation. In some embodiments, the glycoproteins are VZV gI and variant VZV gE, and the VZV gE polypeptide is a full-length VZV gE polypeptide having an additional sequence at the C-terminus that aids in secretion of the polypeptide (e.g., an IgKappa sequence). In some embodiments, the glycoproteins are VZV gI and variant VZV gE, and the VZV gE polypeptide is a full-length VZV gE polypeptide having an IgKappa sequence and a Y582G mutation, a Y569A mutation, or both a Y582G mutation and a Y569A mutation. In some embodiments, the glycoproteins are VZV gI and variant VZV gE, and the VZV gE polypeptide is a truncated VZV gE polypeptide lacking the anchor domain (ER retention domain) and having an IgKappa sequence. In some embodiments, the variant VZV gE polypeptide is a truncated polypeptide comprising amino acids 1-561 or amino acids 1-573 and having an IgKappa sequence at the C-terminus.

In any of the above-described embodiments, the VZV vaccine may further comprise a live attenuated VZV, a whole inactivated VZV, or a VZV virus-like particle (VLP). In some embodiments, the live attenuated VZV, whole inactivated VZV, or VZV VLP is selected from or derived from the following strains and genotypes: VZV E1 strain, genotypes E1_32_5, E1_Kel, E1_Dumas, E1_Russia 1999, E1_SD, E1_MSP, E1_36, E1_49, E1_BC, E1_NH29; VZV E2 strain, genotypes E2_03-500, E2_2, E2_11, E2_HJO; VZV J strain, genotype pOka; VZV M1 strain, genotype M1_CA123; VZV M2 strain, genotypes M2_8 and M2_DR; and VZV M4 strain, genotypes Spain 4242, France 4415, and Italy 4053.

Alternate RNA vaccines comprising RNA polynucleotides encoding other viral protein components of VZV, for example, tegument proteins are encompassed by the present disclosure. Thus, some embodiments of the present disclosure provide VZV vaccines that include at least one ribonucleic acid (RNA) polynucleotide having an open reading frame encoding at least one VZV tegument protein. Some embodiments of the present disclosure provide VZV vaccines that include at least one RNA polynucleotide having an open reading frame encoding at least one VZV tegument protein and at least one VZV glycoprotein. Some embodiments of the present disclosure provide VZV vaccines that include at least one RNA polynucleotide having an open reading frame encoding at least one VZV tegument protein and at least one RNA polynucleotide having an open reading frame encoding at least one VZV glycoprotein. In some embodiments, RNA vaccines comprise RNA (e.g., mRNA) polynucleotide(s) encoding one or more VZV tegument protein(s) and one or more VZV glycoprotein(s) selected from VZV gE, gI, gB, gH, gK, gL, gC, gN, and gM polypeptides. In some embodiments, the VZV glycoprotein is a VZV gE polypeptide. In some embodiments, the VZV glycoprotein is a VZV gI polypeptide. In some embodiments, the VZV glycoprotein is a variant VZV gE polypeptide, such as any of the variant VZV gE polypeptides disclosed herein. In some embodiments, the VZV glycoproteins are VZV gE glycoproteins and VZV gI glycoproteins.

In some embodiments, at least one RNA polynucleotide is encoded by at least one nucleic acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 41 and homologs having at least 80% (e.g., 85%, 90%, 95%, 98%, 99%) identity with a nucleic acid sequence selected from SEQ ID NO: 1-8 and 41. In some embodiments, at least one RNA polynucleotide is encoded by at least one nucleic acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 41 and homologs having at least 90% (e.g., 90%, 91%, 92%, 93%, 94%, 95%, 96%, 97%, 98%, 99%, 99.8% or 99.9%) identity with a nucleic acid sequence selected from SEQ ID NO: 1-8 and 41. In some embodiments, at least one RNA polynucleotide is encoded by at least one fragment of a nucleic acid sequence (e.g., a fragment having an antigenic sequence or at least one epitope) selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 41 and homologs having at least 80% (e.g., 85%, 90%, 95%, 98%, 99%) identity with a nucleic acid sequence selected from SEQ ID NO: 1-8 and 41. In some embodiments, at least one RNA polynucleotide is encoded by at least one epitope of a nucleic acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 41.

In some embodiments, at least one RNA polynucleotide is a gE polypeptide encoded by SEQ ID NO: 1. In some embodiments, at least one RNA polynucleotide is a gI polypeptide encoded by SEQ ID NO: 2. In some embodiments, at least one RNA polynucleotide is a truncated gE polypeptide encoded by SEQ ID NO: 3. In some embodiments, at least one RNA polynucleotide is a truncated gE polypeptide encoded by SEQ ID NO: 5. In some embodiments, at least one RNA polynucleotide is a truncated gE polypeptide having Y569A mutation encoded by SEQ ID NO: 6. In some embodiments, at least one RNA polynucleotide is a gE polypeptide having an AEAADA sequence SEQ ID NO: 58 encoded by SEQ ID NO: 7. In some embodiments, at least one RNA polynucleotide is a gE polypeptide having a Y582G mutation and a AEAADA sequence (SEQ ID NO: 58) encoded by SEQ ID NO: 8. In some embodiments, at least one RNA polynucleotide is a gE polypeptide encoded by SEQ ID NO: 41.

In some embodiments, at least one RNA (e.g., mRNA) polynucleotide encodes an antigenic polypeptide having at least 90% identity to the amino acid sequence of any one of SEQ ID NO: 10, 14, 18, 22, 26, 30, 34, 38, 42 and 45-55. In some embodiments, at least one RNA (e.g., mRNA) polynucleotide encodes an antigenic polypeptide having at least 95% identity to the amino acid sequence of any one of SEQ ID NO: 10, 14, 18, 22, 26, 30, 34, 38, 42 and 45-55. In some embodiments, at least one RNA polynucleotide encodes an antigenic polypeptide having at least 96% identity to the amino acid sequence of any one of SEQ ID NO: 10, 14, 18, 22, 26, 30, 34, 38, 42 and 45-55. In some embodiments, at least one RNA (e.g., mRNA) polynucleotide encodes an antigenic polypeptide having at least 97% identity to the amino acid sequence of any one of SEQ ID NO: 10, 14, 18, 22, 26, 30, 34, 38, 42 and 45-55. In some embodiments, at least one RNA (e.g., mRNA) polynucleotide encodes an antigenic polypeptide having at least 98% identity to the amino acid sequence of any one of SEQ ID NO: 10, 14, 18, 22, 26, 30, 34, 38, 42 and 45-55. In some embodiments, at least one RNA (e.g., mRNA) polynucleotide encodes an antigenic polypeptide having at least 99% identity to the amino acid sequence of any one of SEQ ID NO: 10, 14, 18, 22, 26, 30, 34, 38, 42 and 45-55.

In some embodiments, the open reading frame from which the VZV polypeptide is encoded is codon-optimized. In some embodiments, the at least one RNA polynucleotide encodes an antigenic protein of any one of SEQ ID NO: 10, 14, 18, 22, 26, 30, 34, 38, 42 and 45-55, and wherein the RNA polynucleotide is codon-optimized mRNA. In some embodiments, the at least one RNA polynucleotide comprises a mRNA sequence identified by any one of SEQ ID NO: 92-108. In some embodiments, the mRNA sequence identified by any one of SEQ ID NO: 92-108 is codon optimized to encode antigenic VZV polypeptides that are as immunogenic, or more immunogenic than, the antigenic VZV polypeptides encoded by any one of SEQ ID NO: 92-108.

In some embodiments, the at least one RNA (e.g., mRNA) polynucleotide encodes an antigenic protein of SEQ ID NO: 10, wherein the RNA (e.g., mRNA) polynucleotide has less than 80% identity to wild-type mRNA sequence. In some embodiments, the at least one RNA polynucleotide encodes an antigenic protein of SEQ ID NO: 10, wherein the RNA (e.g., mRNA) polynucleotide has greater than 80% identity to wild-type mRNA sequence, but does not include wild-type mRNA sequence. In some embodiments, the at least one RNA (e.g., mRNA) polynucleotide encodes an antigenic protein of SEQ ID NO: 42, wherein the RNA e.g., mRNA) polynucleotide has less than 80% identity to wild-type mRNA sequence. In some embodiments, the at least one RNA (e.g., mRNA) polynucleotide encodes an antigenic protein of SEQ ID NO: 42, wherein the RNA polynucleotide has greater than 80% identity to wild-type mRNA sequence, but does not include wild-type mRNA sequence. In some embodiments, the at least one RNA (e.g., mRNA) polynucleotide encodes an antigenic protein of SEQ ID NO: 14, wherein the RNA (e.g., mRNA) polynucleotide has less than 80% identity to wild-type mRNA sequence. In some embodiments, the at least one RNA (e.g., mRNA) polynucleotide encodes an antigenic protein of SEQ ID NO: 14, wherein the RNA (e.g., mRNA) polynucleotide has greater than 80% identity to wild-type mRNA sequence, but does not include wild-type mRNA sequence. In some embodiments, the at least one RNA (e.g., mRNA) polynucleotide encodes an antigenic protein of SEQ ID NO: 26, wherein the RNA polynucleotide has less than 80% identity to wild-type mRNA sequence. In some embodiments, the at least one RNA (e.g., mRNA) polynucleotide encodes an antigenic protein of SEQ ID NO: 26, wherein the RNA (e.g., mRNA) polynucleotide has greater than 80% identity to wild-type mRNA sequence, but does not include wild-type mRNA sequence. In some embodiments, the at least one RNA (e.g., mRNA) polynucleotide encodes an antigenic protein of SEQ ID NO: 30, wherein the RNA polynucleotide has less than 80% identity to wild-type mRNA sequence. In some embodiments, the at least one RNA polynucleotide encodes an antigenic protein of SEQ ID NO: 30, wherein the RNA (e.g., mRNA) polynucleotide has greater than 80% identity to wild-type mRNA sequence, but does not include wild-type mRNA sequence. In some embodiments, the at least one RNA (e.g., mRNA) polynucleotide is encoded by a sequence selected from any one of SEQ ID NO: 1-8 and SEQ ID NO 41 and includes at least one chemical modification.

In some embodiments, the VZV vaccine is multivalent. In some embodiments, the RNA polynucleotide comprises a polynucleotide sequence derived from VZV E1 strain, including, for example, any one or more of genotypes E1_32_5, E1_Kel, E1_Dumas, E1_Russia 1999, E1_SD, E1_MSP, E1_36, E1_49, E1_BC, and E1_NH29. In some embodiments, the RNA (e.g., mRNA) polynucleotide comprises a polynucleotide sequence derived from VZV E2 strain, including, for example, any one or more of genotypes E2_03-500, E2_2, E2_11, and E2_HJO. In some embodiments, the RNA (e.g., mRNA) polynucleotide comprises a polynucleotide sequence derived from VZV J strain, including, for example, genotype pOka. In some embodiments, the RNA (e.g., mRNA) polynucleotide comprises a polynucleotide sequence derived from VZV M1 strain, including, for example, genotype M1_CA123. In some embodiments, the RNA (e.g., mRNA) polynucleotide comprises a polynucleotide sequence derived from VZV M2 strain, including, for example, genotypes M2_8 and M2_DR. In some embodiments, the RNA (e.g., mRNA) polynucleotide comprises a polynucleotide sequence derived from VZV M4 strain, including, for example, any one or more of genotypes Spain 4242, France 4415, and Italy 4053.

Some embodiments of the present disclosure provide a VZV vaccine that includes at least one ribonucleic acid (RNA) polynucleotide having an open reading frame encoding at least one VZV antigenic polypeptide and at least one 5' terminal cap. In some embodiments, a 5' terminal cap is 7mG(5')ppp(5')NlmpNp. Some embodiments of the present disclosure provide a VZV vaccine that includes at least one RNA (e.g., mRNA) polynucleotide having an open reading frame encoding at least one VZV antigenic polypeptide, wherein the at least one RNA (e.g., mRNA) polynucleotide has at least one chemical modification. In some embodiments, the at least one RNA (e.g., mRNA) polynucleotide further comprises a second chemical modification. In some embodiments, the at least one RNA (e.g., mRNA) polynucleotide having at least one chemical modification has a 5' terminal cap. In some embodiments, the at least one chemical modification is selected from pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In some embodiments, every (100%) of the uridines of the at least one RNA polynucleotide comprises a chemical modification, such as a N1-methylpseudouridine modification or a N1-ethylpseudouridine modification.

Some embodiments of the present disclosure provide a VZV vaccine that includes at least one ribonucleic acid (RNA) polynucleotide having an open reading frame encoding at least one VZV antigenic polypeptide, wherein at least 80% (e.g., 85%, 90%, 95%, 98%, 99%, 100%) of the uracil in the open reading frame have a chemical modification, optionally wherein the vaccine is formulated in a lipid nanoparticle. In some embodiments, 100% of the uracil in the open reading frame have a chemical modification. In some embodiments, a chemical modification is in the 5-position of the uracil. In some embodiments, a chemical modification is a N1-methyl pseudouridine. In some embodiments, 100% of the uracil in the open reading frame are modified to include N1-methyl pseudouridine.

Some embodiments of the present disclosure provide a VZV vaccine that is formulated within a cationic lipid nanoparticle. In some embodiments, the cationic lipid nanoparticle comprises a cationic lipid, a PEG-modified lipid, a sterol and a non-cationic lipid. In some embodiments, a cationic lipid is an ionizable cationic lipid and the non-cationic lipid is a neutral lipid, and the sterol is a cholesterol. In some embodiments, a cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl]heptadecan-8-amine.

In some embodiments, the lipid is

In some embodiments, the lipid is

In some embodiments, at least one cationic lipid selected from compounds of Formula (I):

(I)

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a carbocycle, heterocycle, —OR, —O$(CH_2)_n$N$(R)_2$, —C(O)OR, —OC(O)R, —CX$_3$, —CX$_2$H, —CXH$_2$, —CN, —N$(R)_2$, —C(O)N$(R)_2$, —N(R)C(O)R, —N(R)S(O)$_2$R, —N(R)C(O)N$(R)_2$, —N(R)C(S)N$(R)_2$, —N(R)R$_8$, —O$(CH_2)_n$OR, —N(R)C(=NR$_9$)N$(R)_2$, —N(R)C(=CHR$_9$)N$(R)_2$, —OC(O)N$(R)_2$, —N(R)C(O)OR, —N(OR)C(O)R, —N(OR)S(O)$_2$R, —N(OR)C(O)OR, —N(OR)C(O)N$(R)_2$, —N(OR)C(S)N$(R)_2$, —N(OR)C(=NR$_9$)N$(R)_2$, —C(=NR$_9$)N$(R)_2$, —C(=NR$_9$)R, —C(O)N(R)OR, and —C(R)N$(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_n$Q, —$(CH_2)_n$CHQR, —CHQR, or —CQ$(R)_2$, then (i) Q is not —N$(R)_2$ when n is 1, 2, 3, 4 or 5, or (ii) Q is not 5, 6, or 7-membered heterocycloalkyl when n is 1 or 2.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M' R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5 to 14-membered heteroaryl having one or more heteroatoms selected from N, O, and S, —OR, —O$(CH_2)_n$N$(R)_2$, —C(O)OR, —OC(O)R, —CX$_3$, —CX$_2$H, —CXH$_2$, —CN, —C(O)N$(R)_2$, —N(R)C(O)R, —N(R)S(O)$_2$R, —N(R)C(O)N$(R)_2$, —N(R)C(S)N$(R)_2$, —CRN$(R)_2$C(O)OR, —N(R)R$_8$, —O$(CH_2)_n$OR, —N(R)C(=NR$_9$)N$(R)_2$, —N(R)C(=CHR$_9$)N$(R)_2$, —OC(O)N$(R)_2$, —N(R)C(O)OR, —N(OR)C(O)R, —N(OR)S(O)$_2$R, —N(OR)C(O)OR, —N(OR)C(O)N$(R)_2$, —N(OR)C(S)N$(R)_2$, —N(OR)C(=NR$_9$)N$(R)_2$, —N(OR)C(=CHR$_9$)N$(R)_2$, —C(=NR$_9$)N$(R)_2$, —C(=NR$_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M' R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —CQ$(R)_2$, and unsubstituted $C_{1-6}$ alkyl, where Q is selected from a $C_{3-6}$ carbocycle, a 5 to 14-membered heterocycle having one or more heteroatoms selected from N, O, and S, —OR, —$O(CH_2)_nN(R)_2$, —$C(O)OR$, —$OC(O)R$, —$CX_3$, —$CX_2H$, —$CXH_2$, —CN, —$C(O)N(R)_2$, —$N(R)C(O)R$, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —$N(R)C(=NR_9)N(R)_2$, —$N(R)C(=CHR_9)N(R)_2$, —$OC(O)N(R)_2$, —$N(R)C(O)OR$, —$N(OR)C(O)R$, —$N(OR)S(O)_2R$, —$N(OR)C(O)OR$, —$N(OR)C(O)N(R)_2$, —$N(OR)C(S)N(R)_2$, —$N(OR)C(=NR_9)N(R)_2$, —$N(OR)C(=CHR_9)N(R)_2$, —$C(=NR_9)R$, —$C(O)N(R)OR$, and —$C(=NR_9)N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M' R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —CQ$(R)_2$, and unsubstituted $C_{1-6}$ alkyl, where Q is selected from a $C_{3-6}$ carbocycle, a 5 to 14-membered heteroaryl having one or more heteroatoms selected from N, O, and S, —OR, —$O(CH_2)_nN(R)_2$, —$C(O)OR$, —$OC(O)R$, —$CX_3$, —$CX_2H$, —$CXH_2$, —CN, —$C(O)N(R)_2$, —$N(R)C(O)R$, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —$N(R)C(=NR_9)N(R)_2$, —$N(R)C(=CHR_9)N(R)_2$, —$OC(O)N(R)_2$, —$N(R)C(O)OR$, —$N(OR)C(O)R$, —$N(OR)S(O)_2R$, —$N(OR)C(O)OR$, —$N(OR)C(O)N(R)_2$, —$N(OR)C(S)N(R)_2$, —$N(OR)C(=NR_9)N(R)_2$, —$N(OR)C(=CHR_9)N(R)_2$, —$C(=NR_9)R$, —$C(O)N(R)OR$, and —$C(=NR_9)N(R)_2$, and each n is independently selected from 1, 2, 3, 4, and 5; and when Q is a 5 to 14-membered heterocycle and (i) $R_4$ is —$(CH_2)_nQ$ in which n is 1 or 2, or (ii) $R_4$ is —$(CH_2)_nCHQR$ in which n is 1, or (iii) $R_4$ is-CHQR, and —CQ$(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR″, —YR″, and —R″M′ R′;

R_2 and R_3 are independently selected from the group consisting of H, $C_{2-14}$ alkyl, $C_{2-14}$ alkenyl, —R*YR″, —YR″, and —R*OR″, or $R_2$ and $R_3$, together with the atom to which they are attached, form a heterocycle or carbocycle;

$R_4$ is —$(CH_2)_nQ$ or —$(CH_2)$·CHQR, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M′ are independently selected from —C(O)O—, —OC(O)—, —C(O)N(R′)—, —N(R′)C(O)—, —C(O)—, —C(S)—, —C(S)S—, —SC(S)—, —CH (OH)—, —P(O)(OR′)O—, —S(O)_2—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R′ is independently selected from the group consisting of $C_{1-18}$ alkyl, $C_{2-18}$ alkenyl, —R*YR″, —YR″, and H;

each R″ is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR″, —YR″, and —R″M′ R′;

R_2 and R_3 are independently selected from the group consisting of $C_{1-14}$ alkyl, $C_{2-14}$ alkenyl, —R*YR″, —YR″, and —R*OR″, or $R_2$ and $R_3$, together with the atom to which they are attached, form a heterocycle or carbocycle;

$R_4$ is selected from the group consisting of —$(CH_2)_nQ$, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M′ are independently selected from —C(O)O—, —OC(O)—, —C(O)N(R′)—, —N(R′)C(O)—, —C(O)—, —C(S)—, —C(S)S—, —SC(S)—, —CH (OH)—, —P(O)(OR′)O—, —S(O)_2—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R′ is independently selected from the group consisting of $C_{1-18}$ alkyl, $C_{2-18}$ alkenyl, —R*YR″, —YR″, and H;

each R″ is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

(IA)

or a salt or isomer thereof, wherein 1 is selected from 1, 2, 3, 4, and 5; m is selected from 5, 6, 7, 8, and 9; $M_1$ is a bond or M′; $R_4$ is unsubstituted $C_{1-3}$ alkyl, or —$(CH_2)_nQ$, in which Q is OH, —$NHC(S)N(R)_2$, —$NHC(O)N(R)_2$, —$N(R)C(O)R$, —$N(R)S(O)_2R$, —$N(R)R_8$, —$NHC(=NR_9)N(R)_2$, —$NHC(=CHR_9)N$ $(R)_2$, —$OC(O)N(R)_2$, —$N(R)C(O)OR$, heteroaryl or heterocycloalkyl; M and M′ are independently selected from —C(O)O—, —OC(O)—, —C(O)N(R′)—, —P(O)(OR′)O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, the cationic lipid nanoparticle has a molar ratio of about 20-60% cationic lipid, about 5-25% non-cationic lipid, about 25-55% sterol, and about 0.5-15% PEG-modified lipid. In some embodiments, the nanoparticle has a polydispersity value of less than 0.4. In some embodiments, the nanoparticle has a net neutral charge at a neutral pH value. In some embodiments, the nanoparticle has a mean diameter of 50-200 nm.

Some embodiments of the present disclosure provide methods of inducing an antigen specific immune response in a subject, comprising administering to the subject a VZV RNA (e.g., mRNA) vaccine in an amount effective to produce an antigen specific immune response. In some embodiments, an antigen specific immune response comprises a T cell response or a B cell response. In some embodiments, an antigen specific immune response comprises a T cell response and a B cell response. In some embodiments, a method of producing an antigen specific immune response involves a single administration of the vaccine. In some embodiments, a method further includes administering to the subject a booster dose of the vaccine. In some embodiments, a vaccine is administered to the subject by intradermal or intramuscular injection.

Also provided herein are VZV RNA (e.g., mRNA) vaccines for use in a method of inducing an antigen specific immune response in a subject, the method comprising administering the vaccine to the subject in an amount effective to produce an antigen specific immune response.

Further provided herein are uses of VZV RNA (e.g., mRNA) vaccines in the manufacture of a medicament for use in a method of inducing an antigen specific immune response in a subject, the method comprising administering the vaccine to the subject in an amount effective to produce an antigen specific immune response.

Some aspects of the present disclosure provide methods of preventing or treating VZV infection comprising administering to a subject the VZV RNA (e.g., mRNA) vaccine of the present disclosure. In some embodiments, the VZV RNA (e.g., mRNA) vaccine is formulated in an effective amount to produce an antigen specific immune response in a subject.

Some embodiments of the present disclosure provide methods of inducing an antigen specific immune response in a subject, the methods comprising administering to a subject a VZV RNA (e.g., mRNA) vaccine as provided herein in an effective amount to produce an antigen specific immune response in a subject.

In some embodiments, an anti-VZV antigenic polypeptide antibody titer produced in the subject is increased by at least 1 log relative to a control. In some embodiments, the anti-VZV antigenic polypeptide antibody titer produced in the subject is increased by 1-3 log relative to a control.

In some embodiments, the anti-VZV antigenic polypeptide antibody titer produced in the subject is increased at least 2 times relative to a control. In some embodiments, the anti-VZV antigenic polypeptide antibody titer produced in the subject is increased at least 5 times relative to a control. In some embodiments, the anti-VZV antigenic polypeptide antibody titer produced in the subject is increased at least 10 times relative to a control. In some embodiments, the anti-VZV antigenic polypeptide antibody titer produced in the subject is increased 2-10 times relative to a control.

In some embodiments, the control is an anti-VZV antigenic polypeptide antibody titer produced in a subject who has not been administered VZV vaccine. In some embodiments, the control is an anti-VZV antigenic polypeptide antibody titer produced in a subject who has been administered a live attenuated or inactivated VZV vaccine. In some embodiments, the control is an anti-VZV antigenic polypeptide antibody titer produced in a subject who has been administered a recombinant or purified VZV protein vaccine. In some embodiments, the control is an anti-VZV antigenic polypeptide antibody titer produced in a subject who has been administered an VZV virus-like particle (VLP) vaccine.

In some embodiments, the effective amount is a dose equivalent to at least a 2-fold reduction in the standard of care dose of a recombinant VZV protein vaccine, wherein an anti-VZV antigenic polypeptide antibody titer produced in the subject is equivalent to an anti-VZV antigenic polypeptide antibody titer produced in a control subject administered the standard of care dose of a recombinant or purified VZV protein vaccine, a live attenuated or inactivated VZV vaccine, or a VZV VLP vaccine.

In some embodiments, the effective amount is a dose equivalent to at least a 4-fold reduction in the standard of care dose of a recombinant VZV protein vaccine, wherein an anti-VZV antigenic polypeptide antibody titer produced in the subject is equivalent to an anti-VZV antigenic polypeptide antibody titer produced in a control subject administered the standard of care dose of a recombinant or purified VZV protein vaccine, a live attenuated or inactivated VZV vaccine, or a VZV VLP vaccine.

In some embodiments, the effective amount is a dose equivalent to at least a 10-fold reduction in the standard of care dose of a recombinant VZV protein vaccine, wherein an anti-VZV antigenic polypeptide antibody titer produced in the subject is equivalent to an anti-VZV antigenic polypeptide antibody titer produced in a control subject administered the standard of care dose of a recombinant or purified VZV protein vaccine, a live attenuated or inactivated VZV vaccine, or a VZV VLP vaccine.

In some embodiments, the effective amount is a dose equivalent to at least a 100-fold reduction in the standard of care dose of a recombinant VZV protein vaccine, wherein an anti-VZV antigenic polypeptide antibody titer produced in the subject is equivalent to an anti-VZV antigenic polypeptide antibody titer produced in a control subject administered the standard of care dose of a recombinant or purified VZV protein vaccine, a live attenuated or inactivated VZV vaccine, or a VZV VLP vaccine.

In some embodiments, the effective amount is a dose equivalent to at least a 1000-fold reduction in the standard of care dose of a recombinant VZV protein vaccine, wherein an anti-VZV antigenic polypeptide antibody titer produced in the subject is equivalent to an anti-VZV antigenic polypeptide antibody titer produced in a control subject administered the standard of care dose of a recombinant or purified VZV protein vaccine, a live attenuated or inactivated VZV vaccine, or a VZV VLP vaccine.

In some embodiments, the effective amount is a dose equivalent to a 2-fold to 1000-fold reduction in the standard of care dose of a recombinant VZV protein vaccine, wherein an anti-VZV antigenic polypeptide antibody titer produced in the subject is equivalent to an anti-VZV antigenic polypeptide antibody titer produced in a control subject administered the standard of care dose of a recombinant or purified VZV protein vaccine, a live attenuated or inactivated VZV vaccine, or a VZV VLP vaccine.

In some embodiments, the effective amount is a total dose of 25 µg to 1000 µg, or 50 µg to 1000 µg or 25 to 200 µg. In some embodiments, the effective amount is a total dose of 50 µg, 100 µg, 200 µg, 400 µg, 800 µg, or 1000 µg. In some embodiments, the effective amount is a total dose of 200 µg. In some embodiments, the effective amount is a total dose of 50 µg to 400 µg. In some embodiments, the effective amount is a total dose of 50 µg, 100 µg, 150 µg, 200 µg, 250 µg, 300 µg, 350 µg or 400 µg. In some embodiments, the effective amount is a dose of 25 µg administered to the subject a total of two times. In some embodiments, the effective amount is a dose of 50 µg administered to the subject a total of two times. In some embodiments, the effective amount is a dose of 100 µg administered to the subject a total of two times. In some embodiments, the effective amount is a dose of 200 µg administered to the subject a total of two times. In some embodiments, the effective amount is a dose of 400 µg administered to the subject a total of two times. In some embodiments, the effective amount is a dose of 500 µg administered to the subject a total of two times.

In some embodiments, the efficacy (or effectiveness) of the VZV RNA (e.g., mRNA) vaccine against VZV is greater than 60%.

Vaccine efficacy may be assessed using standard analyses (see, e.g., Weinberg et al., J Infect Dis. 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy} = (ARU - ARV)/ARU \times 100;$$

and $$\text{Efficacy} = (1 - RR) \times 100.$$

Likewise, vaccine effectiveness may be assessed using standard analyses (see, e.g., Weinberg et al., *J Infect Dis.* 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

$$\text{Effectiveness} = (1 - OR) \times 100.$$

In some embodiments, the efficacy (or effectiveness) of the VZV RNA (e.g., mRNA) vaccine against VZV is greater than 65%. In some embodiments, the efficacy (or effectiveness) of the vaccine against VZV is greater than 70%. In some embodiments, the efficacy (or effectiveness) of the vaccine against VZV is greater than 75%. In some embodiments, the efficacy (or effectiveness) of the vaccine against VZV is greater than 80%. In some embodiments, the efficacy (or effectiveness) of the vaccine against VZV is greater than 85%. In some embodiments, the efficacy (or effectiveness) of the vaccine against VZV is greater than 90%.

In some embodiments, the vaccine immunizes the subject against VZV up to 1 year (e.g. for a single VZV season). In some embodiments, the vaccine immunizes the subject against VZV for up to 2 years. In some embodiments, the vaccine immunizes the subject against VZV for more than 2 years. In some embodiments, the vaccine immunizes the subject against VZV for more than 3 years. In some embodiments, the vaccine immunizes the subject against VZV for more than 4 years. In some embodiments, the vaccine immunizes the subject against VZV for 5-10 years.

In some embodiments, the subject administered an VZV RNA (e.g., mRNA) vaccine is between the ages of about 12 months old and about 10 years old (e.g., about 1, 2, 3, 4, 5, 6, 7, 8, 9 or 10 years old). In some embodiments, the subject administered an VZV RNA (e.g., mRNA) vaccine is between the ages of about 12 months old and about 15 months old (e.g., about 12, 12.5, 13, 13.5, 14, 14.5 or 15 months old). In some embodiments, the subject administered an VZV RNA (e.g., mRNA) vaccine is between the ages of about 4 years old and about 6 years old (e.g., about 4, 4.5, 5, 5.6, or 6 years old).

In some embodiments, the subject is a young adult between the ages of about 20 years and about 50 years (e.g., about 20, 25, 30, 35, 40, 45 or 50 years old).

In some embodiments, the subject is an elderly subject about 60 years old, about 70 years old, or older (e.g., about 60, 65, 70, 75, 80, 85 or 90 years old).

In some embodiments, the subject has been exposed to VZV, is infected with (has) VZV, or is at risk of infection by VZV.

In some embodiments, the subject is immunocompromised (has an impaired immune system, e.g., has an immune disorder or autoimmune disorder).

Some aspects of the present disclosure provide varicella zoster virus (VZV) RNA (e.g., mRNA) vaccines containing a signal peptide linked to a VZV antigenic polypeptide. Thus, in some embodiments, the VZV RNA (e.g., mRNA) vaccines contain at least one ribonucleic acid (RNA) polynucleotide having an open reading frame encoding a signal peptide linked to a VZV antigenic peptide. Also provided herein are nucleic acids encoding the VZV RNA (e.g., mRNA) vaccines disclosed herein.

Other aspects of the present disclosure provide varicella zoster virus (VZV) vaccines containing a signal peptide linked to a VZV antigenic polypeptide. In some embodiments, the VZV antigenic polypeptide is a VZV glycoprotein. In some embodiments, the VZV glycoprotein is selected from VZV gE, gI, gB, gH, gK, gL, gC, gN, and gM. In some embodiments, the VZV glycoprotein is VZV gE or a variant VZV gE polypeptide.

In some embodiments, the signal peptide is a IgE signal peptide. In some embodiments, the signal peptide is an IgE HC (Ig heavy chain epsilon-1) signal peptide. In some embodiments, the signal peptide has the sequence MDWTWILFLVAAATRVHS (SEQ ID NO: 56). In some embodiments, the signal peptide is an IgGκ signal peptide. In some embodiments, the signal peptide has the sequence METPAQLLFLLLLWLPDTTG (SEQ ID NO: 57). In some embodiments, the signal peptide is selected from: a Japanese encephalitis PRM signal sequence (MLG-SNSGQRVVFTILLLLVAPAYS; SEQ ID NO: 109), VSVg protein signal sequence (MKCLLYLAFLFIGVNCA; SEQ ID NO: 110) and Japanese encephalitis JEV signal sequence (MWLVSLAIVTACAGA; SEQ ID NO: 111).

Further provided herein are nucleic acids encoding VZV vaccines disclosed herein. Such VZV vaccines include at least one ribonucleic acid (RNA) (e.g., mRNA) polynucleotide having an open reading frame encoding a signal peptide linked to a VZV antigenic polypeptide. In some embodiments, the VZV antigenic peptide is a VZV glycoprotein. In some embodiments, the VZV glycoprotein is selected from VZV gE, gI, gB, gH, gK, gL, gC, gN, and gM. In some embodiments, the VZV antigenic peptide is a VZV gE or a variant of the gE polypeptide.

In some embodiments, an effective amount of an VZV RNA (e.g., mRNA) vaccine (e.g., a single dose of the VZV vaccine) results in a 2 fold to 200 fold (e.g., about 2, 3, 4, 5, 6, 7, 8, 9, 10, 20, 30, 40, 50, 60, 70, 80, 90, 100, 110, 120, 130, 140, 150, 160, 170, 180, 190 or 200 fold) increase in serum neutralizing antibodies against VZV, relative to a control. In some embodiments, a single dose of the VZV RNA (e.g., mRNA) vaccine results in an about 5 fold, 50 fold, or 150 fold increase in serum neutralizing antibodies against VZV, relative to a control. In some embodiments, a single dose of the VZV RNA (e.g., mRNA) vaccine results in an about 2 fold to 10 fold, or an about 40 to 60 fold increase in serum neutralizing antibodies against VZV, relative to a control.

In some embodiments, efficacy of RNA vaccines RNA (e.g., mRNA) can be significantly enhanced when combined with a flagellin adjuvant, in particular, when one or more antigen-encoding mRNAs is combined with an mRNA encoding flagellin.

RNA (e.g., mRNA) vaccines combined with the flagellin adjuvant (e.g., mRNA-encoded flagellin adjuvant) have superior properties in that they may produce much larger antibody titers and produce responses earlier than commercially available vaccine formulations. While not wishing to be bound by theory, it is believed that the RNA vaccines, for example, as mRNA polynucleotides, are better designed to produce the appropriate protein conformation upon translation, for both the antigen and the adjuvant, as the RNA (e.g., mRNA) vaccines co-opt natural cellular machinery. Unlike traditional vaccines, which are manufactured ex vivo and may trigger unwanted cellular responses, RNA (e.g., mRNA) vaccines are presented to the cellular system in a more native fashion.

Some embodiments of the present disclosure provide RNA (e.g., mRNA) vaccines that include at least one RNA (e.g., mRNA) polynucleotide having an open reading frame encoding at least one antigenic polypeptide and at least one RNA (e.g., mRNA polynucleotide) having an open reading frame encoding a flagellin adjuvant.

In some embodiments, at least one flagellin polypeptide (e.g., encoded flagellin polypeptide) is a flagellin protein. In some embodiments, at least one flagellin polypeptide (e.g., encoded flagellin polypeptide) is an immunogenic flagellin fragment. In some embodiments, at least one flagellin polypeptide and at least one antigenic polypeptide are encoded by a single RNA (e.g., mRNA) polynucleotide. In other embodiments, at least one flagellin polypeptide and at least one antigenic polypeptide are each encoded by a different RNA polynucleotide.

In some embodiments at least one flagellin polypeptide has at least 80%, at least 85%, at least 90%, or at least 95% identity to a flagellin polypeptide having a sequence of any one of SEQ ID NO: 115-117.

In some embodiments the nucleic acid vaccines described herein are chemically modified. In other embodiments the nucleic acid vaccines are unmodified.

In some embodiments, the RNA polynucleotide is any one of SEQ ID NO: 1-8 and 41 and includes at least one chemical modification. In other embodiments, the RNA polynucleotide is any one of SEQ ID NO: 1-8 and 41 and does not include any nucleotide modifications, or is unmodified. In yet other embodiments, the at least one RNA polynucleotide encodes an antigenic protein of any one of SEQ ID NO: 10, 14, 18, 22, 26, 30, 34, 38, 42 and 45-55 and includes at least one chemical modification. In other embodiments, the RNA polynucleotide encodes an antigenic protein of any one of SEQ ID NO: 10, 14, 18, 22, 26, 30, 34, 38, 42 and 45-55 and does not include any nucleotide modifications, or is unmodified.

In some embodiments, the RNA polynucleotide comprises a sequence of any one of SEQ ID NO: 142-150. In some embodiments, the RNA polynucleotide comprises a sequence of any one of SEQ ID NO: 142-150 and includes at least one chemical modification. In other embodiments, the RNA polynucleotide comprises a sequence of any one of SEQ ID NO: 142-150 and does not include any nucleotide modifications, or is unmodified.

Yet other aspects provide compositions for and methods of vaccinating a subject comprising administering to the subject a nucleic acid vaccine comprising one or more RNA polynucleotides having an open reading frame encoding a first antigenic VZV polypeptide, wherein the RNA poly-nucleotide does not include a stabilization element, and wherein an adjuvant is not co-formulated or co-administered with the vaccine.

In other aspects the invention is a composition for or method of vaccinating a subject comprising administering to the subject a nucleic acid vaccine comprising one or more RNA polynucleotides having an open reading frame encoding a first antigenic polypeptide wherein a dosage of between 10 µg/kg and 400 µg/kg of the nucleic acid vaccine is administered to the subject. In some embodiments the dosage of the RNA polynucleotide is 1-5 µg, 5-10 µg, 10-15 µg, 15-20 µg, 10-25 µg, 20-25 µg, 20-50 µg, 30-50 µg, 40-50 µg, 40-60 µg, 60-80 µg, 60-100 µg, 50-100 µg, 80-120 µg, 40-120 µg, 40-150 µg, 50-150 µg, 50-200 µg, 80-200 µg, 100-200 µg, 120-250 µg, 150-250 µg, 180-280 µg, 200-300 µg, 50-300 µg, 80-300 µg, 100-300 µg, 40-300 µg, 50-350 µg, 100-350 µg, 200-350 µg, 300-350 µg, 320-400 µg, 40-380 µg, 40-100 µg, 100-400 µg, 200-400 µg, or 300-400 µg per dose. In some embodiments, the nucleic acid vaccine is administered to the subject by intradermal or intramuscular injection. In some embodiments, the nucleic acid vaccine is administered to the subject on day zero. In some embodiments, a second dose of the nucleic acid vaccine is administered to the subject on day twenty one.

In some embodiments, a dosage of 25 micrograms of the RNA polynucleotide is included in the nucleic acid vaccine administered to the subject. In some embodiments, a dosage of 100 micrograms of the RNA polynucleotide is included in the nucleic acid vaccine administered to the subject. In some embodiments, a dosage of 50 micrograms of the RNA polynucleotide is included in the nucleic acid vaccine administered to the subject. In some embodiments, a dosage of 75 micrograms of the RNA polynucleotide is included in the nucleic acid vaccine administered to the subject. In some embodiments, a dosage of 150 micrograms of the RNA polynucleotide is included in the nucleic acid vaccine administered to the subject. In some embodiments, a dosage of 400 micrograms of the RNA polynucleotide is included in the nucleic acid vaccine administered to the subject. In some embodiments, a dosage of 200 micrograms of the RNA polynucleotide is included in the nucleic acid vaccine administered to the subject. In some embodiments, the RNA polynucleotide accumulates at a 100 fold higher level in the local lymph node in comparison with the distal lymph node. In other embodiments the nucleic acid vaccine is chemically modified and in other embodiments the nucleic acid vaccine is not chemically modified.

Aspects of the invention provide a nucleic acid vaccine comprising one or more RNA polynucleotides having an open reading frame encoding a first antigenic polypeptide, wherein the RNA polynucleotide does not include a stabilization element, and a pharmaceutically acceptable carrier or excipient, wherein an adjuvant is not included in the vaccine. In some embodiments, the stabilization element is a histone stem-loop. In some embodiments, the stabilization element is a nucleic acid sequence having increased GC content relative to wild type sequence.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for seroprotection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

Also provided are nucleic acid vaccines comprising one or more RNA polynucleotides having an open reading frame encoding a first antigenic polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide. In some embodiments, the RNA polynucleotide is formulated to produce a neutralizing antibodies within one week of a single administration. In some embodiments, the adjuvant is selected from a cationic peptide and an immunostimulatory nucleic acid. In some embodiments, the cationic peptide is protamine.

Aspects provide nucleic acid vaccines comprising one or more RNA polynucleotides having an open reading frame comprising at least one chemical modification or optionally no chemical modification, the open reading frame encoding a first antigenic polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no chemical modification, the open reading frame encoding a first antigenic polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Aspects of the invention also provide a unit of use vaccine, comprising between 10 ug and 400 µg of one or more RNA polynucleotides having an open reading frame comprising at least one chemical modification or optionally no chemical modification, the open reading frame encoding a first antigenic polypeptide, and a pharmaceutically acceptable carrier or excipient, formulated for delivery to a human subject. In some embodiments, the vaccine further comprises a cationic lipid nanoparticle.

Aspects of the invention provide methods of creating, maintaining or restoring antigenic memory to a VZV strain in an individual or population of individuals comprising administering to said individual or population an antigenic memory booster nucleic acid vaccine comprising (a) at least one RNA polynucleotide, said polynucleotide comprising at least one chemical modification or optionally no chemical modification and two or more codon-optimized open reading frames, said open reading frames encoding a set of reference antigenic polypeptides, and (b) optionally a pharmaceutically acceptable carrier or excipient. In some embodiments, the vaccine is administered to the individual via a route selected from the group consisting of intramuscular administration, intradermal administration and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

Aspects of the invention provide methods of vaccinating a subject comprising administering to the subject a single dosage of between 25 µg/kg and 400 µg/kg of a nucleic acid vaccine comprising one or more RNA polynucleotides having an open reading frame encoding a first antigenic polypeptide in an effective amount to vaccinate the subject.

Other aspects provide nucleic acid vaccines comprising one or more RNA polynucleotides having an open reading frame comprising at least one chemical modification, the open reading frame encoding a first antigenic polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Other aspects provide nucleic acid vaccines comprising an LNP formulated RNA polynucleotide having an open reading frame comprising no modified nucleotides (unmodified), the open reading frame encoding a first antigenic polypeptide, wherein the vaccine has at least 10 fold less RNA polynucleotide than is required for an unmodified mRNA vaccine not formulated in a LNP to produce an equivalent antibody titer. In some embodiments, the RNA polynucleotide is present in a dosage of 25-100 micrograms.

The data presented in the Examples demonstrate significant enhanced immune responses using the formulations of the invention. The data demonstrated the effectiveness of both chemically modified and unmodified RNA vaccines of the invention. Surprisingly, in contrast to prior art reports that it was preferable to use chemically unmodified mRNA formulated in a carrier for the production of vaccines, it was discovered herein that chemically modified mRNA-LNP vaccines required a much lower effective mRNA dose than unmodified mRNA, i.e., tenfold less than unmodified mRNA when formulated in carriers other than LNP. Both the chemically modified and unmodified RNA vaccines of the invention produce better immune responses than mRNA vaccines formulated in a different lipid carrier.

In other aspects the invention encompasses a method of treating an elderly subject age 60 years or older comprising administering to the subject a nucleic acid vaccine comprising one or more RNA polynucleotides having an open reading frame encoding a VZV antigenic polypeptide in an effective amount to vaccinate the subject.

In other aspects the invention encompasses a method of treating a young subject age 17 years or younger comprising administering to the subject a nucleic acid vaccine comprising one or more RNA polynucleotides having an open reading frame encoding a VZV antigenic polypeptide in an effective amount to vaccinate the subject.

In other aspects the invention encompasses a method of treating an adult subject comprising administering to the subject a nucleic acid vaccine comprising one or more RNA polynucleotides having an open reading frame encoding a VZV antigenic polypeptide in an effective amount to vaccinate the subject.

In preferred aspects, vaccines of the invention (e.g., LNP-encapsulated mRNA vaccines) produce prophylactically- and/or therapeutically-efficacious levels, concentrations and/or titers of antigen-specific antibodies in the blood or serum of a vaccinated subject. As defined herein, the term antibody titer refers to the amount of antigen-specific antibody produces in s subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, etc.

In exemplary embodiments of the invention, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.)

In exemplary aspects of the invention, antigen-specific antibodies are measured in units of μg/ml or are measured in units of IU/L (International Units per liter) or mIU/ml (milli International Units per ml). In exemplary embodiments of the invention, an efficacious vaccine produces >0.5 μg/ml, >0.1 μg/ml, >0.2 μg/ml, >0.35 μg/ml, >0.5 μg/ml, >1 μg/ml, >2 μg/ml, >5 μg/ml or >10 μg/ml. In exemplary embodiments of the invention, an efficacious vaccine produces >10 mIU/ml, >20 mIU/ml, >50 mIU/ml, >100 mIU/ml, >200 mIU/ml, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 3 depicts the study design and injection schedule for the immunization of BALB/C mice with MC3 formulated mRNA encoded VZV gE antigens.

FIGS. 11A and 11B is SEQ ID NO: 58.

FIGS. 12A and 12B is SEQ ID NO: 58.

FIG. 13 is SEQ ID NO: 58.

FIG. 14A is SEQ ID NO: 58.

FIGS. 15A and 15B is SEQ ID NO: 58.

FIGS. 19A-19B are Western blots showing detection of VZV-gE-del_574_Y569A antigens in the lysates of HeLa cells 16 hours post transfection. Expression of the VZV-gE-del_574_Y569A antigen was detected in HeLa cells transfected with the VZV-gE_574_Y569A mRNA construct and in HeLa cells transfected with the VZV-gE-del_574_Y569A-v7 mRNA construct.

FIGS. 20A-20B are graphs showing the expression (FIG. 20A) and localization (FIG. 20B) of the VZV-gE-del_574_Y569A antigen expressed in HeLa cells transfected with either the VZV-gE-del_574_Y569A mRNA construct or the VZV-gE-del_574_Y569A-v7 mRNA construct.

FIG. 22A shows the injection schedule for Table 6. FIG. 22B shows the injection table for Table 7.

DETAILED DESCRIPTION

Figure 1:
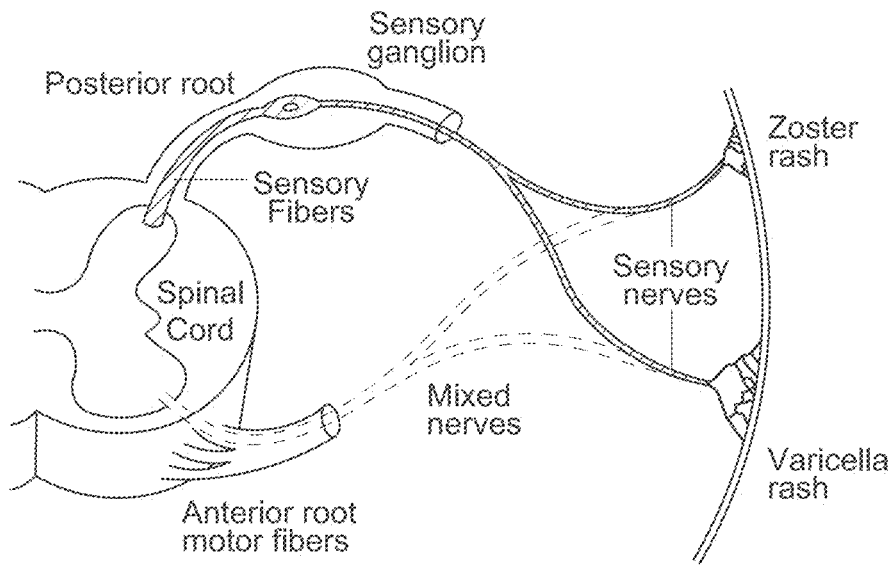
FIG. 1 is a schematic depicting a proposed Varicella zoster virus pathway.

Embodiments of the present disclosure provide RNA (e.g., mRNA) vaccines that include at least one RNA (e.g., mRNA) polynucleotide encoding a varicella zoster virus (VZV) antigen. There are at least five clades of varicella zoster virus (VZV). Clades 1 and 3 include European/North American strains; clade 2 includes Asian strains, especially from Japan; and clade 5 appears to be based in India. Clade 4 includes some strains from Europe, but its geographic origins need further clarification. Phylogenetic analysis of VZV genomic sequences resolves wild-type strains into 9 genotypes (E1, E2, J, M1, M2, M3, M4, VIII and IX). Sequence analysis of 342 clinical varicella and zoster specimens from 18 European countries identified the following distribution of VZV genotypes: E1, 221 (65%); E2, 87 (25%); M1, 20 (6%); M2, 3 (1%); M4, and 11 (3%). No M3 or J strains were observed. Of 165 clinical varicella and zoster isolates from Australia and New Zealand, 67 of 127 eastern Australian isolates were E1, 30 were E2, 16 were J, 10 were M1, and 4 were M2; 25 of 38 New Zealand isolates were E1, 8 were E2, and 5 were M1.

VZV is an alphaherpesvirus that exists as a spherical multilayered structure approximately 200 nm in diameter. The viral genome is surrounded by a protein capsid structure that is covered by an amorphous layer of tegument proteins. These two structures are surrounded by a lipid envelope that is studded with viral glycoproteins, each about 8 nm in length, that are displayed on the exterior of the virion, and encloses the 100 nm nucleocapsid which is comprised of 162 hexameric and pentameric capsomeres arranged in an icosahedral form. The tegument, which is comprised of virally-encoded proteins and enzymes, is located in the space between the nucleocapsid and the viral envelope. The viral envelope is acquired from host cell membranes and contains viral-encoded glycoproteins.

The VZV genome is a single, linear, duplex DNA molecule of 124,884 base pairs having at least 70 open reading frames. The genome has 2 predominant isomers, depending on the orientation of the S segment, P (prototype) and IS (inverted S), which are present with equal frequency for a total frequency of 90-95%. The L segment can also be inverted resulting in a total of four linear isomers (IL and ILS).

VZV is closely related to the herpes simplex viruses (HSV), sharing much genome homology. The VZV genome is the smallest of the human herpesviruses and encodes at least 71 unique proteins (ORF0-ORF68) with three more opening reading frames (ORF69-ORF71) that duplicate earlier open reading frames (ORF64-62, respectively). Only a fraction of the encoded proteins form the structure of the virus particle. Among those proteins are nine glycoproteins: ORF5 (gK), ORF9A (gN), ORF14 (gC), ORF31 (gB), ORF37 (gH), ORF50 (gM), ORF60 (gL), ORF67 (gI), and ORF68 (gE). The known envelope glycoproteins (gB, gC, gE, gH, gI, gK, gL, gN, and gM) correspond with those in HSV; however, there is no equivalent of HSV gD. VZV also fails to produce the LAT (latency-associated transcripts) that play an important role in establishing HSV latency (herpes simplex virus). The encoded glycoproteins gE, gI, gB, gH, gK, gL, gC, gN, and gM function in different steps of the viral replication cycle. The most abundant glycoprotein found in infected cells, as well as in the mature virion, is glycoprotein E (gE, ORF 68), which is a major component of the virion envelope and is essential for viral replication. Glycoprotein I (gI, ORG 67) forms a complex with gE in infected cells, which facilitates the endocytosis of both glycoproteins and directs them to the trans-Golgi network (TGN) where the final viral envelope is acquired. Glycoprotein I (gI) is required within the TGN for VZV envelopment and for efficient membrane fusion during VZV replication. VZV gE and gI are found complexed together on the infected host cell surface. Glycoprotein B (ORF 31), which is the second most prevalent glycoprotein and thought to play a role in virus entry, binds to neutralizing antibodies. Glycoprotein H is thought to have a fusion function facilitating cell to cell spread of the virus. Antibodies to gE, gB, and gH are prevalent after natural infection and following vaccination and have been shown to neutralize viral activity in vitro.

Embodiments of the present disclosure provide RNA (e.g., mRNA) vaccines that include at least one polynucleotide encoding at least one VZV antigenic polypeptide. The VZV RNA vaccines provided herein may be used to induce a balanced immune response, comprising both cellular and humoral immunity, without many of the risks associated with DNA vaccines and live attenuated vaccines. The various RNA (e.g., mRNA) vaccines disclosed herein produced an immune response in BALB/C mice, the results of which are discussed in detail in the Examples section. Specifically, RNA (e.g., mRNA) polynucleotide vaccines having an open reading frame encoding one or more of a variety of VZV antigens produced significant immune response, relative to a traditional VZV vaccine (e.g. attenuated VZV virus). The VZV RNA (e.g., mRNA) polynucleotide vaccines disclosed herein encoding either VZV gE or variant VZV gE demonstrated significant immune response after two administrations when administered intramuscularly (IM) or intradermally (ID). The VZV glycoproteins and tegument proteins have been shown to be antigenic. VZV glycoproteins, fragments thereof, and epitopes thereof are encompassed within the present disclosure.

The entire contents of International Application No. PCT/US2015/027400, International Publication No. WO2015/164674A, are incorporated herein by reference.

It has been discovered that the mRNA vaccines described herein are superior to current vaccines in several ways. First, the lipid nanoparticle (LNP) delivery is superior to other formulations including a protamine base approach described in the literature and no additional adjuvants are to be necessary. The use of LNPs enables the effective delivery of chemically modified or unmodified mRNA vaccines. Additionally it has been demonstrated herein that both modified and unmodified LNP formulated mRNA vaccines were superior to conventional vaccines by a significant degree. In some embodiments the mRNA vaccines of the invention are superior to conventional vaccines by a factor of at least 10 fold, 20 fold, 40 fold, 50 fold, 100 fold, 500 fold or 1,000 fold.

Although attempts have been made to produce functional RNA vaccines, including mRNA vaccines and self-replicating RNA vaccines, the therapeutic efficacy of these RNA vaccines have not yet been fully established. Quite surprisingly, the inventors have discovered, according to aspects of the invention a class of formulations for delivering mRNA vaccines in vivo that results in significantly enhanced, and in many respects synergistic, immune responses including enhanced antigen generation and functional antibody production with neutralization capability. These results can be achieved even when significantly lower doses of the mRNA are administered in comparison with mRNA doses used in other classes of lipid based formulations. The formulations of the invention have demonstrated significant unexpected in vivo immune responses sufficient to establish the efficacy of functional mRNA vaccines as prophylactic and therapeutic agents. Additionally, self-replicating RNA vaccines rely on viral replication pathways to deliver enough RNA to a cell to produce an immunogenic response. The formulations of the invention do not require viral replication to produce enough protein to result in a strong immune response. Thus, the mRNA of the invention are not self-replicating RNA and do not include components necessary for viral replication.

The invention involves, in some aspects, the surprising finding that lipid nanoparticle (LNP) formulations significantly enhance the effectiveness of mRNA vaccines, including chemically modified and unmodified mRNA vaccines. The efficacy of mRNA vaccines formulated in LNP was examined in vivo using several distinct antigens. The results presented herein demonstrate the unexpected superior efficacy of the mRNA vaccines formulated in LNP over other commercially available vaccines.

In addition to providing an enhanced immune response, the formulations of the invention generate a more rapid immune response with fewer doses of antigen than other vaccines tested.

The mRNA-LNP formulations of the invention also produce quantitatively and qualitatively better immune responses than vaccines formulated in a different carriers. The data described herein demonstrate that the formulations of the invention produced significant unexpected improvements over existing VZV antigen vaccines, including significantly higher levels of IgG production by mRNA chemically modified and unmodified VZV vaccines formulated in LNP compared to VARIVAX and ZOSTAVAX. The onset of IgG production was significantly more rapid for the chemically modified LNP mRNA vaccines than the unmodified or commercially available vaccines tested.

Additionally, the mRNA-LNP formulations of the invention are superior to other vaccines even when the dose of mRNA is lower than other vaccines. The data demonstrate that all gE variants LNP mRNA vaccines induced much stronger immune response than ZOSTAVAX® after the two 10 µg doses as well as after the two 2 µg doses. When the sera were diluted more than 100 fold, the antibody titer is higher in VZV gE LNP mRNA vaccinated mice sera than in ZOSTAVAX® vaccinated mice sera, suggesting that the VZV gE LNP mRNA vaccines induced much stronger immune response than ZOSTAVAX® in mice.

The results in mice were consistent with the immunogenicity observed in non-human primates. Rhesus monkeys were primed with chemically modified VZV LNP mRNA vaccines or ZOSTAVAX®. The mRNA vaccines provided higher anti-gE titers than ZOSTAVAX® and produced reasonable frequency of CD4 T-cells producing IFNγ, IL-2 or TNFα cells, unlike the ZOSTAVAX® group. The data also demonstrated that a single dose of mRNA vaccination after ZOSTAVAX® exposure was equivalent to two doses of mRNA vaccination in inducing comparable T-cell responses.

Some of the LNP used in the studies described herein has been used previously to deliver siRNA in various animal models as well as in humans. In view of the observations made in association with the siRNA delivery of LNP formulations, the fact that LNP is useful in vaccines is quite surprising. It has been observed that therapeutic delivery of siRNA formulated in LNP causes an undesirable inflammatory response associated with a transient IgM response, typically leading to a reduction in antigen production and a compromised immune response. In contrast to the findings observed with siRNA, the LNP-mRNA formulations of the invention are demonstrated herein to generate enhanced IgG levels, sufficient for prophylactic and therapeutic methods rather than transient IgM responses.

Antigens/Antigenic Polypeptides

In some embodiments, an antigenic polypeptide is a VZV glycoprotein. For example, a VZV glycoprotein may be VZV gE, gI, gB, gH, gK, gL, gC, gN, or gM. In some embodiments, the antigenic polypeptide is a VZV gE polypeptide. In some embodiments, the antigenic polypeptide is a VZV gI polypeptide. In some embodiments, the antigenic polypeptide is a VZV gB polypeptide. In some embodiments, the antigenic polypeptide is a VZV gH polypeptide. In some embodiments, the antigenic polypeptide is a VZV gK polypeptide. In some embodiments, the antigenic polypeptide is a VZV gL polypeptide. In some embodiments, the antigenic polypeptide is a VZV gC polypeptide. In some embodiments, the antigenic polypeptide is a VZV gN poly-peptide. In some embodiments, the antigenic polypeptide is a VZV gM polypeptide.

In some embodiments, the antigenic polypeptide com-prises two or more glycoproteins. The two or more glyco-proteins can be encoded by a single RNA polynucleotide or can be encoded by two or more RNA polynucleotides, for example, each glycoprotein encoded by a separate RNA polynucleotide. In some embodiments, the two or more glycoproteins can be any combination of VZV gE, gI, gB, gH, gK, gL, gC, gN, and gM polypeptides. In some embodi-ments, the two or more glycoproteins can be any combina-tion of VZV gE and a glycoprotein selected from gI, gB, gH, gK, gL, gC, gN, and gM polypeptides. In some embodi-ments, the two or more glycoproteins can be any combina-tion of VZV gI and a glycoprotein selected from gE, gB, gH, gK, gL, gC, gN, and gM polypeptides. In some embodi-ments, the two or more glycoproteins can be any combina-tion of VZV gE, gI, and a glycoprotein selected from gB, gH, gK, gL, gC, gN, and gM polypeptides. In some embodi-ments, the two or more VZV glycoproteins are gE and gI. Alternate RNA vaccines comprising RNA polynucleotides encoding other viral protein components of VZV, for example, tegument proteins are encompassed by the present disclosure. Thus, some embodiments of the present disclo-sure provide VZV vaccines that include at least one ribo-nucleic acid (RNA) polynucleotide having an open reading frame encoding at least one VZV tegument protein. In some embodiments, the antigenic polypeptide is a VZV tegument protein. In other embodiments, the antigenic fragment(s) of the VZV vaccine may be at least one VZV tegument polypeptide and at least one VZV glycoprotein polypeptide, for example any VZV glycoprotein selected from gE, gI, gB, gH, gK, gL, gC, gN, and gM.

The present disclosure includes variant VZV antigenic polypeptides. In some embodiments, the variant VZV anti-genic polypeptide is a variant VZV gE polypeptide. The variant VZV gE polypeptides are designed to avoid ER/golgi retention of polypeptides, leading to increased surface expression of the antigen. In some embodiments, the variant gE polypeptides are truncated to remove the ER retention portion or the cytoplasmic tail portion of the polypeptide. In some embodiments, the variant VZV gE polypeptides are mutated to reduce VZV polypeptide localization to the ER/golgi/TGN. Such modifications inhibit ER trapping and, as such, expedite trafficking to the cell membrane.

Thus, in some embodiments, the VZV glycoprotein is a variant gE polypeptide. VZV gE has targeting sequences for the TGN in its C-terminus and is transported from the ER to the TGN in infected and gE-transfected cells. Most gE in the TGN appears to be retrieved by endocytosis from the plasma membrane and delivered to the TGN by endosomes, which is followed by recycling to the plasma membranes. gE is accumulated in TGN, along with other VZV proteins (e.g., tegument proteins) associated with the production of fully enveloped VZV virions. Thus, mutations to reduce TGN localization and endocytosis aids in the trafficking of gE to the cell membrane.

The variant VZV gE polypeptide can be any truncated polypeptide lacking the anchor domain (ER retention domain). For example, the variant VZV gE polypeptide can be a truncated VZV gE polypeptide comprising at least amino acids 1-124, including, for example, amino acids 1-124, 1-140, 1-160, 1-200, 1-250, 1-300, 1-350, 1-360, 1-400, 1-450, 1-500, 1-511, 1-550, and 1-561, as well as polypeptide fragments having fragment sizes within the recited size ranges. In one embodiment, the truncated VZV gE polypeptide comprises amino acids 1-561 of SEQ ID NO: 10. In some embodiments, the variant VZV gE poly-peptide is a truncated polypeptide lacking the carboxy terminal tail domain. Thus in some embodiments, the trun-cated VZV gE polypeptide comprises amino acids 1-573 of SEQ ID NO: 10.

In some embodiments, the variant VZV gE polypeptide has at least one mutation in one or more motif(s) associated with ER retention, wherein the mutation(s) in one or more motif(s) results in decreased retention of the VZV gE polypeptide in the ER and/or golgi. In some embodiments, the variant VZV gE polypeptide has at least one mutation in one or more phosphorylated acidic motif(s). For example, the variant VZV gE polypeptide can be a full-length VZV gE polypeptide having a Y582G mutation, a Y569A mutation, or both a Y582G mutation and a Y569A mutation. Alterna-tively, the variant VZV gE polypeptide can be an antigenic fragment comprising, for example, amino acids 1-573 of VZV gE and having a Y569A mutation. Alternatively, the variant VZV gE polypeptide can be an antigenic fragment having mutation in an acidic phosphorylation motif, such as an SST motif. For example, the variant VZV gE polypeptide can be an antigenic fragment having AEAADA sequence (SEQ ID NO: 58).

In some embodiments, the variant VZV gE polypeptide is a full-length VZV gE polypeptide having additional sequence at the C-terminus which aids in secretion of the polypeptide. For example, the variant VZV gE polypeptide can be a full-length VZV gE polypeptide having an IgKappa sequence at the C-terminus. In some embodiments, the VZV gE polypeptide has additional sequence at the C-terminus that aids in secretion (I., an IgKappa sequence at the C-terminus) and the variant VZV gE polypeptide has at least one mutation in one or more motif(s) associated with ER retention, TGN localization, and/or endocytosis (e.g., a Y582G mutation, a Y569A mutation, or both a Y582G mutation and a Y569A mutation) and/or at least one muta-tion in one or more phosphorylated acidic motif(s). In some embodiments, the variant VZV gE polypeptide is a truncated polypeptide lacking the anchor domain (ER retention domain) and having an additional sequence at the C-termi-nus which aids in secretion of the polypeptide, for example, an IgKappa sequence at the C-terminus. In some embodi-ments, the truncated VZV gE polypeptide comprises amino acids 1-561 of SEQ ID NO: 10 and has an IgKappa sequence at the C-terminus. In some embodiments, the variant VZV gE polypeptide is a truncated polypeptide lacking the car-boxy terminal tail domain and having an additional sequence at the C-terminus that aids in secretion of the polypeptide (e.g., having an IgKappa sequence at the C-terminus). In some embodiments, the truncated VZV gE polypeptide comprises amino acids 1-573 of SEQ ID NO: 10 and has an IgKappa sequence at the C-terminus.

In some embodiments, a VZV antigenic polypeptide is longer than 25 amino acids and shorter than 50 amino acids. The term "antigenic polypeptide" and "antigenic protein" includes immunogenic fragments and epitopes thereof. Thus, polypeptides include gene products, naturally occur-ring polypeptides, synthetic polypeptides, homologs, orthologs, paralogs, fragments and other equivalents, vari-ants, and analogs of the foregoing. A polypeptide may be a single molecule or may be a multi-molecular complex such as a dimer, trimer or tetramer. Polypeptides may also com-prise single chain or multichain polypeptides such as anti-bodies or insulin and may be associated or linked. Most commonly, disulfide linkages are found in multichain poly-peptides. The term polypeptide may also apply to amino acid polymers in which at least one amino acid residue is an artificial chemical analogue of a corresponding naturally-occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants possess at least 50% identity to a native or reference sequence. In some embodiments, variants share at least 80%, or at least 90% identity with a native or reference sequence.

In some embodiments "variant mimics" are provided. As used herein, a "variant mimic" contains at least one amino acid that would mimic an activated sequence. For example, glutamate may serve as a mimic for phosphoro-threonine and/or phosphoro-serine. Alternatively, variant mimics may result in deactivation or in an inactivated product containing the mimic. For example, phenylalanine may act as an inactivating substitution for tyrosine, or alanine may act as an inactivating substitution for serine.

"Orthologs" refers to genes in different species that evolved from a common ancestral gene by speciation. Normally, orthologs retain the same function in the course of evolution.

Identification of orthologs is critical for reliable prediction of gene function in newly sequenced genomes.

"Analogs" is meant to include polypeptide variants that differ by one or more amino acid alterations, for example, substitutions, additions or deletions of amino acid residues that still maintain one or more of the properties of the parent or starting polypeptide.

"Paralogs" are genes (or proteins) related by duplication within a genome. Orthologs retain the same function in the course of evolution, whereas paralogs evolve new functions, even if these are related to the original one.

The present disclosure provides several types of compositions that are polynucleotide or polypeptide based, including variants and derivatives. These include, for example, substitutional, insertional, deletion and covalent variants and derivatives. The term "derivative" is used synonymously with the term "variant," but generally refers to a molecule that has been modified and/or changed in any way relative to a reference molecule or starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support. In alternative embodiments, sequences for (or encoding) signal sequences, termination sequences, transmembrane domains, linkers, multimerization domains (such as, e.g., foldon regions) and the like may be substituted with alternative sequences that achieve the same or a similar function. Such sequences are readily identifiable to one of skill in the art. It should also be understood that some of the sequences provided herein contain sequence tags or terminal peptide sequences (e.g., at the N-terminal or C-terminal ends) that may be deleted, for example, prior to use in the preparation of an RNA (e.g., mRNA) vaccine.

"Substitutional variants" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue, such as lysine, arginine or histidine for another, or the substitution of one acidic residue, such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Features" when referring to polypeptide or polynucleotide are defined as distinct amino acid sequence-based or nucleotide-based components of a molecule respectively. Features of the polypeptides encoded by the polynucleotides include surface manifestations, local conformational shape, folds, loops, half-loops, domains, half-domains, sites, termini or any combination thereof.

As used herein when referring to polypeptides the term "domain" refers to a motif of a polypeptide having one or more identifiable structural or functional characteristics or properties (e.g., binding capacity, serving as a site for protein-protein interactions).

As used herein, when referring to polypeptides the terms "site" as it pertains to amino acid based embodiments, is used synonymously with "amino acid residue" and "amino acid side chain." As used herein, when referring to polynucleotides the terms "site" as it pertains to nucleotide based embodiments, is used synonymously with "nucleotide." A site represents a position within a peptide or polypeptide or polynucleotide that may be modified, manipulated, altered, derivatized or varied within the polypeptide or polynucleotide based molecules.

As used herein, the terms "termini" or "terminus," when referring to polypeptides or polynucleotides, refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N-termini and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of 20, 30, 40, 50, or 100 amino acids that are 40%, 50%, 60%, 70%, 80%, 90%, 95%, or 100% identical to any of the sequences described herein can be utilized in accordance with the present disclosure. In some embodiments, a polypeptide includes 2, 3, 4, 5, 6, 7, 8, 9, 10, or more mutations, as shown in any of the sequences provided or referenced herein. In some embodiments, a protein fragment is longer than 25 amino acids and shorter than 50 amino acids.

Polypeptide or polynucleotide molecules of the present disclosure may share a certain degree of sequence similarity or identity with the reference molecules (e.g., reference polypeptides or reference polynucleotides), for example, with art-described molecules (e.g., engineered or designed molecules or wild-type molecules). The term "identity," as known in the art, refers to a relationship between the sequences of two or more polypeptides or polynucleotides, as determined by comparing the sequences. In the art, identity also means the degree of sequence relatedness between them as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", *Nucleic Acids Res.* 25:3389-3402). Another popular local alignment technique is based on the Smith-Waterman algorithm (Smith, T. F. & Waterman, M. S. (1981) "Identification of common molecular subsequences." *J. Mol. Biol.* 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." *J. Mol. Biol.* 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication.

Nucleic Acids/Polynucleotides

Varicella zoster virus (VZV) vaccines, as provided herein, comprise at least one (one or more) ribonucleic acid (RNA, e.g., mRNA) polynucleotide having an open reading frame encoding at least one VZV antigenic polypeptide. The term "nucleic acid," in its broadest sense, includes any compound and/or substance that comprises a polymer of nucleotides. These polymers are referred to as polynucleotides.

In some embodiments, at least one RNA polynucleotide of a VZV vaccine is encoded by at least one nucleic acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 41.

In some embodiments, at least one RNA (e.g., mRNA) polynucleotide of a VZV vaccine is encoded by at least one fragment of a nucleic acid sequence (e.g., a fragment having an antigenic sequence or at least one epitope) selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 41.

Nucleic acids (also referred to as polynucleotides) may be or may include, for example, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a 0-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or chimeras or combinations thereof.

In some embodiments, polynucleotides of the present disclosure function as messenger RNA (mRNA). "Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo. The skilled artisan will appreciate that, except where otherwise noted, polynucleotide sequences set forth in the instant application will recite "T"s in a representative DNA sequence, but where the sequence represents RNA (e.g., mRNA), the "T"s would be substituted for "U"s. Thus, any of the RNA polynucleotides encoded by a DNA identified by a particular sequence identification number may also comprise the corresponding RNA (e.g., mRNA) sequence encoded by the DNA, where each "T" of the DNA sequence is substituted with "U."

It should be understood that the mRNA polynucleotides of the vaccines as provided herein are synthetic molecules, i.e., they are not naturally-occurring molecules. That is, the mRNA polynucleotides of the present disclosure are isolated mRNA polynucleotides. As is known in the art, "isolated polynucleotides" refer to polynucleotides that are substantially physically separated from other cellular material (e.g., separated from cells and/or systems that produce the polynucleotides) or from other material that hinders their use in the vaccines of the present disclosure. Isolated polynucleotides are substantially pure in that they have been substantially separated from the substances with which they may be associated in living or viral systems. Thus, mRNA polynucleotide vaccines are not associated with living or viral systems, such as cells or viruses. The mRNA polynucleotide vaccines do not include viral components (e.g., viral capsids, viral enzymes, or other viral proteins, for example, those needed for viral-based replication), and the mRNA polynucleotide vaccines are not packaged within, encapsulated within, linked to, or otherwise associated with a virus or viral particle. In some embodiments, the mRNA vaccines comprise a lipid nanoparticle that consists of, or consists essentially of, one or more mRNA polynucleotides (e.g., mRNA polynucleotides encoding one or more VZV antigen (s)).

The basic components of an mRNA molecule typically include at least one coding region, a 5' untranslated region (UTR), a 3' UTR, a 5' cap and a poly-A tail. Polynucleotides of the present disclosure may function as mRNA but can be distinguished from wild-type mRNA in their functional and/or structural design features, which serve to overcome existing problems of effective polypeptide expression using nucleic-acid based therapeutics. In some embodiments, the RNA is a messenger RNA (mRNA) having an open reading frame encoding at least one VZV antigen. In some embodiments, the RNA (e.g., mRNA) further comprises a (at least one) 5' UTR, 3' UTR, a polyA tail and/or a 5' cap.

In some embodiments, a RNA polynucleotide (e.g., mRNA) of a VZV vaccine encodes 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9 or 9-10 antigenic polypeptides. In some embodiments, a RNA polynucleotide (e.g., mRNA) of a VZV RNA (e.g., mRNA) vaccine encodes at least 10, 20, 30, 40, 50, 60, 70, 80, 90 or 100 antigenic polypeptides. In some embodiments, a RNA polynucleotide (e.g., mRNA) of a VZV vaccine encodes at least 100 antigenic polypeptides, or at least 200 antigenic polypeptides. In some embodiments, a RNA polynucleotide (e.g., mRNA) of a VZV vaccine encodes 1-10, 5-15, 10-20, 15-25, 20-30, 25-35, 30-40, 35-45, 40-50, 1-50, 1-100, 2-50 or 2-100 antigenic polypeptides.

Polynucleotides (e.g., mRNAs) of the present disclosure, in some embodiments, are codon optimized. Codon optimization methods are known in the art and may be used as provided herein. For example, any one or more of the sequences SEQ ID NO: 11, 15, 19, 23, 27, 31, 35, 39, 62, 66, 70, 74, 78, 82, 86, 90 or any one or more of the sequences of SEQ ID NO: 92-108 may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, a codon optimized sequence (e.g., a codon-optimized sequence any one of SEQ ID NO: 92-108) shares less than 95% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 90% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 85% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 80% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 75% sequence identity to a naturally-occurring or wild-type sequence (e.g., a naturally-occurring or wild-type mRNA sequence encoding a polypeptide or protein of interest (e.g., an antigenic protein or polypeptide)).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares between 65% and 75% or about 80% sequence identity to a naturally-occurring or wild-type sequence (e.g., a naturally-occurring or wild-type mRNA sequence encoding a polypeptide or protein of interest (e.g., an antigenic protein or polypeptide)).

In some embodiments, a codon-optimized sequence (e.g., a codon-optimized sequence of any one of SEQ ID NO: 92-108) encodes an antigenic polypeptide that is as immunogenic as, or more immunogenic than (e.g., at least 10%, at least 20%, at least 30%, at least 40%, at least 50%, at least 100%, or at least 200% more), than an antigenic polypeptide encoded by a (non-codon-optimized) sequence of any one of SEQ ID NO: 92-108.

In some embodiments, the VZV vaccine includes at least one RNA polynucleotide having an open reading frame encoding at least one VZV antigenic polypeptide having at least one modification, at least one 5' terminal cap, and is formulated within a lipid nanoparticle. 5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp (5') G [the ARCA cap];G(5')ppp(5')A; G(5')ppp(5')G; m7G (5')ppp(5')A; m7G(5')ppp(5')G (New England BioLabs, Ipswich, MA). 5'-capping of modified RNA may be completed post-transcriptionally using a Vaccinia Virus Capping Enzyme to generate the "Cap 0" structure: m7G(5')ppp(5')G (New England BioLabs, Ipswich, MA). Cap 1 structure may be generated using both Vaccinia Virus Capping Enzyme and a 2'-O methyl-transferase to generate: m7G(5')ppp(5') G-2'-O-methyl. Cap 2 structure may be generated from the Cap 1 structure followed by the 2'-O-methylation of the 5'-antepenultimate nucleotide using a 2'-0 methyl-transferase. Cap 3 structure may be generated from the Cap 2 structure followed by the 2'-O-methylation of the 5'-preantepenultimate nucleotide using a 2'-O methyl-transferase. Enzymes may be derived from a recombinant source.

When transfected into mammalian cells, the modified mRNAs have a stability of between 12-18 hours, or greater than 18 hours, e.g., 24, 36, 48, 60, 72, or greater than 72 hours.

In some embodiments a codon optimized RNA may be one in which the levels of G/C are enhanced. The G/C-content of nucleic acid molecules (e.g., mRNA) may influence the stability of the RNA. RNA having an increased amount of guanine (G) and/or cytosine (C) residues may be functionally more stable than RNA containing a large amount of adenine (A) and thymine (T) or uracil (U) nucleotides. As an example, WO2002/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Signal Peptides

In some embodiments, antigenic polypeptides encoded by VZV polynucleotides comprise a signal peptide. Signal peptides, comprising the N-terminal 15-60 amino acids of proteins, are typically needed for the translocation across the membrane on the secretory pathway and thus universally control the entry of most proteins both in eukaryotes and prokaryotes to the secretory pathway. Signal peptides generally include of three regions: an N-terminal region of differing length, which usually comprises positively charged amino acids; a hydrophobic region; and a short carboxy-terminal peptide region. In eukaryotes, the signal peptide of a nascent precursor protein (pre-protein) directs the ribosome to the rough endoplasmic reticulum (ER) membrane and initiates the transport of the growing peptide chain across it. The signal peptide is not responsible for the final destination of the mature protein, however. Secretory proteins devoid of further address tags in their sequence are by default secreted to the external environment. Signal peptides are cleaved from precursor proteins by an endoplasmic reticulum (ER)-resident signal peptidase or they remain uncleaved and function as a membrane anchor. During recent years, a more advanced view of signal peptides has evolved, showing that the functions and immunodominance of certain signal peptides are much more versatile than previously anticipated.

Signal peptides typically function to facilitate the targeting of newly synthesized protein to the endoplasmic reticulum (ER) for processing. ER processing produces a mature Envelope protein, wherein the signal peptide is cleaved, typically by a signal peptidase of the host cell. A signal peptide may also facilitate the targeting of the protein to the cell membrane. VZV vaccines of the present disclosure may comprise, for example, RNA polynucleotides encoding an artificial signal peptide, wherein the signal peptide coding sequence is operably linked to and is in frame with the coding sequence of the VZV antigenic polypeptide. Thus, VZV vaccines of the present disclosure, in some embodiments, produce an antigenic polypeptide comprising a VZV antigenic polypeptide fused to a signal peptide. In some embodiments, a signal peptide is fused to the N-terminus of the VZV antigenic polypeptide. In some embodiments, a signal peptide is fused to the C-terminus of the VZV antigenic polypeptide.

In some embodiments, the signal peptide fused to the VZV antigenic polypeptide is an artificial signal peptide. In some embodiments, an artificial signal peptide fused to the VZV antigenic polypeptide encoded by the VZV RNA (e.g., mRNA) vaccine is obtained from an immunoglobulin protein, e.g., an IgE signal peptide or an IgG signal peptide. In some embodiments, a signal peptide fused to the VZV antigenic polypeptide encoded by a VZV RNA (e.g., mRNA) vaccine is an Ig heavy chain epsilon-1 signal peptide (IgE HC SP) having the sequence of: MDWTWIL-FLVAAATRVHS (SEQ ID NO: 56). In some embodiments, a signal peptide fused to a VZV antigenic polypeptide encoded by the VZV RNA (e.g., mRNA) vaccine is an IgGk chain V-III region HAH signal peptide (IgGk SP) having the sequence of METPAQLLFLLLLWLPDTTG (SEQ ID NO: 57). In some embodiments, the VZV antigenic polypeptide encoded by a VZV RNA (e.g., mRNA) vaccine has an amino acid sequence set forth in one of 10, 14, 18, 22, 26, 30, 34, 38, 42 and 45-55 fused to a signal peptide of any one of SEQ ID NO: 56, 57, 109, 110 and 111. The examples disclosed herein are not meant to be limiting and any signal peptide that is known in the art to facilitate targeting of a protein to ER for processing and/or targeting of a protein to the cell membrane may be used in accordance with the present disclosure.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide may have a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

A signal peptide is typically cleaved from the nascent polypeptide at the cleavage junction during ER processing. The mature VZV antigenic polypeptide produce by VZV RNA vaccine of the present disclosure typically does not comprise a signal peptide.

Chemical Modifications

RNA (e.g., mRNA) vaccines of the present disclosure comprise, in some embodiments, at least one ribonucleic acid (RNA) polynucleotide having an open reading frame encoding at least one respiratory syncytial virus (VZV) antigenic polypeptide, wherein said RNA comprises at least one chemical modification.

The terms "chemical modification" and "chemically modified" refer to modification with respect to adenosine (A), guanosine (G), uridine (U), thymidine (T) or cytidine (C) ribonucleosides or deoxyribonucleosides in at least one of their position, pattern, percent or population. Generally, these terms do not refer to the ribonucleotide modifications in naturally occurring 5'-terminal mRNA cap moieties.

Modifications of polynucleotides include, without limitation, those described herein, and include, but are expressly not limited to, those modifications that comprise chemical modifications. Polynucleotides (e.g., RNA polynucleotides, such as mRNA polynucleotides) may comprise modifications that are naturally-occurring, non-naturally-occurring or the polynucleotide may comprise a combination of naturally-occurring and non-naturally-occurring modifications. Polynucleotides may include any useful modification, for example, of a sugar, a nucleobase, or an internucleoside linkage (e.g., to a linking phosphate, to a phosphodiester linkage or to the phosphodiester backbone).

With respect to a polypeptide, the term "modification" refers to a modification relative to the canonical set of 20 amino acids. Polypeptides, as provided herein, are also considered "modified" if they contain amino acid substitutions, insertions or a combination of substitutions and insertions.

Polynucleotides (e.g., RNA polynucleotides, such as mRNA polynucleotides), in some embodiments, comprise various (more than one) different modifications. In some embodiments, a particular region of a polynucleotide contains one, two or more (optionally different) nucleoside or nucleotide modifications. In some embodiments, a modified RNA polynucleotide (e.g., a modified mRNA polynucleotide), introduced to a cell or organism, exhibits reduced degradation in the cell or organism, respectively, relative to an unmodified polynucleotide. In some embodiments, a modified RNA polynucleotide (e.g., a modified mRNA polynucleotide), introduced into a cell or organism, may exhibit reduced immunogenicity in the cell or organism, respectively (e.g., a reduced innate response).

Polynucleotides (e.g., RNA polynucleotides, such as mRNA polynucleotides), in some embodiments, comprise non-natural modified nucleotides that are introduced during synthesis or post-synthesis of the polynucleotides to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a polynucleotide may be chemically modified.

The present disclosure provides for modified nucleosides and nucleotides of a polynucleotide (e.g., RNA polynucleotides, such as mRNA polynucleotides). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A nucleotide" refers to a nucleoside, including a phosphate group. Modified nucleotides may by synthesized by any useful method, such as, for example, chemically, enzymatically, or recombinantly, to include one or more modified or non-natural nucleosides. Polynucleotides may comprise a region or regions of linked nucleosides. Such regions may have variable backbone linkages. The linkages may be standard phosphodiester linkages, in which case the polynucleotides would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those polynucleotides having at least one chemical modification. One example of such non-standard base pairing is the base pairing between the modified nucleotide inosine and adenine, cytosine or uracil. Any combination of base/sugar or linker may be incorporated into polynucleotides of the present disclosure.

Modifications of polynucleotides (e.g., RNA polynucleotides, such as mRNA polynucleotides), including but not limited to chemical modification, that are useful in the compositions, vaccines, methods and synthetic processes of the present disclosure include, but are not limited to the following: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6, N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo)adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl)cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azido-cytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseduouridine;

1-ethyl-pseudouridine; 2'-O-methyluridine; 2'-O-methylp-seudouridine; 2'-O-methyluridine; 2-thio-2'-O-methyluridine; 3-(3-amino-3-carboxypropyl)uridine; 3,2'-O-dimethyluridine; 3-Methyl-pseudoUridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine), 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uracil; N1-ethyl-pseudo-uracil; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2(thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio)pseudouracil; 1 substituted pseudouracil; 1-(aminoalkylamino-carbonylethylenyl)-2-(thio)-pseudouracil; 1-Methyl-3-(3-amino-3-carboxypropyl)pseudouridine TP; 1-Methyl-3-(3-amino-3-carboxypropyl)pseudo-UTP; 1-Methyl-pseudo-UTP; 1-Ethyl-pseudo-UTP; 2 (thio)pseudouracil; 2' deoxy uridine; 2' fluorouridine; 2-(thio)uracil; 2,4-(dithio)psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl) uracil; 4 (thio)pseudouracil; 4-(thio)pseudouracil; 4-(thio) uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio) uracil; 5 (methylaminomethyl)-4 (thio)uracil; 5 (propynyl) uracil; 5 (trifluoromethyl)uracil; 5-(2-aminopropyl)uracil; 5-(alkyl)-2-(thio)pseudouracil; 5-(alkyl)-2,4 (dithio) pseudouracil; 5-(alkyl)-4 (thio)pseudouracil; 5-(alkyl) pseudouracil; 5-(alkyl)uracil; 5-(alkynyl)uracil; 5-(allylamino)uracil; 5-(cyanoalkyl)uracil; 5-(dialkylaminoalkyl) uracil; 5-(dimethylaminoalkyl)uracil; 5-(guanidiniumalkyl) uracil; 5-(halo)uracil; 5-(1,3-diazole-1-alkyl)uracil; 5-(methoxy)uracil; 5-(methoxycarbonylmethyl)-2-(thio) uracil; 5-(methoxycarbonyl-methyl)uracil; 5-(methyl) 2(thio)uracil; 5-(methyl) 2,4 (dithio)uracil; 5-(methyl) 4

(thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio)uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl) pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3, 4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl) pseudo-UTP; 1-(4-Amino-butyl)pseudo-UTP; 1-(4-Amino-phenyl)pseudo-UTP; 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonylbenzyl)pseudouridine TP; 1-(4-Methoxybenzyl)pseudouridine TP; 1-(4-Methoxy-benzyl)pseudo-UTP; 1-(4-Methoxy-phenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1(4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl}pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctylpseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl)pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thiopseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}]propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine;1-(aza)-2-(thio)-3-(aza)-phenoxazin-1-yl: 1,3-(diaza)-2-(oxo)-phenthiazin-1-yl;1,3-(diaza)-2-(oxo)-phenoxazin-1-yl;1,3,5-(triaza)-2,6-(dioxa)-naphthalene;2 (amino)purine;2,4,5-(trimethyl)phenyl;2'methyl, 2'amino, 2'azido, 2'fluro-cytidine;2'methyl, 2'amino, 2'azido, 2'fluro-adenine;2'methyl, 2'amino, 2'azido, 2'fluro-uridine; 2'-amino-2'-deoxyribose; 2-amino-6-Chloro-purine; 2-azainosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl)isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinyl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of pseudouridine ($\Psi$), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1$\psi$), 1-ethyl-pseudouridine (e1$\psi$), 5-methoxy-uridine (mo5U), 5-methyl-cytidine (m5C), $\alpha$-thio-guanosine, $\alpha$-thio-adenosine, 5-cyano uridine, 4'-thio uridine 7-deaza-adenine, 1-methyl-adenosine (m1$\psi$), 2-methyl-adenine (m2A), N6-methyl-adenosine (m6A), and 2,6-Diaminopurine, (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, 2,8-dimethyladenosine, 2-geranylthiouridine, 2-lysidine, 2-selenouridine, 3-(3-amino-3-carboxypropyl)-5,6-dihydrouridine, 3-(3-amino-3-carboxypropyl)pseudouridine, 3-methylpseudouridine, 5-(carboxyhydroxymethyl)-2'-O-methyluridine methyl ester, 5-aminomethyl-2-geranylthiouridine, 5-aminomethyl-2-selenouridine, 5-aminomethyluridine, 5-carbamoylhydroxymethyluridine, 5-carbamoylmethyl-2-thiouridine, 5-carboxymethyl-2-thiouridine, 5-carboxymethylaminomethyl-2-geranylthiouridine, 5-carboxymethylaminomethyl-2-selenouridine, 5-cyanomethyluridine, 5-hydroxycytidine, 5-methylaminomethyl-2-geranylthiouridine, 7-aminocarboxypropyl-demethylwyosine, 7-aminocarboxypropylwyosine, 7-aminocarboxypropylwyosine methyl ester, 8-methyladenosine, N4,N4-dimethylcytidine, N6-formyladenosine, N6-hydroxymethyladenosine, agmatidine, cyclic N6-threonylcarbamoyladenosine, glutamyl-queuosine, methylated undermodified hydroxywybutosine, N4,N4,2'-O-trimethylcytidine, geranylated 5-methylaminomethyl-2-thiouridine, geranylated 5-carboxymethylaminomethyl-2-thiouridine, Qbase, preQ0base, preQ1base, and combinations of two or more thereof. In some embodiments, the at least one chemically modified nucleoside is selected from the group consisting of pseudouridine, 1-methyl-pseudouridine, 1-ethyl-pseudouridine, 5-methylcytosine, 5-methoxyuridine, and a combination thereof. In some embodiments, the polyribonucleotide (e.g., RNA polyribonucleotide, such as mRNA polyribonucleotide) includes a combination of at least two (e.g., 2, 3, 4 or more) of the aforementioned modified nucleobases. In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of 1-methyl-pseudouridine (m1$\psi$), 1-ethyl-pseudouridine (e1$\psi$), 5-methoxy-uridine (mo5U), 5-methyl-cytidine (m5C), pseudouridine ($\Psi$), $\alpha$-thio-guanosine and $\alpha$-thio-adenosine. In some embodiments, the polyribonucleotide includes a combination of at least two (e.g., 2, 3, 4 or more) of the aforementioned modified nucleobases, including but not limited to chemical modifications.

In some embodiments, polynucleotides (e.g., RNA polynucleotides, such as mRNA polynucleotides) comprise pseudouridine ($\Psi$) and 5-methyl-cytidine (m5C). In some embodiments, the polyribonucleotides (e.g., RNA, such as mRNA) comprise 1-methyl-pseudouridine (m1$\psi$). In some embodiments, the polyribonucleotides (e.g., RNA, such as mRNA) comprise 1-ethyl-pseudouridine (e1$\psi$). In some embodiments, the polyribonucleotides (e.g., RNA, such as mRNA) comprise 1-methyl-pseudouridine (m1$\psi$) and 5-methyl-cytidine (m5C). In some embodiments, the polyribonucleotides (e.g., RNA, such as mRNA) comprise 1-ethyl-pseudouridine (e1$\psi$) and 5-methyl-cytidine (m5C). In some embodiments, the polyribonucleotides (e.g., RNA, such as mRNA) comprise 2-thiouridine (s2U). In some embodiments, the polyribonucleotides (e.g., RNA, such as mRNA) comprise 2-thiouridine and 5-methyl-cytidine (m5C). In some embodiments, the polyribonucleotides (e.g., RNA, such as mRNA) comprise methoxy-uridine (mo5U). In some embodiments, the polyribonucleotides (e.g., RNA, such as mRNA) comprise 5-methoxy-uridine (mo5U) and 5-methyl-cytidine (m5C). In some embodiments, the polyribonucleotides (e.g., RNA, such as mRNA) comprise 2'-O-methyl uridine. In some embodiments, the polyribonucleotides (e.g., RNA, such as mRNA) comprise 2'-O-methyl uridine and 5-methyl-cytidine (m5C). In some embodiments, the polyribonucleotides (e.g., RNA, such as mRNA) comprise N6-methyl-adenosine (m6A). In some embodiments, the polyribonucleotides (e.g., RNA, such as mRNA) comprise N6-methyl-adenosine (m6A) and 5-methyl-cytidine (m5C).

In some embodiments, polynucleotides (e.g., RNA polynucleotides, such as mRNA polynucleotides) are uniformly modified (e.g., fully modified, modified throughout the entire sequence) for a particular modification. For example, a polynucleotide can be uniformly modified with 1-methyl-pseudouridine, meaning that all uridine residues in the mRNA sequence are replaced with 1-methyl-pseudouridine. Similarly, a polynucleotide can be uniformly modified for any type of nucleoside residue present in the sequence by replacement with a modified residue such as those set forth above.

Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), and 2-thio-5-methyl-cytidine.

In some embodiments, a modified nucleobase is a modified uridine. Exemplary nucleobases and nucleosides having a modified uridine include 1-methyl-pseudouridine (m1$\psi$), 1-ethyl-pseudouridine (e1$\psi$), 5-methoxy uridine, 2-thio uridine, 5-cyano uridine, 2'-O-methyl uridine and 4'-thio uridine.

In some embodiments, a modified nucleobase is a modified adenine. Exemplary nucleobases and nucleosides having a modified adenine include 7-deaza-adenine, 1-methyl-adenosine (m1A), 2-methyl-adenine (m2A), and N6-methyl-adenosine (m6A).

In some embodiments, a modified nucleobase is a modified guanine. Exemplary nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, and 7-methyl-8-oxo-guanosine.

The polynucleotides of the present disclosure may be partially or fully modified along the entire length of the molecule. For example, one or more or all or a given type of nucleotide (e.g., purine or pyrimidine, or any one or more or all of A, G, U, C) may be uniformly modified in a polynucleotide of the invention, or in a given predetermined sequence region thereof (e.g., in the mRNA including or excluding the polyA tail). In some embodiments, all nucleotides X in a polynucleotide of the present disclosure (or in a given sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The polynucleotide may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The polynucleotides may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the polynucleotides may contain a modified pyrimidine such as a modified uracil or cytosine. In some embodiments, at least 5%, at least 10%, at least 25%, at least 50%, at least 80%, at least 90% or 100% of the uracil in the polynucleotide is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the polynucleotide is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

Thus, in some embodiments, the RNA vaccines comprise a 5'UTR element, an optionally codon optimized open reading frame, and a 3'UTR element, a poly(A) sequence and/or a polyadenylation signal wherein the RNA is not chemically modified.

In some embodiments, the modified nucleobase is a modified uracil. Exemplary nucleobases and nucleosides having a modified uracil include pseudouridine ($\Psi$), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine (hosU), 5-aminoallyl-uridine, 5-halo-uridine (e.g., 5-iodo-uridineor 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s2U$), 5-aminomethyl-2-thio-uridine ($nm^5s2U$), 5-methylaminomethyl-uridine ($mnm^5U$), 5-methylaminomethyl-2-thio-uridine ($mnm^5s2U$), 5-methylaminomethyl-2-selenouridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s2U$), 5-propynyl-uridine, 1-propynyl-pseudouridine, 5-taurinomethyl-uridine ($\tau m^5U$), 1-taurinomethyl-pseudouridine, 5-taurinomethyl-2-thio-uridine($\tau m^5s2U$), 1-taurinomethyl-4-thio-pseudouridine, 5-methyl-uridine ($m^5U$, i.e., having the nucleobase deoxythymine), 1-methyl-pseudouridine ($m^1\psi$), 1-ethyl-pseudouridine ($e1\psi$), 5-methyl-2-thio-uridine ($m^5s2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3\psi$), 5-(isopentenylaminomethyl)uridine ($inm^5U$), 5-(isopentenylaminomethyl)-2-thio-uridine ($inm^5s2U$), $\alpha$-thio-uridine, 2'-O-methyl-uridine (Um), 5,2'-O-dimethyl-uridine ($m^5Um$), 2'-O-methyl-pseudouridine ($\psi m$), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine ($m^3C$), N4-acetyl-cytidine ($ac^4C$), 5-formyl-cytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine ($s^2C$), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thiozebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k_2C$), $\alpha$-thio-cytidine, 2'-O-methyl-cytidine (Cm), 5,2'-O-dimethyl-cytidine ($m^5Cm$), N4-acetyl-2'-O-methyl-cytidine ($ac^4Cm$), N4,2'-O-dimethyl-cytidine ($m^4Cm$), 5-formyl-2'-O-methyl-cytidine ($f^5Cm$), N4,N4,2'-O-trimethyl-cytidine ($m^4_2Cm$), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine ($m^1A$), 2-methyl-adenine ($m^2A$), N6-methyl-adenosine ($m^6A$), 2-methylthio-N6-methyl-adenosine ($ms^2m^6A$), N6-isopentenyl-adenosine ($i^6A$), 2-methylthio-N6-isopentenyl-adenosine ($ms^2i^6A$), N6-(cis-hydroxyisopentenyl)adenosine ($io^6A$), 2-methylthio-N6-(cis-hydroxyisopentenyl) adenosine ($ms^2io^6A$), N6-glycinylcarbamoyl-adenosine ($g^6A$), N6-threonylcarbamoyl-adenosine ($t^6A$), N6-methyl-N6-threonylcarbamoyl-adenosine ($m^6t^6A$), 2-methylthio-N6-threonylcarbamoyl-adenosine ($ms^296A$), N6,N6-dimethyl-adenosine ($m^6_2A$), N6-hydroxynorvalylcarbamoyl-adenosine ($hn^6A$), 2-methylthio-N6-hydroxynorvalylcarbamoyl-adenosine ($ms^2hn^6A$), N6-acetyl-adenosine ($ac^6A$), 7-methyl-adenine, 2-methylthio-adenine, 2-methoxy-adenine, $\alpha$-thio-adenosine, 2'-O-methyl-adenosine (Am), N6,2'-O-dimethyl-adenosine ($m^6Am$), N6,N6,2'-O-trimethyl-adenosine ($m^6_2Am$), 1,2'-O-dimethyl-adenosine ($m^1Am$), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include inosine (I), 1-methyl-inosine ($m^1I$), wyosine (imG), methylwyosine (mimG), 4-demethyl-wyosine (imG-14), isowyosine (imG2), wybutosine (yW), peroxywybutosine ($o_2yW$), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine ($preQ_0$), 7-aminomethyl-7-deaza-guanosine ($preQ_1$), archaeosine ($G^+$), 7-deaza-8-aza-guanosine, 6-thio-guanosine, 6-thio-7-deaza-guanosine, 6-thio-7-deaza-8-aza-guanosine, 7-methyl-guanosine ($m^7G$), 6-thio-7-methyl-guanosine, 7-methyl-inosine, 6-methoxy-guanosine, 1-methyl-guanosine ($m^1G$), N2-methyl-guanosine ($m^2G$), N2,N2-dimethyl-guanosine ($m^22G$), N2,7-dimethyl-guanosine ($m^{2,7}G$), N2, N2,7-dimethyl-guanosine ($m^{2,2,7}G$), 8-oxo-guanosine, 7-methyl-8-oxo-guanosine, 1-methyl-6-thio-guanosine, N2-methyl-6-thio-guanosine, N2,N2-dimethyl-6-thio-guanosine, $\alpha$-thio-guanosine, 2'-O-methyl-guanosine (Gm), N2-methyl-2'-O-methyl-guanosine ($m^2Gm$), N2,N2-dimethyl-2'-O-methyl-guanosine ($m^2Gm$), 1-methyl-2'-O-methyl-guanosine (mGm), N2,7-dimethyl-2'-O-methyl-guanosine ($m^{2,7}Gm$), 2'-O-methyl-inosine (Im), 1,2'-O-dimethyl-inosine ($m^1Im$), 2'-O-ribosylguanosine (phosphate) (Gr(p)), 1-thio-guanosine, 06-methyl-guanosine, 2'-F-ara-guanosine, and 2'-F-guanosine.

In Vitro Transcription of RNA (e.g., mRNA)

VZV vaccines of the present disclosure comprise at least one RNA polynucleotide, such as a mRNA (e.g., modified mRNA). mRNA, for example, is transcribed in vitro from template DNA, referred to as an "in vitro transcription template." In some embodiments, the at least one RNA polynucleotide has at least one chemical modification. The at least one chemical modification may include, but is expressly not limited to, any modification described herein.

In vitro transcription of RNA is known in the art and is described in International Publication WO2014/152027, which is incorporated by reference herein in its entirety. For example, in some embodiments, the RNA transcript is generated using a non-amplified, linearized DNA template in an in vitro transcription reaction to generate the RNA transcript. In some embodiments the RNA transcript is capped via enzymatic capping. In some embodiments the RNA transcript is purified via chromatographic methods, e.g., use of an oligo dT substrate. Some embodiments exclude the use of DNase. In some embodiments the RNA transcript is synthesized from a non-amplified, linear DNA template coding for the gene of interest via an enzymatic in vitro transcription reaction utilizing a T7 phage RNA polymerase and nucleotide triphosphates of the desired chemistry. Any number of RNA polymerases or variants may be used in the method of the present invention. The polymerase may be selected from, but is not limited to, a phage RNA polymerase, e.g., a T7 RNA polymerase, a T3 RNA polymerase, a SP6 RNA polymerase, and/or mutant polymerases such as, but not limited to, polymerases able to incorporate modified nucleic acids and/or modified nucleotides, including chemically modified nucleic acids and/or nucleotides.

In some embodiments a non-amplified, linearized plasmid DNA is utilized as the template DNA for in vitro transcription. In some embodiments, the template DNA is isolated DNA. In some embodiments, the template DNA is cDNA. In some embodiments, the cDNA is formed by reverse transcription of a RNA polynucleotide, for example, but not limited to VZV RNA, e.g. VZV mRNA. In some embodiments, Cells, e.g., bacterial cells, e.g., E. coli, e.g., DH-1 cells are transfected with the plasmid DNA template. In some embodiments, the transfected cells are cultured to replicate the plasmid DNA which is then isolated and purified. In some embodiments, the DNA template includes a RNA polymerase promoter, e.g., a T7 promoter located 5' to and operably linked to the gene of interest.

In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA or RNA beginning with a start codon (e.g., methionine (ATG or AUG)), and ending with a stop codon (e.g., TAA, TAG or TGA, or UAA, UAG or UGA) and typically encodes a polypeptide (e.g., protein). It will be understood that the sequences disclosed herein may further comprise additional elements, e.g., 5' and 3' UTRs, but that those elements, unlike the ORF, need not necessarily be present in a vaccine of the present disclosure.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophos- phates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, and/or export of the mRNA from the nucleus and translation.

In some embodiments, a polynucleotide includes 200 to 3,000 nucleotides. For example, a polynucleotide may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

Methods of Treatment

Provided herein are compositions (e.g., pharmaceutical compositions), methods, kits and reagents for prevention and/or treatment of VZV in humans and other mammals. VZV RNA vaccines can be used as therapeutic or prophy- lactic agents. They may be used in medicine to prevent and/or treat infectious disease. In exemplary aspects, the VZV RNA vaccines of the invention are used to provide prophylactic protection from varicella and herpes zoster. Varicella is an acute infectious disease caused by VZV. The primary varicella zoster virus infection that results in chick- enpox (varicella) may result in complications, including viral or secondary bacterial pneumonia. Even when the clinical symptoms of chickenpox have resolved, VZV remains dormant in the nervous system of the infected person in the trigeminal and dorsal root ganglia and may reactivate later in life, travelling from the sensory ganglia back to the skin where it produces a disease (rash) known as shingles or herpes zoster, and can also cause a number of neurologic conditions ranging from aseptic meningitis to encephalitis. The VZV vaccines of the present disclosure can be used to prevent and/or treat both the primary infection (Chicken pox) and also the re-activated viral infection (shingles or herpes zoster) and may be particularly useful for prevention and/or treatment of immunocompromised and elderly patients to prevent or to reduce the severity and/or duration of herpes zoster.

Prophylactic protection from VZV can be achieved fol- lowing administration of a VZV RNA vaccine of the present disclosure. Vaccines can be administered once, twice, three times, four times or more but it is likely sufficient to administer the vaccine once (optionally followed by a single booster). It is possible, although less desirable, to administer the vaccine to an infected individual to achieve a therapeutic response. Dosing may need to be adjusted accordingly.

A method of eliciting an immune response in a subject against a VZV is provided in aspects of the present disclo- sure. The method involves administering to the subject a VZV RNA vaccine comprising at least one RNA (e.g., mRNA) polynucleotide having an open reading frame encoding at least one VZV antigenic polypeptide, thereby inducing in the subject an immune response specific to VZV antigenic polypeptide, wherein anti-antigenic polypeptide antibody titer in the subject is increased following vaccina- tion relative to anti-antigenic polypeptide antibody titer in a subject vaccinated with a prophylactically effective dose of a traditional vaccine against the VZV. An "anti-antigenic polypeptide antibody" is a serum antibody the binds spe- cifically to the antigenic polypeptide.

A prophylactically effective dose is a therapeutically effective dose that prevents infection with the virus at a clinically acceptable level. In some embodiments, the thera- peutically effective dose is a dose listed in a package insert for the vaccine. A traditional vaccine, as used herein, refers to a vaccine other than the mRNA vaccines of the present disclosure. For instance, a traditional vaccine includes, but is not limited, to live microorganism vaccines, killed micro- organism vaccines, subunit vaccines, protein antigen vac- cines, DNA vaccines, VLP vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

A method of eliciting an immune response in a subject against a VZV is provided in aspects of the invention. The method involves administering to the subject a VZV RNA vaccine comprising at least one RNA polynucleotide having an open reading frame encoding at least one VZV antigenic polypeptide, thereby inducing in the subject an immune response specific to VZV antigenic polypeptide, wherein anti-antigenic polypeptide antibody titer in the subject is increased following vaccination relative to anti-antigenic polypeptide antibody titer in a subject vaccinated with a prophylactically effective dose of a traditional vaccine against the VZV. An "anti-antigenic polypeptide antibody" is a serum antibody the binds specifically to the antigenic polypeptide.

A prophylactically effective dose is a therapeutically effective dose that prevents infection with the virus at a clinically acceptable level. In some embodiments the thera- peutically effective dose is a dose listed in a package insert for the vaccine. A traditional vaccine, as used herein, refers to a vaccine other than the mRNA vaccines of the invention. For instance, a traditional vaccine includes but is not limited to live microorganism vaccines, killed microorganism vac- cines, subunit vaccines, protein antigen vaccines, DNA vaccines, etc.

In some embodiments the anti-antigenic polypeptide anti- body titer in the subject is increased 1 log to 10 log following vaccination relative to anti-antigenic polypeptide antibody titer in a subject vaccinated with a prophylactically effective dose of a traditional vaccine against the VZV.

In some embodiments the anti-antigenic polypeptide anti- body titer in the subject is increased 1 log following vacci- nation relative to anti-antigenic polypeptide antibody titer in a subject vaccinated with a prophylactically effective dose of a traditional vaccine against the VZV.

In some embodiments the anti-antigenic polypeptide anti- body titer in the subject is increased 2 log following vacci- nation relative to anti-antigenic polypeptide antibody titer in a subject vaccinated with a prophylactically effective dose of a traditional vaccine against the VZV.

In some embodiments the anti-antigenic polypeptide anti- body titer in the subject is increased 3 log following vacci- nation relative to anti-antigenic polypeptide antibody titer in a subject vaccinated with a prophylactically effective dose of a traditional vaccine against the VZV.

In some embodiments the anti-antigenic polypeptide antibody titer in the subject is increased 5 log following vaccination relative to anti-antigenic polypeptide antibody titer in a subject vaccinated with a prophylactically effective dose of a traditional vaccine against the VZV.

In some embodiments the anti-antigenic polypeptide antibody titer in the subject is increased 10 log following vaccination relative to anti-antigenic polypeptide antibody titer in a subject vaccinated with a prophylactically effective dose of a traditional vaccine against the VZV.

A method of eliciting an immune response in a subject against a VZV is provided in other aspects of the invention. The method involves administering to the subject a VZV RNA vaccine comprising at least one RNA polynucleotide having an open reading frame encoding at least one VZV antigenic polypeptide, thereby inducing in the subject an immune response specific to VZV antigenic polypeptide, wherein the immune response in the subject is equivalent to an immune response in a subject vaccinated with a traditional vaccine against the VZV at 2 times to 100 times the dosage level relative to the RNA vaccine.

In some embodiments the immune response in the subject is equivalent to an immune response in a subject vaccinated with a traditional vaccine at twice the dosage level relative to the VZV RNA vaccine.

In some embodiments the immune response in the subject is equivalent to an immune response in a subject vaccinated with a traditional vaccine at three times the dosage level relative to the VZV RNA vaccine.

In some embodiments the immune response in the subject is equivalent to an immune response in a subject vaccinated with a traditional vaccine at 4 times the dosage level relative to the VZV RNA vaccine.

In some embodiments the immune response in the subject is equivalent to an immune response in a subject vaccinated with a traditional vaccine at 5 times the dosage level relative to the VZV RNA vaccine.

In some embodiments the immune response in the subject is equivalent to an immune response in a subject vaccinated with a traditional vaccine at 10 times the dosage level relative to the VZV RNA vaccine.

In some embodiments the immune response in the subject is equivalent to an immune response in a subject vaccinated with a traditional vaccine at 50 times the dosage level relative to the VZV RNA vaccine.

In some embodiments the immune response in the subject is equivalent to an immune response in a subject vaccinated with a traditional vaccine at 100 times the dosage level relative to the VZV RNA vaccine.

In some embodiments the immune response in the subject is equivalent to an immune response in a subject vaccinated with a traditional vaccine at 10 times to 1000 times the dosage level relative to the VZV RNA vaccine.

In some embodiments the immune response in the subject is equivalent to an immune response in a subject vaccinated with a traditional vaccine at 100 times to 1000 times the dosage level relative to the VZV RNA vaccine.

In other embodiments the immune response is assessed by determining [protein] antibody titer in the subject.

In other aspects the invention is a method of eliciting an immune response in a subject against a VZV by administering to the subject a VZV RNA vaccine comprising at least one RNA polynucleotide having an open reading frame encoding at least one VZV antigenic polypeptide, thereby inducing in the subject an immune response specific to VZV antigenic polypeptide, wherein the immune response in the subject is induced 2 days to 10 weeks earlier relative to an immune response induced in a subject vaccinated with a prophylactically effective dose of a traditional vaccine against the VZV. In some embodiments the immune response in the subject is induced in a subject vaccinated with a prophylactically effective dose of a traditional vaccine at 2 times to 100 times the dosage level relative to the RNA vaccine.

In some embodiments the immune response in the subject is induced 2 days earlier relative to an immune response induced in a subject vaccinated with a prophylactically effective dose of a traditional vaccine.

In some embodiments the immune response in the subject is induced 3 days earlier relative to an immune response induced in a subject vaccinated a prophylactically effective dose of a traditional vaccine.

In some embodiments the immune response in the subject is induced 1 week earlier relative to an immune response induced in a subject vaccinated with a prophylactically effective dose of a traditional vaccine.

In some embodiments the immune response in the subject is induced 2 weeks earlier relative to an immune response induced in a subject vaccinated with a prophylactically effective dose of a traditional vaccine.

In some embodiments the immune response in the subject is induced 3 weeks earlier relative to an immune response induced in a subject vaccinated with a prophylactically effective dose of a traditional vaccine.

In some embodiments the immune response in the subject is induced 5 weeks earlier relative to an immune response induced in a subject vaccinated with a prophylactically effective dose of a traditional vaccine.

In some embodiments the immune response in the subject is induced 10 weeks earlier relative to an immune response induced in a subject vaccinated with a prophylactically effective dose of a traditional vaccine.

A method of v eliciting an immune response in a subject against a VZV by administering to the subject a VZV RNA vaccine having an open reading frame encoding a first antigenic polypeptide, wherein the RNA polynucleotide does not include a stabilization element, and wherein an adjuvant is not co-formulated or co-administered with the vaccine.

Flagellin Adjuvants

Flagellin is an approximately 500 amino acid monomeric protein that polymerizes to form the flagella associated with bacterial motion. Flagellin is expressed by a variety of flagellated bacteria (*Salmonella typhimurium* for example) as well as non-flagellated bacteria (such as *Escherichia coli*). Sensing of flagellin by cells of the innate immune system (dendritic cells, macrophages, etc.) is mediated by the Toll-like receptor 5 (TLR5) as well as by Nod-like receptors (NLRs) Ipaf and Naip5. TLRs and NLRs have been identified as playing a role in the activation of innate immune response and adaptive immune response. As such, flagellin provides an adjuvant effect in a vaccine.

The nucleotide and amino acid sequences encoding known flagellin polypeptides are publicly available in the NCBI GenBank database. The flagellin sequences from *S. typhimurium, H. pylori, V. cholera, S. marcesens, S. flexneri, T. pallidum, L. pneumophila, B. burgdorferei, C. difficile, R. meliloti, A. tumefaciens, R. lupini, B. clarridgeiae, P. Mirabilis, B. subtilus, L. monocytogenes, P. aeruginosa*, and *E. coli*, among others are known.

A flagellin polypeptide, as used herein, refers to a full length flagellin protein, immunogenic fragments thereof, and peptides having at least 50% sequence identify to a flagellin protein or immunogenic fragments thereof. Exemplary flagellin proteins include flagellin from *Salmonella typhi* (UniPro Entry number: Q56086), *Salmonella typhimurium* (A0A0C9DG09), *Salmonella enteritidis* (A0A0C9BAB7), and *Salmonella choleraesuis* (Q6V2X8), and SEQ ID NO: 115-117. In some embodiments, the flagellin polypeptide has at least 60%, 70%, 75%, 80%, 90%, 95%, 97%, 98%, or 99% sequence identify to a flagellin protein or immunogenic fragments thereof.

In some embodiments, the flagellin polypeptide is an immunogenic fragment. An immunogenic fragment is a portion of a flagellin protein that provokes an immune response. In some embodiments, the immune response is a TLR5 immune response. An example of an immunogenic fragment is a flagellin protein in which all or a portion of a hinge region has been deleted or replaced with other amino acids. For example, an antigenic polypeptide may be inserted in the hinge region. Hinge regions are the hypervariable regions of a flagellin. Hinge regions of a flagellin are also referred to as "D3 domain or region, "propeller domain or region," "hypervariable domain or region" and "variable domain or region." "At least a portion of a hinge region," as used herein, refers to any part of the hinge region of the flagellin, or the entirety of the hinge region. In other embodiments an immunogenic fragment of flagellin is a 20, 25, 30, 35, or 40 amino acid C-terminal fragment of flagellin.

The flagellin monomer is formed by domains DO through D3. DO and D1, which form the stem, are composed of tandem long alpha helices and are highly conserved among different bacteria. The D1 domain includes several stretches of amino acids that are useful for TLR5 activation. The entire D1 domain or one or more of the active regions within the domain are immunogenic fragments of flagellin. Examples of immunogenic regions within the D1 domain include residues 88-114 and residues 411-431 (in *Salmonella typhimurium* FliC flagellin. Within the 13 amino acids in the 88-100 region, at least 6 substitutions are permitted between *Salmonella* flagellin and other flagellin proteins that still preserve TLR5 activation. Thus, immunogenic fragments of flagellin include flagellin like sequences that activate TLR5 and contain a 13 amino acid motif that is 53% or more identical to the *Salmonella* sequence in 88-100 of FliC (LQRVRELAVQSAN; SEQ ID NO: 118).

In some embodiments, the RNA (e.g., mRNA) vaccine includes an RNA that encodes a fusion protein of flagellin and one or more antigenic polypeptides. A "fusion protein" as used herein, refers to a linking of two components of the construct. In some embodiments, a carboxy-terminus of the antigenic polypeptide is fused or linked to an amino terminus of the flagellin polypeptide. In other embodiments, an amino-terminus of the antigenic polypeptide is fused or linked to a carboxy-terminus of the flagellin polypeptide. The fusion protein may include, for example, one, two, three, four, five, six or more flagellin polypeptides linked to one, two, three, four, five, six or more antigenic polypeptides. When two or more flagellin polypeptides and/or two or more antigenic polypeptides are linked such a construct may be referred to as a "multimer."

Each of the components of a fusion protein may be directly linked to one another or they may be connected through a linker. For instance, the linker may be an amino acid linker. The amino acid linker encoded for by the RNA (e.g., mRNA) vaccine to link the components of the fusion protein may include, for instance, at least one member selected from the group consisting of a lysine residue, a glutamic acid residue, a serine residue and an arginine residue. In some embodiments the linker is 1-30, 1-25, 1-25, 5-10, 5, 15, or 5-20 amino acids in length.

In other embodiments the RNA (e.g., mRNA) vaccine includes at least two separate RNA polynucleotides, one encoding one or more antigenic polypeptides and the other encoding the flagellin polypeptide. The at least two RNA polynucleotides may be co-formulated in a carrier such as a lipid nanoparticle.

Therapeutic and Prophylactic Compositions

Provided herein are compositions (e.g., pharmaceutical compositions), methods, kits and reagents for prevention, treatment or diagnosis of VZV in humans and other mammals, for example. VZV RNA (e.g., mRNA) vaccines can be used as therapeutic or prophylactic agents. They may be used in medicine to prevent and/or treat infectious disease. In some embodiments, the VZV vaccines of the invention can be envisioned for use in the priming of immune effector cells, for example, to activate peripheral blood mononuclear cells (PBMCs) ex vivo, which are then infused (re-infused) into a subject.

In exemplary embodiments, a VZV vaccine containing RNA polynucleotides as described herein can be administered to a subject (e.g., a mammalian subject, such as a human subject), and the RNA polynucleotides are translated in vivo to produce an antigenic polypeptide.

The VZV RNA vaccines may be induced for translation of a polypeptide (e.g., antigen or immunogen) in a cell, tissue or organism. In exemplary embodiments, such translation occurs in vivo, although there can be envisioned embodiments where such translation occurs ex vivo, in culture or in vitro. In exemplary embodiments, the cell, tissue or organism is contacted with an effective amount of a composition containing a VZV RNA vaccine that contains a polynucleotide that has at least one a translatable region encoding an antigenic polypeptide.

An "effective amount" of the VZV RNA vaccine is provided based, at least in part, on the target tissue, target cell type, means of administration, physical characteristics of the polynucleotide (e.g., size, and extent of modified nucleosides) and other components of the VZV RNA vaccine, and other determinants. In general, an effective amount of the VZV RNA vaccine composition provides an induced or boosted immune response as a function of antigen production in the cell. In general, an effective amount of the VZV RNA vaccine containing RNA polynucleotides having at least one chemical modifications are preferably more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation from the polynucleotide, decreased nucleic acid degradation (as demonstrated, for example, by increased duration of protein translation from a modified polynucleotide), or altered antigen specific immune response of the host cell.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

In some embodiments, RNA vaccines (including polynucleotides and their encoded polypeptides) in accordance with the present disclosure may be used for treatment or prevention of VZV.

VZV RNA vaccines may be administered prophylactically or therapeutically as part of an active immunization scheme to healthy individuals or early in infection during the incubation phase or during active infection after onset of symptoms. In some embodiments, the amount of RNA vaccines of the present disclosure provided to a cell, a tissue or a subject may be an amount effective for immune prophylaxis.

VZV RNA (e.g., mRNA) vaccines may be administrated with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, VZV RNA vaccines may be administered intramuscularly, intranasally or intradermally, similarly to the administration of inactivated vaccines known in the art.

The VZV RNA vaccines may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers and produce responses early than commercially available anti-virals.

Provided herein are pharmaceutical compositions including VZV RNA vaccines and RNA vaccine compositions and/or complexes optionally in combination with one or more pharmaceutically acceptable excipients.

VZV RNA (e.g., mRNA) vaccines may be formulated or administered alone or in conjunction with one or more other components. For instance, VZV RNA vaccines (vaccine compositions) may comprise other components including, but not limited to, adjuvants.

In some embodiments, VZV RNA vaccines do not include an adjuvant (they are adjuvant free).

VZV RNA (e.g., mRNA) vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, VZV RNA vaccines are administered to humans, human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigenic polypeptides.

Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

VZV RNA vaccines can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with VZV RNA vaccines (e.g., for transplantation into a subject), hyaluronidase, nanoparticle mimics and combinations thereof.

Stabilizing Elements

Naturally-occurring eukaryotic mRNA molecules have been found to contain stabilizing elements, including, but not limited to untranslated regions (UTR) at their 5'-end (5'UTR) and/or at their 3'-end (3'UTR), in addition to other structural features, such as a 5'-cap structure or a 3'-poly(A) tail. Both the 5'UTR and the 3'UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing. The 3'-poly(A) tail is typically a stretch of adenine nucleotides added to the 3'-end of the transcribed mRNA. It can comprise up to about 400 adenine nucleotides. In some embodiments the length of the 3'-poly(A) tail may be an essential element with respect to the stability of the individual mRNA.

In some embodiments the RNA vaccine may include one or more stabilizing elements. Stabilizing elements may include for instance a histone stem-loop. A stem-loop binding protein (SLBP), a 32 kDa protein has been identified. It is associated with the histone stem-loop at the 3'-end of its histone messages in both the nucleus and the cytoplasm. Its expression level is regulated by the cell cycle; it peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, the RNA vaccines include a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. It has been found that the synergistic effect of the combination of poly(A) and at least one histone stem-loop does not depend on the order of the elements or the length of the poly(A) sequence.

In some embodiments, the RNA vaccine does not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. In some embodiments, the nucleic acid does not include an intron.

In some embodiments, the RNA vaccine may or may not contain an enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In other embodiments the RNA vaccine may have one or more AU-rich sequences removed. These sequences, sometimes referred to as AURES are destabilizing sequences found in the 3'UTR. The AURES may be removed from the RNA vaccines. Alternatively the AURES may remain in the RNA vaccine.

Nanoparticle Formulations

In some embodiments, VZV RNA (e.g., mRNA) vaccines are formulated in a nanoparticle. In some embodiments, VZV RNA vaccines are formulated in a lipid nanoparticle. In some embodiments, VZV RNA vaccines are formulated in a lipid-polycation complex, referred to as a cationic lipid nanoparticle. The formation of the lipid nanoparticle may be accomplished by methods known in the art and/or as described in U.S. Publication No. 2012/0178702, herein incorporated by reference in its entirety. As a non-limiting example, the polycation may include a cationic peptide or a polypeptide such as, but not limited to, polylysine, polyornithine and/or polyarginine and the cationic peptides described in International Publication No. WO2012/013326 or U.S. Publication No. US2013/0142818; each of which is herein incorporated by reference in its entirety. In some embodiments, VZV RNA vaccines are formulated in a lipid nanoparticle that includes a non-cationic lipid such as, but not limited to, cholesterol or dioleoyl phosphatidylethanolamine (DOPE).

A lipid nanoparticle formulation may be influenced by, but not limited to, the selection of the cationic lipid component, the degree of cationic lipid saturation, the nature of the PEGylation, ratio of all components and biophysical parameters such as size. In one example by Semple et al. (*Nature Biotech.* 2010 28:172-176; herein incorporated by reference in its entirety), the lipid nanoparticle formulation is composed of 57.1% cationic lipid, 7.1% dipalmitoylphosphatidylcholine, 34.3% cholesterol, and 1.4% PEG-c-DMA. As another example, changing the composition of the cationic lipid was shown to more effectively deliver siRNA to various antigen presenting cells (Basha et al. *Mol Ther.* 2011 19:2186-2200; herein incorporated by reference in its entirety).

In some embodiments, lipid nanoparticle formulations may comprise 35 to 45% cationic lipid, 40% to 50% cationic lipid, 50% to 60% cationic lipid and/or 55% to 65% cationic lipid. In some embodiments, the ratio of lipid to RNA (e.g., mRNA) in lipid nanoparticles may be 5:1 to 20:1, 10:1 to 25:1, 15:1 to 30:1 and/or at least 30:1.

In some embodiments, the ratio of PEG in the lipid nanoparticle formulations may be increased or decreased and/or the carbon chain length of the PEG lipid may be modified from C14 to C18 to alter the pharmacokinetics and/or biodistribution of the lipid nanoparticle formulations. As a non-limiting example, lipid nanoparticle formulations may contain 0.5% to 3.0%, 1.0% to 3.5%, 1.5% to 4.0%, 2.0% to 4.5%, 2.5% to 5.0% and/or 3.0% to 6.0% of the lipid molar ratio of PEG-c-DOMG (R-3-[(o-methoxy-poly(ethyleneglycol)2000)carbamoyl)]-1,2-dimyristyloxypropyl-3-amine) (also referred to herein as PEG-DOMG) as compared to the cationic lipid, DSPC and cholesterol. In some embodiments, the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In some embodiments, a VZV RNA (e.g., mRNA) vaccine formulation is a nanoparticle that comprises at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, (12Z,15Z)—N,N-dimethyl-2-nonylhenicosa-12,15-dien-1-amine, N,N-dimethyl-1-[(1S,2R)-2-octylcyclopropyl]heptadecan-8-amine, PEGylated lipids and amino alcohol lipids.

In some embodiments, the cationic lipid is

In some embodiments, the cationic lipid is

In some embodiments, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in U.S. Publication No. US2013/0150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US2013/0150625); 2-amino-3-[(9Z)-octadec-9-en-1-yloxy]-2-{[(9Z)-octadec-9-en-1-yloxy]methyl}propan-1-ol (Compound 2 in US2013/0150625); 2-amino-3-[(9Z,12Z)-octadeca-9,12-dien-1-yloxy]-2-[(octyloxy)methyl]propan-1-ol (Compound 3 in US2013/0150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US2013/0150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate, and further comprise a neutral lipid, a sterol and a molecule capable of reducing particle aggregation, for example a PEG or PEG-modified lipid.

In some embodiments, a lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate; (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of 20-60% cationic lipid:5-25% neutral lipid (non-cationic lipid): 25-55% sterol; 0.5-15% PEG-lipid.

In some embodiments, a lipid nanoparticle formulation includes 25% to 75% on a molar basis of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)

butanoyl)oxy)heptadecanedioate, e.g., 35 to 65%, 45 to 65%, 60%, 57.5%, 50% or 40% on a molar basis.

In some embodiments, a lipid nanoparticle formulation includes 0.5% to 15% on a molar basis of the neutral lipid, e.g., 3 to 12%, 5 to 10% or 15%, 10%, or 7.5% on a molar basis. Examples of neutral lipids include, without limitation, DSPC, POPC, DPPC, DOPE and SM. In some embodiments, the formulation includes 5% to 50% on a molar basis of the sterol (e.g., 15 to 45%, 20 to 40%, 40%, 38.5%, 35%, or 31% on a molar basis. A non-limiting example of a sterol is cholesterol. In some embodiments, a lipid nanoparticle formulation includes 0.5% to 20% on a molar basis of the PEG or PEG-modified lipid (e.g., 0.5 to 10%, 0.5 to 5%, 1.5%, 0.5%, 1.5%, 3.5%, or 5% on a molar basis. In some embodiments, a PEG or PEG modified lipid comprises a PEG molecule of an average molecular weight of 2,000 Da. In some embodiments, a PEG or PEG modified lipid comprises a PEG molecule of an average molecular weight of less than 2,000, for example around 1,500 Da, around 1,000 Da, or around 500 Da. Non-limiting examples of PEG-modified lipids include PEG-distearoyl glycerol (PEG-DMG) (also referred herein as PEG-$C_{14}$ or $C_{14}$-PEG), PEG-cDMA (further discussed in Reyes et al. *J. Controlled Release,* 107, 276-287 (2005) the content of which is herein incorporated by reference in its entirety).

In some embodiments, lipid nanoparticle formulations include 25-75% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 0.5-15% of the neutral lipid, 5-50% of the sterol, and 0.5-20% of the PEG or PEG-modified lipid on a molar basis.

In some embodiments, lipid nanoparticle formulations include 35-65% of a cationic lipid selected from the group consisting of 2,2-dilinoleyl-4-dimethylaminoethyl-[1,3]-di-oxolane (DLin-KC2-DMA), dilinoleyl-methyl-4-dimethyl-aminobutyrate (DLin-MC3-DMA), and di((Z)-non-2-en-1-yl) 9-((4-(dimethylamino)butanoyl)oxy)heptadecanedioate, 3-12% of the neutral lipid, 15-45% of the sterol, and 0.5-10% of the PEG or PEG-modified lipid on a molar basis.

In some embodiments, lipid nanoparticle formulations include 45-65% of a cationic lipid selected from the group consisting of 2,2-dilinoleyl-4-dimethylaminoethyl-[1,3]-di-oxolane (DLin-KC2-DMA), dilinoleyl-methyl-4-dimethyl-aminobutyrate (DLin-MC3-DMA), and di((Z)-non-2-en-1-yl) 9-((4-(dimethylamino)butanoyl)oxy)heptadecanedioate, 5-10% of the neutral lipid, 25-40% of the sterol, and 0.5-10% of the PEG or PEG-modified lipid on a molar basis.

In some embodiments, lipid nanoparticle formulations include 60% of a cationic lipid selected from the group consisting of 2,2-dilinoleyl-4-dimethylaminoethyl-[1,3]-di-oxolane (DLin-KC2-DMA), dilinoleyl-methyl-4-dimethyl-aminobutyrate (DLin-MC3-DMA), and di((Z)-non-2-en-1-yl) 9-((4-(dimethylamino)butanoyl)oxy)heptadecanedioate, 7.5% of the neutral lipid, 31% of the sterol, and 1.5% of the PEG or PEG-modified lipid on a molar basis.

In some embodiments, lipid nanoparticle formulations include 50% of a cationic lipid selected from the group consisting of 2,2-dilinoleyl-4-dimethylaminoethyl-[1,3]-di-oxolane (DLin-KC2-DMA), dilinoleyl-methyl-4-dimethyl-aminobutyrate (DLin-MC3-DMA), and di((Z)-non-2-en-1-yl) 9-((4-(dimethylamino)butanoyl)oxy)heptadecanedioate, 10% of the neutral lipid, 38.5% of the sterol, and 1.5% of the PEG or PEG-modified lipid on a molar basis.

In some embodiments, lipid nanoparticle formulations include 50% of a cationic lipid selected from the group consisting of 2,2-dilinoleyl-4-dimethylaminoethyl-[1,3]-di-oxolane (DLin-KC2-DMA), dilinoleyl-methyl-4-dimethyl-aminobutyrate (DLin-MC3-DMA), and di((Z)-non-2-en-1-yl) 9-((4-(dimethylamino)butanoyl)oxy)heptadecanedioate, 10% of the neutral lipid, 35% of the sterol, 4.5% or 5% of the PEG or PEG-modified lipid, and 0.5% of the targeting lipid on a molar basis.

In some embodiments, lipid nanoparticle formulations include 40% of a cationic lipid selected from the group consisting of 2,2-dilinoleyl-4-dimethylaminoethyl-[1,3]-di-oxolane (DLin-KC2-DMA), dilinoleyl-methyl-4-dimethyl-aminobutyrate (DLin-MC3-DMA), and di((Z)-non-2-en-1-yl) 9-((4-(dimethylamino)butanoyl)oxy)heptadecanedioate, 15% of the neutral lipid, 40% of the sterol, and 5% of the PEG or PEG-modified lipid on a molar basis.

In some embodiments, lipid nanoparticle formulations include 57.2% of a cationic lipid selected from the group consisting of 2,2-dilinoleyl-4-dimethylaminoethyl-[1,3]-di-oxolane (DLin-KC2-DMA), dilinoleyl-methyl-4-dimethyl-aminobutyrate (DLin-MC3-DMA), and di((Z)-non-2-en-1-yl) 9-((4-(dimethylamino)butanoyl)oxy)heptadecanedioate, 7.1% of the neutral lipid, 34.3% of the sterol, and 1.4% of the PEG or PEG-modified lipid on a molar basis.

In some embodiments, lipid nanoparticle formulations include 57.5% of a cationic lipid selected from the PEG lipid is PEG-cDMA (PEG-cDMA is further discussed in Reyes et al. (J. Controlled Release, 107, 276-287 (2005), the content of which is herein incorporated by reference in its entirety), 7.5% of the neutral lipid, 31.5% of the sterol, and 3.5% of the PEG or PEG-modified lipid on a molar basis.

In some embodiments, lipid nanoparticle formulations consists essentially of a lipid mixture in molar ratios of 20-70% cationic lipid: 5-45% neutral lipid: 20-55% choles-terol: 0.5-15% PEG-modified lipid. In some embodiments, lipid nanoparticle formulations consists essentially of a lipid mixture in a molar ratio of 20-60% cationic lipid:5-25% neutral lipid (non-cationic lipid): 25-55% cholesterol: 0.5-15% PEG-modified lipid.

In some embodiments, the molar lipid ratio is 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Non-limiting examples of lipid nanoparticle compositions and methods of making them are described, for example, in Semple et al. (2010) Nat. Biotechnol. 28:172-176; Jayarama et al. (2012), Angew. Chem. Int. Ed., 51: 8529-8533; and Maier et al. (2013) Molecular Therapy 21, 1570-1578 (the contents of each of which are incorporated herein by reference in their entirety).

In some embodiments, lipid nanoparticle formulations may comprise a cationic lipid, a PEG lipid and a structural lipid and optionally comprise a non-cationic lipid. As a non-limiting example, a lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, a lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, DLin-KC2-DMA, DLin-MC3-DMA and di((Z)-non-2-en-1-yl) 9-((4-(dimethylamino)butanoyl)oxy) heptadecanedioate.

In some embodiments, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, the lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, DLin-KC2-DMA, DLin-MC3-DMA and di((Z)-non-2-en-1-yl) 9-((4-(dimethylamino)butanoyl)oxy) heptadecanedioate.

In some embodiments, the lipid nanoparticle formulations described herein may comprise a cationic lipid, a non-cationic lipid, a PEG lipid and a structural lipid. As a non-limiting example, the lipid nanoparticle comprise 50% of the cationic lipid DLin-KC2-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DMG and 38.5% of the structural lipid cholesterol. As yet another non-limiting example, the lipid nanoparticle comprise 55% of the cationic lipid di((Z)-non-2-en-1-yl) 9-((4-(dimethylamino)butanoyl) oxy)heptadecanedioate, 10% of the non-cationic lipid DSPC, 2.5% of the PEG lipid PEG-DMG and 32.5% of the structural lipid cholesterol.

Relative amounts of the active ingredient, the pharmaceutically acceptable excipient, and/or any additional ingredients in a vaccine composition may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the RNA vaccine composition may comprise the polynucleotide described herein, formulated in a lipid nanoparticle comprising MC3, Cholesterol, DSPC and PEG2000-DMG, the buffer trisodium citrate, sucrose and water for injection. As a non-limiting example, the composition comprises: 2.0 mg/mL of drug substance (e.g., polynucleotides encoding VZV), 21.8 mg/mL of MC3, 10.1 mg/mL of cholesterol, 5.4 mg/mL of DSPC, 2.7 mg/mL of PEG2000-DMG, 5.16 mg/mL of trisodium citrate, 71 mg/mL of sucrose and 1.0 mL of water for injection.

In some embodiments, a nanoparticle (e.g., a lipid nanoparticle) has a mean diameter of 10-500 nm, 20-400 nm, 30-300 nm, 40-200 nm. In some embodiments, a nanoparticle (e.g., a lipid nanoparticle) has a mean diameter of 50-150 nm, 50-200 nm, 80-100 nm or 80-200 nm.

Liposomes, Lipoplexes, and Lipid Nanoparticles

In some embodiments, the RNA vaccine pharmaceutical compositions may be formulated in liposomes such as, but not limited to, DiLa2 liposomes (Marina Biotech, Bothell, WA), SMARTICLES® (Marina Biotech, Bothell, WA), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); herein incorporated by reference in its entirety) and hyaluronan-coated liposomes (Quiet Therapeutics, Israel).

In some embodiments, the RNA vaccines may be formulated in a lyophilized gel-phase liposomal composition as described in U.S. Publication No. US2012/0060293, herein incorporated by reference in its entirety.

The nanoparticle formulations may comprise a phosphate conjugate. The phosphate conjugate may increase in vivo circulation times and/or increase the targeted delivery of the nanoparticle. Phosphate conjugates for use with the present invention may be made by the methods described in International Publication No. WO2013/033438 or U.S. Publication No. US2013/0196948, the content of each of which is herein incorporated by reference in its entirety. As a non-limiting example, the phosphate conjugates may include a compound of any one of the formulas described in International Publication No. WO2013/033438, herein incorporated by reference in its entirety.

The nanoparticle formulation may comprise a polymer conjugate. The polymer conjugate may be a water soluble conjugate. The polymer conjugate may have a structure as described in U.S. Publication No. 2013/0059360, the content of which is herein incorporated by reference in its entirety. In some aspects, polymer conjugates with the polynucleotides of the present invention may be made using the methods and/or segmented polymeric reagents described in U.S. Publication No. 2013/0072709, herein incorporated by reference in its entirety. In other aspects, the polymer conjugate may have pendant side groups comprising ring moieties such as, but not limited to, the polymer conjugates described in U.S. Publication No. US2013/0196948, the contents of which is herein incorporated by reference in its entirety.

The nanoparticle formulations may comprise a conjugate to enhance the delivery of nanoparticles of the present invention in a subject. Further, the conjugate may inhibit phagocytic clearance of the nanoparticles in a subject. In some aspects, the conjugate may be a "self" peptide designed from the human membrane protein CD47 (e.g., the "self" particles described by Rodriguez et al (*Science* 2013, 339, 971-975), herein incorporated by reference in its entirety). As shown by Rodriguez et al. the self peptides delayed macrophage-mediated clearance of nanoparticles which enhanced delivery of the nanoparticles. In other aspects, the conjugate may be the membrane protein CD47 (e.g., see Rodriguez et al. *Science* 2013, 339, 971-975, herein incorporated by reference in its entirety). Rodriguez et al. showed that, similarly to "self" peptides, CD47 can increase the circulating particle ratio in a subject as compared to scrambled peptides and PEG coated nanoparticles.

In some embodiments, the RNA vaccines of the present invention are formulated in nanoparticles which comprise a conjugate to enhance the delivery of the nanoparticles of the present invention in a subject. The conjugate may be the CD47 membrane or the conjugate may be derived from the CD47 membrane protein, such as the "self" peptide described previously. In other embodiments, the nanoparticle may comprise PEG and a conjugate of CD47 or a derivative thereof. In yet other embodiments, the nanoparticle may comprise both the "self" peptide described above and the membrane protein CD47.

In some embodiments, a "self" peptide and/or CD47 protein may be conjugated to a virus-like particle or pseudovirion, as described herein for delivery of the RNA vaccines of the present invention.

In other embodiments, RNA vaccine pharmaceutical compositions comprising the polynucleotides of the present invention and a conjugate, which may have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in U.S. Publication No. US2013/0184443, the content of which is herein incorporated by reference in its entirety.

The nanoparticle formulations may be a carbohydrate nanoparticle comprising a carbohydrate carrier and a RNA vaccine. As a non-limiting example, the carbohydrate carrier may include, but is not limited to, an anhydride-modified phytoglycogen or glycogen-type material, phytoglycogen octenyl succinate, phytoglycogen beta-dextrin, anhydride-modified phytoglycogen beta-dextrin. (See e.g., International Publication No. WO2012/109121, the content of which is herein incorporated by reference in its entirety).

Nanoparticle formulations of the present invention may be coated with a surfactant or polymer in order to improve the delivery of the particle. In some embodiments, the nanoparticle may be coated with a hydrophilic coating such as, but not limited to, PEG coatings and/or coatings that have a neutral surface charge. The hydrophilic coatings may help to deliver nanoparticles with larger payloads such as, but not limited to, RNA vaccines within the central nervous system. As a non-limiting example nanoparticles comprising a hydrophilic coating and methods of making such nanoparticles are described in U.S. Publication No. US2013/0183244, the content of which is herein incorporated by reference in its entirety.

In some embodiments, the lipid nanoparticles of the present invention may be hydrophilic polymer particles. Non-limiting examples of hydrophilic polymer particles and methods of making hydrophilic polymer particles are described in U.S. Publication No. US2013/0210991, the content of which is herein incorporated by reference in its entirety.

In other embodiments, the lipid nanoparticles of the present invention may be hydrophobic polymer particles.

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In some embodiments, the internal ester linkage may be located on either side of the saturated carbo.

In some embodiments, an immune response may be elicited by delivering a lipid nanoparticle which may include a nanospecies, a polymer and an immunogen. (U.S. Publication No. 2012/0189700 and International Publication No. WO2012/099805, each of which is herein incorporated by reference in its entirety).

The polymer may encapsulate the nanospecies or partially encapsulate the nanospecies. The immunogen may be a recombinant protein, a modified RNA and/or a polynucleotide described herein. In some embodiments, the lipid nanoparticle may be formulated for use in a vaccine such as, but not limited to, against a pathogen.

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosal tissue within seconds or within a few hours. Large polymeric nanoparticles (200 nm to 500 nm in diameter) which have been coated densely with a low molecular weight polyethylene glycol (PEG) diffused through mucus only 4 to 6-fold lower than the same particles diffusing in water (Lai et al. PNAS 2007 104(5):1482-487; Lai et al. Adv Drug Deliv Rev. 2009 61(2): 158-171; each of which is herein incorporated by reference in its entirety). The transport of nanoparticles may be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier may be made as described in U.S. Pat. No. 8,241,670 or International Publication No. WO2013/110028, the content of each of which is herein incorporated by reference in its entirety.

The lipid nanoparticle engineered to penetrate mucus may comprise a polymeric material (e.g., a polymeric core) and/or a polymer-vitamin conjugate and/or a tri-block co-polymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of biocompatible polymers are described in International Publication No. WO2013/116804, the content of which is herein incorporated by reference in its entirety. The polymeric material may additionally be irradiated. As a non-limiting example, the polymeric material may be gamma irradiated (see e.g., International Publication No. WO2012/082165, herein incorporated by reference in its entirety). Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D, L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), PEG-PLGA-PEG and trimethylene carbonate, polyvinylpyrrolidone. The lipid nanoparticle may be coated or associated with a copolymer such as, but not limited to, a block co-polymer (such as a branched polyether-polyamide block copolymer described in International Publication No. WO2013/012476, herein incorporated by reference in its entirety), and (poly(ethylene glycol))-(poly(propylene oxide))-(poly(ethylene glycol)) triblock copolymer (see e.g., U.S. Publication 2012/0121718, U.S. Publication 2010/0003337 and U.S. Pat. No. 8,263,665, each of which is herein incorporated by reference in its entirety). The co-polymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. *Angew. Chem. Int. Ed.* 2011 50:25972600, the content of which is herein incorporated by reference in its entirety). A non-limiting scalable method to produce nanoparticles which can penetrate human mucus is described by Xu et al. (see e.g., *J Control Release* 2013, 170(2):279-86, the content of which is herein incorporated by reference in its entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

In some embodiments, the RNA (e.g., mRNA) vaccine pharmaceutical compositions may be formulated in liposomes such as, but not limited to, DiLa2 liposomes (Marina Biotech, Bothell, WA), SMARTICLES® (Marina Biotech, Bothell, WA), neutral DOPC (1,2-dioleoyl-sn-glycero-3-phosphocholine) based liposomes (e.g., siRNA delivery for ovarian cancer (Landen et al. *Cancer Biology & Therapy* 2006 5(12)1708-1713, herein incorporated by reference in its entirety)) and hyaluronan-coated liposomes (Quiet Therapeutics, Israel).

In some embodiments, the RNA vaccines may be formulated in a lyophilized gel-phase liposomal composition as described in U.S. Publication No. US2012/0060293, herein incorporated by reference in its entirety.

The nanoparticle formulations may comprise a phosphate conjugate. The phosphate conjugate may increase in vivo circulation times and/or increase the targeted delivery of the nanoparticle. Phosphate conjugates for use with the present invention may be made by the methods described in International Publication No. WO2013/033438 or U.S. Publication No. 2013/0196948, the content of each of which is herein incorporated by reference in its entirety. As a non-limiting example, the phosphate conjugates may include a compound of any one of the formulas described in International Publication No. WO2013/033438, herein incorporated by reference in its entirety.

The nanoparticle formulation may comprise a polymer conjugate. The polymer conjugate may be a water soluble conjugate. The polymer conjugate may have a structure as described in U.S. Application No. 2013/0059360, the content of which is herein incorporated by reference in its entirety. In some aspects, polymer conjugates with the polynucleotides of the present invention may be made using the methods and/or segmented polymeric reagents described in U.S. Patent Application No. 2013/0072709, herein incorporated by reference in its entirety. In other aspects, the polymer conjugate may have pendant side groups comprising ring moieties such as, but not limited to, the polymer conjugates described in U.S. Publication No. US2013/0196948, the content of which is herein incorporated by reference in its entirety.

The nanoparticle formulations may comprise a conjugate to enhance the delivery of nanoparticles of the present invention in a subject. Further, the conjugate may inhibit phagocytic clearance of the nanoparticles in a subject. In some aspects, the conjugate may be a "self" peptide designed from the human membrane protein CD47 (e.g., the "self" particles described by Rodriguez et al. (*Science* 2013, 339, 971-975), herein incorporated by reference in its entirety). As shown by Rodriguez et al. the self peptides delayed macrophage-mediated clearance of nanoparticles which enhanced delivery of the nanoparticles. In other aspects, the conjugate may be the membrane protein CD47 (e.g., see Rodriguez et al. *Science* 2013, 339, 971-975, herein incorporated by reference in its entirety). Rodriguez et al. showed that, similarly to "self" peptides, CD47 can increase the circulating particle ratio in a subject as compared to scrambled peptides and PEG coated nanoparticles.

In some embodiments, the RNA vaccines of the present invention are formulated in nanoparticles that comprise a conjugate to enhance the delivery of the nanoparticles of the present disclosure in a subject. The conjugate may be the CD47 membrane or the conjugate may be derived from the CD47 membrane protein, such as the "self" peptide described previously. In other aspects the nanoparticle may comprise PEG and a conjugate of CD47 or a derivative thereof. In yet other aspects, the nanoparticle may comprise both the "self" peptide described above and the membrane protein CD47.

In other aspects, a "self" peptide and/or CD47 protein may be conjugated to a virus-like particle or pseudovirion, as described herein for delivery of the RNA vaccines of the present invention.

In other embodiments, RNA vaccine pharmaceutical compositions comprising the polynucleotides of the present invention and a conjugate which may have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in U.S. Publication No. US2013/0184443, the content of which is herein incorporated by reference in its entirety.

The nanoparticle formulations may be a carbohydrate nanoparticle comprising a carbohydrate carrier and a RNA (e.g., mRNA) vaccine. As a non-limiting example, the carbohydrate carrier may include, but is not limited to, an anhydride-modified phytoglycogen or glycogen-type material, phytoglycogen octenyl succinate, phytoglycogen beta-dextrin, anhydride-modified phytoglycogen beta-dextrin. (See e.g., International Publication No. WO2012/109121; the content of which is herein incorporated by reference in its entirety).

Nanoparticle formulations of the present invention may be coated with a surfactant or polymer in order to improve the delivery of the particle. In some embodiments, the nanoparticle may be coated with a hydrophilic coating such as, but not limited to, PEG coatings and/or coatings that have a neutral surface charge. The hydrophilic coatings may help to deliver nanoparticles with larger payloads such as, but not limited to, RNA vaccines within the central nervous system. As a non-limiting example nanoparticles comprising a hydrophilic coating and methods of making such nanoparticles are described in U.S. Publication No. US2013/0183244, the content of which is herein incorporated by reference in its entirety.

In some embodiments, the lipid nanoparticles of the present invention may be hydrophilic polymer particles. Non-limiting examples of hydrophilic polymer particles and methods of making hydrophilic polymer particles are described in U.S. Publication No. US2013/0210991, the content of which is herein incorporated by reference in its entirety.

In other embodiments, the lipid nanoparticles of the present invention may be hydrophobic polymer particles.

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In some embodiments, the internal ester linkage may be located on either side of the saturated carbo.

In some embodiments, an immune response may be elicited by delivering a lipid nanoparticle which may include a nanospecies, a polymer and an immunogen (U.S. Publication No. 2012/0189700 and International Publication No. WO2012/099805, each of which is herein incorporated by reference in its entirety).

The polymer may encapsulate the nanospecies or partially encapsulate the nanospecies. The immunogen may be a recombinant protein, a modified RNA and/or a polynucleotide described herein. In some embodiments, the lipid nanoparticle may be formulated for use in a vaccine such as, but not limited to, against a pathogen.

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosal tissue within seconds or within a few hours. Large polymeric nanoparticles (200 nm-500 nm in diameter) which have been coated densely with a low molecular weight polyethylene glycol (PEG) diffused through mucus only 4 to 6-fold lower than the same particles diffusing in water (Lai et al. *PNAS* 2007 104(5):1482-487; Lai et al. *Adv Drug Deliv Rev.* 2009 61(2): 158-171; each of which is herein incorporated by reference in its entirety). The transport of nanoparticles may be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier may be made as described in U.S. Pat. No. 8,241,670 or International Publication No. WO2013/110028, the content of each of which is herein incorporated by reference in its entirety.

The lipid nanoparticle engineered to penetrate mucus may comprise a polymeric material (i.e. a polymeric core) and/or a polymer-vitamin conjugate and/or a tri-block co-polymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of biocompatible polymers are described in International Publication No. WO2013/116804, the content of which is herein incorporated by reference in its entirety. The polymeric material may additionally be irradiated. As a non-limiting example, the polymeric material may be gamma irradiated (see e.g., International Publication No. WO2012/082165, herein incorporated by reference in its entirety). Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), PEG-PLGA-PEG and trimethylene carbonate, polyvinylpyrrolidone. The lipid nanoparticle may be coated or associated with a copolymer such as, but not limited to, a block co-polymer (such as a branched polyether-polyamide block copolymer described in International Publication No. WO2013/012476, herein incorporated by reference in its entirety), and (poly(ethylene glycol))-(poly(propylene oxide))-(poly(ethylene glycol)) triblock copolymer (see e.g., U.S. Publication 2012/0121718 and U.S. Publication 2010/0003337 and U.S. Pat. No. 8,263,665; each of which is herein incorporated by reference in its entirety). The copolymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. *Angew. Chem. Int.* Ed. 2011 50:25972600; the content of which is herein incorporated by reference in its entirety). A non-limiting scalable method to produce nanoparticles which can penetrate human mucus is described by Xu et al. (see e.g., *J Control Release* 2013, 170(2):279-86, the content of which is herein incorporated by reference in its entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

The lipid nanoparticle engineered to penetrate mucus may include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase. The surface altering agent may be embedded or enmeshed in the particle's surface or disposed (e.g., by coating, adsorption, covalent linkage, or other process) on the surface of the lipid nanoparticle (see e.g., U.S. Publication 2010/0215580 and U.S. Publication 2008/0166414 and US2013/0164343 the content of each of which is herein incorporated by reference in its entirety).

In some embodiments, the mucus penetrating lipid nanoparticles may comprise at least one polynucleotide described herein. The polynucleotide may be encapsulated in the lipid nanoparticle and/or disposed on the surface of the particle. The polynucleotide may be covalently coupled to the lipid nanoparticle. Formulations of mucus penetrating lipid nanoparticles may comprise a plurality of nanoparticles. Further, the formulations may contain particles which may interact with the mucus and alter the structural and/or adhesive properties of the surrounding mucus to decrease mucoadhesion which may increase the delivery of the mucus penetrating lipid nanoparticles to the mucosal tissue.

In other embodiments, the mucus penetrating lipid nanoparticles may be a hypotonic formulation comprising a mucosal penetration enhancing coating. The formulation may be hypotonic for the epithelium to which it is being delivered.

Non-limiting examples of hypotonic formulations may be found in International Publication No. WO2013/110028, the content of which is herein incorporated by reference in its entirety.

In some embodiments, in order to enhance the delivery through the mucosal barrier the RNA vaccine formulation may comprise or be a hypotonic solution. Hypotonic solutions were found to increase the rate at which mucoinert particles such as, but not limited to, mucus-penetrating particles, were able to reach the vaginal epithelial surface (see e.g., Ensign et al. *Biomaterials* 2013, 34(28):6922-9, the content of which is herein incorporated by reference in its entirety).

In some embodiments, the RNA vaccine is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, MA), and polyethylenimine (PEI) or protamine-based targeted and non-targeted delivery of nucleic acids (Aleku et al. *Cancer Res.* 2008 68:9788-9798; Strumberg et al. *Int J Clin Pharmacol Ther* 2012 50:76-78; Santel et al., *Gene Ther* 2006 13:1222-1234; Santel et al., *Gene Ther* 2006 13:1360-1370; Gutbier et al., *Pulm Pharmacol. Ther.* 2010 23:334-344; Kaufmann et al. *Microvasc Res* 2010 80:286-293; Weide et al. *J Immunother.* 2009 32:498-507; Weide et al. *J Immunother.* 2008 31:180-188; Pascolo, *Expert Opin. Biol. Ther.* 4:1285-1294; Fotin-Mleczek et al., 2011 *J. Immunother.* 34:1-15; Song et al., *Nature Biotechnol.* 2005, 23:709-717; Peer et al., *Proc Natl Acad Sci USA.* 2007 6; 104:4095-4100; deFougerolles *Hum Gene Ther.* 2008 19:125-132; each of which is incorporated herein by reference in its entirety).

In some embodiments, such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. *Mol Ther.* 2010 18:1357-1364; Song et al., *Nat Biotechnol.* 2005 23:709-717; Judge et al., *J Clin Invest.* 2009 119:661-673; Kaufmann et al., *Microvasc Res* 2010 80:286-293; Santel et al., *Gene Ther* 2006 13:1222-1234; Santel et al., *Gene Ther* 2006 13:1360-1370; Gutbier et al., *Pulm Pharmacol. Ther.* 2010 23:334-344; Basha et al., *Mol. Ther.* 2011 19:2186-2200; Fenske and Cullis, *Expert Opin Drug Deliv.* 2008 5:25-44; Peer et al., *Science.* 2008 319:627-630; Peer and Lieberman, *Gene Ther.* 2011 18:1127-1133; each of which is incorporated herein by reference in its entirety). One example of passive targeting of formulations to liver cells includes the DLin-DMA, DLin-KC2-DMA and DLin-MC3-DMA-based lipid nanoparticle formulations which have been shown to bind to apolipoprotein E and promote binding and uptake of these formulations into hepatocytes in vivo (Akinc et al. *Mol Ther.* 2010 18:1357-1364; herein incorporated by reference in its entirety). Formulations can also be selectively targeted through expression of different ligands on their surface as exemplified by, but not limited by, folate, transferrin, N-acetylgalactosamine (GalNAc), and antibody targeted approaches (Kolhatkar et al., *Curr Drug Discov Technol.* 2011 8:197-206; Musacchio and Torchilin, *Front Biosci.* 2011 16:1388-1412; Yu et al., *Mol Membr Biol.* 2010 27:286-298; Patil et al., *Crit Rev Ther Drug Carrier Syst.* 2008 25:1-61; Benoit et al., *Biomacromolecules.* 2011 12:2708-2714; Zhao et al., *Expert Opin Drug Deliv.* 2008 5:309-319; Akinc et al., *Mol Ther.* 2010 18:1357-1364; Srinivasan et al., *Methods Mol Biol.* 2012 820:105-116;

Ben-Arie et al., *Methods Mol Biol.* 2012 757:497-507; Peer 2010 *J Control Release.* 20:63-68; Peer et al., *Proc Natl Acad Sci USA.* 2007 104:4095-4100; Kim et al., *Methods Mol Biol.* 2011 721:339-353; Subramanya et al., *Mol Ther.* 2010 18:2028-2037; Song et al., *Nat Biotechnol.* 2005 23:709-717; Peer et al., *Science.* 2008 319:627-630; Peer and Lieberman, *Gene Ther.* 2011 18:1127-1133; each of which is incorporated herein by reference in its entirety).

In some embodiments, the RNA (e.g., mRNA) vaccine is formulated as a solid lipid nanoparticle. A solid lipid nanoparticle (SLN) may be spherical with an average diameter between to 1000 nm. SLN possess a solid lipid core matrix that can solubilize lipophilic molecules and may be stabilized with surfactants and/or emulsifiers. In other embodiments, the lipid nanoparticle may be a self-assembly lipid-polymer nanoparticle (see Zhang et al., *ACS Nano,* 2008, 2 (8), pp 1696-1702; the content of which is herein incorporated by reference in its entirety). As a non-limiting example, the SLN may be the SLN described in International Publication No. WO2013/105101, the content of which is herein incorporated by reference in its entirety. As another non-limiting example, the SLN may be made by the methods or processes described in International Publication No. WO2013/105101, the content of which is herein incorporated by reference in its entirety.

Liposomes, lipoplexes, or lipid nanoparticles may be used to improve the efficacy of polynucleotides directed protein production as these formulations may be able to increase cell transfection by the RNA vaccine; and/or increase the translation of encoded protein. One such example involves the use of lipid encapsulation to enable the effective systemic delivery of polyplex plasmid DNA (Heyes et al., *Mol Ther.* 2007 15:713-720; herein incorporated by reference in its entirety). The liposomes, lipoplexes, or lipid nanoparticles may also be used to increase the stability of the polynucleotide.

In some embodiments, the RNA (e.g., mRNA) vaccines of the present invention can be formulated for controlled release and/or targeted delivery. As used herein, "controlled release" refers to a pharmaceutical composition or compound release profile that conforms to a particular pattern of release to effect a therapeutic outcome. In some embodiments, the RNA vaccines may be encapsulated into a delivery agent described herein and/or known in the art for controlled release and/or targeted delivery. As used herein, the term "encapsulate" means to enclose, surround or encase. As it relates to the formulation of the compounds of the invention, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention may be enclosed, surrounded or encased within the delivery agent. "Partially encapsulation" means that less than 10, 10, 20, 30, 40 50 or less of the pharmaceutical composition or compound of the invention may be enclosed, surrounded or encased within the delivery agent. Advantageously, encapsulation may be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the present disclosure are encapsulated in the delivery agent.

In some embodiments, the controlled release formulation may include, but is not limited to, tri-block co-polymers. As a non-limiting example, the formulation may include two different types of tri-block co-polymers (International Pub. No. WO2012/131104 and WO2012/131106; the contents of each of which is herein incorporated by reference in its entirety).

In other embodiments, the RNA vaccines may be encapsulated into a lipid nanoparticle or a rapidly eliminated lipid nanoparticle and the lipid nanoparticles or a rapidly eliminated lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, FL), HYLENEX® (Halozyme Therapeutics, San Diego CA), surgical sealants such as fibrinogen polymers (Ethicon Inc. Cornelia, GA), TISSELL® (Baxter International, Inc. Deerfield, IL), PEG-based sealants, and COSEAL® (Baxter International, Inc Deerfield, IL).

In other embodiments, the lipid nanoparticle may be encapsulated into any polymer known in the art which may form a gel when injected into a subject. As another non-limiting example, the lipid nanoparticle may be encapsulated into a polymer matrix which may be biodegradable.

In some embodiments, the RNA vaccine formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In some embodiments, the RNA (e.g., mRNA) vaccine controlled release and/or targeted delivery formulation may comprise at least one degradable polyester which may contain polycationic side chains. Degradable polyesters include, but are not limited to, poly(serine ester), poly(L-lactide-co-L-lysine), poly(4-hydroxy-L-proline ester), and combinations thereof. In other embodiments, the degradable polyesters may include a PEG conjugation to form a PEGylated polymer.

In some embodiments, the RNA vaccine controlled release and/or targeted delivery formulation comprising at least one polynucleotide may comprise at least one PEG and/or PEG related polymer derivatives as described in U.S. Pat. No. 8,404,222, herein incorporated by reference in its entirety.

In other embodiments, the RNA vaccine controlled release delivery formulation comprising at least one polynucleotide may be the controlled release polymer system described in U.S. Publication No. 2013/0130348, herein incorporated by reference in its entirety.

In some embodiments, the RNA (e.g., mRNA)vaccines of the present invention may be encapsulated in a therapeutic nanoparticle, referred to herein as "therapeutic nanoparticle RNA vaccines." Therapeutic nanoparticles may be formulated by methods described herein and known in the art such as, but not limited to, International Publication Nos. WO2010/005740, WO2010/030763, WO2010/005721, WO2010/005723, WO2012/054923, U.S. Publication Nos. US2011/0262491, US2010/0104645, US2010/0087337, US2010/0068285, US2011/0274759, US2010/0068286, US2012/0288541, US2013/0123351 and US2013/0230567 and U.S. Pat. Nos. 8,206,747, 8,293,276, 8,318,208 and 8,318,211, the content of each of which is herein incorporated by reference in its entirety. In other embodiments, therapeutic polymer nanoparticles may be identified by the methods described in U.S. Publication No. US2012/0140790, the content of which is herein incorporated by reference in its entirety.

In some embodiments, the therapeutic nanoparticle RNA vaccine may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the polynucleotides of the present invention (see International Publication No. 2010/075072 and U.S. Publication Nos. US2010/0216804, US2011/0217377 and US2012/0201859, each of which is herein incorporated by reference in its entirety). In another non-limiting example, the sustained release formulation may comprise agents which permit persistent bioavailability such as, but not limited to, crystals, macromolecular gels and/or particulate suspensions (see U.S. Publication No. US2013/0150295, the content of which is herein incorporated by reference in its entirety).

In some embodiments, the therapeutic nanoparticle RNA vaccines may be formulated to be target specific. As a non-limiting example, the therapeutic nanoparticles may include a corticosteroid (see International Publication No. WO2011/084518, herein incorporated by reference in its entirety). As a non-limiting example, the therapeutic nanoparticles may be formulated in nanoparticles described in International Publication Nos. WO2008/121949, WO2010/005726, WO2010/005725, WO2011/084521 and U.S. Publication Nos. US2010/0069426, US2012/0004293 and US2010/0104655, each of which is herein incorporated by reference in its entirety.

In some embodiments, the nanoparticles of the present invention may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In some embodiments, the therapeutic nanoparticle comprises a diblock copolymer. In some embodiments, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof. In yet other embodiments, the diblock copolymer may be a high-X diblock copolymer such as those described in International Publication No. WO2013/120052, the content of which is herein incorporated by reference in its entirety.

As a non-limiting example, the therapeutic nanoparticle comprises a PLGA-PEG block copolymer (see U.S. Publication No. US2012/0004293 and U.S. Pat. No. 8,236,330, each of which is herein incorporated by reference in its entirety). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012/166923, the content of each of which is herein incorporated by reference in its entirety). In yet another non-limiting example, the therapeutic nanoparticle is a stealth nanoparticle or a target-specific stealth nanoparticle as described in U.S. Publication No. 2013/0172406, the content of which is herein incorporated by reference in its entirety.

In some embodiments, the therapeutic nanoparticle may comprise a multiblock copolymer (see e.g., U.S. Pat. Nos. 8,263,665 and 8,287,910 and U.S. Publication No. 2013/0195987, the content of each of which is herein incorporated by reference in its entirety).

In yet another non-limiting example, the lipid nanoparticle comprises the block copolymer PEG-PLGA-PEG (see e.g., the thermosensitive hydrogel (PEG-PLGA-PEG) used as a TGF-beta1 gene delivery vehicle in Lee et al. "Thermosensitive Hydrogel as a TGF-β1 Gene Delivery Vehicle Enhances Diabetic Wound Healing." *Pharmaceutical Research*, 2003 20(12): 1995-2000; and used as a controlled gene delivery system in Li et al. "Controlled Gene Delivery System Based on Thermosensitive Biodegradable Hydrogel" *Pharmaceutical Research* 2003 20(6):884-888; and Chang et al., "Non-ionic amphiphilic biodegradable PEG-PLGA-PEG copolymer enhances gene delivery efficiency in rat skeletal muscle." *J Controlled Release*. 2007 118:245-253; each of which is herein incorporated by reference in its entirety). The RNA (e.g., mRNA) vaccines of the present disclosure may be formulated in lipid nanoparticles comprising the PEG-PLGA-PEG block copolymer.

In some embodiments, the block copolymers described herein may be included in a polyion complex comprising a non-polymeric micelle and the block copolymer. (see e.g., U.S. Publication No. 2012/0076836, herein incorporated by reference in its entirety).

In some embodiments, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly (acrylic acid), poly(methacrylic acid), polycyanoacrylates and combinations thereof.

In some embodiments, the therapeutic nanoparticles may comprise at least one poly(vinyl ester) polymer. The poly (vinyl ester) polymer may be a copolymer such as a random copolymer.

As a non-limiting example, the random copolymer may have a structure such as those described in International Publication No. WO2013/032829 or U.S. Publication No. 2013/0121954, the content of which is herein incorporated by reference in its entirety. In some aspects, the poly(vinyl ester) polymers may be conjugated to the polynucleotides described herein.

In some embodiments, the therapeutic nanoparticle may comprise at least one diblock copolymer. The diblock copolymer may be, but it not limited to, a poly(lactic) acid-poly (ethylene)glycol copolymer (see e.g., International Publication No. WO2013/044219; herein incorporated by reference in its entirety). As a non-limiting example, the therapeutic nanoparticle may be used to treat cancer (see International publication No. WO2013/044219, herein incorporated by reference in its entirety).

In some embodiments, the therapeutic nanoparticles may comprise at least one cationic polymer described herein and/or known in the art.

In some embodiments, the therapeutic nanoparticles may comprise at least one amine-containing polymer such as, but not limited to polylysine, polyethyleneimine, poly(amido-amine) dendrimers, poly(beta-amino esters) (see e.g., U.S. Pat. No. 8,287,849, herein incorporated by reference in its entirety) and combinations thereof. In other embodiments, the nanoparticles described herein may comprise an amine cationic lipid such as those described in International Publication No. WO2013/059496, the content of which is herein incorporated by reference in its entirety. In some aspects the cationic lipids may have an amino-amine or an amino-amide moiety.

In some embodiments, the therapeutic nanoparticles may comprise at least one degradable polyester, which may contain polycationic side chains. Degradable polyesters include, but are not limited to, poly(serine ester), poly(L-lactide-co-L-lysine), poly(4-hydroxy-L-proline ester), and combinations thereof. In other embodiments, the degradable polyesters may include a PEG conjugation to form a PEGy-lated polymer.

In other embodiments, the therapeutic nanoparticle may include a conjugation of at least one targeting ligand. The targeting ligand may be any ligand known in the art such as, but not limited to, a monoclonal antibody (Kirpotin et al, *Cancer Res.* 2006 66:6732-6740, herein incorporated by reference in its entirety).

In some embodiments, the therapeutic nanoparticle may be formulated in an aqueous solution, which may be used to target cancer (see International Publication No. WO2011/084513 and U.S. Publication No. 2011/0294717, each of which is herein incorporated by reference in its entirety).

In some embodiments, the therapeutic nanoparticle RNA vaccines, e.g., therapeutic nanoparticles comprising at least one RNA vaccine may be formulated using the methods described by Podobinski et al in U.S. Pat. No. 8,404,799, the content of which is herein incorporated by reference in its entirety.

In some embodiments, the RNA (e.g., mRNA) vaccines may be encapsulated in, linked to and/or associated with synthetic nanocarriers. Synthetic nanocarriers include, but are not limited to, those described in International Publication Nos. WO2010/005740, WO2012/149454 and WO2013/019669, and U.S. Publication Nos. US2011/0262491, US2010/0104645, US2010/0087337 and US2012/0244222, each of which is herein incorporated by reference in its entirety. The synthetic nanocarriers may be formulated using methods known in the art and/or described herein. As a non-limiting example, the synthetic nanocarriers may be formulated by the methods described in International Publication Nos. WO2010/005740, WO2010/030763 and WO2012/13501, and U.S. Publication Nos. US2011/0262491, US2010/0104645, US2010/0087337 and US2012/024422, each of which is herein incorporated by reference in its entirety. In other embodiments, the synthetic nanocarrier formulations may be lyophilized by methods described in International Publication No. WO2011/072218 and U.S. Pat. No. 8,211,473, the content of each of which is herein incorporated by reference in its entirety. In yet other embodiments, formulations of the present invention, including, but not limited to, synthetic nanocarriers, may be lyophilized or reconstituted by the methods described in U.S. Publication No. 2013/0230568, the content of which is herein incorporated by reference in its entirety.

In some embodiments, the synthetic nanocarriers may contain reactive groups to release the polynucleotides described herein (see International Publication No. WO2012/092552 and U.S. Publication No. US2012/0171229, each of which is herein incorporated by reference in its entirety).

In some embodiments, the synthetic nanocarriers may contain an immunostimulatory agent to enhance the immune response from delivery of the synthetic nanocarrier. As a non-limiting example, the synthetic nanocarrier may comprise a Th1 immunostimulatory agent which may enhance a Th1-based response of the immune system (see International Publication No. WO2010/123569 and U.S. Publication No. 2011/0223201, each of which is herein incorporated by reference in its entirety).

In some embodiments, the synthetic nanocarriers may be formulated for targeted release. In some embodiments, the synthetic nanocarrier is formulated to release the polynucleotides at a specified pH and/or after a desired time interval. As a non-limiting example, the synthetic nanoparticle may be formulated to release the RNA vaccines after 24 hours and/or at a pH of 4.5 (see International Publication Nos. WO2010/138193 and WO2010/138194 and U.S. Publication Nos. US2011/0020388 and US2011/0027217, each of which is herein incorporated by reference in their entireties).

In some embodiments, the synthetic nanocarriers may be formulated for controlled and/or sustained release of the polynucleotides described herein. As a non-limiting example, the synthetic nanocarriers for sustained release may be formulated by methods known in the art, described herein and/or as described in International Publication No. WO2010/138192 and U.S. Publication No. 2010/0303850, each of which is herein incorporated by reference in its entirety.

In some embodiments, the RNA vaccine may be formulated for controlled and/or sustained release wherein the formulation comprises at least one polymer that is a crystalline side chain (CYSC) polymer. CYSC polymers are described in U.S. Pat. No. 8,399,007, herein incorporated by reference in its entirety.

In some embodiments, the synthetic nanocarrier may be formulated for use as a vaccine. In some embodiments, the synthetic nanocarrier may encapsulate at least one polynucleotide which encode at least one antigen. As a non-limiting example, the synthetic nanocarrier may include at least one antigen and an excipient for a vaccine dosage form (see International Publication No. WO2011/150264 and U.S. Publication No. 2011/0293723, each of which is herein incorporated by reference in its entirety). As another non-limiting example, a vaccine dosage form may include at least two synthetic nanocarriers with the same or different antigens and an excipient (see International Publication No. WO2011/150249 and U.S. Publication No. 2011/0293701, each of which is herein incorporated by reference in its entirety). The vaccine dosage form may be selected by methods described herein, known in the art and/or described in International Publication No. WO2011/150258 and U.S. Publication No. US2012/0027806, each of which is herein incorporated by reference in its entirety).

In some embodiments, the synthetic nanocarrier may comprise at least one polynucleotide which encodes at least one adjuvant. As non-limiting example, the adjuvant may comprise dimethyldioctadecylammonium-bromide, dimethyldioctadecylammonium-chloride, dimethyldioctadecylammonium-phosphate or dimethyldioctadecylammonium-acetate (DDA) and an apolar fraction or part of said apolar fraction of a total lipid extract of a *mycobacterium* (see e.g., U.S. Pat. No. 8,241,610; herein incorporated by reference in its entirety). In other embodiments, the synthetic nanocarrier may comprise at least one polynucleotide and an adjuvant. As a non-limiting example, the synthetic nanocarrier comprising and adjuvant may be formulated by the methods described in International Publication No. WO2011/150240 and U.S. Publication No. US2011/0293700, each of which is herein incorporated by reference in its entirety.

In some embodiments, the synthetic nanocarrier may encapsulate at least one polynucleotide which encodes a peptide, fragment or region from a virus. As a non-limiting example, the synthetic nanocarrier may include, but is not limited to, the nanocarriers described in International Publication Nos. WO2012/024621, WO2012/02629, WO2012/024632 and U.S. Publication No. US2012/0064110, US2012/0058153 and US2012/0058154, each of which is herein incorporated by reference in its entirety.

In some embodiments, the synthetic nanocarrier may be coupled to a polynucleotide which may be able to trigger a humoral and/or cytotoxic T lymphocyte (CTL) response (See e.g., International Publication No. WO2013/019669, herein incorporated by reference in its entirety).

In some embodiments, the RNA vaccine may be encapsulated in, linked to and/or associated with zwitterionic lipids. Non-limiting examples of zwitterionic lipids and methods of using zwitterionic lipids are described in U.S. Publication No. 2013/0216607, the content of which is herein incorporated by reference in its entirety. In some aspects, the zwitterionic lipids may be used in the liposomes and lipid nanoparticles described herein.

In some embodiments, the RNA vaccine may be formulated in colloid nanocarriers as described in U.S. Publication No. 2013/0197100, the content of which is herein incorporated by reference in its entirety.

In some embodiments, the nanoparticle may be optimized for oral administration. The nanoparticle may comprise at least one cationic biopolymer such as, but not limited to, chitosan or a derivative thereof. As a non-limiting example, the nanoparticle may be formulated by the methods described in U.S. Publication No. 2012/0282343; herein incorporated by reference in its entirety.

In some embodiments, LNPs comprise the lipid KL52 (an amino-lipid disclosed in U.S. Application Publication No. 2012/0295832 expressly incorporated herein by reference in its entirety). Activity and/or safety (as measured by examining one or more of ALT/AST, white blood cell count and cytokine induction) of LNP administration may be improved by incorporation of such lipids. LNPs comprising KL52 may be administered intravenously and/or in one or more doses. In some embodiments, administration of LNPs comprising KL52 results in equal or improved mRNA and/or protein expression as compared to LNPs comprising MC3.

In some embodiments, RNA vaccine may be delivered using smaller LNPs. Such particles may comprise a diameter from below 0.1 μm up to 100 nm such as, but not limited to, less than 0.1 μm, less than 1.0 μm, less than 5 μm, less than 10 μm, less than 15 μm, less than 20 μm, less than 25 μm, less than 30 μm, less than 35 μm, less than 40 μm, less than 50 μm, less than 55 μm, less than 60 μm, less than 65 μm, less than 70 μm, less than 75 μm, less than 80 μm, less than 85 μm, less than 90 μm, less than 95 μm, less than 100 μm, less than 125 μm, less than 150 μm, less than 175 μm, less than 200 μm, less than 225 μm, less than 250 μm, less than 275 μm, less than 300 μm, less than 325 μm, less than 350 μm, less than 375 μm, less than 400 μm, less than 425 μm, less than 450 μm, less than 475 μm, less than 500 μm, less than 525 μm, less than 550 μm, less than 575 μm, less than 600 μm, less than 625 μm, less than 650 μm, less than 675 μm, less than 700 μm, less than 725 μm, less than 750 μm, less than 775 μm, less than 800 μm, less than 825 μm, less than 850 μm, less than 875 μm, less than 900 μm, less than 925 μm, less than 950 μm, or less than 975 μm.

In other embodiments, RNA (e.g., mRNA) vaccines may be delivered using smaller LNPs which may comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nm, from about 20 to about 50 nm, from about 30 to about 50 nm, from about 40 to about 50 nm, from about 20 to about 60 nm, from about 30 to about 60 nm, from about to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

In some embodiments, such LNPs are synthesized using methods comprising microfluidic mixers. Exemplary microfluidic mixers may include, but are not limited to a slit interdigital micromixer including, but not limited to those manufactured by Microinnova (Allerheiligen bei Wildon, Austria) and/or a staggered herringbone micromixer (SHM) (Zhigaltsev, I. V. et al., Bottom-up design and synthesis of limit size lipid nanoparticle systems with aqueous and triglyceride cores using millisecond microfluidic mixing have been published (Langmuir. 2012. 28:3633-40; Belliveau, N. M. et al., Microfluidic synthesis of highly potent limit-size lipid nanoparticles for in vivo delivery of siRNA. *Molecular Therapy-Nucleic Acids*. 2012. 1:e37; Chen, D. et al., Rapid discovery of potent siRNA-containing lipid nanoparticles enabled by controlled microfluidic formulation. *J Am Chem Soc*. 2012. 134(16):6948-51; each of which is herein incorporated by reference in its entirety).

In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method may also comprise a surface for fluid mixing wherein the surface changes orientations during fluid cycling. Methods of generating LNPs using SHM include those disclosed in U.S. Application Publication Nos. 2004/0262223 and 2012/0276209, each of which is expressly incorporated herein by reference in their entirety.

In some embodiments, the RNA vaccine of the present invention may be formulated in lipid nanoparticles created using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet (IJMM) from the Institut für Mikrotechnik Mainz GmbH, Mainz Germany).

In some embodiments, the RNA (e.g., mRNA) vaccines of the present disclosure may be formulated in lipid nanoparticles created using microfluidic technology (see Whitesides, George M. The Origins and the Future of Microfluidics. *Nature,* 2006 442: 368-373; and Abraham et al. Chaotic Mixer for Microchannels. *Science,* 2002 295: 647-651; each of which is herein incorporated by reference in its entirety). As a non-limiting example, controlled microfluidic formulation includes a passive method for mixing streams of steady pressure-driven flows in micro channels at a low Reynolds number (see e.g., Abraham et al. Chaotic Mixer for Microchannels. *Science,* 2002 295: 647651; which is herein incorporated by reference in its entirety).

In some embodiments, the RNA (e.g., mRNA) vaccines of the present invention may be formulated in lipid nanoparticles created using a micromixer chip such as, but not limited to, those from Harvard Apparatus (Holliston, MA) or Dolomite Microfluidics (Royston, UK). A micromixer chip can be used for rapid mixing of two or more fluid streams with a split and recombine mechanism.

In some embodiments, the RNA (e.g., mRNA) vaccines of the invention may be formulated for delivery using the drug encapsulating microspheres described in International Publication No. WO2013/063468 or U.S. Pat. No. 8,440,614, each of which is herein incorporated by reference in its entirety. The microspheres may comprise a compound of the formula (I), (II), (III), (IV), (V) or (VI) as described in International Publication No. WO2013/063468, the content of which is herein incorporated by reference in its entirety. In other aspects, the amino acid, peptide, polypeptide, lipids (APPL) are useful in delivering the RNA vaccines of the invention to cells (see International Publication No. WO2013/063468, the contents of which is herein incorporated by reference in its entirety).

In some embodiments, the RNA (e.g., mRNA) vaccines of the present disclosure may be formulated in lipid nanoparticles having a diameter from about 10 to about 100 nm such as, but not limited to, about 10 to about 20 nm, about 10 to about 30 nm, about 10 to about 40 nm, about to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles may have a diameter from about 10 to 500 nm.

In some embodiments, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some aspects, the lipid nanoparticle may be a limit size lipid nanoparticle described in International Publication No. WO2013/059922, the content of which is herein incorporated by reference in its entirety. The limit size lipid nanoparticle may comprise a lipid bilayer surrounding an aqueous core or a hydrophobic core; where the lipid bilayer may comprise a phospholipid such as, but not limited to, diacylphosphatidylcholine, a diacylphosphatidylethanolamine, a ceramide, a sphingomyelin, a dihydrosphingomyelin, a cephalin, a cerebroside, a C8-C20 fatty acid diacylphophatidylcholine, and 1-palmitoyl-2-oleoyl phosphatidylcholine (POPC). In other aspects the limit size lipid nanoparticle may comprise a polyethylene glycol-lipid such as, but not limited to, DLPE-PEG, DMPE-PEG, DPPC-PEG and DSPE-PEG.

In some embodiments, the RNA vaccines may be delivered, localized and/or concentrated in a specific location using the delivery methods described in International Publication No. WO2013063530, the content of which is herein incorporated by reference in its entirety. As a non-limiting example, a subject may be administered an empty polymeric particle prior to, simultaneously with or after delivering the RNA vaccines to the subject. The empty polymeric particle undergoes a change in volume once in contact with the subject and becomes lodged, embedded, immobilized or entrapped at a specific location in the subject.

In some embodiments, the RNA vaccines may be formulated in an active substance release system (see e.g., U.S. Publication No. US2013/0102545, the contents of which is herein incorporated by reference in its entirety). The active substance release system may comprise 1) at least one nanoparticle bonded to an oligonucleotide inhibitor strand which is hybridized with a catalytically active nucleic acid and 2) a compound bonded to at least one substrate molecule bonded to a therapeutically active substance (e.g., polynucleotides described herein), where the therapeutically active substance is released by the cleavage of the substrate molecule by the catalytically active nucleic acid.

In some embodiments, the RNA (e.g., mRNA) vaccines may be formulated in a nanoparticle comprising an inner core comprising a non-cellular material and an outer surface comprising a cellular membrane. The cellular membrane may be derived from a cell or a membrane derived from a virus. As a non-limiting example, the nanoparticle may be made by the methods described in International Publication No. WO2013/052167, herein incorporated by reference in its entirety. As another non-limiting example, the nanoparticle described in International Publication No. WO2013/052167, herein incorporated by reference in its entirety, may be used to deliver the RNA vaccines described herein.

In some embodiments, the RNA vaccines may be formulated in porous nanoparticle-supported lipid bilayers (protocells). Protocells are described in International Publication No. WO2013/056132, the content of which is herein incorporated by reference in its entirety.

In some embodiments, the RNA vaccines described herein may be formulated in polymeric nanoparticles as described in or made by the methods described in U.S. Pat. Nos. 8,420,123 and 8,518,963 and European Patent No. EP2073848B1, the contents of each of which are herein incorporated by reference in their entirety. As a non-limiting example, the polymeric nanoparticle may have a high glass transition temperature such as the nanoparticles described in or nanoparticles made by the methods described in U.S. Pat.

No. 8,518,963, the content of which is herein incorporated by reference in its entirety. As another non-limiting example, the polymer nanoparticle for oral and parenteral formulations may be made by the methods described in European Patent No. EP2073848B1, the content of which is herein incorporated by reference in its entirety.

In other embodiments, the RNA (e.g., mRNA) vaccines described herein may be formulated in nanoparticles used in imaging. The nanoparticles may be liposome nanoparticles such as those described in U.S. Publication No. 2013/0129636, herein incorporated by reference in its entirety. As a non-limiting example, the liposome may comprise gadolinium(III)2-{4,7-bis-carboxymethyl-10-[(N,N-distearylamidomethyl-N'-amido-methyl]-1,4,7,10-tetra-azacyclododec-1-yl}-acetic acid and a neutral, fully saturated phospholipid component (see e.g., U.S. Publication No US2013/0129636, the contents of which is herein incorporated by reference in its entirety).

In some embodiments, the nanoparticles which may be used in the present invention are formed by the methods described in U.S. Patent Application No. 2013/0130348, the contents of which is herein incorporated by reference in its entirety.

The nanoparticles of the present invention may further include nutrients such as, but not limited to, those which deficiencies can lead to health hazards from anemia to neural tube defects (see e.g., the nanoparticles described in International Patent Publication No. WO2013/072929, the contents of which is herein incorporated by reference in its entirety). As a non-limiting example, the nutrient may be iron in the form of ferrous, ferric salts or elemental iron, iodine, folic acid, vitamins or micronutrients.

In some embodiments, the RNA (e.g., mRNA) vaccines of the present invention may be formulated in a swellable nanoparticle. The swellable nanoparticle may be, but is not limited to, those described in U.S. Pat. No. 8,440,231, the contents of which is herein incorporated by reference in its entirety. As a non-limiting embodiment, the swellable nanoparticle may be used for delivery of the RNA (e.g., mRNA) vaccines of the present invention to the pulmonary system (see e.g., U.S. Pat. No. 8,440,231, the contents of which is herein incorporated by reference in its entirety).

The RNA (e.g., mRNA) vaccines of the present invention may be formulated in polyanhydride nanoparticles such as, but not limited to, those described in U.S. Pat. No. 8,449,916, the contents of which is herein incorporated by reference in its entirety. The nanoparticles and microparticles of the present invention may be geometrically engineered to modulate macrophage and/or the immune response. In some aspects, the geometrically engineered particles may have varied shapes, sizes and/or surface charges in order to incorporated the polynucleotides of the present invention for targeted delivery such as, but not limited to, pulmonary delivery (see e.g., International Publication No. WO2013/082111, the content of which is herein incorporated by reference in its entirety). Other physical features the geometrically engineering particles may have include, but are not limited to, fenestrations, angled arms, asymmetry and surface roughness, charge which can alter the interactions with cells and tissues. As a non-limiting example, nanoparticles of the present invention may be made by the methods described in International Publication No. WO2013/082111, the contents of which is herein incorporated by reference in its entirety.

In some embodiments, the nanoparticles of the present invention may be water soluble nanoparticles such as, but not limited to, those described in International Publication No. WO2013/090601, the content of which is herein incorporated by reference in its entirety. The nanoparticles may be inorganic nanoparticles which have a compact and zwitterionic ligand in order to exhibit good water solubility. The nanoparticles may also have small hydrodynamic diameters (HD), stability with respect to time, pH, and salinity and a low level of non-specific protein binding.

In some embodiments the nanoparticles of the present invention may be developed by the methods described in U.S. Publication No. US2013/0172406, the content of which is herein incorporated by reference in its entirety.

In some embodiments, the nanoparticles of the present invention are stealth nanoparticles or target-specific stealth nanoparticles such as, but not limited to, those described in U.S. Publication No. 2013/0172406, the content of which is herein incorporated by reference in its entirety. The nanoparticles of the present invention may be made by the methods described in U.S. Publication No. 2013/0172406, the content of which is herein incorporated by reference in its entirety.

In other embodiments, the stealth or target-specific stealth nanoparticles may comprise a polymeric matrix. The polymeric matrix may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates or combinations thereof.

In some embodiments, the nanoparticle may be a nanoparticle-nucleic acid hybrid structure having a high density nucleic acid layer. As a non-limiting example, the nanoparticle-nucleic acid hybrid structure may made by the methods described in U.S. Publication No. 2013/0171646, the content of which is herein incorporated by reference in its entirety. The nanoparticle may comprise a nucleic acid such as, but not limited to, polynucleotides described herein and/or known in the art.

At least one of the nanoparticles of the present invention may be embedded in in the core a nanostructure or coated with a low density porous 3-D structure or coating which is capable of carrying or associating with at least one payload within or on the surface of the nanostructure. Non-limiting examples of the nanostructures comprising at least one nanoparticle are described in International Publication No. WO2013/123523, the content of which is herein incorporated by reference in its entirety.

In some embodiments, a nanoparticle comprises compounds of Formula (I):

$$
\tag{I}
$$

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —CQ$(R)_2$, and unsubstituted $C_{1-6}$ alkyl, where Q is selected from a carbocycle, heterocycle, —OR, —$O(CH_2)_nN$ $(R)_2$, —C(O)OR, —OC(O)R, —$CX_3$, —$CX_2H$, —$CXH_2$, —CN, —$N(R)_2$, —C(O)$N(R)_2$, —N(R)C(O) R, —N(R)S(O)$_2$R, —N(R)C(O)$N(R)_2$, —N(R)C(S)N $(R)_2$, —$N(R)R_8$, —$O(CH_2)_nOR$, —N(R)C($=NR_9$)N $(R)_2$, —N(R)C($=CHR_9$)$N(R)_2$, —OC(O)$N(R)_2$, —N(R)C(O)OR, —N(OR)C(O)R, —N(OR)S(O)$_2$R, —N(OR)C(O)OR, —N(OR)C(O)$N(R)_2$, —N(OR)C (S)$N(R)_2$, —N(OR)C($=NR_9$)$N(R)_2$, —N(OR)C ($=CHR_9$)$N(R)_2$, —C($=NR_9$)$N(R)_2$, —C($=NR_9$)R, —C(O)N(R)OR, and —C(R)$N(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH (OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$$N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_nQ$, —$(CH_2)_nCHQR$, —CHQR, or —CQ$(R)_2$, then (i) Q is not —$N(R)_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)

R, —$CX_3$, —$CX_2H$, —$CXH_2$, —CN, —C(O)$N(R)_2$, —N(R)C(O)R, —N(R)S(O)$_2$R, —N(R)C(O)$N(R)_2$, —N(R)C(S)$N(R)_2$, —CRN(R)$_2$C(O)OR, —$N(R)R_8$, —$O(CH_2)_nOR$, —N(R)C($=NR_9$)$N(R)_2$, —N(R)C ($=CHR_9$)$N(R)_2$, —OC(O)$N(R)_2$, —N(R)C(O)OR, —N(OR)C(O)R, —N(OR)S(O)$_2$R, —N(OR)C(O)OR, —N(OR)C(O)$N(R)_2$, —N(OR)C(S)$N(R)_2$, —N(OR)C ($=NR_9$)$N(R)_2$, —N(OR)C($=CHR_9$)$N(R)_2$, —C($=NR_9$)$N(R)_2$, —C($=NR_9$)R, —C(O)N(R)OR, and a 5- to 14-membered heterocycloalkyl having one or more heteroatoms selected from N, O, and S which is substituted with one or more substituents selected from oxo ($=$O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH (OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$$N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —CQ$(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC (O)R, —$CX_3$, —$CX_2H$, —$CXH_2$, —CN, —C(O)$N(R)_2$, —N(R)C(O)R, —N(R)S(O)$_2$R, —N(R)C(O)N $(R)_2$, —N(R)C(S)$N(R)_2$, —CRN(R)$_2$C(O)OR, —N(R)$R_8$, —$O(CH_2)_nOR$, —N(R)C($=NR_9$)$N(R)_2$, —N(R)C ($=CHR_9$)$N(R)_2$, —OC(O)$N(R)_2$, —N(R)C(O)OR, —N(OR)C(O)R, —N(OR)S(O)$_2$R, —N(OR)C(O)OR, —N(OR)C(O)$N(R)_2$, —N(OR)C(S)$N(R)_2$, —N(OR)C $(=NR_9)N(R)_2$, —N(OR)C(=CHR_9)N(R)_2, —C(=NR_9)R, —C(O)N(R)OR, and —C(=NR_9)N(R)_2, and each n is independently selected from 1, 2, 3, 4, and 5; and when Q is a 5- to 14-membered heterocycle and (i) $R_4$ is —(CH_2)_nQ in which n is 1 or 2, or (ii) $R_4$ is —(CH_2)·CHQR in which n is 1, or (iii) $R_4$ is-CHQR, and —CQ(R)_2, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)_2—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO_2, $C_{1-6}$ alkyl, —OR, —S(O)_2R, —S(O)_2N(R)_2, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH_2)_nQ, —(CH_2)_nCHQR, —CHQR, —CQ(R)_2, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH_2)_nN(R)_2, —C(O)OR, —OC(O)R, —CX_3, —CX_2H, —CXH_2, —CN, —C(O)N(R)_2, —N(R)C(O)R, —N(R)S(O)_2R, —N(R)C(O)N(R)_2, —N(R)C(S)N(R)_2, —CRN(R)_2C(O)OR, —N(R)R_8, —O(CH_2)_nOR, —N(R)C(=NR_9)N(R)_2, —N(R)C(=CHR_9)N(R)_2, —OC(O)N(R)_2, —N(R)C(O)OR, —N(OR)C(O)R, —N(OR)S(O)_2R, —N(OR)C(O)OR, —N(OR)C(O)N(R)_2, —N(OR)C(S)N(R)_2, —N(OR)C(=NR_9)N(R)_2, —N(OR)C(=CHR_9)N(R)_2, —C(=NR_9)R, —C(O)N(R)OR, and —C(=NR_9)N(R)_2, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)_2—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO_2, $C_{1-6}$ alkyl, —OR, —S(O)_2R, —S(O)_2N(R)_2, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —(CH_2)_nQ or —(CH_2)·CHQR, where Q is —N(R)_2, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)_2—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR″, —YR″, and —R″M'R';

$R_2$ and $R_3$ are independently selected from the group consisting of $C_{1-14}$ alkyl, $C_{2-14}$ alkenyl, —R*YR″, —YR″, and —R*OR″, or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —CQ(R)$_2$, where Q is —N(R)$_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR″, —YR″, and H;

each R″ is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

(IA)

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

(II)

or a salt or isomer thereof, wherein 1 is selected from 1, 2, 3, 4, and 5; $M_1$ is a bond or M'; $R_4$ is unsubstituted $C_{1-3}$ alkyl, or —$(CH_2)_n$Q, in which n is 2, 3, or 4, and Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (IIe):

(IIa)

(IIb)

(IIc)

, or (IIe)

or a salt or isomer thereof, wherein $R_4$ is as described herein.

In some embodiments, a subset of compounds of Formula (I) includes those of Formula (IId):

(IId)

or a salt or isomer thereof, wherein n is 2, 3, or 4; and m, R', R", and $R_2$ through R are as described herein. For example, each of $R_2$ and $R_3$ may be independently selected from the group consisting of $C_{5-14}$ alkyl and $C_{5-14}$ alkenyl.

In some embodiments, the compound of Formula (I) is selected from the group consisting of:

(Compound 1)

(Compound 2)

(Compound 3)

(Compound 4)

(Compound 5)

(Compound 6)

(Compound 7)

-continued (Compound 8)

(Compound 9)

(Compound 10)

(Compound 11)

(Compound 12)

(Compound 13)

(Compound 14)

(Compound 15)

-continued (Compound 16)

(Compound 17)

(Compound 18)

(Compound 19)

(Compound 20)

(Compound 21)

(Compound 22)

-continued (Compound 23)

(Compound 24)

(Compound 25)

(Compound 26)

(Compound 27)

(Compound 28)

(Compound 29)

-continued (Compound 30)

(Compound 31)

(Compound 32)

(Compound 33)

(Compound 34)

(Compound 35)

(Compound 36)

-continued (Compound 37)

(Compound 38)

(Compound 39)

(Compound 40)

(Compound 41)

(Compound 42)

(Compound 43)

-continued (Compound 44)

(Compound 45)

(Compound 46)

(Compound 47)

(Compound 48)

(Compound 49)

(Compound 50)

-continued (Compound 51)

(Compound 52)

(Compound 53)

(Compound 54)

(Compound 55)

(Compound 56)

(Compound 57)

-continued (Compound 58)

(Compound 59)

(Compound 60)

(Compound 61)

In further embodiments, the compound of Formula (I) is selected from the group consisting of:

(Compound 62)

(Compound 63)

115                                                             116

-continued (Compound 64)

In some embodiments, the compound of Formula (I) is selected from the group consisting of:

(Compound 65)

(Compound 66)

(Compound 67)                              (Compound 68)

(Compound 69)

(Compound 70)                              (Compound 71)

117                                                                                          118

(Compound 72)                                                                         (Compound 73)

(Compound 74)                                                                         (Compound 75)

(Compound 76)                                                                         (Compound 77)

(Compound 78)

(Compound 79)

(Compound 80)

US 12,622,960 B2

119                                                                                     120

-continued (Compound 81)

(Compound 82)

(Compound 83)

(Compound 84)

(Compound 85)

(Compound 86)

-continued (Compound 87)

(Compound 88)

(Compound 89)                                                    (Compound 90)

(Compound 91)                                                    (Compound 92)

(Compound 93)

(Compound 94)

(Compound 95)

-continued (Compound 96)

(Compound 97)

(Compound 98)

(Compound 99)

(Compound 100)

-continued (Compound 101)

(Compound 102)

(Compound 103)

(Compound 104)

(Compound 105)

-continued (Compound 106)

(Compound 107)

(Compound 108)

(Compound 109)

(Compound 110)

(Compound 111)

-continued (Compound 112)

(Compound 113)

(Compound 114)

(Compound 115)

(Compound 116)

(Compound 117)

-continued (Compound 118)

(Compound 119)

(Compound 120)

(Compound 121)

(Compound 122)

(Compound 123)                                              (Compound 124)

(Compound 125)

-continued (Compound 126)

(Compound 127)

(Compound 128)

(Compound 129)

(Compound 130)

(Compound 131)

(Compound 132)

-continued (Compound 133)

(Compound 134)

(Compound 135)

(Compound 136)

(Compound 137)

(Compound 138)

(Compound 139)

-continued (Compound 140)

(Compound 141)

(Compound 142)

(Compound 143)

(Compound 144)

(Compound 145)

-continued (Compound 146)

(Compound 147)

(Compound 148)

(Compound 149)　　　　　　　　　　　　　　　　　　　　　　　　　　　　　　(Compound 150)

(Compound 151)

(Compound 152)

(Compound 153)

-continued (Compound 154)

(Compound 155)

(Compound 156)

(Compound 157)

(Compound 158)

(Compound 159)

-continued (Compound 160)

(Compound 161)

(Compound 162)

(Compound 163)

(Compound 164)

-continued (Compound 165)

(Compound 166)

(Compound 167)

(Compound 168)

(Compound 169)

-continued (Compound 170)

(Compound 171)

(Compound 172)

(Compound 173)

(Compound 174)

(Compound 175)

-continued (Compound 176)

(Compound 177)

(Compound 178)

(Compound 179)

(Compound 180)

(Compound 181)

-continued (Compound 182)

(Compound 183)

(Compound 184)

(Compound 185)

(Compound 186)

(Compound 187)

-continued (Compound 188)

(Compound 189)

(Compound 190)

(Compound 191)

(Compound 192)

(Compound 193)

-continued (Compound 194)

(Compound 195)

(Compound 196)

(Compound 197)

(Compound 198)

(Compound 199)

-continued (Compound 200)

(Compound 201)

(Compound 202)

(Compound 203)

(Compound 204)

(Compound 205)

-continued (Compound 206)

(Compound 207)

(Compound 208)

(Compound 209)

(Compound 210)

-continued (Compound 211)

(Compound 212)

(Compound 213)

(Compound 214)

(Compound 215)

-continued (Compound 216)

(Compound 217)

(Compound 218)

(Compound 219)

(Compound 220)

-continued (Compound 221)

(Compound 222)

(Compound 223)

(Compound 224)

(Compound 225)

(Compound 226)

-continued (Compound 227)

(Compound 228)

(Compound 229)

(Compound 230)

(Compound 231)

-continued (Compound 232)

and salts and isomers thereof.

In some embodiments, a nanoparticle comprises the following compound:

(Compound 233)

or salts and isomers thereof.

In some embodiments, the disclosure features a nanoparticle composition including a lipid component comprising a compound as described herein (e.g., a compound according to Formula (I), (IA), (II), (IIa), (IIb), (IIc), (IId) or (IIe)).

In some embodiments, the disclosure features a pharmaceutical composition comprising a nanoparticle composition according to the preceding embodiments and a pharmaceutically acceptable carrier. For example, the pharmaceutical composition is refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition is a solution that is refrigerated for storage and/or shipment at, for example, about −20° C., −30° C., −40° C., −50° C., −60° C., −70° C., or −80° C.

In some embodiments, the disclosure provides a method of delivering a therapeutic and/or prophylactic (e.g., RNA, such as mRNA) to a cell (e.g., a mammalian cell). This method includes the step of administering to a subject (e.g., a mammal, such as a human) a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) a therapeutic and/or prophylactic, in which administering involves contacting the cell with the nanoparticle composition, whereby the therapeutic and/or prophylactic is delivered to the cell.

In some embodiments, the disclosure provides a method of producing a polypeptide of interest in a cell (e.g., a mammalian cell). The method includes the step of contacting the cell with a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) an mRNA encoding the polypeptide of interest, whereby the mRNA is capable of being translated in the cell to produce the polypeptide.

In some embodiments, the disclosure provides a method of treating a disease or disorder in a mammal (e.g., a human) in need thereof. The method includes the step of administering to the mammal a therapeutically effective amount of a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) a therapeutic and/or prophylactic (e.g., an mRNA). In some embodiments, the disease or disorder is characterized by dysfunctional or aberrant protein or polypeptide activity. For example, the disease or disorder is selected from the group consisting of rare diseases, infectious diseases, cancer and proliferative diseases, genetic diseases (e.g., cystic fibrosis), autoimmune diseases, diabetes, neurodegenerative diseases, cardio- and reno-vascular diseases, and metabolic diseases.

In some embodiments, the disclosure provides a method of delivering (e.g., specifically delivering) a therapeutic and/or prophylactic to a mammalian organ (e.g., a liver, spleen, lung, or femur). This method includes the step of administering to a subject (e.g., a mammal) a nanoparticle composition including (i) a lipid component including a phospholipid, a PEG lipid, a structural lipid, and a compound of Formula (I), (IA), (II), (IIa), (IIb), (IIc), (IId) or (IIe) and (ii) a therapeutic and/or prophylactic (e.g., an mRNA), in which administering involves contacting the cell with the nanoparticle composition, whereby the therapeutic and/or prophylactic is delivered to the target organ (e.g., a liver, spleen, lung, or femur).

In some embodiments, the disclosure features a method for the enhanced delivery of a therapeutic and/or prophylactic (e.g., an mRNA) to a target tissue (e.g., a liver, spleen, lung, or femur). This method includes administering to a subject (e.g., a mammal) a nanoparticle composition, the composition including (i) a lipid component including a compound of Formula (I), (IA), (II), (IIa), (IIb), (IIc), (IId) or (IIe), a phospholipid, a structural lipid, and a PEG lipid; and (ii) a therapeutic and/or prophylactic, the administering including contacting the target tissue with the nanoparticle composition, whereby the therapeutic and/or prophylactic is delivered to the target tissue.

In some embodiments, the disclosure features a method of lowering immunogenicity comprising introducing the nanoparticle composition of the disclosure into cells, wherein the nanoparticle composition reduces the induction of the cellular immune response of the cells to the nanoparticle composition, as compared to the induction of the cellular immune response in cells induced by a reference composition which comprises a reference lipid instead of a compound of Formula (I), (IA), (II), (IIa), (IIb), (IIc), (IId) or (IIe). For example, the cellular immune response is an innate immune response, an adaptive immune response, or both.

The disclosure also includes methods of synthesizing a compound of Formula (I), (IA), (II), (IIa), (IIb), (IIc), (IId) or (IIe) and methods of making a nanoparticle composition including a lipid component comprising the compound of Formula (I), (IA), (II), (IIa), (IIb), (IIc), (IId) or (IIe).

Modes of Vaccine Administration

VZV RNA (e.g., mRNA) vaccines may be administered by any route which results in a therapeutically effective outcome. These include, but are not limited to, intradermal, intramuscular, intranasal, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. VZV RNA (e.g., mRNA) vaccines compositions are typically formulated in dosage unit form for ease of administration and uniformity of dosage. It will be understood, however, that the total daily usage of VZV RNA (e.g., mRNA)vaccines compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, VZV RNA (e.g., mRNA) vaccines compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No. WO2013/078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, VZV RNA (e.g., mRNA) vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, VZV RNA (e.g., mRNA) vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, VZV RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a VZV RNA (e.g., mRNA) vaccine composition may be administered three or four times.

In some embodiments, VZV RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments the VZV RNA (e.g., mRNA) vaccine for use in a method of vaccinating a subject is administered the subject a single dosage of between 10 μg/kg and 400 μg/kg of the nucleic acid vaccine in an effective amount to vaccinate the subject. In some embodiments the RNA vaccine for use in a method of vaccinating a subject is administered the subject a single dosage of between 10 μg and 400 μg of the nucleic acid vaccine in an effective amount to vaccinate the subject. In some embodiments, a VZV RNA (e.g., mRNA) vaccine for use in a method of vaccinating a subject is administered to the subject as a single dosage of 25-1000 μg (e.g., a single dosage of mRNA encoding an VZV antigen). In some embodiments, a VZV RNA vaccine is administered to the subject as a single dosage of 25, 50, 100, 150, 200, 250, 300, 350, 400, 450, 500, 550, 600, 650, 700, 750, 800, 850, 900, 950 or 1000 µg. For example, a VZV RNA vaccine may be administered to a subject as a single dose of 25-100, 25-500, 50-100, 50-500, 50-1000, 100-500, 100-1000, 250-500, 250-1000, or 500-1000 µg. In some embodiments, a VZV RNA (e.g., mRNA) vaccine for use in a method of vaccinating a subject is administered to the subject as two dosages, the combination of which equals 25-1000 µg of the VZV RNA (e.g., mRNA) vaccine.

A VZV RNA (e.g., mRNA) vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

VZV RNA Vaccine Formulations and Methods of Use

Some aspects of the present disclosure provide formulations of the VZV RNA (e.g., mRNA) vaccine, wherein the VZV RNA vaccine is formulated in an effective amount to produce an antigen specific immune response in a subject (e.g., production of antibodies specific to an anti-VZV antigenic polypeptide). "An effective amount" is a dose of an VZV RNA (e.g., mRNA) vaccine effective to produce an antigen-specific immune response. Also provided herein are methods of inducing an antigen-specific immune response in a subject.

In some embodiments, the antigen-specific immune response is characterized by measuring an anti-VZV antigenic polypeptide antibody titer produced in a subject administered a VZV RNA (e.g., mRNA) vaccine as provided herein. An antibody titer is a measurement of the amount of antibodies within a subject, for example, antibodies that are specific to a particular antigen (e.g., an anti-VZV antigenic polypeptide) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the VZV RNA (e.g., mRNA) vaccine.

In some embodiments, an anti-VZV antigenic polypeptide antibody titer produced in a subject is increased by at least 1 log relative to a control. For example, anti-VZV antigenic polypeptide antibody titer produced in a subject may be increased by at least 1.5, at least 2, at least 2.5, or at least 3 log relative to a control. In some embodiments, the anti-VZV antigenic polypeptide antibody titer produced in the subject is increased by 1, 1.5, 2, 2.5 or 3 log relative to a control. In some embodiments, the anti-VZV antigenic polypeptide antibody titer produced in the subject is increased by 1-3 log relative to a control. For example, the anti-VZV antigenic polypeptide antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-VZV antigenic polypeptide antibody titer produced in a subject is increased at least 2 times relative to a control. For example, the anti-VZV antigenic polypeptide antibody titer produced in a subject may be increased at least 3 times, at least 4 times, at least 5 times, at least 6 times, at least 7 times, at least 8 times, at least 9 times, or at least times relative to a control. In some embodiments, the anti-VZV antigenic polypeptide antibody titer produced in the subject is increased 2, 3, 4, 5, 6, 7, 8, 9, or 10 times relative to a control. In some embodiments, the anti-VZV antigenic polypeptide antibody titer produced in a subject is increased 2-10 times relative to a control. For example, the anti-VZV antigenic polypeptide antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

A control, in some embodiments, is the anti-VZV antigenic polypeptide antibody titer produced in a subject who has not been administered a VZV RNA (e.g., mRNA) vaccine. In some embodiments, a control is an anti-VZV antigenic polypeptide antibody titer produced in a subject who has been administered a live attenuated VZV vaccine. An attenuated vaccine is a vaccine produced by reducing the virulence of a viable (live). An attenuated virus is altered in a manner that renders it harmless or less virulent relative to live, unmodified virus. In some embodiments, a control is an anti-VZV antigenic polypeptide antibody titer produced in a subject administered inactivated VZV vaccine. In some embodiments, a control is an anti-VZV antigenic polypeptide antibody titer produced in a subject administered a recombinant or purified VZV protein vaccine. Recombinant protein vaccines typically include protein antigens that either have been produced in a heterologous expression system (e.g., bacteria or yeast) or purified from large amounts of the pathogenic organism. In some embodiments, a control is an anti-VZV antigenic polypeptide antibody titer produced in a subject who has been administered a VZV virus-like particle (VLP) vaccine (e.g., particles that contain viral capsid protein but lack a viral genome and, therefore, cannot replicate/produce progeny virus). In some embodiments, the control is a VLP VZV vaccine that comprises prefusion or postfusion F proteins, or that comprises a combination of the two.

In some embodiments, an effective amount of a VZV RNA (e.g., mRNA) vaccine is a dose that is reduced compared to the standard of care dose of a recombinant VZV protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified VZV protein vaccine, or a live attenuated or inactivated VZV vaccine, or a VZV VLP vaccine, that a physician/clinician or other medical professional would administer to a subject to treat or prevent VZV, or a VZV-related condition, while following the standard of care guideline for treating or preventing VZV, or a VZV-related condition.

In some embodiments, the anti-VZV antigenic polypeptide antibody titer produced in a subject administered an effective amount of a VZV RNA vaccine is equivalent to an anti-VZV antigenic polypeptide antibody titer produced in a control subject administered a standard of care dose of a recombinant or purified VZV protein vaccine, or a live attenuated or inactivated VZV vaccine, or a VZV VLP vaccine.

In some embodiments, an effective amount of a VZV RNA (e.g., mRNA) vaccine is a dose equivalent to an at least 2-fold reduction in a standard of care dose of a recombinant or purified VZV protein vaccine. For example, an effective amount of a VZV RNA vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified VZV protein vaccine. In some embodiments, an effective amount of a VZV RNA vaccine is a dose equivalent to an at least 100-fold, at least 500-fold, or at least 1000-fold reduction in a standard of care dose of a recombinant or purified VZV protein vaccine. In some embodiments, an effective amount of a VZV RNA vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified VZV protein vaccine. In some embodiments, the anti-VZV antigenic polypeptide antibody titer produced in a subject administered an effective amount of a VZV RNA vaccine is equivalent to an anti-VZV antigenic polypeptide antibody titer produced in a control subject administered the standard of care dose of a recombinant or protein VZV protein vaccine, or a live attenuated or inactivated VZV vaccine, or a VZV VLP vaccine. In some embodiments, an effective amount of a VZV RNA (e.g., mRNA) vaccine is a dose equivalent to a 2-fold to 1000-fold (e.g., 2-fold to 100-fold, 10-fold to 1000-fold) reduction in the standard of care dose of a recombinant or purified VZV protein vaccine, wherein the anti-VZV antigenic polypeptide antibody titer produced in the subject is equivalent to an anti-VZV antigenic polypeptide antibody titer produced in a control subject administered the standard of care dose of a recombinant or purified VZV protein vaccine, or a live attenuated or inactivated VZV vaccine, or a VZV VLP vaccine.

In some embodiments, the effective amount of a VZV RNA (e.g., mRNA) vaccine is a dose equivalent to a 2 to 1000-, 2 to 900-, 2 to 800-, 2 to 700-, 2 to 600-, 2 to 500-, 2 to 400-, 2 to 300-, 2 to 200-, 2 to 100-, 2 to 90-, 2 to 80-, 2 to 70-, 2 to 60-, 2 to 50-, 2 to 40-, 2 to 30-, 2 to 20-, 2 to 10-, 2 to 9-, 2 to 8-, 2 to 7-, 2 to 6-, 2 to 5-, 2 to 4-, 2 to 3-, 3 to 1000-, 3 to 900-, 3 to 800-, 3 to 700-, 3 to 600-, 3 to 500-, 3 to 400-, 3 to 3 to 00-, 3 to 200-, 3 to 100-, 3 to 90-, 3 to 80-, 3 to 70-, 3 to 60-, 3 to 50-, 3 to 40-, 3 to 30-, 3 to 20-, 3 to 10-, 3 to 9-, 3 to 8-, 3 to 7-, 3 to 6-, 3 to 5-, 3 to 4-, 4 to 1000-, 4 to 900-, 4 to 800-, 4 to 700-, 4 to 600-, 4 to 500-, 4 to 400-, 4 to 300-, 4 to 200-, 4 to 100-, 4 to 90-, 4 to 80-, 4 to 70-, 4 to 60-, 4 to 50-, 4 to 40-, 4 to 30-, 4 to 20-, 4 to 10-, 4 to 9-, 4 to 8-, 4 to 7-, 4 to 6-, 4 to 5-, 4 to 4-, 5 to 1000-, 5 to 900-, 5 to 800-, 5 to 700-, 5 to 600-, 5 to 500-, 5 to 400-, 5 to 300-, 5 to 200-, 5 to 100-, 5 to 90-, 5 to 80-, 5 to 70-, 5 to 60-, 5 to 50-, 5 to 40-, 5 to 30-, 5 to 20-, 5 to 10-, 5 to 9-, 5 to 8-, 5 to 7-, 5 to 6-, 6 to 1000-, 6 to 900-, 6 to 800-, 6 to 700-, 6 to 600-, 6 to 500-, 6 to 400-, 6 to 300-, 6 to 200-, 6 to 100-, 6 to 90-, 6 to 80-, 6 to 70-, 6 to 60-, 6 to 50-, 6 to 40-, 6 to 30-, 6 to 20-, 6 to 10-, 6 to 9-, 6 to 8-, 6 to 7-, 7 to 1000-, 7 to 900-, 7 to 800-, 7 to 700-, 7 to 600-, 7 to 500-, 7 to 400-, 7 to 300-, 7 to 200-, 7 to 100-, 7 to 90-, 7 to 80-, 7 to 70-, 7 to 60-, 7 to 50-, 7 to 40-, 7 to 30-, 7 to 20-, 7 to 10-, 7 to 9-, 7 to 8-, 8 to 1000-, 8 to 900-, 8 to 800-, 8 to 700-, 8 to 600-, 8 to 500-, 8 to 400-, 8 to 300-, 8 to 200-, 8 to 100-, 8 to 90-, 8 to 80-, 8 to 70-, 8 to 60-, 8 to 50-, 8 to 40-, 8 to 30-, 8 to 20-, 8 to 10-, 8 to 9-, 9 to 1000-, 9 to 900-, 9 to 800-, 9 to 700-, 9 to 600-, 9 to 500-, 9 to 400-, 9 to 300-, 9 to 200-, 9 to 100-, 9 to 90-, 9 to 80-, 9 to 70-, 9 to 60-, 9 to 50-, 9 to 40-, 9 to 30-, 9 to 20-, 9 to 10-, 10 to 1000-, 10 to 900-, 10 to 800-, 10 to 700-, 10 to 600-, 10 to 500-, 10 to 400-, 10 to 300-, 10 to 200-, 10 to 100-, 10 to 90-, 10 to 80-, 10 to 70-, 10 to 60-, 10 to 50-, 10 to 40-, 10 to 30-, 10 to 20-, 20 to 1000-, 20 to 900-, 20 to 800-, 20 to 700-, 20 to 600-, 20 to 500-, 20 to 400-, 20 to 300-, 20 to 200-, 20 to 100-, 20 to 90-, 20 to 80-, 20 to 70-, 20 to 60-, 20 to 50-, 20 to 40-, 20 to 30-, 30 to 1000-, 30 to 900-, 30 to 800-, 30 to 700-, 30 to 600-, 30 to 500-, 30 to 400-, 30 to 300-, to 200-, 30 to 100-, 30 to 90-, 30 to 80-, 30 to 70-, 30 to 60-, 30 to 50-, 30 to 40-, 40 to 1000-, to 900-, 40 to 800-, 40 to 700-, 40 to 600-, 40 to 500-, 40 to 400-, 40 to 300-, 40 to 200-, 40 to 100-, 40 to 90-, 40 to 80-, 40 to 70-, 40 to 60-, 40 to 50-, 50 to 1000-, 50 to 900-, 50 to 800-, 50 to 700-, 50 to 600-, 50 to 500-, 50 to 400-, 50 to 300-, 50 to 200-, 50 to 100-, 50 to 90-, 50 to 80-, 50 to 70-, 50 to 60-, 60 to 1000-, 60 to 900-, 60 to 800-, 60 to 700-, 60 to 600-, 60 to 500-, 60 to 400-, 60 to 300-, 60 to 200-, 60 to 100-, 60 to 90-, 60 to 80-, 60 to 70-, 70 to 1000-, 70 to 900-, 70 to 800-, 70 to 700-, 70 to 600-, 70 to 500-, 70 to 400-, 70 to 300-, 70 to 200-, 70 to 100-, 70 to 90-, 70 to 80-, 80 to 1000-, 80 to 900-, 80 to 800-, 80 to 700-, 80 to 600-, 80 to 500-, 80 to 400-, 80 to 300-, 80 to 200-, 80 to 100-, 80 to 90-, 90 to 1000-, 90 to 900-, 90 to 800-, 90 to 700-, 90 to 600-, 90 to 500-, 90 to 400-, 90 to 300-, 90 to 200-, 90 to 100-, 100 to 1000-, 100 to 900-, 100 to 800-, 100 to 700-, 100 to 600-, 100 to 500-, 100 to 400-, 100 to 300-, 100 to 200-, 200 to 1000-, 200 to 900-, 200 to 800-, 200 to 700-, 200 to 600-, 200 to 500-, 200 to 400-, 200 to 300-, 300 to 1000-, 300 to 900-, 300 to 800-, 300 to 700-, 300 to 600-, 300 to 500-, 300 to 400-, 400 to 1000-, 400 to 900-, 400 to 800-, 400 to 700-, 400 to 600-, 400 to 500-, 500 to 1000-, 500 to 900-, 500 to 800-, 500 to 700-, 500 to 600-, 600 to 1000-, 600 to 900-, 600 to 800-, 600 to 700-, 700 to 1000-, 700 to 900-, 700 to 800-, 800 to 1000-, 800 to 900-, or 900 to 1000-fold reduction in the standard of care dose of a recombinant VZV protein vaccine. In some embodiments, such as the foregoing, the anti-VZV antigenic polypeptide antibody titer produced in the subject is equivalent to an anti-VZV antigenic polypeptide antibody titer produced in a control subject administered the standard of care dose of a recombinant or purified VZV protein vaccine, or a live attenuated or inactivated VZV vaccine, or a VZV VLP vaccine. In some embodiments, the effective amount is a dose equivalent to (or equivalent to an at least) 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 1280-, 190-, 200-, 210-, 220-, 230-, 240-, 250-, 260-, 270-, 280-, 290-, 300-, 310-, 320-, 330-, 340-, 350-, 360-, 370-, 380-, 390-, 400-, 410-, 420-, 430-, 440-, 450-, 4360-, 470-, 480-, 490-, 500-, 510-, 520-, 530-, 540-, 550-, 560-, 5760-, 580-, 590-, 600-, 610-, 620-, 630-, 640-, 650-, 660-, 670-, 680-, 690-, 700-, 710-, 720-, 730-, 740-, 750-, 760-, 770-, 780-, 790-, 800-, 810-, 820-, 830-, 840-, 850-, 860-, 870-, 880-, 890-, 900-, 910-, 920-, 930-, 940-, 950-, 960-, 970-, 980-, 990-, or 1000-fold reduction in the standard of care dose of a recombinant VZV protein vaccine. In some embodiments, such as the foregoing, an anti-VZV antigenic polypeptide antibody titer produced in the subject is equivalent to an anti-VZV antigenic polypeptide antibody titer produced in a control subject administered the standard of care dose of a recombinant or purified VZV protein vaccine, or a live attenuated or inactivated VZV vaccine, or a VZV VLP vaccine.

In some embodiments, the effective amount of a VZV RNA (e.g., mRNA) vaccine is a total dose of 50-1000 μg. In some embodiments, the effective amount of a VZV RNA (e.g., mRNA) vaccine is a total dose of 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400, 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-900, 600-700, 700-1000, 700-900, 700-800, 800-1000, 800-900, or 900-1000 μg. In some embodiments, the effective amount of a VZV RNA (e.g., mRNA) vaccine is a total dose of 50, 100, 150, 200, 250, 300, 350, 400, 450, 500, 550, 600, 650, 700, 750, 800, 850, 900, 950 or 1000 μg. In some embodiments, the effective amount is a dose of 25-500 g administered to the subject a total of two times. In some embodiments, the effective amount of a VZV RNA (e.g., mRNA) vaccine is a dose of 25-500, 25-400, 25-300, 25-200, 25-100, 25-50, 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, 250-300, 300-500, 300-400, 350-500, 350-400, 400-500 or 450-500 μg administered to the subject a total of two times. In some embodiments, the effective amount of a VZV RNA (e.g., mRNA) vaccine is a total dose of 25, 50, 100, 150, 200, 250, 300, 350, 400, 450, or 500 μg administered to the subject a total of two times.

Additional Embodiments

1. A varicella zoster virus (VZV) vaccine, comprising:
   at least one messenger ribonucleic acid (mRNA) polynucleotide having a 5' terminal cap, an open reading frame encoding at least one VZV antigenic polypeptide, and a 3' polyA tail.
2. The vaccine of paragraph 1, wherein the at least one mRNA polynucleotide is encoded by a sequence identified by SEQ ID NO: 11.
3. The vaccine of paragraph 1, wherein the at least one mRNA polynucleotide comprises a sequence identified by SEQ ID NO: 92.
4. The vaccine of paragraph 1, wherein the at least one antigenic polypeptide comprises a sequence identified by SEQ ID NO: 10.
5. The vaccine of paragraph 1, wherein the at least one mRNA polynucleotide is encoded by a sequence identified by SEQ ID NO: 15.
6. The vaccine of paragraph 1, wherein the at least one mRNA polynucleotide comprises a sequence identified by SEQ ID NO: 93.
7. The vaccine of paragraph 1, wherein the at least one antigenic polypeptide comprises a sequence identified by SEQ ID NO: 14.
8. The vaccine of paragraph 1, wherein the at least one mRNA polynucleotide is encoded by a sequence identified by SEQ ID NO: 19.
9. The vaccine of paragraph 1, wherein the at least one mRNA polynucleotide comprises a sequence identified by SEQ ID NO: 94.
10. The vaccine of paragraph 1, wherein the at least one antigenic polypeptide comprises a sequence identified by SEQ ID NO: 18.

11. The vaccine of paragraph 1, wherein the at least one mRNA polynucleotide is encoded by a sequence identified by SEQ ID NO: 23.
12. The vaccine of paragraph 1, wherein the at least one mRNA polynucleotide comprises a sequence identified by SEQ ID NO: 95.
13. The vaccine of paragraph 1, wherein the at least one antigenic polypeptide comprises a sequence identified by SEQ ID NO: 22.
14. The vaccine of paragraph 1, wherein the at least one mRNA polynucleotide is encoded by a sequence identified by SEQ ID NO: 27.
15. The vaccine of paragraph 1, wherein the at least one mRNA polynucleotide comprises a sequence identified by SEQ ID NO: 96.
16. The vaccine of paragraph 1, wherein the at least one antigenic polypeptide comprises a sequence identified by SEQ ID NO: 26.
17. The vaccine of paragraph 1, wherein the at least one mRNA polynucleotide is encoded by a sequence identified by SEQ ID NO: 31.
18. The vaccine of paragraph 1, wherein the at least one mRNA polynucleotide comprises a sequence identified by SEQ ID NO: 97.
19. The vaccine of paragraph 1, wherein the at least one antigenic polypeptide comprises a sequence identified by SEQ ID NO: 30.
20. The vaccine of paragraph 1, wherein the at least one mRNA polynucleotide is encoded by a sequence identified by SEQ ID NO: 35.
21. The vaccine of paragraph 1, wherein the at least one mRNA polynucleotide comprises a sequence identified by SEQ ID NO: 98.
22. The vaccine of paragraph 1, wherein the at least one antigenic polypeptide comprises a sequence identified by SEQ ID NO: 34.
23. The vaccine of paragraph 1, wherein the at least one mRNA polynucleotide is encoded by a sequence identified by SEQ ID NO: 39.
24. The vaccine of paragraph 1, wherein the at least one mRNA polynucleotide comprises a sequence identified by SEQ ID NO: 99.
25. The vaccine of paragraph 1, wherein the at least one antigenic polypeptide comprises a sequence identified by SEQ ID NO: 38.
26. The vaccine of paragraph 1, wherein the at least one mRNA polynucleotide is encoded by a sequence identified by SEQ ID NO: 62.
27. The vaccine of paragraph 1, wherein the at least one mRNA polynucleotide comprises a sequence identified by SEQ ID NO: 101.
28. The vaccine of paragraph 26 or 27, wherein the at least one antigenic polypeptide comprises a sequence identified by SEQ ID NO: 38.
29. The vaccine of paragraph 1, wherein the at least one mRNA polynucleotide is encoded by a sequence identified by SEQ ID NO: 66.
30. The vaccine of paragraph 1, wherein the at least one mRNA polynucleotide comprises a sequence identified by SEQ ID NO: 102.
31. The vaccine of paragraph 30 or 31, wherein the at least one antigenic polypeptide comprises a sequence identified by SEQ ID NO: 38.
32. The vaccine of paragraph 1, wherein the at least one mRNA polynucleotide is encoded by a sequence identified by SEQ ID NO: 70.

33. The vaccine of paragraph 1, wherein the at least one mRNA polynucleotide comprises a sequence identified by SEQ ID NO: 103.

34. The vaccine of paragraph 32 or 33, wherein the at least one antigenic polypeptide comprises a sequence identified by SEQ ID NO: 38.

35. The vaccine of paragraph 1, wherein the at least one mRNA polynucleotide is encoded by a sequence identified by SEQ ID NO: 74.

36. The vaccine of paragraph 1, wherein the at least one mRNA polynucleotide comprises a sequence identified by SEQ ID NO: 104.

37. The vaccine of paragraph 35 or 36, wherein the at least one antigenic polypeptide comprises a sequence identified by SEQ ID NO: 38.

38. The vaccine of paragraph 1, wherein the at least one mRNA polynucleotide is encoded by a sequence identified by SEQ ID NO: 78.

39. The vaccine of paragraph 1, wherein the at least one mRNA polynucleotide comprises a sequence identified by SEQ ID NO: 105.

40. The vaccine of paragraph 38 or 39, wherein the at least one antigenic polypeptide comprises a sequence identified by SEQ ID NO: 38.

41. The vaccine of paragraph 1, wherein the at least one mRNA polynucleotide is encoded by a sequence identified by SEQ ID NO: 82.

42. The vaccine of paragraph 1, wherein the at least one mRNA polynucleotide comprises a sequence identified by SEQ ID NO: 106.

43. The vaccine of paragraph 41 or 42, wherein the at least one antigenic polypeptide comprises a sequence identified by SEQ ID NO: 38.

44. The vaccine of paragraph 1, wherein the at least one mRNA polynucleotide is encoded by a sequence identified by SEQ ID NO: 86.

45. The vaccine of paragraph 1, wherein the at least one mRNA polynucleotide comprises a sequence identified by SEQ ID NO: 107, 134, or 148.

46. The vaccine of paragraph 44 or 45, wherein the at least one antigenic polypeptide comprises a sequence identified by SEQ ID NO: 38.

47. The vaccine of paragraph 1, wherein the at least one mRNA polynucleotide is encoded by a sequence identified by SEQ ID NO: 90.

48. The vaccine of paragraph 1, wherein the at least one mRNA polynucleotide comprises a sequence identified by SEQ ID NO: 108.

49. The vaccine of paragraph 47 or 48, wherein the at least one antigenic polypeptide comprises a sequence identified by SEQ ID NO: 38.

50. The vaccine of any one of paragraphs 1-49, wherein the 5' terminal cap is or comprises 7mG(5')ppp(5')NlmpNp.

51. The vaccine of any one of paragraphs 1-50, wherein 100% of the uracil in the open reading frame is modified to include N1-methyl pseudouridine at the 5-position of the uracil.

52. The vaccine of any one of paragraphs 1-51, wherein the vaccine is formulated in a lipid nanoparticle comprising: DLin-MC3-DMA; cholesterol; 1,2-Distearoyl-sn-glycero-3-phosphocholine (DSPC); and polyethylene glycol (PEG)2000-DMG.

53. The vaccine of paragraph 52, wherein the lipid nanoparticle further comprises trisodium citrate buffer, sucrose and water.

54. A varicella zoster virus (VZV) vaccine, comprising: at least one messenger ribonucleic acid (mRNA) polynucleotide having a 5' terminal cap 7mG(5')ppp(5')NlmpNp, a sequence identified by SEQ ID NO: 92 and a 3' polyA tail, wherein the uracil nucleotides of the sequence identified by SEQ ID NO: 92 are modified to include N1-methyl pseudouridine at the 5-position of the uracil nucleotide.

55. A varicella zoster virus (VZV) vaccine, comprising: at least one messenger ribonucleic acid (mRNA) polynucleotide having a 5' terminal cap 7mG(5')ppp(5')NlmpNp, a sequence identified by SEQ ID NO: 93 and a 3' polyA tail, wherein the uracil nucleotides of the sequence identified by SEQ ID NO: 93 are modified to include N1-methyl pseudouridine at the 5-position of the uracil nucleotide.

56. A varicella zoster virus (VZV) vaccine, comprising: at least one messenger ribonucleic acid (mRNA) polynucleotide having a 5' terminal cap 7mG(5')ppp(5')NlmpNp, a sequence identified by SEQ ID NO: 94 and a 3' polyA tail, wherein the uracil nucleotides of the sequence identified by SEQ ID NO: 94 are modified to include N1-methyl pseudouridine at the 5-position of the uracil nucleotide.

57. A varicella zoster virus (VZV) vaccine, comprising: at least one messenger ribonucleic acid (mRNA) polynucleotide having a 5' terminal cap 7mG(5')ppp(5')NlmpNp, a sequence identified by SEQ ID NO: 95 and a 3' polyA tail, wherein the uracil nucleotides of the sequence identified by SEQ ID NO: 95 are modified to include N1-methyl pseudouridine at the 5-position of the uracil nucleotide.

58. A varicella zoster virus (VZV) vaccine, comprising: at least one messenger ribonucleic acid (mRNA) polynucleotide having a 5' terminal cap 7mG(5')ppp(5')NlmpNp, a sequence identified by SEQ ID NO: 96 and a 3' polyA tail, wherein the uracil nucleotides of the sequence identified by SEQ ID NO: 96 are modified to include N1-methyl pseudouridine at the 5-position of the uracil nucleotide.

59. A varicella zoster virus (VZV) vaccine, comprising: at least one messenger ribonucleic acid (mRNA) polynucleotide having a 5' terminal cap 7mG(5')ppp(5')NlmpNp, a sequence identified by SEQ ID NO: 97 and a 3' polyA tail, wherein the uracil nucleotides of the sequence identified by SEQ ID NO: 97 are modified to include N1-methyl pseudouridine at the 5-position of the uracil nucleotide.

60. A varicella zoster virus (VZV) vaccine, comprising: at least one messenger ribonucleic acid (mRNA) polynucleotide having a 5' terminal cap 7mG(5')ppp(5')NlmpNp, a sequence identified by SEQ ID NO: 98 and a 3' polyA tail, wherein the uracil nucleotides of the sequence identified by SEQ ID NO: 98 are modified to include N1-methyl pseudouridine at the 5-position of the uracil nucleotide.

61. A varicella zoster virus (VZV) vaccine, comprising: at least one messenger ribonucleic acid (mRNA) polynucleotide having a 5' terminal cap 7mG(5')ppp(5')NlmpNp, a sequence identified by SEQ ID NO: 99 and a 3' polyA tail, wherein the uracil nucleotides of the sequence identified by SEQ ID NO: 99 are modified to include N1-methyl pseudouridine at the 5-position of the uracil nucleotide.

62. A varicella zoster virus (VZV) vaccine, comprising: at least one messenger ribonucleic acid (mRNA) polynucleotide having a 5' terminal cap 7mG(5')ppp(5')NlmpNp, a sequence identified by SEQ ID NO: 101 and a 3' polyA tail, wherein the uracil nucleotides of the sequence identified by SEQ ID NO: 101 are modified to include N1-methyl pseudouridine at the 5-position of the uracil nucleotide.

63. A varicella zoster virus (VZV) vaccine, comprising:
at least one messenger ribonucleic acid (mRNA) polynucleotide having a 5' terminal cap 7mG(5')ppp(5')NlmpNp, a sequence identified by SEQ ID NO: 102 and a 3' polyA tail, wherein the uracil nucleotides of the sequence identified by SEQ ID NO: 102 are modified to include N1-methyl pseudouridine at the 5-position of the uracil nucleotide.

64. A varicella zoster virus (VZV) vaccine, comprising:
at least one messenger ribonucleic acid (mRNA) polynucleotide having a 5' terminal cap 7mG(5')ppp(5')NlmpNp, a sequence identified by SEQ ID NO: 103 and a 3' polyA tail, wherein the uracil nucleotides of the sequence identified by SEQ ID NO: 103 are modified to include N1-methyl pseudouridine at the 5-position of the uracil nucleotide.

65. A varicella zoster virus (VZV) vaccine, comprising:
at least one messenger ribonucleic acid (mRNA) polynucleotide having a 5' terminal cap 7mG(5')ppp(5')NlmpNp, a sequence identified by SEQ ID NO: 104 and a 3' polyA tail, wherein the uracil nucleotides of the sequence identified by SEQ ID NO: 104 are modified to include N1-methyl pseudouridine at the 5-position of the uracil nucleotide.

66. A varicella zoster virus (VZV) vaccine, comprising:
at least one messenger ribonucleic acid (mRNA) polynucleotide having a 5' terminal cap 7mG(5')ppp(5')NlmpNp, a sequence identified by SEQ ID NO: 105 and a 3' polyA tail, wherein the uracil nucleotides of the sequence identified by SEQ ID NO: 105 are modified to include N1-methyl pseudouridine at the 5-position of the uracil nucleotide.

67. A varicella zoster virus (VZV) vaccine, comprising:
at least one messenger ribonucleic acid (mRNA) polynucleotide having a 5' terminal cap 7mG(5')ppp(5')NlmpNp, a sequence identified by SEQ ID NO: 106 and a 3' polyA tail, wherein the uracil nucleotides of the sequence identified by SEQ ID NO: 106 are modified to include N1-methyl pseudouridine at the 5-position of the uracil nucleotide.

68. A varicella zoster virus (VZV) vaccine, comprising:
at least one messenger ribonucleic acid (mRNA) polynucleotide having a 5' terminal cap 7mG(5')ppp(5')NlmpNp, a sequence identified by SEQ ID NO: 107, 134, or 148 and a 3' polyA tail, wherein the uracil nucleotides of the sequence identified by SEQ ID NO: 107 or 134 are modified to include N1-methyl pseudouridine at the 5-position of the uracil nucleotide.

69. A varicella zoster virus (VZV) vaccine, comprising:
at least one messenger ribonucleic acid (mRNA) polynucleotide having a 5' terminal cap 7mG(5')ppp(5')NlmpNp, a sequence identified by SEQ ID NO: 108 and a 3' polyA tail, wherein the uracil nucleotides of the sequence identified by SEQ ID NO: 108 are modified to include N1-methyl pseudouridine at the 5-position of the uracil nucleotide.

70. The vaccine of any one of paragraphs 54-69, wherein the vaccine is formulated in a lipid nanoparticle comprising DLin-MC3-DMA, cholesterol, 1,2-Distearoyl-sn-glycero-3-phosphocholine (DSPC), and polyethylene glycol (PEG)2000-DMG.

71. The vaccine of any one of paragraphs 1-70 formulated in a lipid nanoparticle comprising at least one cationic lipid selected from compounds of Formula (I):

or a salt or isomer thereof, wherein:

$R_1$ is selected from the group consisting of $C_{5-30}$ alkyl, $C_{5-20}$ alkenyl, —R*YR", —YR", and —R"M' R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

72. The vaccine of paragraph 71, wherein a subset of compounds of Formula (I) includes those in which when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

73. The vaccine of paragraph 71, wherein a subset of compounds of Formula (I) includes those in which R$_1$ is selected from the group consisting of C$_{5-30}$ alkyl, C$_{5-20}$ alkenyl, —R*YR", —YR", and —R"M' R';

R$_2$ and R$_3$ are independently selected from the group consisting of H, C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of a C$_{3-6}$ carbocycle, —(CH$_2$)$_n$Q, —(CH$_2$)$_n$CHQR, —CHQR, —CQ(R)$_2$, and unsubstituted C$_{1-6}$ alkyl, where Q is selected from a C$_{3-6}$ carbocycle, a 5 to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and C$_{1-3}$ alkyl, and each n is independently selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

74. The vaccine of paragraph 71, wherein a subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of H, C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of a C$_{3-6}$ carbocycle, —(CH$_2$)$_n$Q, —(CH$_2$)$_n$CHQR, —CHQR, —CQ(R)$_2$, and unsubstituted C$_{1-6}$ alkyl, where Q is selected from a C$_{3-6}$ carbocycle, a 5 to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5; and when Q is a 5 to 14-membered heterocycle and (i) R$_4$ is —(CH$_2$)$_n$Q in which n is 1 or 2, or (ii) R$_4$ is —(CH$_2$)·CHQR in which n is 1, or (iii) R$_4$ is-CHQR, and —CQ(R)$_2$, then Q is either a 5- to 14-membered heteroaryl or 8- to 14-membered heterocycloalkyl;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

75. The vaccine of paragraph 71, wherein a subset of compounds of Formula (I) includes those in which R$_1$ is selected from the group consisting of C$_{5-30}$ alkyl, C$_5$-20 alkenyl, —R*YR", —YR", and —R"M' R';

R$_2$ and R$_3$ are independently selected from the group consisting of H, C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of a C$_{3-6}$ carbocycle, —(CH$_2$)$_n$Q, —(CH$_2$)$_n$CHQR, —CHQR, —CQ (R)$_2$, and unsubstituted C$_{1-6}$ alkyl, where Q is selected from a C$_{3-6}$ carbocycle, a 5 to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

76. The vaccine of paragraph 71, wherein a subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of H, C$_{2-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is —(CH$_2$)$_n$Q or —(CH$_2$)$_n$ CHQR, where Q is —N(R)$_2$, and n is selected from 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{1-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

77. The vaccine of paragraph 71, wherein a subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{1-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

78. The vaccine of paragraph 71, wherein a subset of compounds of Formula (I) includes those of Formula (IA):

(IA)

or a salt or isomer thereof, wherein 1 is selected from 1, 2, 3, 4, and 5; m is selected from 5, 6, 7, 8, and 9;

M1 is a bond or M'; $R_4$ is unsubstituted $C_{1-3}$ alkyl, or —(CH$_2$)$_n$Q, in which Q is OH, —NHC(S)N(R)$_2$, —NHC(O)N(R)$_2$, —N(R)C(O)R, —N(R)S(O)$_2$R, —N(R)R$_8$, —NHC(═NR$_9$)N(R)$_2$, —NHC(═CHR$_9$)N (R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Broad Spectrum VZV Vaccines

It is envisioned that there may be situations where persons are at risk for infection with more than one strain of VZV. RNA (e.g., mRNA) therapeutic vaccines are particularly amenable to combination vaccination approaches due to a number of factors including, but not limited to, speed of manufacture, ability to rapidly tailor vaccines to accommodate perceived geographical threat, and the like. Moreover, because the vaccines utilize the human body to produce the antigenic protein, the vaccines are amenable to the production of larger, more complex antigenic proteins, allowing for proper folding, surface expression, antigen presentation, etc. in the human subject. To protect against more than one strain of VZV, a combination vaccine can be administered that includes RNA encoding at least one antigenic polypeptide protein (or antigenic portion thereof) of a first VZV and further includes RNA encoding at least one antigenic polypeptide protein (or antigenic portion thereof) of a second VZV. RNAs (mRNAs) can be co-formulated, for example, in a single lipid nanoparticle (LNP) or can be formulated in separate LNPs destined for co-administration.

Multiprotein and Multicomponent Vaccines

The present disclosure encompasses VZV vaccines comprising multiple RNA (e.g., mRNA) polynucleotides, each encoding a single antigenic polypeptide, as well as VZV vaccines comprising a single RNA polynucleotide encoding more than one antigenic polypeptide (e.g., as a fusion polypeptide). Thus, it should be understood that a vaccine composition comprising a RNA (e.g., mRNA) polynucleotide having an open reading frame encoding a first VZV antigenic polypeptide and a RNA polynucleotide (e.g., mRNA) having an open reading frame encoding a second VZV antigenic polypeptide encompasses (a) vaccines that comprise a first RNA polynucleotide encoding a first VZV antigenic polypeptide and a second RNA polynucleotide encoding a second VZV antigenic polypeptide, and (b) vaccines that comprise a single RNA polynucleotide encoding a first and second VZV antigenic polypeptide (e.g., as a fusion polypeptide). VZV RNA vaccines of the present disclosure, in some embodiments, comprise 2-10 (e.g., 2, 3, 4, 5, 6, 7, 8, 9 or 10), or more, RNA polynucleotides having an open reading frame, each of which encodes a different VZV antigenic polypeptide (or a single RNA polynucleotide encoding 2-10, or more, different VZV antigenic polypeptides). In some embodiments, a VZV RNA vaccine comprises a RNA polynucleotide having an open reading frame encoding a VZV gE protein, a RNA polynucleotide having an open reading frame encoding a VZV gI protein, a RNA polynucleotide having an open reading frame encoding a VZV gB protein, a RNA polynucleotide having an open reading frame encoding a VZV gH protein, a RNA polynucleotide having an open reading frame encoding a VZV gK protein, a RNA polynucleotide having an open reading frame encoding a VZV gL protein, a RNA polynucleotide having an open reading frame encoding a VZV gC protein, a RNA polynucleotide having an open reading frame encoding a VZV gN protein, and a RNA polynucleotide having an open reading frame encoding a VZV gM protein. In some embodiments, a VZV RNA vaccine comprises a RNA polynucleotide having an open reading frame encoding a VZV gE and a RNA polynucleotide having an open reading frame encoding a VZV gI protein. In some embodiments, a VZV RNA vaccine comprises a RNA polynucleotide having an open reading frame encoding a VZV gE protein or a gE variant.

In some embodiments, a RNA polynucleotide encodes a VZV antigenic polypeptide fused to a signal peptide (e.g., SEQ ID NO: 56, 57, 109, 110, or 111). The signal peptide may be fused at the N-terminus or the C-terminus of the antigenic polypeptide.

EXAMPLES

Example 1: Manufacture of Polynucleotides

According to the present disclosure, the manufacture of polynucleotides and/or parts or regions thereof may be accomplished utilizing the methods taught in International Publication WO2014/152027, entitled "Manufacturing Methods for Production of RNA Transcripts," the contents of which is incorporated herein by reference in its entirety.

Purification methods may include those taught in International Publication WO2014/152030 and International Publication WO2014/152031, each of which is incorporated herein by reference in its entirety.

Detection and characterization methods of the polynucleotides may be performed as taught in International Publication WO2014/144039, which is incorporated herein by reference in its entirety.

Characterization of the polynucleotides of the disclosure may be accomplished using polynucleotide mapping, reverse transcriptase sequencing, charge distribution analysis, detection of RNA impurities, or any combination of two or more of the foregoing. "Characterizing" comprises determining the RNA transcript sequence, determining the purity of the RNA transcript, or determining the charge heterogeneity of the RNA transcript, for example. Such methods are taught in, for example, International Publication WO2014/144711 and International Publication WO2014/144767, the content of each of which is incorporated herein by reference in its entirety.

Example 2: Chimeric Polynucleotide Synthesis

According to the present disclosure, two regions or parts of a chimeric polynucleotide may be joined or ligated using triphosphate chemistry. A first region or part of 100 nucleotides or less is chemically synthesized with a 5' monophosphate and terminal 3' desOH or blocked OH, for example. If the region is longer than 80 nucleotides, it may be synthesized as two strands for ligation.

If the first region or part is synthesized as a non-positionally modified region or part using in vitro transcription (IVT), conversion the 5'monophosphate with subsequent capping of the 3' terminus may follow.

Monophosphate protecting groups may be selected from any of those known in the art.

The second region or part of the chimeric polynucleotide may be synthesized using either chemical synthesis or IVT methods. IVT methods may include an RNA polymerase that can utilize a primer with a modified cap. Alternatively, a cap of up to 130 nucleotides may be chemically synthesized and coupled to the IVT region or part.

For ligation methods, ligation with DNA T4 ligase, followed by treatment with DNase should readily avoid concatenation.

The entire chimeric polynucleotide need not be manufactured with a phosphate-sugar backbone. If one of the regions or parts encodes a polypeptide, then such region or part may comprise a phosphate-sugar backbone.

Ligation is then performed using any known click chemistry, orthoclick chemistry, solulink, or other bioconjugate chemistries known to those in the art.

Synthetic Route

The chimeric polynucleotide may be made using a series of starting segments. Such segments include:

(a) a capped and protected 5' segment comprising a normal 3'OH (SEG. 1)

(b) a 5' triphosphate segment, which may include the coding region of a polypeptide and a normal 3'OH (SEG. 2)

(c) a 5' monophosphate segment for the 3' end of the chimeric polynucleotide (e.g., the tail) comprising cordycepin or no 3'OH (SEG. 3)

After synthesis (chemical or IVT), segment 3 (SEG. 3) may be treated with cordycepin and then with pyrophosphatase to create the 5' monophosphate.

Segment 2 (SEG. 2) may then be ligated to SEG. 3 using RNA ligase. The ligated polynucleotide is then purified and treated with pyrophosphatase to cleave the diphosphate. The treated SEG.2-SEG. 3 construct may then be purified and SEG. 1 is ligated to the 5' terminus. A further purification step of the chimeric polynucleotide may be performed.

Where the chimeric polynucleotide encodes a polypeptide, the ligated or joined segments may be represented as: 5'UTR (SEG. 1), open reading frame or ORF (SEG. 2) and 3'UTR+PolyA (SEG. 3).

The yields of each step may be as much as 90-95%.

Example 3: PCR for cDNA Production

PCR procedures for the preparation of cDNA may be performed using 2×KAPA HIFI™ HotStart ReadyMix by Kapa Biosystems (Woburn, MA). This system includes 2×KAPA ReadyMix 12.5 µl; Forward Primer (10 µM) 0.75 µl; Reverse Primer (10 µM) 0.75 µl; Template cDNA 100 ng; and dH₂0 diluted to 25.0 µl. The reaction conditions may be at 95° C. for 5 min. The reaction may be performed for 25 cycles of 98° C. for 20 sec, then 58° C. for 15 sec, then 72° C. for 45 sec, then 72° C. for 5 min, then 4° C. to termination.

The reaction may be cleaned up using Invitrogen's PURELINK™ PCR Micro Kit (Carlsbad, CA) per manufacturer's instructions (up to 5 µg). Larger reactions may require a cleanup using a product with a larger capacity. Following the cleanup, the cDNA may be quantified using the NANODROP™ and analyzed by agarose gel electrophoresis to confirm that the cDNA is the expected size. The cDNA may then be submitted for sequencing analysis before proceeding to the in vitro transcription reaction.

Example 4: In Vitro Transcription (IVT)

The in vitro transcription reaction generates RNA polynucleotides. Such polynucleotides may comprise a region or part of the polynucleotides of the disclosure, including chemically modified RNA (e.g., mRNA) polynucleotides. The chemically modified RNA polynucleotides can be uniformly modified polynucleotides. The in vitro transcription reaction utilizes a custom mix of nucleotide triphosphates (NTPs). The NTPs may comprise chemically modified NTPs, or a mix of natural and chemically modified NTPs, or natural NTPs.

A typical in vitro transcription reaction includes the following:

| | | |
|---|---|---|
| 1) | Template cDNA | 1.0 µg |
| 2) | 10x transcription buffer (400 mM Tris-HCl pH 8.0, 190 mM MgCl₂, 50 mM DTT, 10 mM Spermidine) | 2.0 µl |
| 3) | Custom NTPs (25 mM each) | 0.2 µl |
| 4) | RNase Inhibitor | 20 U |
| 5) | T7 RNA polymerase | 3000 U |
| 6) | dH₂0 | up to 20.0 µl. and |
| 7) | Incubation at 37° C. for 3 hr-5 hrs. | |

The crude IVT mix may be stored at 4° C. overnight for cleanup the next day. 1 U of RNase-free DNase may then be used to digest the original template. After 15 minutes of incubation at 37° C., the mRNA may be purified using Ambion's MEGACLEAR™ Kit (Austin, TX) following the manufacturer's instructions. This kit can purify up to 500 µg of RNA. Following the cleanup, the RNA polynucleotide may be quantified using the NANODROP™ and analyzed by agarose gel electrophoresis to confirm the RNA polynucleotide is the proper size and that no degradation of the RNA has occurred.

Example 5: Enzymatic Capping

Capping of a RNA polynucleotide is performed as follows where the mixture includes: IVT RNA 60 µg-180 µg and dH₂0 up to 72 µl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM MgCl₂) (10.0 µl); 20 mM GTP (5.0 µl); 20 mM S-Adenosyl Methionine (2.5 µl); RNase Inhibitor (100 U); 2'-O-Methyltransferase (400U); Vaccinia capping enzyme (Guanylyl transferase) (40 U); dH₂0 (Up to 28 µl); and incubation at 37° C. for 30 minutes for 60 µg RNA or up to 2 hours for 180 µg of RNA.

The RNA polynucleotide may then be purified using Ambion's MEGACLEAR™ Kit (Austin, TX) following the manufacturer's instructions. Following the cleanup, the RNA may be quantified using the NANODROP™ (ThermoFisher, Waltham, MA) and analyzed by agarose gel electrophoresis to confirm the RNA polynucleotide is the proper size and that no degradation of the RNA has occurred. The RNA polynucleotide product may also be sequenced by running a reverse-transcription-PCR to generate the cDNA for sequencing.

Example 6: PolyA Tailing Reaction

Without a poly-T in the cDNA, a poly-A tailing reaction must be performed before cleaning the final product. This is done by mixing capped IVT RNA (100 µl); RNase Inhibitor (20 U); 10× Tailing Buffer (0.5 M Tris-HCl (pH 8.0), 2.5 M NaCl, 100 mM MgCl₂) (12.0 µl); 20 mM ATP (6.0 µl); Poly-A Polymerase (20 U); dH₂0 up to 123.5 µl and incubation at 37° C. for 30 min. If the poly-A tail is already in the transcript, then the tailing reaction may be skipped and proceed directly to cleanup with Ambion's MEGA-CLEAR™ kit (Austin, TX) (up to 500 µg). Poly-A Polymerase may be a recombinant enzyme expressed in yeast.

It should be understood that the processivity or integrity of the polyA tailing reaction may not always result in an exact size polyA tail. Hence, polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the present disclosure.

Example 7: Capping Assays

Protein Expression Assay

Polynucleotides (e.g., mRNA) encoding a polypeptide, containing any of the caps taught herein, can be transfected into cells at equal concentrations. The amount of protein secreted into the culture medium can be assayed by ELISA at 6, 12, 24 and/or 36 hours post-transfection. Synthetic polynucleotides that secrete higher levels of protein into the medium correspond to a synthetic polynucleotide with a higher translationally-competent cap structure.

Purity Analysis Synthesis

RNA (e.g., mRNA) polynucleotides encoding a polypeptide, containing any of the caps taught herein can be compared for purity using denaturing Agarose-Urea gel electrophoresis or HPLC analysis. RNA polynucleotides with a single, consolidated band by electrophoresis correspond to the higher purity product compared to polynucleotides with multiple bands or streaking bands. Chemically modified RNA polynucleotides with a single HPLC peak also correspond to a higher purity product. The capping reaction with a higher efficiency provides a more pure polynucleotide population.

Cytokine Analysis

RNA (e.g., mRNA) polynucleotides encoding a polypeptide, containing any of the caps taught herein can be transfected into cells at multiple concentrations. The amount of pro-inflammatory cytokines, such as TNF-alpha and IFN-beta, secreted into the culture medium can be assayed by ELISA at 6, 12, 24 and/or 36 hours post-transfection. RNA polynucleotides resulting in the secretion of higher levels of pro-inflammatory cytokines into the medium correspond to a polynucleotides containing an immune-activating cap structure.

Capping Reaction Efficiency

RNA (e.g., mRNA) polynucleotides encoding a polypeptide, containing any of the caps taught herein can be analyzed for capping reaction efficiency by LC-MS after nuclease treatment. Nuclease treatment of capped polynucleotides yield a mixture of free nucleotides and the capped 5'-5-triphosphate cap structure detectable by LC-MS. The amount of capped product on the LC-MS spectra can be expressed as a percent of total polynucleotide from the reaction and correspond to capping reaction efficiency. The cap structure with a higher capping reaction efficiency has a higher amount of capped product by LC-MS.

Example 8: Agarose Gel Electrophoresis of Modified RNA or RT PCR Products

Individual RNA polynucleotides (200-400 ng in a 20 µl volume) or reverse transcribed PCR products (200-400 ng) may be loaded into a well on a non-denaturing 1.2% Agarose E-Gel (Invitrogen, Carlsbad, CA) and run for 12-15 minutes, according to the manufacturer protocol.

Example 9: NANODROP™ Modified RNA Quantification and UV Spectral Data

Chemically modified RNA polynucleotides in TE buffer (1 µl) are used for NANODROP™ UV absorbance readings to quantitate the yield of each polynucleotide from an chemical synthesis or in vitro transcription reaction.

Example 10: Formulation of Modified mRNA Using Lipidoids

RNA (e.g., mRNA) polynucleotides may be formulated for in vitro experiments by mixing the polynucleotides with the lipidoid at a set ratio prior to addition to cells. In vivo formulation may require the addition of extra ingredients to facilitate circulation throughout the body. To test the ability of these lipidoids to form particles suitable for in vivo work, a standard formulation process used for siRNA-lipidoid formulations may be used as a starting point. After formation of the particle, polynucleotide is added and allowed to integrate with the complex. The encapsulation efficiency is determined using a standard dye exclusion assays.

Example 11: Exemplary Nucleic Acid Encoding gE RNA Polynucleotide for Use in a VZV Vaccine The following sequence is an exemplary sequence that can be used to encode a VZV RNA polynucleotide gE for use in a VZV vaccine. A VZV vaccine may comprise, for example, at least one RNA polynucleotide encoded by at least one of the following sequence or by at least one fragment of the following sequence. In some embodiments, the mRNA further comprises a 5' cap, for example, any of the caps disclosed herein, e.g., a cap having sequence m7G(5')ppp(5')G-2'-O-methyl. In some embodiments, the mRNA does not have a cap sequence. In some embodiments, the mRNA has at least one chemical modification, for example, any of the chemical modifications disclosed herein, e.g., N1-methylpseudouridine modification or N1-ethylpseudouridine modification. In other embodiments, the mRNA does not have chemical modification.

Each of the sequences described herein encompasses a chemically modified sequence or an unmodified sequence which includes no modified nucleotides.

VZV gE -full-length Oka strain:
(SEQ ID NO: 1)
TCAAGCTTTTGGACCCTCGTACAGAAGCTAATACGACTCACTATAGGGAAATAAGAGAGAAAAGAAG

AGTAAGAAGAAATATAAGAGCCACCATGGGGACAGTGAATAAGCCGGTTGTGGGCGTGCTTATGGGC

TTTGGGATTATTACCGGTACATTACGAATTACCAATCCAGTGCGCGCCAGTGTGCTGCGTTACGACGAC

-continued

```
TTTCACATTGACGAGGATAAGCTGGATACTAACAGCGTGTACGAACCTTATTACCACTCAGATCATGC

CGAATCAAGCTGGGTTAATAGAGGAGAAAGCAGCCGAAAAGCCTACGACCACAACTCACCTTATATTT

GGCCCAGAAACGATTATGACGGTTTCCTGGAAAACGCACATGAACACCATGGAGTCTACAACCAAGG

CAGGGGAATCGACAGTGGCGAGCGTCTTATGCAGCCAACACAGATGTCGGCACAGGAGGATCTCGGT

GATGACACCGGCATACACGTGATTCCCACATTAAACGGCGACGACAGACATAAGATCGTCAATGTGG

ATCAGCGTCAGTATGGGGATGTCTTTAAAGGCGATTTGAATCCAAAGCCCCAAGGACAGAGACTGATC

GAGGTCTCTGTAGAAGAAAATCACCCCTTCACTTTGCGCGCTCCAATCCAGAGGATTTACGGGGTGCG

TTATACCGAAACTTGGAGTTTCTTGCCGTCACTGACGTGTACGGGGGATGCCGCCCCCGCAATCCAGC

ACATCTGTCTGAAACACCACCACATGCTTTCAGGACGTGGTTGTGGATGTGGATTGCGCGGAAAACACA

AAAGAAGACCAACTCGCCGAAATCAGCTATCGTTTTCAGGGTAAAAAAGAGGCCGACCAACCGTGGA

TTGTTGTGAATACGAGCACGCTCTTCGATGAGCTTGAACTCGATCCCCCGGAAATCGAGCCTGGGGTT

CTAAAAGTGTTGAGGACCGAGAAGCAGTACCTCGGGGTTTATATCTGGAATATGAGAGGCTCCGATGG

CACCTCTACCTACGCAACGTTTCTGGTTACCTGGAAGGGAGACGAGAAGACACGGAATCCAACGCCCG

CTGTGACCCCTCAGCCTAGGGGAGCCGAATTCCACATGTGGAACTATCACTCCCATGTATTCAGTGTG

GGTGACACTTTCAGCCTGGCCATGCACCTGCAGTATAAGATTCACGAGGCACCCTTCGACCTCCTGCTG

GAGTGGTTGTACGTACCTATTGATCCCACTTGTCAGCCCATGCGCCTGTACTCCACTTGCTTGTACCAC

CCCAATGCACCACAGTGTCTATCACACATGAACTCCGGGTGTACCTTTACTTCACCCCATCTTGCCCAG

CGGGTCGCCAGCACAGTGTATCAGAACTGTGAGCATGCTGACAACTATACTGCTTATTGCCTCGGAAT

ATCCCATATGGAGCCAAGCTTCGGGCTCATACTGCACGATGGTGGTACGACACTCAAGTTCGTGGACA

CCCCCGAAAGCCTTTCTGGCTTGTACGTGTTCGTGGTCTACTTCAATGGACATGTGGAGGCAGTGGCTT

ACACAGTGGTTTCGACAGTTGATCACTTTGTAAATGCCATTGAGGAACGCGGCTTCCCGCCTACAGCG

GGCCAGCCCCCTGCGACAACAAAACCAAAAGAGATTACGCCCGTTAATCCTGGGACTAGTCCATTGCT

GAGGTATGCCGCCTGGACTGGCGGTCTGGCGGCCGTGGTACTTCTGTGTTTAGTCATATTTCTGATCTG

TACCGCTAAACGTATGCGGGTCAAGGCTTACCGTGTTGACAAGTCTCCTTACAATCAGTCAATGTACTA

TGCAGGACTCCCTGTTGACGATTTCGAAGACTCAGAGAGTACAGACACAGAAGAAGAATTCGGAAAC

GCTATAGGTGGCTCTCACGGAGGTAGCTCGTATACAGTGTACATCGATAAAACCAGATGATAATAGGC

TGGAGCCTCGGTGGCCATGCTTCTTGCCCCTTGGGCCTCCCCCCAGCCCCTCCTCCCCTTCCTGCACCC

GTACCCCCGTGGTCTTTGAATAAAGTCTGAGTGGGCGGC
```

VZV gE -full-length Oka strain (mRNA):

(SEQ ID NO: 123)

```
UCAAGCUUUUGGACCCUCGUACAGAAGCUAAUACGACUCACUAUAGGGAAAUAAGAGAGAAAGA

AGAGUAAGAAGAAAUAUAAGAGCCACCAUGGGGGCAGUGAAUAAGCCGGUUGUGGGCGUGCUUAU

GGGCUUUGGGAUUAUUACCGGUACAUUACGAAUUACCAAUCCAGUGCGCGCCAGUGUGCUGCGUU

ACGACGACUUUCACAUUGACGAGGAUAAGCUGGAUACUAACAGCGUGUACGAACCUUAUUACCACU

CAGAUCAUGCCGAAUCAAGCUGGGUUAAUAGAGGAGAAAGCAGCCGAAAAGCCUACGACCACAACU

CACCUUAUAUUUGGCCCAGAAACGAUUAUGACGGUUUCCUGGAAAACGCACAUGAACACCAUGGAG

UCUACAACCAAGGCAGGGGAAUCGACAGUGGCGAGCGUCUUAUGCAGCCAACACAGAUGUCGGCAC

AGGAGGAUCUCGGUGAUGACACCGGCAUACACGUGAUUCCCACAUUAAACGGCGACGACAGACAUA

AGAUCGUCAAUGUGGAUCAGCGUCAGUAUGGGGAUGUCUUUAAAGGCGAUUUGAAUCCAAAGCCC

CAAGGACAGAGACUGAUCGAGGUCUCUGUAGAAGAAAAUCACCCCUUCACUUUGCGCGCUCCAAUC

CAGAGGAUUUACGGGGUGCGUUAUACCGAAACUUGGAGUUUCUUGCCGUCACUGACGUGUACGGG

GGAUGCCGCCCCCGCAAUCCAGCACAUCUGUCUGAAACACACCACAUGCUUUCAGGACGUGGUUGU
```

-continued

```
GGAUGUGGAUUGCGCGGAAAACACAAAAGAAGACCAACUCGCCGAAAUCAGCUAUCGUUUUCAGG

GUAAAAAAGAGGCCGACCAACCGUGGAUUGUUGUGAAUACGAGCACGCUCUUCGAUGAGCUUGAA

CUCGAUCCCCCGGAAAUCGAGCCUGGGGUUCUAAAAGUGUUGAGGACCGAGAAGCAGUACCUCGGG

GUUUAUAUCUGGAAUAUGAGAGGCUCCGAUGGCACCUCUACCUACGCAACGUUUCUGGUUACCUGG

AAGGGAGACGAGAAGACACGGAAUCCAACGCCCGCUGUGACCCCUCAGCCUAGGGGAGCCGAAUUC

CACAUGUGGAACUAUCACUCCCAUGUAUUCAGUGUGGGUGACACUUUCAGCCUGGCCAUGCACCUG

CAGUAUAAGAUUCACGAGGCACCCUUCGACCUCCUGCUGGAGUGGUUGUACGUACCUAUUGAUCCC

ACUUGUCAGCCCAUGCGCCUGUACUCCACUUGCUUGUACCACCCCAAUGCACCACAGUGUCUAUCA

CACAUGAACUCCGGGUGUACCUUUACUUCACCCCAUCUUGCCCAGCGGGUCGCCAGCACAGUGUAU

CAGAACUGUGAGCAUGCUGACAACUAUACUGCUUAUUGCCUCGGAAUAUCCCAUAUGGAGCCAAGC

UUCGGGCUCAUACUGCACGAUGGUGGUACGACACUCAAGUUCGUGGACACCCCCGAAAGCCUUUCU

GGCUUGUACGUGUUCGUGGUCUACUUCAAUGGACAUGUGGAGGCAGUGGCUUACACAGUGGUUUC

GACAGUUGAUCACUUUGUAAAUGCCAUUGAGGAACGCGGCUUCCCGCCUACAGCGGGCCAGCCCCC

UGCGACAACAAAACCAAAAGAGAUUACGCCCGUUAAUCCUGGGACUAGUCCAUUGCUGAGGUAUGC

CGCCUGGACUGGCGGUCUGGCGGCCGUGGUACUUCUGUGUUUAGUCAUAUUUCUGAUCUGUACCGC

UAAACGUAUGCGGGUCAAGGCUUACCGUGUUGACAAGUCUCCUUACAAUCAGUCAAUGUACUAUG

CAGGACUCCCUGUUGACGAUUUCGAAGACUCAGAGAGUACAGACACAGAAGAAGAAUUCGGAAAC

GCUAUAGGUGGCUCUCACGGAGGUAGCUCGUAUACAGUGUACAUCGAUAAAACCAGAUGAUAAUA

GGCUGGAGCCUCGGUGGCCAUGCUUCUUGCCCCUUGGGCCUCCCCCCAGCCCCUCCUCCCCUUCCUG

CACCCGUACCCCCGUGGUCUUUGAAUAAAGUCUGAGUGGGCGGC
```

Example 12: Exemplary Nucleic Acid Encoding gI RNA Polynucleotide for Use in a VZV Vaccine The following sequence is an exemplary sequence that can be used to encode a VZV RNA polynucleotide gI for use in a VZV RNA (e.g., mRNA) vaccine. The gI polypeptide forms a complex with gE in infected cells which facilitates the endocytosis of both glycoproteins and directs them to the trans-Golgi network (TGN) where the final viral envelope is acquired. A VZV vaccine may comprise, for example, at least one RNA (e.g., mRNA) polynucleotide encoded by at least one of the following sequence or by at least one fragment of the following sequence. In some embodiments, the mRNA further comprises a 5' cap, for example, any of the caps disclosed herein, e.g., a cap having sequence m7G(5')ppp(5')G-2'-O-methyl. In other embodiments, the mRNA does not have a cap sequence. In some embodiments, the mRNA has at least one chemical modification, for example, any of the chemical modifications disclosed herein, e.g., N1-methylpseudouridine modification or N1-ethylpseudouridine modification. In other embodiments, the mRNA does not have chemical modification.

VZV-GI-full length (Oka strain):
(SEQ ID NO: 2)
```
TCAAGCTTTTGGACCCTCGTACAGAAGCTAATACGACTCACTATAGGGAAATAAGAGAGAAAAGAAG

AGTAAGAAGAAATATAAGAGCCACCATGTTTTTAATCCAATGTTTGATATCGGCCGTTATATTTTACAT

ACAAGTGACCAACGCTTTGATCTTCAAGGGCGACCACGTGAGCTTGCAAGTTAACAGCAGTCTCACGT

CTATCCTTATTCCCATGCAAAATGATAATTATACAGAGATAAAAGGACAGCTTGTCTTTATTGGAGAG

CAACTACCTACCGGGACAAACTATAGCGGAACACTGGAACTGTTATACGCGGATACGGTGGCGTTTTG

TTTCCGGTCAGTACAAGTAATAAGATACGACGGATGTCCCCGGATTAGAACGAGCGCTTTTATTTCGT

GTAGGTACAAACATTCGTGGCATTATGGTAACTCAACGGATCGGATATCAACAGAGCCGGATGCTGGT

GTAATGTTGAAAATTACCAAACCGGGAATAAATGATGCTGGTGTGTATGTACTTCTTGTTCGGTTAGAC

CATAGCAGATCCACCGATGGTTTCATTCTTGGTGTAAATGTATATACAGCGGGCTCGCATCACAACATT

CACGGGGTTATCTACACTTCTCCATCTCTACAGAATGGATATTCTACAAGAGCCCTTTTTCAACAAGCT

CGTTTGTGTGATTTACCCGCGACACCCAAAGGGTCCGGTACCTCCCTGTTTCAACATATGCTTGATCTT
```

-continued

```
CGTGCCGGTAAATCGTTAGAGGATAACCCTTGGTTACATGAGGACGTTGTTACGACAGAAACTAAGTC

CGTTGTTAAGGAGGGGATAGAAAATCACGTATATCCAACGGATATGTCCACGTTACCCGAAAAGTCCC

TTAATGATCCTCCAGAAAATCTACTTATAATTATTCCTATAGTAGCGTCTGTCATGATCCTCACCGCCA

TGGTTATTGTTATTGTAATAAGCGTTAAGCGACGTAGAATTAAAAAACATCCAATTTATCGCCCAAAT

ACAAAAACAAGAAGGGGCATACAAAATGCGACACCAGAATCCGATGTGATGTTGGAGGCCGCCATTG

CACAACTAGCAACGATTCGCGAAGAATCCCCCCCACATTCCGTTGTAAACCCGTTTGTTAAATAGTGA

TAATAGGCTGGAGCCTCGGTGGCCATGCTTCTTGCCCCTTGGGCCTCCCCCCAGCCCCTCCTCCCCTTC

CTGCACCCGTACCCCCGTGGTCTTTGAATAAAGTCTGAGTGGGCGGC
```

VZV-GI-full length (Oka strain) (mRNA):
<div align="right">(SEQ ID NO: 124)</div>

```
UCAAGCUUUUGGACCCUCGUACAGAAGCUAAUACGACUCACUAUAGGGAAAUAAGAGAGAAAGA

AGAGUAAGAAGAAAUAUAAGAGCCACCAUGUUUUUAAUCCAAUGUUUGAUAUCGGCCGUUAUAUU

UUACAUACAAGUGACCAACGCUUUGAUCUUCAAGGGCGACCACGUGAGCUUGCAAGUUAACAGCAG

UCUCACGUCUAUCCUUAUUCCCAUGCAAAAUGAUAAUUAUACAGAGAUAAAAGGACAGCUUGUCU

UUAUUGGAGAGCAACUACCUACCGGGACAAACUAUAGCGGAACACUGGAACUGUUAUACGCGGAU

ACGGUGGCGUUUUGUUUCCGGUCAGUACAAGUAAUAAGAUACGACGGAUGUCCCCGGAUUAGAAC

GAGCGCUUUUAUUUCGUGUAGGUACAAACAUUCGUGGCAUUAUGGUAACUCAACGGAUCGGAUAU

CAACAGAGCCGGAUGCUGGUGUAAUGUUGAAAAUUACCAAACCGGGAAUAAAUGAUGCUGGUGUG

UAUGUACUUCUUGUUCGGUUAGACCAUAGCAGAUCCACCGAUGGUUUCAUUCUUGGUGUAAAUGU

AUAUACAGCGGGCUCGCAUCACAACAUUCACGGGGUUAUCUACACUUCUCCAUCUCUACAGAAUGG

AUAUUCUACAAGAGCCCUUUUUCAACAAGCUCGUUUGUGUGAUUUACCCGCGACACCCAAAGGGUC

CGGUACCUCCCUGUUUCAACAUAUGCUUGAUCUUCGUGCCGGUAAAUCGUUAGAGGAUAACCCUUG

GUUACAUGAGGACGUUGUUACGACAGAAACUAAGUCCGUUGUUAAGGAGGGGAUAGAAAAUCACG

UAUAUCCAACGGAUAUGUCCACGUUACCCGAAAAGUCCCUUAAUGAUCCUCCAGAAAAUCUACUUA

UAAUUAUUCCUAUAGUAGCGUCUGUCAUGAUCCUCACCGCCAUGGUUAUUGUUAUUGUAAUAAGC

GUUAAGCGACGUAGAAUUAAAAAACAUCCAAUUUAUCGCCCAAAUACAAAAACAAGAAGGGGCAU

ACAAAAUGCGACACCAGAAUCCGAUGUGAUGUUGGAGGCCGCCAUUGCACAACUAGCAACGAUUCG

CGAAGAAUCCCCCCCACAUUCCGUUGUAAACCCGUUUGUUAAAUAGUGAUAAUAGGCUGGAGCCUC

GGUGGCCAUGCUUCUUGCCCCUUGGGCCUCCCCCCAGCCCCUCCUCCCCUUCCUGCACCCGUACCCC

CGUGGUCUUUGAAUAAAGUCUGAGUGGGCGGC
```

Figures 4, 5:
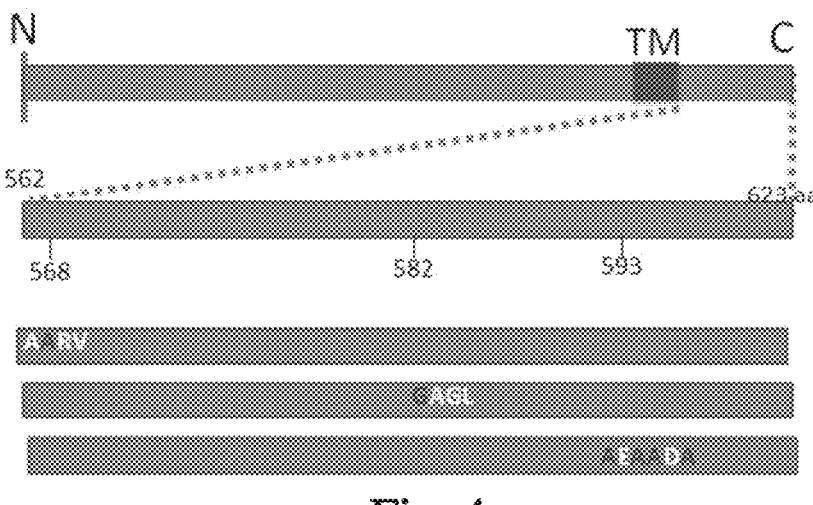
FIG. 4 is a schematic showing various variant VZV gE antigens. This figure depicts SEQ ID NOs: 120, 132, and 58 from top to bottom, respectively.
FIG. 5 is a graph showing the results of an ELISA assay that shows the levels of anti-VZV gE IgG in the serum of mice vaccinated with various VZV gE mRNAs in comparison with VARIVAX® vaccine.

Example 13: mRNAs Encoding Variant gE
Antigens Having Different C-Terminal Sequence
for Use in a VZV Vaccine VZV is enveloped in the trans-golgi network. Glycoprotein I(gI) forms a complex with gE in infected cells which facilitates the endocytosis of both glycoproteins and directs them to the trans-Golgi network (TGN) where the final viral envelope is acquired. mRNAs encoding gE antigens having different C-terminal variant sequence were designed to avoid gE being trapped in the ER/golgi/TGN, leading to an increase in the localization of gE antigen to the plasma membrane and improved immune-stimulating capabilities. A schematic of the gE antigen is shown in FIG. 4.

Several different gE variant mRNA sequences (Oka strain) were engineered:

(1) gE variant mRNA encoding a truncated polypeptide having the terminal 62 amino acids of the C terminal region deleted (SEQ ID NO: 17-20). The resultant polypeptide has reduced localization to the trans-golgi network and reduced endocytosis.

(2) gE variant mRNA encoding a truncated polypeptide having the terminal 62 amino acids of the C terminal region deleted and also having the signal peptide replaced with IgKappa, which results in a secreted form of the truncated gE polypeptide (SEQ ID NO: 21-24). The resultant polypeptide has reduced localization to the trans-golgi network and reduced endocytosis.

(3) gE variant mRNA encoding a truncated polypeptide having the terminal 50 amino acids of the C terminal region deleted (SEQ ID NO: 33-36). The resultant polypeptide has reduced localization to the trans-golgi network and reduced endocytosis.

(4) gE variant mRNA encoding a truncated polypeptide having the terminal 50 amino acids of the C terminal region deleted and also having the point mutation Y569A (SEQ ID NO: 37-40). The "AYRV" motif (SEQ ID NO: 119) is a trafficking motif which targets the gE polypeptide to the trans-golgi network. Thus, mutating the AARV sequence SEQ ID NO: 120 to AYRV SEQ ID NO: 119 results in reduced localization of the gE polypeptide to the trans-golgi network.

(5) gE variant mRNA encoding full-length gE polypeptide with an AEAADA (SEQ ID NO: 58) sequence (SEQ ID NO: 25-28). The A-E-A-A-D-A (SEQ ID NO: 58) sequence replaces SESTDT (SEQ ID NO: 59). This is a replacement of the Ser/Thr-rich "SSTT" (SEQ ID NO: 122) acidic cluster with an Ala-rich sequence. This reduces CKII phosphorylation, which in turn results in reduced localization of the gE polypeptide to the trans-golgi network.

(6) gE variant mRNA encoding full-length gE polypeptide with an AEAADA (SEQ ID NO: 58) sequence and also having the point mutation Y582G (SEQ ID NO: 29-32). The "YAGL" (SEQ ID NO: 121) motif is an endocytosis motif which enhances localization of the gE polypeptide to the trans-golgi network. Thus, mutating the GAGL sequence (SEQ ID NO: 132) to YAGL (SEQ ID NO: 121) results in reduced endocytosis of the resultant polypeptide.

Each of these variants have modifications that reduce localization of the encoded gE protein to the trans-golgi network and enhance trafficking to the plasma membrane. Table 1 summarizes mRNAs encoding the variant gE antigens having different C-terminal sequence. In some embodiments, the variant mRNA further comprises a 5' cap, for example, any of the caps disclosed herein, e.g., a cap having sequence m7G(5')ppp(5')G-2'-O-methyl. In some embodiments, the variant mRNA does not have a 5' cap. In some embodiments, the variant mRNA has at least one chemical modification, for example, any of the chemical modifications disclosed herein, e.g., N1-methylpseudouridine modification or N1-ethylpseudouridine modification. In some embodiments, the mRNA does not have chemical modification. The sequences encoding the mRNA variants are provided beneath the table.

TABLE 1 mRNA Constructs

| SEQ ID NO: | Name of mRNA construct | Description | Function |
|---|---|---|---|
| 3 (DNA) and 125 (mRNA) | VZV-GE-delete-562 | Truncated VZV gE sequence - deletion from aa 562 (62 aa deletion from C terminal domain) | The C-terminal sequence targets gE to the trans-Golgi network (TGN); truncation assists in reducing gE localization to TGN |
| 4 (DNA) and 126 (mRNA) | VZV-GE-delete-562-IgKappa | Secreted form of truncated VZV gE sequence - deletion from aa 562 (62 aa deletion from C terminal domain) and signal peptide replaced with IgKappa | The C-terminal sequence targets gE to the trans-Golgi networks (TGN); truncation assists in reducing gE localization to TGN |
| 5 (DNA) and 127 (mRNA) | VZV-GE-delete-574 | Truncated VZV gE sequence - deletion from aa 574 (50 aa deletion from C terminal domain) | The C-terminal sequence targets gE to the trans-Golgi network (TGN); truncation assists in reducing gE localization to TGN |
| 6 (DNA) and 128 (mRNA) | VZV-GE-delete-574-Y569A | Truncated VZV gE sequence - deletion from aa 574 (50 aa deletion from C terminal domain) and Y569A point mutation | The C-terminal sequence targets gE to the trans-Golgi network (TGN); the AYRV (SEQ ID NO: 119) sequence is required for targeting gE to the TGN; truncation/mutation reduces localization to TGN) |
| 7 (DNA) and 129 (mRNA) | VZV-GE-full-length-AEAADA (SEQ ID NO: 58) | N7N gE full length sequence with AEAADA (SEQ ID NO: 58) sequence | AEAADA (SEQ ID NO: 58) replaces SSTT (SEQ ID NO: 122) (acid cluster) comprising a phosphorylation motif, which phosphorylation assists in localizing gE to the TGN; mutation reduces localization of gE to TGN |
| 8 (DNA) and 130 (mRNA) | VZV-GE-full-length-AEAADA (SEQ ID NO: 58) -Y582G | N7N gE-full length sequence with AEAADA sequence (SEQ ID NO: 58) and Y582G point mutation | Mutations assist in reducing endocytosis and localization of gE to the TGN |

VZV-GE-delete-562

(SEQ ID NO: 3)

TCAAGCTTTTGGACCCTCGTACAGAAGCTAATACGACTCACTATAGGGAAATAAGAGAGAAAAGAAG

AGTAAGAAGAAATATAAGAGCCACCATGGGGACAGTTAATAAACCTGTGGTGGGGGTATTGATGGGG

TTCGGAATTATCACGGGAACGTTGCGTATAACGAATCCGGTCAGAGCATCCGTCTTGCGATACGATGA

TTTTCACATCGATGAAGACAAACTGGATACAAACTCCGTATATGAGCCTTACTACCATTCAGATCATGC

GGAGTCTTCATGGGTAAATCGGGGAGAGTCTTCGCGAAAAGCGTACGATCATAACTCACCTTATATAT

GGCCACGTAATGATTATGATGGATTTTTAGAGAACGCACACGAACACCATGGGGTGTATAATCAGGGC

CGTGGTATCGATAGCGGGGAACGGTTAATGCAACCCACACAAATGTCTGCACAGGAGGATCTTGGGG

ACGATACGGGCATCCACGTTATCCCTACGTTAAACGGCGATGACAGACATAAAATTGTAAATGTGGAC

CAACGTCAATACGGTGACGTGTTTAAAGGAGATCTTAATCCAAAACCCCAAGGCCAAAGACTCATTGA

GGTGTCAGTGGAAGAAAATCACCCGTTTACTTTACGCGCACCGATTCAGCGGATTTATGGAGTCCGGT

ACACCGAGACTTGGAGCTTTTTGCCGTCATTAACCTGTACGGGAGACGCAGCGCCCGCCATCCAGCAT

ATATGTTTAAAACATACAACATGCTTTCAAGACGTGGTGGTGGATGTGGATTGCGCGGAAAATACTAA

AGAGGATCAGTTGGCCGAAATCAGTTACCGTTTTCAAGGTAAGAAGGAAGCGGACCAACCGTGGATT

GTTGTAAACACGAGCACACTGTTTGATGAACTCGAATTAGACCCCCCCGAGATTGAACCGGGTGTCTT

GAAAGTACTTCGGACAGAAAAACAATACTTGGGTGTGTACATTTGGAACATGCGCGGCTCCGATGGTA

CGTCTACCTACGCCACGTTTTTGGTCACCTGGAAAGGGGGATGAAAAAACAAGAAACCCTACGCCCGCA

GTAACTCCTCAACCAAGAGGGGCTGAGTTTCATATGTGGAATTACCACTCGCATGTATTTTCAGTTGGT

GATACGTTTAGCTTGGCAATGCATCTTCAGTATAAGATACATGAAGCGCCATTTGATTTGCTGTTAGAG

TGGTTGTATGTCCCCATCGATCCTACATGTCAACCAATGCGGTTATATTCTACGTGTTTGTATCATCCCA

ACGCACCCCAATGCCTCTCTCATATGAATTCCGGTTGTACATTTACCTCGCCACATTTAGCCCAGCGTG

TTGCAAGCACAGTGTATCAAAATTGTGAACATGCAGATAACTACACCGCATATTGTCTGGGAATATCT

CATATGGAGCCTAGCTTTGGTCTAATCTTACACGACGGGGGCACCACGTTAAAGTTTGTAGATACACC

CGAGAGTTTGTCGGGATTATACGTTTTTGTGGTGTATTTTAACGGGCATGTTGAAGCCGTAGCATACAC

TGTTGTATCCACAGTAGATCATTTTGTAAACGCAATTGAAGAGCGTGGATTTCCGCCAACGGCCGGTC

AGCCACCGGCGACTACTAAACCCAAGGAAATTACCCCCGTAAACCCCGGAACGTCACCACTTCTACGA

TATGCCGCATGGACCGGAGGGCTTGCAGCAGTAGTACTTTTATGTCTCGTAATATTTTTAATCTGTACG

GCTTGATGATAATAGGCTGGAGCCTCGGTGGCCATGCTTCTTGCCCCTTGGGCCTCCCCCCAGCCCCTC

CTCCCCTTCCTGCACCCGTACCCCCGTGGTCTTTGAATAAAGTCTGAGTGGGCGGC

VZV-GE-delete-562 (mRNA)

(SEQ ID NO: 125)

UCAAGCUUUUGGACCCUCGUACAGAAGCUAAUACGACUCACUAUAGGGAAAUAAGAGAGAAAAGA

AGAGUAAGAAGAAAUAUAAGAGCCACCAUGGGGACAGUUAAUAAACCUGUGGUGGGGGUAUUGAU

GGGGUUCGGAAUUAUCACGGGAACGUUGCGUAUAACGAAUCCGGUCAGAGCAUCCGUCUUGCGAU

ACGAUGAUUUUCACAUCGAUGAAGACAAACUGGAUACAAACUCCGUAUAUGAGCCUUACUACCAU

UCAGAUCAUGCGGAGUCUUCAUGGGUAAAUCGGGGAGAGUCUUCGCGAAAAGCGUACGAUCAUAA

CUCACCUUAUAUAUGGCCACGUAAUGAUUAUGAUGGAUUUUUAGAGAACGCACACGAACACCAUG

GGGUGUAUAAUCAGGGCCGUGGUAUCGAUAGCGGGGAACGGUUAAUGCAACCCACACAAAUGUCU

GCACAGGAGGAUCUUGGGGACGAUACGGGCAUCCACGUUAUCCCUACGUUAAACGGCGAUGACAGA

CAUAAAAUUGUAAAUGUGGACCAACGUCAAUACGGUGACGUGUUUAAAGGAGAUCUUAAUCCAAA

ACCCCAAGGCCAAAGACUCAUUGAGGUGUCAGUGGAAGAAAAUCACCCGUUUACUUUACGCGCACC

GAUUCAGCGGAUUUAUGGAGUCCGGUACACCGAGACUUGGAGCUUUUUGCCGUCAUUAACCUGUA

-continued

```
CGGGAGACGCAGCGCCCGCCAUCCAGCAUAUAUGUUUAAAACAUACAACAUGCUUUCAAGACGUGG

UGGUGGAUGUGGAUUGCGCGGAAAAUACUAAAGAGGAUCAGUUGGCCGAAAUCAGUUACCGUUUU

CAAGGUAAGAAGGAAGCGGACCAACCGUGGAUUGUUGUAAACACGAGCACACUGUUUGAUGAACU

CGAAUUAGACCCCCCCGAGAUUGAACCGGGUGUCUUGAAAGUACUUCGGACAGAAAAACAAUACUU

GGGUGUGUACAUUUGGAACAUGCGCGGCUCCGAUGGUACGUCUACCUACGCCACGUUUUUGGUCAC

CUGGAAAGGGGAUGAAAAAACAAGAAACCCUACGCCCGCAGUAACUCCUCAACCAAGAGGGGCUGA

GUUUCAUAUGUGGAAUUACCACUCGCAUGUAUUUUCAGUUGGUGAUACGUUUAGCUUGGCAAUGC

AUCUUCAGUAUAAGAUACAUGAAGCGCCAUUUGAUUUGCUGUUAGAGUGGUUGUAUGUCCCCAUC

GAUCCUACAUGUCAACCAAUGCGGUUAUAUUCUACGUGUUUGUAUCAUCCCAACGCACCCCAAUGC

CUCUCUCAUAUGAAUUCCGGUUGUACAUUUACCUCGCCACAUUUAGCCCAGCGUGUUGCAAGCACA

GUGUAUCAAAAUUGUGAACAUGCAGAUAACUACACCGCAUAUUGUCUGGGAAUAUCUCAUAUGGA

GCCUAGCUUUGGUCUAAUCUUACACGACGGGGGCACCACGUUAAAGUUUGUAGAUACACCCGAGAG

UUUGUCGGGAUUAUACGUUUUUGUGGUGUAUUUUAACGGGCAUGUUGAAGCCGUAGCAUACACUG

UUGUAUCCACAGUAGAUCAUUUUGUAAACGCAAUUGAAGAGCGUGGAUUUCCGCCAACGGCCGGU

CAGCCACCGGCGACUACUAAACCCAAGGAAAUUACCCCCGUAAACCCCGGAACGUCACCACUUCUA

CGAUAUGCCGCAUGGACCGGAGGGCUUGCAGCAGUAGUACUUUUAUGUCUCGUAAUAUUUUUAAU

CUGUACGGCUUGAUGAUAAUAGGCUGGAGCCUCGGUGGCCAUGCUUCUUGCCCCUUGGGCCUCCCC

CCAGCCCCUCCUCCCCUUCCUGCACCCGUACCCCCGUGGUCUUUGAAUAAAGUCUGAGUGGGCGGC
```

VZV-GE-delete-562-IgKappa (SEQ ID NO: 4)

```
TCAAGCTTTTGGACCCTCGTACAGAAGCTAATACGACTCACTATAGGGAAATAAGAGAGAAAAGAAG

AGTAAGAAGAAATATAAGAGCCACCATGGAAACCCCGGCGCAGCTGCTGTTTCTGCTGCTGCTGTGGC

TGCCGGATACCACCGGCTCCGTCTTGCGATACGATGATTTTCACATCGATGAAGACAAACTGGATACA

AACTCCGTATATGAGCCTTACTACCATTCAGATCATGCGGAGTCTTCATGGGTAAATCGGGGAGAGTC

TTCGCGAAAAGCGTACGATCATAACTCACCTTATATATGGCCACGTAATGATTATGATGGATTTTTAGA

GAACGCACACGAACACCATGGGGTGTATAATCAGGGCCGTGGTATCGATAGCGGGGAACGGTTAATG

CAACCCACACAAATGTCTGCACAGGAGGATCTTGGGGACGATACGGGCATCCACGTTATCCCTACGTT

AAACGGCGATGACGACATAAAATTGTAAATGTGGACCAACGTCAATACGGTGACGTGTTTAAAGGA

GATCTTAATCCAAAACCCCAAGGCCAAAGACTCATTGAGGTGTCAGTGGAAGAAAATCACCCGTTTAC

TTTACGCGCACCGATTCAGCGGATTTATGGAGTCCGGTACACCGAGACTTGGAGCTTTTTGCCGTCATT

AACCTGTACGGGAGACGCAGCGCCCGCCATCCAGCATATATGTTTAAAACATACAACATGCTTTCAAG

ACGTGGTGGTGGATGTGGATTGCGCGGAAAATACTAAAGAGGATCAGTTGGCCGAAATCAGTTACCGT

TTTCAAGGTAAGAAGGAAGCGGACCAACCGTGGATTGTTGTAAACACGAGCACACTGTTTGATGAACT

CGAATTAGACCCCCCCGAGATTGAACCGGGTGTCTTGAAAGTACTTCGGACAGAAAAACAATACTTGG

GTGTGTACATTTGGAACATGCGCGGCTCCGATGGTACGTCTACCTACGCCACGTTTTTGGTCACCTGGA

AAGGGGATGAAAAAACAAGAAACCCTACGCCCGCAGTAACTCCTCAACCAAGAGGGGCTGAGTTTCA

TATGTGGAATTACCACTCGCATGTATTTTCAGTTGGTGATACGTTTAGCTTGGCAATGCATCTTCAGTA

TAAGATACATGAAGCGCCATTTGATTTGCTGTTAGAGTGGTTGTATGTCCCCATCGATCCTACATGTCA

ACCAATGCGGTTATATTCTACGTGTTTGTATCATCCCAACGCACCCCAATGCCTCTCTCATATGAATTC

CGGTTGTACATTTACCTCGCCACATTTAGCCCAGCGTGTTGCAAGCACAGTGTATCAAAATTGTGAACA

TGCAGATAACTACACCGCATATTGTCTGGGAATATCTCATATGGAGCCTAGCTTTGGTCTAATCTTACA
```

-continued

CGACGGGGGCACCACGTTAAAGTTTGTAGATACACCCGAGAGTTTGTCGGGATTATACGTTTTTGTGG

TGTATTTTAACGGGCATGTTGAAGCCGTAGCATACACTGTTGTATCCACAGTAGATCATTTTGTAAACG

CAATTGAAGAGCGTGGATTTCCGCCAACGGCCGGTCAGCCACCGGCGACTACTAAACCCAAGGAAATT

ACCCCCGTAAACCCCGGAACGTCACCACTTCTACGATATGCCGCATGGACCGGAGGGCTTGCAGCAGT

AGTACTTTTATGTCTCGTAATATTTTTAATCTGTACGGCTTGATGATAATAGGCTGGAGCCTCGGTGGC

CATGCTTCTTGCCCCTTGGGCCTCCCCCCAGCCCCTCCTCCCCTTCCTGCACCCGTACCCCCGTGGTCTT

TGAATAAAGTCTGAGTGGGCGGC

VZV-GE-delete-562-IgKappa (mRNA)

(SEQ ID NO: 126)

UCAAGCUUUUGGACCCUCGUACAGAAGCUAAUACGACUCACUAUAGGGAAAUAAGAGAGAAAAGA

AGAGUAAGAAGAAAUAUAAGAGCCACCAUGGAAACCCCGGCGCAGCUGCUGUUUCUGCUGCUGCUG

UGGCUGCCGGAUACCACCGGCUCCGUCUUGCGAUACGAUGAUUUUCACAUCGAUGAAGACAAACUG

GAUACAAACUCCGUAUAUGAGCCUUACUACCAUUCAGAUCAUGCGGAGUCUUCAUGGGUAAAUCG

GGGAGAGUCUUCGCGAAAAGCGUACGAUCAUAACUCACCUUAUAUAUGGCCACGUAAUGAUUAUG

AUGGAUUUUUAGAGAACGCACACGAACACCAUGGGGGUGUAUAAUCAGGGCCGUGGGUAUCGAUAGC

GGGGAACGGUUAAUGCAACCCACACAAAUGUCUGCACAGGAGGAUCUUGGGGACGAUACGGGCAU

CCACGUUAUCCCUACGUUAAACGGCGAUGACAGACAUAAAAUUGUAAAUGUGGACCAACGUCAAU

ACGGUGACGUGUUUAAAGGAGAUCUUAAUCCAAAACCCCAAGGCCAAAGACUCAUUGAGGUGUCA

GUGGAAGAAAAUCACCCGUUUACUUUACGCGCACCGAUUCAGCGGAUUUAUGGAGUCCGGUACACC

GAGACUUGGAGCUUUUUGCCGUCAUUAACCUGUACGGGAGACGCAGCGCCCGCCAUCCAGCAUAUA

UGUUUAAAACAUACAACAUGCUUUCAAGACGUGGUGGUGGAUGUGGAUUGCGCGGAAAAUACUAA

AGAGGAUCAGUUGGCCGAAAUCAGUUACCGUUUUCAAGGUAAGAAGGAAGCGGACCAACCGUGGA

UUGUUGUAAACACGAGCACACUGUUUGAUGAACUCGAAUUAGACCCCCCCGAGAUUGAACCGGGUG

UCUUGAAAGUACUUCGGACAGAAAAACAAUACUUGGGGUGUGUACAUUUGGAACAUGCGCGGCUCC

GAUGGUACGUCUACCUACGCCACGUUUUUGGUCACCUGGAAAGGGGAUGAAAAAACAAGAAACCC

UACGCCCGCAGUAACUCCUCAACCAAGAGGGGCUGAGUUUCAUAUGUGGAAUUACCACUCGCAUGU

AUUUUCAGUUGGUGAUACGUUUAGCUUGGCAAUGCAUCUUCAGUAUAAGAUACAUGAAGCGCCAU

UUGAUUUGCUGUUAGAGUGGUUGUAUGUCCCCAUCGAUCCUACAUGUCAACCAAUGCGGUUAUAU

UCUACGUGUUUGUAUCAUCCCAACGCACCCCAAUGCCUCUCUCAUAUGAAUUCCGGUUGUACAUUU

ACCUCGCCACAUUUAGCCCAGCGUGUUGCAAGCACAGUGUAUCAAAAUUGUGAACAUGCAGAUAAC

UACACCGCAUAUUGUCUGGGAAUAUCUCAUAUGGAGCCUAGCUUUGGUCUAAUCUUACACGACGG

GGGCACCACGUUAAAGUUUGUAGAUACACCCGAGAGUUUGUCGGGAUUAUACGUUUUUGUGGUGU

AUUUUAACGGGCAUGUUGAAGCCGUAGCAUACACUGUUGUAUCCACAGUAGAUCAUUUUGUAAAC

GCAAUUGAAGAGCGUGGAUUUCCGCCAACGGCCGGUCAGCCACCGGCGACUACUAAACCCAAGGAA

AUUACCCCCGUAAACCCCGGAACGUCACCACUUCUACGAUAUGCCGCAUGGACCGGAGGGCUUGCA

GCAGUAGUACUUUUAUGUCUCGUAAUAUUUUUAAUCUGUACGGCUUGAUGAUAAUAGGCUGGAGC

CUCGGUGGCCAUGCUUCUUGCCCCUUGGGCCUCCCCCCAGCCCCUCCUCCCCUUCCUGCACCCGUAC

CCCCGUGGUCUUUGAAUAAAGUCUGAGUGGGCGGC

VZV-GE- delete-574

(SEQ ID NO: 5)

TCAAGCTTTTGGACCCTCGTACAGAAGCTAATACGACTCACTATAGGGAAATAAGAGAGAAAAGAAG

AGTAAGAAGAAATATAAGAGCCACCATGGGGACAGTTAATAAACCTGTGGTGGGGGTATTGATGGGG

TTCGGAATTATCACGGGAACGTTGCGTATAACGAATCCGGTCAGAGCATCCGTCTTGCGATACGATGA

-continued

```
TTTTCACATCGATGAAGACAAACTGGATACAAACTCCGTATATGAGCCTTACTACCATTCAGATCATGC

GGAGTCTTCATGGGTAAATCGGGGAGAGTCTTCGCGAAAAGCGTACGATCATAACTCACCTTATATAT

GGCCACGTAATGATTATGATGGATTTTTAGAGAACGCACACGAACACCATGGGGTGTATAATCAGGGC

CGTGGTATCGATAGCGGGGAACGGTTAATGCAACCCACACAAATGTCTGCACAGGAGGATCTTGGGG

ACGATACGGGCATCCACGTTATCCCTACGTTAAACGGCGATGACAGACATAAAATTGTAAATGTGGAC

CAACGTCAATACGGTGACGTGTTTAAAGGAGATCTTAATCCAAAACCCCAAGGCCAAAGACTCATTGA

GGTGTCAGTGGAAGAAAATCACCCGTTTACTTTACGCGCACCGATTCAGCGGATTTATGGAGTCCGGT

ACACCGAGACTTGGAGCTTTTTGCCGTCATTAACCTGTACGGGAGCGCAGCGCCCGCCATCCAGCAT

ATATGTTTAAAACATACAACATGCTTTCAAGACGTGGTGGTGGATGTGGATTGCGCGGAAAATACTAA

AGAGGATCAGTTGGCCGAAATCAGTTACCGTTTTCAAGGTAAGAAGGAAGCGGACCAACCGTGGATT

GTTGTAAACACGAGCACACTGTTTGATGAACTCGAATTAGACCCCCCCGAGATTGAACCGGGTGTCTT

GAAAGTACTTCGGACAGAAAAACAATACTTGGGTGTGTACATTTGGAACATGCGCGGCTCCGATGGTA

CGTCTACCTACGCCACGTTTTTGGTCACCTGGAAAGGGGATGAAAAAACAAGAAACCCTACGCCCGCA

GTAACTCCTCAACCAAGAGGGGCTGAGTTTCATATGTGGAATTACCACTCGCATGTATTTTCAGTTGGT

GATACGTTTAGCTTGGCAATGCATCTTCAGTATAAGATACATGAAGCGCCATTTGATTTGCTGTTAGAG

TGGTTGTATGTCCCCATCGATCCTACATGTCAACCAATGCGGTTATATTCTACGTGTTTGTATCATCCCA

ACGCACCCCAATGCCTCTCTCATATGAATTCCGGTTGTACATTTACCTCGCCACATTTAGCCCAGCGTG

TTGCAAGCACAGTGTATCAAAATTGTGAACATGCAGATAACTACACCGCATATTGTCTGGGAATATCT

CATATGGAGCCTAGCTTTGGTCTAATCTTACACGACGGGGGCACCACGTTAAAGTTTGTAGATACACC

CGAGAGTTTGTCGGGATTATACGTTTTTGTGGTGTATTTTAACGGGCATGTTGAAGCCGTAGCATACAC

TGTTGTATCCACAGTAGATCATTTTGTAAACGCAATTGAAGAGCGTGGATTTCCGCCAACGGCCGGTC

AGCCACCGGCGACTACTAAACCCAAGGAAATTACCCCCGTAAACCCCGGAACGTCACCACTTCTACGA

TATGCCGCATGGACCGGAGGGCTTGCAGCAGTAGTACTTTTATGTCTCGTAATATTTTTAATCTGTACG

GCTAAACGAATGAGGGTTAAAGCCTATAGGGTAGACAAGTGATGATAATAGGCTGGAGCCTCGGTGG

CCATGCTTCTTGCCCCTTGGGCCTCCCCCCAGCCCCTCCTCCCCTTCCTGCACCCGTACCCCCGTGGTCT

TTGAATAAAGTCTGAGTGGGCGGC
```

VZV-GE- delete-574 (mRNA)

(SEQ ID NO: 127)

```
UCAAGCUUUUGGACCCUCGUACAGAAGCUAAUACGACUCACUAUAGGGAAAUAAGAGAGAAAAGA

AGAGUAAGAAGAAAUAUAAGAGCCACCAUGGGGCAGUUAAUAAACCUGUGGUGGGGGUAUUGAU

GGGGUUCGGAAUUAUCACGGGAACGUUGCGUAUAACGAAUCCGGUCAGAGCAUCCGUCUUGCGAU

ACGAUGAUUUUCACAUCGAUGAAGACAAACUGGAUACAAACUCCGUAUAUGAGCCUUACUACCAU

UCAGAUCAUGCGGAGUCUUCAUGGGUAAAUCGGGGAGAGUCUUCGCGAAAAGCGUACGAUCAUAA

CUCACCUUAUAUAUGGCCACGUAAUGAUUAUGAUGGAUUUUUAGAGAACGCACACGAACACCAUG

GGGUGUAUAAUCAGGGCCGUGGUAUCGAUAGCGGGGAACGGUUAAUGCAACCCACACAAAUGUCU

GCACAGGAGGAUCUUGGGGACGAUACGGGCAUCCACGUUAUCCCUACGUUAAACGGCGAUGACAGA

CAUAAAAUUGUAAAUGUGGACCAACGUCAAUACGGUGACGUGUUUAAAGGAGAUCUUAAUCCAAA

ACCCCAAGGCCAAAGACUCAUUGAGGUGUCAGUGGAAGAAAAUCACCCGUUUACUUUACGCGCACC

GAUUCAGCGGAUUUAUGGAGUCCGGUACACCGAGACUUGGAGCUUUUUGCCGUCAUUAACCUGUA

CGGGAGACGCAGCGCCCGCCAUCCAGCAUAUAUGUUUAAAACAUACAACAUGCUUUCAAGACGUGG

UGGUGGAUGUGGAUUGCGCGGAAAAUACUAAAGAGGAUCAGUUGGCCGAAAUCAGUUACCGUUUU
```

-continued

```
CAAGGUAAGAAGGAAGCGGACCAACCGUGGAUUGUUGUAAACACGAGCACACUGUUUGAUGAACU

CGAAUUAGACCCCCCCGAGAUUGAACCGGGUGUCUUGAAAGUACUUCGGACAGAAAAACAAUACUU

GGGUGUGUACAUUUGGAACAUGCGCGGCUCCGAUGGUACGUCUACCUACGCCACGUUUUUGGUCAC

CUGGAAAGGGGAUGAAAAAACAAGAAACCCUACGCCCGCAGUAACUCCUCAACCAAGAGGGGCUGA

GUUUCAUAUGUGGAAUUACCACUCGCAUGUAUUUUCAGUUGGUGAUACGUUUAGCUUGGCAAUGC

AUCUUCAGUAUAAGAUACAUGAAGCGCCAUUUGAUUUGCUGUUAGAGUGGUUGUAUGUCCCCAUC

GAUCCUACAUGUCAACCAAUGCGGUUAUAUUCUACGUGUUUGUAUCAUCCCAACGCACCCCAAUGC

CUCUCUCAUAUGAAUUCCGGUUGUACAUUUACCUCGCCACAUUUAGCCCAGCGUGUUGCAAGCACA

GUGUAUCAAAAUUGUGAACAUGCAGAUAACUACACCGCAUAUUGUCUGGGAAUAUCUCAUAUGGA

GCCUAGCUUUGGUCUAAUCUUACACGACGGGGGCACCACGUUAAAGUUUGUAGAUACACCCGAGAG

UUUGUCGGGAUUAUACGUUUUUGUGGUGUAUUUUAACGGGCAUGUUGAAGCCGUAGCAUACACUG

UUGUAUCCACAGUAGAUCAUUUUUGUAAACGCAAUUGAAGAGCGUGGAUUUCCGCCAACGGCCGGU

CAGCCACCGGCGACUACUAAACCCAAGGAAAUUACCCCCGUAAACCCCGGAACGUCACCACUUCUA

CGAUAUGCCGCAUGGACCGGAGGGCUUGCAGCAGUAGUACUUUUAUGUCUCGUAAUAUUUUUAAU

CUGUACGGCUAAACGAAUGAGGGUUAAAGCCUAUAGGGUAGACAAGUGAUGAUAAUAGGCUGGAG

CCUCGGUGGCCAUGCUUCUUGCCCCUUGGGCCUCCCCCCAGCCCCUCCUCCCCUUCCUGCACCCGUA

CCCCCGUGGUCUUUGAAUAAAGUCUGAGUGGGCGGC
```

VZV-GE- delete-574-Y569A (SEQ ID NO: 6)

```
TCAAGCTTTTGGACCCTCGTACAGAAGCTAATACGACTCACTATAGGGAAATAAGAGAGAAAAGAAG

AGTAAGAAGAAATATAAGAGCCACCATGGGGACAGTTAATAAACCTGTGGTGGGGGTATTGATGGGG

TTCGGAATTATCACGGGAACGTTGCGTATAACGAATCCGGTCAGAGCATCCGTCTTGCGATACGATGA

TTTTCACATCGATGAAGACAAACTGGATACAAACTCCGTATATGAGCCTTACTACCATTCAGATCATGC

GGAGTCTTCATGGGTAAATCGGGGAGAGTCTTCGCGAAAAGCGTACGATCATAACTCACCTTATATAT

GGCCACGTAATGATTATGATGGATTTTTAGAGAACGCACACGAACACCATGGGGTGTATAATCAGGGC

CGTGGTATCGATAGCGGGGAACGGTTAATGCAACCCACACAAATGTCTGCACAGGAGGATCTTGGGG

ACGATACGGGCATCCACGTTATCCCTACGTTAAACGGCGATGACAGACATAAAATTGTAAATGTGGAC

CAACGTCAATACGGTGACGTGTTTAAAGGAGATCTTAATCCAAAACCCCAAGGCCAAAGACTCATTGA

GGTGTCAGTGGAAGAAAATCACCCGTTTACTTTACGCGCACCGATTCAGCGGATTTATGGAGTCCGGT

ACACCGAGACTTGGAGCTTTTTGCCGTCATTAACCTGTACGGGAGACGCAGCGCCCGCCATCCAGCAT

ATATGTTTAAAACATACAACATGCTTTCAAGACGTGGTGGTGGATGTGGATTGCGCGGAAAATACTAA

AGAGGATCAGTTGGCCGAAATCAGTTACCGTTTTCAAGGTAAGAAGGAAGCGGACCAACCGTGGATT

GTTGTAAACACGAGCACACTGTTTGATGAACTCGAATTAGACCCCCCCGAGATTGAACCGGGTGTCTT

GAAAGTACTTCGGACAGAAAAACAATACTTGGGTGTGTACATTTGGAACATGCGCGGCTCCGATGGTA

CGTCTACCTACGCCACGTTTTTGGTCACCTGGAAAGGGGATGAAAAAACAAGAAACCCTACGCCCGCA

GTAACTCCTCAACCAAGAGGGGCTGAGTTTCATATGTGGAATTACCACTCGCATGTATTTTCAGTTGGT

GATACGTTTAGCTTGGCAATGCATCTTCAGTATAAGATACATGAAGCGCCATTTGATTTGCTGTTAGAG

TGGTTGTATGTCCCCATCGATCCTACATGTCAACCAATGCGGTTATATTCTACGTGTTTGTATCATCCCA

ACGCACCCCAATGCCTCTCTCATATGAATTCCGGTTGTACATTTACCTCGCCACATTTAGCCCAGCGTG

TTGCAAGCACAGTGTATCAAAATTGTGAACATGCAGATAACTACACCGCATATTGTCTGGGAATATCT

CATATGGAGCCTAGCTTTGGTCTAATCTTACACGACGGGGGCACCACGTTAAAGTTTGTAGATACACC

CGAGAGTTTGTCGGGATTATACGTTTTTGTGGTGTATTTTAACGGGCATGTTGAAGCCGTAGCATACAC
```

-continued

```
TGTTGTATCCACAGTAGATCATTTTGTAAACGCAATTGAAGAGCGTGGATTTCCGCCAACGGCCGGTC

AGCCACCGGCGACTACTAAACCCAAGGAAATTACCCCCGTAAACCCCGGAACGTCACCACTTCTACGA

TATGCCGCATGGACCGGAGGGCTTGCAGCAGTAGTACTTTTATGTCTCGTAATATTTTTAATCTGTACG

GCTAAACGAATGAGGGTTAAAGCCGCCAGGGTAGACAAGTGATGATAATAGGCTGGAGCCTCGGTGG

CCATGCTTCTTGCCCCTTGGGCCTCCCCCCAGCCCCTCCTCCCCTTCCTGCACCCGTACCCCCGTGGTCT

TTGAATAAAGTCTGAGTGGGCGGC
```

VZV-GE- delete-574-Y569A (mRNA)

(SEQ ID NO: 128)
```
UCAAGCUUUUGGACCCUCGUACAGAAGCUAAUACGACUCACUAUAGGGAAAUAAGAGAGAAAAGA

AGAGUAAGAAGAAAUAUAAGAGCCACCAUGGGGACAGUUAAUAAACCUGUGGUGGGGGUAUUGAU

GGGGUUCGGAAUUAUCACGGGAACGUUGCGUAUAACGAAUCCGGUCAGAGCAUCCGUCUUGCGAU

ACGAUGAUUUUCACAUCGAUGAAGACAAACUGGAUACAAACUCCGUAUAUGAGCCUUACUACCAU

UCAGAUCAUGCGGAGUCUUCAUGGGUAAAUCGGGGAGAGUCUUCGCGAAAAGCGUACGAUCAUAA

CUCACCUUAUAUAUGGCCACGUAAUGAUUAUGAUGGAUUUUUAGAGAACGCACACGAACACCAUG

GGGUGUAUAAUCAGGGCCGUGGGUAUCGAUAGCGGGGAACGGUUAAUGCAACCCACACAAAUGUCU

GCACAGGAGGAUCUUGGGGACGAUACGGGCAUCCACGUUAUCCCUACGUUAAACGGCGAUGACAGA

CAUAAAAUUGUAAAUGUGGACCAACGUCAAUACGGUGACGUGUUUAAAGGAGAUCUUAAUCCAAA

ACCCCAAGGCCAAAGACUCAUUGAGGUGUCAGUGGAAGAAAAUCACCCGUUUACUUUACGCGCACC

GAUUCAGCGGAUUUAUGGAGUCCGGUACACCGAGACUUGGAGCUUUUUGCCGUCAUUAACCUGUA

CGGGAGACGCAGCGCCCGCCAUCCAGCAUAUAUGUUUAAAACAUACAACAUGCUUUCAAGACGUGG

UGGUGGAUGUGGAUUGCGCGGAAAAAUACUAAAGAGGAUCAGUUGGCCGAAAUCAGUUACCGUUUU

CAAGGUAAGAAGGAAGCGGACCAACCGUGGAUUGUUGUAAACACGAGCACACUGUUUGAUGAACU

CGAAUUAGACCCCCCCGAGAUUGAACCGGGUGUCUUGAAAGUACUUCGGACAGAAAAACAAUACUU

GGGUGUGUACAUUUGGAACAUGCGCGGCUCCGAUGGUACGUCUACCUACGCCACGUUUUUGGUCAC

CUGGAAAGGGGAUGAAAAAACAAGAAACCCUACGCCCGCAGUAACUCCUCAACCAAGAGGGGCUGA

GUUUCAUAUGUGGAAUUACCACUCGCAUGUAUUUUCAGUUGGUGAUACGUUUAGCUUGGCAAUGC

AUCUUCAGUAUAAGAUACAUGAAGCGCCAUUUGAUUUGCUGUUAGAGUGGUUGUAUGUCCCCAUC

GAUCCUACAUGUCAACCAAUGCGGUUAUAUUCUACGUGUUUGUAUCAUCCCAACGCACCCCAAUGC

CUCUCUCAUAUGAAUUCCGGUUGUACAUUUACCUCGCCACAUUUAGCCCAGCGUGUUGCAAGCACA

GUGUAUCAAAAUUGUGAACAUGCAGAUAACUACACCGCAUAUUGUCUGGGAAUAUCUCAUAUGGA

GCCUAGCUUUGGUCUAAUCUUACACGACGGGGGCACCACGUUAAAGUUUGUAGAUACACCCGAGAG

UUUGUCGGGAUUAUACGUUUUUGUGGGUGUAUUUUAACGGGCAUGUUGAAGCCGUAGCAUACACUG

UUGUAUCCACAGUAGAUCAUUUUGUAAACGCAAUUGAAGAGCGUGGAUUUCCGCCAACGGCCGGU

CAGCCACCGGCGACUACUAAACCCAAGGAAAUUACCCCCGUAAACCCCGGAACGUCACCACUUCUA

CGAUAUGCCGCAUGGACCGGAGGGCUUGCAGCAGUAGUACUUUUAUGUCUCGUAAUAUUUUUAAU

CUGUACGGCUAAACGAAUGAGGGUUAAAGCCGCCAGGGUAGACAAGUGAUGAUAAUAGGCUGGAG

CCUCGGUGGCCAUGCUUCUUGCCCCUUGGGCCUCCCCCCAGCCCCUCCUCCCCUUCCUGCACCCGUA

CCCCCGUGGUCUUUGAAUAAAGUCUGAGUGGGCGGC
```

VZV-gE-full length-AEAADA (SEQ ID NO: 58)

(SEQ ID NO: 7)
```
TCAAGCTTTTGGACCCTCGTACAGAAGCTAATACGACTCACTATAGGGAAATAAGAGAGAAAAGAAG

AGTAAGAAGAAATATAAGAGCCACCATGGGGACAGTTAATAAACCTGTGGTGGGGGTATTGATGGGG
```

-continued

TTCGGAATTATCACGGGAACGTTGCGTATAACGAATCCGGTCAGAGCATCCGTCTTGCGATACGATGA

TTTTCACATCGATGAAGACAAACTGGATACAAACTCCGTATATGAGCCTTACTACCATTCAGATCATGC

GGAGTCTTCATGGGTAAATCGGGGAGAGTCTTCGCGAAAAGCGTACGATCATAACTCACCTTATATAT

GGCCACGTAATGATTATGATGGATTTTTAGAGAACGCACACGAACACCATGGGGTGTATAATCAGGGC

CGTGGTATCGATAGCGGGGAACGGTTAATGCAACCCACACAAATGTCTGCACAGGAGGATCTTGGGG

ACGATACGGGCATCCACGTTATCCCTACGTTAAACGGCGATGACAGACATAAAATTGTAAATGTGGAC

CAACGTCAATACGGTGACGTGTTTAAAGGAGATCTTAATCCAAAACCCCAAGGCCAAAGACTCATTGA

GGTGTCAGTGGAAGAAAATCACCCGTTTACTTTACGCGCACCGATTCAGCGGATTTATGGAGTCCGGT

ACACCGAGACTTGGAGCTTTTTGCCGTCATTAACCTGTACGGGAGACGCAGCGCCCGCCATCCAGCAT

ATATGTTTAAAACATACAACATGCTTTCAAGACGTGGTGGTGGATGTGGATTGCGCGGAAAATACTAA

AGAGGATCAGTTGGCCGAAATCAGTTACCGTTTTCAAGGTAAGAAGGAAGCGGACCAACCGTGGATT

GTTGTAAACACGAGCACACTGTTTGATGAACTCGAATTAGACCCCCCCGAGATTGAACCGGGTGTCTT

GAAAGTACTTCGGACAGAAAAACAATACTTGGGTGTGTACATTTGGAACATGCGCGGCTCCGATGGTA

CGTCTACCTACGCCACGTTTTTGGTCACCTGGAAAGGGGATGAAAAAACAAGAAACCCTACGCCCGCA

GTAACTCCTCAACCAAGAGGGGCTGAGTTTCATATGTGGAATTACCACTCGCATGTATTTTCAGTTGGT

GATACGTTTAGCTTGGCAATGCATCTTCAGTATAAGATACATGAAGCGCCATTTGATTTGCTGTTAGAG

TGGTTGTATGTCCCCATCGATCCTACATGTCAACCAATGCGGTTATATTCTACGTGTTTGTATCATCCCA

ACGCACCCCAATGCCTCTCTCATATGAATTCCGGTTGTACATTTACCTCGCCACATTTAGCCCAGCGTG

TTGCAAGCACAGTGTATCAAAATTGTGAACATGCAGATAACTACACCGCATATTGTCTGGGAATATCT

CATATGGAGCCTAGCTTTGGTCTAATCTTACACGACGGGGGCACCACGTTAAAGTTTGTAGATACACC

CGAGAGTTTGTCGGGATTATACGTTTTTGTGGTGTATTTTAACGGGCATGTTGAAGCCGTAGCATACAC

TGTTGTATCCACAGTAGATCATTTTGTAAACGCAATTGAAGAGCGTGGATTTCCGCCAACGGCCGGTC

AGCCACCGGCGACTACTAAACCCAAGGAAATTACCCCCGTAAACCCCGGAACGTCACCACTTCTACGA

TATGCCGCATGGACCGGAGGGCTTGCAGCAGTAGTACTTTTATGTCTCGTAATATTTTTAATCTGTACG

GCTAAACGAATGAGGGTTAAAGCCTATAGGGTAGACAAGTCCCCGTATAACCAAAGCATGTATTACGC

TGGCCTTCCAGTGGACGATTTCGAGGACGCCGAAGCCGCCGATGCCGAAGAAGAGTTTGGTAACGCG

ATTGGAGGGAGTCACGGGGGTTCGAGTTACACGGTGTATATAGATAAGACCCGGTGATGATAATAGG

CTGGAGCCTCGGTGGCCATGCTTCTTGCCCCTTGGGCCTCCCCCCAGCCCCTCCTCCCCTTCCTGCACCC

GTACCCCCGTGGTCTTTGAATAAAGTCTGAGTGGGCGGC

VZV-gE-full length-AEAADA (SEQ ID NO: 58) (mRNA)

(SEQ ID NO: 129)

UCAAGCUUUUGGACCCUCGUACAGAAGCUAAUACGACUCACUAUAGGGAAAUAAGAGAGAAAGA

AGAGUAAGAAGAAAUAUAAGAGCCACCAUGGGGACAGUUAAUAAACCUGUGGUGGGGGUAUUGAU

GGGGUUCGGAAUUAUCACGGGAACGUUGCGUAUAACGAAUCCGGUCAGAGCAUCCGUCUUGCGAU

ACGAUGAUUUUCACAUCGAUGAAGACAAACUGGAUACAAACUCCGUAUAUGAGCCUUACUACCAU

UCAGAUCAUGCGGAGUCUUCAUGGGUAAAUCGGGGAGAGUCUUCGCGAAAAGCGUACGAUCAUAA

CUCACCUUAUAUAUGGCCACGUAAUGAUUAUGAUGGAUUUUUAGAGAACGCACACGAACACCAUG

GGGUGUAUAAUCAGGGCCGUGGUAUCGAUAGCGGGGAACGGUUAAUGCAACCCACACAAAUGUCU

GCACAGGAGGAUCUUGGGGGACGAUACGGGCAUCCACGUUAUCCCUACGUUAAACGGCGAUGACAGA

CAUAAAAUUGUAAAUGUGGACCAACGUCAAUACGGUGACGUGUUUAAAGGAGAUCUUAAUCCAAA

ACCCCAAGGCCAAAGACUCAUUGAGGUGUCAGUGGAAGAAAAUCACCCGUUUACUUUACGCGCACC

GAUUCAGCGGAUUUAUGGAGUCCGGUACACCGAGACUUGGAGCUUUUUGCCGUCAUUAACCUGUA

CGGGAGACGCAGCGCCCGCCAUCCAGCAUAUAUGUUUAAAACAUACAACAUGCUUUCAAGACGUGG

UGGUGGAUGUGGAUUGCGCGGAAAAUACUAAAGAGGAUCAGUUGGCCGAAAUCAGUUACCGUUUU

CAAGGUAAGAAGGAAGCGGACCAACCGUGGAUUGUUGUAAACACGAGCACACUGUUUGAUGAACU

CGAAUUAGACCCCCCCGAGAUUGAACCGGGUGUCUUGAAAGUACUUCGGACAGAAAAACAAUACUU

GGGUGUGUACAUUUGGAACAUGCGCGGCUCCGAUGGUACGUCUACCUACGCCACGUUUUUGGUCAC

CUGGAAAGGGGAUGAAAAAACAAGAAACCCUACGCCCGCAGUAACUCCUCAACCAAGAGGGGCUGA

GUUUCAUAUGUGGAAUUACCACUCGCAUGUAUUUUCAGUUGGUGAUACGUUUAGCUUGGCAAUGC

AUCUUCAGUAUAAGAUACAUGAAGCGCCAUUUGAUUUGCUGUUAGAGUGGUUGUAUGUCCCCAUC

GAUCCUACAUGUCAACCAAUGCGGUUAUAUUCUACGUGUUUGUAUCAUCCCAACGCACCCCAAUGC

CUCUCUCAUAUGAAUUCCGGUUGUACAUUUACCUCGCCACAUUUAGCCCAGCGUGUUGCAAGCACA

GUGUAUCAAAAUUGUGAACAUGCAGAUAACUACACCGCAUAUUGUCUGGGAAUAUCUCAUAUGGA

GCCUAGCUUUGGUCUAAUCUUACACGACGGGGGCACCACGUUAAAGUUUGUAGAUACACCCGAGAG

UUUGUCGGGAUUAUACGUUUUUGUGGUGUAUUUUAACGGGCAUGUUGAAGCCGUAGCAUACACUG

UUGUAUCCACAGUAGAUCAUUUUGUAAACGCAAUUGAAGAGCGUGGAUUUCCGCCAACGGCCGGU

CAGCCACCGGCGACUACUAAACCCAAGGAAAUUACCCCCGUAAACCCCGGAACGUCACCACUUCUA

CGAUAUGCCGCAUGGACCGGAGGGCUUGCAGCAGUAGUACUUUUAUGUCUCGUAAUAUUUUUAAU

CUGUACGGCUAAACGAAUGAGGGUUAAAGCCUAUAGGGUAGACAAGUCCCCGUAUAACCAAAGCA

UGUAUUACGCUGGCCUUCCAGUGGACGAUUUCGAGGACGCCGAAGCCGCCGAUGCCGAAGAAGAGU

UUGGUAACGCGAUUGGAGGGAGUCACGGGGGUUCGAGUUACACGGUGUAUAUAGAUAAGACCCGG

UGAUGAUAAUAGGCUGGAGCCUCGGUGGCCAUGCUUCUUGCCCCUUGGGCCUCCCCCCAGCCCCUC

CUCCCCUUCCUGCACCCGUACCCCCGUGGUCUUUGAAUAAAGUCUGAGUGGGCGGC

VZV-GE-full-AEAADA (SEQ ID NO: 58)-Y582G (SEQ ID NO: 8)
TCAAGCTTTTGGACCCTCGTACAGAAGCTAATACGACTCACTATAGGGAAATAAGAGAGAAAAGAAG

AGTAAGAAGAAATATAAGAGCCACCATGGGGACAGTTAATAAACCTGTGGTGGGGGGTATTGATGGGG

TTCGGAATTATCACGGGAACGTTGCGTATAACGAATCCGGTCAGAGCATCCGTCTTGCGATACGATGA

TTTTCACATCGATGAAGACAAACTGGATACAAACTCCGTATATGAGCCTTACTACCATTCAGATCATGC

GGAGTCTTCATGGGTAAATCGGGGAGAGTCTTCGCGAAAAGCGTACGATCATAACTCACCTTATATAT

GGCCACGTAATGATTATGATGGATTTTTAGAGAACGCACACGAACACCATGGGGTGTATAATCAGGGC

CGTGGTATCGATAGCGGGGAACGGTTAATGCAACCCACACAAATGTCTGCACAGGAGGATCTTGGGG

ACGATACGGGCATCCACGTTATCCCTACGTTAAACGGCGATGACAGACATAAAATTGTAAATGTGGAC

CAACGTCAATACGGTGACGTGTTTAAAGGAGATCTTAATCCAAAACCCCAAGGCCAAAGACTCATTGA

GGTGTCAGTGGAAGAAAATCACCCGTTTACTTTACGCGCACCGATTCAGCGGATTTATGGAGTCCGGT

ACACCGAGACTTGGAGCTTTTTGCCGTCATTAACCTGTACGGGAGACGCAGCGCCCGCCATCCAGCAT

ATATGTTTAAAACATACAACATGCTTTCAAGACGTGGTGGTGGATGTGGATTGCGCGGAAAATACTAA

AGAGGATCAGTTGGCCGAAATCAGTTACCGTTTTCAAGGTAAGAAGGAAGCGGACCAACCGTGGATT

GTTGTAAACACGAGCACACTGTTTGATGAACTCGAATTAGACCCCCCCGAGATTGAACCGGGTGTCTT

GAAAGTACTTCGGACAGAAAAACAATACTTGGGTGTGTACATTTGGAACATGCGCGGCTCCGATGGTA

CGTCTACCTACGCCACGTTTTTGGTCACCTGGAAAGGGGATGAAAAAACAAGAAACCCTACGCCCGCA

GTAACTCCTCAACCAAGAGGGGCTGAGTTTCATATGTGGAATTACCACTCGCATGTATTTTCAGTTGGT

GATACGTTTAGCTTGGCAATGCATCTTCAGTATAAGATACATGAAGCGCCATTTGATTTGCTGTTAGAG

-continued
TGGTTGTATGTCCCCATCGATCCTACATGTCAACCAATGCGGTTATATTCTACGTGTTTGTATCATCCCA

ACGCACCCCAATGCCTCTCTCATATGAATTCCGGTTGTACATTTACCTCGCCACATTTAGCCCAGCGTG

TTGCAAGCACAGTGTATCAAAATTGTGAACATGCAGATAACTACACCGCATATTGTCTGGGAATATCT

CATATGGAGCCTAGCTTTGGTCTAATCTTACACGACGGGGGCACCACGTTAAAGTTTGTAGATACACC

CGAGAGTTTGTCGGGATTATACGTTTTTGTGGTGTATTTTAACGGGCATGTTGAAGCCGTAGCATACAC

TGTTGTATCCACAGTAGATCATTTTGTAAACGCAATTGAAGAGCGTGGATTTCCGCCAACGGCCGGTC

AGCCACCGGCGACTACTAAACCCAAGGAAATTACCCCCGTAAACCCCGGAACGTCACCACTTCTACGA

TATGCCGCATGGACCGGAGGGCTTGCAGCAGTAGTACTTTTATGTCTCGTAATATTTTTAATCTGTACG

GCTAAACGAATGAGGGTTAAAGCCTATAGGGTAGACAAGTCCCCGTATAACCAAAGCATGTATGGCG

CTGGCCTTCCAGTGGACGATTTCGAGGACGCCGAAGCCGCCGATGCCGAAGAAGAGTTTGGTAACGCG

ATTGGAGGGAGTCACGGGGGTTCGAGTTACACGGTGTATATAGATAAGACCCGGTGATGATAATAGG

CTGGAGCCTCGGTGGCCATGCTTCTTGCCCCTTGGGCCTCCCCCCAGCCCCTCCTCCCCTTCCTGCACCC

GTACCCCCGTGGTCTTTGAATAAAGTCTGAGTGGGCGGC

VZV-GE-full-AEAADA (SEQ ID NO: 58)-Y582G (mRNA)

(SEQ ID NO: 130)
UCAAGCUUUUGGACCCUCGUACAGAAGCUAAUACGACUCACUAUAGGGAAAUAAGAGAGAAAAGA

AGAGUAAGAAGAAAUAUAAGAGCCACCAUGGGGACAGUUAAUAAACCUGUGGUGGGGGUAUUGAU

GGGGUUCGGAAUUAUCACGGGAACGUUGCGUAUAACGAAUCCGGUCAGAGCAUCCGUCUUGCGAU

ACGAUGAUUUUCACAUCGAUGAAGACAAACUGGAUACAAACUCCGUAUAUGAGCCUUACUACCAU

UCAGAUCAUGCGGAGUCUUCAUGGGGUAAAUCGGGGAGAGUCUUCGCGAAAAGCGUACGAUCAUAA

CUCACCUUAUAUAUGGCCACGUAAUGAUUAUGAUGGAUUUUUAGAGAACGCACACGAACACCAUG

GGGUGUAUAAUCAGGGCCGUGGGUAUCGAUAGCGGGGAACGGUUAAUGCAACCCACACAAAUGUCU

GCACAGGAGGAUCUUGGGGACGAUACGGGCAUCCACGUUAUCCCUACGUUAAACGGCGAUGACAGA

CAUAAAAAUUGUAAAUGUGGACCAACGUCAAUACGGUGACGUGUUUAAAGGAGAUCUUAAUCCAAA

ACCCCAAGGCCAAAGACUCAUUGAGGUGUCAGUGGAAGAAAAUCACCCGUUUACUUUACGCGCACC

GAUUCAGCGGAUUUAUGGAGUCCGGUACACCGAGACUUGGAGCUUUUUGCCGUCAUUAACCUGUA

CGGGAGACGCAGCGCCCGCCAUCCAGCAUAUAUGUUUAAAACAUACAACAUGCUUUCAAGACGUGG

UGGUGGAUGUGGAUUGCGCGGAAAAAUACUAAAGAGGAUCAGUUGGCCGAAAUCAGUUACCGUUUU

CAAGGUAAGAAGGAAGCGGACCAACCGUGGAUUGUUGUAAACACGAGCACACUGUUUGAUGAACU

CGAAUUAGACCCCCCCGAGAUUGAACCGGGUGUCUUGAAAGUACUUCGGACAGAAAAACAAUACUU

GGGUGUGUACAUUUGGAACAUGCGCGGCUCCGAUGGUACGUCUACCUACGCCACGUUUUUGGUCAC

CUGGAAAGGGGAUGAAAAAACAAGAAACCCUACGCCCGCAGUAACUCCUCAACCAAGAGGGGCUGA

GUUUCAUAUGUGGAAUUACCACUCGCAUGUAUUUUCAGUUGGUGAUACGUUUAGCUUGGCAAUGC

AUCUUCAGUAUAAGAUACAUGAAGCGCCAUUUGAUUUGCUGUUAGAGUGGUUGUAUGUCCCCAUC

GAUCCUACAUGUCAACCAAUGCGGUUAUAUUCUACGUGUUUGUAUCAUCCCAACGCACCCCAAUGC

CUCUCUCAUAUGAAUUCCGGUUGUACAUUUACCUCGCCACAUUUAGCCCAGCGUGUUGCAAGCACA

GUGUAUCAAAAUUGUGAACAUGCAGAUAACUACACCGCAUAUUGUCUGGGAAUAUCUCAUAUGGA

GCCUAGCUUUGGUCUAAUCUUACACGACGGGGGCACCACGUUAAAGUUUGUAGAUACACCCGAGAG

UUUGUCGGGAUUAUACGUUUUUGUGGUGUAUUUUAACGGGCAUGUUGAAGCCGUAGCAUACACUG

UUGUAUCCACAGUAGAUCAUUUUGUAAACGCAAUUGAAGAGCGUGGAUUUCCGCCAACGGCCGGU

CAGCCACCGGCGACUACUAAACCCAAGGAAAUUACCCCCGUAAACCCCGGAACGUCACCACUUCUA

CGAUAUGCCGCAUGGACCGGAGGGCUUGCAGCAGUAGUACUUUUAUGUCUCGUAAUAUUUUUAAU

-continued

CUGUACGGCUAAACGAAUGAGGGUUAAAGCCUAUAGGGUAGACAAGUCCCCGUAUAACCAAAGCA

UGUAUGGCGCUGGCCUUCCAGUGGACGAUUUCGAGGACGCCGAAGCCGCCGAUGCCGAAGAAGAGU

UUGGUAACGCGAUUGGAGGGAGUCACGGGGGUUCGAGUUACACGGUGUAUAUAGAUAAGACCCGG

UGAUGAUAAUAGGCUGGAGCCUCGUGGCCAUGCUUCUUGCCCCUUGGGCCUCCCCCCAGCCCCUC

CUCCCCUUCCUGCACCCGUACCCCCGUGGUCUUUGAAUAAAGUCUGAGUGGGCGGC

VZV_gE_Oka_hIgkappa
                                                          (SEQ ID NO: 41)
TCAAGCTTTTGGACCCTCGTACAGAAGCTAATACGACTCACTATAGGGAAATAAGAGAGAAAAGAAG

AGTAAGAAGAAATATAAGAGCCACCATGGAGACTCCCGCTCAGCTACTGTTCCTCCTGCTCCTTTGGC

TGCCTGATACTACAGGCTCTGTTTTGCGGTACGACGACTTTCACATCGATGAGGACAAGCTCGACACT

AATAGCGTGTATGAGCCCTACTACCATTCAGATCACGCCGAGTCCTCTTGGGTGAACAGGGGTGAAAG

TTCTAGGAAAGCCTATGATCACAACAGCCCTTATATTTGGCCACGGAATGATTACGACGGATTTCTCG

AAAATGCCCACGAGCATCACGGAGTGTACAACCAGGGCCGTGGAATCGACTCTGGGGAGAGATTGAT

GCAACCTACACAGATGAGCGCCCAGGAAGATCTCGGGGATGATACAGGAATTCACGTTATCCCTACAT

TAAACGGAGATGACCGCCACAAAATCGTCAATGTCGATCAAAGACAGTATGGAGATGTGTTCAAAGG

CGATCTCAACCCTAAGCCGCAGGGCCAGAGACTCATTGAGGTGTCTGTCGAAGAGAACCACCCTTTCA

CTCTGCGCGCTCCCATTCAGAGAATCTATGGAGTTCGCTATACGGAGACTTGGTCATTCCTTCCTTCCC

TGACATGCACCGGAGACGCCGCCCCTGCCATTCAGCACATATGCCTGAAACATACCACCTGTTTCCAG

GATGTGGTGGTTGATGTTGATTGTGCTGAAAATACCAAGGAAGACCAACTGGCCGAGATTAGTTACCG

GTTCCAAGGGAAAAAGGAAGCCGACCAGCCATGGATTGTGGTTAATACAAGCACTCTGTTCGATGAGC

TCGAGCTGGATCCCCCCGAGATAGAACCCGGAGTTCTGAAAGTGCTCCGGACAGAAAAACAATATCTG

GGAGTCTACATATGGAACATGCGCGGTTCCGATGGGACCTCCACTTATGCAACCTTTCTCGTCACGTGG

AAGGGAGATGAGAAAACTAGGAATCCCACACCCGCTGTCACACCACAGCCAAGAGGGGCTGAGTTCC

ATATGTGGAACTATCATAGTCACGTGTTTAGTGTCGGAGATACGTTTTCATTGGCTATGCATCTCCAGT

ACAAGATTCATGAGGCTCCCTTCGATCTGTTGCTTGAGTGGTTGTACGTCCCGATTGACCCGACCTGCC

AGCCCATGCGACTGTACAGCACCTGTCTCTACCATCCAAACGCTCCGCAATGTCTGAGCCACATGAAC

TCTGGGTGTACTTTCACCAGTCCCCACCTCGCCCAGCGGGTGGCCTCTACTGTTTACCAGAACTGTGAG

CACGCCGACAACTACACCGCATACTGCCTCGGTATTTCTCACATGGAACCCTCCTTCGGACTCATCCTG

CACGATGGGGGCACTACCCTGAAGTTCGTTGATACGCCAGAATCTCTGTCTGGGCTCTATGTTTTCGTG

GTCTACTTCAATGGCCATGTCGAGGCCGTGGCCTATACTGTCGTTTCTACCGTGGATCATTTTGTGAAC

GCCATCGAAGAACGGGGATTCCCCCCTACGGCAGGCCAGCCGCCTGCAACCACCAAGCCCAAGGAAA

TAACACCAGTGAACCCTGGCACCTCACCTCTCCTAAGATATGCCGCGTGGACAGGGGGACTGGCGGCA

GTGGTGCTCCTCTGTCTCGTGATCTTTCTGATCTGTACAGCCAAGAGGATGAGGGTCAAGGCTTATAGA

GTGGACAAGTCCCCCTACAATCAGTCAATGTACTACGCCGGCCTTCCCGTTGATGATTTTGAGGATTCC

GAGTCCACAGATACTGAGGAAGAGTTCGGTAACGCTATAGGCGGCTCTCACGGGGGTTCAAGCTACAC

GGTTTACATTGACAAGACACGCTGATAATAGGCTGGAGCCTCGGTGGCCATGCTTCTTGCCCCTTGGG

CCTCCCCCCAGCCCCTCCTCCCCTTCCTGCACCCGTACCCCCGTGGTCTTTGAATAAAGTCTGAGTGGG

CGGC

VZV_gE_Oka_hIgkappa (mRNA)
                                                         (SEQ ID NO: 131)
UCAAGCUUUUGGACCCUCGUACAGAAGCUAAUACGACUCACUAUAGGGAAAUAAGAGAGAAAAGA

AGAGUAAGAAGAAAUAUAAGAGCCACCAUGGAGACUCCCGCUCAGCUACUGUUCCUCCUGCUCCUU

-continued

UGGCUGCCUGAUACUACAGGCUCUGUUUUGCGGUACGACGACUUUCACAUCGAUGAGGACAAGCUC

GACACUAAUAGCGUGUAUGAGCCCUACUACCAUUCAGAUCACGCCGAGUCCUCUUGGGUGAACAGG

GGUGAAAGUUCUAGGAAAGCCUAUGAUCACAACAGCCCUUAUAUUUGGCCACGGAAUGAUUACGA

CGGAUUUCUCGAAAAUGCCCACGAGCAUCACGGAGUGUACAACCAGGGCCGUGGAAUCGACUCUGG

GGAGAGAUUGAUGCAACCUACACAGAUGAGCGCCCAGGAAGAUCUCGGGGAUGAUACAGGAAUUC

ACGUUAUCCCUACAUUAAACGGAGAUGACCGCCACAAAAUCGUCAAUGUCGAUCAAAGACAGUAUG

GAGAUGUGUUCAAAGGCGAUCUCAACCCUAAGCCGCAGGGCCAGAGACUCAUUGAGGUGUCUGUCG

AAGAGAACCACCCUUUCACUCUGCGCGCUCCCAUUCAGAGAAUCUAUGGAGUUCGCUAUACGGAGA

CUUGGUCAUUCCUUCCUUCCCUGACAUGCACCGGAGACGCCGCCCCUGCCAUUCAGCACAUAUGCC

UGAAACAUACCACCUGUUUCCAGGAUGUGGUGGUUGAUGUUGAUUGUGCUGAAAAUACCAAGGAA

GACCAACUGGCCGAGAUUAGUUACCGGUUCCAAGGGAAAAAGGAAGCCGACCAGCCAUGGAUUGU

GGUUAAUACAAGCACUCUGUUCGAUGAGCUCGAGCUGGAUCCCCCCGAGAUAGAACCCGGAGUUCU

GAAAGUGCUCCGGACAGAAAAACAAUAUCUGGGAGUCUACAUAUGGAACAUGCGCGGUUCCGAUG

GGACCUCCACUUAUGCAACCUUUCUCGUCACGUGGAAGGGAGAUGAGAAAACUAGGAAUCCCACAC

CCGCUGUCACACCACAGCCAAGAGGGGCUGAGUUCCAUAUGUGGAACUAUCAUAGUCACGUGUUUA

GUGUCGGAGAUACGUUUUCAUUGGCUAUGCAUCUCCAGUACAAGAUUCAUGAGGCUCCCUUCGAUC

UGUUGCUUGAGUGGUUGUACGUCCCGAUUGACCCGACCUGCCAGCCCAUGCGACUGUACAGCACCU

GUCUCUACCAUCCAAACGCUCCGCAAUGUCUGAGCCACAUGAACUCUGGGUGUACUUUCACCAGUC

CCCACCUCGCCCAGCGGGUGGCCUCUACUGUUUACCAGAACUGUGAGCACGCCGACAACUACACCG

CAUACUGCCUCGGUAUUUCUCACAUGGAACCCUCCUUCGGACUCAUCCUGCACGAUGGGGGCACUA

CCCUGAAGUUCGUUGAUACGCCCAGAACUCUGUCUGGGCUCUAUGUUUUCGUGGUCUACUUCAAUG

GCCAUGUCGAGGCCGUGGCCUAUACUGUCGUUUCUACCGUGGAUCAUUUUGUGAACGCCAUCGAAG

AACGGGAUUCCCCCCUACGGCAGGCCAGCCGCCUGCAACCACCAAGCCCAAGGAAAUAACACCAG

UGAACCCUGGCACCUCACCUCUCCUAAGAUAUGCCGCGUGGACAGGGGGACUGGCGGCAGUGGUGC

UCCUCUGUCUCGUGAUCUUUCUGAUCUGUACAGCCAAGAGGAUGAGGGUCAAGGCUUAUAGAGUG

GACAAGUCCCCCUACAAUCAGUCAAUGUACUACGCCGGCCUUCCCGUUGAUGAUUUUGAGGAUUCC

GAGUCCACAGAUACUGAGGAAGAGUUCGGUAACGCUAUAGGCGGCUCUCACGGGGGUUCAAGCUA

CACGGUUUACAUUGACAAGACACGCUGAUAAUAGGCUGGAGCCUCGGUGGCCAUGCUUCUUGCCCC

UUGGGCCUCCCCCCAGCCCCUCCUCCCCUUCCUGCACCCGUACCCCCGUGGUCUUUGAAUAAAGUCU

GAGUGGGCGGC

TABLE 2

| mRNA Name(s) | Sequence, NT (5′ UTR, ORF, 3′ UTR) | ORF Sequence, AA | ORF Sequence, NT | mRNA Sequence (assumes T100 tail) |
|---|---|---|---|---|
| | Sequences of Variant VZV gE Constructs | | | |
| VZ-V_gE_Oka | SEQ ID NO: 9<br>TCAAGCTTTTGG<br>ACCCTCGTACAG<br>AAGCTAATACGA<br>CTCACTATAGGG<br>AAATAAGAGAGA<br>AAAGAAGAGTAA<br>GAAGAAATATAA<br>GAGCCACCATGG<br>GGACAGTGAATA<br>AGCCGGTTGTGG | SEQ ID NO: 10<br>MGTVNKPVVGVLMGFGI<br>ITGTLRITNPVRASVLR<br>YDDFHIDEDKLDTNSVY<br>EPYYHSDHAESSWVNRG<br>ESSRKAYDHNSPYIWPR<br>NDYDGFLENAHEHHGVY<br>NQGRGIDSGERLMQPTQ<br>MSAQEDLGDDTGIHVIP<br>TLNGDDRHKIVNVDQRQ<br>YGDVFKGDLNPKPQGQR | SEQ ID NO: 11<br>ATGGGGACAGTGAATAA<br>GCCGGTTGTGGGCGTGC<br>TTATGGGCTTTGGGATT<br>ATTACCGGTACATTACG<br>AATTACCAATCCAGTGC<br>GCGCCAGTGTGCTGCGT<br>TACGACGACTTTCACAT<br>TGACGAGGATAAGCTGG<br>ATACTAACAGCGTGTAC<br>GAACCTTATTACCACTC | SEQ ID NO: 12<br>G*GGGAAATAAG<br>AGAGAAAAGAAG<br>AGTAAGAAGAAA<br>TATAAGAGCCAC<br>CATGGGGACAGT<br>GAATAAGCCGGT<br>TGTGGGCGTGCT<br>TATGGGCTTTGG<br>GATTATTACCGG<br>TACATTACGAAT |

TABLE 2-continued

| | | | |
|---|---|---|---|
| GCGTGCTTATGG | LIEVSVEENHPFTLRAP | AGATCATGCCGAATCAA | TACCAATCCAGT |
| GCTTTGGGATTA | IQRIYGVRYTETWSFLP | GCTGGGTTAATAGAGGA | GCGCGCCAGTGT |
| TTACCGGTACAT | SLTCTGDAAPAIQHICL | GAAAGCAGCCGAAAAGC | GCTGCGTTACGA |
| TACGAATTACCA | KHTTCFQDVVVDVDCAE | CTACGACCACAACTCAC | CGACTTTCACAT |
| ATCCAGTGCGCG | NTKEDQLAEISYRFQGK | CTTATATTTGGCCCAGA | TGACGAGGATAA |
| CCAGTGTGCTGC | KEADQPWIVVNTSTLFD | AACGATTATGACGGTTT | GCTGGATACTAA |
| GTTACGACGACT | ELELDPPEIEPGVLKVL | CCTGGAAAACGCACATG | CAGCGTGTACGA |
| TTCACATTGACG | RTEKQYLGVYIWNMRGS | AACACCATGGAGTCTAC | ACCTTATTACCA |
| AGGATAAGCTGG | DGTSTYATFLVTWKGDE | AACCAAGGCAGGGGAAT | CTCAGATCATGC |
| ATACTAACAGCG | KTRNPTPAVTPQPRGAE | CGACAGTGGCGAGCGTC | CGAATCAAGCTG |
| TGTACGAACCTT | FHMWNYHSHVFSVGDTF | TTATGCAGCCAACACAG | GGTTAATAGAGG |
| ATTACCACTCAG | SLAMHLQYKIHEAPFDL | ATGTCGGCACAGGAGGA | AGAAAGCAGCCG |
| ATCATGCCGAAT | LLEWLYVPIDPTCQPMR | TCTCGGTGATGACACCG | AAAAGCCTACGA |
| CAAGCTGGGTTA | LYSTCLYHPNAPQCLSH | GCATACACGTGATTCCC | CCACAACTCACC |
| ATAGAGGAGAAA | MNSGCTFTSPHLAQRVA | ACATTAAACGGCGACGA | TTTATATTTGGCC |
| GCAGCCGAAAAG | STVYQNCEHADNYTAYC | CAGACATAAGATCGTCA | CAGAAACGATTA |
| CCTACGACCACA | LGISHMEPSFGLILHDG | ATGTGGATCAGCGTCAG | TGACGGTTTCCT |
| ACTCACCTTATA | GTTLKFVDTPESLSGLY | TATGGGGATGTCTTTAA | GGAAAACGCACA |
| TTTGGCCCAGAA | VFVVYFNGHVEAVAYTV | AGGCGATTTGAATCCAA | TGAACACCATGG |
| ACGATTATGACG | VSTVDHFVNAIEERGFP | AGCCCCAAGGACAGAGA | AGTCTACAACCA |
| GTTTCCTGGAAA | PTAGQPPATTKPKEITP | CTGATCGAGGTCTCTGT | AGGCAGGGGAAT |
| ACGCACATGAAC | VNPGTSPLLRYAAWTGG | AGAAGAAAATCACCCCT | CGACAGTGGCGA |
| ACCATGGAGTCT | LAAVVLLCLVIFLICTA | TCACTTTGCGCGCTCCA | GCGTCTTATGCA |
| ACAACCAAGGCA | KRMRVKAYRVDKSPYNQ | ATCCAGAGGATTTACGG | GCCAACACAGAT |
| GGGGAATCGACA | SMYYAGLPVDDFEDSES | GGTGCGTTATACCGAAA | GTCGGCACAGGA |
| GTGGCGAGCGTC | TDTEEEFGNAIGGSHGG | CTTGGAGTTTCTTGCCG | GGATCTCGGTGA |
| TTATGCAGCCAA | SSYTVYIDKTR | TCACTGACGTGTACGGG | TGACACCGGCAT |
| CACAGATGTCGG | | GGATGCCGCCCCCGCAA | ACACGTGATTCC |
| CACAGGAGGATC | | TCCAGCACATCTGTCTG | CACATTAAACGG |
| TCGGTGATGACA | | AAACACACCACATGCTT | CGACGACAGACA |
| CCGGCATACACG | | TCAGGACGTGGTTGTGG | TAAGATCGTCAA |
| TGATTCCCACAT | | ATGTGGATTGCGCGGAA | TGTGGATCAGCG |
| TAAACGGCGACG | | AACACAAAAGAAGACCA | TCAGTATGGGGA |
| ACAGACATAAGA | | ACTCGCCGAAATCAGCT | TGTCTTTAAAGG |
| TCGTCAATGTGG | | ATCGTTTTCAGGGTAAA | CGATTTGAATCC |
| ATCAGCGTCAGT | | AAAGAGGCCGACCAACC | AAAGCCCCAAGG |
| ATGGGGATGTCT | | GTGGATTGTTGTGAATA | ACAGAGACTGAT |
| TTAAAGGCGATT | | CGAGCACGCTCTTCGAT | CGAGGTCTCTGT |
| TGAATCCAAAGC | | GAGCTTGAACTCGATCC | AGAAGAAAATCA |
| CCCAAGGACAGA | | CCCGGAAATCGAGCCTG | CCCCTTCACTTT |
| GACTGATCGAGG | | GGGTTCTAAAAGTGTTG | GCGCGCTCCAAT |
| TCTCTGTAGAAA | | AGGACCGAGAAGCAGTA | CCAGAGGATTTA |
| AAAATCACCCCT | | CCTCGGGGTTTATATCT | CGGGGTGCGTTA |
| TCACTTTGCGCG | | GGAATATGAGAGGCTCC | TACCGAAACTTG |
| CTCCAATCCAGA | | GATGGCACCTCTACCTA | GAGTTTCTTGCC |
| GGATTTACGGGG | | CGCAACGTTTCTGGTTA | GTCACTGACGTG |
| TGCGTTATACCG | | CCTGGAAGGGAGACGAG | TACGGGGGATGC |
| AAACTTGGAGTT | | AAGACACGGAATCCAAC | CGCCCCCGCAAT |
| TCTTGCCGTCAC | | GCCCGCTGTGACCCCTC | CCAGCACATCTG |
| TGACGTTACGGG | | AGCCTAGGGGAGCCGAA | TCTGAAACACAC |
| GGGATGCCGCCC | | TTCCACATGTGGAACTA | CACATGCTTTCA |
| CCGCAATCCAGC | | TCACTCCCATGTATTCA | GGACGTGGTTGT |
| ACATCTGTCTGA | | GTGTGGGTGACACTTTC | GGATGTGGATTG |
| AACACACCACAT | | AGCCTGGCCATGCACCT | CGCAGGAAAACAC |
| GCTTTCAGGACG | | GCAGTATAAGATTCACG | AAAAGAAGACCA |
| TGGTTGTGGATG | | AGGCACCCTTCGACCTC | ACTCGCCGAAAT |
| TGGATTGCGCGG | | CTGCTGGAGTGGTTGTA | CAGCTATCGTTT |
| AAAACACAAAAG | | CGTACCTATTGATCCCA | TCAGGGTAAAAA |
| AAGACCAACTCG | | CTTGTCAGCCCATGCGC | AGAGGCCGACCA |
| CCGAAATCAGCT | | CTGTACTCCACTTGCTT | ACCGTGGATTGT |
| ATCGTTTTCAGG | | GTACCACCCCAATGCAC | TGTGAATACGAG |
| GTAAAAAAGAGG | | CACAGTGTCTATCACAC | CACGCTCTTCGA |
| CCGACCAACCGT | | ATGAACTCCGGGTGTAC | TGAGCTTGAACT |
| GGATTGTTGTGA | | CTTTACTTCACCCCATC | CGATCCCCCGGA |
| ATACGAGCACGC | | TTGCCCAGCGGGTCGCC | AATCGAGCCTGG |
| TCTTCGATGAGC | | AGCACAGTGTATCAGAA | GGTTCTAAAAGT |
| TTGAACTCGATC | | CTGTGAGCATGCTGACA | GTTGAGGACCGA |
| CCCCGGAAATCG | | ACTATACTGCTTATTGC | GAAGCAGTACCT |
| AGCCTGGGGTTC | | CTCGGAATATCCCATAT | CGGGGTTTATAT |
| TAAAAGTGTTGA | | GGAGCCAAGCTTCGGGC | CTGGAATATGAG |
| GGACCGAGAAGC | | TCATACTGCACGATGGT | AGGCTCCGATGG |
| AGTACCTCGGGG | | GGTACGACACTCAAGTT | CACCTCTACCTA |
| TTTATATCTGGA | | CGTGGACACCCCCGAAA | CGCAACGTTTCT |
| ATATGAGAGGCT | | GCCTTTCTGGCTTGTAC | GGTTACCTGGAA |
| CCGATGGCACCT | | GTGTTCGTGGTCTACTT | GGGAGACGAGAA |
| CTACCTACGCAA | | CAATGGACATGTGGAGG | GACACGGAATCC |
| CGTTTCTGGTTA | | CAGTGGCTTACACAGTG | AACGCCCGCTGT |
| CCTGGAAGGGAG | | GTTTCGACAGTTGATCA | GACCCCTCAGCC |
| ACGAGAAGACAC | | CTTTGTAAATGCCATTG | TAGGGGAGCCGA |
| GGAATCCAACGC | | AGGAACGCGGCTTCCCG | ATTCCACATGTG |

TABLE 2-continued

| | | |
|---|---|---|
| CCGCTGTGACCC | CCTACAGCGGGCCAGCC | GAACTATCACTC |
| CTCAGCCTAGGG | CCCTGCGACAACAAAAC | CCATGTATTCAG |
| GAGCCGAATTCC | CAAAAGAGATTACGCCC | TGTGGGTGACAC |
| ACATGTGGAACT | GTTAATCCTGGGACTAG | TTTCAGCCTGGC |
| ATCACTCCCATG | TCCATTGCTGAGGTATG | CATGCACCTGCA |
| TATTCAGTGTGG | CCGCCTGGACTGGCGGT | GTATAAGATTCA |
| GTGACACTTTCA | CTGGCGGCCGTGGTACT | CGAGGCACCCTT |
| GCCTGGCCATGC | TCTGTGTTTAGTCATAT | CGACCTCCTGCT |
| ACCTGCAGTATA | TTCTGATCTGTACCGCT | GGAGTGGTTGTA |
| AGATTCACGAGG | AAACGTATGCGGGTCAA | CGTACCTATTGA |
| CACCCTTCGACC | GGCTTACCGTGTTGACA | TCCCACTTGTCA |
| TCCTGCTGGAGT | AGTCTCCTTACAATCAG | GCCCATGCGCCT |
| GGTTGTACGTAC | TCAATGTACTATGCAGG | GTACTCCACTTG |
| CTATTGATCCCA | ACTCCCTGTTGACGATT | CTTGTACCACCC |
| CTTGTCAGCCCA | TCGAAGACTCAGAGAGT | CAATGCACCACA |
| TGCGCCTGTACT | ACAGACACAGAAGAAGA | GTGTCTATCACA |
| CCACTTGCTTGT | ATTCGGAAACGCTATAG | CATGAACTCCGG |
| ACCACCCCAATG | GTGGCTCTCACGGAGGT | GTGTACCTTTAC |
| CACCACAGTGTC | AGCTCGTATACAGTGTA | TTCACCCCATCT |
| TATCACACATGA | CATCGATAAAACCAGA | TGCCCAGCGGGT |
| ACTCCGGGTGTA | | CGCCAGCACAGT |
| CCTTTACTTCAC | | GTATCAGAACTG |
| CCCATCTTGCCC | | TGAGCATGCTGA |
| AGCGGGTCGCCA | | CAACTATACTGC |
| GCACAGTGTATC | | TTATTGCCTCGG |
| AGAACTGTGAGC | | AATATCCCATAT |
| ATGCTGACAACT | | GGAGCCAAGCTT |
| ATACTGCTTATT | | CGGGCTCATACT |
| GCCTCGGAATAT | | GCACGATGGTGG |
| CCCATATGGAGC | | TACGACACTCAA |
| CAAGCTTCGGGC | | GTTCGTGGACAC |
| TCATACTGCACG | | CCCCGAAAGCCT |
| ATGGTGGTACGA | | TTCTGGCTTGTA |
| CACTCAAGTTCG | | CGTGTTCGTGGT |
| TGGACACCCCCG | | CTACTTCAATGG |
| AAAGCCTTTCTG | | ACATGTGGAGGC |
| GCTTGTACGTGT | | AGTGGCTTACAC |
| TCGTGGTCTACT | | AGTGGTTTCGAC |
| TCAATGGACATG | | AGTTGATCACTT |
| TGGAGGCAGTGG | | TGTAAATGCCAT |
| CTTACACAGTGG | | TGAGGAACGCGG |
| TTTCGACAGTTG | | CTTCCCGCCTAC |
| ATCACTTTGTAA | | AGCGGGCCAGCC |
| ATGCCATTGAGG | | CCCTGCGACAAC |
| AACGCGGCTTCC | | AAAACCAAAAGA |
| CGCCTACAGCGG | | GATTACGCCCGT |
| GCCAGCCCCCTG | | TAATCCTGGGAC |
| CGACAACAAAAC | | TAGTCCATTGCT |
| CAAAAGAGATTA | | GAGGTATGCCGC |
| CGCCCGTTAATC | | CTGGACTGGCGG |
| CTGGGACTAGTC | | TCTGGCGGCCGT |
| CATTGCTGAGGT | | GGTACTTCTGTG |
| ATGCCGCCTGGA | | TTTAGTCATATT |
| CTGGCGGTCTGG | | TCTGATCTGTAC |
| CGGCCGTGGTAC | | CGCTAAACGTAT |
| TTCTGTGTTTAG | | GCGGGTCAAGGC |
| TCATATTTCTGA | | TTACCGTGTTGA |
| TCTGTACCGCTA | | CAAGTCTCCTTA |
| AACGTATGCGGG | | CAATCAGTCAAT |
| TCAAGGCTTACC | | GTACTATGCAGG |
| GTGTTGACAAGT | | ACTCCCTGTTGA |
| CTCCTTACAATC | | CGATTTCGAAGA |
| AGTCAATGTACT | | CTCAGAGAGTAC |
| ATGCAGGACTCC | | AGACACAGAAGA |
| CTGTTGACGATT | | AGAATTCGGAAA |
| TCGAAGACTCAG | | CGCTATAGGTGG |
| AGAGTACAGACA | | CTCTCACGGAGG |
| CAGAAGAAGAAT | | TAGCTCGTATAC |
| TCGGAAACGCTA | | AGTGTACATCGA |
| TAGGTGGCTCTC | | TAAAACCAGATG |
| ACGGAGGTAGCT | | ATAATAGGCTGG |
| CGTATACAGTGT | | AGCCTCGGTGGC |
| ACATCGATAAAA | | CATGCTTCTTGC |
| CCAGATGATAAT | | CCCTTGGGCCTC |
| AGGCTGGAGCCT | | CCCCCAGCCCCT |
| CGGTGGCCATGC | | CCTCCCCTTCCT |
| TTCTTGCCCCTT | | GCACCCGTACCC |
| GGGCCTCCCCCC | | CCGTGGTCTTTG |
| AGCCCCTCCTCC | | AATAAAGTCTGA |
| CCTTCCTGCACC | | GTGGGCGGCAAA |

TABLE 2-continued

```
CGTACCCCCGTG                                                            AAAAAAAAAAAA
GTCTTTGAATAA                                                            AAAAAAAAAAAA
AGTCTGAGTGGG                                                            AAAAAAAAAAAA
CGGC                                                                    AAAAAAAAAAAA
                                                                        AAAAAAAAAAAA
                                                                        AAAAAAAAAAAA
                                                                        AAAAAAAAAAAA
                                                                        AAAAAAAAAAAA
                                                                        ATCTAG
```

```
VZV_gE_Oka_hIgkappa    SEQ ID NO: 13       SEQ ID NO: 14        SEQ ID NO: 15        SEQ ID NO: 16
                       TCAAGCTTTTGG        METPAQLLFLLLLWLPD    ATGGAGACTCCCGCTCA    G*GGGAAATAAG
                       ACCCTCGTACAG        TTGSVLRYDDFHIDEDK    GCTACTGTTCCTCCTGC    AGAGAAAAGAAG
                       AAGCTAATACGA        LDTNSVYEPYYHSDHAE    TCCTTTGGCTGCCTGAT    AGTAAGAAGAAA
                       CTCACTATAGGG        SSWVNRGESSRKAYDHN    ACTACAGGCTCTGTTTT    TATAAGAGCCAC
                       AAATAAGAGAGA        SPYIWPRNDYDGFLENA    GCGGTACGACGACTTTC    CATGGAGACTCC
                       AAAGAAGAGTAA        HEHHGVYNQGRGIDSGE    ACATCGATGAGGACAAG    CGCTCAGCTACT
                       GAAGAAATATAA        RLMQPTQMSAQEDLGDD    CTCGACACTAATAGCGT    GTTCCTCCTGCT
                       GAGCCACCATGG        TGIHVIPTLNGDDRHKI    GTATGAGCCCTACTACC    CCTTTGGCTGCC
                       AGACTCCCGCTC        VNVDQRQYGDVFKGDLN    ATTCAGATCACGCCGAG    TGATACTACAGG
                       AGCTACTGTTCC        PKPQGQRLIEVSVEENH    TCCTCTTGGGTGAACAG    CTCTGTTTTGCG
                       TCCTGCTCCTTT        PFTLRAPIQRIYGVRYT    GGGTGAAAGTTCTAGGA    GTACGACGACTT
                       GGCTGCCTGATA        ETWSFLPSLTCTGDAAP    AAGCCTATGATCACAAC    TCACATCGATGA
                       CTACAGGCTCTG        AIQHICLKHTTCFQDVV    AGCCCTTATATTTGGCC    GGACAAGCTCGA
                       TTTTGCGGTACG        VDVDCAENTKEDQLAEI    ACGGAATGATTACGACG    CACTAATAGCGT
                       ACGACTTTCACA        SYRFQGKKEADQPWIVV    GATTTCTCGAAAATGCC    GTATGAGCCCTA
                       TCGATGAGGACA        NTSTLFDELELDPPEIE    CACGAGCATCACGGAGT    CTACCATTCAGA
                       AGCTCGACACTA        PGVLKVLRTEKQYLGVY    GTACAACCAGGGCCGTG    TCACGCCGAGTC
                       ATAGCGTGTATG        IWNMRGSDGTSTYATFL    GAATCGACTCTGGGGAG    CTCTTGGGTGAA
                       AGCCCTACTACC        VTWKGDEKTRNPTPAVT    AGATTGATGCAACCTAC    CAGGGGTGAAAG
                       ATTCAGATCACG        PQPRGAEFHMWNYHSHV    ACAGATGAGCGCCCAGG    TTCTAGGAAAGC
                       CCGAGTCCTCTT        FSVGDTFSLAMHLQYKI    AAGATCTCGGGGATGAT    CTATGATCACAA
                       GGGTGAACAGGG        HEAPFDLLLEWLYVPID    ACAGGAATTCACGTTAT    CAGCCCTTATAT
                       GTGAAAGTTCTA        PTCQPMRLYSTCLYHPN    CCCTACATTAAACGGAG    TTGGCCACGGAA
                       GGAAAGCCTATG        APQCLSHMNSGCTFTSP    ATGACCGCCACAAAATC    TGATTACGACGG
                       ATCACAACAGCC        HLAQRVASTVYQNCEHA    GTCAATGTCGATCAAAG    ATTTCTCGAAAA
                       CTTATATTTGGC        DNYTAYCLGISHMEPSF    ACAGTATGGAGATGTGT    TGCCCACGAGCA
                       CACGGAATGATT        GLILHDGGTTLKFVDTP    TCAAAGGCGATCTCAAC    TCACGGAGTGTA
                       ACGACGGATTTC        ESLSGLYVFVVYFNGHV    CCTAAGCCGCAGGGCCA    CAACCAGGGCCG
                       TCGAAAATGCCC        EAVAYTVVSTVDHFVNA    GAGACTCATTGAGGTGT    TGGAATCGACTC
                       ACGAGCATCACG        IEERGFPPTAGQPPATT    CTGTCGAAGAGAACCAC    TGGGGAGAGATT
                       GAGTGTACAACC        KPKEITPVNPGTSPLLR    CCTTTCACTCTGCACGC    GATGCAACCTAC
                       AGGGCCGTGGAA        YAAWTGGLAAVVLLCLV    TCCCATTCAGAGAATCT    ACAGATGAGCGC
                       TCGACTCTGGGG        IFLICTAKRMRVKAYRV    ATGGAGTTCGCTATACG    CCAGGAAGATCT
                       AGAGATTGATGC        DKSPYNQSMYYAGLPVD    GAGACTTGGTCATTCCT    CGGGGATGATAC
                       AACCTACACAGA        DFEDSESTDTEEEFGNA    TCCTTCCCTGACATGCA    AGGAATTCACGT
                       TGAGCGCCCAGG        IGGSHGGSSYTVYIDKT    CCGGAGACGCCGCCCCT    TATCCCTACATT
                       AAGATCTCGGGG        R                    GCCATTCAGCACATATG    AAACGGAGATGA
                       ATGATACAGGAA                             CCTGAAACATACCACCT    CCGCCACAAAAT
                       TTCACGTTATCC                             GTTTCCAGGATGTGGTG    CGTCAATGTCGA
                       CTACATTAAACG                             GTTGATGTTGATTGTGC    TCAAAGACAGTA
                       GAGATGACCGCC                             TGAAAATACCAAGGAAG    TGGAGATGTGTT
                       ACAAAATCGTCA                             ACCAACTGGCCGAGATT    CAAAGGCGATCT
                       ATGTCGATCAAA                             AGTTACCGGTTCCAAGG    CAACCCTAAGCC
                       GACAGTATGGAG                             GAAAAAGGAAGCCGACC    GCAGGGCCAGAG
                       ATGTGTTCAAAG                             AGCCATGGATTGTGGTT    ACTCATTGAGGT
                       GCGATCTCAACC                             AATACAAGCACTCTGTT    GTCTGTCGAAGA
                       CTAAGCCGCAGG                             CGATGAGCTCGAGCTGG    GAACCACCCTTT
                       GCCAGAGACTCA                             ATCCCCCCGAGATAGAA    CACTCTGCGCGC
                       TTGAGGTGTCTG                             CCCGGAGTTCTGAAAGT    TCCCATTCAGAG
                       TCGAAGAGAACC                             GCTCCGGACAGAAAAAC    AATCTATGGAGT
                       ACCCTTTCACTC                             AATATCTGGGAGTCTAC    TCGCTATACGGA
                       TGCGCGCTCACA                             ATATGGAACATGCGCGG    GACTTGGTCATT
                       TTCAGAGAATCT                             TTCCGATGGGACCTCCA    CCTTCCTTCCCT
                       ATGGAGTTCGCT                             CTTATGCAACCTTTCTC    GACATGCACCGG
                       ATACGGAGACTT                             GTCACGTGGAAGGGAGA    AGACGCCGCCCC
                       GGTCATTCCTTC                             TGAGAAAACTAGGAATC    TGCCATTCAGCA
                       CTTCCCTGACAT                             CCACACCCGCTGTCACA    CATATGCCTGAA
                       GCACCGGAGACG                             CCACAGCCAAGAGGGGC    ACATACCACCTG
                       CCGCCCCTGCCA                             TGAGTTCCATATGTGGA    TTTCCAGGATGT
                       TTCAGCACATAT                             ACTATCATAGTCACGTG    GGTGGTTGATGT
                       GCCTGAAACATA                             TTTAGTGTCGGAGATAC    TGATTGTGCTGA
                       CCACCTGTTTCC                             GTTTTCATTGGCTATGC    AAATACCAAGGA
                       AGGATGTGGTGG                             ATCTCCAGTACAAGATT    AGACCAACTGGC
                       TTGATGTTGATT                             CATGAGGCTCCCTTCGA    CGAGATTAGTTA
                       GTGCTGAAAATA                             TCTGTTGCTTGAGTGGT    CCGGTTCCAAGG
                       CCAAGGAAGACC                             TGTACGTCCCGATTGAC    GAAAAAGGAAGC
                       AACTGGCCGAGA                             CCGACCTGCCAGCCCAT    CGACCAGCCATG
                       TTAGTTACCGGT                             GCGACTGTACAGCACCT    GATTGTGGTTAA
                       TCCAAGGGAAAA                             GTCTCTACCATCCAAAC    TACAAGCACTCT
```

| | | |
|---|---|---|
| AGGAAGCCGACC | GCTCCGCAATGTCTGAG | GTTCGATGAGCT |
| AGCCATGGATTG | CCACATGAACTCTGGGT | CGAGCTGGATCC |
| TGGTTAATACAA | GTACTTTCACCAGTCCC | CCCCGAGATAGA |
| GCACTCTGTTCG | CACCTCGCCCAGCGGGT | ACCCGGAGTTCT |
| ATGAGCTCGAGC | GGCCTCTACTGTTTACC | GAAAGTGCTCCG |
| TGGATCCCCCCG | AGAACTGTGAGCACGCC | GACAGAAAAACA |
| AGATAGAACCCG | GACAACTACACCGCATA | ATATCTGGGAGT |
| GAGTTCTGAAAG | CTGCCTCGGTATTTCTC | CTACATATGGAA |
| TGCTCCGGACAG | ACATGGAACCCTCCTTC | CATGCGCGGTTC |
| AAAAACAATATC | GGACTCATCCTGCACGA | CGATGGGACCTC |
| TGGGAGTCTACA | TGGGGGCACTACCCTGA | CACTTATGCAAC |
| TATGGAACATGC | AGTTCGTTGATACGCCA | CTTTCTCGTCAC |
| GCGGTTCCGATG | GAATCTCTGTCTGGGCT | GTGGAAGGGAGA |
| GGACCTCCACTT | CTATGTTTTCGTGGTCT | TGAGAAAACTAG |
| ATGCAACCTTTC | ACTTCAATGGCCATGTC | GAATCCCACACC |
| TCGTCACGTGGA | GAGGCCGTGGCCTATAC | CGCTGTCACACC |
| AGGGAGATGAGA | TGTCGTTTCTACCGTGG | ACAGCCAAGAGG |
| AAACTAGGAATC | ATCATTTTGTGAACGCC | GGCTGAGTTCCA |
| CCACACCCGCTG | ATCGAAGAACGGGGATT | TATGTGGAACTA |
| TCACACCACAGC | CCCCCCTACGGCAGGCC | TCATAGTCACGT |
| CAAGAGGGGTCG | AGCCGCCTGCAACCACC | GTTTAGTGTCGG |
| AGTTCCATATGT | AAGCCCAAGGAAATAAC | AGATACGTTTTC |
| GGAACTATCATA | ACCAGTGAACCCTGGCA | ATTGGCTATGCA |
| GTCACGTGTTTA | CCTCACCTCTCCTAAGA | TCTCCAGTACAA |
| GTGTCGGAGATA | TATGCCGCGTGGACAGG | GATTCATGAGGC |
| CGTTTTCATTGG | GGGACTGGCGGCAGTGG | TCCCTTCGATCT |
| CTATGCATCTCC | TGCTCCTCTGTCTCGTG | GTTGCTTGAGTG |
| AGTACAAGATTC | ATCTTTCTGATCTGTAC | GTTGTACGTCCC |
| ATGAGGCTCCCT | AGCCAAGAGGATGAGGG | GATTGACCCGAC |
| TCGATCTGTTGC | TCAAGGCTTATAGAGTG | CTGCCAGCCCAT |
| TTGAGTGGTTGT | GACAAGTCCCCCTACAA | GCGACTGTACAG |
| ACGTCCCGATTG | TCAGTCAATGTACTACG | CACCTGTCTCTA |
| ACCCGACCTGCC | CCGGCCTTCCCGTTGAT | CCATCCAAACGC |
| AGCCCATGCGAC | GATTTTGAGGATTCCGA | TCCGCAATGTCT |
| TGTACAGCACCT | GTCCACAGATACTGAGG | GAGCCACATGAA |
| GTCTCTACCATC | AAGAGTTCGGTAACGCT | CTCTGGGTGTAC |
| CAAACGCTCCGC | ATAGGCGGCTCTCACGG | TTTCACCAGTCC |
| AATGTCTGAGCC | GGGTTCAAGCTACACGG | CCACCTCGCCCA |
| ACATGAACTCTG | TTTACATTGACAAGACA | GCGGGTGGCCTC |
| GGTGTACTTTCA | CGC | TACTGTTTACCA |
| CCAGTCCCCACC | | GAACTGTGAGCA |
| TCGCCCAGCGGG | | CGCCGACAACTA |
| TGGCCTCTACTG | | CACCGCATACTG |
| TTTACCAGAACT | | CCTCGGTATTTC |
| GTGAGCACGCCG | | TCACATGGAACC |
| ACAACTACACCG | | CTCCTTCGGACT |
| CATACTGCCTCG | | CATCCTGCACGA |
| GTATTTCTCACA | | TGGGGGCACTAC |
| TGGAACCCTCCT | | CCTGAAGTTCGT |
| TCGGACTCATCC | | TGATACGCCAGA |
| TGCACGATGGGG | | ATCTCTGTCTGG |
| GCACTACCCTGA | | GCTCTATGTTTT |
| AGTTCGTTGATA | | CGTGGTCTACTT |
| CGCCAGAATCTC | | CAATGGCCATGT |
| TGTCTGGGCTCT | | CGAGGCCGTGGC |
| ATGTTTTCGTGG | | CTATACTGTCGT |
| TCTACTTCAATG | | TTCTACCGTGGA |
| GCCATGTCGAGG | | TCATTTTGTGAA |
| CCGTGGCCTATA | | CGCCATCGAAGA |
| CTGTCGTTTCTA | | ACGGGGATTCCC |
| CCGTGGATCATT | | CCCTACGGCAGG |
| TTGTGAACGCCA | | CCAGCCGCCTGC |
| TCGAAGAACGGG | | AACCACCAAGCC |
| GATTCCCCCCTA | | CAAGGAAATAAC |
| CGGCAGGCCAGC | | ACCAGTGAACCC |
| CGCCTGCAACCA | | TGGCACCTCACC |
| CCAAGCCCAAGG | | TCTCCTAAGATA |
| AAATAACACCAG | | TGCCGCGTGGAC |
| TGAACCCTGGCA | | AGGGGGACTGGC |
| CCTCACCTCTCC | | GGCAGTGGTGCT |
| TAAGATATGCCG | | CCTCTGTCTCGT |
| CGTGGACAGGGG | | GATCTTTCTGAT |
| GACTGGCGGCAG | | CTGTACAGCCAA |
| TGGTGCTCCTCT | | GAGGATGAGGGT |
| GTCTCGTGATCT | | CAAGGCTTATAG |
| TTCTGATCTGTA | | AGTGGACAAGTC |
| CAGCCAAGAGGA | | CCCCTACAATCA |
| TGAGGGTCAAGG | | GTCAATGTACTA |
| CTTATAGAGTGG | | CGCCGGCCTTCC |
| ACAAGTCCCCCT | | CGTTGATGATTT |

```
ACAATCAGTCAA                                                              TGAGGATTCCGA
TGTACTACGCCG                                                              GTCCACAGATAC
GCCTTCCCGTTG                                                              TGAGGAAGAGTT
ATGATTTTGAGG                                                              CGGTAACGCTAT
ATTCCGAGTCCA                                                              AGGCGGCTCTCA
CAGATACTGAGG                                                              CGGGGGTTCAAG
AAGAGTTCGGTA                                                              CTACACGGTTTA
ACGCTATAGGCG                                                              CATTGACAAGAC
GCTCTCACGGGG                                                              ACGCTGATAATA
GTTCAAGCTACA                                                              GGCTGGAGCCTC
CGGTTTACATTG                                                              GGTGGCCATGCT
ACAAGACACGCT                                                              TCTTGCCCCTTG
GATAATAGGCTG                                                              GGCCTCCCCCCA
GAGCCTCGGTGG                                                              GCCCCTCCTCCC
CCATGCTTCTTG                                                              CTTCCTGCACCC
CCCCTTGGGCCT                                                              GTACCCCCGTGG
CCCCCCAGCCCC                                                              TCTTTGAATAAA
TCCTCCCCTTCC                                                              GTCTGAGTGGGC
TGCACCCGTACC                                                              GGCAAAAAAAAA
CCCGTGGTCTTT                                                              AAAAAAAAAAAA
GAATAAAGTCTG                                                              AAAAAAAAAAAA
AGTGGGCGGC                                                                AAAAAAAAAAAA
                                                                          AAAAAAAAAAAA
                                                                          AAAAAAAAAAAA
                                                                          AAAAAAAAAAAA
                                                                          AAAAAAATCTAG
```

|  | SEQ ID NO: 17 | SEQ ID NO: 18 | SEQ ID NO: 19 | SEQ ID NO: 20 |
|---|---|---|---|---|
| VZV-GE-delete-562 | TCAAGCTTTTGG | MGTVNKPVVGVLMGFGI | ATGGGGACAGTTAATAA | G*GGGAAATAAG |
|  | ACCCTCGTACAG | ITGTLRITNPVRASVLR | ACCTGTGGTGGGGGTAT | AGAGAAAAGAAG |
|  | AAGCTAATACGA | YDDFHIDEDKLDTNSVY | TGATGGGGTTCGGAATT | AGTAAGAAGAAA |
|  | CTCACTATAGGG | EPYYHSDHAESSWVNRG | ATCACGGGAACGTTGCG | TATAAGAGCCAC |
|  | AAATAAGAGAGA | ESSRKAYDHNSPYIWPR | TATAACGAATCCGGTCA | CATGGGGACAGT |
|  | AAAGAAGAGTAA | NDYDGFLENAHEHHGVY | GAGCATCCGTCTTGCGA | TAATAAACCTGT |
|  | GAAGAAATATAA | NQGRGIDSGERLMQPTQ | TACGATGATTTTCACAT | GGTGGGGGTATT |
|  | GAGCCACCATGG | MSAQEDLGDDTGIHVIP | CGATGAAGACAAACTGG | GATGGGGTTCGG |
|  | GGACAGTTAATA | TLNGDDRHKIVNVDQRQ | ATACAAACTCCGTATAT | AATTATCACGGG |
|  | AACCTGTGGTGG | YGDVFKGDLNPKPQGQR | GAGCCTTACTACCATTC | AACGTTGCGTAT |
|  | GGGTATTGATGG | LIEVSVEENHPFTLRAP | AGATCATGCGGAGTCTT | AACGAATCCGGT |
|  | GGTTCGGAATTA | IQRIYGVRYTETWSFLP | CATGGGTAAATCGGGGA | CAGAGCATCCGT |
|  | TCACGGGAACGT | SLTCTGDAAPAIQHICL | GAGTCTTCGCGAAAAGC | CTTGCGATACGA |
|  | TGCGTATAACGA | KHTTCFQDVVVDVDCAE | GTACGATCATAACTCAC | TGATTTTCACAT |
|  | ATCCGGTCAGAG | NTKEDQLAEISYRFQGK | CTTATATATGGCCACGT | CGATGAAGACAA |
|  | CATCCGTCTTGC | KEADQPWIVVNTSTLFD | AATGATTATGATGGATT | ACTGGATACAAA |
|  | GATACGATGATT | ELELDPPEIEPGVLKVL | TTTAGAGAACGCACACG | CTCCGTATATGA |
|  | TTCACATCGATG | RTEKQYLGVYIWNMRGS | AACACCATGGGGTGTAT | GCCTTACTACCA |
|  | AAGACAAACTGG | DGTSTYATFLVTWKGDE | AATCAGGGCCGTGGTAT | TTCAGATCATGC |
|  | ATACAAACTCCG | KTRNPTPAVTPQPRGAE | CGATAGCGGGGAACGGT | GGAGTCTTCATG |
|  | TATATGGACCTT | FHMWNYHSHVFSVGDTF | TAATGCAACCCACACAA | GGTAAATCGGGG |
|  | ACTACCATTCAG | SLAMHLQYKIHEAPFDL | ATGTCTGCACAGGAGGA | AGAGTCTTCGCG |
|  | ATCATGCGGAGT | LLEWLYVPIDPTCQPMR | TCTTGGGGACGATACGG | AAAAGCGTACGA |
|  | CTTCATGGGTAA | LYSTCLYHPNAPQCLSH | GCATCCACGTTATCCCT | TCATAACTCACC |
|  | ATCGGGGAGAGT | MNSGCTFTSPHLAQRVA | ACGTTAAATCGGCGATGA | TTATATATGGCC |
|  | CTTCGCGAAAAG | STVYQNCEHADNYTAYC | CAGACATAAAATTGTAA | ACGTAATGATTA |
|  | CGTACGATCATA | LGISHMEPSFGLILHDG | ATGTGGACCAACGTCAA | TGATGGATTTTT |
|  | ACTCACCTTATA | GTTLKFVDTPESLSGLY | TACGGTGACGTGTTTAA | AGAGAACGCACA |
|  | TATGGCCACGTA | VFVVYFNGHVEAVAYTV | AGGAGATCTTAATCCAA | CGAACACCATGG |
|  | ATGATTATGATG | VSTVDHFVNAIEERGFP | AACCCCAAGGCCAAAGA | GGTGTATAATCA |
|  | GATTTTTAGAGA | PTAGQPPATTKPKEITP | CTCATTGAGGTGTCAGT | GGGCCGTGGTAT |
|  | ACGCACACGAAC | VNPGTSPLLRYAAWTGG | GGAAGAAATCACCCGT | CGATAGCGGGGA |
|  | ACCATGGGGTGT | LAAVVLLCLVIFLICTA* | TTACTTTACGCGCACCG | ACGGTTAATGCA |
|  | ATAATCAGGGCC |  | ATTCAGCGGATTTATGG | ACCCACACAAAT |
|  | GTGGTATCGATA |  | AGTCCGGTACACCGAGA | GTCTGCACAGGA |
|  | GCGGGGAACGGT |  | CTTGGAGCTTTTTGCCG | GGATCTTGGGGA |
|  | TAATGCAACCCA |  | TCATTAACCTGTACGGG | CGATACGGGCAT |
|  | CACAAATGTCTG |  | AGACGCAGCGCCCGCCA | CCACGTTATCCC |
|  | CACAGGAGGATC |  | TCCAGCATATATGTTTA | TACGTTAAACGG |
|  | TTGGGGACGATA |  | AAACATACAACATGCTT | CGATGACAGACA |
|  | CGGGCATCCACG |  | TCAAGACGTGGTGGTGG | TAAAATTGTAAA |
|  | TTATCCCTACGT |  | ATGTGGATTGCGCGGAA | TGTGGACCAACG |
|  | TAAACGGCGATG |  | AATACTAAAGAGGATCA | TCAATACGGTGA |
|  | ACAGACATAAAA |  | GTTGGCCGAAATCAGTT | CGTGTTAAAGG |
|  | TTGTAAATGTGG |  | ACCGTTTTCAAGGTAAG | AGATCTTAATCC |
|  | ACCAACGTCAAT |  | AAGGAAGCGGACCAACC | AAAACCCCAAGG |
|  | ACGGTGACGTGT |  | GTGGATTGTTGTAAACA | CCAAAGACTCAT |
|  | TTAAAGGAGATC |  | CGAGCACACTGTTTGAT | TGAGGTGTCAGT |
|  | TTAATCCAAAAC |  | GAACTCGAATTAGACCC | GGAAGAAAATCA |
|  | CCCAAGGCCAAA |  | CCCCGAGATTGAACCGG | CCCGTTTACTTT |
|  | GACTCATTGAGG |  | GTGTCTTGAAAGTACTT | ACGCGCACCGAT |

TABLE 2-continued

| | | |
|---|---|---|
| TGTCAGTGGAAG | CGGACAGAAAAACAATA | TCAGCGGATTTA |
| AAAATCACCCGT | CTTGGGTGTGTACATTT | TGGAGTCCGGTA |
| TTACTTTACGCG | GGAACATGCGCGGCTCC | CACCGAGACTTG |
| CACCGATTCAGC | GATGGTACGTCTACCTA | GAGCTTTTTGCC |
| GGATTTATGGAG | CGCCACGTTTTTGGTCA | GTCATTAACCTG |
| TCCGGTACACCG | CCTGGAAAGGGGATGAA | TACGGGAGACGC |
| AGACTTGGAGCT | AAAACAAGAAACCCTAC | AGCGCCCGCCAT |
| TTTTGCCGTCAT | GCCCGCAGTAACTCCTC | CCAGCATATATG |
| TAACCTGTACGG | AACCAAGAGGGGCTGAG | TTTAAAACATAC |
| GAGACGCAGCGC | TTTCATATGTGGAATTA | AACATGCTTTCA |
| CCGCCATCCAGC | CCACTCGCATGTATTTT | AGACGTGGTGGT |
| ATATATGTTTAA | CAGTTGGTGATACGTTT | GGATGTGGATTG |
| AACATACAACAT | AGCTTGGCAATGCATCT | CGCGGAAAATAC |
| GCTTTCAAGACG | TCAGTATAAGATACATG | TAAAGAGGATCA |
| TGGTGGTGGATG | AAGCGCCATTTGATTTG | GTTGGCCGAAAT |
| TGGATTGCGCGG | CTGTTAGAGTGGTTGTA | CAGTTACCGTTT |
| AAAATACTAAAG | TGTCCCCATCGATCCTA | TCAAGGTAAGAA |
| AGGATCAGTTGG | CATGTCAACCAATGCGG | GGAAGCGGACCA |
| CCGAAATCAGTT | TTATATTCTACGTGTTT | ACCGTGGATTGT |
| ACCGTTTTCAAG | GTATCATCCCAACGCAC | TGTAAACACGAG |
| GTAAGAAGGAAG | CCCAATGCCTCTCTCAT | CACACTGTTTGA |
| CGGACCAACCGT | ATGAATTCCGGTTGTAC | TGAACTCGAATT |
| GGATTGTTGTAA | ATTTACCTCGCCACATT | AGACCCCCCCGA |
| ACACGAGCACAC | TAGCCCAGCGTGTTGCA | GATTGAACCGGG |
| TGTTTGATGAAC | AGCACAGTGTATCAAAA | TGTCTTGAAAGT |
| TCGAATTAGACC | TTGTGAACATGCAGATA | ACTTCGGACAGA |
| CCCCCGAGATTG | ACTACACCGCATATTGT | AAAACAATACTT |
| AACCGGGTGTCT | CTGGGAATATCTCATAT | GGGTGTGTACAT |
| TGAAAGTACTTC | GGAGCCTAGCTTTGGTC | TTGGAACATGCG |
| GGACAGAAAAAC | TAATCTTACACGACGGG | CGGCTCCGATGG |
| AATACTTGGGTG | GGCACCACGTTAAAGTT | TACGTCTACCTA |
| TGTACATTTGGA | TGTAGATACACCCGAGA | CGCCACGTTTTT |
| ACATGCGGGCT | GTTTGTCGGGATTATAC | GGTCACCTGGAA |
| CCGATGGTACGT | GTTTTTGTGGTGTATTT | AGGGGATGAAAA |
| CTACCTACGCCA | TAACGGGCATGTTGAAG | AACAAGAAACCC |
| CGTTTTTGGTCA | CCGTAGCATACACTGTT | TACGCCCGCAGT |
| CCTGGAAAGGGG | GTATCCACAGTAGATCA | AACTCCTCAACC |
| ATGAAAAACAA | TTTTGTAAACGCAATTG | AAGAGGGGCTGA |
| GAAACCCTACGC | AAGAGCGTGGATTTCCG | GTTTCATATGTG |
| CCGCAGTAACTC | CCAACGGCCGGTCAGCC | GAATTACCACTC |
| CTCAACCAAGAG | ACCGGCGACTACTAAAC | GCATGTATTTTC |
| GGGCTGAGTTTC | CCAAGGAAATTACCCCC | AGTTGGTGATAC |
| ATATGTGGAATT | GTAAACCCCGGAACGTC | GTTTAGCTTGGC |
| ACCACTCGCATG | ACCACTTCTACGATATG | AATGCATCTTCA |
| TATTTTCAGTTG | CCGCATGGACCGGAGGG | GTATAAGATACA |
| GTGATACGTTTA | CTTGCAGCAGTAGTACT | TGAAGCGCCATT |
| GCTTGGCAATGC | TTTATGTCTCGTAATAT | TGATTTGCTGTT |
| ATCTTCAGTATA | TTTTAATCTGTACGGCT | AGAGTGGTTGTA |
| AGATACATGAAG | TGA | TGTCCCCATCGA |
| CGCCATTTGATT | | TCCTACATGTCA |
| TGCTGTTAGAGT | | ACCAATGCGGTT |
| GGTTGTATGTCC | | ATATTCTACGTG |
| CCATCGATCCTA | | TTTGTATCATCC |
| CATGTCAACCAA | | CAACGCACCCCA |
| TGCGGTTATATT | | ATGCCTCTCTCA |
| CTACGTGTTTGT | | TATGAATTCCGG |
| ATCATCCCAACG | | TTGTACATTTAC |
| CACCCCAATGCC | | CTCGCCACATTT |
| TCTCTCATATGA | | AGCCCAGCGTGT |
| ATTCCGGTTGTA | | TGCAAGCACAGT |
| CATTTACCTCGC | | GTATCAAAATTG |
| CACATTTAGCCC | | TGAACATGCAGA |
| AGCGTGTTGCAA | | TAACTACACCGC |
| GCACAGTGTATC | | ATATTGTCTGGG |
| AAAATTGTGAAC | | AATATCTCATAT |
| ATGCAGATAACT | | GGAGCCTAGCTT |
| ACACCGCATATT | | TGGTCTAATCTT |
| GTCTGGGAATAT | | ACACGACGGGGG |
| CTCATATGGAGC | | CACCACGTTAAA |
| CTAGCTTTGGTC | | GTTTGTAGATAC |
| TAATCTTACACG | | ACCCGAGAGTTT |
| ACGGGGGCACCA | | GTCGGGATTATA |
| CGTTAAAGTTTG | | CGTTTTTGTGGT |
| TAGATACACCCG | | GTATTTTAACGG |
| AGAGTTTGTCGG | | GCATGTTGAAGC |
| GATTATACGTTT | | CGTAGCATACAC |
| TTGTGGTGTATT | | TGTTGTATCCAC |
| TTAACGGGCATG | | AGTAGATCATTT |
| TTGAAGCCGTAG | | TGTAAACGCAAT |
| CATACACTGTTG | | TGAAGAGCGTGG |

TABLE 2-continued

| | | | |
|---|---|---|---|
| | TATCCACAGTAG | | ATTTCCGCCAAC |
| | ATCATTTTGTAA | | GGCCGGTCAGCC |
| | ACGCAATTGAAG | | ACCGGCGACTAC |
| | AGCGTGGATTTC | | TAAACCCAAGGA |
| | CGCCAACGGCCG | | AATTACCCCCGT |
| | GTCAGCCACCGG | | AAACCCCGGAAC |
| | CGACTACTAAAC | | GTCACCACTTCT |
| | CCAAGGAAATTA | | ACGATATGCCGC |
| | CCCCCGTAAACC | | ATGGACCGGAGG |
| | CCGGAACGTCAC | | GCTTGCAGCAGT |
| | CACTTCTACGAT | | AGTACTTTTATG |
| | ATGCCGCATGGA | | TCTCGTAATATT |
| | CCGGAGGGCTTG | | TTTAATCTGTAC |
| | CAGCAGTAGTAC | | GGCTTGATGATA |
| | TTTTATGTCTCG | | ATAGGCTGGAGC |
| | TAATATTTTAA | | CTCGGTGGCCAT |
| | TCTGTACGGCTT | | GCTTCTTGCCCC |
| | GATGATAATAGG | | TTGGGCCTCCCC |
| | CTGGAGCCTCGG | | CCAGCCCCTCCT |
| | TGGCCATGCTTC | | CCCCTTCCTGCA |
| | TTGCCCCTTGGG | | CCCGTACCCCCG |
| | CCTCCCCCCAGC | | TGGTCTTTGAAT |
| | CCCTCCTCCCCT | | AAAGTCTGAGTG |
| | TCCTGCACCCGT | | GGCGGCAAAAAA |
| | ACCCCGTGGTC | | AAAAAAAAAAAA |
| | TTTGAATAAAGT | | AAAAAAAAAAAA |
| | CTGAGTGGGCGG | | AAAAAAAAAAAA |
| | C | | AAAAAAAAAAAA |
| | | | AAAAAAAAAAAA |
| | | | AAAAAAAAAAAA |
| | | | AAAAAAAAAAAA |
| | | | AAAAAAAAAATC |
| | | | TAG |

| | SEQ ID NO: 21 | SEQ ID NO: 22 | SEQ ID NO: 23 | SEQ ID NO: 24 |
|---|---|---|---|---|
| VZV-GE- | TCAAGCTTTTGG | METPAQLLFLLLLWLPD | ATGGAAACCCCGGCGCA | G*GGGAAATAAG |
| delete- | ACCCTCGTACAG | TTGSVLRYDDFHIDEDK | GCTGCTGTTTCTGCTGC | AGAGAAAAGAAG |
| 562- | AAGCTAATACGA | LDTNSVYEPYYHSDHAE | TGCTGTGGCTGCCGGAT | AGTAAGAAGAAA |
| replacedSP- | CTCACTATAGGG | SSWVNRGESSRKAYDHN | ACCACCGGCTCCGTCTT | TATAAGAGCCAC |
| withIgKaPPa | AAATAAGAGAGA | SPYIWPRNDYDGFLENA | GCGATACGATGATTTTC | CATGGAAACCCC |
| | AAAGAAGAGTAA | HEHHGVYNQGRGIDSGE | ACATCGATGAAGACAAA | GGCGCAGCTGCT |
| | GAAGAAATATAA | RLMQPTQMSAQEDLGDD | CTGGATACAAACTCCGT | GTTTCTGCTGCT |
| | GAGCCACCATGG | TGIHVIPTLNGDDRHKI | ATATGAGCCTTACTACC | GCTGTGGCTGCC |
| | AAACCCCGGCGC | VNVDQRQYGDVFKGDLN | ATTCAGATCATGCGGAG | GGATACCACCGG |
| | AGCTGCTGTTTC | PKPQGQRLIEVSVEENH | TCTTCATGGGTAAATCG | CTCCGTCTTGCG |
| | TGCTGCTGGATA | PFTLRAPIQRIYGVRYT | GGGGAGAGTCTTCGCGAA | ATACGATGATTT |
| | GGCTGCCGGATA | ETWSFLPSLTCTGDAAP | AAGCGTACGATCATAAC | TCACATCGATGA |
| | CCACCGGCTCCG | AIQHICLKHTTCFQDVV | TCACCTTATATATGGCC | AGACAAACTGGA |
| | TCTTGCGATACG | VDVDCAENTKEDQLAEI | ACGTAATGATTATGATG | TACAAACTCCGT |
| | ATGATTTTCACA | SYRFQGKKEADQPWIVV | GATTTTTAGAGAACGCA | ATATGAGCCTTA |
| | TCGATGAAGACA | NTSTLFDELELDPPEIE | CACGAACACCATGGGGT | CTACCATTCAGA |
| | AACTGGATACAA | PGVLKVLRTEKQYLGVY | GTATAATCAGGGCCGTG | TCATGCGGAGTC |
| | ACTCCGTATATG | IWNMRGSDGTSTYATFL | GTATCGATAGCGGGGAA | TTCATGGGTAAA |
| | AGCCTTACTACC | VTWKGDEKTRNPTPAVT | CGGTTAATGCAACCCAC | TCGGGGAGAGTC |
| | ATTCAGATCATG | PQPRGAEFHMWNYHSHV | ACAAATGTCTGCACAGG | TTCGCGAAAAGC |
| | CGGAGTCTTCAT | FSVGDTFSLAMHLQYKI | AGGATCTTGGGGACGAT | GTACGATCATAA |
| | GGGTAAATCGGG | HEAPFDLLLEWLYVPID | ACGGGCATCCACGTTAT | CTCACCTTATAT |
| | GAGAGTCTTCGC | PTCQPMRLYSTCLYHPN | CCCTACGTTAAACGGCG | ATGGCCACGTAA |
| | GAAAAGCGTACG | APQCLSHMNSGCTFTSP | ATGACAGACATAAAATT | TGATTATGATGG |
| | ATCATAACTCAC | HLAQRVASTVYQNCEHA | GTAAATGTGGACCAACG | ATTTTTAGAGAA |
| | CTTATATATGGC | DNYTAYCLGISHMEPSF | TCAATACGGTGACGTGT | CGCACACGAACA |
| | CACGTAATGATT | GLILHDGGTTLKFVDTP | TTAAAGGAGATCTTAAT | CCATGGGGTGTA |
| | ATGATGGATTTT | ESLSGLYVFVVYFNGHV | CCAAAACCCCAAGGCCA | TAATCAGGGCCG |
| | TAGAGAACGCAC | EAVAYTVVSTVDHFVNA | AAGACTCATTGAGGTGT | TGGTATCGGATAG |
| | ACGAACACCATG | IEERGFPPTAGQPPATT | CAGTGGAAGAAAATCAC | CGGGGAACGGTT |
| | GGGTGTATAATC | KPKEITPVNPGTSPLLR | CCGTTTACTTTACGCGC | AATGCAACCCAC |
| | AGGGCCGTGGTA | YAAWTGGLAAVVLLCLV | ACCGATTCAGCGGATTT | ACAAATGTCTGC |
| | TCGATAGCGGGG | IFLICTA* | ATGGAGTCCGGTACACC | ACAGGAGGATCT |
| | AACGGTTAATGC | | GAGACTTGGAGCTTTTT | TGGGGACGATAC |
| | AACCCACACAAA | | GCCGTCATTAACCTGTA | GGGCATCCACGT |
| | TGTCTGCACAGG | | CGGGAGACGCAGCGCCC | TATCCCTACGTT |
| | AGGATCTTGGGG | | GCCATCCAGCATATATG | AAACGGCGATGA |
| | ACGATACGGGCA | | TTTAAAACATACAACAT | CAGACATAAAAT |
| | TCCACGTTATCC | | GCTTTCAAGACGTGGTG | TGTAAATGTGGA |
| | CTACGTTAAACG | | GTGGATGTGGATTGCGC | CCAACGTCAATA |
| | GCGATGACAGAC | | GGAAAATACTAAAGAGG | CGGTGACGTGTT |
| | ATAAAATTGTAA | | ATCAGTTGGCCGAAATC | TAAAGGAGATCT |
| | ATGTGGACCAAC | | AGTTACCGTTTTCAAGG | TAATCCAAAACC |
| | GTCAATACGGTG | | TAAGAAGGAAGCGGACC | CCAAGGCCAAAG |
| | ACGTGTTTAAAG | | AACCGTGGATTGTTGTA | ACTCATTGAGGT |

TABLE 2-continued

| | | |
|---|---|---|
| GAGATCTTAATC | AACACGAGCACACTGTT | GTCAGTGGAAGA |
| CAAAACCCCAAG | TGATGAACTCGAATTAG | AAATCACCCGTT |
| GCCAAAGACTCA | ACCCCCCCGAGATTGAA | TACTTTACGCGC |
| TTGAGGTGTCAG | CCGGGTGTCTTGAAAGT | ACCGATTCAGCG |
| TGGAAGAAAATC | ACTTCGGACAGAAAAAC | GATTTATGGAGT |
| ACCCGTTTACTT | AATACTTGGGTGTGTAC | CCGGTACACCGA |
| TACGCGCACCGA | ATTTGGAACATGCGCGG | GACTTGGAGCTT |
| TTCAGCGGATTT | CTCCGATGGTACGTCTA | TTTGCCGTCATT |
| ATGGAGTCCGGT | CCTACGCCACGTTTTTG | AACCTGTACGGG |
| ACACCGAGACTT | GTCACCTGGAAAGGGGA | AGACGCAGCGCC |
| GGAGCTTTTTGC | TGAAAAAACAAGAAACC | CGCCATCCAGCA |
| CGTCATTAACCT | CTACGCCCGCAGTAACT | TATATGTTTAAA |
| GTACGGGAGACG | CCTCAACCAAGAGGGGC | ACATACAACATG |
| CAGCGCCCGCCA | TGAGTTTCATATGTGGA | CTTTCAAGACGT |
| TCCAGCATATAT | ATTACCACTCGCATGTA | GGTGGTGGATGT |
| GTTTAAAACATA | TTTTCAGTTGGTGATAC | GGATTGCGCGGA |
| CAACATGCTTTC | GTTTAGCTTGGCAATGC | AAATACTAAAGA |
| AAGACGTGGTGG | ATCTTCAGTATAAGATA | GGATCAGTTGGC |
| TGGATGTGGATT | CATGAAGCGCCATTTGA | CGAAATCAGTTA |
| GCGCGGAAAATA | TTTGCTGTTAGAGTGGT | CCGTTTTCAAGG |
| CTAAAGAGGATC | TGTATGTCCCCATCGAT | TAAGAAGGAAGC |
| AGTTGGCCGAAA | CCTACATGTCAACCAAT | GGACCAACCGTG |
| TCAGTTACCGTT | GCGGTTATATTCTACGT | GATTGTTGTAAA |
| TTCAAGGTAAGA | GTTTGTATCATCCCAAC | CACGAGCACACT |
| AGGAAGCGGACC | GCACCCCAATGCCTCTC | GTTTGATGAACT |
| AACCGTGGATTG | TCATATGAATTCCGGTT | CGAATTAGACCC |
| TTGTAAACACGA | GTACATTTACCTCGCCA | CCCCGAGATTGA |
| GCACACTGTTTG | CATTTAGCCCAGCGTGT | ACCGGGTGTCTT |
| ATGAACTCGAAT | TGCAAGCACAGTGTATC | GAAAGTACTTCG |
| TAGACCCCCCCG | AAAATTGTGAACATGCA | GACAGAAAAACA |
| AGATTGAACCGG | GATAACTACACCGCATA | ATACTTGGGTGT |
| GTGTCTTGAAAG | TTGTCTGGGAATATCTC | GTACATTTGGAA |
| TACTTCGGACAG | ATATGGAGCCTAGCTTT | CATGCGCGGCTC |
| AAAAACAATACT | GGTCTAATCTTACACGA | CGATGGTACGTC |
| TGGGTGTGTACA | CGGGGGCACCACGTTAA | TACCTACGCCAC |
| TTTGGAACATGC | AGTTTGTAGATACACCC | GTTTTTGGTCAC |
| GCGGCTCCGATG | GAGAGTTTGTCGGGATT | CTGGAAAGGGGA |
| GTACGTCTACCT | ATACGTTTTTGTGGTGT | TGAAAAAACAAG |
| ACGCCACGTTTT | ATTTTAACGGGCATGTT | AAACCCTACGCC |
| TGGTCACCTGGA | GAAGCCGTAGCATACAC | CGCAGTAACTCC |
| AAGGGGATGAAA | TGTTGTATCCACAGTAG | TCAACCAAGAGG |
| AAACAAGAAACC | ATCATTTTGTAAACGCA | GGCTGAGTTTCA |
| CTACGCCCGCAG | ATTGAAGAGCGTGGATT | TATGTGGAATTA |
| TAACTCCTCAAC | TCCGCCAACGGCCGGTC | CCACTCGCATGT |
| CAAGAGGGGCTG | AGCCACCGGCGACTACT | ATTTTCAGTTGG |
| AGTTTCATATGT | AAACCCAAGGAAATTAC | TGATACGTTTAG |
| GGAATTACCACT | CCCCGTAAACCCCGGAA | CTTGGCAATGCA |
| CGCATGTATTTT | CGTCACCACTTCTACGA | TCTTCAGTATAA |
| CAGTTGGTGATA | TATGCCGCATGGACCGG | GATACATGAAGC |
| CGTTTAGCTTGG | AGGGCTTGCAGCAGTAG | GCCATTTGATTT |
| CAATGCATCTTC | TACTTTTATGTCTCGTA | GCTGTTAGAGTG |
| AGTATAAGATAC | ATATTTTTAATCTGTAC | GTTGTATGTCCC |
| ATGAAGCGCCAT | GGCTTGA | CATCGATCCTAC |
| TTGATTTGCTGT | | ATGTCAACCAAT |
| TAGAGTGGTTGT | | GCGGTTATATTC |
| ATGTCCCCATCG | | TACGTGTTTGTA |
| ATCCTACATGTC | | TCATCCCAACGC |
| AACCAATGCGGT | | ACCCCAATGCCT |
| TATATTCTACGT | | CTCTCATATGAA |
| GTTTGTATCATC | | TTCCGGTTGTAC |
| CCAACGCACCCC | | ATTTACCTCGCC |
| AATGCCTCTCTC | | ACATTTAGCCCA |
| ATATGAATTCCG | | GCGTGTTGCAAG |
| GTTGTACATTTA | | CACAGTGTATCA |
| CCTCGCCACATT | | AAATTGTGAACA |
| TAGCCCAGCGTG | | TGCAGATAACTA |
| TTGCAAGCACAG | | CACCGCATATTG |
| TGTATCAAAATT | | TCTGGGAATATC |
| GTGAACATGCAG | | TCATATGGAGCC |
| ATAACTACACCG | | TAGCTTTGGTCT |
| CATATTGTCTGG | | AATCTTACACGA |
| GAATATCTCATA | | CGGGGGCACCAC |
| TGGAGCCTAGCT | | GTTAAAGTTTGT |
| TTGGTCTAATCT | | AGATACACCCGA |
| TACACGACGGGG | | GAGTTTGTCGGG |
| GCACCACGTTAA | | ATTATACGTTTT |
| AGTTTGTAGATA | | TGTGGTGTATTT |
| CACCCGAGAGTT | | TAACGGGCATGT |
| TGTCGGGATTAT | | TGAAGCCGTAGC |
| ACGTTTTTGTGG | | ATACACTGTTGT |

TABLE 2-continued

| | | | |
|---|---|---|---|
| | TGTATTTTAACG | | ATCCACAGTAGA |
| | GGCATGTTGAAG | | TCATTTTGTAAA |
| | CCGTAGCATACA | | CGCAATTGAAGA |
| | CTGTTGTATCCA | | GCGTGGATTTCC |
| | CAGTAGATCATT | | GCCAACGGCCGG |
| | TTGTAAACGCAA | | TCAGCCACCGGC |
| | TTGAAGAGCGTG | | GACTACTAAACC |
| | GATTTCCGCCAA | | CAAGGAAATTAC |
| | CGGCCGGTCAGC | | CCCCGTAAACCC |
| | CACCGGCGACTA | | CGGAACGTCACC |
| | CTAAACCCAAGG | | ACTTCTACGATA |
| | AAATTACCCCCG | | TGCCGCATGGAC |
| | TAAACCCCGGAA | | CGGAGGGCTTGC |
| | CGTCACCACTTC | | AGCAGTAGTACT |
| | TACGATATGCCG | | TTTATGTCTCGT |
| | CATGGACCGGAG | | AATATTTTTAAT |
| | GGCTTGCAGCAG | | CTGTACGGCTTG |
| | TAGTACTTTTAT | | ATGATAATAGGC |
| | GTCTCGTAATAT | | TGGAGCCTCGGT |
| | TTTTAATCTGTA | | GGCCATGCTTCT |
| | CGGCTTGATGAT | | TGCCCCTTGGGC |
| | AATAGGCTGGAG | | CTCCCCCCAGCC |
| | CCTCGGTGGCCA | | CCTCCTCCCCTT |
| | TGCTTCTTGCCC | | CCTGCACCCGTA |
| | CTTGGGCCTCCC | | CCCCCGTGGTCT |
| | CCCAGCCCCTCC | | TTGAATAAAGTC |
| | TCCCCTTCCTGC | | TGAGTGGGCGGC |
| | ACCCGTACCCCC | | AAAAAAAAAAAA |
| | GTGGTCTTTGAA | | AAAAAAAAAAAA |
| | TAAAGTCTGAGT | | AAAAAAAAAAAA |
| | GGGCGGC | | AAAAAAAAAAAA |
| | | | AAAAAAAAAAAA |
| | | | AAAAAAAAAAAA |
| | | | AAAAAAAAAAAA |
| | | | AAAAAAAAAAAA |
| | | | AAAATCTAG |

| | SEQ ID NO: 25 | SEQ ID NO: 26 | SEQ ID NO: 27 | SEQ ID NO: 28 |
|---|---|---|---|---|
| VZV-GE-<br>full_with_AEAADA<br>(SEQ ID NO: 58) | TCAAGCTTTTGG | MGTVNKPVVGVLMGFGI | ATGGGGACAGTTAATAA | G*GGGAAATAAG |
| | ACCCTCGTACAG | ITGTLRITNPVRASVLR | ACCTGTGGTGGGGGTAT | AGAGAAAAGAAG |
| | AAGCTAATACGA | YDDFHIDEDKLDTNSVY | TGATGGGGGTTCGGAATT | AGTAAGAAGAAA |
| | CTCACTATAGGG | EPYYHSDHAESSWVNRG | ATCACGGAACGTTGCG | TATAAGAGCCAC |
| | AAATAAGAGAGA | ESSRKAYDHNSPYIWPR | TATAACGAATCCGGTCA | CATGGGGACAGT |
| | AAAGAAGAGTAA | NDYDGFLENAHEHHGVY | GAGCATCCGTCTTGCGA | TAATAAACCTGT |
| | GAAGAAATATAA | NQGRGIDSGERLMQPTQ | TACGATGATTTTCACAT | GGTGGGGGTATT |
| | GAGCCACCATGG | MSAQEDLGDDTGIHVIP | CGATGAAGACAAACTGG | GATGGGGTTCGG |
| | GGACAGTTAATA | TLNGDDRHKIVNVDQRQ | ATACAAACTCCGTATAT | AATTATCACGGG |
| | AACCTGTGGTGG | YGDVFKGDLNPKPQGQR | GAGCCTTACTACCATTC | AACGTTGCGTAT |
| | GGGTATTGATGG | LIEVSVEENHPFTLRAP | AGATCATGCGGAGTCTT | AACGAATCCGGT |
| | GGTTCGGAATTA | IQRIYGVRYTETWSFLP | CATGGGTAAATCGGGGA | CAGAGCATCCGT |
| | TCACGGGAACGT | SLTCTGDAAPAIQHICL | GAGTCTTCGCGAAAAGC | CTTGCGATACGA |
| | TGCGTATAACGA | KHTTCFQDVVVVDVDCAE | GTACGATCATAACTCAC | TGATTTTCACAT |
| | ATCCGGTCAGAG | NTKEDQLAEISYRFQGK | CTTATATATGGCCACGT | CGATGAAGACAA |
| | CATCCGTCTTGC | KEADQPWIVVNTSTLFD | AATGATTATGATGGATT | ACTGGATACAAA |
| | GATACGATGATT | ELELDPPEIEPGVLKVL | TTTAGAGAACGCACACG | CTCCGTATATGA |
| | TTCACATCGATG | RTEKQYLGVYIWNMRGS | AACACCATGGGGTGTAT | GCCTTACTACCA |
| | AAGACAAACTGG | DGTSTYATFLVTWKGDE | AATCAGGGCCGTGGTAT | TTCAGATCATGC |
| | ATACAAACTCCG | KTRNPTPAVTPQPRGAE | CGATAGCGGGGAACGGT | GGAGTCTTCATG |
| | TATATGAGCCTT | FHMWNYHSHVFSVGDTF | TAATGCAACCCACACAA | GGTAAATCGGGG |
| | ACTACCATTCAG | SLAMHLQYKIHEAPFDL | ATGTCTGCACAGGAGGA | AGAGTCTTCGCG |
| | ATCATGCGGAGT | LLEWLYVPIDPTCQPMR | TCTTGGGGACGATACGG | AAAAGCGTACGA |
| | CTTCATGGGTAA | LYSTCLYHPNAPQCLSH | GCATCCACGTTATCCCT | TCATAACTCACC |
| | ATCGGGGATGGT | MNSGCTFTSPHLAQRVA | ACGTTAAACGGCGATGA | TTATATATGGCC |
| | CTTCGCGAAAAG | STVYQNCEHADNYTAYC | CAGACATAAAATTGTAA | ACGTAATGATTA |
| | CGTACGATCATA | LGISHMEPSFGLILHDG | ATGTGGACCAACGTCAA | TGATGGATTTTT |
| | ACTCACCTTATA | GTTLKFVDTPESLSGLY | TACGGTGACGTGTTTAA | AGAGAACGCACA |
| | TATGGCCACGT | VFVVYFNGHVEAVAYTV | AGGAGATCTTAATCCAA | CGAACACCATGG |
| | ATGATTATGATG | VSTVDHFVNAIEERGFP | AACCCCAAGGCCAAAGA | GGTGTATAATCA |
| | GATTTTTAGAGA | PTAGQPPATTKPKEITP | CTCATTGAGGTGTCAGT | GGGCCGTGGTAT |
| | ACGCACACGAAC | VNPGTSPLLRYAAWTGG | GGAAGAAATCACCCGT | CGATAGCGGGGA |
| | ACCATGGGGTGT | LAAVLLCLVIFLICTA | TTACTTTACGCGCACCG | ACGGTTAATGCA |
| | ATAATCAGGGCC | KRMRVKAYRVDKSPYNQ | ATTCAGCGGATTTATGG | ACCCACACAAAT |
| | GTGGTATCGATA | SMYYAGLPVDDFEDAEA | AGTCCGGTACACCGAGA | GTCTGCACAGGA |
| | GCGGGGAACGGT | ADAEEEFGNAIGGSHGG | CTTGGAGCTTTTTGCCG | GGATCTTGGGGA |
| | TAATGCAACCCA | SSYTVYIDKTR* | TCATTAACCTGTACGGG | CGATACGGGCAT |
| | CACAAATGTCTG | | AGACGCAGCGCCCGCCA | CCACGTTATCCC |
| | CACAGGAGGATC | | TCCAGCATATATGTTTA | TACGTTAAACGG |
| | TTGGGGACGATA | | AAACATACAACATGCTT | CGATGACAGACA |
| | CGGGCATCCACG | | TCAAGACGTGGTGGTGG | TAAAATTGTAAA |
| | TTATCCCTACGT | | ATGTGGATTGCGCGGAA | TGTGGACCAACG |

TABLE 2-continued

| | | |
|---|---|---|
| TAAACGGCGATG | AATACTAAAGAGGATCA | TCAATACGGTGA |
| ACAGACATAAAA | GTTGGCCGAAATCAGTT | CGTGTTTAAAGG |
| TTGTAAATGTGG | ACCGTTTTCAAGGTAAG | AGATCTTAATCC |
| ACCAACGTCAAT | AAGGAAGCGGACCAACC | AAAACCCCAAGG |
| ACGGTGACGTGT | GTGGATTGTTGTAAACA | CCAAAGACTCAT |
| TTAAAGGAGATC | CGAGCACACTGTTTGAT | TGAGGTGTCAGT |
| TTAATCCAAAAC | GAACTCGAATTAGACCC | GGAAGAAAATCA |
| CCCAAGGCCAAA | CCCCGAGATTGAACCGG | CCCGTTTACTTT |
| GACTCATTGAGG | GTGTCTTGAAAGTACTT | ACGCGCACCGAT |
| TGTCAGTGGAAG | CGGACAGAAAACAATA | TCAGCGGATTTA |
| AAAATCACCCGT | CTTGGGTGTGTACATTT | TGGAGTCCGGTA |
| TTACTTTACGCG | GGAACATGCGCGGCTCC | CACCGAGACTTG |
| CACCGATTCAGC | GATGGTACGTCTACCTA | GAGCTTTTTGCC |
| GGATTTATGGAG | CGCCACGTTTTTGGTCA | GTCATTAACCTG |
| TCCGGTACACCG | CCTGGAAAGGGGATGAA | TACGGGAGACGC |
| AGACTTGGAGCT | AAAACAAGAAACCCTAC | AGCGCCCGCCAT |
| TTTTGCCGTCAT | GCCCGCAGTAACTCCTC | CCAGCATATATG |
| TAACCTGTACGG | AACCAAGAGGGGCTGAG | TTTAAAACATAC |
| GAGACGCAGCGC | TTTCATATGTGGAATTA | AACATGCTTTCA |
| CCGCCATCCAGC | CCACTCGCATGTATTTT | AGACGTGGTGGT |
| ATATATGTTTAA | CAGTTGGTGATACGTTT | GGATGTGGATTG |
| AACATACAACAT | AGCTTGGCAATGCATCT | CGCGGAAAATAC |
| GCTTTCAAGACG | TCAGTATAAGATACATG | TAAAGAGGATCA |
| TGGTGGTGGATG | AAGCGCCATTTGATTTG | GTTGGCCGAAAT |
| TGGATTGCGCGG | CTGTTAGAGTGGTTGTA | CAGTTACCGTTT |
| AAAATACTAAAG | TGTCCCCATCGATCCTA | TCAAGGTAAGAA |
| AGGATCAGTTGG | CATGTCAACCAATGCGG | GGAAGCGGACCA |
| CCGAAATCAGTT | TTATATTCTACGTGTTT | ACCGTGGATTGT |
| ACCGTTTTCAAG | GTATCATCCCAACGCAC | TGTAAACACGAG |
| GTAAGAAGGAAG | CCCAATGCCTCTCTCAT | CACACTGTTTGA |
| CGGACCAACCGT | ATGAATTCCGGTTGTAC | TGAACTCGAATT |
| GGATTGTTGTAA | ATTTACCTCGCCACATT | AGACCCCCCGA |
| ACACGAGCACAC | TAGCCCAGCGTGTTGCA | GATTGAACCGGG |
| TGTTTGATGAAC | AGCACAGTGTATCAAAA | TGTCTTGAAAGT |
| TCGAATTAGACC | TTGTGAACATGCAGATA | ACTTCGGACAGA |
| CCCCCGAGATTG | ACTACACCGCATATTGT | AAAACAATACTT |
| AACGGGTGTCT | CTGGGAATATCTCATAT | GGGTGTGTACAT |
| TGAAAGTACTTC | GGAGCCTAGCTTTGGTC | TTGGAACATGCG |
| GGACAGAAAAAC | TAATCTTACACGACGGG | CGGCTCCGATGG |
| AATACTTGGGTG | GGCACCACGTTAAAGTT | TACGTCTACCTA |
| TGTACATTTGGA | TGTAGATACACCCGAGA | CGCCACGTTTTT |
| ACATGCGCGGCT | GTTTGTCGGGATTATAC | GGTCACCTGGAA |
| CCGATGGTACGT | GTTTTTTGTGGTGTATTT | AGGGGATGAAAA |
| CTACCTACGCCA | TAACGGGCATGTTGAAG | AACAAGAAACCC |
| CGTTTTTGGTCA | CCGTAGCATACACTGTT | TACGCCCGCAGT |
| CCTGGAAAGGGG | GTATCCACAGTAGATCA | AACTCCTCAACC |
| ATGAAAAAACAA | TTTTGTAAACGCAATTG | AAGAGGGGCTGA |
| GAAACCCTACGC | AAGAGCGTGGATTTCCG | GTTTCATATGTG |
| CCGCAGTAACTC | CCAACGGCCGGTCAGCC | GAATTACCACTC |
| CTCAACCAAGAG | ACCGGCGACTACTAAAC | GCATGTATTTTC |
| GGGCTGAGTTTC | CCAAGGAAATTACCCCC | AGTTGGTGATAC |
| ATATGTGGAATT | GTAAACCCCGGAACGTC | GTTTAGCTTGGC |
| ACCACTCGCATG | ACCACTTCTACGATATG | AATGCATCTTCA |
| TATTTTGGTTG | CCGCATGGACCGGAGGG | GTATAAGATACA |
| GTGATACGTTTA | CTTGCAGCAGTAGTACT | TGAAGCGCCATT |
| GCTTGGCAATGC | TTTATGTCTCGTAATAT | TGATTTGCTGTT |
| ATCTTCAGTATA | TTTTAATCTGTACGGCT | AGAGTGGTTGTA |
| AGATACATGAAG | AAACGAATGAGGGTTAA | TGTCCCCATCGA |
| CGCCATTTGATT | AGCCTATAGGGTAGACA | TCCTACATGTCA |
| TGCTGTTAGAGT | AGTCCCCGTATAACCAA | ACCAATGCGGTT |
| GGTTGTATGTCC | AGCATGTATTACGCTGG | ATATTCTACGTG |
| CCATCGATCCTA | CCTTCCAGTGGACGATT | TTTGTATCATCC |
| CATGTCAACCAA | TCGAGGACGCCGAAGCC | CAACGCACCCCA |
| TGCGGTTATATT | GCCGATGCCGAAGAAGA | ATGCCTCTCTCA |
| CTACGTGTTTGT | GTTTGGTAACGCGATTG | TATGAATTCCGG |
| ATCATCCCAACG | GAGGGAGTCACGGGGGT | TTGTACATTTAC |
| CACCCAATGCC | TCGAGTTACACGGTGTA | CTCGCCACATTT |
| TCTCTCATATGA | TATAGATAAGACCCGGT | AGCCCAGCGTGT |
| ATTCCGGTTGTA | GA | TGCAAGCACAGT |
| CATTTACCTCGC | | GTATCAAAATTG |
| CACATTTAGCCC | | TGAACATGCAGA |
| AGCGTGTTGCAA | | TAACTACACCGC |
| GCACAGTGTATC | | ATATTGTCTGGG |
| AAAATTGTGAAC | | AATATCTCATAT |
| ATGCAGATAACT | | GGAGCCTAGCTT |
| ACACCGCATATT | | TGGTCTAATCTT |
| GTCTGGGAATAT | | ACACGACGGGGG |
| CTCATATGGAGC | | CACCACGTTAAA |
| CTAGCTTTGGTC | | GTTTGTAGATAC |
| TAATCTTACACG | | ACCCGAGAGTTT |

TABLE 2-continued

| | |
|---|---|
| ACGGGGGCACCA | GTCGGGATTATA |
| CGTTAAAGTTTG | CGTTTTTGTGGT |
| TAGATACACCCG | GTATTTTAACGG |
| AGAGTTTGTCGG | GCATGTTGAAGC |
| GATTATACGTTT | CGTAGCATACAC |
| TTGTGGTGTATT | TGTTGTATCCAC |
| TTAACGGGCATG | AGTAGATCATTT |
| TTGAAGCCGTAG | TGTAAACGCAAT |
| CATACACTGTTG | TGAAGAGCGTGG |
| TATCCACAGTAG | ATTTCCGCCAAC |
| ATCATTTTGTAA | GGCCGGTCAGCC |
| ACGCAATTGAAG | ACCGGCGACTAC |
| AGCGTGGATTTC | TAAACCCAAGGA |
| CGCCAACGGCCG | AATTACCCCCGT |
| GTCAGCCACCGG | AAACCCCGGAAC |
| CGACTACTAAAC | GTCACCACTTCT |
| CCAAGGAAATTA | ACGATATGCCGC |
| CCCCCGTAAACC | ATGGACCGGAGG |
| CCGGAACGTCAC | GCTTGCAGCAGT |
| CACTTCTACGAT | AGTACTTTTATG |
| ATGCCGCATGGA | TCTCGTAATATT |
| CCGGAGGGCTTG | TTTAATCTGTAC |
| CAGCAGTAGTAC | GGCTAAACGAAT |
| TTTTATGTCTCG | GAGGGTTAAAGC |
| TAATATTTTTAA | CTATAGGGTAGA |
| TCTGTACGGCTA | CAAGTCCCCGTA |
| AACGAATGAGGG | TAACCAAAGCAT |
| TTAAAGCCTATA | GTATTACGCTGG |
| GGGTAGACAAGT | CCTTCCAGTGGA |
| CCCCGTATAACC | CGATTTCGAGGA |
| AAAGCATGTATT | CGCCGAAGCCGC |
| ACGCTGGCCTTC | CGATGCCGAAGA |
| CAGTGGACGATT | AGAGTTTGGTAA |
| TCGAGGACGCCG | CGCGATTGGAGG |
| AAGCCGCCGATG | GAGTCACGGGGG |
| CCGAAGAAGAGT | TTCGAGTTACAC |
| TTGGTAACGCGA | GGTGTATATAGA |
| TTGGAGGGGAGTC | TAAGACCCGGTG |
| ACGGGGGTTCGA | ATGATAATAGGC |
| GTTACACGGTGT | TGGAGCCTCGGT |
| ATATAGATAAGA | GGCCATGCTTCT |
| CCCGGTGATGAT | TGCCCCTTGGGC |
| AATAGGCTGGAG | CTCCCCCCAGCC |
| CCTCGGTGGCCA | CCTCCTCCCCTT |
| TGCTTCTTGCCC | CCTGCACCCGTA |
| CTTGGGCCTCCC | CCCCCGTGGTCT |
| CCCAGCCCCTCC | TTGAATAAAGTC |
| TCCCCTTCCTGC | TGAGTGGGCGGC |
| ACCCGTACCCCC | AAAAAAAAAAAA |
| GTGGTCTTTGAA | AAAAAAAAAAAA |
| TAAAGTCTGAGT | AAAAAAAAAAAA |
| GGGCGGC | AAAAAAAAAAAA |
| | AAAAAAAAAAAA |
| | AAAAAAAAAAAA |
| | AAAAAAAAAAAA |
| | AAAAAAAAAAAA |
| | AAAATCTAG |

| | SEQ ID NO: 29 | SEQ ID NO: 30 | SEQ ID NO: 31 | SEQ ID NO: 32 |
|---|---|---|---|---|
| VZV-GE-full_with_AEAADA (SEQ ID NO: 58)_and_Y582G | TCAAGCTTTTGG | MGTVNKPVVGVLMGFGI | ATGGGGACAGTTAATAA | G*GGGAAATAAG |
| | ACCCTCGTACAG | ITGTLRITNPVRASVLR | ACCTGTGGTGGGGGTAT | AGAGAAAGAAG |
| | AAGCTAATACGA | YDDFHIDEDKLDTNSVY | TGATGGGGTTCGGAATT | AGTAAGAAGAAA |
| | CTCACTATAGGG | EPYYHSDHAESSWVNRG | ATCACGGGAACGTTGCG | TATAAGAGCCAC |
| | AAATAAGAGAGA | ESSRKAYDHNSPYIWPR | TATAACGAATCCGGTCA | CATGGGGACAGT |
| | AAAGAAGAGTAA | NDYDGFLENAHEHHGVY | GAGCATCCGTCTTGCGA | TAATAAACCTGT |
| | GAAGAAATATAA | NQGRGIDSGERLMQPTQ | TACGATGATTTTCACAT | GGTGGGGGTATT |
| | GAGCCACCATGG | MSAQEDLGDDTGIHVIP | CGATGAAGACAAACTGG | GATGGGGTTCGG |
| | GGACAGTTAATA | TLNGDDRHKIVNVDQRQ | ATACAAACTCCGTATAT | AATTATCACGGG |
| | AACCTGTGGTGG | YGDVFKGDLNPKPQGQR | GAGCCTTACTACCATTC | AACGTTGCGTAT |
| | GGGTATTGATGG | LIEVSVEENHPFTLRAP | AGATCATGCGGAGTCTT | AACGAATCCGGT |
| | GGTTCGGAATTA | IQRIYGVRYTETWSFLP | CATGGGTAAATCGGGGA | CAGAGCATCCGT |
| | TCACGGGAACGT | SLTCTGDAAPAIQHICL | GAGTCTTCGCGAAAAGC | CTTGCGATACGA |
| | TGCGTATAACGA | KHTTCFQDVVVDVDCAE | GTACGATCATAACTCAC | TGATTTTCACAT |
| | ATCCGGTCAGAG | NTKEDQLAEISYRFQGK | CTTATATATGGCCACGT | CGATGAAGACAA |
| | CATCCGTCTTGC | KEADQPWIVVNTSTLFD | AATGATTATGATGGATT | ACTGGATACAAA |
| | GATACGATGATT | ELELDPPEIEPGVLKVL | TTTAGAGAACGCACACG | CTCCGTATATGA |
| | TTCACATCGATG | RTEKQYLGVYIWNMRGS | AACACCATGGGTGTAT | GCCTTACTACCA |
| | AAGACAAACTGG | DGTSTYATFLVTWKGDE | AATCAGGGCCGTGGTAT | TTCAGATCATGC |
| | ATACAAACTCCG | KTRNPTPAVTPQPRGAE | CGATAGCGGGGAACGGT | GGAGTCTTCATG |
| | TATATGAGCCTT | FHMWNYHSHVFSVGDTF | TAATGCAACCCACACAA | GGTAAATCGGGG |

TABLE 2-continued

| | | | |
|---|---|---|---|
| ACTACCATTCAG | SLAMHLQYKIHEAPFDL | ATGTCTGCACAGGAGGA | AGAGTCTTCGCG |
| ATCATGCGGAGT | LLEWLYVPIDPTCQPMR | TCTTGGGGACGATACGG | AAAAGCGTACGA |
| CTTCATGGGTAA | LYSTCLYHPNAPQCLSH | GCATCCACGTTATCCCT | TCATAACTCACC |
| ATCGGGGAGAGT | MNSGCTFTSPHLAQRVA | ACGTTAAACGGCGATGA | TTATATATGGCC |
| CTTCGCGAAAAG | STVYQNCEHADNYTAYC | CAGACATAAAATTGTAA | ACGTAATGATTA |
| CGTACGATCATA | LGISHMEPSFGLILHDG | ATGTGGACCAACGTCAA | TGATGGATTTTT |
| ACTCACCTTATA | GTTLKFVDTPESLSGLY | TACGGTGACGTGTTTAA | AGAGAACGCACA |
| TATGGCCACGTA | VFVVYFNGHVEAVAYTV | AGGGAGATCTTAATCCAA | CGAACACCATGG |
| ATGATTATGATG | VSTVDHFVNAIEERGFP | AACCCCAAGGCCAAAGA | GGTGTATAATCA |
| GATTTTTAGAGA | PTAGQPPATTKPKEITP | CTCATTGAGGTGTCAGT | GGGCCGTGGTAT |
| ACGCACACGAAC | VNPGTSPLLRYAAWTGG | GGAAGAAAATCACCCGT | CGATAGCGGGGA |
| ACCATGGGGTGT | LAAVVLLCLVIFLICTA | TTACTTTACGCGCACCG | ACGGTTAATGCA |
| ATAATCAGGGCC | KRMRVKAYRVDKSPYNQ | ATTCAGCGGATTTATGG | ACCCACACAAAT |
| GTGGTATCGATA | SMYGAGLPVDDFEDAEA | AGTCCGGTACACCGAGA | GTCTGCACAGGA |
| GCGGGGAACGGT | ADAEEEFGNAIGGSHGG | CTTGGAGCTTTTTGCCG | GGATCTTGGGGA |
| TAATGCAACCCA | SSYTVYIDKTR* | TCATTAACCTGTACGGG | CGATACGGGCAT |
| CACAAATGTCTG | | AGACGCAGCGCCCGCCA | CCACGTTATCCC |
| CACAGGAGGATC | | TCCAGCATATATGTTTA | TACGTTAAACGG |
| TTGGGGACGATA | | AAACATACAACATGCTT | CGATGACAGACA |
| CGGGCATCCACG | | TCAAGACGTGGTGGTGG | TAAAATTGTAAA |
| TTATCCCTACGT | | ATGTGGATTGCGCGGAA | TGTGGACCAACG |
| TAAACGGCGATG | | AATACTAAAGAGGATCA | TCAATACGGTGA |
| ACAGACATAAAA | | GTTGGCCGAAATCAGTT | CGTGTTTAAAGG |
| TTGTAAATGTGG | | ACCGTTTTCAAGGTAAG | AGATCTTAATCC |
| ACCAACGTCAAT | | AAGGAAGCGGACCAACC | AAAACCCCAAGG |
| ACGGTGACGTGT | | GTGGATTGTTGTAAACA | CCAAAGACTCAT |
| TTAAAGGAGATC | | CGAGCACACTGTTTGAT | TGAGGTGTCAGT |
| TTAATCCAAAAC | | GAACTCGAATTAGACCC | GGAAGAAAATCA |
| CCCAAGGCCAAA | | CCCCGAGATTGAACCGG | CCCGTTTACTTT |
| GACTCATTGAGG | | GTGTCTTGAAAGTACTT | ACGCGCACCGAT |
| TGTCAGTGGAAG | | CGGACAGAAAACAATA | TCAGCGGATTTA |
| AAAATCACCCGT | | CTTGGGTGTGTACATTT | TGGAGTCCGGTA |
| TTACTTTACGCG | | GGAACATGCGCGGCTCC | CACCGAGACTTG |
| CACCGATTCAGC | | GATGGTACGTCTACCTA | GAGCTTTTTGCC |
| GGATTTATGGAG | | CGCCACGTTTTTGGTCA | GTCATTAACCTG |
| TCCGGTACACCG | | CCTGGAAAGGGGATGAA | TACGGGAGACGC |
| AGACTTGGAGCT | | AAAACAAGAAACCCTAC | AGCGCCCGCCAT |
| TTTTGCCGTCAT | | GCCCGCAGTAACTCCTC | CCAGCATATATG |
| TAACCTGTACGG | | AACCAAGAGGGGCTGAG | TTTAAAACATAC |
| GAGACGCAGCGC | | TTTCATATGTGGAATTA | AACATGCTTTCA |
| CCGCCATCCAGC | | CCACTCGCATGTATTTT | AGACGTGGTGGT |
| ATATATGTTTAA | | CAGTTGGTGATACGTTT | GGATGTGGATTG |
| AACATACAACAT | | AGCTTGGCAATGCATCT | CGCGGAAAATAC |
| GCTTTCAAGACG | | TCAGTATAAGATACATG | TAAAGAGGATCA |
| TGGTGGTGGATG | | AAGCGCCATTTGATTTG | GTTGGCCGAAAT |
| TGGATTGCGCGG | | CTGTTAGAGTGGTTGTA | CAGTTACCGTTT |
| AAAATACTAAAG | | TGTCCCCATCGATCCTA | TCAAGGTAAGAA |
| AGGATCAGTTGG | | CATGTCAACCAATGCGG | GGAAGCGGACCA |
| CCGAAATCAGTT | | TTATATTCTACGTGTTT | ACCGTGGATTGT |
| ACCGTTTCAAG | | GTATCATCCCAACGCAC | TGTAAACACGAG |
| GTAAGAAGGAAG | | CCCAATGCCTCTCTCAT | CACACTGTTTGA |
| CGGACCAACCGT | | ATGAATTCCGGTTGTAC | TGAACTCGAATT |
| GGATTGTTGTAA | | ATTTACCTCGCCACATT | AGACCCCCCGA |
| ACACGAGCACAC | | TAGCCCAGCGTGTTGCA | GATTGAACCGGG |
| TGTTTGATGAAC | | AGCACAGTGTATCAAAA | TGTCTTGAAAGT |
| TCGAATTAGACC | | TTGTGAACATGCAGATA | ACTTCGGACAGA |
| CCCCCGAGATTG | | ACTACACCGCATATTGT | AAAACAATACTT |
| AACCGGGTGTCT | | CTGGGAATATCTCATAT | GGGTGTGTACAT |
| TGAAAGTACTTC | | GGAGCCTAGCTTTGGTC | TTGGAACATGCG |
| GGACAGAAAAC | | TAATCTTACACGACGGG | CGGCTCCGATGG |
| AATACTTGGGTG | | GGCACCACGTTAAAGTT | TACGTCTACCTA |
| TGTACATTTGGA | | TGTAGATACACCCGAGA | CGCCACGTTTTT |
| ACATGCGCGGCT | | GTTTGTCGGGATTATAC | GGTCACCTGGAA |
| CCGATGGTACGT | | GTTTTTGTGGTGTATTT | AGGGGATGAAAA |
| CTACCTACGCCA | | TAACGGGCATGTTGAAG | AACAAGAAACCC |
| CGTTTTTGGTCA | | CCGTAGCATACACTGTT | TACGCCCGCAGT |
| CCTGGAAGGGG | | GTATCCACAGTAGATCA | AACTCCTCAACC |
| ATGAAAAACAA | | TTTTGTAAACGCAATTG | AAGAGGGGCTGA |
| GAAACCCTACGC | | AAGAGCGTGGATTCCG | GTTTCATATGTG |
| CCGCAGTAACTC | | CCAACGGCCGGTCAGCC | GAATTACCACTC |
| CTCAACCAAGAG | | ACCGGCGACTACTAAAC | GCATGTATTTTC |
| GGGCTGAGTTTC | | CCAAGGAAATTACCCCC | AGTTGGTGATAC |
| ATATGTGGAATT | | GTAAACCCCGGAACGTC | GTTTAGCTTGGC |
| ACCACTCGCATG | | ACCACTTCTACGATATG | AATGCATCTTCA |
| TATTTTCAGTTG | | CCGCATGGACCGGAGGG | GTATAAGATACA |
| GTGATACGTTTA | | CTTGCAGCAGTAGTACT | TGAAGCGCCATT |
| GCTTGGCAATGC | | TTTATGTCTCGTAATAT | TGATTTGCTGTT |
| ATCTTCAGTATA | | TTTTAATCTGTACGGCT | AGAGTGGTTGTA |
| AGATACATGAAG | | AAACGAATGAGGGTTAA | TGTCCCCATCGA |
| CGCCATTTGATT | | AGCCTATAGGGTAGACA | TCCTACATGTCA |

TGCTGTTAGAGT
GGTTGTATGTCC
CCATCGATCCTA
CATGTCAACCAA
TGCGGTTATATT
CTACGTGTTTGT
ATCATCCCAACG
CACCCCAATGCC
TCTCTCATATGA
ATTCCGGTTGTA
CATTTACCTCGC
CACATTTAGCCC
AGCGTGTTGCAA
GCACAGTGTATC
AAAATTGTGAAC
ATGCAGATAACT
ACACCGCATATT
GTCTGGGAATAT
CTCATATGGAGC
CTAGCTTTGGTC
TAATCTTACACG
ACGGGGGCACCA
CGTTAAAGTTTG
TAGATACACCCG
AGAGTTTGTCGG
GATTATACGTTT
TTGTGGTGTATT
TTAACGGGCATG
TTGAAGCCGTAG
CATACACTGTTG
TATCCACAGTAG
ATCATTTTGTAA
ACGCAATTGAAG
AGCGTGGATTTC
CGCCAACGGCCG
GTCAGCCACCGG
CGACTACTAAAC
CCAAGGAAATTA
CCCCCGTAAACC
CCGGAACGTCAC
CACTTCTACGAT
ATGCCGCATGGA
CCGGAGGGCTTG
CAGCAGTAGTAC
TTTTATGTCTCG
TAATATTTTTAA
TCTGTACGGCTA
AACGAATGAGGG
TTAAAGCCTATA
GGGTAGACAAGT
CCCCGTATAACC
AAAGCATGTATG
GCGCTGGCCTTC
CAGTGGACGATT
TCGAGGACGCCG
AAGCCGCCGATG
CCGAAGAAGAGT
TTGGTAACGCGA
TTGGAGGGAGTC
ACGGGGGTTCGA
GTTACACGGTGT
ATATAGATAAGA
CCCGGTGATGAT
AATAGGCTGGAG
CCTCGGTGGCCA
TGCTTCTTGCCC
CTTGGGCCTCCC
CCCAGCCCTCC
TCCCCTTCCTGC
ACCCGTACCCCC
GTGGTCTTTGAA
TAAAGTCTGAGT
GGGCGGC

AGTCCCCGTATAACCAA
AGCATGTATGGCGCTGG
CCTTCCAGTGGACGATT
TCGAGGACGCCGAAGCC
GCCGATGCCGAAGAAGA
GTTTGGTAACGCGATTG
GAGGGAGTCACGGGGGT
TCGAGTTACACGGTGTA
TATAGATAAGACCCGGT
GA

ACCAATGCGGTT
ATATTCTACGTG
TTTGTATCATCC
CAACGCACCCCA
ATGCCTCTCTCA
TATGAATTCCGG
TTGTACATTTAC
CTCGCCACATTT
AGCCCAGCGTGT
TGCAAGCACAGT
GTATCAAAATTG
TGAACATGCAGA
TAACTACACCGC
ATATTGTCTGGG
AATATCTCATAT
GGAGCCTAGCTT
TGGTCTAATCTT
ACACGACGGGGG
CACCACGTTAAA
GTTTGTAGATAC
ACCCGAGAGTTT
GTCGGGATTATA
CGTTTTTGTGGT
GTATTTTAACGG
GCATGTTGAAGC
CGTAGCATACAC
TGTTGTATCCAC
AGTAGATCATTT
TGTAAACGCAAT
TGAAGAGCGTGG
ATTTCCGCCAAC
GGCCGGTCAGCC
ACCGGCGACTAC
TAAACCCAAGGA
AATTACCCCCGT
AAACCCCGGAAC
GTCACCACTTCT
ACGATATGCCGC
ATGGACCGGAGG
GCTTGCAGCAGT
AGTACTTTTATG
TCTCGTAATATT
TTTAATCTGTAC
GGCTAAACGAAT
GAGGGTTAAAGC
CTATAGGGTAGA
CAAGTCCCCGTA
TAACCAAAGCAT
GTATGGCGCTGG
CCTTCCAGTGGA
CGATTTCGAGGA
CGCCGAAGCCGC
CGATGCCGAAGA
AGAGTTTGGTAA
CGCGATTGGAGG
GAGTCACGGGGG
TTCGAGTTACAC
GGTGTATATAGA
TAAGACCCGGTG
ATGATAATAGGC
TGGAGCCTCGGT
GGCCATGCTTCT
TGCCCCTTGGGC
CTCCCCCCAGCC
CCTCCTCCCCTT
CCTGCACCCGTA
CCCCCGTGGTCT
TTGAATAAAGTC
TGAGTGGGCGGC
AAAAAAAAAAAA
AAAAAAAAAAAA
AAAAAAAAAAAA
AAAAAAAAAAAA
AAAAAAAAAAAA
AAAAAAAAAAAA
AAAAAAAAAAAA
AAAAAAAAAAAA
AAAATCTAG

TABLE 2-continued

| | SEQ ID NO: 33 | SEQ ID NO: 34 | SEQ ID NO: 35 | SEQ ID NO: 36 |
|---|---|---|---|---|
| VZV-GE-truncated-delete_from_574 | TCAAGCTTTTGG | MGTVNKPVVGVLMGFGI | ATGGGGACAGTTAATAA | G*GGGAAATAAG |
| | ACCCTCGTACAG | ITGTLRITNPVRASVLR | ACCTGTGGTGGGGGTAT | AGAGAAAAGAAG |
| | AAGCTAATACGA | YDDFHIDEDKLDTNSVY | TGATGGGGTTCGGAATT | AGTAAGAAGAAA |
| | CTCACTATAGGG | EPYYHSDHAESSWVNRG | ATCACGGGAACGTTGCG | TATAAGAGCCAC |
| | AAATAAGAGAGA | ESSRKAYDHNSPYIWPR | TATAACGAATCCGGTCA | CATGGGGACAGT |
| | AAAGAAGAGTAA | NDYDGFLENAHEHHGVY | GAGCATCCGTCTTGCGA | TAATAAACCTGT |
| | GAAGAAATATAA | NQGRGIDSGERLMQPTQ | TACGATGATTTTCACAT | GGTGGGGGTATT |
| | GAGCCACCATGG | MSAQEDLGDDTGIHVIP | CGATGAAGACAAACTGG | GATGGGGGTTCGG |
| | GGACAGTTAATA | TLNGDDRHKIVNVDQRQ | ATACAAACTCCGTATAT | AATTATCACGGG |
| | AACCTGTGGTGG | YGDVFKGDLNPKPQGQR | GAGCCTTACTACCATTC | AACGTTGCGTAT |
| | GGGTATTGATGG | LIEVSVEENHPFTLRAP | AGATCATGCGGAGTCTT | AACGAATCCGGT |
| | GGTTCGGAATTA | IQRIYGVRYTETWSFLP | CATGGGTAAATCGGGGA | CAGAGCATCCGT |
| | TCACGGGAACGT | SLTCTGDAAPAIQHICL | GAGTCTTCGCGAAAAGC | CTTGCGATACGA |
| | TGCGTATAACGA | KHTTCFQDVVVDVDCAE | GTACGATCATAACTCAC | TGATTTTCACAT |
| | ATCCGGTCAGAG | NTKEDQLAEISYRFQGK | CTTATATATGGCCACGT | CGATGAAGACAA |
| | CATCCGTCTTGC | KEADQPWIVVNTSTLFD | AATGATTATGATGGATT | ACTGGATACAAA |
| | GATACGATGATT | ELELDPPEIEPGVLKVL | TTTAGAGAACGCACACG | CTCCGTATATGA |
| | TTCACATCGATG | RTEKQYLGVYIWNMRGS | AACACCATGGGGTGTAT | GCCTTACTACCA |
| | AAGACAAACTGG | DGTSTYATFLVTWKGDE | AATCAGGGCCGTGGTAT | TTCAGATCATGC |
| | ATACAAACTCCG | KTRNPTPAVTPQPRGAE | CGATAGCGGGGAACGGT | GGAGTCTTCATG |
| | TATATGAGCCTT | FHMWNYHSHVFSVGDTF | TAATGCAACCCACACAA | GGTAAATCGGGG |
| | ACTACCATTCAG | SLAMHLQYKIHEAPFDL | ATGTCTGCACAGGAGGA | AGAGTCTTCGCG |
| | ATCATGCGGAGT | LLEWLYVPIDPTCQPMR | TCTTGGGGACGATACGG | AAAAGCGTACGA |
| | CTTCATGGGTAA | LYSTCLYHPNAPQCLSH | GCATCCACGTTATCCCT | TCATAACTCACC |
| | ATCGGGGAGAGT | MNSGCTFTSPHLAQRVA | ACGTTAAACGGCGATGA | TTATATATGGCC |
| | CTTCGCGAAAAG | STVYQNCEHADNYTAYC | CAGACATAAAATTGTAA | ACGTAATGATTA |
| | CGTACGATCATA | LGISHMEPSFGLILHDG | ATGTGGACCAACGTCAA | TGATGGATTTTT |
| | ACTCACCTTATA | GTTLKFVDTPESLSGLY | TACGGTGACGTGTTTAA | AGAGAACGCACA |
| | TATGGCCACGTA | VFVVYFNGHVEAVAYTV | AGGAGATCTTAATCCAA | CGAACACCATGG |
| | ATGATTATGATG | VSTVDHFVNAIEERGFP | AACCCCAAGGCCAAAGA | GGTGTATAATCA |
| | GATTTTTAGAGA | PTAGQPPATTKPKEITP | CTCATTGAGGTGTCAGT | GGGCCGTGGTAT |
| | ACGCACACGAAC | VNPGTSPLLRYAAWTGG | GGAAGAAAATCACCCGT | CGATAGCGGGGA |
| | ACCATGGGGTGT | LAAVVLLCLVIFLICTA | TTACTTTACGCGCACCG | ACGGTTAATGCA |
| | ATAATCAGGGCC | KRMRVKAYRVDK* | ATTCAGCGGATTTATGG | ACCCACACAAAT |
| | GTGGTATCGATA | | AGTCCGGTACACCGAGA | GTCTGCACAGGA |
| | GCGGGGAACGGT | | CTTGGAGCTTTTTGCCG | GGATCTTGGGGA |
| | TAATGCAACCCA | | TCATTAACCTGTACGGG | CGATACGGGCAT |
| | CACAAATGTCTG | | AGACGCAGCGCCCGCCA | CCACGTTATCCC |
| | CACAGGAGGATC | | TCCAGCATATATGTTTA | TACGTTAAACGG |
| | TTGGGGACGATA | | AAACATACAACATGCTT | CGATGACAGACA |
| | CGGGCATCCACG | | TCAAGACGTGGTGGTGG | TAAAATTGTAAA |
| | TTATCCCTACGT | | ATGTGGATTGCGCGGAA | TGTGGACCAACG |
| | TAAACGGCGATG | | AATACTAAAGAGGATCA | TCAATACGGTGA |
| | ACAGACATAAAA | | GTTGGCCGAAATCAGTT | CGTGTTTAAAGG |
| | TTGTAAATGTGG | | ACCGTTTTCAAGGTAAG | AGATCTTAATCC |
| | ACCAACGTCAAT | | AAGGAAGCGGACCAACC | AAAACCCCAAGG |
| | ACGGTGACGTGT | | GTGGATTGTTGTAAACA | CCAAAGACTCAT |
| | TTAAAGGAGATC | | CGAGCACACTGTTTGAT | TGAGGTGTCAGT |
| | TTAATCAAACCA | | GAACTCGAATTAGACCC | GGAAGAAAATCA |
| | CCCAAGGCCAAA | | CCCCGAGATTGAACCGG | CCCGTTTACTTT |
| | GACTCATTGAGG | | GTGTCTTGAAAGTACTT | ACGCGCACCGAT |
| | TGTCAGTGGAAG | | CGGACAGAAAACAATA | TCAGCGGATTTA |
| | AAAATCACCCGT | | CTTGGGTGTGTACATTT | TGGAGTCCGGTA |
| | TTACTTTACGCG | | GGAACATGCGCGGCTCC | CACCGAGACTTG |
| | CACCGATTCAGC | | GATGGTACGTCTACCTA | GAGCTTTTTGCC |
| | GGATTTATGGAG | | CGCCACGTTTTTGGTCA | GTCATTAACCTG |
| | TCCGGTACACCG | | CCTGGAAAGGGGATGAA | TACGGGGAGACGC |
| | AGACTTGGAGCT | | AAAACAAGAAACCCTAC | AGCGCCCGCCAT |
| | TTTTGCCGTCAT | | GCCCGCAGTAACTCCTC | CCAGCATATATG |
| | TAACCTGTACGG | | AACCAAGAGGGCTGAG | TTTAAAACATAC |
| | GAGACGCAGCGC | | TTTCATATGTGGAATTA | AACATGCTTTCA |
| | CCGCCATCCAGC | | CCACTCGCATGTATTTT | AGACGTGGTGGT |
| | ATATATGTTTAA | | CAGTTGGTGATACGTTT | GGATGTGGATTG |
| | AACATACAACAT | | AGCTTGGCAATGCATCT | CGCGGAAAATAC |
| | GCTTTCAAGACG | | TCAGTATAAGATACATG | TAAAGAGGATCA |
| | TGGTGGTGGATG | | AAGCGCCATTTGATTTG | GTTGGCCGAAAT |
| | TGGATTGCGCGG | | CTGTTAGAGTGGTTGTA | CAGTTACCGTTT |
| | AAAATACTAAAG | | TGTCCCCATCGATCCTA | TCAAGGTAAGAA |
| | AGGATCAGTTGG | | CATGTCAACCAATGCGG | GGAAGCGGACCA |
| | CCGAAATCAGTT | | TTATATTCTACGTGTTT | ACCGTGGATTGT |
| | ACCGTTTTCAAG | | GTATCATCCCAACGCAC | TGTAAACACGAG |
| | GTAAGAAGGAAG | | CCCAATGCCTCTCTCAT | CACACTGTTTGA |
| | CGGACCAACCGT | | ATGAATTCCGGTTGTAC | TGAACTCGAATT |
| | GGATTGTTGTAA | | ATTTACCTCGCCACATT | AGACCCCCCGAG |
| | ACACGAGCACAC | | TAGCCCAGCGTGTTGCA | GATTGAACCGGG |
| | TGTTTGATGAAC | | AGCACAGTGTATCAAAA | TGTCTTGAAAGT |
| | TCGAATTAGACC | | TTGTGAACATGCAGATA | ACTTCGGACAGA |
| | CCCCCGAGATTG | | ACTACACCGCATATTGT | AAAACAATACTT |
| | AACCGGGTGTCT | | CTGGGAATATCTCATAT | GGGTGTGTACAT |

TABLE 2-continued

TGAAAGTACTTC
GGACAGAAAAAC
AATACTTGGGTG
TGTACACGTTGGA
ACATGCGCGGCT
CCGATGGTACGT
CTACCTACGCCA
CGTTTTTGGTCA
CCTGGAAAGGGG
ATGAAAAAACAA
GAAACCCTACGC
CCGCAGTAACTC
CTCAACCAAGAG
GGGCTGAGTTTC
ATATGTGGAATT
ACCACTCGCATG
TATTTTCAGTTG
GTGATACGTTTA
GCTTGGCAATGC
ATCTTCAGTATA
AGATACATGAAG
CGCCATTTGATT
TGCTGTTAGAGT
GGTTGTATGTCC
CCATCGATCCTA
CATGTCAACCAA
TGCGGTTATATT
CTACGTGTTTGT
ATCATCCCAACG
CACCCCAATGCC
TCTCTCATATGA
ATTCCGGTTGTA
CATTTACCTCGC
CACATTTAGCCC
AGCGTGTTGCAA
GCACAGTGTATC
AAAATTGTGAAC
ATGCAGATAACT
ACACCGCATATT
GTCTGGGAATAT
CTCATATGGAGC
CTAGCTTTGGTC
TAATCTTACACG
ACGGGGGCACCA
CGTTAAAGTTTG
TAGATACACCCG
AGAGTTTGTCGG
GATTATACGTTT
TTGTGGTGTATT
TTAACGGGCATG
TTGAAGCCGTAG
CATACACTGTTG
TATCCACAGTAG
ATCATTTTGTAA
ACGCAATTGAAG
AGCGTGGATTTC
CGCCAACGGCCG
GTCAGCCACCGG
CGACTACTAAAC
CCAAGGAAATTA
CCCCCGTAAACC
CCGGAACGTCAC
CACTTCTACGAT
ATGCCGCATGGA
CCGGAGGGCTTG
CAGCAGTAGTAC
TTTTATGTCTCG
TAATATTTTTAA
TCTGTACGGCTA
AACGAATGAGGG
TTAAAGCCTATA
GGGTAGACAAGT
GATGATAATAGG
CTGGAGCCTCGG
TGGCCATGCTTC
TTGCCCCTTGGG
CCTCCCCCCAGC
CCCTCCTCCCCT
TCCTGCACCCGT
ACCCCCGTGGTC

GGAGCCTAGCTTTGGTC
TAATCTTACACGACGGG
GGCACCACGTTAAAGTT
TGTAGATACACCCGAGA
GTTTGTCGGGATTATAC
GTTTTTGTGGTGTATTT
TAACGGGCATGTTGAAG
CCGTAGCATACACTGTT
GTATCCACAGTAGATCA
TTTTGTAAACGCAATTG
AAGAGCGTGGATTTCCG
CCAACGGCCGGTCAGCC
ACCGGCGACTACTAAAC
CCAAGGAAATTACCCCC
GTAAACCCCGGAACGTC
ACCACTTCTACGATATG
CCGCATGGACCGGAGGG
CTTGCAGCAGTAGTACT
TTTATGTCTCGTAATAT
TTTTAATCTGTACGGCT
AAACGAATGAGGGTTAA
AGCCTATAGGGTAGACA
AGTGA

TTGGAACATGCG
CGGCTCCGATGG
TACGTCTACCTA
CGCCACGTTTTT
GGTCACCTGGAA
AGGGGATGAAAA
AACAAGAAACCC
TACGCCCGCAGT
AACTCCTCAACC
AAGAGGGGCTGA
GTTTCATATGTG
GAATTACCACTC
GCATGTATTTTC
AGTTGGTGATAC
GTTTAGCTTGGC
AATGCATCTTCA
GTATAAGATACA
TGAAGCGCCATT
TGATTTGCTGTT
AGAGTGGTTGTA
TGTCCCCATCGA
TCCTACATGTCA
ACCAATGCGGTT
ATATTCTACGTG
TTTGTATCATCC
CAACGCACCCCA
ATGCCTCTCTCA
TATGAATTCCGG
TTGTACATTTAC
CTCGCCACATTT
AGCCCAGCGTGT
TGCAAGCACAGT
GTATCAAAATTG
TGAACATGCAGA
TAACTACACCGC
ATATTGTCTGGG
AATATCTCATAT
GGAGCCTAGCTT
TGGTCTAATCTT
ACACGACGGGGG
CACCACGTTAAA
GTTTGTAGATAC
ACCCGAGAGTTT
GTCGGGATTATA
CGTTTTTGTGGT
GTATTTTAACGG
GCATGTTGAAGC
CGTAGCATACAC
TGTTGTATCCAC
AGTAGATCATTT
TGTAAACGCAAT
TGAAGAGCGTGG
ATTTCCGCCAAC
GGCCGGTCAGCC
ACCGGCGACTAC
TAAACCCAAGGA
AATTACCCCCGT
AAACCCCGGAAC
GTCACCACTTCT
ACGATATGCCGC
ATGGACCGGAGG
GCTTGCAGCAGT
AGTACTTTTATG
TCTCGTAATATT
TTTAATCTGTAC
GGCTAAACGAAT
GAGGGTTAAAGC
CTATAGGGTAGA
CAAGTGATGATA
ATAGGCTGGAGC
CTCGGTGGCCAT
GCTTCTTGCCCC
TTGGGCCTCCCC
CCAGCCCCTCCT
CCCCTTCCTGCA
CCCGTACCCCCG
TGGTCTTTGAAT
AAAGTCTGAGTG
GGCGGCAAAAAA
AAAAAAAAAAAA

TABLE 2-continued

| | | | |
|---|---|---|---|
| | TTTGAATAAAGT | | AAAAAAAAAAAA |
| | CTGAGTGGGCGG | | AAAAAAAAAAAA |
| | C | | AAAAAAAAAAAA |
| | | | AAAAAAAAAAAA |
| | | | AAAAAAAAAAAA |
| | | | AAAAAAAAAAAA |
| | | | AAAAAAAAAATC |
| | | | TAG |

| | SEQ ID NO: 37 | SEQ ID NO: 38 | SEQ ID NO: 39 | SEQ ID NO: 40 |
|---|---|---|---|---|
| VZV-GE-<br>truncated-<br>delete_from_574_-_Y569A | TCAAGCTTTTGG | MGTVNKPVVGVLMGFGI | ATGGGGACAGTTAATAA | G*GGGAAATAAG |
| | ACCCTCGTACAG | ITGTLRITNPVRASVLR | ACCTGTGGTGGGGGTAT | AGAGAAAAGAAG |
| | AAGCTAATACGA | YDDFHIDEDKLDTNSVY | TGATGGGGTTCGGAATT | AGTAAGAAGAAA |
| | CTCACTATAGGG | EPYYHSDHAESSWVNRG | ATCACGGGAACGTTGCG | TATAAGAGCCAC |
| | AAATAAGAGAGA | ESSRKAYDHNSPYIWPR | TATAACGAATCCGGTCA | CATGGGGACAGT |
| | AAAGAAGAGTAA | NDYDGFLENAHEHHGVY | GAGCATCCGTCTTGCGA | TAATAAACCTGT |
| | GAAGAAATATAA | NQGRGIDSGERLMQPTQ | TACGATGATTTTCACAT | GGTGGGGGTATT |
| | GAGCCACCATGG | MSAQEDLGDDTGIHVIP | CGATGAAGACAAACTGG | GATGGGGTTCGG |
| | GGACAGTTAATA | TLNGDDRHKIVNVDQRQ | ATACAAACTCCGTATAT | AATTATCACGGG |
| | AACCTGTGGTGG | YGDVFKGDLNPKPQGQR | GAGCCTTACTACCATTC | AACGTTGCGTAT |
| | GGGTATTGATGG | LIEVSVEENHPFTLRAP | AGATCATGCGGAGTCTT | AACGAATCCGGT |
| | GGTTCGGAATTA | IQRIYGVRYTETWSFLP | CATGGGTAAATCGGGGA | CAGAGCATCCGT |
| | TCACGGGAACGT | SLTCTGDAAPAIQHICL | GAGTCTTCGCGAAAAGC | CTTGCGATACGA |
| | TGCGTATAACGA | KHTTCFQDVVVDVDCAE | GTACGATCATAACTCAC | TGATTTTCACAT |
| | ATCCGGTCAGAG | NTKEDQLAEISYRFQGK | CTTATATATGGCCACGT | CGATGAAGACAA |
| | CATCCGTCTTGC | KEADQPWIVVNTSTLFD | AATGATTATGATGGATT | ACTGGATACAAA |
| | GATACGATGATT | ELELDPPEIEPGVLKVL | TTTAGAGAACGCACACG | CTCCGTATATGA |
| | TTCACATCGATG | RTEKQYLGVYIWNMRGS | AACACCATGGGGTGTAT | GCCTTACTACCA |
| | AAGACAAACTGG | DGTSTYATFLVTWKGDE | AATCAGGGCCGTGGTAT | TTCAGATCATGC |
| | ATACAAACTCCG | KTRNPTPAVTPQPRGAE | CGATAGCGGGGAACGGT | GGAGTCTTCATG |
| | TATATGAGCCTT | FHMWNYHSHVFSVGDTF | TAATGCAACCCACACAA | GGTAAATCGGGG |
| | ACTACCATTCAG | SLAMHLQYKIHEAPFDL | ATGTCTGCACAGGAGGA | AGAGTCTTCGCG |
| | ATCATGCGGAGT | LLEWLYVPIDPTCQPMR | TCTTGGGGACGATACGG | AAAAGCGTACGA |
| | CTTCATGGGTAA | LYSTCLYHPNAPQCLSH | GCATCCACGTTATCCCT | TCATAACTCACC |
| | ATCGGGGAGAGT | MNSGCTFTSPHLAQRVA | ACGTTAAACGGCGATGA | TTATATATGGCC |
| | CTTCGCGAAAAG | STVYQNCEHADNYTAYC | CAGACATAAAATTGTAA | ACGTAATGATTA |
| | CGTACGATCATA | LGISHMEPSFGLILHDG | ATGTGGACCAACGTCAA | TGATGGATTTTT |
| | ACTCACCTTATA | GTTLKFVDTPESLSGLY | TACGGTGACGTGTTTAA | AGAGAACGCACA |
| | TATGGCCACGTA | VFVVYFNGHVEAVAYTV | AGGAGATCTTAATCCAA | CGAACACCATGG |
| | ATGATTATGATG | VSTVDHFVNAIEERGFP | AACCCCAAGGCCAAAGA | GGTGTATAATCA |
| | GATTTTTAGAGA | PTAGQPPATTKPKEITP | CTCATTGAGGTGTCAGT | GGGCCGTGGTAT |
| | ACGCACGCAAC | VNPGTSPLLRYAAWTGG | GGAAGAAAATCACCCGT | CGATAGCGGGGA |
| | ACCATGGGGTGT | LAAVVLLCLVIFLICTA | TTACTTTACGCGCACCG | ACGGTTAATGCA |
| | ATAATCAGGGCC | KRMRVKAARVDK* | ATTCAGCGGATTTATGG | ACCCACACAAAT |
| | GTGGTATCGATA | | AGTCCGGTACACCGAGA | GTCTGCACAGGA |
| | GCGGGGAACGGT | | CTTGGAGCTTTTTGCCG | GGATCTTGGGGA |
| | TAATGCAACCCA | | TCATTAACCTGTACGGG | CGATACGGGCAT |
| | CACAAATGTCTG | | AGACGCAGCGCCCGCCA | CCACGTTATCCC |
| | CACAGGAGGATC | | TCCAGCATATATGTTTA | TACGTTAAACGG |
| | TTGGGGACGATC | | AAACATACAACATGCTT | CGATGACAGACA |
| | CGGGCATCCACG | | TCAAGACGTGGTGGTGG | TAAAATTGTAAA |
| | TTATCCCTACGT | | ATGTGGATTGCGCGGAA | TGTGGACCAACG |
| | TAAACGGCGATG | | AATACTAAAGAGGATCA | TCAATACGGTGA |
| | ACAGACATAAAA | | GTTGGCCGAAATCAGTT | CGTGTTTAAAGG |
| | TTGTAAATGTGG | | ACCGTTTTCAAGGTAAG | AGATCTTAATCC |
| | ACCAACGTCAAT | | AAGGAAGCGGACCAACC | AAAACCCCAAGG |
| | ACGGTGACGTGT | | GTGGATTGTTGTAAACA | CCAAAGACTCAT |
| | TTAAAGGAGATC | | CGAGCACACTGTTTGAT | TGAGGTGTCAGT |
| | TTAATCCAAAAC | | GAACTCGAATTAGACCC | GGAAGAAAATCA |
| | CCCAAGGCCAAA | | CCCCGAGATTGAACCGG | CCCGTTTACTTT |
| | GACTCATTGAGG | | GTGTCTTGAAAGTACTT | ACGCGCACCGAT |
| | TGTCAGTGGAAG | | CGGACAGAAAAACAATA | TCAGCGGATTTA |
| | AAAATCACCCGT | | CTTGGGTGTGTACATTT | TGGAGTCCGGTA |
| | TTACTTTACGCG | | GGAACATGCGCGGCTCC | CACCGAGACTTG |
| | CACCGATTCAGC | | GATGGTACGTCTACCTA | GAGCTTTTTGCC |
| | GGATTTATGGAG | | CGCCACGTTTTTGGTCA | GTCATTAACCTG |
| | TCCGGTACACCG | | CCTGGAAAGGGGATGAA | TACGGGAGACGC |
| | AGACTTGGAGCT | | AAAACAAGAAACCCTAC | AGCGCCCGCCAT |
| | TTTTGCCGTCAT | | GCCCGCAGTAACTCCTC | CCAGCATATATG |
| | TAACCTGTACGG | | AACCAAGAGGGGCTGAG | TTTAAAACATAC |
| | GAGACGCAGCGC | | TTTCATATGTGGAATTA | AACATGCTTTCA |
| | CCGCCATCCAGC | | CCACTCGCATGTATTTT | AGACGTGGTGGT |
| | ATATATGTTTAA | | CAGTTGGTGATACGTTT | GGATGTGGATTG |
| | AACATACAACAT | | AGCTTGGCAATGCATCT | CGCGGAAAATAC |
| | GCTTTCAAGACG | | TCAGTATAAGATACATG | TAAAGAGGATCA |
| | TGGTGGTGGATG | | AAGCGCCATTTGATTTG | GTTGGCCGAAAT |
| | TGGATTGCGCGG | | CTGTTAGAGTGGTTGTA | CAGTTACCGTTT |
| | AAAATACTAAAG | | TGTCCCCATCGATCCTA | TCAAGGTAAGAA |
| | AGGATCAGTTGG | | CATGTCAACCAATGCGG | GGAAGCGGACCA |
| | CCGAAATCAGTT | | TTATATTCTACGTGTTT | ACCGTGGATTGT |

TABLE 2-continued

| | | |
|---|---|---|
| ACCGTTTTCAAG | GTATCATCCCAACGCAC | TGTAAACACGAG |
| GTAAGAAGGAAG | CCCAATGCCTCTCTCAT | CACACTGTTTGA |
| CGGACCAACCGT | ATGAATTCCGGTTGTAC | TGAACTCGAATT |
| GGATTGTTGTAA | ATTTACCTCGCCACATT | AGACCCCCCCGA |
| ACACGAGCACAC | TAGCCCAGCGTGTTGCA | GATTGAACCGGG |
| TGTTTGATGAAC | AGCACAGTGTATCAAAA | TGTCTTGAAAGT |
| TCGAATTAGACC | TTGTGAACATGCAGATA | ACTTCGGACAGA |
| CCCCCGAGATTG | ACTACACCGCATATTGT | AAAACAATACTT |
| AACCGGGTGTCT | CTGGGAATATCTCATAT | GGGTGTGTACAT |
| TGAAAGTACTTC | GGAGCCTAGCTTTGGTC | TTGGAACATGCG |
| GGACAGAAAAAC | TAATCTTACACGACGGG | CGGCTCCGATGG |
| AATACTTGGGTG | GGCACCACGTTAAAGTT | TACGTCTACCTA |
| TGTACATTTGGA | TGTAGATACACCCGAGA | CGCCACGTTTTT |
| ACATGCGCGGCT | GTTTGTCGGGATTATAC | GGTCACCTGGAA |
| CCGATGGTACGT | GTTTTTGTGGTGTATTT | AGGGGATGAAAA |
| CTACCTACGCCA | TAACGGGCATGTTGAAG | AACAAGAAACCC |
| CGTTTTTGGTCA | CCGTAGCATACACTGTT | TACGCCCGCAGT |
| CCTGGAAAGGGG | GTATCCACAGTAGATCA | AACTCCTCAACC |
| ATGAAAAAACAA | TTTTGTAAACGCAATTG | AAGAGGGGCTGA |
| GAAACCCTACGC | AAGAGCGTGGATTTCCG | GTTTCATATGTG |
| CCGCAGTAACTC | CCAACGGCCGGTCAGCC | GAATTACCACTC |
| CTCAACCAAGAG | ACCGGCGACTACTAAAC | GCATGTATTTTC |
| GGGCTGAGTTTC | CCAAGGAAATTACCCCC | AGTTGGTGATAC |
| ATATGTGGAATT | GTAAACCCCGGAACGTC | GTTTAGCTTGGC |
| ACCACTCGACTG | ACCACTTCTACGATATG | AATGCATCTTCA |
| TATTTTCAGTTG | CCGCATGGACCGGAGGG | GTATAAGATACA |
| GTGATACGTTTA | CTTGCAGCAGTAGTACT | TGAAGCGCCATT |
| GCTTGGCAATGC | TTTATGTCTCGTAATAT | TGATTTGCTGTT |
| ATCTTCAGTATA | TTTTAATCTGTACGGCT | AGAGTGGTTGTA |
| AGATACATGAAG | AAACGAATGAGGGTTAA | TGTCCCCATCGA |
| CGCCATTTGATT | AGCCGCCAGGGTAGACA | TCCTACATGTCA |
| TGCTGTTAGAGT | AGTGA | ACCAATGCGGTT |
| GGTTGTATGTCC | | ATATTCTACGTG |
| CCATCGATCCTA | | TTTGTATCATCC |
| CATGTCAACCAA | | CAACGCACCCCA |
| TGCGGTTATATT | | ATGCCTCTCTCA |
| CTACGTGTTTGT | | TATGAATTCCGG |
| ATCATCCCAACG | | TTGTACATTTAC |
| CACCCCAATGCC | | CTCGCCACATTT |
| TCTCTCATATGA | | AGCCCAGCGTGT |
| ATTCCGGTTGTA | | TGCAAGCACAGT |
| CATTTACCTCGC | | GTATCAAAATTG |
| CACATTTAGCCC | | TGAACATGCAGA |
| AGCGTGTTGCAA | | TAACTACACCGC |
| GCACAGTGTATC | | ATATTGTCTGGG |
| AAAATTGTGAAC | | AATATCTCATAT |
| ATGCAGATAACT | | GGAGCCTAGCTT |
| ACACCGCATATT | | TGGTCTAATCTT |
| GTCTGGGAATAT | | ACACGACGGGGG |
| CTCATATGGAGC | | CACCACGTTAAA |
| CTAGCTTTGGTC | | GTTTGTAGATAC |
| TAATCTTACACG | | ACCCGAGAGTTT |
| ACGGGGGCACCA | | GTCGGGATTATA |
| CGTTAAAGTTTG | | CGTTTTTGTGGT |
| TAGATACACCCG | | GTATTTTAACGG |
| AGAGTTTGTCGG | | GCATGTTGAAGC |
| GATTATACGTTT | | CGTAGCATACAC |
| TTGTGGTGTATT | | TGTTGTATCCAC |
| TTAACGGGCATG | | AGTAGATCATTT |
| TTGAAGCCGTAG | | TGTAAACGCAAT |
| CATACACTGTTG | | TGAAGAGCGTGG |
| TATCCACAGTAG | | ATTTCCGCCAAC |
| ATCATTTTGTAA | | GGCCGGTCAGCC |
| ACGCAATTGAAG | | ACCGGCGACTAC |
| AGCGTGGATTTC | | TAAACCCAAGGA |
| CGCCAACGGCCG | | AATTACCCCCGT |
| GTCAGCCACCGG | | AAACCCCGGAAC |
| CGACTACTAAAC | | GTCACCACTTCT |
| CCAAGGAAATTA | | ACGATATGCCGC |
| CCCCCGTAAACC | | ATGGACCGGAGG |
| CCGGAACGTCAC | | GCTTGCAGCAGT |
| CACTTCTACGAT | | AGTACTTTTATG |
| ATGCCGCATGGA | | TCTCGTAATATT |
| CCGGAGGGCTTG | | TTTAATCTGTAC |
| CAGCAGTAGTAC | | GGCTAAACGAAT |
| TTTTATGTCTCG | | GAGGGTTAAAGC |
| TAATATTTTTAA | | CGCCAGGGTAGA |
| TCTGTACGGCTA | | CAAGTGATGATA |
| AACGAATGAGGG | | ATAGGCTGGAGC |
| TTAAAGCCGCCA | | CTCGGTGGCCAT |

TABLE 2-continued

| GGGTAGACAAGT | | | GCTTCTTGCCCC |
| GATGATAATAGG | | | TTGGGCCTCCCC |
| CTGGAGCCTCGG | | | CCAGCCCCTCCT |
| TGGCCATGCTTC | | | CCCCTTCCTGCA |
| TTGCCCCTTGGG | | | CCCGTACCCCCG |
| CCTCCCCCCAGC | | | TGGTCTTTGAAT |
| CCCTCCTCCCCT | | | AAAGTCTGAGTG |
| TCCTGCACCCGT | | | GGCGGCAAAAAA |
| ACCCCCGTGGTC | | | AAAAAAAAAAAA |
| TTTGAATAAAGT | | | AAAAAAAAAAAA |
| CTGAGTGGGCGG | | | AAAAAAAAAAAA |
| C | | | AAAAAAAAAAAA |
| | | | AAAAAAAAAAAA |
| | | | AAAAAAAAAAAA |
| | | | AAAAAAAAAAAA |
| | | | AAAAAAAAAATC |
| | | | TAG |

| | SEQ ID NO: 2 | SEQ ID NO: 42 | SEQ ID NO: 43 | SEQ ID NO: 44 |
|---|---|---|---|---|
| VZV-GI-full | TCAAGCTTTTGG | MFLIQCLISAVIFYIQV | ATGTTTTTAATCCAATG | G*GGGAAATAAG |
| | ACCCTCGTACAG | TNALIFKGDHVSLQVNS | TTTGATATCGGCCGTTA | AGAGAAAAGAAG |
| | AAGCTAATACGA | SLTSILIPMQNDNYTEI | TATTTTACATACAAGTG | AGTAAGAAGAAA |
| | CTCACTATAGGG | KGQLVFigEQLPTGTNY | ACCAACGCTTTGATCTT | TATAAGAGCCAC |
| | AAATAAGAGAGA | SGTLELLYADTVAFCFR | CAAGGGCGACCACGTGA | CATGTTTTTAAT |
| | AAAGAAGAGTAA | SVQVIRYDGCPRIRTSA | GCTTGCAAGTTAACAGC | CCAATGTTTGAT |
| | GAAGAAATATAA | FISCRYKHSWHYGNSTD | AGTCTCACGTCTATCCT | ATCGGCCGTTAT |
| | GAGCCACCATGT | RISTEPDAGVMLKITKP | TATTCCCATGCAAAATG | ATTTTACATACA |
| | TTTTAATCCAAT | GINDAGVYVLLVRLDHS | ATAATTATACAGAGATA | AGTGACCAACGC |
| | GTTTGATATCGG | RSTDGFILGVNVYTAGS | AAAGGACAGCTTGTCTT | TTTGATCTTCAA |
| | CCGTTATATTTT | HHNIHGVIYTSPSLQNG | TATTGGAGAGCAACTAC | GGGCGACCACGT |
| | ACATACAAGTGA | YSTRALFQQARLCDLPA | CTACCGGGACAAACTAT | GAGCTTGCAAGT |
| | CCAACGCTTTGA | TPKGSGTSLFQHMLDLR | AGCGGAACACTGGAACT | TAACAGCAGTCT |
| | TCTTCAAGGGCG | AGKSLEDNPWLHEDVVT | GTTATACGCGGATACGG | CACGTCTATCCT |
| | ACCACGTGAGCT | TETKSVVKEGIENHVYP | TGGCGTTTTGTTTCCGG | TATTCCCATGCA |
| | TGCAAGTTAACA | TDMSTLPEKSLNDPPEN | TCAGTACAAGTAATAAG | AAATGATAATTA |
| | GCAGTCTCACGT | LLIIIPIVASVMILTAM | ATACGACGGATGTCCCC | TACAGAGATAAA |
| | CTATCCTTATTC | VIVIVISVKRRRIKKHP | GGATTAGAACGAGCGCT | AGGACAGCTTGT |
| | CCATGCAAAATG | IYRPNTKTRRGIQNATP | TTTATTTCGTGTAGGTA | CTTTATTGGAGA |
| | ATAATTATACAG | ESDVMLEAAIAQLATIR | CAAACATTCGTGGCATT | GCAACTACCTAC |
| | AGATAAAAGGAC | EESPPHSVVNPFVK* | ATGGTAACTCAACGGAT | CGGGACAAACTA |
| | AGCTTGTCTTTA | | CGGATATCAACAGAGCC | TAGCGGAACACT |
| | TTGGAGAGCAAC | | GGATGCTGGTGTAATGT | GGAACTGTTATA |
| | TACCTACCGGGA | | TGAAAATTACCAAACCG | CGCGGATACGGT |
| | CAAACTATAGCG | | GGAATAAATGATGCTGG | GGCGTTTTGTTT |
| | GAACACTGGAAC | | TGTGTATGTACTTCTTG | CCGGTCAGTACA |
| | TGTTATACGCGG | | TTCGGTTAGACCATAGC | AGTAATAAGATA |
| | ATACGGTGGCGT | | AGATCCACCGATGGTTT | CGACGGATGTCC |
| | TTTGTTTCCGGT | | CATTCTTGGTGTAAATG | CCGGATTAGAAC |
| | CAGTACAAGTAA | | TATATACAGCGGGCTCG | GAGCGCTTTTAT |
| | TAAGATACGACG | | CATCACAACATTCACGG | TTCGTGTAGGTA |
| | GATGTCCCCGGA | | GGTTATCTACACTTCTC | CAAACATTCGTG |
| | TTAGAACGAGCG | | CATCTCTACAGAATGGA | GCATTATGGTAA |
| | CTTTTATTTCGT | | TATTCTACAAGAGCCCT | CTCAACGGATCG |
| | GTAGGTACAAAC | | TTTTCAACAAGCTCGTT | GATATCAACAGA |
| | ATTCGTGGCATT | | TGTGTGATTTACCCGCG | GCCGGATGCTGG |
| | ATGGTAACTCAA | | ACACCCAAAGGGTCCGG | TGTAATGTTGAA |
| | CGGATCGGATAT | | TACCTCCCTGTTTCAAC | AATTACCAAACC |
| | CAACAGAGCCGG | | ATATGCTTGATCTTCGT | GGGAATAAATGA |
| | ATGCTGGTGTAA | | GCCGGTAAATCGTTAGA | TGCTGGTGTGTA |
| | TGTTGAAAATTA | | GGATAACCCTTGGTTAC | TGTACTTCTTGT |
| | CCAAACCGGGAA | | ATGAGGACGTTGTTACG | TCGGTTAGACCA |
| | TAAATGATGCTG | | ACAGAAACTAAGTCCGT | TAGCAGATCCAC |
| | GTGTGTATGTAC | | TGTTAAGGAGGGGATAG | CGATGGTTTCAT |
| | TTCTTGTTCGGT | | AAAATCACGTATATCCA | TCTTGGTGTAAA |
| | TAGACCATAGCA | | ACGGATATGTCCACGTT | TGTATATACAGC |
| | GATCCACCGATG | | ACCCGAAAAGTCCCTTA | GGGCTCGCATCA |
| | GTTTCATTCTTG | | ATGATCCTCCAGAAAAT | CAACATTCACGG |
| | GTGTAAATGTAT | | CTACTTATAATTATTCC | GGTTATCTACAC |
| | ATACAGCGGGCT | | TATAGTAGCGTCTGTCA | TTCTCCATCTCT |
| | CGCATCACAACA | | TGATCCTCACCGCCATG | ACAGAATGGATA |
| | TTCACGGGGTTA | | GTTATTGTTATTGTAAT | TTCTACAAGAGC |
| | TCTACACTTCTC | | AAGCGTTAAGCGACGTA | CCTTTTTCAACA |
| | CATCTCTACAGA | | GAATTAAAAAACATCCA | AGTCGTTTGTG |
| | ATGGATATTCTA | | ATTTATCGCCCAAATAC | TGATTTACCCGC |
| | CAAGAGCCCTTT | | AAAAACAAGAAGGGGCA | GACACCCAAAGG |
| | TTCAACAAGCTC | | TACAAAATGCGACACCA | GTCCGGTACCTC |
| | GTTTGTGTGATT | | GAATCCGATGTGATGTT | CCTGTTTCAACA |
| | TACCCGCGACAC | | GGAGGCCGCCATTGCAC | TATGCTTGATCT |
| | CCAAAGGGTCCG | | AACTAGCAACGATTCGC | TCGTGCCGGTAA |
| | GTACCTCCCTGT | | GAAGAATCCCCCCCACA | ATCGTTAGAGGA |

TABLE 2-continued

| | | |
|---|---|---|
| TTCAACATATGC | TTCCGTTGTAAACCCGT | TAACCCTTGGTT |
| TTGATCTTCGTG | TTGTTAAATAG | ACATGAGGACGT |
| CCGGTAAATCGT | | TGTTACGACAGA |
| TAGAGGATAACC | | AACTAAGTCCGT |
| CTTGGTTACATG | | TGTTAAGGAGGG |
| AGGACGTTGTTA | | GATAGAAAATCA |
| CGACAGAAACTA | | CGTATATCCAAC |
| AGTCCGTTGTTA | | GGATATGTCCAC |
| AGGAGGGGATAG | | GTTACCCGAAAA |
| AAAATCACGTAT | | GTCCCTTAATGA |
| ATCCAACGGATA | | TCCTCCAGAAAA |
| TGTCCACGTTAC | | TCTACTTATAAT |
| CCGAAAAGTCCC | | TATTCCTATAGT |
| TTAATGATCCTC | | AGCGTCTGTCAT |
| CAGAAAATCTAC | | GATCCTCACCGC |
| TTATAATTATTC | | CATGGTTATTGT |
| CTATAGTAGCGT | | TATTGTAATAAG |
| CTGTCATGATCC | | CGTTAAGCGACG |
| TCACCGCCATGG | | TAGAATTAAAAA |
| TTATTGTTATTG | | ACATCCAATTTA |
| TAATAAGCGTTA | | TCGCCCAAATAC |
| AGCGACGTAGAA | | AAAAACAAGAAG |
| TTAAAAAACATC | | GGGCATACAAAA |
| CAATTTATCGCC | | TGCGACACCAGA |
| CAAATACAAAAA | | ATCCGATGTGAT |
| CAAGAAGGGGCA | | GTTGGAGGCCGC |
| TACAAAATGCGA | | CATTGCACAACT |
| CACCAGAATCCG | | AGCAACGATTCG |
| ATGTGATGTTGG | | CGAAGAATCCCC |
| AGGCCGCCATTG | | CCCACATTCCGT |
| CACAACTAGCAA | | TGTAAACCCGTT |
| CGATTCGCGAAG | | TGTTAAATAGTG |
| AATCCCCCCCAC | | ATAATAGGCTGG |
| ATTCCGTTGTAA | | AGCCTCGGTGGC |
| ACCCGTTTGTTA | | CATGCTTCTTGC |
| AATAGTGATAAT | | CCCTTGGGCCTC |
| AGGCTGGAGCCT | | CCCCCAGCCCCT |
| CGGTGGCCATGC | | CCTCCCCTTCCT |
| TTCTTGCCCCTT | | GCACCCGTACCC |
| GGGCCTCCCCCC | | CCGTGGTCTTTG |
| AGCCCCTCCTCC | | AATAAAGTCTGA |
| CCTTCCTGCACC | | GTGGGCGGCAAA |
| CGTACCCCCGTG | | AAAAAAAAAAAA |
| GTCTTTGAATAA | | AAAAAAAAAAAA |
| AGTCTGAGTGGG | | AAAAAAAAAAAA |
| CGGC | | AAAAAAAAAAAA |
| | | AAAAAAAAAAAA |
| | | AAAAAAAAAAAA |
| | | AAAAAAAAAAAA |
| | | AAAAAAAAAAAA |
| | | ATCTAG |

| | SEQ ID NO: 60 | SEQ ID NO: 61 | SEQ ID NO: 62 | SEQ ID NO: 63 |
|---|---|---|---|---|
| VZV-GE-truncated-delete_from_574_-_Y569A Variant 1 | GGGAAAATAAGAG | MGTVNKPVVGVLMGFGI | ATGGGCACCGTGAACAA | GGGAAAATAAGAG |
| | AGAAAAGAAGAG | ITGTLRITNPVRASVLR | GCCCGTCGTGGGCGTGC | AGAAAAGAAGAG |
| | TAAGAAGAAATA | YDDFHIDEDKLDTNSVY | TGATGGGCTTCGGCATC | TAAGAAGAAATA |
| | TAAGAGCCACCA | EPYYHSDHAESSWVNRG | ATCACCGGCACCCTGCG | TAAGAGCCACCA |
| | TGGGCACCGTGA | ESSRKAYDHNSPYIWPR | GATCACCAATCCTGTGC | TGGGCACCGTGA |
| | ACAAGCCCGTCG | NDYDGFLENAHEHHGVY | GGGCCAGCGTGCTGAGA | ACAAGCCCGTCG |
| | TGGGCGTGCTGA | NQGRGIDSGERLMQPTQ | TACGACGACTTCCACAT | TGGGCGTGCTGA |
| | TGGGCTTCGGCA | MSAQEDLGDDTGIHVIP | CGACGAGGACAAGCTGG | TGGGCTTCGGCA |
| | TCATCACCGGCA | TLNGDDRHKIVNVDQRQ | ACACCAACAGCGTGTAC | TCATCACCGGCA |
| | CCCTGCGGATCA | YGDVFKGDLNPKPQGQR | GAGCCCTACTACCACAG | CCCTGCGGATCA |
| | CCAATCCTGTGC | LIEVSVEENHPFTLRAP | CGACCACGCCGAGAGCA | CCAATCCTGTGC |
| | GGGCCAGCGTGC | IQRIYGVRYTETWSFLP | GCTGGGTCAACAGAGGC | GGGCCAGCGTGC |
| | TGAGATACGACG | SLTCTGDAAPAIQHICL | GAGTCCAGCCGGAAGGC | TGAGATACGACG |
| | ACTTCCACATCG | KHTTCFQDVVVDVDCAE | CTACGATCTGGCCCCGG | ACTTCCACATCG |
| | ACGAGGACAAGC | NTKEDQLAEISYRFQGK | AACGACTACGACGGCTT | ACGAGGACAAGC |
| | TGGACACCAACA | KEADQPWIVVNTSTLFD | CCTGGAAAATGCCCACG | TGGACACCAACA |
| | GCGTGTACGAGC | ELELDPPEIEPGVLKVL | AGCACCACGGCGTGTAC | GCGTGTACGAGC |
| | CCTACTACCACA | RTEKQYLGVYIWNMRGS | AACCAGGGCAGAGGCAT | CCTACTACCACA |
| | GCGACCACGCCG | DGTSTYATFLVTWKGDE | CGACAGCGGCGAGAGAC | GCGACCACGCCG |
| | AGAGCAGCTGGG | KTRNPTPAVTPQPRGAE | TGATGCAGCCCACCCAG | AGAGCAGCTGGG |
| | TCAACAGAGGCG | FHMWNYHSHVFSVGDTF | ATGAGCGCCCAGGAAGA | TCAACAGAGGCG |
| | AGTCCAGCCGGA | SLAMHLQYKIHEAPFDL | TCTGGGCGACGACACCG | AGTCCAGCCGGA |
| | AGGCCTACGACC | LLEWLYVPIDPTCQPMR | GCATCCACGTGATCCCT | AGGCCTACGACC |
| | ACAACAGCCCCT | LYSTCLYHPNAPQCLSH | ACCCTGAACGGCGACGA | ACAACAGCCCCT |
| | ACATCTGGCCCC | MNSGCTFTSPHLAQRVA | CCGGCACAAGATCGTGA | ACATCTGGCCCC |
| | GGAACGACTACG | STVYQNCEHADNYTAYC | ACGTGGACCAGCGGCAG | GGAACGACTACG |
| | ACGGCTTCCTGG | LGISHMEPSFGLILHDG | | ACGGCTTCCTGG |

TABLE 2-continued

| | | | |
|---|---|---|---|
| AAAATGCCCACG | GTTLKFVDTPESLSGLY | TACGGCGACGTGTTCAA | AAAATGCCCACG |
| AGCACCACGGCG | VFVVYFNGHVEAVAYTV | GGGCGACCTGAACCCCA | AGCACCACGGCG |
| TGTACAACCAGG | VSTVDHFVNAIEERGFP | AGCCCCAGGGACAGCGG | TGTACAACCAGG |
| GCAGAGGCATCG | PTAGQPPATTKPKEITP | CTGATTGAGGTGTCCGT | GCAGAGGCATCG |
| ACAGCGGCGAGA | VNPGTSPLLRYAAWTGG | GGAAGAGAACCACCCCT | ACAGCGGCGAGA |
| GACTGATGCAGC | LAAVVLLCLVIFLICTA | TCACCCTGAGAGCCCCT | GACTGATGCAGC |
| CCACCCAGATGA | KRMRVKAARVDK | ATCCAGCGGATCTACGG | CCACCCAGATGA |
| GCGCCCAGGAAG | | CGTGCGCTATACCGAGA | GCGCCCAGGAAG |
| ATCTGGGCGACG | | CTTGGAGCTTCCTGCCC | ATCTGGGCGACG |
| ACACCGGCATCC | | AGCCTGACCTGTACTGG | ACACCGGCATCC |
| ACGTGATCCCTA | | CGACGCCGCTCCTGCCA | ACGTGATCCCTA |
| CCCTGAACGGCG | | TCCAGCACATCTGCCTG | CCCTGAACGGCG |
| ACGACCGGCACA | | AAGCACACCACCTGTTT | ACGACCGGCACA |
| AGATCGTGAACG | | CCAGGACGTGGTGGTGG | AGATCGTGAACG |
| TGGACCAGCGGC | | ACGTGGACTGCGCCGAG | TGGACCAGCGGC |
| AGTACGGCGACG | | AACACCAAAGAGGACCA | AGTACGGCGACG |
| TGTTCAAGGGCG | | GCTGGCCGAGATCAGCT | TGTTCAAGGGCG |
| ACCTGAACCCCA | | ACCGGTTCCAGGGCAAG | ACCTGAACCCCA |
| AGCCCCAGGGAC | | AAAGAGGCCGACCAGCC | AGCCCCAGGGAC |
| AGCGGCTGATTG | | CTGGATCGTCGTGAACA | AGCGGCTGATTG |
| AGGTGTCCGTGG | | CCAGCACCCTGTTCGAC | AGGTGTCCGTGG |
| AAGAGAACCACC | | GAGCTGGAACTGGACCC | AAGAGAACCACC |
| CCTTCACCCTGA | | TCCCGAGATCGAACCCG | CCTTCACCCTGA |
| GAGCCCCTATCC | | GGGTGCTGAAGGTGCTG | GAGCCCCTATCC |
| AGCGGATCTACG | | CGGACCGAGAAGCAGTA | AGCGGATCTACG |
| GCGTGCGCTATA | | CCTGGGAGTGTACATCT | GCGTGCGCTATA |
| CCGAGACTTGGA | | GGAACATGCGGGGCAGC | CCGAGACTTGGA |
| GCTTCCTGCCCA | | GACGGCACCTCTACCTA | GCTTCCTGCCCA |
| GCCTGACCTGTA | | CGCCACCTTCCTCGTGA | GCCTGACCTGTA |
| CTGGCGACGCCG | | CCTGGAAGGGCGACGAG | CTGGCGACGCCG |
| CTCCTGCCATCC | | AAAACCCGGAACCCTAC | CTCCTGCCATCC |
| AGCACATCTGCC | | CCCTGCCGTGACCCCTC | AGCACATCTGCC |
| TGAAGCACACCA | | AGCCTAGAGGCGCCGAG | TGAAGCACACCA |
| CCTGTTTCCAGG | | TTTCACATGTGGAATTA | CCTGTTTCCAGG |
| ACGTGGTGGTGG | | CCACAGCCACGTGTTCA | ACGTGGTGGTGG |
| ACGTGGACTGCG | | GCGTGGGCGACACCTTC | ACGTGGACTGCG |
| CCGAGAACACCA | | TCCCTGGCCATGCATCT | CCGAGAACACCA |
| AAGAGGACCAGC | | GCAGTACAAGATCCACG | AAGAGGACCAGC |
| TGGCCGAGATCA | | AGGCCCCTTTCGACCTG | TGGCCGAGATCA |
| GCTACCGGTTCC | | CTGCTGGAATGGCTGTA | GCTACCGGTTCC |
| AGGGCAAGAAAG | | CGTGCCCATCGACCCTA | AGGGCAAGAAAG |
| AGGCCGACCAGC | | CCTGCCAGCCCATGCGG | AGGCCGACCAGC |
| CCTGGATCGTCG | | CTGTACTCCACCTGTCT | CCTGGATCGTCG |
| TGAACACCAGCA | | GTACCACCCCAACGCCC | TGAACACCAGCA |
| CCCTGTTCGACG | | CTCAGTGCCTGAGCCAC | CCCTGTTCGACG |
| AGCTGGAACTGG | | ATGAATAGCGGCTGCAC | AGCTGGAACTGG |
| ACCCTCCCGAGA | | CTTCACCAGCCCTCACC | ACCCTCCCGAGA |
| TCGAACCCGGGG | | TGGCTCAGAGGGTGGCC | TCGAACCCGGGG |
| TGCTGAAGGTGC | | AGCACCGTGTACCAGAA | TGCTGAAGGTGC |
| TGCGGACCGAGA | | TTGCGAGCACGCCGACA | TGCGGACCGAGA |
| AGCAGTACCTGG | | ACTACACCGCCTACTGC | AGCAGTACCTGG |
| GAGTGTACATCT | | CTGGGCATCAGCCACAT | GAGTGTACATCT |
| GGAACATGCGGG | | GGAACCCAGCTTCGGCC | GGAACATGCGGG |
| GCAGCGACGGCA | | TGATCCTGCACGATGGC | GCAGCGACGGCA |
| CCTCTACCTACG | | GGCACCACCCTGAAGTT | CCTCTACCTACG |
| CCACCTTCCTCG | | CGTGGACACCCTGAGT | CCACCTTCCTCG |
| TGACCTGGAAGG | | CCCTGAGCGGCCTGTAC | TGACCTGGAAGG |
| GCGACGAGAAAA | | GTGTTCGTGGTGTACTT | GCGACGAGAAAA |
| CCCGGAACCCTA | | CAACGGCCACGTGGAAG | CCCGGAACCCTA |
| CCCCTGCCGTGA | | CCGTGGCCTACACCGTG | CCCCTGCCGTGA |
| CCCCTCAGCCTA | | GTGTCCACCGTGGACCA | CCCCTCAGCCTA |
| GAGGCGCCGAGT | | CTTCGTGAACGCCATCG | GAGGCGCCGAGT |
| TTCACATGTGGA | | AGGAACGGGGCTTCCCT | TTCACATGTGGA |
| ATTACCACAGCC | | CCAACTGCTGGACAGCC | ATTACCACAGCC |
| ACGTGTTCAGCG | | TCCTGCCACCACCAAGC | ACGTGTTCAGCG |
| TGGGCGACACCT | | CCAAAGAAATCACCCCT | TGGGCGACACCT |
| TCTCCCTGGCCA | | GTGAACCCCGGCACCAG | TCTCCCTGGCCA |
| TGCATCTGCAGT | | CCCACTGCTGCGCTATG | TGCATCTGCAGT |
| ACAAGATCCACG | | CTGCTTGGACAGGCGGA | ACAAGATCCACG |
| AGGCCCCTTTCG | | CTGGCTGCTGTGGTGCT | AGGCCCCTTTCG |
| ACCTGCTGCTGG | | GCTGTGCCTCGTGATTT | ACCTGCTGCTGG |
| AATGGCTGTACG | | TCCTGATCTGCACCGCC | AATGGCTGTACG |
| TGCCCATCGACC | | AAGCGGATGAGAGTGAA | TGCCCATCGACC |
| CTACCTGCCAGC | | GGCCGCCAGAGTGGACA | CTACCTGCCAGC |
| CCATGCGGCTGT | | AG | CCATGCGGCTGT |
| ACTCCACCTGTC | | | ACTCCACCTGTC |
| TGTACCACCCCA | | | TGTACCACCCCA |
| ACGCCCCTCAGT | | | ACGCCCCTCAGT |
| GCCTGAGCCACA | | | GCCTGAGCCACA |
| TGAATAGCGGCT | | | TGAATAGCGGCT |

TABLE 2-continued

| | |
|---|---|
| GCACCTTCACCA | GCACCTTCACCA |
| GCCCTCACCTGG | GCCCTCACCTGG |
| CTCAGAGGGTGG | CTCAGAGGGTGG |
| CCAGCACCGTGT | CCAGCACCGTGT |
| ACCAGAATTGCG | ACCAGAATTGCG |
| AGCACGCCGACA | AGCACGCCGACA |
| ACTACACCGCCT | ACTACACCGCCT |
| ACTGCCTGGGCA | ACTGCCTGGGCA |
| TCAGCCACATGG | TCAGCCACATGG |
| AACCCAGCTTCG | AACCCAGCTTCG |
| GCCTGATCCTGC | GCCTGATCCTGC |
| ACGATGGCGGCA | ACGATGGCGGCA |
| CCACCCTGAAGT | CCACCCTGAAGT |
| TCGTGGACACCC | TCGTGGACACCC |
| CTGAGTCCCTGA | CTGAGTCCCTGA |
| GCGGCCTGTACG | GCGGCCTGTACG |
| TGTTCGTGGTGT | TGTTCGTGGTGT |
| ACTTCAACGGCC | ACTTCAACGGCC |
| ACGTGGAAGCCG | ACGTGGAAGCCG |
| TGGCCTACACCG | TGGCCTACACCG |
| TGGTGTCCACCG | TGGTGTCCACCG |
| TGGACCACTTCG | TGGACCACTTCG |
| TGAACGCCATCG | TGAACGCCATCG |
| AGGAACGGGGCT | AGGAACGGGGCT |
| TCCCTCCAACTG | TCCCTCCAACTG |
| CTGGACAGCCTC | CTGGACAGCCTC |
| CTGCCACCACCA | CTGCCACCACCA |
| AGCCCAAAGAAA | AGCCCAAAGAAA |
| TCACCCCTGTGA | TCACCCCTGTGA |
| ACCCCGGCACCA | ACCCCGGCACCA |
| GCCCACTGCTGC | GCCCACTGCTGC |
| GCTATGCTGCTT | GCTATGCTGCTT |
| GGACAGGCGGAC | GGACAGGCGGAC |
| TGGCTGCTGTGG | TGGCTGCTGTGG |
| TGCTGCTGTGCC | TGCTGCTGTGCC |
| TCGTGATTTTCC | TCGTGATTTTCC |
| TGATCTGCACCG | TGATCTGCACCG |
| CCAAGCGGATGA | CCAAGCGGATGA |
| GAGTGAAGGCCG | GAGTGAAGGCCG |
| CCAGAGTGGACA | CCAGAGTGGACA |
| AGTGATAATAGG | AGTGATAATAGG |
| CTGGAGCCTCGG | CTGGAGCCTCGG |
| TGGCCATGCTTC | TGGCCATGCTTC |
| TTGCCCCTTGGG | TTGCCCCTTGGG |
| CCTCCCCCCAGC | CCTCCCCCCAGC |
| CCCTCCTCCCCT | CCCTCCTCCCCT |
| TCCTGCACCCGT | TCCTGCACCCGT |
| ACCCCCGTGGTC | ACCCCCGTGGTC |
| TTTGAATAAAGT | TTTGAATAAAGT |
| CTGAGTGGGCGG | CTGAGTGGGCGG |
| C | CAAAAAAAAAAA |
| | AAAAAAAAAAAA |
| | AAAAAAAAAAAA |
| | AAAAAAAAAAAA |
| | AAAAAAAAAAAA |
| | AAAAAAAAAAAA |
| | AAAAAAAAAAAA |
| | AAAAAAAAAAAA |
| | AAAAATCTAG |

| | SEQ ID NO: 64 | SEQ ID NO: 65 | SEQ ID NO: 66 | SEQ ID NO: 67 |
|---|---|---|---|---|
| VZV-GE- | GGGAAATAAGAG | MGTVNKPVVGVLMGFGI | ATGGGGACAGTTAATAA | GGGAAATAAGAG |
| truncated- | AGAAAAGAAGAG | ITGTLRITNPVRASVLR | ACCTGTGGTGGGGGTAT | AGAAAAGAAGAG |
| delete_from_574_-_Y569A | TAAGAAGAAATA | YDDFHIDEDKLDTNSVY | TGATGGGGTTCGGAATT | TAAGAAGAAATA |
| Variant 2 | TAAGAGCCACCA | EPYYHSDHAESSWVNRG | ATCACGGGAACGTTGCG | TAAGAGCCACCA |
| | TGGGGACAGTTA | ESSRKAYDHNSPYIWPR | TATAACGAATCCGGTCA | TGGGGACAGTTA |
| | ATAAACCTGTGG | NDYDGFLENAHEHHGVY | GAGCATCCGTCTTGCGA | ATAAACCTGTGG |
| | TGGGGGTATTGA | NQGRGIDSGERLMQPTQ | TACGATGATTTTCACAT | TGGGGGTATTGA |
| | TGGGGTTCGGAA | MSAQEDLGDDTGIHVIP | CGATGAAGACAAACTGG | TGGGGTTCGGAA |
| | TTATCACGGGAA | TLNGDDRHKIVNVDQRQ | ATACAAACTCCGTATAT | TTATCACGGGAA |
| | CGTTGCGTATAA | YGDVFKGDLNPKPQGQR | GAGCCTTACTACCATTC | CGTTGCGTATAA |
| | CGAATCCGGTCA | LIEVSVEENHPFTLRAP | AGATCATGCGGAGTCTT | CGAATCCGGTCA |
| | GAGCATCCGTCT | IQRIYGVRYTETWSFLP | CATGGGTAAATCGGGGA | GAGCATCCGTCT |
| | TGCGATACGATG | SLTCTGDAAPAIQHICL | GAGTCTTCGCGAAAAGC | TGCGATACGATG |
| | ATTTTCACATCG | KHTTCFQDVVVDVDCAE | GTACGATCATAACTCAC | ATTTTCACATCG |
| | ATGAAGACAAAC | NTKEDQLAEISYRFQGK | CTTATATATGGCCACGT | ATGAAGACAAAC |
| | TGGATACAAACT | KEADQPWIVVNTSTLFD | AATGATTATGATGGATT | TGGATACAAACT |
| | CCGTATATGAGC | ELELDPPEIEPGVLKVL | TTTAGAGAACGCACACG | CCGTATATGAGC |
| | CTTACTACCATT | RTEKQYLGVYIWNMRGS | AACACCATGGGTGTAT | CTTACTACCATT |
| | CAGATCATGCGG | DGTSYATFLVTWKGDE | AATCAGGGCCGTGGTAT | CAGATCATGCGG |

TABLE 2-continued

| | | | |
|---|---|---|---|
| AGTCTTCATGGG | KTRNPTPAVTPQPRGAE | CGATAGCGGGGAACGGT | AGTCTTCATGGG |
| TAAATCGGGGAG | PHMWNYHSHVFSVGDTF | TAATGCAACCCACACAA | TAAATCGGGGAG |
| AGTCTTCGCGAA | SLAMHLQYKIHEAPFDL | ATGTCTGCACAGGAGGA | AGTCTTCGCGAA |
| AAGCGTACGATC | LLEWLYVPIDPTCQPMR | TCTTGGGGACGATACGG | AAGCGTACGATC |
| ATAACTCACCTT | LYSTCLYHPNAPQCLSH | GCATCCACGTTATCCCT | ATAACTCACCTT |
| ATATATGGCCAC | MNSGCTFTSPHLAQRVA | ACGTTAAACGGCGATGA | ATATATGGCCAC |
| GTAATGATTATG | STVYQNCEHADNYTAYC | CAGACATAAAATTGTAA | GTAATGATTATG |
| ATGGATTTTTAG | LGISHMEPSFGLILHDG | ATGTGGACCAACGTCAA | ATGGATTTTTAG |
| AGAACGCACACG | GTTLKFVDTPESLSGLY | TACGGTGACGTGTTTAA | AGAACGCACACG |
| AACACCATGGGG | VFVVYFNGHVEAVAYTV | AGGAGATCTTAATCCAA | AACACCATGGGG |
| TGTATAATCAGG | VSTVDHFVNAIEERGFP | AACCCCAAGGCCAAAGA | TGTATAATCAGG |
| GCCGTGGTATCG | PTAGQPPATTKPKEITP | CTCATTGAGGTGTCAGT | GCCGTGGTATCG |
| ATAGCGGGGAAC | VNPGTSPLLRYAAWTGG | GGAAGAAAATCACCCGT | ATAGCGGGGAAC |
| GGTTAATGCAAC | LAAVVLLCLVIFLICTA | TTACTTTACGCGCACCG | GGTTAATGCAAC |
| CCACACAAATGT | KRMRVKAARVDK | ATTCAGCGGATTTATG | CCACACAAATGT |
| CTGCACAGGAGG | | AGTCCGGTACACCGAGA | CTGCACAGGAGG |
| ATCTTGGGGACG | | CTTGGAGCTTTTTGCCG | ATCTTGGGGACG |
| ATACGGGCATCC | | TCATTAACCTGTACGGG | ATACGGGCATCC |
| ACGTTATCCCTA | | AGACGCAGCGCCCGCCA | ACGTTATCCCTA |
| CGTTAAACGGCG | | TCCAGCATATATGTTTA | CGTTAAACGGCG |
| ATGACAGACATA | | AAACATACAACATGCTT | ATGACAGACATA |
| AAATTGTAAATG | | TCAAGACGTGGTGGTGG | AAATTGTAAATG |
| TGGACCAACGTC | | ATGTGGATTGCGCGGAA | TGGACCAACGTC |
| AATACGGTGACG | | AATACTAAAGAGGATCA | AATACGGTGACG |
| TGTTTAAAGGAG | | GTTGGCCGAAATCAGTT | TGTTTAAAGGAG |
| ATCTTAATCCAA | | ACCGTTTTCAAGGTAAG | ATCTTAATCCAA |
| AACCCCAAGGCC | | AAGGAAGCGGACCAACC | AACCCCAAGGCC |
| AAAGACTCATTG | | GTGGATTGTTGTAAACA | AAAGACTCATTG |
| AGGTGTCAGTGG | | CGAGCACACTGTTTGAT | AGGTGTCAGTGG |
| AAGAAAATCACC | | GAACTCGAATTAGACCC | AAGAAAATCACC |
| CGTTTACTTTAC | | CCCCGAGATTGAACCGG | CGTTTACTTTAC |
| GCGCACCGATTC | | GTGTCTTGAAAGTACTT | GCGCACCGATTC |
| AGCGGATTTATG | | CGGACAGAGAAACAATA | AGCGGATTTATG |
| GAGTCCGGTACA | | CTTGGGTGTGTACATTT | GAGTCCGGTACA |
| CCGAGACTTGGA | | GGAACATGCGCGGCTCC | CCGAGACTTGGA |
| GCTTTTTGCCGT | | GATGGTACGTCTACCTA | GCTTTTTGCCGT |
| CATTAACCTGTA | | CGCCACGTTTTTGGTCA | CATTAACCTGTA |
| CGGGAGACGCAG | | CCTGGAAAGGGGATGAG | CGGGAGACGCAG |
| CGCCCGCCATCC | | AAGACAAGAAACCCTAC | CGCCCGCCATCC |
| AGCATATATGTT | | GCCCGCAGTAACTCCTC | AGCATATATGTT |
| TAAAACATACAA | | AACCAAGAGGGGCTGAG | TAAAACATACAA |
| CATGCTTTCAAG | | TTTCATATGTGGAATTA | CATGCTTTCAAG |
| ACGTGGTGGTGG | | CCACTCGCATGTATTTT | ACGTGGTGGTGG |
| ATGTGGATTGCG | | CAGTTGGTGATACGTTT | ATGTGGATTGCG |
| CGGAAAATACTA | | AGCTTGGCAATGCATCT | CGGAAAATACTA |
| AAGAGGATCAGT | | TCAGTATAAGATACATG | AAGAGGATCAGT |
| TGGCCGAAATCA | | AAGCGCCATTTGATTTG | TGGCCGAAATCA |
| GTTACCGTTTTC | | CTGTTAGAGTGGTTGTA | GTTACCGTTTTC |
| AAGGTAAGAAGG | | TGTCCCCATCGATCCTA | AAGGTAAGAAGG |
| AAGCGGACCAAC | | CATGTCAACCAATGCGG | AAGCGGACCAAC |
| CGTGGATTGTTG | | TTATATTCTACGTGTTT | CGTGGATTGTTG |
| TAAACACGAGCA | | GTATCATCCCAACGCAC | TAAACACGAGCA |
| CACTGTTTGATG | | CCCAATGCCTCTCTCAT | CACTGTTTGATG |
| AACTCGAATTAG | | ATGAATTCCGGTTGTAC | AACTCGAATTAG |
| ACCCCCCCGAGA | | ATTTACCTCGCCACATT | ACCCCCCCGAGA |
| TTGAACCGGGTG | | TAGCCCAGCGTGTTGCA | TTGAACCGGGTG |
| TCTTGAAAGTAC | | AGCACAGTGTATCAAAA | TCTTGAAAGTAC |
| TTCGGACAGAGA | | TTGTGAACATGCAGATA | TTCGGACAGAGA |
| AACAATACTTGG | | ACTACACCGCATATTGT | AACAATACTTGG |
| GTGTGTACATTT | | CTGGGAATATCTCATAT | GTGTGTACATTT |
| GGAACATGCGCG | | GGAGCCTAGCTTTGGTC | GGAACATGCGCG |
| GCTCCGATGGTA | | TAATCTTACACGACGGG | GCTCCGATGGTA |
| CGTCTACCTACG | | GGCACCACGTTAAAGTT | CGTCTACCTACG |
| CCACGTTTTTGG | | TGTAGATACACCCGAGA | CCACGTTTTTGG |
| TCACCTGGAAAG | | GTTTGTCGGGATTATAC | TCACCTGGAAAG |
| GGGATGAGAAGA | | GTTTTTGTGGTGTATTT | GGGATGAGAAGA |
| CAAGAAACCCTA | | TAACGGGCATGTTGAAG | CAAGAAACCCTA |
| CGCCCGCAGTAA | | CCGTAGCATACACTGTT | CGCCCGCAGTAA |
| CTCCTCAACCAA | | GTATCCACAGTAGATCA | CTCCTCAACCAA |
| GAGGGGCTGAGT | | TTTTGTAAACGCAATTG | GAGGGGCTGAGT |
| TTCATATGTGGA | | AAGAGCGTGGATTTCCG | TTCATATGTGGA |
| ATTACCACTCGC | | CCAACGGCCGGTCAGCC | ATTACCACTCGC |
| ATGTATTTTCAG | | ACCGGCGACTACTAAAC | ATGTATTTTCAG |
| TTGGTGATACGT | | CCAAGGAAATTACCCCC | TTGGTGATACGT |
| TTAGCTTGGCAA | | GTAAACCCCGGAACGTC | TTAGCTTGGCAA |
| TGCATCTTCAGT | | ACCACTTCTACGATATG | TGCATCTTCAGT |
| ATAAGATACATG | | CCGCATGGACCGGAGGG | ATAAGATACATG |
| AAGCGCCATTTG | | CTTGCAGCAGTAGTACT | AAGCGCCATTTG |
| ATTTGCTGTTAG | | TTTATGTCTCGTAATAT | ATTTGCTGTTAG |
| AGTGGTTGTATG | | TTTTAATCTGTACGGCT | AGTGGTTGTATG |

TABLE 2-continued

```
TCCCCATCGATC                          AAACGAATGAGGGTTAA   TCCCCATCGATC
CTACATGTCAAC                          AGCCGCCAGGGTAGACA   CTACATGTCAAC
CAATGCGGTTAT                          AG                  CAATGCGGTTAT
ATTCTACGTGTT                                              ATTCTACGTGTT
TGTATCATCCCA                                              TGTATCATCCCA
ACGCACCCCAAT                                              ACGCACCCCAAT
GCCTCTCTCATA                                              GCCTCTCTCATA
TGAATTCCGGTT                                              TGAATTCCGGTT
GTACATTTACCT                                              GTACATTTACCT
CGCCACATTTAG                                              CGCCACATTTAG
CCCAGCGTGTTG                                              CCCAGCGTGTTG
CAAGCACAGTGT                                              CAAGCACAGTGT
ATCAAAATTGTG                                              ATCAAAATTGTG
AACATGCAGATA                                              AACATGCAGATA
ACTACACCGCAT                                              ACTACACCGCAT
ATTGTCTGGGAA                                              ATTGTCTGGGAA
TATCTCATATGG                                              TATCTCATATGG
AGCCTAGCTTTG                                              AGCCTAGCTTTG
GTCTAATCTTAC                                              GTCTAATCTTAC
ACGACGGGGCA                                               ACGACGGGGCA
CCACGTTAAAGT                                              CCACGTTAAAGT
TTGTAGATACAC                                              TTGTAGATACAC
CCGAGAGTTTGT                                              CCGAGAGTTTGT
CGGGATTATACG                                              CGGGATTATACG
TTTTTGTGGTGT                                              TTTTTGTGGTGT
ATTTTAACGGGC                                              ATTTTAACGGGC
ATGTTGAAGCCG                                              ATGTTGAAGCCG
TAGCATACACTG                                              TAGCATACACTG
TTGTATCCACAG                                              TTGTATCCACAG
TAGATCATTTTG                                              TAGATCATTTTG
TAAACGCAATTG                                              TAAACGCAATTG
AAGAGCGTGGAT                                              AAGAGCGTGGAT
TTCCGCCAACGG                                              TTCCGCCAACGG
CCGGTCAGCCAC                                              CCGGTCAGCCAC
CGGCGACTACTA                                              CGGCGACTACTA
AACCCAAGGAAA                                              AACCCAAGGAAA
TTACCCCCGTAA                                              TTACCCCCGTAA
ACCCCGGAACGT                                              ACCCCGGAACGT
CACCACTTCTAC                                              CACCACTTCTAC
GATATGCCGCAT                                              GATATGCCGCAT
GGACCGGAGGGC                                              GGACCGGAGGGC
TTGCAGCAGTAG                                              TTGCAGCAGTAG
TACTTTTATGTC                                              TACTTTTATGTC
TCGTAATATTTT                                              TCGTAATATTTT
TAATCTGTACGG                                              TAATCTGTACGG
CTAAACGAATGA                                              CTAAACGAATGA
GGGTTAAAGCCG                                              GGGTTAAAGCCG
CCAGGGTAGACA                                              CCAGGGTAGACA
AGTGATAATAGG                                              AGTGATAATAGG
CTGGAGCCTCGG                                              CTGGAGCCTCGG
TGGCCATGCTTC                                              TGGCCATGCTTC
TTGCCCCTTGGG                                              TTGCCCCTTGGG
CCTCCCCCCAGC                                              CCTCCCCCCAGC
CCCTCCTCCCCT                                              CCCTCCTCCCCT
TCCTGCACCCGT                                              TCCTGCACCCGT
ACCCCCGTGGTC                                              ACCCCCGTGGTC
TTTGAATAAAGT                                              TTTGAATAAAGT
CTGAGTGGGCGG                                              CTGAGTGGGCGG
C                                                         CAAAAAAAAAAA
                                                          AAAAAAAAAAAA
                                                          AAAAAAAAAAAA
                                                          AAAAAAAAAAAA
                                                          AAAAAAAAAAAA
                                                          AAAAAAAAAAAA
                                                          AAAAAAAAAAAA
                                                          AAAAAAAAAAAA
                                                          AAAAATCTAG
```

| | SEQ ID NO: 68 | SEQ ID NO: 69 | SEQ ID NO: 70 | SEQ ID NO: 71 |
|---|---|---|---|---|
| VZV-GE-truncated-delete_from_574_-_Y569A Variant 3 | GGGAAATAAGAG<br>AGAAAAGAAGAG<br>TAAGAAGAAATA<br>TAAGAGCCACCA<br>TGGGGACAGTTA<br>ATAAACCTGTGG<br>TGGGGGTATTGA<br>TGGGGTTCGGAA<br>TTATCACGGGAA<br>CGTTGCGTATAA<br>CGAATCCGGTCA | MGTVNKPVVGVLMGFGI<br>ITGTLRITNPVRASVLR<br>YDDFHIDEDKLDTNSVY<br>EPYYHSDHAESSWVNRG<br>ESSRKAYDHNSPYIWPR<br>NDYDGFLENAHEHHGVY<br>NQGRGIDSGERLMQPTQ<br>MSAQEDLGDDTGIHVIP<br>TLNGDDRHKIVNVDQRQ<br>YGDVFKGDLNPKPQGQR<br>LIEVSVEENHPFTLRAP | ATGGGGACAGTTAATAA<br>ACCTGTGGTGGGGGTAT<br>TGATGGGGTTCGGAATT<br>ATCACGGGAACGTTGCG<br>TATAACGAATCCGGTCA<br>GAGCATCCGTCTTGCGA<br>TACGATGATTTTCACAT<br>CGATGAAGACAAACTGG<br>ATACAAACTCCGTATAT<br>GAGCCTTACTACCATTC<br>AGATCATGCGGAGTCTT | GGGAAATAAGAG<br>AGAAAAGAAGAG<br>TAAGAAGAAATA<br>TAAGAGCCACCA<br>TGGGGACAGTTA<br>ATAAACCTGTGG<br>TGGGGGTATTGA<br>TGGGGTTCGGAA<br>TTATCACGGGAA<br>CGTTGCGTATAA<br>CGAATCCGGTCA |

TABLE 2-continued

| | | | |
|---|---|---|---|
| GAGCATCCGTCT | IQRIYGVRYTETWSFLP | CATGGGTAAATCGGGGA | GAGCATCCGTCT |
| TGCGATACGATG | SLTCTGDAAPAIQHICL | GAGTCTTCGCGAAAAGC | TGCGATACGATG |
| ATTTTCACATCG | KHTTCFQDVVVDVDCAE | GTACGATCATAACTCAC | ATTTTCACATCG |
| ATGAAGACAAAC | NTKEDQLAEISYRFQGK | CTTATATATGGCCACGT | ATGAAGACAAAC |
| TGGATACAAACT | KEADQPWIVVNTSTLFD | AATGATTATGATGGATT | TGGATACAAACT |
| CCGTATATGAGC | ELELDPPEIEPGVLKVL | TTTAGAGAACGCACACG | CCGTATATGAGC |
| CTTACTACCATT | RTEKQYLGVYIWNMRGS | AACACCATGGGGTGTAT | CTTACTACCATT |
| CAGATCATGCGG | DGTSTYATFLVTWKGDE | AATCAGGGCCGTGGTAT | CAGATCATGCGG |
| AGTCTTCATGGG | KTRNPTPAVTPQPRGAE | CGATAGCGGGGAACGGT | AGTCTTCATGGG |
| TAAATCGGGGAG | FHMWNYHSHVFSVGDTF | TAATGCAACCCACACAA | TAAATCGGGGAG |
| AGTCTTCGCGAA | SLAMHLQYKIHEAPFDL | ATGTCTGCACAGGAGGA | AGTCTTCGCGAA |
| AAGCGTACGATC | LLEWLYVPIDPTCQPMR | TCTTGGGGACGATACGG | AAGCGTACGATC |
| ATAACTCACCTT | LYSTCLYHPNAPQCLSH | GCATCCACGTTATCCCT | ATAACTCACCTT |
| ATATATGGCCAC | MNSGCTFTSPHLAQRVA | ACGTTAAACGGCGATGA | ATATATGGCCAC |
| GTAATGATTATG | STVYQNCEHADNYTAYC | CAGACATAAAATTGTAA | GTAATGATTATG |
| ATGGATTTTTAG | LGISHMEPSFGLILHDG | ATGTGGACCAACGTCAA | ATGGATTTTTAG |
| AGAACGCACACG | GTTLKFVDTPESLSGLY | TACGGTGACGTGTTTAA | AGAACGCACACG |
| AACACCATGGGG | VFVVYFNGHVEAVAYTV | AGGAGATCTTAATCCAA | AACACCATGGGG |
| TGTATAATCAGG | VSTVDHFVNAIEERGFP | AACCCCAAGGCCAAAGA | TGTATAATCAGG |
| GCCGTGGTATCG | PTAGQPPATTKPKEITP | CTCATTGAGGTGTCAGT | GCCGTGGTATCG |
| ATAGCGGGGAAC | VNPGTSPLLRYAAWTGG | GGAAGAAAATCACCCGT | ATAGCGGGGAAC |
| GGTTAATGCAAC | LAAVVLLCLVIFLICTA | TTACTTTACGCGCACCG | GGTTAATGCAAC |
| CCACACAAATGT | KRMRVKAARVDK | ATTCAGCGGATTTATGG | CCACACAAATGT |
| CTGCACAGGAGG | | AGTCCGGTACACCGAGA | CTGCACAGGAGG |
| ATCTTGGGGACG | | CTTGGAGCTTTTTGCCG | ATCTTGGGGACG |
| ATACGGGCATCC | | TCATTAACCTGTACGGG | ATACGGGCATCC |
| ACGTTATCCCTA | | AGACGCAGCGCCCGCCA | ACGTTATCCCTA |
| CGTTAAACGGCG | | TCCAGCATATATGTTTA | CGTTAAACGGCG |
| ATGACAGACATA | | AAACATACAACATGCTT | ATGACAGACATA |
| AAATTGTAAATG | | TCAAGACGTGGTGGTGG | AAATTGTAAATG |
| TGGACCAACGTC | | ATGTGGATTGCGCGGAA | TGGACCAACGTC |
| AATACGGTGACG | | AATACTAAAGAGGATCA | AATACGGTGACG |
| TGTTTAAAGGAG | | GTTGGCCGAAATCAGTT | TGTTTAAAGGAG |
| ATCTTAATCCAA | | ACCGTTTTCAAGGTAAG | ATCTTAATCCAA |
| AACCCCAAGGCC | | AAGGAAGCGGACCAACC | AACCCCAAGGCC |
| AAAGACTCATTG | | GTGGATTGTTGTAAACA | AAAGACTCATTG |
| AGGTGTCAGTGG | | CGAGCACACTGTTTGAT | AGGTGTCAGTGG |
| AAGAAAATCACC | | GAACTCGAATTAGACCC | AAGAAAATCACC |
| CGTTTACTTTAC | | ACCCGAGATTGAACCGG | CGTTTACTTTAC |
| GCGCACCGATTC | | GTGTCTTGAAAGTACTT | GCGCACCGATTC |
| AGCGGATTTATG | | CGGACAGAGAAACAATA | AGCGGATTTATG |
| GAGTCCGGTACA | | CTTGGGTGTGTACATTT | GAGTCCGGTACA |
| CCGAGACTTGGA | | GGAACATGCGCGGCTCC | CCGAGACTTGGA |
| GCTTTTTGCCGT | | GATGGTACGTCTACCTA | GCTTTTTGCCGT |
| CATTAACCTGTA | | CGCCACGTTTTTGGTCA | CATTAACCTGTA |
| CGGGAGACGCAG | | CCTGGAAAGGGGATGAG | CGGGAGACGCAG |
| CGCCCGCCATCC | | AAGACAAGAAACCCTAC | CGCCCGCCATCC |
| AGCATATATGTT | | GCCCGCAGTAACTCCTC | AGCATATATGTT |
| TAAAACATACAA | | AACCAAGAGGGGCTGAG | TAAAACATACAA |
| CATGCTTTCAAG | | TTTCATATGTGGAATTA | CATGCTTTCAAG |
| ACGTGGTGGTGG | | CCACTCGCATGTATTTT | ACGTGGTGGTGG |
| ATGTGGATTGCG | | CAGTTGGTGATACGTTT | ATGTGGATTGCG |
| CGGAAAAATACTA | | AGCTTGGCAATGCATCT | CGGAAAAATACTA |
| AAGAGGATCAGT | | TCAGTATAAGATACATG | AAGAGGATCAGT |
| TGGCCGAAATCA | | AAGCGCCATTTGATTTG | TGGCCGAAATCA |
| GTTACCGTTTTC | | CTGTTAGAGTGGTTGTA | GTTACCGTTTTC |
| AAGGTAAGAAGG | | TGTCCCCATCGATCCTA | AAGGTAAGAAGG |
| AAGCGGACCAAC | | CATGTCAACCAATGCGG | AAGCGGACCAAC |
| CGTGGATTGTTG | | TTATATTCTACGTGTTT | CGTGGATTGTTG |
| TAAACACGAGCA | | GTATCATCCCAACGCAC | TAAACACGAGCA |
| CACTGTTTGATG | | CCCAATGCCTCTCTCAT | CACTGTTTGATG |
| AACTCGAATTAG | | ATGAATTCCGGTTGTAC | AACTCGAATTAG |
| ACCCACCCGAGA | | ATTTACCTCGCCACATT | ACCCACCCGAGA |
| TTGAACCGGGTG | | TAGCCCAGCGTGTTGCA | TTGAACCGGGTG |
| TCTTGAAAGTAC | | AGCACAGTGTATCAAAA | TCTTGAAAGTAC |
| TTCGGACAGAGA | | TTGTGAACATGCAGATA | TTCGGACAGAGA |
| AACAATACTTGG | | ACTACACCGCATATTGT | AACAATACTTGG |
| GTGTGTACATTT | | CTGGGAATATCTCATAT | GTGTGTACATTT |
| GGAACATGCGCG | | GGAGCCTAGCTTTGGTC | GGAACATGCGCG |
| GCTCCGATGGTA | | TAATCTTACACGACGGG | GCTCCGATGGTA |
| CGTCTACCTACG | | GGCACCACGTTAAAGTT | CGTCTACCTACG |
| CCACGTTTTTGG | | TGTAGATACACCCGAGA | CCACGTTTTTGG |
| TCACCTGGAAAG | | GTTTGTCGGGATTATAC | TCACCTGGAAAG |
| GGGATGAGAAGA | | GTTTTTGTGGTGTATTT | GGGATGAGAAGA |
| CAAGAAACCCTA | | TAACGGGCATGTTGAAG | CAAGAAACCCTA |
| CGCCCGCAGTAA | | CCGTAGCATACACTGTT | CGCCCGCAGTAA |
| CTCCTCAACCAA | | GTATCCACAGTAGATCA | CTCCTCAACCAA |
| GAGGGGCTGAGT | | TTTTGTAAACGCAATTG | GAGGGGCTGAGT |
| TTCATATGTGGA | | AAGAGCGTGGATTTCCG | TTCATATGTGGA |
| ATTACCACTCGC | | CCAACGGCCGGTCAGCC | ATTACCACTCGC |

TABLE 2-continued

```
ATGTATTTTCAG          ACCGGCGACTACTAAAC     ATGTATTTTCAG
TTGGTGATACGT          CCAAGGAAATTACCCCC     TTGGTGATACGT
TTAGCTTGGCAA          GTAAACCCCGGAACGTC     TTAGCTTGGCAA
TGCATCTTCAGT          ACCACTTCTACGATATG     TGCATCTTCAGT
ATAAGATACATG          CCGCATGGACCGGAGGG     ATAAGATACATG
AAGCGCCATTTG          CTTGCAGCAGTAGTACT     AAGCGCCATTTG
ATTTGCTGTTAG          TTTATGTCTCGTAATAT     ATTTGCTGTTAG
AGTGGTTGTATG          TTTTAATCTGTACGGCT     AGTGGTTGTATG
TCCCCATCGATC          AAACGAATGAGGGTTAA     TCCCCATCGATC
CTACATGTCAAC          AGCCGCCAGGGTAGACA     CTACATGTCAAC
CAATGCGGTTAT          AG                    CAATGCGGTTAT
ATTCTACGTGTT                                ATTCTACGTGTT
TGTATCATCCCA                                TGTATCATCCCA
ACGCACCCAAT                                 ACGCACCCAAT
GCCTCTCTCATA                                GCCTCTCTCATA
TGAATTCCGGTT                                TGAATTCCGGTT
GTACATTTACCT                                GTACATTTACCT
CGCCACATTTAG                                CGCCACATTTAG
CCCAGCGTGTTG                                CCCAGCGTGTTG
CAAGCACAGTGT                                CAAGCACAGTGT
ATCAAAATTGTG                                ATCAAAATTGTG
AACATGCAGATA                                AACATGCAGATA
ACTACACCGCAT                                ACTACACCGCAT
ATTGTCTGGGAA                                ATTGTCTGGGAA
TATCTCATATGG                                TATCTCATATGG
AGCCTAGCTTTG                                AGCCTAGCTTTG
GTCTAATCTTAC                                GTCTAATCTTAC
ACGACGGGGGCA                                ACGACGGGGGCA
CCACGTTAAAGT                                CCACGTTAAAGT
TTGTAGATACAC                                TTGTAGATACAC
CCGAGAGTTTGT                                CCGAGAGTTTGT
CGGGATTATACG                                CGGGATTATACG
TTTTTGTGGTGT                                TTTTTGTGGTGT
ATTTTAACGGGC                                ATTTTAACGGGC
ATGTTGAAGCCG                                ATGTTGAAGCCG
TAGCATACACTG                                TAGCATACACTG
TTGTATCCACAG                                TTGTATCCACAG
TAGATCATTTTG                                TAGATCATTTTG
TAAACGCAATTG                                TAAACGCAATTG
AAGAGCGTGGAT                                AAGAGCGTGGAT
TTCCGCCAACGG                                TTCCGCCAACGG
CCGGTCAGCCAC                                CCGGTCAGCCAC
CGGCGACTACTA                                CGGCGACTACTA
AACCCAAGGAAA                                AACCCAAGGAAA
TTACCCCCGTAA                                TTACCCCCGTAA
ACCCCGGAACGT                                ACCCCGGAACGT
CACCACTTCTAC                                CACCACTTCTAC
GATATGCCGCAT                                GATATGCCGCAT
GGACCGGAGGGC                                GGACCGGAGGGC
TTGCAGCAGTAG                                TTGCAGCAGTAG
TACTTTTATGTC                                TACTTTTATGTC
TCGTAATATTTT                                TCGTAATATTTT
TAATCTGTACGG                                TAATCTGTACGG
CTAAACGAATGA                                CTAAACGAATGA
GGGTTAAAGCCG                                GGGTTAAAGCCG
CCAGGGTAGACA                                CCAGGGTAGACA
AGTGATAATAGG                                AGTGATAATAGG
CTGGAGCCTCGG                                CTGGAGCCTCGG
TGGCCATGCTTC                                TGGCCATGCTTC
TTGCCCCTTGGG                                TTGCCCCTTGGG
CCTCCCCCCAGC                                CCTCCCCCCAGC
CCCTCCTCCCCT                                CCCTCCTCCCCT
TCCTGCACCCGT                                TCCTGCACCCGT
ACCCCGTGGTC                                 ACCCCGTGGTC
TTTGAATAAAGT                                TTTGAATAAAGT
CTGAGTGGGCGG                                CTGAGTGGGCGG
C                                           CAAAAAAAAAAA
                                            AAAAAAAAAAAA
                                            AAAAAAAAAAAA
                                            AAAAAAAAAAAA
                                            AAAAAAAAAAAA
                                            AAAAAAAAAAAA
                                            AAAAAAAAAAAA
                                            AAAAAAAAAAAA
                                            AAAAATCTAG
```

TABLE 2-continued

| | SEQ ID NO: 72 | SEQ ID NO: 73 | SEQ ID NO: 74 | SEQ ID NO: 75 |
|---|---|---|---|---|
| VZV-GE-truncated-delete_from_574_-_Y569A Variant 4 | GGGAAATAAGAG | MGTVNKPVVGVLMGFGI | ATGGGGACAGTTAATAA | GGGAAATAAGAG |
| | AGAAAAGAAGAG | ITGTLRITNPVRASVLR | ACCTGTGGTGGGGGTAT | AGAAAAGAAGAG |
| | TAAGAAGAAATA | YDDFHIDEDKLDTNSVY | TGATGGGGTTCGGAATT | TAAGAAGAAATA |
| | TAAGAGCCACCA | EPYYHSDHAESSWVNRG | ATCACGGGAACGTTGCG | TAAGAGCCACCA |
| | TGGGGACAGTTA | ESSRKAYDHNSPYIWPR | TATAACGAATCCGGTCA | TGGGGACAGTTA |
| | ATAAACCTGTGG | NDYDGFLENAHEHHGVY | GAGCATCCGTCTTGCGA | ATAAACCTGTGG |
| | TGGGGGTATTGA | NQGRGIDSGERLMQPTQ | TACGATGATTTTCACAT | TGGGGGTATTGA |
| | TGGGGTTCGGAA | MSAQEDLGDDTGIHVIP | CGATGAAGACAAACTGG | TGGGGTTCGGAA |
| | TTATCACGGGAA | TLNGDDRHKIVNVDQRQ | ATACAAACTCCGTATAT | TTATCACGGGAA |
| | CGTTGCGTATAA | YGDVFKGDLNPKPQGQR | GAGCCTTACTACCATTC | CGTTGCGTATAA |
| | CGAATCCGGTCA | LIEVSVEENHPFTLRAP | AGATCATGCGGAGTCTT | CGAATCCGGTCA |
| | GAGCATCCGTCT | IQRIYGVRYTETWSFLP | CATGGGTAAATCGGGGA | GAGCATCCGTCT |
| | TGCGATACGATG | SLTCTGDAAPAIQHICL | GAGTCTTCGCGAAAGGC | TGCGATACGATG |
| | ATTTTCACATCG | KHTTCFQDVVVDVDCAE | GTACGATCATAACTCAC | ATTTTCACATCG |
| | ATGAAGACAAAC | NTKEDQLAEISYRFQGK | CTTATATATGGCCACGT | ATGAAGACAAAC |
| | TGGATACAAACT | KEADQPWIVVNTSTLFD | AATGATTATGATGGATT | TGGATACAAACT |
| | CCGTATATGAGC | ELELDPPEIEPGVLKVL | TTTAGAGAACGCACACG | CCGTATATGAGC |
| | CTTACTACCATT | RTEKQYLGVYIWNMRGS | AACACCATGGGGTGTAT | CTTACTACCATT |
| | CAGATCATGCGG | DGTSTYATFLVTWKGDE | AATCAGGGCCGTGGTAT | CAGATCATGCGG |
| | AGTCTTCATGGG | KTRNPTPAVTPQPRGAE | CGATAGCGGGGAACGGT | AGTCTTCATGGG |
| | TAAATCGGGGAG | FHMWNYHSHVFSVGDTF | TAATGCAACCCACACAA | TAAATCGGGGAG |
| | AGTCTTCGCGAA | SLAMHLQYKIHEAPFDL | ATGTCTGCACAGGAGGA | AGTCTTCGCGAA |
| | AGGCGTACGATC | LLEWLYVPIDPTCQPMR | TCTTGGGGACGATACGG | AGGCGTACGATC |
| | ATAACTCACCTT | LYSTCLYHPNAPQCLSH | GCATCCACGTTATCCCT | ATAACTCACCTT |
| | ATATATGGCCAC | MNSGCTFTSPHLAQRVA | ACGTTAAACGGCGATGA | ATATATGGCCAC |
| | GTAATGATTATG | STVYQNCEHADNYTAYC | CAGACATAAGATTGTAA | GTAATGATTATG |
| | ATGGATTTTTAG | LGISHMEPSFGLILHDG | ATGTGGACCAACGTCAA | ATGGATTTTTAG |
| | AGAACGCACACG | GTTLKFVDTPESLSGLY | TACGGTGACGTGTTTAA | AGAACGCACACG |
| | AACACCATGGGG | VFVVYFNGHVEAVAYTV | AGGAGATCTTAATCCAA | AACACCATGGGG |
| | TGTATAATCAGG | VSTVDHFVNAIEERGFP | AGCCCCAAGGCCAAAGA | TGTATAATCAGG |
| | GCCGTGGTATCG | PTAGQPPATTKPKEITP | CTCATTGAGGTGTCAGT | GCCGTGGTATCG |
| | ATAGCGGGGAAC | VNPGTSPLLRYAAWTGG | GGAAGAGAATCACCCGT | ATAGCGGGGAAC |
| | GGTTAATGCAAC | LAAVVLLCLVIFLICTA | TTACTTTACGCGCACCG | GGTTAATGCAAC |
| | CCACACAAATGT | KRMRVKAARVDK | ATTCAGCGGATTTATGG | CCACACAAATGT |
| | CTGCACAGGAGG | | AGTCCGGTACACCGAGA | CTGCACAGGAGG |
| | ATCTTGGGGACG | | CTTGGAGCTTTTTGCCG | ATCTTGGGGACG |
| | ATACGGGCATCC | | TCATTAACCTGTACGGG | ATACGGGCATCC |
| | ACGTTATCCCTA | | AGACGCAGCGCCCGCCA | ACGTTATCCCTA |
| | CGTTAAACGGCG | | TCCAGCATATATGTTTA | CGTTAAACGGCG |
| | ATGACAGACATA | | AAGCATACAACATGCTT | ATGACAGACATA |
| | AGATTGTAAATG | | TCAAGACGTGGTGGTGG | AGATTGTAAATG |
| | TGGACCAACGTC | | ATGTGGATTGCGCGGAG | TGGACCAACGTC |
| | AATACGGTGACG | | AATACTAAAGAGGATCA | AATACGGTGACG |
| | TGTTTAAAGGAG | | GTTGGCCGAAATCAGTT | TGTTTAAAGGAG |
| | ATCTTAATCCAA | | ACCGTTTTCAAGGTAAG | ATCTTAATCCAA |
| | AGCCCCAAGGCC | | AAGGAAGCGGACCAACC | AGCCCCAAGGCC |
| | AAAGACTCATTG | | GTGGATTGTTGTAAACA | AAAGACTCATTG |
| | AGGTGTCAGTGG | | CGAGCACACTGTTTGAT | AGGTGTCAGTGG |
| | AAGAGAATCACC | | GAACTCGAATTAGACCC | AAGAGAATCACC |
| | CGTTTACTTTAC | | CCCCGAGATTGAACCGG | CGTTTACTTTAC |
| | GCGCACCGATTC | | GTGTCTTGAAAGTACTT | GCGCACCGATTC |
| | AGCGGATTTATG | | CGGACAGAGAAACAATA | AGCGGATTTATG |
| | GAGTCCGGTACA | | CTTGGGTGTGTACATTT | GAGTCCGGTACA |
| | CCGAGACTTGGA | | GGAACATGCGCGGCTCC | CCGAGACTTGGA |
| | GCTTTTTGCCGT | | GATGGTACGTCTACCTA | GCTTTTTGCCGT |
| | CATTAACCTGTA | | CGCCACGTTTTTGGTCA | CATTAACCTGTA |
| | CGGGGAGACGCAG | | CCTGGAAAGGGGATGAG | CGGGGAGACGCAG |
| | CGCCCGCCATCC | | AAGACAAGAAACCCTAC | CGCCCGCCATCC |
| | AGCATATATGTT | | GCCCGCAGTAACTCCTC | AGCATATATGTT |
| | TAAAGCATACAA | | AACCAAGAGGGCTGAG | TAAAGCATACAA |
| | CATGCTTTCAAG | | TTTCATATGTGGAATTA | CATGCTTTCAAG |
| | ACGTGGTGGTGG | | CCACTCGCATGTATTTT | ACGTGGTGGTGG |
| | ATGTGGATTGCG | | CAGTTGGTGATACGTTT | ATGTGGATTGCG |
| | CGGAGAATACTA | | AGCTTGGCAATGCATCT | CGGAGAATACTA |
| | AAGAGGATCAGT | | TCAGTATAAGATACATG | AAGAGGATCAGT |
| | TGGCCGAAATCA | | AAGCGCCATTTGATTTG | TGGCCGAAATCA |
| | GTTACCGTTTTC | | CTGTTAGAGTGGTTGTA | GTTACCGTTTTC |
| | AAGGTAAGAAGG | | TGTCCCCATCGATCCTA | AAGGTAAGAAGG |
| | AAGCGGACCAAC | | CATGTCAACCAATGCGG | AAGCGGACCAAC |
| | CGTGGATTGTTG | | TTATATTCTACGTGTTT | CGTGGATTGTTG |
| | TAAACACGAGCA | | GTATCATCCCAACGCAC | TAAACACGAGCA |
| | CACTGTTTGATG | | CCCAATGCCTCTCTCAT | CACTGTTTGATG |
| | AACTCGAATTAG | | ATGAATTCCGGTTGTAC | AACTCGAATTAG |
| | ACCCCCCCGAGA | | ATTTACCTCGCCACATT | ACCCCCCCGAGA |
| | TTGAACCGGGTG | | TAGCCCAGCGTGTTGCA | TTGAACCGGGTG |
| | TCTTGAAAGTAC | | AGCACAGTGTATCAGAA | TCTTGAAAGTAC |
| | TTCGGACAGAGA | | TTGTGAACATGCAGATA | TTCGGACAGAGA |
| | AACAATACTTGG | | ACTACACCGCATATTGT | AACAATACTTGG |
| | GTGTGTACATTT | | CTGGGAATATCTCATAT | GTGTGTACATTT |

TABLE 2-continued

| | | |
|---|---|---|
| GGAACATGCGCG | GGAGCCTAGCTTTGGTC | GGAACATGCGCG |
| GCTCCGATGGTA | TAATCTTACACGACGGG | GCTCCGATGGTA |
| CGTCTACCTACG | GGCACCACGTTAAAGTT | CGTCTACCTACG |
| CCACGTTTTTGG | TGTAGATACACCCGAGA | CCACGTTTTTGG |
| TCACCTGGAAAG | GTTTGTCGGGATTATAC | TCACCTGGAAAG |
| GGGATGAGAAGA | GTTTTTGTGGTGTATTT | GGGATGAGAAGA |
| CAAGAAACCCTA | TAACGGGCATGTTGAAG | CAAGAAACCCTA |
| CGCCCGCAGTAA | CCGTAGCATACACTGTT | CGCCCGCAGTAA |
| CTCCTCAACCAA | GTATCCACAGTAGATCA | CTCCTCAACCAA |
| GAGGGGCTGAGT | TTTTGTAAACGCAATTG | GAGGGGCTGAGT |
| TTCATATGTGGA | AAGAGCGTGGATTTCCG | TTCATATGTGGA |
| ATTACCACTCGC | CCAACGGCCGGTCAGCC | ATTACCACTCGC |
| ATGTATTTTCAG | ACCGGCGACTACTAAAC | ATGTATTTTCAG |
| TTGGTGATACGT | CCAAGGAAATTACCCCC | TTGGTGATACGT |
| TTAGCTTGGCAA | GTAAACCCCGGAACGTC | TTAGCTTGGCAA |
| TGCATCTTCAGT | ACCACTTCTACGATATG | TGCATCTTCAGT |
| ATAAGATACATG | CCGCATGGACCGGAGGG | ATAAGATACATG |
| AAGCGCCATTTG | CTTGCAGCAGTAGTACT | AAGCGCCATTTG |
| ATTTGCTGTTAG | TTTATGTCTCGTAATAT | ATTTGCTGTTAG |
| AGTGGTTGTATG | TTTTAATCTGTACGGCT | AGTGGTTGTATG |
| TCCCCATCGATC | AAACGAATGAGGGTTAA | TCCCCATCGATC |
| CTACATGTCAAC | AGCCGCCAGGGTAGACA | CTACATGTCAAC |
| CAATGCGGTTAT | AG | CAATGCGGTTAT |
| ATTCTACGTGTT | | ATTCTACGTGTT |
| TGTATCATCCCA | | TGTATCATCCCA |
| ACGCACCCCAAT | | ACGCACCCCAAT |
| GCCTCTCTCATA | | GCCTCTCTCATA |
| TGAATTCCGGTT | | TGAATTCCGGTT |
| GTACATTTACCT | | GTACATTTACCT |
| CGCCACATTTAG | | CGCCACATTTAG |
| CCCAGCGTGTTG | | CCCAGCGTGTTG |
| CAAGCACAGTGT | | CAAGCACAGTGT |
| ATCAGAATTGTG | | ATCAGAATTGTG |
| AACATGCAGATA | | AACATGCAGATA |
| ACTACACCGCAT | | ACTACACCGCAT |
| ATTGTCTGGGAA | | ATTGTCTGGGAA |
| TATCTCATATGG | | TATCTCATATGG |
| AGCCTAGCTTTG | | AGCCTAGCTTTG |
| GTCTAATCTTAC | | GTCTAATCTTAC |
| ACGACGGGGGCA | | ACGACGGGGGCA |
| CCACGTTAAAGT | | CCACGTTAAAGT |
| TTGTAGATACAC | | TTGTAGATACAC |
| CCGAGAGTTTGT | | CCGAGAGTTTGT |
| CGGGATTATACG | | CGGGATTATACG |
| TTTTTGTGGTGT | | TTTTTGTGGTGT |
| ATTTTAACGGGC | | ATTTTAACGGGC |
| ATGTTGAAGCCG | | ATGTTGAAGCCG |
| TAGCATACACTG | | TAGCATACACTG |
| TTGTATCCACAG | | TTGTATCCACAG |
| TAGATCATTTTG | | TAGATCATTTTG |
| TAAACGCAATTG | | TAAACGCAATTG |
| AAGAGCGTGGAT | | AAGAGCGTGGAT |
| TTCCGCCAACGG | | TTCCGCCAACGG |
| CCGGTCAGCCAC | | CCGGTCAGCCAC |
| CGGCGACTACTA | | CGGCGACTACTA |
| AACCCAAGGAAA | | AACCCAAGGAAA |
| TTACCCCGTAA | | TTACCCCGTAA |
| ACCCCGGAACGT | | ACCCCGGAACGT |
| CACCACTTCTAC | | CACCACTTCTAC |
| GATATGCCGCAT | | GATATGCCGCAT |
| GGACCGGAGGGC | | GGACCGGAGGGC |
| TTGCAGCAGTAG | | TTGCAGCAGTAG |
| TACTTTTATGTC | | TACTTTTATGTC |
| TCGTAATATTTT | | TCGTAATATTTT |
| TAATCTGTACGG | | TAATCTGTACGG |
| CTAAACGAATGA | | CTAAACGAATGA |
| GGGTTAAAGCCG | | GGGTTAAAGCCG |
| CCAGGGTAGACA | | CCAGGGTAGACA |
| AGTGATAATAGG | | AGTGATAATAGG |
| CTGGAGCCTCGG | | CTGGAGCCTCGG |
| TGGCCATGCTTC | | TGGCCATGCTTC |
| TTGCCCCTTGGG | | TTGCCCCTTGGG |
| CCTCCCCCCAGC | | CCTCCCCCCAGC |
| CCCTCCTCCCCT | | CCCTCCTCCCCT |
| TCCTGCACCCGT | | TCCTGCACCCGT |
| ACCCCCGTGGTC | | ACCCCCGTGGTC |
| TTTGAATAAAGT | | TTTGAATAAAGT |
| CTGAGTGGGCGG | | CTGAGTGGGCGG |
| C | | CAAAAAAAAAAA |
| | | AAAAAAAAAAAA |

TABLE 2-continued

|  | | | | AAAAAAAAAAAA |
| --- | --- | --- | --- | --- |
|  | | | | AAAAAAAAAAAA |
|  | | | | AAAAAAAAAAAA |
|  | | | | AAAAAAAAAAAA |
|  | | | | AAAAAAAAAAAA |
|  | | | | AAAAAAAAAAAA |
|  | | | | AAAAATCTAG |
|  | SEQ ID NO: 76 | SEQ ID NO: 77 | SEQ ID NO: 78 | SEQ ID NO: 79 |
| VZV-GE-<br>truncated-<br>delete_from_574_-_Y569A<br>Variant 5 | GGGAAATAAGAG | MGTVNKPVVGVLMGFGI | ATGGGGACAGTTAATAA | GGGAAATAAGAG |
|  | AGAAAAGAAGAG | ITGTLRITNPVRASVLR | ACCTGTGGTGGGGGTAT | AGAAAAGAAGAG |
|  | TAAGAAGAAATA | YDDFHIDEDKLDTNSVY | TGATGGGGTTCGGAATT | TAAGAAGAAATA |
|  | TAAGAGCCACCA | EPYYHSDHAESSWVNRG | ATCACGGGAACGTTGCG | TAAGAGCCACCA |
|  | TGGGGACAGTTA | ESSRKAYDHNSPYIWPR | TATAACGAATCCGGTCA | TGGGGACAGTTA |
|  | ATAAACCTGTGG | NDYDGFLENAHEHHGVY | GAGCATCCGTCTTGCGA | ATAAACCTGTGG |
|  | TGGGGGTATTGA | NQGRGIDSGERLMQPTQ | TACGATGATTTTCACAT | TGGGGGTATTGA |
|  | TGGGGTTCGGAA | MSAQEDLGDDTGIHVIP | CGATGAAGACAAACTGG | TGGGGTTCGGAA |
|  | TTATCACGGGAA | TLNGDDRHKIVNVDQRQ | ATACAAACTCCGTATAT | TTATCACGGGAA |
|  | CGTTGCGTATAA | YGDVFKGDLNPKPQGQR | GAGCCTTACTACCATTC | CGTTGCGTATAA |
|  | CGAATCCGGTCA | LIEVSVEENHPFTLRAP | AGATCATGCGGAGTCTT | CGAATCCGGTCA |
|  | GAGCATCCGTCT | IQRIYGVRYTETWSFLP | CATGGGTAAATCGGGGA | GAGCATCCGTCT |
|  | TGCGATACGATG | SLTCTGDAAPAIQHICL | GAGTCTTCGCGAAAGGC | TGCGATACGATG |
|  | ATTTTCACATCG | KHTTCFQDVVVDVDCAE | GTACGATCATAACTCAC | ATTTTCACATCG |
|  | ATGAAGACAAAC | NTKEDQLAEISYRFQGK | CTTATATATGGCCACGT | ATGAAGACAAAC |
|  | TGGATACAAACT | KEADQPWIVVNTSTLFD | AATGATTATGATGGATT | TGGATACAAACT |
|  | CCGTATATGAGC | ELELDPPEIEPGVLKVL | TTTAGAGAACGCACACG | CCGTATATGAGC |
|  | CTTACTACCATT | RTEKQYLGVYIWNMRGS | AACACCATGGGGTGTAT | CTTACTACCATT |
|  | CAGATCATGCGG | DGTSTYATFLVTWKGDE | AATCAGGGCCGTGGTAT | CAGATCATGCGG |
|  | AGTCTTCATGGG | KTRNPTPAVTPQPRGAE | CGATAGCGGGGAACGGT | AGTCTTCATGGG |
|  | TAAATCGGGGAG | FHMWNYHSHVFSVGDTF | TAATGCAACCCACACAA | TAAATCGGGGAG |
|  | AGTCTTCGCGAA | SLAMHLQYKIHEAPFDL | ATGTCTGCACAGGAGGA | AGTCTTCGCGAA |
|  | AGGCGTACGATC | LLEWLYVPIDPTCQPMR | TCTTGGGGACGATACGG | AGGCGTACGATC |
|  | ATAACTCACCTT | LYSTCLYHPNAPQCLSH | GCATCCACGTTATCCCT | ATAACTCACCTT |
|  | ATATATGGCCAC | MNSGCTFTSPHLAQRVA | ACGTTAAACGGCGATGA | ATATATGGCCAC |
|  | GTAATGATTATG | STVYQNCEHADNYTAYC | CAGACATAAGATTGTAA | GTAATGATTATG |
|  | ATGGATTTTTAG | LGISHMEPSFGLILHDG | ATGTGGACCAACGTCAA | ATGGATTTTTAG |
|  | AGAACGCACACG | GTTLKFVDTPESLSGLY | TACGGTGACGTGTTTAA | AGAACGCACACG |
|  | AACACCATGGGG | VFVVYFNGHVEAVAYTV | AGGAGATCTTAATCCAA | AACACCATGGGG |
|  | TGTATAATCAGG | VSTVDHFVNAIEERGFP | AGCCCCAAGGCCAAAGA | TGTATAATCAGG |
|  | GCCGTGGTATCG | PTAGQPPATTKPKEITP | CTCATTGAGGTGTCAGT | GCCGTGGTATCG |
|  | ATAGCGGGGAAC | VNPGTSPLLRYAAWTGG | GGAAGAGAATCACCCGT | ATAGCGGGGAAC |
|  | GGTTAATGCAAC | LAAVVLLCLVIFLICTA | TTACTTTACGCGCACCG | GGTTAATGCAAC |
|  | CCACACAAATGT | KRMRVKAARVDK | ATTCAGCGGATTTATGG | CCACACAAATGT |
|  | CTGCACAGGAGG | | AGTCCGGTACACCGAGA | CTGCACAGGAGG |
|  | ATCTTGGGGACG | | CTTGGAGCTTTTTGCCG | ATCTTGGGGACG |
|  | ATACGGGCATCC | | TCATTAACCTGTACGGG | ATACGGGCATCC |
|  | ACGTTATCCCTA | | AGACGCAGCGCCCGCCA | ACGTTATCCCTA |
|  | CGTTAAACGGCG | | TCCAGCATATATGTTTA | CGTTAAACGGCG |
|  | ATGACAGACATA | | AAGCATACAACATGCTT | ATGACAGACATA |
|  | AGATTGTAAATG | | TCAAGACGTGGTGGTGG | AGATTGTAAATG |
|  | TGGACCAACGTC | | ATGTGGATTGCGCGGAG | TGGACCAACGTC |
|  | AATACGGTGACG | | AATACTAAAGAGGATCA | AATACGGTGACG |
|  | TGTTTAAAGGAG | | GTTGGCCGAAATCAGTT | TGTTTAAAGGAG |
|  | ATCTTAATCCAA | | ACCGTTTTCAAGGTAAG | ATCTTAATCCAA |
|  | AGCCCCAAGGCC | | AAGGAAGCGGACCAACC | AGCCCCAAGGCC |
|  | AAAGACTCATTG | | GTGGATTGTTGTAAACA | AAAGACTCATTG |
|  | AGGTGTCAGTGG | | CGAGCACACTGTTTGAT | AGGTGTCAGTGG |
|  | AAGAGAATCACC | | GAACTCGAATTAGACCC | AAGAGAATCACC |
|  | CGTTTACTTTAC | | ACCCGAGATTGAACCGG | CGTTTACTTTAC |
|  | GCGCACCGATTC | | GTGTCTTGAAAGTACTT | GCGCACCGATTC |
|  | AGCGGATTTATG | | CGGACAGAGAAACAATA | AGCGGATTTATG |
|  | GAGTCCGGTACA | | CTTGGGTGTGTACATTT | GAGTCCGGTACA |
|  | CCGAGACTTGGA | | GGAACATGCGCGGCTCC | CCGAGACTTGGA |
|  | GCTTTTTGCCGT | | GATGGTACGTCTACCTA | GCTTTTTGCCGT |
|  | CATTAACCTGTA | | CGCCACGTTTTTGGTCA | CATTAACCTGTA |
|  | CGGGAGACGCAG | | CCTGGAAAGGGGATGAG | CGGGAGACGCAG |
|  | CGCCCGCCATCC | | AAGACAAGAAACCCTAC | CGCCCGCCATCC |
|  | AGCATATATGTT | | GCCCGCAGTAACTCCTC | AGCATATATGTT |
|  | TAAAGCATACAA | | AACCAAGAGGGCTGAG | TAAAGCATACAA |
|  | CATGCTTTCAAG | | TTTCATATGTGGAATTA | CATGCTTTCAAG |
|  | ACGTGGTGGTGG | | CCACTCGCATGTATTTT | ACGTGGTGGTGG |
|  | ATGTGGATTGCG | | CAGTTGGTGATACGTTT | ATGTGGATTGCG |
|  | CGGAGAATACTA | | AGCTTGGCAATGCATCT | CGGAGAATACTA |
|  | AAGAGGATCAGT | | TCAGTATAAGATACATG | AAGAGGATCAGT |
|  | TGGCCGAAATCA | | AAGCGCCATTTGATTTG | TGGCCGAAATCA |
|  | GTTACCGTTTTC | | CTGTTAGAGTGGTTGTA | GTTACCGTTTTC |
|  | AAGGTAAGAAGG | | TGTCCCCATCGATCCTA | AAGGTAAGAAGG |
|  | AAGCGGACCAAC | | CATGTCAACCAATGCGG | AAGCGGACCAAC |
|  | CGTGGATTGTTG | | TTATATTCTACGTGTTT | CGTGGATTGTTG |
|  | TAAACACGAGCA | | GTATCATCCCAACGCAC | TAAACACGAGCA |

TABLE 2-continued

| | | |
|---|---|---|
| CACTGTTTGATG | CCCAATGCCTCTCTCAT | CACTGTTTGATG |
| AACTCGAATTAG | ATGAATTCCGGTTGTAC | AACTCGAATTAG |
| ACCCACCCGAGA | ATTTACCTCGCCACATT | ACCCACCCGAGA |
| TTGAACCGGGTG | TAGCCCAGCGTGTTGCA | TTGAACCGGGTG |
| TCTTGAAAGTAC | AGCACAGTGTATCAGAA | TCTTGAAAGTAC |
| TTCGGACAGAGA | TTGTGAACATGCAGATA | TTCGGACAGAGA |
| AACAATACTTGG | ACTACACCGCATATTGT | AACAATACTTGG |
| GTGTGTACATTT | CTGGGAATATCTCATAT | GTGTGTACATTT |
| GGAACATGCGCG | GGAGCCTAGCTTTGGTC | GGAACATGCGCG |
| GCTCCGATGGTA | TAATCTTACACGACGGG | GCTCCGATGGTA |
| CGTCTACCTACG | GGCACCACGTTAAAGTT | CGTCTACCTACG |
| CCACGTTTTTGG | TGTAGATACACCCGAGA | CCACGTTTTTGG |
| TCACCTGGAAAG | GTTTGTCGGGATTATAC | TCACCTGGAAAG |
| GGGATGAGAAGA | GTTTTTGTGGTGTATTT | GGGATGAGAAGA |
| CAAGAAACCCTA | TAACGGGCATGTTGAAG | CAAGAAACCCTA |
| CGCCCGCAGTAA | CCGTAGCATACACTGTT | CGCCCGCAGTAA |
| CTCCTCAACCAA | GTATCCACAGTAGATCA | CTCCTCAACCAA |
| GAGGGGCTGAGT | TTTTGTAAACGCAATTG | GAGGGGCTGAGT |
| TTCATATGTGGA | AAGAGCGTGGATTCCG | TTCATATGTGGA |
| ATTACCACTCGC | CCAACGGCCGGTCAGCC | ATTACCACTCGC |
| ATGTATTTTCAG | ACCGGCGACTACTAAAC | ATGTATTTTCAG |
| TTGGTGATACGT | CCAAGGAAATTACCCCC | TTGGTGATACGT |
| TTAGCTTGGCAA | GTAAACCCCGGAACGTC | TTAGCTTGGCAA |
| TGCATCTTCAGT | ACCACTTCTACGATATG | TGCATCTTCAGT |
| ATAAGATACATG | CCGCATGGACCGGAGGG | ATAAGATACATG |
| AAGCGCCATTTG | CTTGCAGCAGTAGTACT | AAGCGCCATTTG |
| ATTTGCTGTTAG | TTTATGTCTCGTAATAT | ATTTGCTGTTAG |
| AGTGGTTGTATG | TTTTAATCTGTACGGCT | AGTGGTTGTATG |
| TCCCCATCGATC | AAACGAATGAGGGTTAA | TCCCCATCGATC |
| CTACATGTCAAC | AGCCGCCAGGGTAGACA | CTACATGTCAAC |
| CAATGCGGTTAT | AG | CAATGCGGTTAT |
| ATTCTACGTGTT | | ATTCTACGTGTT |
| TGTATCATCCCA | | TGTATCATCCCA |
| ACGCACCCCAAT | | ACGCACCCCAAT |
| GCCTCTCTCATA | | GCCTCTCTCATA |
| TGAATTCCGGTT | | TGAATTCCGGTT |
| GTACATTTACCT | | GTACATTTACCT |
| CGCCACATTTAG | | CGCCACATTTAG |
| CCCAGCGTGTTG | | CCCAGCGTGTTG |
| CAAGCACAGTGT | | CAAGCACAGTGT |
| ATCAGAATTGTG | | ATCAGAATTGTG |
| AACATGCAGATA | | AACATGCAGATA |
| ACTACACCGCAT | | ACTACACCGCAT |
| ATTGTCTGGGAA | | ATTGTCTGGGAA |
| TATCTCATATGG | | TATCTCATATGG |
| AGCCTAGCTTTG | | AGCCTAGCTTTG |
| GTCTAATCTTAC | | GTCTAATCTTAC |
| ACGACGGGGGCA | | ACGACGGGGGCA |
| CCACGTTAAAGT | | CCACGTTAAAGT |
| TTGTAGATACAC | | TTGTAGATACAC |
| CCGAGAGTTTGT | | CCGAGAGTTTGT |
| CGGGATTATACG | | CGGGATTATACG |
| TTTTTGTGGTGT | | TTTTTGTGGTGT |
| ATTTTAACGGGC | | ATTTTAACGGGC |
| ATGTTGAAGCCG | | ATGTTGAAGCCG |
| TAGCATACACTG | | TAGCATACACTG |
| TTGTATCCACAG | | TTGTATCCACAG |
| TAGATCATTTTG | | TAGATCATTTTG |
| TAAACGCAATTG | | TAAACGCAATTG |
| AAGAGCGTGGAT | | AAGAGCGTGGAT |
| TTCCGCCAACGG | | TTCCGCCAACGG |
| CCGGTCAGCCAC | | CCGGTCAGCCAC |
| CGGCGACTACTA | | CGGCGACTACTA |
| AACCCAAGGAAA | | AACCCAAGGAAA |
| TTACCCCCGTAA | | TTACCCCCGTAA |
| ACCCCGGAACGT | | ACCCCGGAACGT |
| CACCACTTCTAC | | CACCACTTCTAC |
| GATATGCCGCAT | | GATATGCCGCAT |
| GGACCGGAGGGC | | GGACCGGAGGGC |
| TTGCAGCAGTAG | | TTGCAGCAGTAG |
| TACTTTTATGTC | | TACTTTTATGTC |
| TCGTAATATTTT | | TCGTAATATTTT |
| TAATCTGTACGG | | TAATCTGTACGG |
| CTAAACGAATGA | | CTAAACGAATGA |
| GGGTTAAAGCCG | | GGGTTAAAGCCG |
| CCAGGGTAGACA | | CCAGGGTAGACA |
| AGTGATAATAGG | | AGTGATAATAGG |
| CTGGAGCCTCGG | | CTGGAGCCTCGG |
| TGGCCATGCTTC | | TGGCCATGCTTC |
| TTGCCCCTTGGG | | TTGCCCCTTGGG |

TABLE 2-continued

| | | | | |
|---|---|---|---|---|
| | CCTCCCCCCAGC | | | CCTCCCCCCAGC |
| | CCCTCCTCCCCT | | | CCCTCCTCCCCT |
| | TCCTGCACCCGT | | | TCCTGCACCCGT |
| | ACCCCCGTGGTC | | | ACCCCCGTGGTC |
| | TTTGAATAAAGT | | | TTTGAATAAAGT |
| | CTGAGTGGGCGG | | | CTGAGTGGGCGG |
| | C | | | CAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAATCTAG |
| | SEQ ID NO: 80 | SEQ ID NO: 81 | SEQ ID NO: 82 | SEQ ID NO: 83 |
| VZV-GE- | GGGAAATAAGAG | MGTVNKPVVGVLMGFGI | ATGGGGACAGTTAATAA | GGGAAATAAGAG |
| truncated- | AGAAAAGAAGAG | ITGTLRITNPVRASVLR | ACCTGTGGTGGGGGGTAT | AGAAAAGAAGAG |
| delete_from_574_-_Y569A | TAAGAAGAAATA | YDDFHIDEDKLDTNSVY | TGATGGGGTTCGGAATT | TAAGAAGAAATA |
| Variant 6 | TAAGAGCCACCA | EPYYHSDHAESSWVNRG | ATCACGGGAACGTTGCG | TAAGAGCCACCA |
| | TGGGGACAGTTA | ESSRKAYDHNSPYIWPR | TATAACGAATCCGGTCA | TGGGGACAGTTA |
| | ATAAACCTGTGG | NDYDGFLENAHEHHGVY | GAGCATCCGTCTTGCGA | ATAAACCTGTGG |
| | TGGGGGTATTGA | NQGRGIDSGERLMQPTQ | TACGATGATTTTCACAT | TGGGGGTATTGA |
| | TGGGGTTCGGAA | MSAQEDLGDDTGIHVIP | CGATGAAGACAAACTGG | TGGGGTTCGGAA |
| | TTATCACGGGAA | TLNGDDRHKIVNVDQRQ | ATACAAACTCCGTATAT | TTATCACGGGAA |
| | CGTTGCGTATAA | YGDVFKGDLNPKPQGQR | GAGCCTTACTACCATTC | CGTTGCGTATAA |
| | CGAATCCGGTCA | LIEVSVEENHPFTLRAP | AGATCATGCGGAGTCTT | CGAATCCGGTCA |
| | GAGCATCCGTCT | IQRIYGVRYTETWSFLP | CATGGGTAAATCGGGGA | GAGCATCCGTCT |
| | TGCGATACGATG | SLTCTGDAAPAIQHICL | GAGTCTTCGCGAAAAGC | TGCGATACGATG |
| | ATTTTCACATCG | KHTTCFQDVVVDVDCAE | GTACGATCATAACTCAC | ATTTTCACATCG |
| | ATGAAGACAAAC | NTKEDQLAEISYRFQGK | CTTATATATGGCCACGT | ATGAAGACAAAC |
| | TGGATACAAACT | KEADQPWIVVNTSTLFD | AATGATTATGATGGATT | TGGATACAAACT |
| | CCGTATATGAGC | ELELDPPEIEPGVLKVL | TTTAGAGAACGCACACG | CCGTATATGAGC |
| | CTTACTACCATT | RTEKQYLGVYIWNMRGS | AACACCATGGGGTGTAT | CTTACTACCATT |
| | CAGATCATGCGG | DGTSTYATFLVTWKGDE | AATCAGGGCCGTGGTAT | CAGATCATGCGG |
| | AGTCTTCATGGG | KTRNPTPAVTPQPRGAE | CGATAGCGGGGAACGGT | AGTCTTCATGGG |
| | TAAATCGGGGAG | FHMWNYHSHVFSVGDTF | TAATGCAACCCACACAA | TAAATCGGGGAG |
| | AGTCTTCGCGAA | SLAMHLQYKIHEAPFDL | ATGTCTGCACAGGAGGA | AGTCTTCGCGAA |
| | AAGCGTACGATC | LLEWLYVPIDPTCQPMR | TCTTGGGGACGATACGG | AAGCGTACGATC |
| | ATAACTCACCTT | LYSTCLYHPNAPQCLSH | GCATCCACGTTATCCCT | ATAACTCACCTT |
| | ATATATGGCCAC | MNSGCTFTSPHLAQRVA | ACGTTAAACGGCGATGA | ATATATGGCCAC |
| | GTAATGATTATG | STVYQNCEHADNYTAYC | CAGACATAAAATTGTAA | GTAATGATTATG |
| | ATGGATTTTTAG | LGISHMEPSFGLILHDG | ATGTGGACCAACGTCAA | ATGGATTTTTAG |
| | AGAACGCACACG | GTTLKFVDTPESLSGLY | TACGGTGACGTGTTTAA | AGAACGCACACG |
| | AACACCATGGGG | VFVVYFNGHVEAVAYTV | AGGAGATCTTAATCCAA | AACACCATGGGG |
| | TGTATAATCAGG | VSTVDHFVNAIEERGFP | AACCCCAAGGCCAAAGA | TGTATAATCAGG |
| | GCCGTGGTATCG | PTAGQPPATTKPKEITP | CTCATTGAGGTGTCAGT | GCCGTGGTATCG |
| | ATAGCGGGGAAC | VNPGTSPLLRYAAWTGG | GGAAGAAAATCACCCGT | ATAGCGGGGAAC |
| | GGTTAATGCAAC | LAAVVLLCLVIFLICTA | TTACTTTACGCGCACCG | GGTTAATGCAAC |
| | CCACACAAATGT | KRMRVKAARVDK | ATTCAGCGGATTTATGG | CCACACAAATGT |
| | CTGCACAGGAGG | | AGTCCGGTACACCGAGA | CTGCACAGGAGG |
| | ATCTTGGGGACG | | CTTGGAGCTTTTTGCCG | ATCTTGGGGACG |
| | ATACGGGCATCC | | TCATTAACCTGTACGGG | ATACGGGCATCC |
| | ACGTTATCCCTA | | AGACGCAGCGCCCGCCA | ACGTTATCCCTA |
| | CGTTAAACGGCG | | TCCAGCATATATGTTTA | CGTTAAACGGCG |
| | ATGACAGACATA | | AAGCATACAACATGCTT | ATGACAGACATA |
| | AAATTGTAAATG | | TCAAGACGTGGTGGTGG | AAATTGTAAATG |
| | TGGACCAACGTC | | ATGTGGATTGCGCGGAA | TGGACCAACGTC |
| | AATACGGTGACG | | AATACTAAAGAGGATCA | AATACGGTGACG |
| | TGTTTAAAGGAG | | GTTGGCCGAAATCAGTT | TGTTTAAAGGAG |
| | ATCTTAATCCAA | | ACCGTTTTCAAGGTAAG | ATCTTAATCCAA |
| | AACCCCAAGGCC | | AAGGAAGCGGACCAACC | AACCCCAAGGCC |
| | AAAGACTCATTG | | GTGGATTGTTGTAAACA | AAAGACTCATTG |
| | AGGTGTCAGTGG | | CGAGCACACTGTTTGAT | AGGTGTCAGTGG |
| | AAGAAAATCACC | | GAACTCGAATTAGACCC | AAGAAAATCACC |
| | CGTTTACTTTAC | | CCCCGAGATTGAACCGG | CGTTTACTTTAC |
| | GCGCACCGATTC | | GTGTCTTGAAAGTACTT | GCGCACCGATTC |
| | AGCGGATTTATG | | CGGACAGAGAAACAATA | AGCGGATTTATG |
| | GAGTCCGGTACA | | CTTGGGTGTGTACATTT | GAGTCCGGTACA |
| | CCGAGACTTGGA | | GGAACATGCGCGGCTCC | CCGAGACTTGGA |
| | GCTTTTTGCCGT | | GATGGTACGTCTACCTA | GCTTTTTGCCGT |
| | CATTAACCTGTA | | CGCCACGTTTTTGGTCA | CATTAACCTGTA |
| | CGGGAGACGCAG | | CCTGGAAAGGGGATGAG | CGGGAGACGCAG |
| | CGCCCGCCATCC | | AAGACAAGAAACCCTAC | CGCCCGCCATCC |
| | AGCATATATGTT | | GCCCGCAGTAACTCCTC | AGCATATATGTT |
| | TAAAGCATACAA | | AACCAAGAGGGGCTGAG | TAAAGCATACAA |
| | CATGCTTTCAAG | | TTTCATATGTGGAATTA | CATGCTTTCAAG |
| | ACGTGGTGGTGG | | CCACTCGCATGTATTTT | ACGTGGTGGTGG |
| | ATGTGGATTGCG | | CAGTTGGTGATACGTTT | ATGTGGATTGCG |

TABLE 2-continued

| | | |
|---|---|---|
| CGGAAAATACTA | AGCTTGGCAATGCATCT | CGGAAAATACTA |
| AAGAGGATCAGT | TCAGTATAAGATACATG | AAGAGGATCAGT |
| TGGCCGAAATCA | AAGCGCCATTTGATTTG | TGGCCGAAATCA |
| GTTACCGTTTTC | CTGTTAGAGTGGTTGTA | GTTACCGTTTTC |
| AAGGTAAGAAGG | TGTCCCCATCGATCCTA | AAGGTAAGAAGG |
| AAGCGGACCAAC | CATGTCAACCAATGCGG | AAGCGGACCAAC |
| CGTGGATTGTTG | TTATATTCTACGTGTTT | CGTGGATTGTTG |
| TAAACACGAGCA | GTATCATCCCAACGCAC | TAAACACGAGCA |
| CACTGTTTGATG | CCCAATGCCTCTCTCAT | CACTGTTTGATG |
| AACTCGAATTAG | ATGAATTCCGGTTGTAC | AACTCGAATTAG |
| ACCCCCCCGAGA | ATTTACCTCGCCACATT | ACCCCCCCGAGA |
| TTGAACCGGGTG | TAGCCCAGCGTGTTGCA | TTGAACCGGGTG |
| TCTTGAAAGTAC | AGCACAGTGTATCAGAA | TCTTGAAAGTAC |
| TTCGGACAGAGA | TTGTGAACATGCAGATA | TTCGGACAGAGA |
| AACAATACTTGG | ACTACACCGCATATTGT | AACAATACTTGG |
| GTGTGTACATTT | CTGGGAATATCTCATAT | GTGTGTACATTT |
| GGAACATGCGCG | GGAGCCTAGCTTTGGTC | GGAACATGCGCG |
| GCTCCGATGGTA | TAATCTTACACGACGGG | GCTCCGATGGTA |
| CGTCTACCTACG | GGCACCACGTTAAAGTT | CGTCTACCTACG |
| CCACGTTTTTGG | TGTAGATACACCCGAGA | CCACGTTTTTGG |
| TCACCTGGAAAG | GTTTGTCGGGATTATAC | TCACCTGGAAAG |
| GGGATGAGAAGA | GTTTTTGTGGTGTATTT | GGGATGAGAAGA |
| CAAGAAACCCTA | TAACGGGCATGTTGAAG | CAAGAAACCCTA |
| CGCCCGCAGTAA | CCGTAGCATACACTGTT | CGCCCGCAGTAA |
| CTCCTCAACCAA | GTATCCACAGTAGATCA | CTCCTCAACCAA |
| GAGGGGCTGAGT | TTTTGTAAACGCAATTG | GAGGGGCTGAGT |
| TTCATATGTGGA | AAGAGCGTGGATTTCCG | TTCATATGTGGA |
| ATTACCACTCGC | CCAACGGCCGGTCAGCC | ATTACCACTCGC |
| ATGTATTTTCAG | ACCGGCGACTACTAAAC | ATGTATTTTCAG |
| TTGGTGATACGT | CCAAGGAAATTACCCCC | TTGGTGATACGT |
| TTAGCTTGGCAA | GTAAACCCCGGAACGTC | TTAGCTTGGCAA |
| TGCATCTTCAGT | ACCACTTCTACGTATATG | TGCATCTTCAGT |
| ATAAGATACATG | CCGCATGGACCGGAGGG | ATAAGATACATG |
| AAGCGCCATTTG | CTTGCAGCAGTAGTACT | AAGCGCCATTTG |
| ATTTGCTGTTAG | TTTATGTCTCGTAATAT | ATTTGCTGTTAG |
| AGTGGTTGTATG | TTTTAATCTGTACGGCT | AGTGGTTGTATG |
| TCCCCATCGATC | AAACGAATGAGGGTTAA | TCCCCATCGATC |
| CTACATGTCAAC | AGCCGCCAGGGTAGACA | CTACATGTCAAC |
| CAATGCGGTTAT | AG | CAATGCGGTTAT |
| ATTCTACGTGTT | | ATTCTACGTGTT |
| TGTATCATCCCA | | TGTATCATCCCA |
| ACGCACCCCAAT | | ACGCACCCCAAT |
| GCCTCTCTCATA | | GCCTCTCTCATA |
| TGAATTCCGGTT | | TGAATTCCGGTT |
| GTACATTTACCT | | GTACATTTACCT |
| CGCCACATTTAG | | CGCCACATTTAG |
| CCCAGCGTGTTG | | CCCAGCGTGTTG |
| CAAGCACAGTGT | | CAAGCACAGTGT |
| ATCAGAATTGTG | | ATCAGAATTGTG |
| AACATGCAGATA | | AACATGCAGATA |
| ACTACACCGCAT | | ACTACACCGCAT |
| ATTGTCTGGGAA | | ATTGTCTGGGAA |
| TATCTCATATGG | | TATCTCATATGG |
| AGCCTAGCTTTG | | AGCCTAGCTTTG |
| GTCTAATCTTAC | | GTCTAATCTTAC |
| ACGACGGGGGCA | | ACGACGGGGGCA |
| CCACGTTAAAGT | | CCACGTTAAAGT |
| TTGTAGATACAC | | TTGTAGATACAC |
| CCGAGAGTTTGT | | CCGAGAGTTTGT |
| CGGGATTATACG | | CGGGATTATACG |
| TTTTTGTGGTGT | | TTTTTGTGGTGT |
| ATTTTAACGGGC | | ATTTTAACGGGC |
| ATGTTGAAGCCG | | ATGTTGAAGCCG |
| TAGCATACACTG | | TAGCATACACTG |
| TTGTATCCACAG | | TTGTATCCACAG |
| TAGATCATTTTG | | TAGATCATTTTG |
| TAAACGCAATTG | | TAAACGCAATTG |
| AAGAGCGTGGAT | | AAGAGCGTGGAT |
| TTCCGCCAACGG | | TTCCGCCAACGG |
| CCGGTCAGCCAC | | CCGGTCAGCCAC |
| CGGCGACTACTA | | CGGCGACTACTA |
| AACCCAAGGAAA | | AACCCAAGGAAA |
| TTACCCCCGTAA | | TTACCCCCGTAA |
| ACCCCGGAACGT | | ACCCCGGAACGT |
| CACCACTTCTAC | | CACCACTTCTAC |
| GATATGCCGCAT | | GATATGCCGCAT |
| GGACCGGAGGGC | | GGACCGGAGGGC |
| TTGCAGCAGTAG | | TTGCAGCAGTAG |
| TACTTTTATGTC | | TACTTTTATGTC |
| TCGTAATATTTT | | TCGTAATATTTT |

| | |
|---|---|
| TAATCTGTACGG | TAATCTGTACGG |
| CTAAACGAATGA | CTAAACGAATGA |
| GGGTTAAAGCCG | GGGTTAAAGCCG |
| CCAGGGTAGACA | CCAGGGTAGACA |
| AGTGATAATAGG | AGTGATAATAGG |
| CTGGAGCCTCGG | CTGGAGCCTCGG |
| TGGCCATGCTTC | TGGCCATGCTTC |
| TTGCCCCTTGGG | TTGCCCCTTGGG |
| CCTCCCCCCAGC | CCTCCCCCCAGC |
| CCCTCCTCCCCT | CCCTCCTCCCCT |
| TCCTGCACCCGT | TCCTGCACCCGT |
| ACCCCGTGGTC | ACCCCGTGGTC |
| TTTGAATAAAGT | TTTGAATAAAGT |
| CTGAGTGGGCGG | CTGAGTGGGCGG |
| C | CAAAAAAAAAAA |
| | AAAAAAAAAAAA |
| | AAAAAAAAAAAA |
| | AAAAAAAAAAAA |
| | AAAAAAAAAAAA |
| | AAAAAAAAAAAA |
| | AAAAAAAAAAAA |
| | AAAAAAAAAAAA |
| | AAAAATCTAG |

|  | SEQ ID NO: 84 | SEQ ID NO: 85 | SEQ ID NO: 86 | SEQ ID NO: 87 |
|---|---|---|---|---|
| VZV-GE-<br>truncated-<br>delete_from_574_-_Y569A<br>Variant 7 | GGGAAATAAGAG | MGTVNKPVVGVLMGFGI | ATGGGGACAGTTAATAA | GGGAAATAAGAG |
| | AGAAAAGAAGAG | ITGTLRITNPVRASVLR | ACCTGTGGTGGGGGTAT | AGAAAAGAAGAG |
| | TAAGAAGAAATA | YDDFHIDEDKLDTNSVY | TGATGGGGGTTCGGAATT | TAAGAAGAAATA |
| | TAAGAGCCACCA | EPYYHSDHAESSWVNRG | ATCACGGGAACGTTGCG | TAAGAGCCACCA |
| | TGGGGACAGTTA | ESSRKAYDHNSPYIWPR | TATAACGAATCCGGTCA | TGGGGACAGTTA |
| | ATAAACCTGTGG | NDYDGFLENAHEHHGVY | GAGCATCCGTCTTGCGA | ATAAACCTGTGG |
| | TGGGGGTATTGA | NQGRGIDSGERLMQPTQ | TACGATGATTTTCACAT | TGGGGGTATTGA |
| | TGGGGTTCGGAA | MSAQEDLGDDTGIHVIP | CGATGAAGACAAACTGG | TGGGGTTCGGAA |
| | TTATCACGGGAA | TLNGDDRHKIVNVDQRQ | ATACAAACTCCGGTATAT | TTATCACGGGAA |
| | CGTTGCGTATAA | YGDVFKGDLNPKPQGQR | GAGCCTTACTACCATTC | CGTTGCGTATAA |
| | CGAATCCGGTCA | LIEVSVEENHPFTLRAP | AGATCATGCGGAGTCTT | CGAATCCGGTCA |
| | GAGCATCCGTCT | IQRIYGVRYTETWSFLP | CATGGGTAAATCGGGGA | GAGCATCCGTCT |
| | TGCGATACGATG | SLTCTGDAAPAIQHICL | GAGTCTTCGCGAAAAGC | TGCGATACGATG |
| | ATTTTCACATCG | KHTTCFQDVVVDVDCAE | GTACGATCATAACTCAC | ATTTTCACATCG |
| | ATGAAGACAAAC | NTKEDQLAEISYRFQGK | CTTATATATGGCCACGT | ATGAAGACAAAC |
| | TGGATACAAACT | KEADQPWIVVNTSTLFD | AATGATTATGATGGATT | TGGATACAAACT |
| | CCGTATATGAGC | ELELDPPEIEPGVLKVL | TTTAGAGAACGCACACG | CCGTATATGAGC |
| | CTTACTACCATT | RTEKQYLGVYIWNMRGS | AACACCATGGGGTGTAT | CTTACTACCATT |
| | CAGATCATGCGG | DGTSTYATFLVTWKGDE | AATCAGGGCCGTGGTAT | CAGATCATGCGG |
| | AGTCTTCATGGG | KTRNPTPAVTPQPRGAE | CGATAGCGGGGAACGGT | AGTCTTCATGGG |
| | TAAATCGGGGAG | FHMWNYHSHVFSVGDTF | TAATGCAACCCACACAA | TAAATCGGGGAG |
| | AGTCTTCGCGAA | SLAMHLQYKIHEAPFDL | ATGTCTGCACAGGAGGA | AGTCTTCGCGAA |
| | AAGCGTACGATC | LLEWLYVPIDPTCQPMR | TCTTGGGGACGATACGG | AAGCGTACGATC |
| | ATAACTCACCTT | LYSTCLYHPNAPQCLSH | GCATCCACGTTATCCCT | ATAACTCACCTT |
| | ATATATGGCCAC | MNSGCTFTSPHLAQRVA | ACGTTAAACGGCCGATGA | ATATATGGCCAC |
| | GTAATGATTATG | STVYQNCEHADNYTAYC | CAGACATAAAATTGTAA | GTAATGATTATG |
| | ATGGATTTTTAG | LGISHMEPSFGLILHDG | ATGTGGACCAACGTCAA | ATGGATTTTTAG |
| | AGAACGCACACG | GTTLKFVDTPESLSGLY | TACGGTGACGTGTTTAA | AGAACGCACACG |
| | AACACCATGGGG | VFVVYFNGHVEAVAYTV | AGGAGATCTTAATCCAA | AACACCATGGGG |
| | TGTATAATCAGG | VSTVDHFVNAIEERGFP | AACCCCAAGGCCAAGA | TGTATAATCAGG |
| | GCCGTGGTATCG | PTAGQPPATTKPKEITP | CTCATTGAGGTGTCAGT | GCCGTGGTATCG |
| | ATAGCGGGGAAC | VNPGTSPLLRYAAWTGG | GGAAGAAAATCACCCGT | ATAGCGGGGAAC |
| | GGTTAATGCAAC | LAAVVLLCLVIFLICTA | TTACTTTACGCGCACCG | GGTTAATGCAAC |
| | CCACACAAATGT | KRMRVKAARVDK | ATTCAGCGGATTTATGG | CCACACAAATGT |
| | CTGCACAGGAGG | | AGTCCGGTACACCGAGA | CTGCACAGGAGG |
| | ATCTTGGGGACG | | CTTGGAGCTTTTTGCCG | ATCTTGGGGACG |
| | ATACGGGCATCC | | TCATTAACCTGTACGGG | ATACGGGCATCC |
| | ACGTTATCCCTA | | AGACGCAGCGCCCGCCA | ACGTTATCCCTA |
| | CGTTAAACGGCG | | TCCAGCATATATGTTTA | CGTTAAACGGCG |
| | ATGACAGACATA | | AAGCATACAACATGCTT | ATGACAGACATA |
| | AAATTGTAAATG | | TCAAGACGTGGTGGTGG | AAATTGTAAATG |
| | TGGACCAACGTC | | ATGTGGATTGCGCGGAA | TGGACCAACGTC |
| | AATACGGTGACG | | AATACTAAAGAGGATCA | AATACGGTGACG |
| | TGTTTAAAGGAG | | GTTGGCCGAAATCAGTT | TGTTTAAAGGAG |
| | ATCTTAATCCAA | | ACCGTTTTCAAGGTAAG | ATCTTAATCCAA |
| | AACCCCAAGGCC | | AAGGAAGCGGACCAACC | AACCCCAAGGCC |
| | AAAGACTCATTG | | GTGGATTGTTGTAAACA | AAAGACTCATTG |
| | AGGTGTCAGTGG | | CGAGCACACTGTTTGAT | AGGTGTCAGTGG |
| | AAGAAAATCACC | | GAACTCGAATTAGACCC | AAGAAAATCACC |
| | CGTTTACTTTAC | | ACCCGAGATTGAACCGG | CGTTTACTTTAC |
| | GCGCACCGATTC | | GTGTCTTGAAAGTACTT | GCGCACCGATTC |
| | AGCGGATTTATG | | CGGACAGAGAAACAATA | AGCGGATTTATG |
| | GAGTCCGGTACA | | CTTGGGTGTGTACATTT | GAGTCCGGTACA |
| | CCGAGACTTGGA | | GGAACATGCGCGGCTCC | CCGAGACTTGGA |
| | GCTTTTTGCCGT | | GATGGTACGTCTACCTA | GCTTTTTGCCGT |

TABLE 2-continued

| | | |
|---|---|---|
| CATTAACCTGTA | CGCCACGTTTTTGGTCA | CATTAACCTGTA |
| CGGGAGACGCAG | CCTGGAAAGGGGATGAG | CGGGAGACGCAG |
| CGCCCGCCATCC | AAGACAAGAAACCCTAC | CGCCCGCCATCC |
| AGCATATATGTT | GCCCGCAGTAACTCCTC | AGCATATATGTT |
| TAAAGCATACAA | AACCAAGAGGGGCTGAG | TAAAGCATACAA |
| CATGCTTTCAAG | TTTCATATGTGGAATTA | CATGCTTTCAAG |
| ACGTGGTGGTGG | CCACTCGCATGTATTTT | ACGTGGTGGTGG |
| ATGTGGATTGCG | CAGTTGGTGATACGTTT | ATGTGGATTGCG |
| CGGAAAATACTA | AGCTTGGCAATGCATCT | CGGAAAATACTA |
| AAGAGGATCAGT | TCAGTATAAGATACATG | AAGAGGATCAGT |
| TGGCCGAAATCA | AAGCGCCATTTGATTTG | TGGCCGAAATCA |
| GTTACCGTTTTC | CTGTTAGAGTGGTTGTA | GTTACCGTTTTC |
| AAGGTAAGAAGG | TGTCCCCATCGATCCTA | AAGGTAAGAAGG |
| AAGCGGACCAAC | CATGTCAACCAATGCGG | AAGCGGACCAAC |
| CGTGGATTGTTG | TTATATTCTACGTGTTT | CGTGGATTGTTG |
| TAAACACGAGCA | GTATCATCCCAACGCAC | TAAACACGAGCA |
| CACTGTTTGATG | CCCAATGCCTCTCTCAT | CACTGTTTGATG |
| AACTCGAATTAG | ATGAATTCCGGTTGTAC | AACTCGAATTAG |
| ACCCACCCGAGA | ATTTACCTCGCCACATT | ACCCACCCGAGA |
| TTGAACCGGGTG | TAGCCCAGCGTGTTGCA | TTGAACCGGGTG |
| TCTTGAAAGTAC | AGCACAGTGTATCAGAA | TCTTGAAAGTAC |
| TTCGGACAGAGA | TTGTGAACATGCAGATA | TTCGGACAGAGA |
| AACAATACTTGG | ACTACACCGCATATTGT | AACAATACTTGG |
| GTGTGTACATTT | CTGGGAATATCTCATAT | GTGTGTACATTT |
| GGAACATGCGCG | GGAGCCTAGCTTTGGTC | GGAACATGCGCG |
| GCTCCGATGGTA | TAATCTTACACGACGGG | GCTCCGATGGTA |
| CGTCTACCTACG | GGCACCACGTTAAAGTT | CGTCTACCTACG |
| CCACGTTTTTGG | TGTAGATACACCCGAGA | CCACGTTTTTGG |
| TCACCTGGAAAG | GTTTGTCGGGATTATAC | TCACCTGGAAAG |
| GGGATGAGAAGA | GTTTTTGTGGTGTATTT | GGGATGAGAAGA |
| CAAGAAACCCTA | TAACGGGCATGTTGAAG | CAAGAAACCCTA |
| CGCCCGCAGTAA | CCGTAGCATACACTGTT | CGCCCGCAGTAA |
| CTCCTCAACCAA | GTATCCACAGTAGATCA | CTCCTCAACCAA |
| GAGGGGCTGAGT | TTTTGTAAACGCAATTG | GAGGGGCTGAGT |
| TTCATATGTGGA | AAGAGCGTGGATTCCG | TTCATATGTGGA |
| ATTACCACTCGC | CCAACGGCCGGTCAGCC | ATTACCACTCGC |
| ATGTATTTTCAG | ACCGGCGACTACTAAAC | ATGTATTTTCAG |
| TTGGTGATACGT | CCAAGGAAATTACCCCC | TTGGTGATACGT |
| TTAGCTTGGCAA | GTAAACCCCGGAACGTC | TTAGCTTGGCAA |
| TGCATCTTCAGT | ACCACTTCTACGATATG | TGCATCTTCAGT |
| ATAAGATACATG | CCGCATGGACCGGAGGG | ATAAGATACATG |
| AAGCGCCATTTG | CTTGCAGCAGTAGTACT | AAGCGCCATTTG |
| ATTTGCTGTTAG | TTTATGTCTCGTAATAT | ATTTGCTGTTAG |
| AGTGGTTGTATG | TTTTAATCTGTACGGCT | AGTGGTTGTATG |
| TCCCCATCGATC | AAACGAATGAGGGTTAA | TCCCCATCGATC |
| CTACATGTCAAC | AGCCGCCAGGGTAGACA | CTACATGTCAAC |
| CAATGCGGTTAT | AG | CAATGCGGTTAT |
| ATTCTACGTGTT | | ATTCTACGTGTT |
| TGTATCATCCCA | | TGTATCATCCCA |
| ACGCACCCCAAT | | ACGCACCCCAAT |
| GCCTCTCTCATA | | GCCTCTCTCATA |
| TGAATTCCGGTT | | TGAATTCCGGTT |
| GTACATTTACCT | | GTACATTTACCT |
| CGCCACATTTAG | | CGCCACATTTAG |
| CCCAGCGTGTTG | | CCCAGCGTGTTG |
| CAAGCACAGTGT | | CAAGCACAGTGT |
| ATCAGAATTGTG | | ATCAGAATTGTG |
| AACATGCAGATA | | AACATGCAGATA |
| ACTACACCGCAT | | ACTACACCGCAT |
| ATTGTCTGGGAA | | ATTGTCTGGGAA |
| TATCTCATATGG | | TATCTCATATGG |
| AGCCTAGCTTTG | | AGCCTAGCTTTG |
| GTCTAATCTTAC | | GTCTAATCTTAC |
| ACGACGGGGCA | | ACGACGGGGCA |
| CCACGTTAAAGT | | CCACGTTAAAGT |
| TTGTAGATACAC | | TTGTAGATACAC |
| CCGAGAGTTTGT | | CCGAGAGTTTGT |
| CGGGATTATACG | | CGGGATTATACG |
| TTTTTGTGGTGT | | TTTTTGTGGTGT |
| ATTTTAACGGGC | | ATTTTAACGGGC |
| ATGTTGAAGCCG | | ATGTTGAAGCCG |
| TAGCATACACTG | | TAGCATACACTG |
| TTGTATCCACAG | | TTGTATCCACAG |
| TAGATCATTTTG | | TAGATCATTTTG |
| TAAACGCAATTG | | TAAACGCAATTG |
| AAGAGCGTGGAT | | AAGAGCGTGGAT |
| TTCCGCCAACGG | | TTCCGCCAACGG |
| CCGGTCAGCCAC | | CCGGTCAGCCAC |
| CGGCGACTACTA | | CGGCGACTACTA |
| AACCCAAGGAAA | | AACCCAAGGAAA |

TABLE 2-continued

| | | | |
|---|---|---|---|
| TTACCCCCGTAA | | | TTACCCCCGTAA |
| ACCCCGGAACGT | | | ACCCCGGAACGT |
| CACCACTTCTAC | | | CACCACTTCTAC |
| GATATGCCGCAT | | | GATATGCCGCAT |
| GGACCGGAGGGC | | | GGACCGGAGGGC |
| TTGCAGCAGTAG | | | TTGCAGCAGTAG |
| TACTTTTATGTC | | | TACTTTTATGTC |
| TCGTAATATTTT | | | TCGTAATATTTT |
| TAATCTGTACGG | | | TAATCTGTACGG |
| CTAAACGAATGA | | | CTAAACGAATGA |
| GGGTTAAAGCCG | | | GGGTTAAAGCCG |
| CCAGGGTAGACA | | | CCAGGGTAGACA |
| AGTGATAATAGG | | | AGTGATAATAGG |
| CTGGAGCCTCGG | | | CTGGAGCCTCGG |
| TGGCCATGCTTC | | | TGGCCATGCTTC |
| TTGCCCCTTGGG | | | TTGCCCCTTGGG |
| CCTCCCCCCAGC | | | CCTCCCCCCAGC |
| CCCTCCTCCCCT | | | CCCTCCTCCCCT |
| TCCTGCACCCGT | | | TCCTGCACCCGT |
| ACCCCCGTGGTC | | | ACCCCCGTGGTC |
| TTTGAATAAAGT | | | TTTGAATAAAGT |
| CTGAGTGGGCGG | | | CTGAGTGGGCGG |
| C | | | CAAAAAAAAAAA |
| | | | AAAAAAAAAAAA |
| | | | AAAAAAAAAAAA |
| | | | AAAAAAAAAAAA |
| | | | AAAAAAAAAAAA |
| | | | AAAAAAAAAAAA |
| | | | AAAAAAAAAAAA |
| | | | AAAAAAAAAAAA |
| | | | AAAAATCTAG |

| | SEQ ID NO: 88 | SEQ ID NO: 89 | SEQ ID NO: 90 | SEQ ID NO: 91 |
|---|---|---|---|---|
| VZV-GE-truncated-delete_from_574_-_Y569A Variant 8 | GGGAAATAAGAG | MGTVNKPVVGVLMGFGI | ATGGGGACAGTTAATAA | GGGAAATAAGAG |
| | AGAAAAGAAGAG | ITGTLRITNPVRASVLR | ACCTGTGGTGGGCGTAT | AGAAAAGAAGAG |
| | TAAGAAGAAATA | YDDFHIDEDKLDTNSVY | TGATGGGGTTCGGAATT | TAAGAAGAAATA |
| | TAAGAGCCACCA | EPYYHSDHAESSWVNRG | ATCACGGGAACGTTGCG | TAAGAGCCACCA |
| | TGGGGACAGTTA | ESSRKAYDHNSPYIWPR | TATAACGAATCCGGTCA | TGGGGACAGTTA |
| | ATAAACCTGTGG | NDYDGFLENAHEHHGVY | GAGCATCCGTCTTGCGA | ATAAACCTGTGG |
| | TGGGCGTATTGA | NQGRGIDSGERLMQPTQ | TACGATGATTTTCACAT | TGGGCGTATTGA |
| | TGGGGTTCGGAA | MSAQEDLGDDTGIHVIP | CGATGAAGACAAACTGG | TGGGGTTCGGAA |
| | TTATCACGGGAA | TLNGDDRHKIVNVDQRQ | ATACAAACTCCGTATAT | TTATCACGGGAA |
| | CGTTGCGTATAA | YGDVFKGDLNPKPQGQR | GAGCCTTACTACCATTC | CGTTGCGTATAA |
| | CGAATCCGGTCA | LIEVSVEENHPFTLRAP | AGATCATGCGGAGTCTT | CGAATCCGGTCA |
| | GAGCATCCGTCT | IQRIYGVRYTETWSFLP | CATGGGTAAATCGGGGA | GAGCATCCGTCT |
| | TGCGATACGATG | SLTCTGDAAPAIQHICL | GAGTCTTCGCGAAAGGC | TGCGATACGATG |
| | ATTTTCACATCG | KHTTCFQDVVVDVDCAE | GTACGATCATAACTCAC | ATTTTCACATCG |
| | ATGAAGACAAAC | NTKEDQLAEISYRFQGK | CTTATATATGGCCACGT | ATGAAGACAAAC |
| | TGGATACAAACT | KEADQPWIVVNTSTLFD | AATGATTATGATGGATT | TGGATACAAACT |
| | CCGTATATGAGC | ELELDPPEIEPGVLKVL | CTTAGAGAACGCACACG | CCGTATATGAGC |
| | CTTACTACCATT | RTEKQYLGVYIWNMRGS | AACACCATGGGGTGTAT | CTTACTACCATT |
| | CAGATCATGCGG | DGTSTYATFLVTWKGDE | AATCAGGGCCGTGGTAT | CAGATCATGCGG |
| | AGTCTTCATGGG | KTRNPTPAVTPQPRGAE | CGATAGCGGGGAACGGT | AGTCTTCATGGG |
| | TAAATCGGGGAG | FHMWNYHSHVFSVGDTF | TAATGCAACCCACACAA | TAAATCGGGGAG |
| | AGTCTTCGCGAA | SLAMHLQYKIHEAPFDL | ATGCTGCACAGGAGGA | AGTCTTCGCGAA |
| | AGGCGTACGATC | LLEWLYVPIDPTCQPMR | TCTTGGGGACGATACGG | AGGCGTACGATC |
| | ATAACTCACCTT | LYSTCLYHPNAPQCLSH | GCATCCACGTTATCCCT | ATAACTCACCTT |
| | ATATATGGCCAC | MNSGCTFTSPHLAQRVA | ACGTTAAACGGCGATGA | ATATATGGCCAC |
| | GTAATGATTATG | STVYQNCEHADNYTAYC | CAGACATAAGATTGTAA | GTAATGATTATG |
| | ATGGATTCTTAG | LGISHMEPSFGLILHDG | ATGTGGACCAACGTCAA | ATGGATTCTTAG |
| | AGAACGCACACG | GTTLKFVDTPESLSGLY | TACGGTGACGTGTTTAA | AGAACGCACACG |
| | AACACCATGGGG | VFVVYFNGHVEAVAYTV | AGGAGATCTTAATCCAA | AACACCATGGGG |
| | TGTATAATCAGG | VSTVDHFVNAIEERGFP | AGCCCCAAGGCCAAAGA | TGTATAATCAGG |
| | GCCGTGGTATCG | PTAGQPPATTKPKEITP | CTCATTGAGGTGTCAGT | GCCGTGGTATCG |
| | ATAGCGGGGAAC | VNPGTSPLLRYAAWTGG | GGAAGAGAATCACCCGT | ATAGCGGGGAAC |
| | GGTTAATGCAAC | LAAVVLLCLVIFLICTA | TTACTTTACGCGCACCG | GGTTAATGCAAC |
| | CCACACAAATGT | KRMRVKAARVDK | ATTCAGCGGATTTATGG | CCACACAAATGT |
| | CTGCACAGGAGG | | AGTCCGGTACACCGAGA | CTGCACAGGAGG |
| | ATCTTGGGGACG | | CTTGGAGCTTCTTGCCG | ATCTTGGGGACG |
| | ATACGGGCATCC | | TCATTAACCTGTACGGG | ATACGGGCATCC |
| | ACGTTATCCCTA | | AGACGCAGCGCCCGCCA | ACGTTATCCCTA |
| | CGTTAAACGGCG | | TCCAGCATATATGTTTA | CGTTAAACGGCG |
| | ATGACAGACATA | | AAGCATACAACATGCTT | ATGACAGACATA |
| | AGATTGTAAATG | | TCAAGACGTGGTGGTGG | AGATTGTAAATG |
| | TGGACCAACGTC | | ATGTGGATTGCGCGGAG | TGGACCAACGTC |
| | AATACGGTGACG | | AATACTAAAGAGGATCA | AATACGGTGACG |
| | TGTTTAAAGGAG | | GTTGGCCGAAATCAGTT | TGTTTAAAGGAG |
| | ATCTTAATCCAA | | ACCGTTTTCAAGGTAAG | ATCTTAATCCAA |
| | AGCCCCAAGGCC | | AAGGAAGCGGACCAACC | AGCCCCAAGGCC |
| | AAAGACTCATTG | | GTGGATTGTTGTAAACA | AAAGACTCATTG |

TABLE 2-continued

| | | |
|---|---|---|
| AGGTGTCAGTGG | CGAGCACACTGTTTGAT | AGGTGTCAGTGG |
| AAGAGAATCACC | GAACTCGAATTAGACCC | AAGAGAATCACC |
| CGTTTACTTTAC | ACCCGAGATTGAACCGG | CGTTTACTTTAC |
| GCGCACCGATTC | GTGTCTTGAAAGTACTT | GCGCACCGATTC |
| AGCGGATTTATG | CGGACAGAGAAACAATA | AGCGGATTTATG |
| GAGTCCGGTACA | CTTGGGTGTGTACATTT | GAGTCCGGTACA |
| CCGAGACTTGGA | GGAACATGCGCGGCTCC | CCGAGACTTGGA |
| GCTTCTTGCCGT | GATGGTACGTCTACCTA | GCTTCTTGCCGT |
| CATTAACCTGTA | CGCCACGTTCTTGGTCA | CATTAACCTGTA |
| CGGGAGACGCAG | CCTGGAAAGGGGATGAG | CGGGAGACGCAG |
| CGCCCGCCATCC | AAGACAAGAAACCCTAC | CGCCCGCCATCC |
| AGCATATATGTT | GCCCGCAGTAACTCCTC | AGCATATATGTT |
| TAAAGCATACAA | AACCAAGAGGGGCTGAG | TAAAGCATACAA |
| CATGCTTTCAAG | TTTCATATGTGGAATTA | CATGCTTTCAAG |
| ACGTGGTGGTGG | CCACTCGCATGTATTTT | ACGTGGTGGTGG |
| ATGTGGATTGCG | CAGTTGGTGATACGTTT | ATGTGGATTGCG |
| CGGAGAATACTA | AGCTTGGCAATGCATCT | CGGAGAATACTA |
| AAGAGGATCAGT | TCAGTATAAGATACATG | AAGAGGATCAGT |
| TGGCCGAAATCA | AAGCGCCATTTGATTTG | TGGCCGAAATCA |
| GTTACCGTTTTC | CTGTTAGAGTGGTTGTA | GTTACCGTTTTC |
| AAGGTAAGAAGG | TGTCCCCATCGATCCTA | AAGGTAAGAAGG |
| AAGCGGACCAAC | CATGTCAACCAATGCGG | AAGCGGACCAAC |
| CGTGGATTGTTG | TTATATTCTACGTGTTT | CGTGGATTGTTG |
| TAAACACGAGCA | GTATCATCCCAACGCAC | TAAACACGAGCA |
| CACTGTTTGATG | CCCAATGCCTCTCTCAT | CACTGTTTGATG |
| AACTCGAATTAG | ATGAATTCCGGTTGTAC | AACTCGAATTAG |
| ACCCACCCGAGA | ATTTACCTCGCCACATT | ACCCACCCGAGA |
| TTGAACCGGGTG | TAGCCCAGCGTGTTGCA | TTGAACCGGGTG |
| TCTTGAAAGTAC | AGCACAGTGTATCAGAA | TCTTGAAAGTAC |
| TTCGGACAGAGA | TTGTGAACATGCAGATA | TTCGGACAGAGA |
| AACAATACTTGG | ACTACACCGCATATTGT | AACAATACTTGG |
| GTGTGTACATTT | CTGGGAATATCTCATAT | GTGTGTACATTT |
| GGAACATGCGCG | GGAGCCTAGCTTTGGTC | GGAACATGCGCG |
| GCTCCGATGGTA | TAATCTTACACGACGGA | GCTCCGATGGTA |
| CGTCTACCTACG | GGCACCACGTTAAAGTT | CGTCTACCTACG |
| CCACGTTCTTGG | TGTAGATACACCCGAGA | CCACGTTCTTGG |
| TCACCTGGAAAG | GTTTGTCGGGATTATAC | TCACCTGGAAAG |
| GGGATGAGAAGA | GTCTTTGTGGTGTATTT | GGGATGAGAAGA |
| CAAGAAACCCTA | TAACGGGCATGTTGAAG | CAAGAAACCCTA |
| CGCCCGCAGTAA | CCGTAGCATACACTGTT | CGCCCGCAGTAA |
| CTCCTCAACCAA | GTATCCACAGTAGATCA | CTCCTCAACCAA |
| GAGGGGCTGAGT | TTTTGTAAACGCAATTG | GAGGGGCTGAGT |
| TTCATATGTGGA | AAGAGCGTGGATTTCCG | TTCATATGTGGA |
| ATTACCACTCGC | CCAACGGCCGGTCAGCC | ATTACCACTCGC |
| ATGTATTTTCAG | ACCGGCGACTACTAAAC | ATGTATTTTCAG |
| TTGGTGATACGT | CCAAGGAAATTACGCCC | TTGGTGATACGT |
| TTAGCTTGGCAA | GTAAACCCCGGAACGTC | TTAGCTTGGCAA |
| TGCATCTTCAGT | ACCACTTCTACGATATG | TGCATCTTCAGT |
| ATAAGATACATG | CCGCATGGACCGGAGGG | ATAAGATACATG |
| AAGCGCCATTTG | CTTGCAGCAGTAGTACT | AAGCGCCATTTG |
| ATTTGCTGTTAG | TTTATGTCTCGTAATAT | ATTTGCTGTTAG |
| AGTGGTTGTATG | TCTTAATCGTACGGCT | AGTGGTTGTATG |
| TCCCCATCGATC | AAACGAATGAGGGTTAA | TCCCCATCGATC |
| CTACATGTCAAC | AGCCGCCAGGGTAGACA | CTACATGTCAAC |
| CAATGCGGTTAT | AG | CAATGCGGTTAT |
| ATTCTACGTGTT | | ATTCTACGTGTT |
| TGTATCATCCCA | | TGTATCATCCCA |
| ACGCACCCCAAT | | ACGCACCCCAAT |
| GCCTCTCTCATA | | GCCTCTCTCATA |
| TGAATTCCGGTT | | TGAATTCCGGTT |
| GTACATTTACCT | | GTACATTTACCT |
| CGCCACATTTAG | | CGCCACATTTAG |
| CCCAGCGTGTTG | | CCCAGCGTGTTG |
| CAAGCACAGTGT | | CAAGCACAGTGT |
| ATCAGAATTGTG | | ATCAGAATTGTG |
| AACATGCAGATA | | AACATGCAGATA |
| ACTACACCGCAT | | ACTACACCGCAT |
| ATTGTCTGGGAA | | ATTGTCTGGGAA |
| TATCTCATATGG | | TATCTCATATGG |
| AGCCTAGCTTTG | | AGCCTAGCTTTG |
| GTCTAATCTTAC | | GTCTAATCTTAC |
| ACGACGGAGGCA | | ACGACGGAGGCA |
| CCACGTTAAAGT | | CCACGTTAAAGT |
| TTGTAGATACAC | | TTGTAGATACAC |
| CCGAGAGTTTGT | | CCGAGAGTTTGT |
| CGGGATTATACG | | CGGGATTATACG |
| TCTTTGTGGTGT | | TCTTTGTGGTGT |
| ATTTTAACGGGC | | ATTTTAACGGGC |
| ATGTTGAAGCCG | | ATGTTGAAGCCG |
| TAGCATACACTG | | TAGCATACACTG |

TABLE 2-continued

| | |
|---|---|
| TTGTATCCACAG | TTGTATCCACAG |
| TAGATCATTTTG | TAGATCATTTTG |
| TAAACGCAATTG | TAAACGCAATTG |
| AAGAGCGTGGAT | AAGAGCGTGGAT |
| TTCCGCCAACGG | TTCCGCCAACGG |
| CCGGTCAGCCAC | CCGGTCAGCCAC |
| CGGCGACTACTA | CGGCGACTACTA |
| AACCCAAGGAAA | AACCCAAGGAAA |
| TTACGCCCGTAA | TTACGCCCGTAA |
| ACCCCGGAACGT | ACCCCGGAACGT |
| CACCACTTCTAC | CACCACTTCTAC |
| GATATGCCGCAT | GATATGCCGCAT |
| GGACCGGAGGGC | GGACCGGAGGGC |
| TTGCAGCAGTAG | TTGCAGCAGTAG |
| TACTTTTATGTC | TACTTTTATGTC |
| TCGTAATATTCT | TCGTAATATTCT |
| TAATCTGTACGG | TAATCTGTACGG |
| CTAAACGAATGA | CTAAACGAATGA |
| GGGTTAAAGCCG | GGGTTAAAGCCG |
| CCAGGGTAGACA | CCAGGGTAGACA |
| AGTGATAATAGG | AGTGATAATAGG |
| CTGGAGCCTCGG | CTGGAGCCTCGG |
| TGGCCATGCTTC | TGGCCATGCTTC |
| TTGCCCCTTGGG | TTGCCCCTTGGG |
| CCTCCCCCCAGC | CCTCCCCCCAGC |
| CCCTCCTCCCCT | CCCTCCTCCCCT |
| TCCTGCACCCGT | TCCTGCACCCGT |
| ACCCCCGTGGTC | ACCCCCGTGGTC |
| TTTGAATAAAGT | TTTGAATAAAGT |
| CTGAGTGGGCGG | CTGAGTGGGCGG |
| C | CAAAAAAAAAAA |
| | AAAAAAAAAAAA |
| | AAAAAAAAAAAA |
| | AAAAAAAAAAAA |
| | AAAAAAAAAAAA |
| | AAAAAAAAAAAA |
| | AAAAAAAAAAAA |
| | AAAAAAAAAAAA |
| | AAAAATCTAG |

VZV mRNA Sequences

| mRNA Name(s) | mRNA Sequence (assumes T100 tail) | SEQ ID NO |
|---|---|---|
| VZV_gE_Oka | G*GGGAAAUAAGAGAGAAAAGAAGAGUAAGAAGAAAUAUAAGA<br>GCCACCAUGGGGACAGUGAAUAAGCCGGUUGUGGGCGUGCUUAU<br>GGGCUUUGGGAUUAUUACCGGUACAUUACGAAUUACCAAUCCAG<br>UGCGCGCCAGUGUGCUGCGUUACGACGACUUUCACAUUGACGAG<br>GAUAAGCUGGAUACUAACAGCGUGUACGAACCUUAUUACCACUC<br>AGAUCAUGCCGAAUCAAGCUGGGUUAAUAGAGGAGAAAGCAGC<br>CGAAAAGCCUACGACCACAACUCACCUUAUAUUUGGCCCAGAAA<br>CGAUUAUGACGGUUUCCUGGAAAACGCACAUGAACACCAUGGAG<br>UCUACAACCAAGGCAGGGGAAUCGACAGUGGCGAGCGUCUUAUG<br>CAGCCAACACAGAUGUCGGCACAGGAGGAUCUCGGUGAUGACAC<br>CGGCAUACACGUGAUUCCCACAUUAAACGGCGACGACAGACAUA<br>AGAUCGUCAAUGUGGAUCAGCGUCAGUAUGGGGAUGUCUUUAA<br>AGGCGAUUUGAAUCCAAAGCCCCAAGGACAGAGACUGAUCGAGG<br>UCUCUGUAGAAGAAAAUCACCCCUUCACUUUGCGCGCUCCAAUC<br>CAGAGGAUUUACGGGGUGCGUUAUACCGAAACUUGGAGUUUCU<br>UGCCGUCACUGACGUGUACGGGGGAUGCCGCCCCCGCAAUCCAG<br>CACAUCUGUCUGAAACACACCACAUGCUUUCAGGACGUGGUUGU<br>GGAUGUGGAUUGCGCGGAAAACACAAAAGAAGACCAACUCGCCG<br>AAAUCAGCUAUCGUUUUCAGGGUAAAAAAGAGGCCGACCAACCG<br>UGGAUUGUUGUGAAUACGAGCACGCUCUUCGAUGAGCUUGAAC<br>UCGAUCCCCCGGAAAUCGAGCCUGGGGUUCUAAAAGUGUUGAGG<br>ACCGAGAAGCAGUACCUCGGGGUUUAUAUCUGGAAUAUGAGAG<br>GCUCCGAUGGCACCUCUACCUACGCAACGUUUCUGGUUACCUGG<br>AAGGGAGACGAGAAGACACGGAAUCCAACGCCCGCUGUGACCCC<br>UCAGCCUAGGGGAGCCGAAUUCCACAUGUGGAACUAUCACUCCC<br>AUGUAUUCAGUGUGGGUGACACUUUCAGCCUGGCCAUGCACCUG<br>CAGUAUAAGAUUCACGAGGCACCCUUCGACCUCCUGCUGGAGUG<br>GUUGUACGUACCUAUUGAUCCCACUUGUCAGCCCAUGCGCCUGU<br>ACUCCACUUGCUUGUACCACCCCAAUGCACCACAGUGUCUAUCA<br>CACAUGAACUCCGGGUGUACCUUUACUUCACCCCAUCUUGCCCA<br>GCGGGUCGCCAGCACAGUGUAUCAGAACUGUGAGCAUGCUGACA<br>ACUAUACUGCUUAUUGCCUCGGAAUAUCCCAUAUGGAGCCAAGC<br>UUCGGGCUCAUACUGCACGAUGGUGGUACGACACUCAAGUUCGU<br>GGACACCCCCGAAAGCCUUUCUGGCUUGUACGUGUUCGUGGUCU<br>ACUUCAAUGGACAUGUGGAGGCAGUGGCUUACACAGUGGGUUUC | 92 |

TABLE 2-continued

```
GACAGUUGAUCACUUUGUAAAUGCCAUUGAGGAACGCGGCUUCC
CGCCUACAGCGGGCCAGCCCCCUGCGACAACAAAACCAAAAGAG
AUUACGCCCGUUAAUCCUGGGACUAGUCCAUUGCUGAGGUAUGC
CGCCUGGACUGGCGGUCUGGCGGCCGUGGGUACUUCUGUGUUUAG
UCAUAUUUCUGAUCUGUACCGCUAAACGUAUGCGGGUCAAGGCU
UACCGUGUUGACAAGUCUCCUUACAAUCAGUCAAUGUACUAUGC
AGGACUCCCUGUUGACGAUUUCGAAGACUCAGAGAGUACAGACA
CAGAAGAAGAAUUCGGAAACGCUAUAGGUGGCUCUCACGGAGG
UAGCUCGUAUACAGUGUACAUCGAUAAAACCAGAUGAUAAUAG
GCUGGAGCCUCGGUGGCCAUGCUUCUUGCCCCUUGGGCCUCCCC
CCAGCCCCUCCUCCCCUUCCUGCACCCGUACCCCCGUGGUCUUUG
AAUAAAGUCUGAGUGGGCGGCAAAAAAAAAAAAAAAAAAAAAAAA
AAAAAAAAAAAAAAAAAAAAAAAAAAAAAAAAAAAAAAAAAAA
AAAAAAAAAAAAAAAAAAAAAAAAAAAAAAAAAAAUCUAG
```

VZV_gE_full_indel_fixed

```
G*GGGAAUAAGAGAGAAAAGAAGAGUAAGAAGAAAUAUAAGA
GCCACCAUGGGGACAGUUAAUAAACCUGUGGGUGGGGGUAUUGA
UGGGGUUCGGAAUUAUCACGGGAACGUUGCGUAUAACGAAUCC
GGUCAGAGCAUCCGUCUUGCGAUACGAUGAUUUUCACAUCGAUG
AAGACAAACUGGAUACAAACUCCGUAUAUGAGCCUUACUACCAU
UCAGAUCAUGCGGAGUCUUCAUGGGUAAAUCGGGGAGAGUCUU
CGCGAAAAGCGUACGAUCAUAACUCACCUUAUAUAUGGCCACGU
AAUGAUUAUGAUGGAUUUUUAGAGAACGCACACGAACACCAUG
GGGUGUAUAAUCAGGGCCGUGGUAUCGAUAGCGGGGAACGGUU
AAUGCAACCCACACAAAUGUCUGCACAGGAGGAUCUUGGGGACG
AUACGGGCAUCCACGUUAUCCCUACGUUAAACGGCGAUGACAGA
CAUAAAAUUGUAAAUGUGGACCAACGUCAAUACGGUGACGUGU
UUAAAGGAGAUCUUAAUCCAAAACCCCAAGGCCAAAGACUCAUU
GAGGUGUCAGUGGAAGAAAAUCACCCGUUUUACUUUACGCGCACC
GAUUCAGCGGAUUUAUGGAGUCCGGUACACCGAGACUUGGAGCU
UUUUGCCGUCAUUAACCUGUACGGGAGACGCAGCGCCCGCCAUC
CAGCAUAUAUGUUUAAAGCAUACAACAUGCUUUCAAGACGUGG
UGGUGGAUGUGGAUUGCGCGGAAAAUACUAAAGAGGAUCAGUU
GGCCGAAAUCAGUUACCGUUUUCAAGGUAAGAAGGAAGCGGACC
AACCGUGGAUUGUUGUAAACACGAGCACACUGUUUGAUGAACUC
GAAUUAGACCCACCCGAGAUUGAACCGGGUGUCUUGAAAGUACU
UCGGACAGAGAAACAAUACUUGGGUGUGUACAUUUGGAACAUG
CGCGGCUCCGAUGGUACGUCUACCUACGCCACGUUUUUGGUCAC
CUGGAAAGGGGAUGAGAAGACAAGAAACCCUACGCCCGCAGUAA
CUCCUCAACCAAGAGGGGCUGAGUUUCAUAUGUGGAAUUACCAC
UCGCAUGUAUUUUCAGUUGGUGAUACGUUUAGCUUGGCAAUGC
AUCUUCAGUAUAAGAUACAUGAAGCGCCAUUUGAUUUGCUGUU
AGAGUGGUUGUAUGUCCCCAUCGAUCCUACAUGUCAACCAAUGC
GGUUAUAUUCUACGUGUUUGUAUCAUCCCAACGCCACCCCAAUGC
CUCUCUCAUAUGAAUUCCGGUUGUACAUUUACCUCGCCACAUUU
AGCCCAGCGUGUUGCAAGCACAGUGUAUCAGAAUUGUGAACAUG
CAGAUAACUACACCGCAUAUUGUCUGGGAAUAUCUCAUAUGGAG
CCUAGCUUUGGUCUAAUCUUACACGACGGGGGCCACCACGUUAAA
GUUUGUAGAUACACCCGAGAGUUUGUCGGGAUUAUACGUUUUU
GUGGUGUAUUUUAACGGGCAUGUUGAAGCCGUAGCAUACACUG
UUGUAUCCACAGUAGAUCAUUUUGUAAACGCAAUUGAAGAGCG
UGGAUUUCCGCCAACGGCCGGUCAGCCACCGGCGACUACUAAAC
CCAAGGAAAUUACCCCCGUAAACCCCGGAACGUCACCACUUCUA
CGAUAUGCCGCAUGGACCGGAGGGCUUGCAGCAGUAGUACUUUU
AUGUCUCGUAAUAUUUUUAAUCUGUACGGCUAAACGAAUGAGG
GUUAAAGCCUACAGGGUAGACAAGUCUCCUUACAAUCAGUCAAU
GUACUAUGCAGGACUCCCUGUUGACGAUUUCGAAGACUCAGAGA
GUACAGACACAGAAGAAGAAUUCGGAAACGCUAUAGGUGGCUC
UCACGGAGGUAGCUCGUAUACAGUGUACAUCGAUAAAACCAGA
UGAUAAUAGGCUGGAGCCUCGGUGGCCAUGCUUCUUGCCCCUUG
GGCCUCCCCCAGCCCCUCCUCCCCUUCCUGCACCCGUACCCCCG
UGGUCUUUGAAUAAAGUCUGAGUGGGCGGC
```

VZV_gE_Oka_hIgkappa

```
G*GGGAAUAAGAGAGAAAAGAAGAGUAAGAAGAAAUAUAAGA
GCCACCAUGGAGACUCCCGCUCAGCUACUGUUCCUCCUGCUCCU
UUGGCUGCCUGAUACUACAGGCUCUGUUUUGCGGUACGACGACU
UUCACAUCGAUGAGGACAAGCUCGACACUAAUAGCGUGUAUGAG
CCCUACUACCAUUCAGAUCACGCCGAGUCCUCUUGGGUGAACAG
GGGUGAAAGUUCUAGGAAAGCCUAUGAUCACAACAGCCCUUAUA
UUUGGCCACGGAAUGAUUACGACGGAUUUCUCGAAAAUGCCCAC
GAGCAUCACGGAGUGUACAACCAGGGCCGUGGAAUCGACUCUGG
GGAGAGAUUGAUGCAACCUACACAGAUGAGCGCCCAGGAAGAUC
UCGGGGAUGAUACAGGAAUUCACGUUAUCCCUACAUUAAACGGA
GAUGACCGCCACAAAAUCGUCAAUGUCGAUCAAAGACAGUAUGG
AGAUGUGUUCAAAGGCGAUCUCAACCCUUAAGCCGCAGGGCCAGA
GACUCAUUGAGGGUGUCUGUCGAAGAGAACCACCCUUUCACUCUG
CGCGCUCCCAUUCAGAGAAUCUAUGGAGUUCGCUAUACGGAGAC
UUGGUCAUUCCUUCCUUCCCUGACAUGCACCGGAGACGCCGCCC
CUGCCAUUCAGCACAUAUGCCUGAAACAUACCACCUGUUUCCAG
GAUGUGGUGGUUGAUGUUGAUUGUGCUGAAAAUACCAAGGAAG
```

TABLE 2-continued

```
ACCAACUGGCCGAGAUUAGUUACCGGUUCCAAGGGAAAAAGGAA
GCCGACCAGCCAUGGAUUGUGGUUAAUACAAGCACUCUGUUCGA
UGAGCUCGAGCUGGAUCCCCCCGAGAUAGAACCCGGAGUUCUGA
AAGUGCUCCGGACAGAAAAACAAUAUCUGGGGAGUCUACAUAUG
GAACAUGCGCGGUUCCGAUGGGACCUCCACUUAUGCAACCUUUC
UCGUCACGUGGAAGGGAGAUGAGAAAACUAGGAAUCCCACACCC
GCUGUCACACCACAGCCAAGAGGGGCUGAGUUCCAUAUGUGGAA
CUAUCAUAGUCACGUGUUUAGUGUCGGAGAUACGUUUUCAUUG
GCUAUGCAUCUCCAGUACAAGAUUCAUGAGGCUCCCUUCGAUCU
GUUGCUUGAGUGGUUGUACGUCCCGAUUGACCCGACCUGCCAGC
CCAUGCGACUGUACAGCACCUGUCUCUACCAUCCAAACGCUCCG
CAAUGUCUGAGCCACAUGAACUCUGGGGUGUACUUUCACCAGUCC
CCACCUCGCCCAGCGGGUGGCCUCUACUGUUUACCAGAACUGUG
AGCACGCCGACAACUACACCGCAUACUGCCUCGGUAUUUCUCAC
AUGGAACCCUCCUUCGGACUCAUCCUGCACGAUGGGGGCACUAC
CCUGAAGUUCGUUGAUACGCCAGAAUCUCUGUCUGGGCUCUAUG
UUUUCGUGGUCUACUUCAAUGGCCAUGUCGAGGCCGUGGCCUAU
ACUGUCGUUUCUACCGUGGAUCAUUUUGUGAACGCCAUCGAAGA
ACGGGGAUUCCCCCCUACGGCAGGCCAGCCGCCUGCAACCACCA
AGCCCAAGGAAAUAACACCAGUGAACCCUGGCACCUCACCUCUC
CUAAGAUAUGCCGCGUGGACAGGGGGACUGGCGGCAGUGGUGCU
CCUCUGUCUCGUGAUCUUUCUGAUCUGUACAGCCAAGAGGAUGA
GGGUCAAGGCUUAUAGAGUGGACAAGUCCCCCUACAAUCAGUCA
AUGUACUACGCCGGCCUUCCCGUUGAUGAUUUUGAGGAUUCCGA
GUCCACAGAUACUGAGGAAGAGUUCGGUAACGCUAUAGGCGGCU
CUCACGGGGGUUCAAGCUACACGGUUUACAUUGACAAGACACGC
UGAUAAUAGGCUGGAGCCUCGGUGGCCAUGCUUCUUGCCCCUUG
GGCCUCCCCCCAGCCCCUCCUCCCCUUCCUGCACCCGUACCCCCG
UGGUCUUUGAAUAAAGUCUGAGUGGGCGGCAAAAAAAAAAAAAA
AAAAAAAAAAAAAAAAAAAAAAAAAAAAAAAAAAAAAAAAAAAA
AAAAAAAAAAAAAAAAAAAAAAAAAAAAAAAAAAAAAAAAAAAA
AUCUAG
```

VZV-GE-delete-562

```
G*GGGAAAUAAGAGAGAAAAGAAGAGUAAGAAGAAAUAUAAGA
GCCACCAUGGGGACAGUUAAUAAACCUGUGGUGGGGGGUAUUGA
UGGGGUUCGGAAUUAUCACGGGAACGUUGCGUAUAACGAAUCC
GGUCAGAGCAUCCGUCUUGCGAUACGAUGAUUUUCACAUCGAUG
AAGACAAACUGGAUACAAACUCCGUAUAUGAGCCUUACUACCAU
UCAGAUCAUGCGGAGUCUUCAUGGGUAAAUCGGGGAGAGUCUU
CGCGAAAAGCGUACGAUCAUAACUCACCUUAUAUAUGGCCACGU
AAUGAUUAUGAUGGAUUUUUUAGAGAACGCACACGAACACCAUG
GGGUGUAUAAUCAGGGCCGUGGUAUCGAUAGCGGGGAACGGUU
AAUGCAACCCACACAAAUGUCUGCACAGGAGGAUCUUGGGGACG
AUACGGGCAUCCACGUUAUCCCUACGUUAAACGGCGAUGACAGA
CAUAAAAAUUGUAAAUGUGGACCAACGUCAAUACGGUGACGUGU
UUAAAGGAGAUCUUAAUCCAAAACCCCAAGGCCAAAGACUCAUU
GAGGUGUCAGUGGAAGAAAAUCACCCGUUUACUUUACGCGCACC
GAUUCAGCGGAUUUAUGGAGUCCGGUACACCGAGACUUGGAGCU
UUUUGCCGUCAUUAACCUGUACGGGAGACGCAGCGCCCGCCAUC
CAGCAUAUAUGUUUAAAACAUACAACAUGCUUUCAAGACGUGG
UGGUGGAUGUGGAUUGCGCGGAAAAAUACUAAAGAGGAUCAGUU
GGCCGAAAUCAGUUACCGUUUUCAAGGUAAGAAGGAAGCGGACC
AACCGUGGAUUGUUGUAAAACACGAGCACACUGUUUGAUGAACUC
GAAUUAGACCCCCCCGAGAUUGAACCGGGUGUCUUGAAAGUACU
UCGGACAGAAAAACAAUACUUGGGUGUGUACAUUUGGAACAUG
CGCGGCUCCGAUGGUACGUCUACCUACGCCACGUUUUUGGUCAC
CUGGAAAGGGAUGAAAAAACAAGAAACCCUACGCCCGCAGUAA
CUCCUCAACCAAGAGGGGCUGAGUUUCAUAUGUGGAAUUACCAC
UCGCAUGUAUUUUCAGUUGGUGAUACGUUUAGCUUGGCAAUGC
AUCUUCAGUAUAAGAUACAUGAAGCGCCAUUUGAUUUGCUGUU
AGAGUGGUUGUAUGUCCCCAUCGAUCCUACAUGUCAACCAAUGC
GGUUAUAUUCUACGUGUUUGUAUCAUCCCAACGCACCCCAAUGC
CUCUCUCAUAUGAAUUCCGGUUGUACAUUUACCUCGCCACAUUU
AGCCCAGCGUGUUGCAAGCACAGUGUAUCAAAAAUUGUGAACAUG
CAGAUAACUACACCGCAUAUUGUCUGGGAAUAUCUCAUAUGGAG
CCUAGCUUUGGUCUAAUCUUACACGACGGGGGCACCACGUUAAA
GUUUGUAGAUACACCCGAGAGUUUGUCGGGAUUAUACGUUUUU
GUGGGUGUAUUUUAACGGGCAUGUUGAAGCCGUAGCAUACACUG
UUGUAUCCACAGUAGAUCAUUUUGUAAACGCAAUUGAAGAGCG
UGGAUUUCCGCCAACGGCCGGUCAGCCACCGGCGACUACUAAAC
CCAAGGAAAUUACCCCCGUAAACCCCGGAACGUCACCACUUCUA
CGAUAUGCCGCAUGGACCGGAGGGCUUGCAGCAGUAGUACUUUU
AUGUCUCGUAAUAUUUUUAAUCUGUACGGCUUGAUGAUAAUAG
GCUGGAGCCUCGGUGGCCAUGCUUCUUGCCCCUUGGGCCUCCCCC
CCAGCCCCUCCUCCCCUUCCUGCACCCGUACCCCCGUGGUCUUUG
AAUAAAGUCUGAGUGGGCGGCAAAAAAAAAAAAAAAAAAAAAA
AAAAAAAAAAAAAAAAAAAAAAAAAAAAAAAAAAAAAAAAAAAA
AAAAAAAAAAAAAAAAAAAAAAAAAAAAAAAAAAUCUA
```

94

TABLE 2-continued

VZV-GE-delete-562-
replacedSP-withIgKappa

G*GGGAAAUAAGAGAGAAAAGAAGAGUAAGAAGAAAUAUAAGA
GCCACCAUGGAAACCCCGGCGCAGCUGCUGUUUCUGCUGCUGCU
GUGGCUGCCGGAUACCACCGGCUCCGUCUUGCGAUACGAUGAUU
UUCACAUCGAUGAAGACAAACUGGAUACAAACUCCGUAUAUGAG
CCUUACUACCAUUCAGAUCAUGCGGAGUCUUCAUGGGUAAAUCG
GGGAGAGUCUUCGCGAAAAGCGUACGAUCAUAACUCACCUUAUA
UAUGGCCACGUAAUGAUUAUGAUGGAUUUUUAGAGAACGCACA
CGAACACCAUGGGGUGUAUAAUCAGGGCCGUGGUAUCGAUAGCG
GGGAACGGUUAAUGCAACCCACACAAAUGUCUGCACAGGAGGAU
CUUGGGGACGAUACGGGCAUCCACGUUAUCCCUACGUUAAACGG
CGAUGACAGACAUAAAAUUGUAAAUGUGGACCAACGUCAUAC
GGUGACGUGUUUAAAGGAGAUCUUAAUCCAAAACCCCAAGGCCA
AAGACUCAUUGAGGUGUCAGUGGAAGAAAAUCACCCGUUUACU
UUACGCGCACCGAUUCAGCGGAUUUAUGGAGUCCGGUACACCGA
GACUUGGAGCUUUUUGCCGUCAUUAACCUGUACGGGAGACGCAG
CGCCCGCCAUCCAGCAUAUAUGUUUAAAACAUACAACAUGCUUU
CAAGACGUGGUGGUGGAUGUGGAUUGCGCGGAAAAUACUAAAG
AGGAUCAGUUGGCCGAAAUCAGUUACCGUUUUCAAGGUAAGAA
GGAAGCGGACCAACCGUGGAUUGUUGUAAACACGAGCACACUGU
UUGAUGAACUCGAAUUAGACCCCCCCGAGAUUGAACCGGGUGUC
UUGAAAGUACUUCGGACAGAAAAACAAUACUUGGGUGUGUACA
UUUGGAACAUGCGCGGCUCCGAUGGUACGUCUACCUACGCCACG
UUUUUGGUCACCUGGAAAGGGGAUGAAAAAACAAGAAACCCUA
CGCCCGCAGUAACUCCUCAACCAAGAGGGGCUGAGUUUCAUAUG
UGGAAUUACCACUCGCAUGUAUUUUCAGUUGGUGAUACGUUUA
GCUUGGCAAUGCAUCUUCAGUAUAAGAUACAUGAAGCGCCAUUU
GAUUUGCUGUUAGAGUGGUUGUAUGUCCCCAUCGAUCCUACAUG
UCAACCAAUGCGGUUAUAUUCUACGUGUUUGUAUCAUCCCAACG
CACCCCAAUGCCUCUCUCAUAUGAAUUCCGGUUGUACAUUUACC
UCGCCACAUUUAGCCCAGCGUGUUGCAAGCACAGUGUAUCAAAA
UUGUGAACAUGCAGAUAACUACACCGCAUAUUGUCUGGGAAUA
UCUCAUAUGGAGCCUAGCUUUGGUCUAAUCUUUACACGACGGGGG
CACCACGUUAAAGUUUGUAGAUACACCCGAGAGUUUGUCGGGAU
UAUACGUUUUUGUGGUGUAUUUUAACGGGCAUGUUGAAGCCGU
AGCAUACACUGUUGUAUCCACAGUAGAUCAUUUUGUAAACGCAA
UUGAAGAGCGUGGAUUUCCGCCAACGGCCGGUCAGCCACCGGCG
ACUACUAAACCCAAGGAAAUUACCCCCGUAAACCCCGGAACGUC
ACCACUUCUACGAUAUGCCGCAUGGACCGGAGGGCUUGCAGCAG
UAGUACUUUUAUGUCUCGUAAUAUUUUUAAUCUGUACGGCUUG
AUGAUAAUAGGCUGGAGCCUCGGUGGCCAUGCUUCUUGCCCCUU
GGGCCUCCCCCCAGCCCCUCCUCCCCUUCCUGCCACCCGUACCCCC
GUGGUCUUUGAAUAAAGUCUGAGUGGGCGGCAAAAAAAAAAA
AAAAAAAAAAAAAAAAAAAAAAAAAAAAAAAAAAAAAAAAA
AAAAAAAAAAAAAAAAAAAAAAAAAAAAAAAAAAAAAAAAA
AAUCUAG

95

VZV-GE-
full_with_AEAADA
(SEQ ID NO: 58)

G*GGGAAAUAAGAGAGAAAAGAAGAGUAAGAAGAAAUAUAAGA
GCCACCAUGGGGGCACAGUUAAUAAACCUGUGGUGGGGGUAUUGA
UGGGGUUCGGAAUUAUCACGGGAACGUUGCGUAUAACGAAUCC
GGUCAGAGCAUCCGUCUUGCGAUACGAUGAUUUUCACAUCGAUG
AAGACAAACUGGAUACAAACUCCGUAUAUGAGCCUUACUACCAU
UCAGAUCAUGCGGAGUCUUCAUGGGUAAAUCGGGGAGAGUCUU
CGCGAAAAGCGUACGAUCAUAACUCACCUUAUAUAUGGCCACGU
AAUGAUUAUGAUGGAUUUUUAGAGAACGCACACGAACACCAUG
GGGUGUAUAAUCAGGGCCGUGGUAUCGAUAGCGGGGAACGGUU
AAUGCAACCCACACAAAUGUCUGCACAGGAGGAUCUUGGGGACG
AUACGGGCAUCCACGUUAUCCCUACGUUAAACGGCGAUGACAGA
CAUAAAAUUGUAAAUGUGGACCAACGUCAUAACGGUGACGUGU
UUAAAGGAGAUCUUAAUCCAAAACCCCAAGGCCAAAGACUCAUU
GAGGUGUCAGUGGAAGAAAAUCACCCGUUUACUUUACGCGCACC
GAUUCAGCGGAUUUAUGGAGUCCGGUACACCGAGACUUGGAGCU
UUUUGCCGUCAUUAACCUGUACGGGAGACGCAGCGCCCGCCAUC
CAGCAUAUAUGUUUAAAACAUACAACAUGCUUUCAAGACGUGG
UGGUGGAUGUGGAUUGCGCGGAAAAUACUAAAGAGGAUCAGUU
GGCCGAAAUCAGUUACCGUUUUCAAGGUAAGAAGGAAGCGGACC
AACCGUGGAUUGUUGUAAACACGAGCACACUGUUUGAUGAACUC
GAAUUAGACCCCCCCGAGAUUGAACCGGGUGUCUUGAAAGUACU
UCGGACAGAAAAACAAUACUUGGGUGUGUACAUUUGGAACAUG
CGCGGCUCCGAUGGUACGUCUACCUACGCCACGUUUUUGGUCAC
CUGGAAAGGGGAUGAAAAAACAAGAAACCCUACGCCCGCAGUAA
CUCCUCAACCAAGAGGGGCUGAGUUUCAUAUGUGGAAUUACCAC
UCGCAUGUAUUUUCAGUUGGUGAUACGUUUAGCUUGGCAAUGC
AUCUUCAGUAUAAGAUACAUGAAGCGCCAUUUGAUUUGCUGUU
AGAGUGGUUGUAUGUCCCCAUCGAUCCUACAUGUCAACCAAUGC
GGUUAUAUUCUACGUGUUUGUAUCAUCCCAACGCACCCCAAUGC
CUCUCUCAUAUGAAUUCCGGUUGUACAUUUACCUCGCCACAUUU
AGCCCAGCGUGUUGCAAGCACAGUGUAUCAAAAUUGUGAACAUG
CAGAUAACUACACCGCAUAUUGUCUGGGAAUAUCUCAUAUGGAG
CCUAGCUUUGGUCUAAUCUUUACACGACGGGGGCACCACGUUAAA

```
GUUUGUAGAUACACCCGAGAGUUUGUCGGGAUUAUACGUUUUU
GUGGUGUAUUUUAACGGGCAUGUUGAAGCCGUAGCAUACACUG
UUGUAUCCACAGUAGAUCAUUUUGUAAACGCAAUUGAAGAGCG
UGGAUUUCCGCCAACGGCCGGUCAGCCACCGGCGACUACUAAAC
CCAAGGAAAUUACCCCCGUAAACCCCGGAACGUCACCACUUCUA
CGAUAUGCCGCAUGGACCGGAGGGCUUGCAGCAGUAGUACUUUU
AUGUCUCGUAAUAUUUUUAAUCUGUACGGCUAAACGAAUGAGG
GUUAAAGCCUAUAGGGUAGACAAGUCCCCGUAUAACCAAAGCAU
GUAUUACGCUGGCCUUCCAGUGGACGAUUUCGAGGACGCCGAAG
CCGCCGAUGCCGAAGAAGAGUUUGGUAACGCGAUUGGAGGGAG
UCACGGGGGUUCGAGUUACACGGUGUAUAUAGAUAAGACCCGG
UGAUGAUAAUAGGCUGGAGCCUCGGUGGCCAUGCUUCUUGCCCC
UUGGGCCUCCCCCCAGCCCCUCCUCCCCUUCCUGCACCCGUACCC
CCGUGGUCUUUGAAUAAAGUCUGAGUGGGCGGCAAAAAAAAAA
AAAAAAAAAAAAAAAAAAAAAAAAAAAAAAAAAAAAAAAAAA
AAAAAAAAAAAAAAAAAAAAAAAAAAAAAAAAAAAAAAAAAA
AAAAUCUAG
```

VZV-GE-
full_with_AEAADA
(SEQ ID NO: 58)_and_Y582G

```
G*GGGAAAUAAGAGAGAAAAGAAGAGUAAGAAGAAAUAUAAGA
GCCACCAUGGGGCACAGUUAAUAAACCUGUGGUGGGGGUAUUGA
UGGGGUUCGGAAUUAUCACGGGAACGUUGCGUAUAACGAAUCC
GGUCAGAGCAUCCGUCUUGCGAUACGAUGAUUUUCACAUCGAUG
AAGACAAACUGGAUACAAACUCCGUAUAUGAGCCUUACUACCAU
UCAGAUCAUGCGGAGUCUUCAUGGGUAAAUCGGGGAGAGUCUU
CGCGAAAAGCGUACGAUCAUAACUCACCUUAUAUAUGGCCACGU
AAUGAUUAUGAUGGAUUUUUAGAGAACGCACACGAACACCAUG
GGGUGUAUAAUCAGGGCCGUGGUAUCGAUAGCGGGGAACGGUU
AAUGCAACCCACACAAAUGUCUGCACAGGAGGAUCUUGGGGACG
AUACGGGCAUCCACGUUAUCCCUACGUUAAACGGCGAUGACAGA
CAUAAAAUUGUAAAUGUGGACCAACGUCAAUACGGUGACGUGU
UUAAAGGAGAUCUUAAUCCAAAACCCCAAGGCCAAAGACUCAUU
GAGGUGUCAGUGGAAGAAAAUCACCCGUUUACUUUACGCGCACC
GAUUCAGCGGAUUUAUGGAGUCCGGUACACCGAGACUUGGAGCU
UUUUGCCGUCAUUAACCUGUACGGGAGACGCAGCGCCCGCCAUC
CAGCAUAUAUGUUUAAAACAUACAACAUGCUUUCAAGACGUGG
UGGUGGAUGUGGAUUGCGCGGAAAAAUACUAAAGAGGAUCAGUU
GGCCGAAAUCAGUUACCGUUUUCAAGGUAAGAAGGAAGCGGACC
AACCGUGGAUUGUUGUAAACACGAGCCACUGUUUGAUGAACUC
GAAUUAGACCCCCCCGAGAUUGAACCGGGUGUCUUGAAAGUACU
UCGGACAGAAAAACAAUACUUGGGUGUGUACAUUUGGAACAUG
CGCGGCUCCGAUGGUACGUCUACCUACGCCACGUUUUUGGUCAC
CUGGAAAGGGGAUGAAAAAACAAGAAACCCUACGCCCGCAGUAA
CUCCUCAACCAAGAGGGGCUGAGUUUCAUAUGUGGAAUUACCAC
UCGCAUGUAUUUUCAGUUGGUGAUACGUUUAGCUUGGCAAUGC
AUCUUCAGUAUAAGAUACAUGAAGCGCCAUUUGAUUUGCUGUU
AGAGUGGUUGUAUGUCCCCAUCGAUCCUACAUGUCAACCAAUGC
GGUUAUAUUCUACGUGUUUUGUAUCAUCCCAACGCACCCCAAUGC
CUCUCUCAUAUGAAUUCCGGUUGUACAUUUACCUCGCCACAUUU
AGCCCAGCGUGUUGCAAGCACAGUGUAUCAAAAUUGUGAACAUG
CAGAUAACUACACCGCAUAUUGUCUGGGAAUAUCUCAUAUGGAG
CCUAGCUUUGGUCUAAUCUUACACGACGGGGGGCACCACGUUAAA
GUUUGUAGAUACACCCGAGAGUUUGUCGGGAUUAUACGUUUUU
GUGGUGUAUUUUAACGGGCAUGUUGAAGCCGUAGCAUACACUG
UUGUAUCCACAGUAGAUCAUUUUGUAAACGCAAUUGAAGAGCG
UGGAUUUCCGCCAACGGCCGGUCAGCCACCGGCGACUACUAAAC
CCAAGGAAAUUACCCCCGUAAACCCCGGAACGUCACCACUUCUA
CGAUAUGCCGCAUGGACCGGAGGGCUUGCAGCAGUAGUACUUUU
AUGUCUCGUAAUAUUUUUAAUCUGUACGGCUAAACGAAUGAGG
GUUAAAGCCUAUAGGGUAGACAAGUCCCCGUAUAACCAAAGCAU
GUAUGGCGCUGGCCUUCCAGUGGACGAUUUCGAGGACGCCGAAG
CCGCCGAUGCCGAAGAAGAGUUUGGUAACGCGAUUGGAGGGAG
UCACGGGGGUUCGAGUUACACGGUGUAUAUAGAUAAGACCCGG
UGAUGAUAAUAGGCUGGAGCCUCGGUGGCCAUGCUUCUUGCCCC
UUGGGCCUCCCCCCAGCCCCUCCUCCCCUUCCUGCACCCGUACCC
CCGUGGUCUUUGAAUAAAGUCUGAGUGGGCGGCAAAAAAAAAA
AAAAAAAAAAAAAAAAAAAAAAAAAAAAAAAAAAAAAAAAAA
AAAAAAAAAAAAAAAAAAAAAAAAAAAAAAAAAAAAAAAAAA
AAAAUCUAG
```

97

VZV-GE-
Truncated-
delete_from_574

```
G*GGGAAAUAAGAGAGAAAAGAAGAGUAAGAAGAAAUAUAAGA
GCCACCAUGGGGACAGUUAAUAAACCUGUGGUGGGGGUAUUGA
UGGGGUUCGGAAUUAUCACGGGAACGUUGCGUAUAACGAAUCC
GGUCAGAGCAUCCGUCUUGCGAUACGAUGAUUUUCACAUCGAUG
AAGACAAACUGGAUACAAACUCCGUAUAUGAGCCUUACUACCAU
UCAGAUCAUGCGGAGUCUUCAUGGGUAAAUCGGGGAGAGUCUU
CGCGAAAAGCGUACGAUCAUAACUCACCUUAUAUAUGGCCACGU
AAUGAUUAUGAUGGAUUUUUAGAGAACGCACACGAACACCAUG
GGGUGUAUAAUCAGGGCCGUGGUAUCGAUAGCGGGGAACGGUU
AAUGCAACCCACACAAAUGUCUGCACAGGAGGAUCUUGGGGACG
AUACGGGCAUCCACGUUAUCCCUACGUUAAACGGCGAUGACAGA
```

98

TABLE 2-continued

```
CAUAAAAUUGUAAAUGUGGACCAACGUCAAUACGGUGACGUGU
UUAAAGGAGAUCUUAAUCCAAAACCCCAAGGCCAAAGACUCAUU
GAGGUGUCAGUGGAAGAAAAUCACCCGUUUACUUUACGCGCACC
GAUUCAGCGGAUUUAUGGAGUCCGGUACACCGAGACUUGGAGCU
UUUUGCCGUCAUUAACCUGUACGGGAGACGCAGCGCCCGCCAUC
CAGCAUAUAUGUUUAAAACAUACAACAUGCUUUCAAGACGUGG
UGGUGGAUGUGGAUUGCGCGGAAAAUACUAAAGAGGAUCAGUU
GGCCGAAAUCAGUUACCGUUUUCAAGGUAAGAAGGAAGCGGACC
AACCGUGGAUUGUUGUAAACACGAGCACACUGUUUGAUGAACUC
GAAUUAGACCCCCCCGAGAUUGAACCGGGUGUCUUGAAAGUACU
UCGGACAGAAAAACAAUACUUGGGUGUGUACAUUUGGAACAUG
CGCGGCUCCGAUGGUACGUCUACCUACGCCACGUUUUUGGUCAC
CUGGAAAGGGGAUGAAAAAACAAGAAACCCUACGCCCGCAGUAA
CUCCUCAACCAAGAGGGGCUGAGUUUCAUAUGUGGAAUUACCAC
UCGCAUGUAUUUUCAGUUGGUGAUACGUUUAGCUUGGCAAUGC
AUCUUCAGUAUAAGAUACAUGAAGCGCCAUUUGAUUUGCUGUU
AGAGUGGUUGUAUGUCCCCAUCGAUCCUACAUGUCAACCAAUGC
GGUUAUAUUCUACGUGUUUGUAUCAUCCCAACGCACCCCAAUGC
CUCUCUCAUAUGAAUUCCGGUUGUACAUUUACCUCGCCACAUUU
AGCCCAGCGUGUUGCAAGCACAGUGUAUCAAAAUUGUGAACAUG
CAGAUAACUACACCGCAUAUUGUCUGGGAAUAUCUCAUAUGGAG
CCUAGCUUUGGUCUAAUCUUACACGACGGGGGCACCACGUUAAA
GUUUGUAGAUACACCCGAGAGUUUGUCGGGAUUAUACGUUUUU
GUGGUGUAUUUUAACGGGCAUGUUGAAGCCGUAGCAUACACUG
UUGUAUCCACAGUAGAUCAUUUUGUAAACGCAAUUGAAGAGCG
UGGAUUUCCGCCAACGGCCGGUCAGCCACCGGCGACUACUAAAC
CCAAGGAAAUUACCCCCGUAAACCCCGGAACGUCACCACUUCUA
CGAUAUGCCGCAUGGACCGGAGGGCUUGCAGCAGUAGUACUUUU
AUGUCUCGUAAUAUUUUUAAUCUGUACGGCUAAACGAAUGAGG
GUUAAAGCCUAUAGGGUAGACAAGUGAUGAUAAUAGGCUGGAG
CCUCGGUGGCCAUGCUUCUUGCCCCUUGGGCCUCCCCCCAGCCCC
UCCUCCCCUUCCUGCACCCGUACCCCCGUGGUCUUUGAAUAAAG
UCUGAGUGGGCGGCAAAAAAAAAAAAAAAAAAAAAAAAAAAA
AAAAAAAAAAAAAAAAAAAAAAAAAAAAAAAAAAAAAAAA
AAAAAAAAAAAAAAAAAAAAAAAAAAAAUCUAG
```

| VZV-GE-<br>Truncated-<br>delete_from_574_-_Y569A | ```
G*GGGAAAUAAGAGAGAAAAGAAGAGUAAGAAGAAAUAUAAGA
GCCACCAUGGGGACAGUUAAUAAAACCUGUGGUGGGGGGUAUUGA
UGGGGUUCGGAAUUAUCACGGGAACGUUGCGUAUAACGAAUCC
GGUCAGAGCAUCCGUCUUGCGAUACGAUGAUUUUCACAUCGAUG
AAGACAAACUGGAUACAAACUCCGUAUAUGAGCCUUACUACCAU
UCAGAUCAUGCGGAGUCUUCAUGGGUAAAUCGGGGAGAGUCUU
CGCGAAAAGCGUACGAUCAUAACUCACCUUAUAUAUGGCCACGU
AAUGAUUAUGAUGGAUUUUUAGAGAACGCACACGAACACCAUG
GGGUGUAUAAUCAGGGCCGUGGUUAUCGAUAGCGGGGAACGGUU
AAUGCAACCCACACAAAUGUCUGCACAGGAGGAUCUUGGGGACG
AUACGGGCAUCCACGUUAUCCCUACGUUAAACGGCGAUGACAGA
CAUAAAAUUGUAAAUGUGGACCAACGUCAAUACGGUGACGUGU
UUAAAGGAGAUCUUAAUCCAAAACCCCAAGGCCAAAGACUCAUU
GAGGUGUCAGUGGAAGAAAAUCACCCGUUUACUUUACGCGCACC
GAUUCAGCGGAUUUAUGGAGUCCGGUACACCGAGACUUGGAGCU
UUUUGCCGUCAUUAACCUGUACGGGAGACGCAGCGCCCGCCAUC
CAGCAUAUAUGUUUAAAACAUACAACAUGCUUUCAAGACGUGG
UGGUGGAUGUGGAUUGCGCGGAAAAUACUAAAGAGGAUCAGUU
GGCCGAAAUCAGUUACCGUUUUCAAGGUAAGAAGGAAGCGGACC
AACCGUGGAUUGUUGUAAACACGAGCACACUGUUUGAUGAACUC
GAAUUAGACCCCCCCGAGAUUGAACCGGGUGUCUUGAAAGUACU
UCGGACAGAAAAACAAUACUUGGGUGUGUACAUUUGGAACAUG
CGCGGCUCCGAUGGUACGUCUACCUACGCCACGUUUUUGGUCAC
CUGGAAAGGGGAUGAAAAAACAAGAAACCCUACGCCCGCAGUAA
CUCCUCAACCAAGAGGGGCUGAGUUUCAUAUGUGGAAUUACCAC
UCGCAUGUAUUUUCAGUUGGUGAUACGUUUAGCUUGGCAAUGC
AUCUUCAGUAUAAGAUACAUGAAGCGCCAUUUGAUUUGCUGUU
AGAGUGGUUGUAUGUCCCCAUCGAUCCUACAUGUCAACCAAUGC
GGUUAUAUUCUACGUGUUUGUAUCAUCCCAACGCACCCCAAUGC
CUCUCUCAUAUGAAUUCCGGUUGUACAUUUACCUCGCCACAUUU
AGCCCAGCGUGUUGCAAGCACAGUGUAUCAAAAUUGUGAACAUG
CAGAUAACUACACCGCAUAUUGUCUGGGAAUAUCUCAUAUGGAG
CCUAGCUUUGGUCUAAUCUUACACGACGGGGGCACCACGUUAAA
GUUUGUAGAUACACCCGAGAGUUUGUCGGGAUUAUACGUUUUU
GUGGUGUAUUUUAACGGGCAUGUUGAAGCCGUAGCAUACACUG
UUGUAUCCACAGUAGAUCAUUUUGUAAACGCAAUUGAAGAGCG
UGGAUUUCCGCCAACGGCCGGUCAGCCACCGGCGACUACUAAAC
``` | 99 |

TABLE 2-continued

```
CCAAGGAAAUUACCCCCGUAAACCCCGGAACGUCACCACUUCUA
CGAUAUGCCGCAUGGACCGGAGGGCUUGCAGCAGUAGUACUUUU
AUGUCUCGUAAUAUUUUUAAUCUGUACGGCUAAACGAAUGAGG
GUUAAAGCCGCCAGGGUAGACAAGUGAUGAUAAUAGGCUGGAG
CCUCGGUGGCCAUGCUUCUUGCCCCUUGGGCCUCCCCCCAGCCCC
UCCUCCCCUUCCUGCACCCGUACCCCCGUGGUCUUUGAAUAAAG
UCUGAGUGGGCGGCAAAAAAAAAAAAAAAAAAAAAAAAAAAAAA
AAAAAAAAAAAAAAAAAAAAAAAAAAAAAAAAAAAAAAAAAAAA
AAAAAAAAAAAAAAAAAAAAAAAAAAAAUCUAG
```

VZV-GE-
Truncated-
delete_from_574_-_Y569A
(ORF)

```
AUGGGGACAGUUAAUAAACCUGUGGUGGGGGUAUUGAUGGGGU
UCGGAAUUAUCACGGGAACGUUGCGUAUAACGAAUCCGGUCAGA
GCAUCCGUCUUGCGAUACGAUGAUUUUCACAUCGAUGAAGACAA
ACUGGAUACAAACUCCGUAUAUGAGCCUUACUACCAUUCAGAUC
AUGCGGAGUCUUCAUGGGUAAAUCGGGGAGAGUCUUCGCGAAA
AGCGUACGAUAAUCAUAACUCACCUUAUAUAUGGGCCACGUAAUG
AUUAUGAUGGAUUUUUAGAGAACGCACACGAACACCAUGGGGU
GUAUAAUCAGGGCCGUGGUAUCGAUAGCGGGGAACGGUUAAUG
CAACCCCACACAAAUGUCUGCACAGGAGGAUCUUGGGGACGAUAC
GGGCAUCCACGUUAUCCCUACGUUAAACGGCGAUGACAGACAUA
AAAUUGUAAAUGUGGACCAACGUCAAUACGGUGACGUGUUUAA
AGGAGAUCUUAAUCCAAAACCCCAAGGCCAAAGACUCAUUGAGG
UGUCAGUGGAAGAAAAUCACCCGUUUACUUUACGCGCACCGAUU
CAGCGGAUUUAUGGAGUCCGGUACACCGAGACUUGGAGCUUUUU
GCCGUCAUUAACCUGUACGGGAGACGCAGCGCCCGCCAUCCAGC
AUAUAUGUUUAAAACAUACAACAUGCUUUCAAGACGUGGUGGU
GGAUGUGGAUUGCGCGGAAAAUACUAAAGAGGAUCAGUUGGCC
GAAAUCAGUUACCGUUUUCAAGGUAAGAAGGAAGCGGACCAACC
GUGGAUUGUUGUAAACACGAGCACACUGUUUGAUGAACUCGAA
UUAGACCCCCCCGAGAUUGAACCGGGUGUCUUGAAAGUACUUCG
GACAGAAAAACAAUACUUGGGUGUGUACAUUUGGAACAUGCGC
GGCUCCGAUGGUACGUCUACCUACGCCACGUUUUUGGUCACCUG
GAAAGGGGAUGAAAAAACAAGAAACCCUACGCCCGCAGUAACUC
CUCAACCAAGAGGGGCUGAGUUUCAUAUGUGGAAUUACCACUCG
CAUGUAUUUUCAGUUGGUGAUACGUUUAGCUUGGCAAUGCAUC
UUCAGUAUAAGAUACAUGAAGCGCCAUUUGAUUUGCUGUUAGA
GUGGUUGUAUGUCCCCAUCGAUCCUACAUGUCAACCAAUGCGGU
UAUAUUCUACGUGUUUGUAUCAUCCCAACGCACCCCAAUGCCUC
UCUCAUAUGAAUUCCGGUUGUACAUUUACCUCGCCACAUUUAGC
CCAGCGUGUUGCAAGCACAGUGUAUCAAAAUUGUGAACAUGCAG
AUAACUACACCGCAUAUUGUCUGGGAAUAUCUCAUAUGGAGCCU
AGCUUUGGUCUAAUCUUACGACGGGGGCACCCACGUUAAAGUU
UGUAGAUACACCCGAGAGUUUGUCGGGAUUAUACGUUUUUGUG
GUGUAUUUUAACGGGCAUGUUGAAGCCGUAGCAUCACUGUUG
UAUCCACAGUAGAUCAUUUUGUAAACGCAAUUGAAGAGCGUGG
AUUUCCGCCAACGGCCGGUCAGCCACCGGCGACUACUAAACCCA
AGGAAAUUACCCCCGUAAACCCCGGAACGUCACCACUUCUACGA
UAUGCCGCAUGGACCGGAGGGCUUGCAGCAGUAGUACUUUUAUG
UCUCGUAAUAUUUUUAAUCUGUACGGCUAAACGAAUGAGGGUU
AAAGCCGCCAGGGUAGACAAGUGAUGAUAAUAGGCUGGAGCCUC
GGUGGCCAUGCUUCUUGCCCCUUGGGCCUCCCCCCAGCCCCUCCU
CCCCUUCCUGCACCCGUACCCCCGUGGUCUUUGAAUAAAGUCUG
AGUGGGCGGC
```

133

VZV-GI-full

```
G*GGGAAAUAAGAGAGAAAAGAAGAGUAAGAAGAAAUAUAAGA
GCCACCAUGUUUUUUAAUCCAAUGUUUGAUAUCGGCCGUUAUAUU
UUACAUACAAGUGACCAACGCUUUGAUCUUCAAGGGCGACCACG
UGAGCUUGCAAGUUAACAGCAGUCUCACGUCUAUCCUUAUUCCC
AUGCAAAAUGAUAAUUAUACAGAGAUAAAAGGACAGCUUGUCU
UUAUUGGAGAGCAACUACCUACCGGGACAAACUAUAGCGGAACA
CUGGAACUGUUAUACGCGGAUACGGUGGCGUUUUGUUUCCGGUC
AGUACAAGUAAUAAGAUACGACGGAUGUCCCCGGAUUAGAACG
AGCGCUUUUAUUUCGUGUAGGUACAAACAUUCGUGGCAUUAUG
GUAACUCAACGGAUCGGAUAUCAACAGAGCCGGAUGCUGGUGUA
AUGUUGAAAAUUACCAAACCGGGAAUAAAUGAUGCUGGUGUGU
AUGUACUUCUUGUUCGGUUAGACCAUAGCAGAUCCACCGAUGGU
UUCAUUCUUGGUGUAAAUGUAUAUUACAGCGGGCUCGCUCACAA
CAUUCACGGGGUUAUCUACACUUCUCCAUCUCUACAGAAUGGAU
AUUCUACAAGAGCCCUUUUUCAACAAGCUCGUUUGUGUGAUUUA
CCCGCGACACCCAAAGGGUCCGGUACCUCCCUGUUUCAACAUAU
GCUUGAUCUUCGUGCCGGUAAAUCGUUUAGAGGGAUAACCCUUGGU
UACAUGAGGACGUUGUUACGACAGAAACUAAGUCCGUUGUUAA
GGAGGGGAUAGAAAUCACGUAUAUCCAACGGAUAUGUCCACG
UUACCCGAAAAGUCCCUUAAUGAUCCUCCAGAAAAUCUACUUAU
AAUUAUUCCUAUAGUAGCGUCUGUCAUGAUCCUCACCGCCAUGG
UUAUUGUAUUGUAAUAAGCGUUAAGCGACGUAGAAUUAAAAA
ACAUCCAAUUUAUCGCCCAAAUACAAAAACAAGAAGGGGCAUAC
AAAAUGCGACACCAGAAUCCGAUGUGAUGUUGGAGGCCGCCAUU
GCACAACUAGCAACGAUUCGCGAAGAAUCCCCCCCACAUUCCGU
UGUAAACCCGUUUGUGUAAAUAGUGAUAAUAGGCUGGAGCCUCG
```

100

TABLE 2-continued

GUGGCCAUGCUUCUUGCCCCUUGGGCCUCCCCCCCAGCCCCUCCUC
CCCUUCCUGCACCCGUACCCCCGUGGUCUUUGAAUAAAGUCUGA
GUGGGCGGCAAAAAAAAAAAAAAAAAAAAAAAAAAAAAAAAAAA
AAAAAAAAAAAAAAAAAAAAAAAAAAAAAAAAAAAAAAAAAAA
AAAAAAAAAAAAAAAAAAAAAAAUCUAG

VZV-GE-
Truncated-
delete from_574_-_Y569A
Variant 1

G*GGGAAAUAAGAGAGAAAAGAAGAGAUAAGAAGAAAUAUAAGA
GCCACCAUGGGCACCGUGAACAAGCCCGUCGUGGGCGUGCUGAU
GGGCUUCGGCAUCAUCACCGGCACCCUGCGGGAUCACCAAUCCUG
UGCGGGCCAGCGUGCUGAGAUACGACGACUUCCACAUCGACGAG
GACAAGCUGGACACCAACAGCGUGUACGAGCCCUACUACCACAG
CGACCACGCCGAGAGCAGCUGGGUCAACAGAGGCGAGUCCAGCC
GGAAGGCCUACGACCACAACAGCCCCUACAUCUGGCCCCGGAAC
GACUACGACGGCUUCCUGGAAAAUGCCCACGAGCACCACGGCGU
GUACAACCAGGGCAGAGGCAUCGACAGCGGCGAGAGACUGAUGC
AGCCCACCCAGAUGAGCGCCCAGGAAGAUCUGGGCGACGACACC
GGCAUCCACGUGAUCCCUACCCUGAACGGCGACGACCGGCACAA
GAUCGUGAACGUGGACCAGCGGCAGUACGGCGACGUGUUCAAGG
GCGACCUGAACCCCAAGCCCCAGGGACAGCGGCUGAUUGAGGUG
UCCGUGGAAGAGAACCACCCCUUCACCCUGAGAGCCCCUAUCCA
GCGGAUCUACGGCGUGCGCUAUACCGAGACUUGGAGCUUCCUGC
CCAGCCUGACCGUACUGGCGACGCCGCUCCUGCCCAUCCAGCAC
AUCUGCCUGAAGCACACCACCUGUUUCAGGACGUGGUGGUGGA
CGUGGACUGCGCCGAGAACACCAAAGAGGACCAGCUGGCCGAGA
UCAGCUACCGGUUCCAGGGCAAGAAAGAGGCCGACCAGCCCUGG
AUCGUCGUGAACACCAGCACCCUGUUCGACGAGCUGGAACUGGA
CCCUCCCGAGAUCGAACCCGGGGUGCUGAAGGUGCUGCGGACCG
AGAAGCAGUACCUGGGAGUGUACAUCUGGAACAUGCGGGGCAGC
GACGGCACCUCUACCUACGCCCACCUUCCUCGUGACCUGGAAGGG
CGACGAGAAAACCCGGAACCCUACCCCUGCCGUGACCCCUCAGC
CUAGAGGCGCCGAGUUUCACAUGUGGAAUUACCACAGCCACGUG
UUCAGCGUGGGCGACACCUUCUCCCUGGCCAUGCAUCUGCAGUA
CAAGAUCCACGAGGCCCUUUCGACCUGCUGCUGGAAUGGCUGU
ACGUGCCCAUCGACCCUACCUGCCAGCCCAUGCGGCUGUACUCC
ACCUGUCUGUACCACCCCAACGCCCCUCAGUGCCUGAGCCACAU
GAAUAGCGGCUGCACCUUCACCAGCCCUCACCUGGCUCAGAGGG
UGGCCAGCACCGUGUACCAGAAUUGCGAGCACGCCGACAACUAC
ACCGCCUACUGCCUGGGCAUCAGCCACAUGGAACCCAGCUUCGG
CCUGAUCCUGCACGAUGGCGGCACCACCCUGAAGUUCGUGGACA
CCCCUGAGUCCCUGAGCGGCCUGUACGUGUUCGUGGGUGUACUUC
AACGGCCACGUGGAAGCCGUGGCCUACACCGUGGUGUCCACCGU
GGACCACUUCGUGAACGCCAUCGAGGAACGGGGCUUCCCUCCAA
CUGCUGGACAGCCUCCUGCCACCACCAAGCCCAAAGAAAUCACC
CCUGUGAACCCCGGCACCAGCCCACUGCUGCGCUAUGCUGCUUG
GACAGGCGGACUGGCUGCUGUGGGUGCUGCUGUGCCUCGUGAUUU
UCCUGAUCUGCACCGCCAAGCGGAUGAGAGUGAAGGCCGCCAGA
GUGGACAAGUGAUAAUAGGCUGGAGCCUCGGUGGCCAUGCUUCU
UGCCCCUUGGGCCUCCCCCCAGCCCCUCCUCCCCCUUCCUGCACCC
GUACCCCCGUGGUCUUUGAAUAAAGUCUGAGUGGGCGGCAAAAA
AAAAAAAAAAAAAAAAAAAAAAAAAAAAAAAAAAAAAAAAAAA
AAAAAAAAAAAAAAAAAAAAAAAAAAAAAAAAAAAAAAAAAAA
AAAAAAAAAUCUAG

101

VZV-GE-
Truncated-
delete_from_574_-_Y569A
Variant 2

G*GGGAAAUAAGAGAGAAAAGAAGAGUAAGAAGAAAUAUAAGA
GCCACCAUGGGGACAGUUAAUAAACCUGUGGUGGGGGUAUUGA
UGGGGUUCGGAAUUAUCACGGGAACGUUGCGUAUAACGAAUCC
GGUCAGAGCAUCCGUCUUGCGAUACGAUGAUUUUCACAUCGAUG
AAGACAAACUGGAUACAAACUCCGUAUAUGAGCCUUACUACCAU
UCAGAUCAUGCGGAGUCUUCAUGGGUAAAUCGGGGAGAGUCUU
CGCGAAAAGCGUACGAUCAUAACUCACCUUUAUAUAUGGCCACGU
AAUGAUUAUGAUGGAUUUUUUAGAGAACGCACACGAACACCAUG
GGGUGUAUAAUCAGGGCCGUGGGUAUCGAUAGCGGGGAACGGUU
AAUGCAACCCACACAAAUGUCUGCACAGGAGGAUCUUGGGGACG
AUACGGGCAUCCACGUUAUCCCUACGUUAAACGGCGAUGACAGA
CAUAAAAUUGUAAAUGUGGACCAACGUCAAUACGGUGACGUGU
UUAAAGGAGAUCUUAAUCCAAAACCCCAAGGCCAAAGACUCAUU
GAGGUGUCAGUGGAAGAAAAUCACCCGUUUUACUUUACGCGCACU
GAUUCAGCGGAUUUAUGGAGUCCGGUACACCGAGACUUGGAGCU
UUUUGCCGUCAUUUAACCUGUACGGGAGACGCAGCGCCCGCCAUC
CAGCAUAUAUGUUUAAAACAUACAACAUGCUUUCAAGACGUGG
UGGUGGAUGUGGAUUGCGCGGAAAAUACUAAAGAGGAUCAGUU
GGCCGAAAUCAGUUACCGUUUUCAAGGUAAGAAGGAAGCGGACC
AACCGUGGAUUGUUGUAAACACGAGCACACUGUUUGAUGAACUC
GAAUUAGACCCCCCCGAGAUUGAACCGGGUGUCUUGAAAGUACU
UCGGACAGAGAAACAAUACUUGGGUGUGUACAUUUGGAACAUG
CGCGGCUCCGAUGGUACGUCUACCUACGCCACGUUUUUGGUCAC
CUGGAAAGGGGAUGAGAAGACAAGAAACCCUACGCCCGCAGUAA
CUCCUCAACCAAGAGGGGCUGAGUUUCAUAUGUGGAAUUACCAC
UCGCAUGUAUUUUCAGUUGGUGAUACGUUUAGCUUGGCAAUGC
AUCUUCAGUAUAAGAUACAUGAAGCGCCAUUUGAUUUGCUGUU

102

TABLE 2-continued

AGAGUGGUUGUAUGUCCCCAUCGAUCCUACAUGUCAACCAAUGC
GGUUAUAUUCUACGUGUUUGUAUCAUCCCAACGCACCCCAAUGC
CUCUCUCAUAUGAAUUCCGGUUGUACAUUUACCUCGCCACAUUU
AGCCCAGCGUGUUGCAAGCACAGUGUAUCAAAAUUGUGAACAUG
CAGAUAACUACACCGCAUAUUGUCUGGGAAUAUCUCAUAUGGAG
CCUAGCUUUGGUCUAAUCUUACACGACGGGGGCACCACGUUAAA
GUUUGUAGAUACACCCGAGAGUUUGUCGGGAUUAUACGUUUUU
GUGGUGUAUUUUAACGGGCAUGUUGAAGCCGUAGCAUACACUG
UUGUAUCCACAGUAGAUCAUUUUGUAAACGCAAUUGAAGAGCG
UGGAUUUCCGCCAACGGCCGGUCAGCCACCGGCGACUACUAAAC
CCAAGGAAAUUACCCCCGUAAACCCCGGAACGUCACCACUUCUA
CGAUAUGCCGCAUGGACCGGAGGGCUUGCAGCAGUAGUACUUUU
AUGUCUCGUAAUAUUUUUAAUCUGUACGGCUAAACGAAUGAGG
GUUAAAGCCGCCAGGGUAGACAAGUGAUAAUAGGCUGGAGCCUC
GGUGGCCAUGCUUCUUGCCCCUUGGGCCUCCCCCCCAGCCCCUCCU
CCCCUUCCUGCACCCGUACCCCCGUGGUCUUUGAAUAAAGUCUG
AGUGGGCGGCAAAAAAAAAAAAAAAAAAAAAAAAAAAAAAA
AAAAAAAAAAAAAAAAAAAAAAAAAAAAAAAAAAAAAAAAA
AAAAAAAAAAAAAAAAAAAAAAAAUCUAG

VZV-GE-
Truncated-
delete_from_574_-_Y569A
Variant 3

G*GGGAAUAAGAGAGAAAAGAAGAGUAAGAAGAAAUAUAAGA        103
GCCACCAUGGGGACAGUUAAUAAACCUGUGGUGGGGGUAUUGA
UGGGGUUCGGAAUUAUCACGGGAACGUUGCGUAUAACGAAUCC
GGUCAGAGCAUCCGUCUUGCGAUACGAUGAUUUUCACAUCGAUG
AAGACAAACUGGAUACAAACUCCGUAUAUGAGCCUUACUACCAU
UCAGAUCAUGCGGAGUCUUCAUGGGUAAAUCGGGGAGAGUCUU
CGCGAAAAGCGUACGAUCAUAACUCACCUUAUAUAUGGCCACGU
AAUGAUUAUGAUGGAUUUUUAGAGAACGCACACGAACACCAUG
GGGUGUAUAAUCAGGGCCGUGGUAUCGAUAGCGGGGAACGGUU
AAUGCAACCCACACAAAUGUCUGCACAGGAGGAUCUUGGGGACG
AUACGGGCAUCCACGUUAUCCCUACGUUAAACGGCGAUGACAGA
CAUAAAAUUGUAAAUGUGGACCAACGUCAAUACGGUGACGUGU
UUAAAGGAGAUCUUAAUCCAAAACCCCAAGGCCAAAGACUCAUU
GAGGUGUCAGUGGAAGAAAAUCACCCGUUUACUUUACGCGCACC
GAUUCAGCGGAUUUAUGGAGUCCGGUACACCGAGACUUGGAGCU
UUUUGCCGUCAUUAACCUGUACGGGAGACGCAGCGCCCGCCAUC
CAGCAUAUAUGUUUAAAACAUACAACAUGCUUUCAAGACGUGG
UGGUUGGAUGUGGGAUUGCGCGGAAAAAUACUAAAGAGGAUCAGUU
GGCCGAAAUCAGUUACCGUUUUCAAGGUAAGAAGGAAGCGGACC
AACCGUGGAUUGUUGUAAACACGAGCACACUGUUUGAUGAACUC
GAAUUAGACCCACCCGAGAUUGAACCGGGUGUCUUGAAAGUACU
UCGGACAGAGAAACAAUACUUGGGUGUGUACAUUUGGAACAUG
CGCGGCUCCGAUGGUACGUCUACCUACGCCACGUUUUUGGUCAC
CUGGAAAGGGGAUGAGAAGACAAGAAACCCUACGCCCGCAGUAA
CUCCUCAACCAAGAGGGGCUGAGUUUCAUAUGUGGAAUUACCAC
UCGCAUGUAUUUUCAGUUGGUGAUACGUUUAGCUUGGCCAAUGC
AUCUUCAGUAUAAGAUACAUGAAGCGCCAUUUGAUUUGCUGUU
AGAGUGGUUGUAUGUCCCCAUCGAUCCUACAUGUCAACCAAUGC
GGUUAUAUUCUACGUGUUUGUAUCAUCCCAACGCACCCCAAUGC
CUCUCUCAUAUGAAUUCCGGUUGUACAUUUACCUCGCCACAUUU
AGCCCAGCGUGUUGCAAGCACAGUGUAUCAAAAUUGUGAACAUG
CAGAUAACUACACCGCAUAUUGUCUGGGAAUAUCUCAUAUGGAG
CCUAGCUUUGGUCUAAUCUUACACGACGGGGGCACCACGUUAAA
GUUUGUAGAUACACCCGAGAGUUUGUCGGGAUUAUACGUUUUU
GUGGUGUAUUUUAACGGGCAUGUUGAAGCCGUAGCAUACACUG
UUGUAUCCACAGUAGAUCAUUUUGUAAACGCAAUUGAAGAGCG
UGGAUUUCCGCCAACGGCCGGUCAGCCACCGGCGACUACUAAAC
CCAAGGAAAUUACCCCCGUAAACCCCGGAACGUCACCACUUCUA
CGAUAUGCCGCAUGGACCGGAGGGCUUGCAGCAGUAGUACUUUU
AUGUCUCGUAAUAUUUUUAAUCUGUACGGCUAAACGAAUGAGG
GUUAAAGCCGCCAGGGUAGACAAGUGAUAAUAGGCUGGAGCCUC
GGUGGCCAUGCUUCUUGCCCCUUGGGCCUCCCCCCCAGCCCCUCCU
CCCCUUCCUGCACCCGUACCCCCGUGGUCUUUGAAUAAAGUCUG
AGUGGGCGGCAAAAAAAAAAAAAAAAAAAAAAAAAAAAAAA
AAAAAAAAAAAAAAAAAAAAAAAAAAAAAAAAAAAAAAAAA
AAAAAAAAAAAAAAAAAAAAAAAAUCUAG

VZV-GE-
Truncated-
delete_from_574_-_Y569A
Variant 4

G*GGGAAUAAGAGAGAAAAGAAGAGUAAGAAGAAAUAUAAGA        104
GCCACCAUGGGGACAGUUAAUAAACCUGUGGUGGGGGUAUUGA
UGGGGUUCGGAAUUAUCACGGGAACGUUGCGUAUAACGAAUCC
GGUCAGAGCAUCCGUCUUGCGAUACGAUGAUUUUCACAUCGAUG
AAGACAAACUGGAUACAAACUCCGUAUAUGAGCCUUACUACCAU
UCAGAUCAUGCGGAGUCUUCAUGGGUAAAUCGGGGAGAGUCUU
CGCGAAAAGCGUACGAUCAUAACUCACCUUAUAUAUGGCCACGU
AAUGAUUAUGAUGGAUUUUUAGAGAACGCACACGAACACCAUG
GGGUGUAUAAUCAGGGCCGUGGUAUCGAUAGCGGGGAACGGUU
AAUGCAACCCACACAAAUGUCUGCACAGGAGGAUCUUGGGGACG
AUACGGGCAUCCACGUUAUCCCUACGUUAAACGGCGAUGACAGA
CAUAAAGAUUGUAAAUGUGGACCAACGUCAAUACGGUGACGUGU
UUAAAGGAGAUCUUAAUCCAAAGCCCCAAGGCCAAAGACUCAUU

TABLE 2-continued

GAGGUGUCAGUGGAAGAGAAUCACCCGUUUACUUUACGCGCACC
GAUUCAGCGGAUUUAUGGAGUCCGGUACACCGAGACUUGGAGCU
UUUUGCCGUCAUUAACCUGUACGGGAGACGCAGCGCCCGCCAUC
CAGCAUAUAUGUUUAAAGCAUACAACAUGCUUUCAAGACGUGG
UGGUGGAUGUGGAUUGCGCGGAGAAUACUAAAGAGGAUCAGUU
GGCCGAAAUCAGUUACCGUUUUCAAGGUAAGAAGGAAGCGGACC
AACCGUGGAUUGUUGUAAACACGAGCACACUGUUUGAUGAACUC
GAAUUAGACCCCCCCGAGAUUGAACCGGGUGUCUUGAAAGUACU
UCGGACAGAGAAACAAUACUUGGGUGUGUACAUUUGGAACAUG
CGCGGCUCCGAUGGUACGUCUACCUACGCCACGUUUUUGGUCAC
CUGGAAAGGGGAUGAGAAGACAAGAAACCCUACGCCCGCAGUAA
CUCCUCAACCAAGAGGGGCUGAGUUUCAUAUGUGGAAUUACCAC
UCGCAUGUAUUUUCAGUUGGUGAUACGUUUAGCUUGGCAAUGC
AUCUUCAGUAUAAGAUACAUGAAGCGCCAUUUGAUUUGCUGUU
AGAGUGGUUGUAUGUCCCCAUCGAUCCUACAUGUCAACCAAUGC
GGUUAUAUUCUACGUGUUUGUAUCAUCCCAACGCACCCCAAUGC
CUCUCUCAUAUGAAUUCCGGUUGUACAUUUACCUCGCCACAUUU
AGCCCAGCGUGUUGCAAGCACAGUGUAUCAGAAUUGUGAACAUG
CAGAUAACUACACCGCAUAUUGUCUGGGAAUAUCUCAUAUGGAG
CCUAGCUUUGGUCUAAUCUUACACGACGGGGGCACCACGUUAAA
GUUUGUAGAUACACCCGAGAGUUUGUCGGGAUUAUACGUUUUU
GUGGUGUAUUUUAACGGGCAUGUUGAAGCCGUAGCAUACACUG
UUGUAUCCACAGUAGAUCAUUUUGUAAACGCAAUUGAAGAGCG
UGGAUUUCCGCCAACGGCCGGUCAGCCACCGGCGACUACUAAAC
CCAAGGAAAUUACCCCCGUAAACCCCGGAACGUCACCACUUCUA
CGAUAUGCCGCAUGGACCGGAGGGCUUGCAGCAGUAGUACUUUU
AUGUCUCGUAAUAUUUUUAAUCUGUACGGCUAAACGAAUGAGG
GUUAAAGCCGCCAGGGUAGACAAGUGAUAAUAGGCUGGAGCCUC
GGUGGCCAUGCUUCUUGCCCCUUGGGCCUCCCCCCAGCCCCUCCU
CCCCUUCCUGCACCCGUACCCCCGUGGGUCUUUGAAUAAAGUCUG
AGUGGGCGGCAAAAAAAAAAAAAAAAAAAAAAAAAAAAAAAAAA
AAAAAAAAAAAAAAAAAAAAAAAAAAAAAAAAAAAAAAAAAAAA
AAAAAAAAAAAAAAAAAAAAAAAUCUAG

VZV-GE-                          G*GGGAAAUAAGAGAGAAAAGAAGAGUAAGAAGAAAUAUAAGA                105
Truncated-                       GCCACCAUGGGGACAGUUAAUAAACCUGUGGUGGGGGGUAUUGA
delete_from_574_-_Y569A          UGGGGUUCGGAAUUAUCACGGGAACGUUGCGUAUAACGAAUCC
Variant 5                        GGUCAGAGCAUCCGUCUUGCGAUACGAUGAUUUUCACAUCGAUG
                                 AAGACAAACUGGAUACAAACUCCGUAUAUGAGCCUUACUACCAU
                                 UCAGAUCAUGCGGAGUCUUCAUGGGUAAAUCGGGGAGAGUCUU
                                 CGCGAAAGGCGUACGAUCAUAACUCACCUUAUAUAUGGCCACGU
                                 AAUGAUUAUGAUGGAUUUUUAGAGAACGCACACGAACACCAUG
                                 GGGUGUAUAAUCAGGGCCGUGGGUAUCGAUAGCGGGGAACGGUU
                                 AAUGCAACCCACACAAAAUGUCUGCACAGGAGGAUCUUGGGGACG
                                 AUACGGGCAUCCACGUUAUCCCUACGUUAAACGGCGAUGACAGA
                                 CAUAAGAUUGUAAAUGUGGACCAACGUCAAUACGGUGACGUGU
                                 UUAAAGGAGAUCUUAAUCCAAAGCCCCAAGGCCAAAGACUCAUU
                                 GAGGUGUCAGUGGAAGAGAAUCACCCGUUUACUUUACGCGCACC
                                 GAUUCAGCGGAUUUAUGGAGUCCGGUACACCGAGACUUGGAGCU
                                 UUUUGCCGUCAUUAACCUGUACGGGAGACGCAGCGCCCGCCAUC
                                 CAGCAUAUAUGUUUAAAGCAUACAACAUGCUUUCAAGACGUGG
                                 UGGUGGAUGUGGAUUGCGCGGAGAAUACUAAAGAGGAUCAGUU
                                 GGCCGAAAUCAGUUACCGUUUUCAAGGUAAGAAGGAAGCGGACC
                                 AACCGUGGAUUGUUGUAAACACGAGCACACUGUUUGAUGAACUC
                                 GAAUUAGACCCACCCGAGAUUGAACCGGGUGUCUUGAAAGUACU
                                 UCGGACAGAGAAACAAUACUUGGGUGUGUACAUUUGGAACAUG
                                 CGCGGCUCCGAUGGUACGUCUACCUACGCCACGUUUUUGGUCAC
                                 CUGGAAAGGGGAUGAGAAGACAAGAAACCCUACGCCCGCAGUAA
                                 CUCCUCAACCAAGAGGGGCUGAGUUUCAUAUGUGGAAUUACCAC
                                 UCGCAUGUAUUUUCAGUUGGUGAUACGUUUAGCUUGGCAAUGC
                                 AUCUUCAGUAUAAGAUACAUGAAGCGCCAUUUGAUUUGCUGUU
                                 AGAGUGGUUGUAUGUCCCCAUCGAUCCUACAUGUCAACCAAUGC
                                 GGUUAUAUUCUACGUGUUUGUAUCAUCCCAACGCACCCCAAUGC
                                 CUCUCUCAUAUGAAUUCCGGUUGUACAUUUACCUCGCCACAUUU
                                 AGCCCAGCGUGUUGCAAGCACAGUGUAUCAGAAUUGUGAACAUG
                                 CAGAUAACUACACCGCAUAUUGUCUGGGAAUAUCUCAUAUGGAG
                                 CCUAGCUUUGGUCUAAUCUUACACGACGGGGGCACCACGUUAAA
                                 GUUUGUAGAUACACCCGAGAGUUUGUCGGGAUUAUACGUUUUU
                                 GUGGUGUAUUUUAACGGGCAUGUUGAAGCCGUAGCAUACACUG
                                 UUGUAUCCACAGUAGAUCAUUUUGUAAACGCAAUUGAAGAGCG
                                 UGGAUUUCCGCCAACGGCCGGUCAGCCACCGGCGACUACUAAAC
                                 CCAAGGAAAUUACCCCCGUAAACCCCGGAACGUCACCACUUCUA
                                 CGAUAUGCCGCAUGGACCGGAGGGCUUGCAGCAGUAGUACUUUU
                                 AUGUCUCGUAAUAUUUUUAAUCUGUACGGCUAAACGAAUGAGG
                                 GUUAAAGCCGCCAGGGUAGACAAGUGAUAAUAGGCUGGAGCCUC
                                 GGUGGCCAUGCUUCUUGCCCCUUGGGCCUCCCCCCAGCCCCUCCU
                                 CCCCUUCCUGCACCCGUACCCCCGUGGGUCUUUGAAUAAAGUCUG
                                 AGUGGGCGGCAAAAAAAAAAAAAAAAAAAAAAAAAAAAAAAAAA
                                 AAAAAAAAAAAAAAAAAAAAAAAAAAAAAAAAAAAAAAAAAAAA
                                 AAAAAAAAAAAAAAAAAAAAAAAUCUAG TABLE 2-continued VZV-GE-
Truncated-
delete_from_574_-_Y569A
Variant 6

G*GGGAAAUAAGAGAGAAAAGAAGAGUAAGAAGAAAUAUAAGA
GCCACCAUGGGGACAGUUAAUAAACCUGUGGUGGGGGUAUUGA
UGGGGUUCGGAAUUAUCACGGGAACGUUGCGUAUAACGAAUCC
GGUCAGAGCAUCCGUCUUGCGAUACGAUGAUUUUCACAUCGAUG
AAGACAAACUGGAUACAAACUCCGUAUAUGAGCCUUACUACCAU
UCAGAUCAUGCGGAGUCUUCAUGGGUAAAUCGGGGAGAGUCUU
CGCGAAAAGCGUACGAUCAUAACUCACCUUAUAUAUGGCCACGU
AAUGAUUAUGAUGGAUUUUUAGAGAACGCACACGAACACCAUG
GGGUGUAUAAUCAGGGCCGUGGUAUCGAUAGCGGGGAACGGUU
AAUGCAACCCACACAAAUGUCUGCACAGGAGGAUCUUGGGGACG
AUACGGGCAUCCACGUUAUCCCUACGUUAAACGGCGAUGACAGA
CAUAAAAUUGUAAAUGUGGACCAACGUCAAUACGGUGACGUGU
UUAAAGGAGAUCUUAAUCCAAAACCCCAAGGCCAAAGACUCAUU
GAGGUGUCAGUGGAAGAAAAUCACCCGUUUACUUUACGCGCACC
GAUUCAGCGGAUUUAUGGAGUCCGGUACACCGAGACUUGGAGCU
UUUUGCCGUCAUUAACCUGUACGGGAGACGCAGCGCCCGCCAUC
CAGCAUAUAUGUUUAAAGCAUACAACAUGCUUUCAAGACGUGG
UGGUGGAUGUGGAUUGCGCGGAAAAUACUAAAGAGGAUCAGUU
GGCCGAAAUCAGUUACCGUUUUCAAGGUAAGAAGGAAGCGGACC
AACCGUGGAUUGUUGUAAACACGAGCACACUGUUUGAUGAACUC
GAAUUAGACCCCCCCGAGAUUGAACCGGGUGUCUUGAAAGUACU
UCGGACAGAGAAACAAUACUUGGGUGUGUACAUUUGGAACAUG
CGCGGCUCCGAUGGUACGUCUACCUACGCCACGUUUUUGGUCAC
CUGGAAAGGGGAUGAGAAGACAAGAAACCCUACGCCCGCAGUAA
CUCCUCAACCAAGAGGGGCUGAGUUUCAUAUGUGGAAUUACCAC
UCGCAUGUAUUUUCAGUUGGUGAUACGUUUAGCUUGGCAAUGC
AUCUUCAGUAUAAGAUACAUGAAGCGCCAUUUGAUUUGCUGUU
AGAGUGGUUGUAUGUCCCCAUCGAUCCUACAUGUCAACCAAUGC
GGUUAUAUUCUACGUGUUUGUAUCAUCCCAACGCACCCCAAUGC
CUCUCUCAUAUGAAUUCCGGUUGUACAUUUACCUCGCCACAUUU
AGCCCAGCGUGUUGCAAGCACAGUGUAUCAGAAUUGUGAACAUG
CAGAUAACUACACCGCAUAUUGUCUGGGAAUAUCUCAUAUGGAG
CCUAGCUUUGGUCUAAUCUUACACGACGGGGGGCACCACGUUAAA
GUUUGUAGAUACACCCGAGAGUUUGUCGGGAUUAUACGUUUUU
GUGGUGUAUUUUAACGGGCAUGUUGAAGCCGUAGCAUACACUG
UUGUAUCCACAGUAGAUCAUUUUGUAAACGCAAUUGAAGAGCG
UGGAUUUCCGCCAACGGCCGGUCAGCCACCGGCGACUACUAAAC
CCAAGGAAAUUACCCCCGUAAACCCCGGAACGUCACCACUUCUA
CGAUAUGCCGCAUGGACCGGAGGGCUUGCAGCAGUAGUACUUUU
AUGUCUCGUAAUAUUUUUAAUCUGUACGGCUAAACGAAUGAGG
GUUAAAGCCGCCAGGGUAGACAAGUGAUAAUAGGCUGGAGCCUC
GGUGGCCAUGCUUCUUGCCCCUUGGGCCUCCCCCCCAGCCCCUCCU
CCCCUUCCUGCACCCGUACCCCCGUGGUCUUUGAAUAAAGUCUG
AGUGGGCGGCAAAAAAAAAAAAAAAAAAAAAAAAAAAAAAAAA
AAAAAAAAAAAAAAAAAAAAAAAAAAAAAAAAAAAAAAAAAAA
AAAAAAAAAAAAAAAAAAAAAAUCUAG

106

VZV-GE-
Truncated-
delete_from_574_-_Y569A
Variant 6
(version 2)

G*GGGAAAUAAGAGAGAAAAGAAGAGUAAGAAGAAAUAUAAGA
GCCACCAUGGGGACAGUUAAUAAACCUGUGGUGGGGGUAUUGA
UGGGGUUCGGAAUUAUCACGGGAACGUUGCGUAUAACGAAUCC
GGUCAGAGCAUCCGUCUUGCGAUACGAUGAUUUUCACAUCGAUG
AAGACAAACUGGAUACAAACUCCGUAUAUGAGCCUUACUACCAU
UCAGAUCAUGCGGAGUCUUCAUGGGUAAAUCGGGGAGAGUCUU
CGCGAAAAGCGUACGAUCAUAACUCACCUUAUAUAUGGCCACGU
AAUGAUUAUGAUGGAUUUUUAGAGAACGCACACGAACACCAUG
GGGUGUAUAAUCAGGGCCGUGGUAUCGAUAGCGGGGAACGGUU
AAUGCAACCCACACAAAUGUCUGCACAGGAGGAUCUUGGGGACG
AUACGGGCAUCCACGUUAUCCCUACGUUAAACGGCGAUGACAGA
CAUAAAAUUGUAAAUGUGGACCAACGUCAAUACGGUGACGUGU
UUAAAGGAGAUCUUAAUCCAAAACCCCAAGGCCAAAGACUCAUU
GAGGUGUCAGUGGAAGAAAAUCACCCGUUUACUUUACGCGCACC
GAUUCAGCGGAUUUAUGGAGUCCGGUACACCGAGACUUGGAGCU
UUUUGCCGUCAUUAACCUGUACGGGAGACGCAGCGCCCGCCAUC
CAGCAUAUAUGUUUAAAGCAUACAACAUGCUUUCAAGACGUGG
UGGUGGAUGUGGAUUGCGCGGAAAAUACUAAAGAGGAUCAGUU
GGCCGAAAUCAGUUACCGUUUUCAAGGUAAGAAGGAAGCGGACC
AACCGUGGAUUGUUGUAAACACGAGCACACUGUUUGAUGAACUC
GAAUUAGACCCCCCCGAGAUUGAACCGGGUGUCUUGAAAGUACU
UCGGACAGAGAAACAAUACUUGGGUGUGUACAUUUGGAACAUG
CGCGGCUCCGAUGGUACGUCUACCUACGCCACGUUUUUGGUCAC
CUGGAAAGGGGAUGAGAAGACAAGAAACCCUACGCCCGCAGUAA
CUCCUCAACCAAGAGGGGCUGAGUUUCAUAUGUGGAAUUACCAC
UCGCAUGUAUUUUCAGUUGGUGAUACGUUUAGCUUGGCAAUGC
AUCUUCAGUAUAAGAUACAUGAAGCGCCAUUUGAUUUGCUGUU
AGAGUGGUUGUAUGUCCCCAUCGAUCCUACAUGUCAACCAAUGC
GGUUAUAUUCUACGUGUUUGUAUCAUCCCAACGCACCCCAAUGC
CUCUCUCAUAUGAAUUCCGGUUGUACAUUUACCUCGCCACAUUU
AGCCCAGCGUGUUGCAAGCACAGUGUAUCAGAAUUGUGAACAUG
CAGAUAACUACACCGCAUAUUGUCUGGGAAUAUCUCAUAUGGAG

136

TABLE 2-continued

CCUAGCUUUGGUCUAAUCUUACACGACGGGGGCACCACGUUAAA
GUUUGUAGAUACACCCGAGAGUUUGUCGGGAUUAUACGUUUUU
GUGGUGUAUUUUAACGGGCAUGUUGAAGCCGUAGCAUACACUG
UUGUAUCCACAGUAGAUCAUUUUGUAAACGCAAUUGAAGAGCG
UGGAUUUCCGCCAACGGCCGGUCAGCCACCGGCGACUACUAAAC
CCAAGGAAAUUACCCCCGUAAACCCCGGAACGUCACCACUUCUA
CGAUAUGCCGCAUGGACCGGAGGGCUUGCAGCAGUAGUACUUUU
AUGUCUCGUAAUAUUUUUAAUCUGUACGGCUAAACGAAUGAGG
GUUAAAGCCGCCAGGGUAGACAAGUGAUAAUAGGCUGGAGCCUC
GGUGGCCAUGCUUCUUGCCCCUUGGGCCUCCCCCCCAGCCCCUCCU
CCCCUUCCUGCACCCGUACCCCCGUGGUCUUUGAAUAAAGUCUG
AGUGGGCGGCAAAAAAAAAAAAAAAAAAAAAAAAAAAAAAAAAAA
AAAAAAAAAAAAAAAAAAAAAAAAAAAAAAAAAAAAAAAAAAAA
AAAAAAAAAAAAAAAAAAAAAAAAAUCUAG

VZV-GE-
Truncated-
delete_from_574_-_Y569A
Variant 7

G*GGGAAUAAGAGAGAAAAGAAGAGUAAGAAGAAAUAUAAGA                    107
GCCACCAUGGGGACAGUUAAUAAACCUGUGGUGGGGGGUAUUGA
UGGGGUUCGGGAAUUAUCACGGGAACGUUGCGUAUAACGAAUCC
GGUCAGAGCAUCCGUCUUGCGAUACGAUGAUUUUCACAUCGAUG
AAGACAAACUGGAUACAAACUCCGUAUAUGAGCCUUACUACCAU
UCAGAUCAUGCGGAGUCUUCAUGGGUAAAUCGGGGAGAGUCUU
CGCGAAAAGCGUACGAUCAUAACUCACCUUAUAUAUGGCCACGU
AAUGAUUAUGAUGGAUUUUUAGAGAACGCACACGAACACCAUG
GGGUGUAUAAUCAGGGCCGUGGUAUCGAUAGCGGGGAACGGUU
AAUGCAACCCACACAAAUGUCUGCACAGGAGGAUCUUGGGGACG
AUACGGGCAUCCACGUUAUCCCUACGUUAAACGGCGAUGACAGA
CAUAAAAUUGUAAAUGUGGACCAACGUCAAUACGGUGACGUGU
UUAAAGGAGAUCUUAAUCCAAAACCCCAAGGCCAAAGACUCAUU
GAGGUGUCAGUGGAAGAAAAUCACCCGUUUUACUUUACGCGCACC
GAUUCAGCGGAUUUAUGGAGUCCGGUACACCGAGACUUGGAGCU
UUUUGCCGUCAUUAACCUGUACGGGAGACGCAGCGCCCGCCAUC
CAGCAUAUAUGUUUAAAGCAUACAACAUGCUUUCAAGACGUGG
UGGUGGAUGUGGAUUGCGCGGAAAAUACUAAAGAGGAUCAGUU
GGCCGAAAUCAGUUACCGUUUUCAAGGUAAGAAGGAAGCGGACC
AACCGUGGAUUGUUGUAAACACGAGCACACUGUUUGAUGAACUC
GAAUUAGACCCACCCGAGAUUGAACCGGGGUGUCUUGAAAAGUACU
UCGGACAGAGAAACAAUACUUGGGUGUGUACAUUUGGAACAUG
CGCGGCUCCGAUGGUACGUCUACCUACGCCACGUUUUUGGUCAC
CUGGAAAGGGGAUGAGAAGACAAGAAACCCUACGCCCGCAGUAA
CUCCUCAACCAAGAGGGGCUGAGUUUCAUAUGUGGAAUUACCAC
UCGCAUGUAUUUUCAGUUGGUGAUACGUUUAGCUUGGCAAUGC
AUCUUCAGUAUAAGAUACAUGAAGCGCCAUUUGAUUUGCUGUU
AGAGUGGUUGUAUGUCCCCAUCGAUCCUACAUGUCAACCAAUGC
GGUUAUAUUCUACGUGUUUGUAUCAUCCCAACGCACCCCAAUGC
CUCUCUCAUAUGAAUUCCGGUUGUACAUUUACCUCGCCACAUUU
AGCCCAGCGUGUUGCAAGCACAGUGUAUCAGAAUUGUGAACAUG
CAGAUAACUACACCGCAUAUUGUCUGGGAAUAUCUCAUAUGGAG
CCUAGCUUUGGUCUAAUCUUACACGACGGGGGCACCACGUUAAA
GUUUGUAGAUACACCCGAGAGUUUGUCGGGAUUAUACGUUUUU
GUGGUGUAUUUUAACGGGCAUGUUGAAGCCGUAGCAUACACUG
UUGUAUCCACAGUAGAUCAUUUUGUAAACGCAAUUGAAGAGCG
UGGAUUUCCGCCAACGGCCGGUCAGCCACCGGCGACUACUAAAC
CCAAGGAAAUUACCCCCGUAAACCCCGGAACGUCACCACUUCUA
CGAUAUGCCGCAUGGACCGGAGGGCUUGCAGCAGUAGUACUUUU
AUGUCUCGUAAUAUUUUUAAUCUGUACGGCUAAACGAAUGAGG
GUUAAAGCCGCCAGGGUAGACAAGUGAUAAUAGGCUGGAGCCUC
GGUGGCCAUGCUUCUUGCCCCUUGGGCCUCCCCCCCAGCCCCUCCU
CCCCUUCCUGCACCCGUACCCCCGUGGUCUUUGAAUAAAGUCUG
AGUGGGCGGCAAAAAAAAAAAAAAAAAAAAAAAAAAAAAAAAAAA
AAAAAAAAAAAAAAAAAAAAAAAAAAAAAAAAAAAAAAAAAAAA
AAAAAAAAAAAAAAAAAAAAAAAAAUCUAG

VZV-GE-
Truncated-
delete_from_574_-_Y569A
Variant 7

AUGGGGACAGUUAAUAAACCUGUGGUGGGGGGUAUUGAUGGGGU                   134
UCGGAAUUAUCACGGGAACGUUGCGUAUAACGAAUCCGGUCAGA
GCAUCCGUCUUGCGAUACGAUGAUUUUCACAUCGAUGAAGACAA
ACUGGAUACAAACUCCGUAUAUGAGCCUUACUACCAUUCAGAUC
AUGCGGAGUCUUCAUGGGUAAAUCGGGGAGAGUCUUCGCGUAC
AGCGUACGAUCAUAACUCACCUUAUAUAUGGCCACGUAAUGAUU
AUGAUGGAUUUUUAGAGAACGCACACGAACACCAUGGGGUGUA
UAAUCAGGGCCGUGGUAUCGAUAGCGGGGAACGGUUAAUGCAA
CCCACACAAAUGUCUGCACAGGAGGAUCUUGGGGACGAUACGGG
CAUCCACGUUAUCCCUACGUUAAACGGCGAUGACAGACAUAAAA
UUGUAAAUGUGGACCAACGUCAAUACGGUGACGUGUUUAAAGG
AGAUCUUAAUCCAAAACCCCAAGGCCAAAGACUCAUUGAGGUGU
CAGUGGAAGAAAAUCACCCGUUUUACUUUACGCGCACCGAUUCAG
CGGAUUUAUGGAGUCCGGUACACCGAGACUUGGAGCUUUUUGCC
GUCAUUAACCUGUACGGGAGACGCAGCGCCCGCCAUCCAGCAUA
UAUGUUUAAAGCAUACAACAUGCUUUCAAGACGUGGUGGUGGA
UGUGGAUUGCGCGGAAAAUACUAAAGAGGAUCAGUUGGCCGAA
AUCAGUUACCGUUUUCAAGGUAAGAAGGAAGCGGACCAACCGUG

TABLE 2-continued

GAUUGUUGUAAACACGAGCACACUGUUUGAUGAACUCGAAUUA
GACCCACCCGAGAUUGAACCGGGUGUCUUGAAAGUACUUCGGAC
AGAGAAACAAUACUUGGGUGUGUACAUUUGGAACAUGCGCGGC
UCCGAUGGUACGUCUACCUACGCCACGUUUUUGGUCACCUGGAA
AGGGGAUGAGAAGACAAGAAACCCUACGCCCGCAGUAACUCCUC
AACCAAGAGGGGCUGAGUUUCAUAUGUGGAAUUACCACUCGCAU
GUAUUUUCAGUUGGUGAUACGUUUAGCUUGGCAAUGCAUCUUC
AGUAUAAGAUACAUGAAGCGCCAUUUGAUUUGCUGUUAGAGUG
GUUGUAUGUCCCCAUCGAUCCUACAUGUCAACCAAUGCGGUUAU
AUUCUACGUGUUUGUAUCAUCCCAACGCACCCCAAUGCCUCUCU
CAUAUGAAUUCCGGUUGUACAUUUACCUCGCCACAUUUAGCCCA
GCGUGUUGCAAGCACAGUGUAUCAGAAUUGUGAACAUGCAGAU
AACUACACCGCAUAUUGUCUGGGAAUAUCUCAUAUGGAGCCUAG
CUUUGGUCUAAUCUUACACGACGGGGGCACCACGUUAAAGUUUG
UAGAUACACCCGAGAGUUUGUCGGGAUUAUACGUUUUUGUGGU
GUAUUUUAACGGGCAUGUUGAAGCCGUAGCAUACACUGUUGUA
UCCACAGUAGAUCAUUUUGUAAACGCAAUUGAAGAGCGUGGAU
UUCCGCCAACGGCCGGUCAGCCACCGGCGACUACUAAACCCAAG
GAAAUUACCCCCGUAAACCCCGGAACGUCACCACUUCUACGAUA
UGCCGCAUGGACCGGAGGGCUUGCAGCAGUAGUACUUUUAUGUC
UCGUAAUAUUUUUAAUCUGUACGGCUAAACGAAUGAGAGGGUUA
AGCCGCCAGGGUAGACAAGUGAUAAUAGGCUGGAGCCUCGGUGG
CCAUGCUUCUUGCCCCUUGGGCCUCCCCCCCAGCCCCUCCUCCCCU
UCCUGCACCCGUACCCCCGUGGUCUUUGAAUAAAGUCUGAGUGG
GCGGC

VZV-GE-                          G*AGAAGAAAUAUAAGAGCCACCAUGGGGGACAGUUAAUAAACCU    108
Truncated-                       GUGGUGGGCGUAUUGAUGGGGUUCGGAAUUAUCACGGGAACGU
delete_from_574_-_Y569A          UGCGUAUAACGAAUCCGUCGAGCAUCCGUCUUGCGAUACGAU
Variant 8                        GAUUUUCACAUCGAUGAAGACAAACUGGAUACAAACUCCGUAUA
                                 UGAGCCUUACUACCAUUCAGAUCAUGCGGAGUCUUUCAUGGGUAA
                                 AUCGGGGAGAGUCUUCGCGAAAGGCGUACGAUCAUAACUCACCU
                                 UAUAUAUGGCCACGUAAUGAUUAUGAUGGGAUUCUUAGAGAACG
                                 CACACGAACACCAUGGGGGUGUAUAAUCAGGGCCGUGGGUAUCGAU
                                 AGCGGGGAACGGUUAAUGCAACCCACACAAAUGUCUGCACAGGA
                                 GGAUCUUGGGGACGAUACGGGCAUCCACGUUAUCCCUACGUUAA
                                 ACGGCGAUGACGACAUAAGAUUGUAAAUGUGGACCAACGUCA
                                 AUACGGUGACGUGUUUAAAGGAGAUCUUAAUCCAAAGCCCCAAG
                                 GCCAAAGACUCAUUGAGGUGUCAGUGGAAGAGAAUCACCCGUUU
                                 ACUUUACGCGCACCGAUUCAGCGGAUUUAUGGAGUCCGGUACAC
                                 CGAGACUUGGAGCUUCUUGCCGUCAUUAACCUGUACGGGAGACG
                                 CAGCGCCCGCCAUCCAGCAUAUAUGUUUAAAGCAUACAACAUGC
                                 UUUCAAGACGUGGUGGUGGAUGUGGAUUGCGCGGAGAAUACUA
                                 AAGAGGAUCAGUUGGCCGAAAUCAGUUACCGUUUUCAAGGUAA
                                 GAAGGAAGCGGACCAACCGUGGAUUGUUGUAAACACGAGCACAC
                                 UGUUUGAUGAACUCGAAUUAGACCCACCCGAGAUUGAACCGGGU
                                 GUCUUGAAAGUACUUCGGACAGAGAAACAAUACUUGGGUGUGU
                                 ACAUUUGGAACAUGCGCGGCUCCGAUGGUACGUCUACCUACGCC
                                 ACGUUCUUGGUCACCUGGAAAGGGGAUGAGAAGACAAGAAACCC
                                 UACGCCCGCAGUAACUCCUCAACCAAGAGGGGCUGAGUUUCAUA
                                 UGUGGAAUUACCACUCGCAUGUAUUUUCAGUUGGUGAUACGUU
                                 UAGCUUGGCAAUGCAUCUUCAGUAUAAGAUACAUGAAGCGCCAU
                                 UUGAUUUGCUGUUAGAGUGGUUGUAUGUCCCCAUCGAUCCUACA
                                 UGUCAACCAAUGCGGUUAUAUUCUACGUGUUUGUAUCAUCCCAA
                                 CGCACCCCAAUGCCUCUCUCAUAUGAAUUCCGGUUGUACAUUUA
                                 CCUCGCCACAUUUAGCCCAGCGUGUUGCAAGCACAGUGUAUCAG
                                 AAUUGUGAACAUGCAGAUAACUACACCGCAUAUUGUCUGGGAA
                                 UAUCUCAUAUGGAGCCUAGCUUUGGUCUAAUCUUACACGACGGA
                                 GGCACCACGUUAAAGUUUGUAGAUACACCCGAGAGUUUGUCGGG
                                 AUUAUACGUCUUUGUGGUGUAUUUUAACGGGCAUGUUGAAGCC
                                 GUAGCAUACACUGUUGUAUCCACAGUAGAUCAUUUUGUAAACGC
                                 AAUUGAAGAGCGUGGAUUUCCGCCAACGGCCGGUCAGCCACCGG
                                 CGACUACUAAACCCAAGGAAAUUACGCCCGUAAACCCCGGAACG
                                 UCACCACUUCUACGAUAUGCCGCAUGGACCGGAGGGCUUGCAGC
                                 AGUAGUACUUUUAUGUCUCGUAAUAUUCUUAAUCUGUACGGCU
                                 AAACGAAUGAGGGUUAAAGCCGCCAGGGUAGACAAGUGAUAAU
                                 AGGCUGGAGCCUCGGUGGCCAUGCUUCUUGCCCCUUGGGCCUCC
                                 CCCCAGCCCCUCCUCCCCUUCCUGCACCCGUACCCCCGUGGUCUU
                                 UGAAUAAAGUCUGAGUGGGCGGCAAAAAAAAAAAAAAAAAAAA
                                 AAAAAAAAAAAAAAAAAAAAAAAAAAAAAAAAAAAAAAAAAA
                                 AAAAAAAAAAAAAAAAAAAAAAAAAAAAAAAAAAAAAUCUAG VZV-GE-                          G*GGGAAUAAGAGAGAAAGAAGAGUAAGAAGAAAUAUAAGA          141
Truncated-                       GCCACCAUGGGGGACAGUUAAUAAACCUGUGGUGGGCGUAUUGA
delete_from_574_-_Y569A          UGGGGUUCGGAAUUAUCACGGGAACGUUGCGUAUAACGAAUCC
Variant 8                        GGUCAGAGCAUCCGUCUUGCGAUACGAUGAUUUUCACAUCGAUG
(5'UTR includes                  AAGACAAACUGGAUACAAACUCCGUAUAUGAGCCUUACUACCAU
promoter region)                 UCAGAUCAUGCGGAGUCUUCAUGGGUAAAUCGGGGAGAGUCUU
                                 CGCGAAAGGCGUACGAUCAUAACUCACCUUAUAUAUGGCCACGU
                                 AAUGAUUAUGAUGGGAUUCUUAGAGAACGCACACGAACACCAUG TABLE 2-continued GGGUGUAUAAUCAGGGCCGUGGUAUCGAUAGCGGGGAACGGUU
AAUGCAACCCACACAAAUGUCUGCACAGGAGGAUCUUGGGGACG
AUACGGGCAUCCACGUUAUCCCUACGUUAAACGGCGAUGACAGA
CAUAAGAUUGUAAAUGUGGACCAACGUCAAUACGGUGACGUGU
UUAAAGGAGAUCUUAAUCCAAAGCCCCAAGGCCAAAGACUCAUU
GAGGUGUCAGUGGAAGAGAAUCACCCGUUUACUUUACGCGCACC
GAUUCAGCGGAUUUAUGGAGUCCGGUACACCGAGACUUGGAGCU
UCUUGCCGUCAUUAACCUGUACGGGAGACGCAGCGCCCGCCAUC
CAGCAUAUAUGUUUAAAGCAUACAACAUGCUUUCAAGACGUGG
UGGUGGAUGUGGAUUGCGCGGAGAAUACUAAAGAGGAUCAGUU
GGCCGAAAUCAGUUACCGUUUUCAAGGUAAGAAGGAAGCGGACC
AACCGUGGAUUGUUGUAAACACGAGCACUGUUUGAUGAACUC
GAAUUAGACCCACCCGAGAUUGAACCGGGUGUCUUGAAAGUACU
UCGGACAGAGAAACAAUACUUGGGUGUGUACAUUUGGAACAUG
CGCGGCUCCGAUGGUACGUCUACCUACGCCACGUUCUUGGUCAC
CUGGAAAGGGGAUGAGAAGACAAGAAACCCUACGCCCGCAGUAA
CUCCUCAACCAAGAGGGGCUGAGUUUCAUAUGUGGAAUUACCAC
UCGCAUGUAUUUUCAGUUGGUGAUACGUUUAGCUUGGCAAUGC
AUCUUCAGUAUAAGAUACAUGAAGCGCCAUUUGAUUUGCUGUU
AGAGUGGUUGUAUGUCCCCAUCGAUCCUACAUGUCAACCAAUGC
GGUUAUAUUCUACGUGUUUGUAUCAUCCCAACGCACCCCAAUGC
CUCUCUCAUAUGAAUUCCGGUUGUACAUUUACCUCGCCACAUUU
AGCCCAGCGUGUUGCAAGCACAGUGUAUCAGAAUUGUGAACAUG
CAGAUAACUACACCGCAUAUUGUCUGGGAAUAUCUCAUAUGGAG
CCUAGCUUUGGUCUAAUCUUACACGACGGAGGCACCACGUUAAA
GUUUGUAGAUACACCCGAGAGUUUGUCGGGAUUAUACGUCUUU
GUGGUGUAUUUUAACGGGCAUGUUGAAGCCGUAGCAUACACUG
UUGUAUCCACAGUAGAUCAUUUUGUAAACGCAAUUGAAGAGCG
UGGAUUUCCGCCAACGGCCGGUCAGCCACCGGCGACUACUAAAC
CCAAGGAAAUUACGCCCGUAAACCCCGGAACGUCACCACUUCUA
CGAUAUGCCGCAUGGACCGGAGGGCUUGCAGCAGUAGUACUUUU
AUGUCUCGUAAUAUUCUUAAUCUGUACGGCUAAACGAAUGAGG
GUUAAAGCCGCCAGGGUAGACAAGUGAUAAAUAGGCUGGAGCCUC
GGUGGCCAUGCUUCUUGCCCCUUGGGCCUCCCCCCAGCCCCUCCU
CCCCUUCCUGCACCCGUACCCCCGUGGUCUUUGAAUAAAGUCUG
AGUGGGCGGCAAAAAAAAAAAAAAAAAAAAAAAAAAAAAAAAA
AAAAAAAAAAAAAAAAAAAAAAAAAAAAAAAAAAAAAAAAAAA
AAAAAAAAAAAAAAAAAAAAAAUCUAG VZV-GE-Truncated-
delete from_574_-_Y569A
Variant 9

G*GGGAAAUAAGAGAGAAAAGAAGAGUAAGAAGAAAUAUAAGA          137
GCCACCAUGGGCACCGUGAACAAGCCUGUUGUGGGCGUGCUGAU
GGGCUUCGGCAUCAUCACAGGCACCCUGCGGAUCACCAAUCCUG
UGCGGGCUAGCGUGCUGAGAUACGACGACUUCCACAUCGACGAG
GACAAGCUGGACACCAACAGCGUGUACGAGCCCUACUACCACAG
CGAUCACGCCGAGUCUAGCUGGGGUCAACAGAGGCGAGAGCAGCA
GAAAGGCCUACGACCAGAACGCCCUUACAUCUGGCCCAGAAAC
GACUACGACGGCUUCCUCGAGAAUGCCCACGAACACCACGGCGU
GUACAAUCAAGGCAGAGGCAUCGACAGCGGCGAGAGACUGAUGC
AGCCUACACAGAUGAGCGCCCAAGAGGACCUGGGAGAUGAUACC
GGCAUCCACGUGAUCCCUACACUGAACGGCGACGACCGGCACAA
GAUCGUGAACGUGGACCAGAGACAGUACGGCGACGUGUUCAAGG
GCGACCUGAAUCCUAAGCCUCAGGGCCAGCGCCUGAUCGAGGUU
UCCGUGGAAGAGAAUCACCCUUUCACACUGCGGGCUCCCAUCCA
GAGAAUCUACGGCGUGCGCUAUACCGAGACAUGGUCCUUUCUGC
CCAGCCUGACAUGUACCGGCGACGCCGCUCCUGCCAUCCAGCAC
AUUUGUCUGAAGCACACCACCUGUUUCCAGGACGUGGUGGUGGA
UGUGGACUGCGCCGAGAACACCAAAGAGGAUCAGCUGGCCGAGA
UCAGCUACCGGUUCCAGGGAAAGAAAGAGGCCGACCAGCCUUGG
AUCGUGGUCAACACCAGCACACUGUUCGACGAGCUGGAACUGGA
CCCUCCUGAGAUUGAACCCGGCGUCCUGAAGGUGCUGAGAACCG
AGAAGCAGUACCUGGGAGUGUACAUCUGGAACAUGAGAGGCAG
CGACGGCACCUCUACCUACGCCACCUUUCUGGUCACAUGGAAGG
GCGACGAAGACCAGAAAUCCCACACCAGCCGUGACACCUCAG
CCUAGAGGCGCCGAAUUUCACAUGUGGAACUACCACUCUCACGU
GUUCAGCGUGGGCGAUACCUUCAGCCUGGCCAUGCAUCUGCAGU
ACAAGAUCCACGAGGCUCCCUUCGACCUGCUGCUGGAAUGGCUG
UACGUGCCCAUCGAUCCUACCUGCCAGCCUAUGCGGCUGUACUC
CACCUGUCUGUAUCACCCUAACGCUCCUCAGUGCCUGAGCCACA
UGAAUAGCGGCUGCACCUUCACAAGCCCUCACCUGGCUCAGCGA
GUGGCCAGCACAGUGUACCAGAAUUGCGAGCACGCCGACAAUUA
CACCGCCUACUGUCUGGGGCAUCAGCCACAUGGAACCUAGCUUCG
GCCUGAUCCUGCACGAUGGCGGCACCACACUGAAGUUCGUGGAC
ACACCUGAGAGCCUGAGCGGCCUGUAUGUGUUUGUGGGUGUACUU
CAACGGCCACGUGGAAGCCGUGGCCUACACCGUGGUGUCUACCG
UGGACCACUUCGUGAACGCCAUCGAGGAAAGAGGCUUCCCUCCA
ACUGCUGGACAGCCUCCUGCCACCACCAAGCCUAAAGAAAUCAC
AACCCGUGAAUCCCGGCACUAGCCCUCUGCUUAGAUACGCCGCUU
GGACAGGCGGACUGGCUGCUGUUGUUCUGCUGUGCCUGGUCAUC
UUCCUGAUCUGCACCGCCAAGCGGAUGAGAGUGAAAGCCGCCAG
AGUGGACAAGUGAUAAUAGGCUGGAGCCUCGGUGGCCAUGCUUC

TABLE 2-continued

```
UUGCCCCUUGGGCCUCCCCCCAGCCCCUCCUCCCCUUCCUGCACC
CGUACCCCCGUGGUCUUUGAAUAAAGUCUGAGUGGGCGGCAAAA
AAAAAAAAAAAAAAAAAAAAAAAAAAAAAAAAAAAAAAAAAAAAA
AAAAAAAAAAAAAAAAAAAAAAAAAAAAAAAAAAAAAAAAAAAAA
AAAAAAAAAAUCUAG
```

G* represents a 5' terminal cap, e.g., 7 mG(5')ppp(5')N1mpNp
All mRNAs contains a 5'-UTR, a 3'UTR, and a polyA tail.
5'-UTR: GGGAAAUAAGAGAGAAAAGAAGAGUAAGAAGAAAUAUAAGAGCCACC (SEQ ID NO: 138)
3'-UTR: UGAUAAUAGGCUGGAGCCUCGGUGGCCAUGCUUCUUGCCCCUUGGGCCUCCCCCCAGCCC-
CUCCUCCCCUUCCUGCACCCGUACCCCCGUGGUCUUUGAAUAAAGUCUGAGUGGGCGGC (SEQ ID NO: 139)
polyA tail: AAAAAAAAAAAAAAAAAAAAAAAAAAAAAAAAAAAAAAAAAAAAAAAAAAAAAAAAAAAAAAAAAAAAAAAAAAAAAAAAAAAUCUAG (SEQ
ID NO: 140)

It should also be understood that the 5' and/or 3' UTR for each construct may be omitted, modified or substituted for a different UTR sequences in any one of the vaccines as provided herein.

Example 14: Variant gE Antigen Distribution in Vero and Mewo Cells

The expression and trafficking of VZV gE antigens having different C terminal variants was investigated in Vero cells and Mewo cells.

Figure 9A:
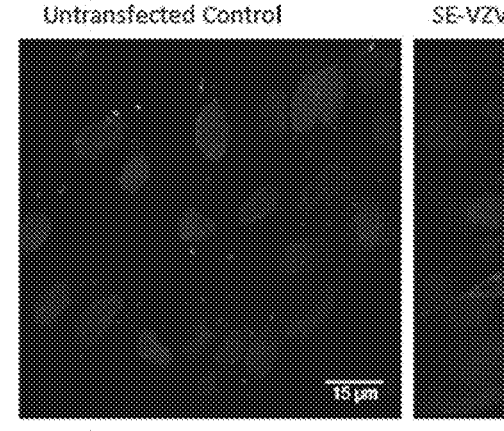
FIGS. 9A-9C show confocal microscopy of MeWo cells stained with antibodies against VZV gE to show VZV gE expression and trafficking. The sequence AEAADA depicted in FIG. 9C is SEQ ID NO: 58.
Figure 9B:
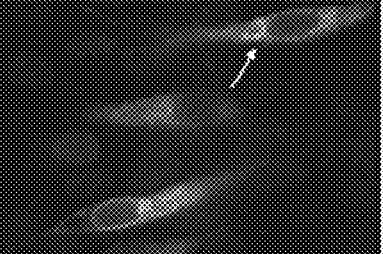
Figure 9C:
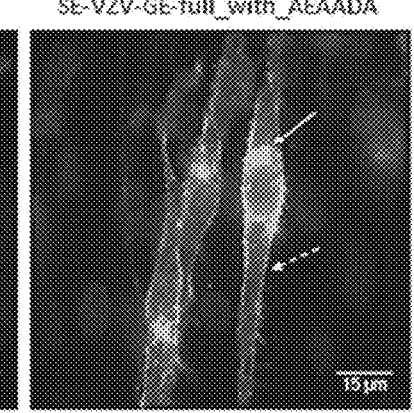
Figure 10A:
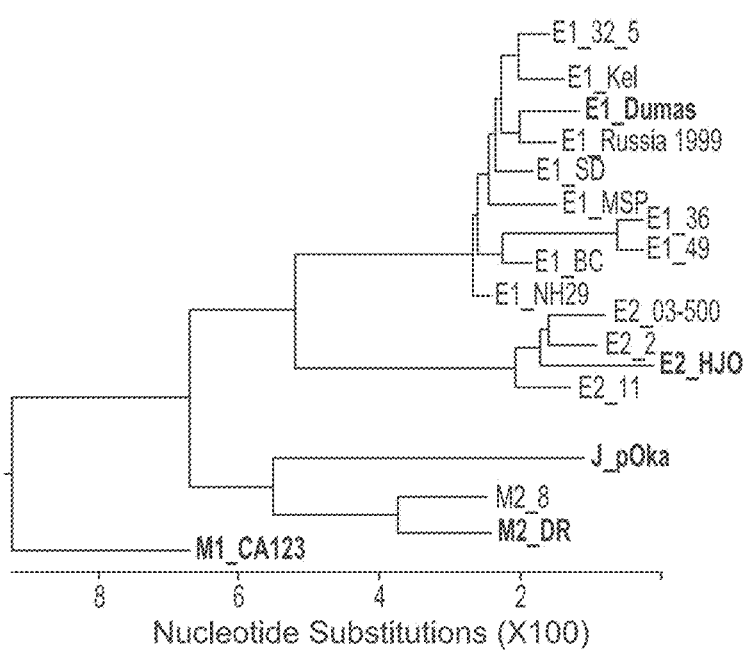
FIGS. 10A and 10B are schematics depicting various VZV wildtype genotypes.
Figure 10B:
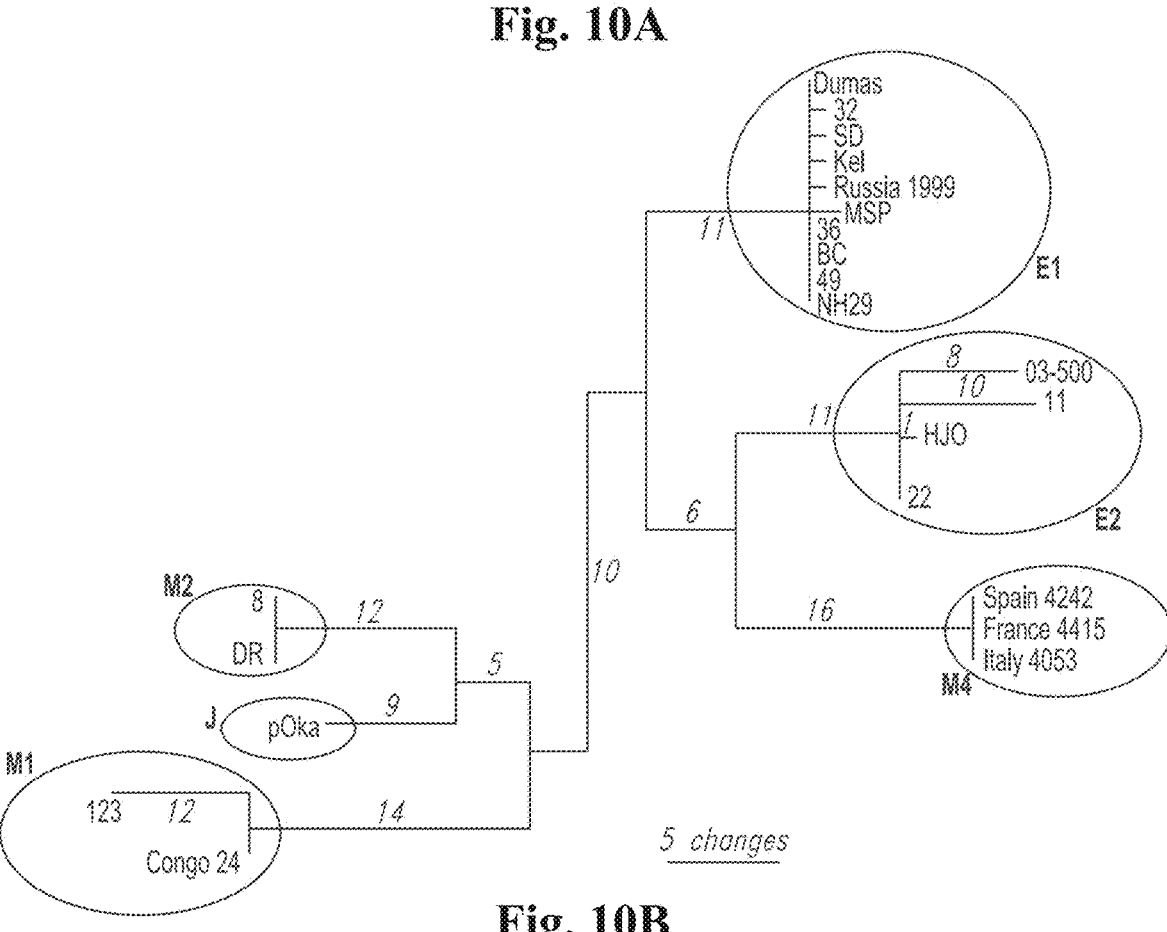

Vero cells are lineages of cells used in cell cultures. The 'Vero' lineage was isolated from kidney epithelial cells extracted from an African green monkey. MeWo cells are human malignant melanoma cells that are susceptible to VZV infection. Vero cells or Mewo cells were transfected with the constructs indicated below in Table 3. The transfected cells were stained with antibodies for gE and for golgi markers GM 130 and golgin. Confocal microscopy was used to visualize the stained cells. The results for the constructs are described in Table 3 ("Cellular localization" column). FIG. 9 provides an exemplary experiment, which shows the results of the following transfected constructs: (1) VZV gE mRNA encoding a VZV gE polypeptide having a 62 amino acid deletion at the C-terminus (encoded by SEQ ID NO: 3); (2) full-length VZV gE mRNA encoding a VZV gE polypeptide having the AEAADA sequence (SEQ ID NO: 58) (encoded by SEQ ID NO: 7); or (3) PBS (as negative control). Using an anti-gE antibody, FIG. 9 shows that the truncated VZV gE polypeptide (having the 62 amino acid C-terminal deletion) localizes to a perinuclear location and organelles. The full-length VZV gE polypeptide having AEAADA sequence (SEQ ID NO: 58) was localized to the golgi and a perinuclear location. Importantly, several of the constructs, e.g., gE-truncated-delete_from_574_Y569A, gE full length with AEAADA (SEQ ID NO: 58), gE full length with AEAADA (SEQ ID NO: 58) and Y582C mutation, gE-truncated-delete_from_574, and gE-truncated-delete_from_574 with Y569A mutation each encoded polypeptides that localized to the cell membrane, indicating that these polypeptides may have enhanced antigenicity.

TABLE 3

Summary of Results for Cellular Trafficking of Variant VZV gE Polypeptides

| Construct | Experimental conditions | Expression | Cellular localization |
|---|---|---|---|
| Full length gE | Vero cells- 500 ng/well, transfected 24 h transfection (C8) Construct = Full length GE | + | shows Golgi localization |
| GE-full with AEAADA (SEQ ID NO: 58) | Vero cells- 500 ng/well, transfected 24 h transfection (C1)- Construct = VZV-GE-full with AEAADA (SEQ ID NO: 58) | +++ | shows Golgi localization and diffuse perinuclear |
| GE-full with AEAADA (SEQ ID NO: 58) and Y582C | Vero cells- 500 ng/well, transfected 24 h transfection (C6) Construct = VZV-GE full_with_AEAADA (SEQ ID NO: 58)_and_Y582G | low | shows organelles and cytoplasmic localization |
| GE-delete-562 | Vero cells- 500 ng/well, transfected 24 h transfection (C2)- Construct = C2 VZV-GE-delete-562 | + | shows perinuclear and organelles |
| GE-delete-562-replaced SP-with IgKappa | Vero cells- 500 ng/well, transfected 24 h transfection (C5) VZV-GE-delete-562-replacedSignal Peptide-with IgKappa | +++ | shows golgi localization and cytoplasmic |
| GE-truncated-delete_from_574 | Vero cells- 500 ng/well, transfected 24 h transfection (C4) - Construct = VZV-GE-truncated-delete_from_574 | ++ | shows Golgi and cytoplasmic localization |
| GE-truncated-delete_from_574_Y569A | Vero cells- 500 ng/well, transfected 24 h transfection (C3)- Construct = VZV-GE-truncated-delete_from_574_Y569A | +++ | shows Golgi and cell membrane localization |
| Full length gE | MeWo cells- 500 ng/well, transfected 24 h transfection (C8) Construct = Full length GE | +++ | shows Golgi localization |

TABLE 3-continued

Summary of Results for Cellular Trafficking of Variant VZV gE Polypeptides

| Construct | Experimental conditions | Expression | Cellular localization |
|---|---|---|---|
| GE-full with AEAADA (SEQ ID NO: 58) | MeWo cells- 500 ng/well, transfected 24 h transfection (C1)- Construct = VZV-GE-full with AEAADA (SEQ ID NO: 58) | +++ | shows Golgi and Membrane localization |
| GE-full with AEAADA (SEQ ID NO: 58) and Y582C | MeWo cells- 500 ng/well, transfected 24 h transfection (C6) Construct = SE-VZV-GE full_with_AEAADA (SEQ ID NO: 58)_and_Y582G | ++ | shows golgi and cell membrane localization |
| GE-delete-562 | MeWo cells- 500 ng/well, transfected 24 h transfection (C2)- Construct = C2 VZV-GE-delete-562 | +++ | shows perinuclear and cytoplasmic localization |
| GE-delete-562-replaced SP-with Ig Kappa | MeWo cells- 500 ng/well, transfected 24 h transfection (C5) VZV-GE-delete-562-replacedSignal Peptide with IgKappa | +++ | shows golgi localization and cytoplasmic |
| GE-truncated-delete_from_574 | MeWo cells- 500 ng/well, transfected 24 h transfection (C4) - Construct = -VZV-GE-truncated-delete_from_574 | +++ | shows Golgi and cell membrane localization |
| GE-truncated-delete_from_574_Y569A | MeWo cells- 500 ng/well, transfected 24 h transfection (C3)- Construct = VZV-GE-truncated-delete_from_574_Y569A | +++ | shows Golgi and cell membrane localization |

Example 15: Immunization of BALB/C Mice with MC3 Formulated mRNA Encoded VZV gE Antigens An immunization study was conducted as an initial evaluation of the effect of MC3-formulated mRNAs encoding VZV antigens as vaccine candidates to achieve immunization in BALB/C mice post intramuscular or intradermal administration.

The candidate vaccines were as follows:

(1) MC3 formulated VZVgE-hIg kappa mRNA having 5' cap: m7G(5')ppp(5')G-2'-O-methyl, N1-methylpseudouridine chemical modification, and the additional hIg Kappa sequence.

(2) MC3 formulated VZV gE mRNA having 5' cap: m7G(5')ppp(5')G-2'-O-methyl and N1-methylpseudouridine chemical modification.

(3) MC3 formulated VZVgE mRNA having 5' cap: m7G (5')ppp(5')G-2'-O-methyl and no chemical modification.

All of the VZV gE mRNAs were strain Oka.

BALB/C mice were given a single 10 µg dose or two 10 µg doses (at day 28) of MC3 formulated VZV gE mRNA (either vaccine (1), (2), or (3) described above) either intramuscularly or intradermally. G5 refers mRNA having N1-methylpseudouridine chemical modification. GO refers to unmodified mRNA. Cap 1 refers to 5' cap: m7G(5')ppp (5')G-2'-O-methyl. Each treatment group contained eight mice. The positive control was VARIVAX® vaccine and the negative control was PBS.

Figure 2:
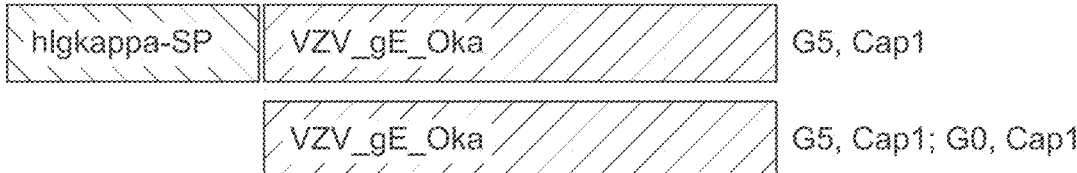
FIG. 2 is a schematic of the constructs encoding VZV gE (strain Oka).

Blood samples were taken to determine the presence/level of serum protein and antibodies. Western blots were performed to detect VZV-gE protein expression at six hours and ELISAs were performed to detect mouse IgGs. Schematics of the constructs encoding VZV gE (strain Oka) are shown in FIG. 2. Schematics of the study's design and schedule of injection are shown in FIG. 3 and Table 3. Table 4 shows the various time points for collection of different samples. Blood was collected for serum protein and antibody determination, while VZV protein expression was surveyed 6 hours post-dosing on day 0 for groups 1-4, 13, and 14, and 6 hours post-dosing on day 28 for groups 2, 4, and 14. Antibody detection assays were performed on day −3, day 14, day 27, day 42, and day 56.

TABLE 4

Injection Schedule

| G# Antigen | Route | N= | Dose (µg) | Dose Vol (µl) | 1$^{st}$ dose | 2$^{nd}$ dose | LNP | mRNA Conc. (mg/ml) | Volume + Overage |
|---|---|---|---|---|---|---|---|---|---|
| 1 VZV-gE-oka-hIgkappa (G5; cap1) (SEQ ID NO: 93) | IM | 8 | 10 | 50 | Day 0 | | MC3 | 0.2 | 1 × 600 µl |
| 2 VZV-gE-oka-hIgkappa (G5; cap1) | IM | 8 | 10 | 50 | Day 0 | Day 28 | MC3 | 0.2 | 2 × 600 µl |

TABLE 4-continued

| | | | | | | | | | | |
|---|---|---|---|---|---|---|---|---|---|---|
| | | | | Injection Schedule | | | | | | |
| G# | Antigen | Route | N= | Dose (µg) | Dose Vol (µl) | 1$^{st}$ dose | 2$^{nd}$ dose | LNP | mRNA Conc. (mg/ml) | Volume + Overage |
| 3 | VZV-gE-oka-hIgkappa (G5; cap1) | ID | 8 | 10 | 50 | Day 0 | | MC3 | 0.2 | 1 × 600 µl |
| 4 | VZV-gE-oka-hIgkappa (G5; cap1) | ID | 8 | 10 | 50 | Day 0 | Day 28 | MC3 | 0.2 | 2 × 600 µl |
| 5 | VZV-gE-oka (G0; cap1) (SEQ ID NO: 92) | IM | 8 | 10 | 50 | Day 0 | | MC3 | 0.2 | 1 × 600 µl |
| 6 | VZV-gE-oka (G0; cap1) | IM | 8 | 10 | 50 | Day 0 | Day 28 | MC3 | 0.2 | 2 × 600 µl |
| 7 | VZV-gE-oka (G0; cap1) | ID | 8 | 10 | 50 | Day 0 | | MC3 | 0.2 | 1 × 600 µl |
| 8 | VZV-gE-oka (G0; cap1) | ID | 8 | 10 | 50 | Day 0 | Day 28 | MC3 | 0.2 | 2 × 600 µl |
| 9 | VZV-gE-oka (G5; cap1) | IM | 8 | 10 | 50 | Day 0 | | MC3 | 0.2 | 1 × 600 µl |
| 10 | VZV-gE-oka (G5; cap1) | IM | 8 | 10 | 50 | Day 0 | Day 28 | MC3 | 0.2 | 2 × 600 µl |
| 11 | VZV-gE-oka (G5; cap1) | ID | 8 | 10 | 50 | Day 0 | | MC3 | 0.2 | 1 × 600 µl |
| 12 | VZV-gE-oka (G5; cap1) | ID | 8 | 10 | 50 | Day 0 | Day 28 | MC3 | 0.2 | 2 × 600 µl |
| 13 | Negative control (PBS) | IM | 6 | / | 50 | Day 0 | | PBS | / | 1 × 600 µl |
| 14 | Negative control (PBS) | IM | 6 | / | 50 | Day 0 | Day 28 | PBS | / | 2 × 600 µl |
| 15 | Positive control (VARIVAX ®) | SC | 6 | 54 (pfu) | 50 | Day 0 | | | / | 1 × 1250 µl |
| 16 | Positive control (VARIVAX ®) | SC | 6 | 54 (pfu) | 50 | Day 0 | Day 28 | | / | |
| 17 | Positive control (VARIVAX ®) | SC | 4 | 675 (pfu) | 100 | Day 0 | | | / | 4 × 220 µl |
| 18 | Positive control (VARIVAX ®) | SC | 4 | 675 (pfu) | 100 | Day 0 | Day 28 | | / | |

TABLE 5

| | | | | | | | | |
|---|---|---|---|---|---|---|---|---|
| | | | | Schedule of Sample Collection | | | | |
| G# | Antigen | Pre-bleed | Day 0 + 6 h | Day 14 | Day 27 | Day 28 + 6 h | Day 42 | Day 56 |
| 1 | N7N-gE-oka-hIgkappa (G5; cap1) | ✓ | ✓ | ✓ | ✓ | | ✓ | ✓ |
| 2 | N7N-gE-oka-hIgkappa (G5; cap1) | ✓ | ✓ | ✓ | ✓ | ✓ | ✓ | ✓ |
| 3 | VZV-gE-oka-hIgkappa (G5; cap1) | ✓ | | ✓ | ✓ | | ✓ | ✓ |
| 4 | VZV-gE-oka-hIgkappa (G5; cap1) | ✓ | | ✓ | ✓ | | ✓ | ✓ |
| 5 | VZV-gE-oka (G0; cap1) | ✓ | | ✓ | ✓ | | ✓ | ✓ |
| 6 | VZV-gE-oka (G0; cap1) | ✓ | | ✓ | ✓ | | ✓ | ✓ |
| 7 | VZV-gE-oka (G0; cap1) | ✓ | | ✓ | ✓ | | ✓ | ✓ |
| 8 | VZV-gE-oka (G0; cap1) | ✓ | | ✓ | ✓ | | ✓ | ✓ |
| 9 | VZV-gE-oka (G5; cap1) | ✓ | | ✓ | ✓ | | ✓ | ✓ |
| 10 | VZV-gE-oka (G5; cap1) | ✓ | | ✓ | ✓ | | ✓ | ✓ |
| 11 | VZV-gE-oka (G5; cap1) | ✓ | | ✓ | ✓ | | ✓ | ✓ |
| 12 | VZV-gE-oka (G5; cap1) | ✓ | | ✓ | ✓ | | ✓ | ✓ |
| 13 | PBS | ✓ | ✓ | ✓ | ✓ | | ✓ | ✓ |
| 14 | PBS | ✓ | ✓ | ✓ | ✓ | ✓ | ✓ | ✓ |

TABLE 5-continued

| | | Schedule of Sample Collection | | | | | | |
|---|---|---|---|---|---|---|---|---|
| G# | Antigen | Pre-bleed | Day 0 + 6 h | Day 14 | Day 27 | Day 28 + 6 h | Day 42 | Day 56 |
| 15 | Positive control | ✓ | | ✓ | ✓ | | ✓ | ✓ |
| 16 | Positive control | ✓ | | ✓ | ✓ | | ✓ | ✓ |
| 17 | Positive control | ✓ | | ✓ | ✓ | | ✓ | ✓ |
| 18 | Positive control | ✓ | | ✓ | ✓ | | ✓ | ✓ |

Example 16: Immunogenicity Study—ELISA

The instant studies were designed to test the immunogenicity in BALB/C mice of candidate VZV vaccines comprising a mRNA polynucleotide encoding glycoprotein gE from VZV. Mice were immunized with various VZV mRNA vaccine formulations at set intervals, and sera were collected after each immunization. The immunization schedule is provided in Table 2 of Example 15. The sera collection schedule is set forth in Table 4 of Example 15.

Enzyme-linked immunosorbent assay (ELISA) Serum antibody titers against VZV glycoprotein E were determined by Enzyme-linked immunosorbent assay (ELISA) using standard methods. In one study, the amount of anti-VZV gE mouse IgG was measured in the pre-bleed and in serum collected at day 14 and day 42 post vaccination in mice vaccinated intramuscularly with two 10 μg doses of either: (1) VZV-gE-hIgkappa (SEQ ID NO: 93) having 5' cap: m7G(5')ppp(5')G-2'-O-methyl and N1-methylpseudouridine chemical modification (#1 in Tables 2 and 3); (2) VZV-gE (SEQ ID NO: 135) having 5' cap: m7G(5')ppp(5')G-2'-O-methyl, and no chemical modification (#6 in Tables 2 and 3) (SEQ ID NO: 135); (3) VZV-gE having 5' cap: m7G(5')ppp (5')G-2'-O-methyl and N1-methylpseudouridine chemical modification (#10 in Tables 2 and 3); (4) VARIVAX® vaccine (positive control); or (5) PBS (negative control).

Figure 6:
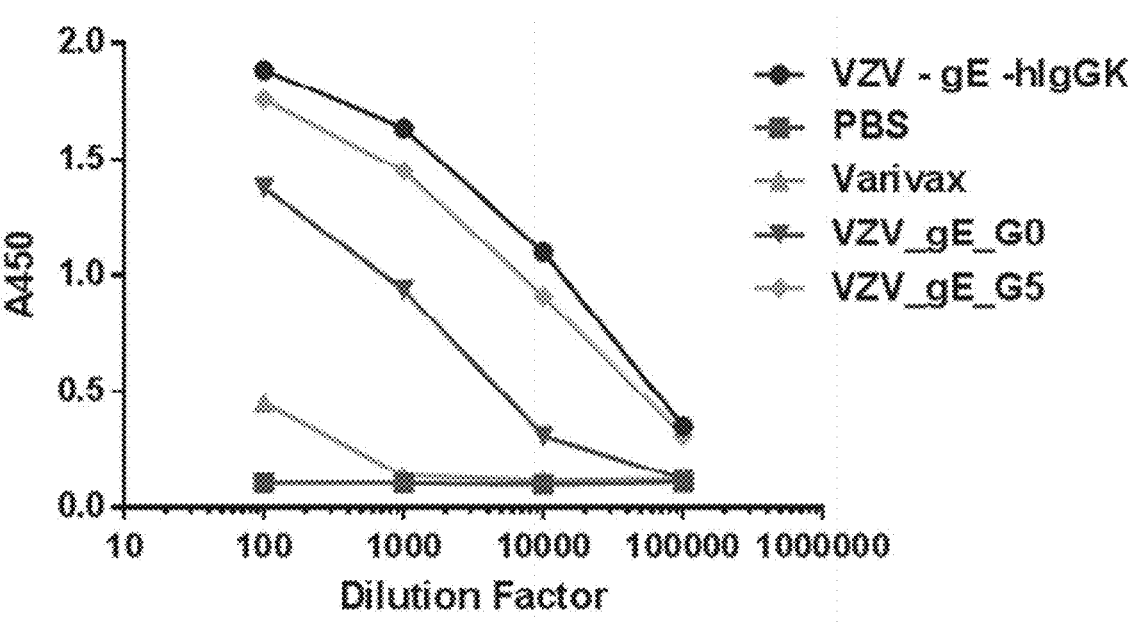
FIG. 6 is a graph showing the results of an ELISA assay indicating the levels of anti-VZV gE IgG in the serum of mice vaccinated with various VZV gE mRNAs in comparison with VARIVAX® vaccine.
Figure 7:
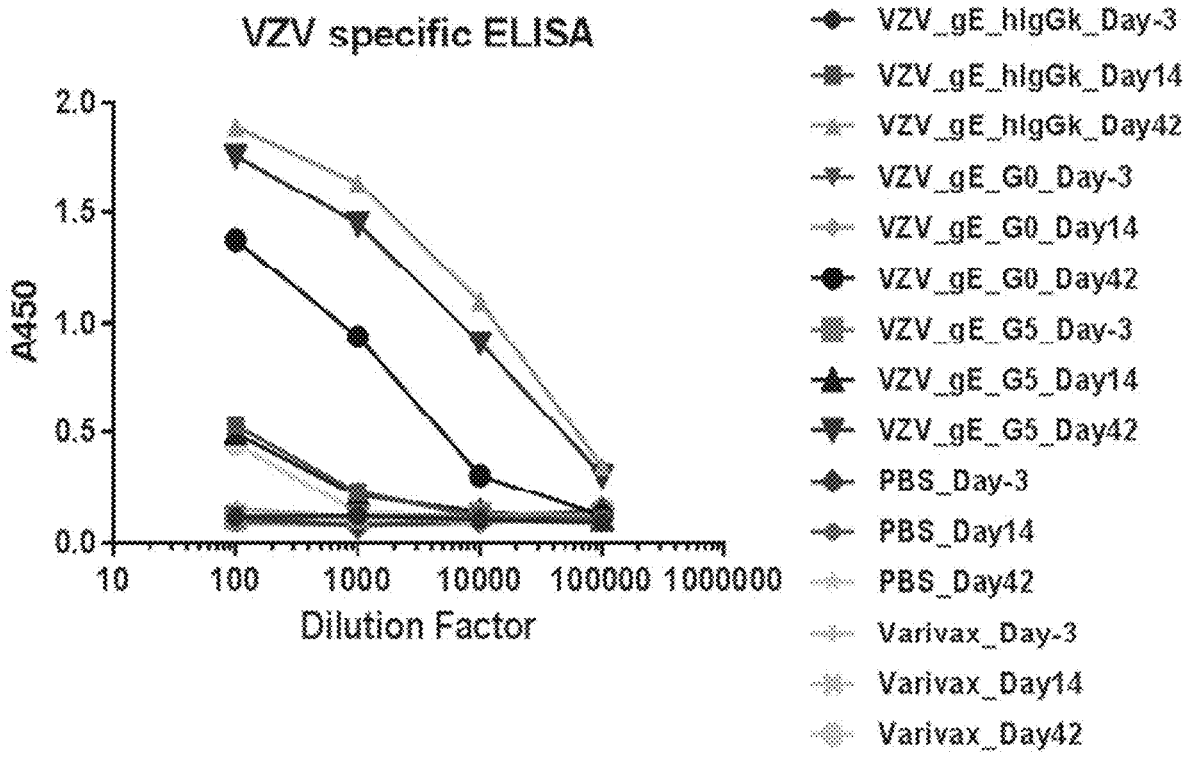
FIG. 7 is a graph showing the results of an ELISA assay indicating the levels of anti-VZV gE IgG in the serum of mice vaccinated with various VZV gE mRNAs in comparison with VARIVAX© vaccine.
Figure 8A:
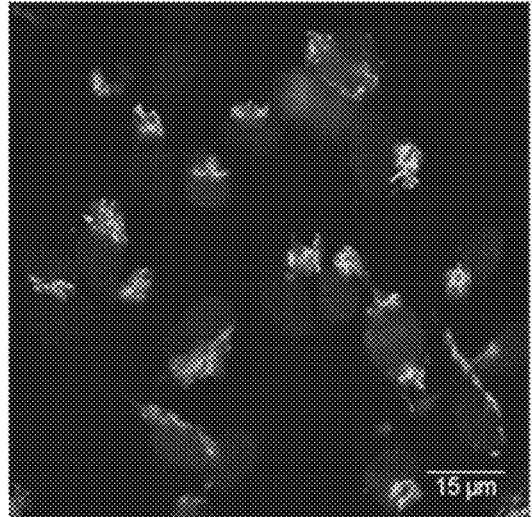
FIGS. 8A and 8B show confocal microscopy of human melanoma (MeWo) cells stained with an antibodies to show the golgi apparatus.
Figure 8B:
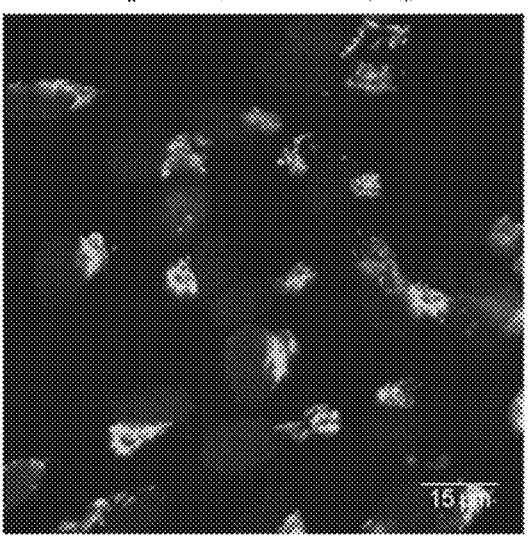

FIGS. 5-7 show that there was a very strong immune response with all mRNA encoded VZV-gE vaccines tested relative to the current VARIVAX® vaccine. FIG. 5 shows that at day 14, the titer for anti-VZV-gE IgG was about 10 μg/mL in the serum of mice vaccinated with vaccine candidate (1) VZV-gE-hIgkappa having 5' cap: m7G(5')ppp(5')G-2'-O-methyl and N1-methylpseudouridine chemical modification and about 50 μg/mL in the serum of mice vaccinated with vaccine candidate (3) VZV-gE having 5' cap: m7G(5')ppp(5')G-2'-O-methyl and N1-methylpseudouridine chemical modification. The level of anti-VZV-gE IgG in the serum of mice vaccinated with VARIVAX® was not detectable at day 14. At day 42, the amount of anti-VZV-gE IgG present in the serum of mice vaccinated with vaccine candidate (1) VZV-gE-hIgkappa having 5' cap: m7G(5')ppp (5')G-2'-O-methyl and N1-methylpseudouridine chemical modification or vaccine candidate (3) VZV-gE having 5' cap: m7G(5')ppp(5')G-2'-O-methyl and N1-methylpseudouridine chemical modification was almost 1000-fold greater than the amount of anti-VZV-gE IgG present in the serum of mice vaccinated with VARIVAX®. The amount of anti-VZV gE IgG present in the serum of mice vaccinated with vaccine candidate (2) VZV-gE having 5' cap: m7G(5')ppp(5')G-2'-O-methyl and no chemical modification was almost 100-fold greater than the amount of anti-VZV-gE IgG present in the serum of mice vaccinated with VARIVAX®. This study indicates that each of the VZV gE mRNA vaccines tested is a more immunogenic vaccine that the current VARIVAX® VZV vaccine.

Example 17: Immunogenicity Study—ELISA

The instant studies were designed to test the immunogenicity in BALB/C mice of candidate VZV vaccines comprising a mRNA polynucleotide encoding glycoprotein gE from VZV. Mice were immunized with various VZV mRNA vaccine formulations at set intervals, and sera were collected after each immunization. The immunization schedule is provided in Table 4 of Example 15. The sera collection schedule is set forth in Table 5 of Example 15.

Serum antibody titers against VZV glycoprotein E was determined by Enzyme-linked immunosorbent assay (ELISA) using standard methods. In a second expanded study, the serum samples were serially diluted to bring the signal within the scope of detectability using ELISA. The amount of anti-VZV gE mouse IgG was measured in serum collected at day 42 post vaccination in mice vaccinated intramuscularly with two 10 μg doses of either: (1) VZV-gE-hIgkappa having 5' cap: m7G(5')ppp(5')G-2'-O-methyl and N1-methylpseudouridine chemical modification (#1 in Tables 2 and 3); (2) VZV-gE having 5' cap: m7G(5')ppp(5') G-2'-O-methyl and no chemical modification (#6 in Tables 2 and 3); (3) VZV-gE having 5' cap: m7G(5')ppp(5')G-2'-O-methyl and N1-methylpseudouridine chemical modification (#10 in Tables 2 and 3); (4) VARIVAX® vaccine (positive control); or (5) PBS (negative control). The concentration of anti-VZV-gE mouse IgG was measured in 10-fold serial dilutions.

FIG. 6 shows that the strongest immune response was found in mice vaccinated with vaccine candidate (1) VZV-gE-hIgkappa having 5' cap: m7G(5')ppp(5')G-2'-O-methyl and N1-methylpseudouridine chemical modification. The second strongest response was found in mice vaccinated with vaccine candidate (3) VZV-gE having 5' cap: m7G(5') ppp(5')G-2'-O-methyl and N1-methylpseudouridine chemical modification. The third strongest response was found in mice vaccinated with vaccine candidate (2) VZV-gE having 5' cap: m7G(5')ppp(5')G-2'-O-methyl and no chemical modification. All three VZV gE mRNA vaccines generated a significantly greater immune response than VARIVAX® vaccine.

FIG. 7 shows the amount of anti-VZV-gE mouse IgG present in mice vaccinated with vaccines (1)-(4) and (5) negative control at day 3, day 14, and day 42 post-vaccination.

Example 18: Immunogenicity Study

The instant studies are designed to test the immunogenicity in BALB/C mice of candidate VZV vaccines comprising a mRNA polynucleotide encoding variant glycoprotein gE from VZV. Mice were immunized with various VZV mRNA vaccine formulations at set intervals, and sera were collected after each immunization at indicated time points.

The immunization schedule is provided in Table 6 below. The sera collection schedule is set forth in Table 7 below.

The amount of anti-VZV gE mouse IgG is measured in serum collected at the times indicated in Table 7 post vaccination in mice vaccinated intramuscularly with two 10 μg or 2 μg doses of the indicated constructs. All mRNAs used have the 5' cap: m7G(5')ppp(5')G-2'-O-methyl and N1-methylpseudouridine chemical modification. ZOSTA-VAX® was used as a positive control and was injected into mice intramuscularly with twice clinical dose of 19400 pfu SC. PBS was used as negative control.

Antibody titers against the VZV gE variant polypeptides in the sera of mice immunized with VZV gE variant mRNA vaccines indicated in Table 6 were determined by enzyme-linked immunosorbent assay (ELISA). To perform the ELISA, wells of a plate were coated with VZV gE antigen (Abcam: ab43050) in PBS. 100 μl of the VZV gE antigen at a concentration of 1, 2, or 4 μg/ml were used for coating overnight at 4° C. The wells were then washed with 300 μl of PBST (PBS with 0.05% tween) 3 times. The VZV gE-coated wells were blocked with 200 μl of blocking butter containing 1% Blotto in PBS for 30 minutes at room temperature. Mice sera containing anti-VZV gE antibodies were diluted 1:2000 and then subject to 1:3 serial dilutions using PBST. The diluted sera were added to the VZV gE-coated wells and incubated for 1 hour at room temperature. A secondary antibody, rabbit anti-mouse conjugated to horseradish peroxidase (HRP, Abcam: ab6728) was diluted 1:1000 in PBST and 100 μl of the secondary antibody containing solution was added to the wells and incubated for 45 minutes at room temperature. 100 μl of HRP substrates, KPL TMB, were added the wells and incubated for 3 minutes at room temperature before 100 μl of a stop solution (2M $H_2SO_4$) was added to stop the HRP reaction. Signals generated from the HRP substrates were measured at A450. The results were shown in FIGS. 11A, 11B, 12A, 12B, 13 and Tables 8 and 9.

Figure 11A:
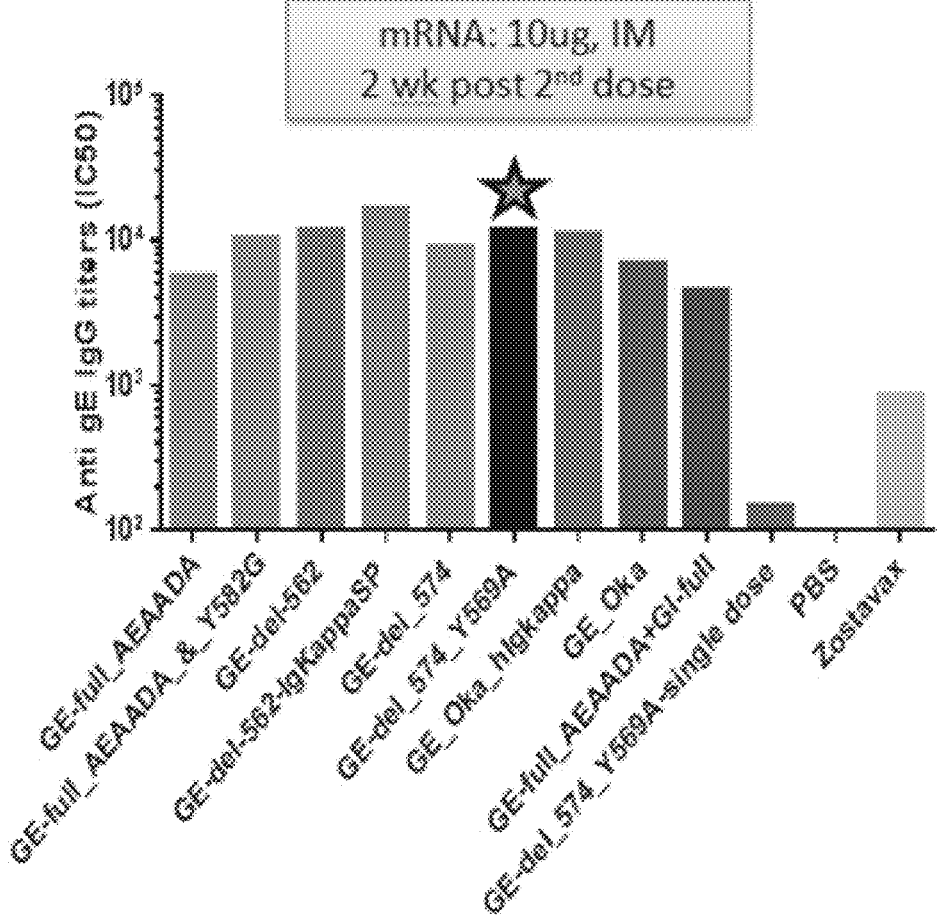
FIGS. 11A and 11B are graphs showing the results of an ELISA assay, which shows the levels of anti-VZV gE IgG in the serum of mice vaccinated with VZV gE variant mRNAs in comparison with ZOSTAVAX® vaccine. The sequence AEAADA depicted throughout
Figure 11B:
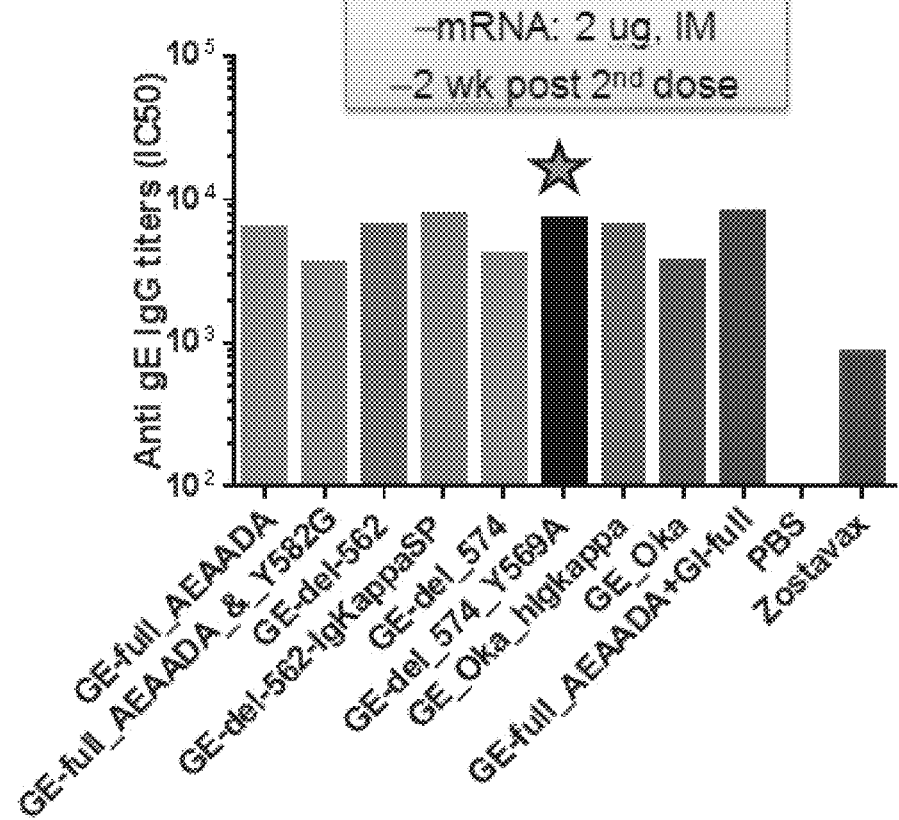

FIG. 11A shows that all gE variants induced much stronger immune response than ZOSTAVAX® after the two 10 μg doses. FIG. 11B show that all gE variants induced much stronger immune response than ZOSTAVAX® after the two 2 μg doses. With both dosages, the gE variants GE-del_574_Y569A and GE-del-562-IgKappaSP induced the strongest immune response and the antibody titer measured in the sera of mice immunized with this gE variant is over 10 times more than the antibody titer measured in the sera of mice immunized with ZOSTAVAX®, indicating that the GE-del_574_Y569A and GE-del_562-IgKappaSP mRNAs are superior vaccine candidates against VZV.

Figure 12A:
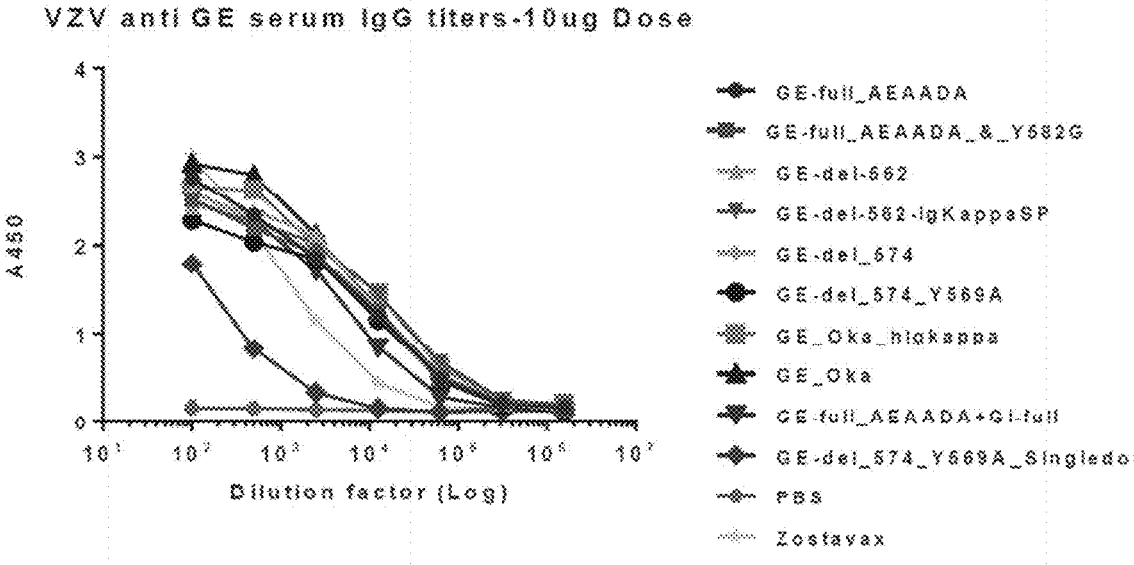
FIGS. 12A and 12B are graphs showing the results of an ELISA assay, which shows the levels of anti-VZV gE IgG in the serum of mice vaccinated with VZV gE variant mRNAs in comparison with ZOSTAVAX® vaccine. The sequence AEAADA depicted throughout
Figure 12B:
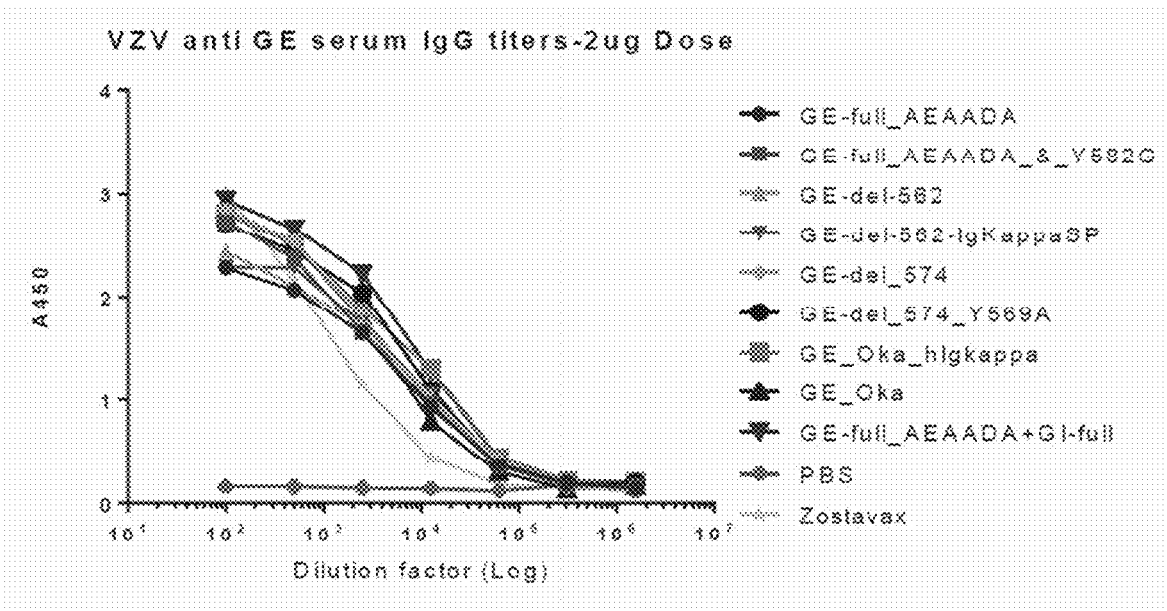

FIG. 12A shows the amount of antibodies in titrated sera collected from mice immunized twice with 10 μg of VZV gE mRNA variants described in Table 6. FIG. 12B shows the amount of antibodies in titrated sera collected from mice immunized twice with 2 μg of VZV gE mRNA variants described in Table 6. When the sera were diluted more than 100 fold, the antibody titer is higher in VZV gE variants vaccinated mice sera than in ZOSTAVAX® vaccinated mice sera, suggesting that the VZV gE mRNA variants induced much stronger immune response than ZOSTAVAX® in mice. All the VZV gE mRNA variants tested showed comparable ability in inducing immune response in mice.

Figure 13:
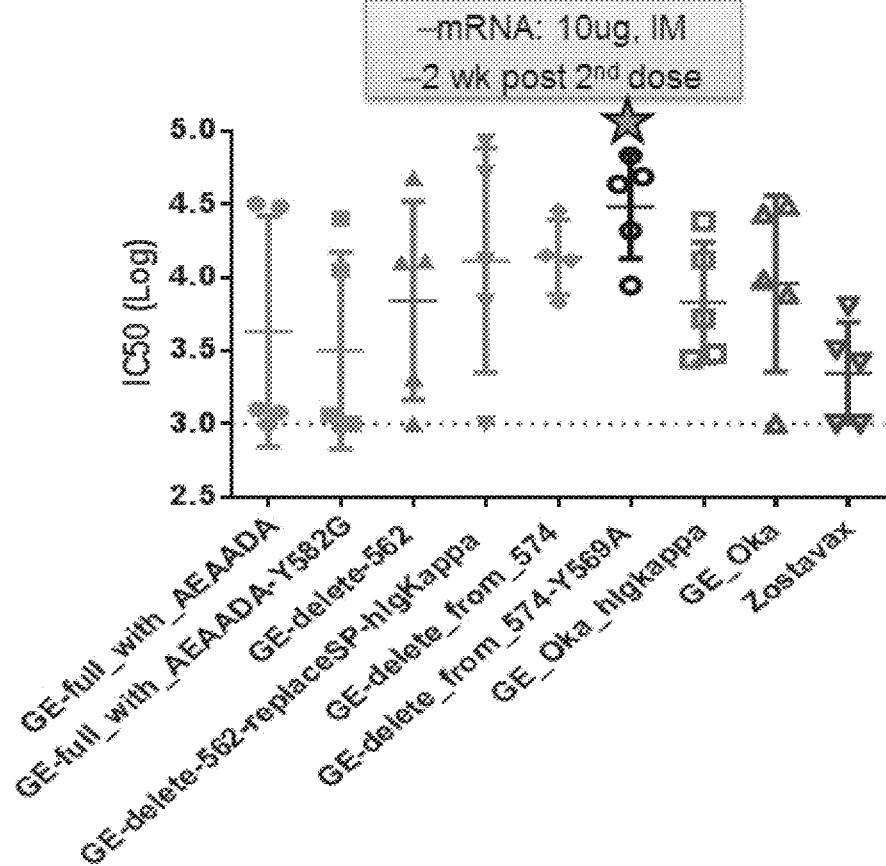
FIG. 13 is a graph showing the results of an ELISA assay measuring the antibody titer in the sera of mice immunized with VZV gE variant mRNA vaccines. Anti-VZV gE response induced by VZV gE variants mRNAs in mice are greater than that of ZOSTAVAX®. The gE variant mRNA for GE-delete_from_574-Y569A induced an immune response that is 1 log greater than ZOSTAVAX®. The sequence AEAADA depicted throughout

FIG. 13 is a graph showing the anti-VZV gE immune response induced by the VZV gE variant mRNA vaccines compared to ZOSTAVAX®. The VZV gE variant GE-delete_from_574-Y569A induced immune response in mice that is about 1 log greater than ZOSTAVAX®.

Table 9 summarizes the reciprocal IgG titer (IC50) in the sera collected from mice immunized with 10 μg or 2 μg of the respective VZV gE mRNAs twice. GE-delete_from_574-Y569A induced strong immune response with either 10 μg or 2 μg dosages. The Geometric Mean Titer (GMT) was used to indicate the immunogenic potential of the VZV gE variant mRNA vaccines. GE-delete_from_574-Y569A showed the highest GMT value, indicating that it is the most efficacious in inducing immune response against VZV gE.

TABLE 6

| | | | | | Dose | | | | |
| | | | | Dosage | Vol | $1^{st}$ | $2^{nd}$ | MC3/ | |
| G# | Antigen | Route | N | (μg) | (μl) | dose | dose | conc | |
|---|---|---|---|---|---|---|---|---|---|
| 1 | SE-VZV-GE-full_with_AEAADA (SEQ ID NO: 58) | IM | 5 | 10 | 50 | Day 0 | Day 28 | 0.2 mg/ml | 2 × 500 |
| 2 | SE-VZV-GE-full_with_AEAADA (SEQ ID NO: 58) | IM | 5 | 2 | 50 | Day 0 | Day 28 | 0.04 mg/ml | 2 × 500 |
| 3 | SE-VZV-GE-full_with_AEAADA (SEQ ID NO: 58)_and_Y582G | IM | 5 | 10 | 50 | Day 0 | Day 28 | 0.2 mg/ml | 2 × 500 |
| 4 | SE-VZV-GE-full_with_AEAADA (SEQ ID NO: 58)_and_Y582G | IM | 5 | 2 | 50 | Day 0 | Day 28 | 0.04 mg/ml | 2 × 500 |
| 5 | SE-VZV-GE-delete-562 | IM | 5 | 10 | 50 | Day 0 | Day 28 | 0.2 mg/ml | 2 × 500 |
| 6 | SE-VZV-GE-delete-562 | IM | 5 | 2 | 50 | Day 0 | Day 28 | 0.04 mg/ml | 2 × 500 |
| 7 | SE-VZV-GE-delete-562-replacedSP-withIgKappa | IM | 5 | 10 | 50 | Day 0 | Day 28 | 0.2 mg/ml | 2 × 500 |
| 8 | SE-VZV-GE-delete-562-replacedSP-withIgKappa | IM | 5 | 2 | 50 | Day 0 | Day 28 | 0.04 mg/ml | 2 × 500 |
| 9 | SE-VZV-GE-truncated-delete_from_574 | IM | 5 | 10 | 50 | Day 0 | Day 28 | 0.2 mg/ml | 2 × 500 |
| 10 | SE-VZV-GE-truncated-delete_from_574 | IM | 5 | 2 | 50 | Day 0 | Day 28 | 0.04 mg/ml | 2 × 500 |
| 11 | SE-VZV-GE-truncated-delete_from_574_—_Y569A | IM | 5 | 10 | 50 | Day 0 | Day 28 | 0.2 mg/ml | 2 × 500 |
| 12 | SE-VZV-GE-truncated-delete_from_574_—_Y569A | IM | 5 | 2 | 50 | Day 0 | Day 28 | 0.04 mg/ml | 2 × 500 |

TABLE 6-continued

| | | | | | Injection Schedule | | | | |
|---|---|---|---|---|---|---|---|---|---|
| G# | Antigen | Route | N | Dosage (μg) | Dose Vol (μl) | $1^{st}$ dose | $2^{nd}$ dose | MC3/ conc | |
| 13 | KB_VZV_gE_Oka_hIgkappa | IM | 5 | 10 | 50 | Day 0 | Day 28 | 0.2 mg/ml | 2 × 500 |
| 14 | KB_VZV_gE_Oka_hIgkappa | IM | 5 | 2 | 50 | Day 0 | Day 28 | 0.04 mg/ml | 2 × 500 |
| 15 | KB_VZV_gE_Oka | IM | 5 | 10 | 50 | Day 0 | Day 28 | 0.2 mg/ml | 2 × 500 |
| 16 | KB_VZV_gE_Oka | IM | 5 | 2 | 50 | Day 0 | Day 28 | 0.04 mg/ml | 2 × 500 |
| 17 | SE-VZV-GI-full | IM | 5 | 10 | 50 | Day 0 | Day 28 | 0.2 mg/ml | 2 × 500 |
| 18 | SE-VZV-GI-full | IM | 5 | 2 | 50 | Day 0 | Day 28 | 0.04 mg/ml | 2 × 500 |
| 19 | SE-VZV-GE-full_with_AEAADA (SEQ ID NO: 58) + SE-VZV-GI-full | IM | 5 | 10 | 50 | Day 0 | Day 28 | 0.2 mg/ml | 2 × 500 |
| 20 | SE-VZV-GE-full_with_AEAADA (SEQ ID NO: 58) + SE-VZV-GI-full | IM | 5 | 2 | 50 | Day 0 | Day 28 | 0.04 mg/ml | 2 × 500 |
| 21 | SE-VZV-GE-truncated-delete_from_574_—_Y569A | IM | 5 | 10 | 50 | Day 0 | No dosing | 0.2 mg/ml | 500 |
| 22 | PBS | IM | 5 | — | 50 | Day 0 | Day 28 | | 2 × 500 |
| 23 | Positive control | SC | 5 | 19400 PFUs | 100 | Day 0 | Day 28 | | 2 × 500 |

TABLE 7

| | | Schedule of Sample Collection | | | | |
|---|---|---|---|---|---|---|
| G# | Antigen | Pre-bleed | Day 14 | Day 27 | Day 42 | Day 56 |
| 1 | SE-VZV-GE-full_with_AEAADA (SEQ ID NO: 58) | ✓ | ✓ | ✓ | ✓ | ✓ |
| 2 | SE-VZV-GE-full_with_AEAADA (SEQ ID NO: 58) | ✓ | ✓ | ✓ | ✓ | ✓ |
| 3 | SE-VZV-GE-full_with_AEAADA (SEQ ID NO: 58)_and_Y582G | ✓ | ✓ | ✓ | ✓ | ✓ |
| 4 | SE-VZV-GE-full_with_AEAADA (SEQ ID NO: 58)_and_Y582G | ✓ | ✓ | ✓ | ✓ | ✓ |
| 5 | SE-VZV-GE-delete-562 | ✓ | ✓ | ✓ | ✓ | ✓ |
| 6 | SE-VZV-GE-delete-562 | ✓ | ✓ | ✓ | ✓ | ✓ |
| 7 | SE-VZV-GE-delete-562-replacedSP-withIgKappa | ✓ | ✓ | ✓ | ✓ | ✓ |
| 8 | SE-VZV-GE-delete-562-replacedSP-withIgKappa | ✓ | ✓ | ✓ | ✓ | ✓ |
| 9 | SE-VZV-GE-truncated-delete_from_574 | ✓ | ✓ | ✓ | ✓ | ✓ |
| 10 | SE-VZV-GE-truncated-delete_from_574 | ✓ | ✓ | ✓ | ✓ | ✓ |
| 11 | SE-VZV-GE-truncated-delete_from_574_—_Y569A | ✓ | ✓ | ✓ | ✓ | ✓ |
| 12 | SE-VZV-GE-truncated-delete_from_574_—_Y569A | ✓ | ✓ | ✓ | ✓ | ✓ |
| 13 | KB_VZV_gE_Oka_hIgkappa | ✓ | ✓ | ✓ | ✓ | ✓ |
| 14 | KB_VZV_gE_Oka_hIgkappa | ✓ | ✓ | ✓ | ✓ | ✓ |
| 15 | KB_VZV_gE_Oka | ✓ | ✓ | ✓ | ✓ | ✓ |
| 16 | KB_VZV_gE_Oka | ✓ | ✓ | ✓ | ✓ | ✓ |
| 17 | SE-VZV-GI-full | ✓ | ✓ | ✓ | ✓ | ✓ |
| 18 | SE-VZV-GI-full | ✓ | ✓ | ✓ | ✓ | ✓ |
| 19 | SE-VZV-GE-full_with_AEAADA (SEQ ID NO: 58) + SE-VZV-GI-full | ✓ | ✓ | ✓ | ✓ | ✓ |
| 20 | SE-VZV-GE-full_with_AEAADA (SEQ ID NO: 58) + SE-VZV-GI-full | ✓ | ✓ | ✓ | ✓ | ✓ |
| 21 | SE-VZV-GE-truncated-delete_from_574_—_Y569A | ✓ | ✓ | ✓ | ✓ | ✓ |
| 22 | PBS | ✓ | ✓ | ✓ | ✓ | ✓ |
| 23 | Positive control | ✓ | ✓ | ✓ | ✓ | ✓ |

TABLE 8

| Summary of IC50 of the different N7N constructs Reciprocal IgG titer (IC50) | | |
| --- | --- | --- |
| Name | 10 ug | 2 ug |
| GE-FULL_AEAADA | 5741 | 6378 |
| GE-FULL_AEAADA_&_Y582G | 10306 | 3556 |
| GE-del-562 | 11672 | 6445 |
| GE-del-562-IaKappaSP | 16490 | 7939 |
| GE-del-574 | 9031 | 4082 |
| GE-del_574_Y569A | 11704 | 7291 |
| GE_Oka_hIgkappa | 11708 | 6448 |
| GE_Oka_hIgkappa | 7045 | 3672 |
| GE-full_AEAADA_GI-full | 4457 | 8242 |
| GE-del_574_Y569A | NA | |
| PBS | NA | NA |
| Zostavax | 860 | 860 |

| Assay controls | plate 1 | plate 2 | % CV | std | mean | CV |
| --- | --- | --- | --- | --- | --- | --- |
| VZV_Ge_Oka_hIgkappa | 12803 | 11078 | 7.22 | 862.5 | 11940.5 | 0.07 |

TABLE 9

| Reciprocal anti-gE IgG titer (IC50) measured by ELISA | | | | | |
| --- | --- | --- | --- | --- | --- |
| Name | IC50 | GMT | Name | IC50 | GMT |
| GE-full_AEAADA | 1188.5 | 4291.4 | GE-del_574_Y569A | 20941.1 | |
| | 31915.4 | | | 48865.2 | |
| | 1261.8 | | | 8810.5 | |
| | 30408.9 | | | 43351.1 | |
| | 1000 | | | 68076.9 | |
| GE-full_AEAADA_&_Y582G | 1150.8 | 3181.3 | GE_Oka_hIgkappa | 24266.1 | 6763.9 |
| | 25351.3 | | | 3026.9 | |
| | 1000 | | | 13213 | |
| | 1000 | | | 5236 | |
| | 11168.6 | | | 2786.1 | |
| GE-del-562 | 1000 | 6921.5 | GE_Oka | 27227 | 9078.2 |
| | 47752.9 | | | 30903 | |
| | 12676.5 | | | 7638.4 | |
| | 12912.2 | | | 1000 | |
| | 2032.4 | | | 9594 | |
| GE-del-562-IgKappaSP | 1000 | 13140.1 | Zostavax | 6397.3 | 2228.4 |
| | 13122 | | | 1000 | |
| | 51760.7 | | | 1000 | |
| | 84918..1 | | | 2660.7 | |
| | 66792 | | | 3228.5 | |
| GE-del_574 | 13091.8 | 13795.9 | | | |
| | 6760.8 | | | | |
| | 14223.3 | | | | |
| | 28774 | | | | |

Example 19: VZV In Vitro Neutralization Assay

A VZV in vitro neutralization assay was performed to evaluate the anti-VZV gE antibodies in neutralizing VZV. The anti-VZV gE antibodies were obtained by collecting the sera of mice vaccinated with VZV gE variant mRNA vaccines. Mice were vaccinated with VZV gE variant mRNA vaccines at dosages or 10 μg or 2 μg as described in Table 6 and sera were collected 2 weeks post $2^{nd}$ immunization.

To perform the assay, mice sera were diluted 1:5 and then subjected to 1:2 serial dilutions. VZV virus were added to the sera and neutralization was allowed to continue for 1 hour at room temperature. ARPE-19 cells were seeded in 96-wells one day before and the virus/serum mixtures were added to ARPE-19 cells at 50-100 pfu per well. The ARPE-19 cells were fixed on the next day and VZV-specific staining was performed. The plates were scanned and analyzed. Results of the VZV in vitro neutralization assay were summarized in Table 10. Values in Table 10 are serum dilutions showing 50% reduction in well-area coverage by VZV virus plaques. No reduction in plaque number was observed. As shown in Table 10, one replicate of serum from mice immunized with GE-delete_from_574-Y569A variant mRNA vaccine was able to reduce well-area coverage by VZV virus plaques at 1:80 dilution.

TABLE 10

| | | In vitro neutralization assay | | |
| --- | --- | --- | --- | --- |
| | 10 ug | | 2 ug | |
| Antigen | Replicate1 | Replicate2 | Replicate1 | Replicate2 |
| SE-VZV-GE-full_with_AEAADA | 20 | 10 | 10 | 10 |
| SE-VZV-GE-full_with_AEAADA_and_Y582G | 40 | 20 | | 10 |
| SE-VZV-GE-delete-562 | 40 | 20 | 20 | 10 |
| SE-VZV-GE-delete-562-replacedSP-withIgKappa | 40 | 40 | 20 | 40 |
| SE-VZV-GE-truncated-delete_from_574 | 80 | 40 | 40 | 20 |
| SE-VZV-GE-truncated-delete_from_574_—_Y569A | 20 | 80 | 10 | 10 |
| KB_VZV_gE_Oka_hIgkappa | 40 | <20 | 20 | 10 |
| KB_VZV_gE_Oka | 160 | 10 | 10 | 10 |
| SE-vzv-GI-full | <10 | <10 | <20 | <20 |
| SE-VZV-GE-full_with_AEAADA + SE-VZV-GI-full | 20 | 10 | — | — |
| SE-VZV-GE-truncated-delete_from_574_—_Y569A | <10 | <10 | — | — |
| PBS | <20 | <20 | | |
| Positive Control | 20 | 20 | | |

Example 20: Immunogenicity in Mice

Herpes zoster (HZ) or shingles is a debilitating disease characterized by a vesicular rash, with the most common complication being post-herpetic neuralgia (PHN). PHN is a constant and severe pain that develops after clearance of the cutaneous outbreak, and can last for several years, thereby contributing to the high morbidity of affected individuals. HZ is caused by reactivation of latent varicella-zoster virus (VZV) from the sensory ganglia. Immune responses generated during primary VZV infection (chickenpox) have been shown to prevent the reactivation of latent VZV. However, the incidence of HZ is strongly associated with advancing age. Several investigations have shown that T cell-mediated immune responses decline with increasing age and during immunosuppression, resulting in reactivation of VZV. Nonetheless, the levels of anti-VZV antibodies remain relatively stable with increasing age, demonstrating that the humoral immune response may not be sufficient for the prevention of HZ. Several studies have reported the induction of VZV-specific CD4+ and CD8+ T cells, with CD4+ T cells dominating the memory response.

The approved vaccine ZOSTAVAX® demonstrates around 60-70% efficacy in 50-60 years adults and declines with age. Recently a subunit adjuvanted vaccine (Shingrix: gE protein +ASO1B) was shown to have ~90% efficacy in all age group of adults 50+. However, this vaccine demonstrated grade 3 severe AE's in 10% of the vaccinated subjects. Shingrix demonstrated about a log fold better T and B cell response after two doses to ZOSTAVAX®. In the present studies mRNA immunization with a gE construct was investigated for immunogenicity in mice and NHP.

Figure 14A:
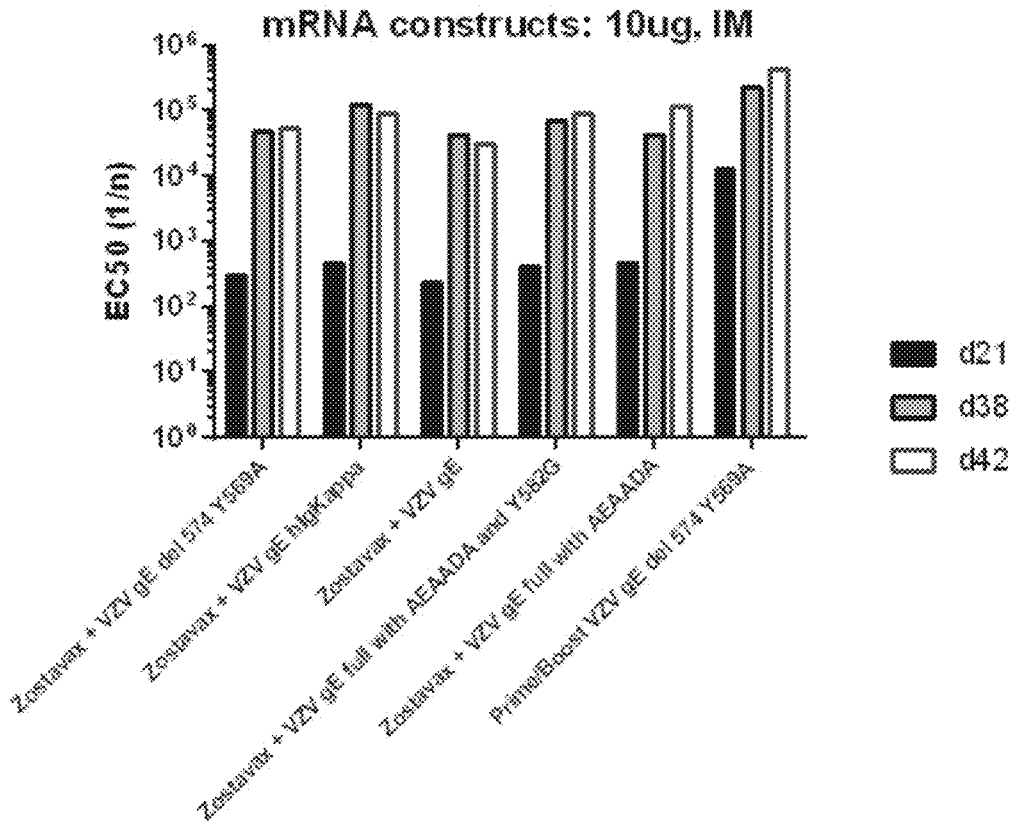
FIG. 14A is a graph showing the results of an ELISA assay, which shows the levels of anti-VZV gE IgG in the serum of mice vaccinated with VZV gE variant mRNAs after primary exposure with ZOSTAVAX® vaccine (groups 1-5) or VZV-gE-del_574_Y569A (group 6). The sequence AEAADA depicted throughout
Figure 14B:
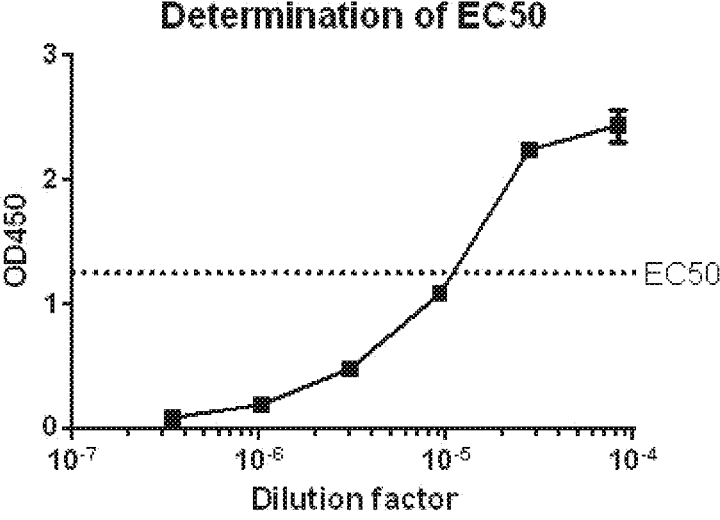
FIG. 14B is a graph showing the determination of EC50.
Figure 15A:
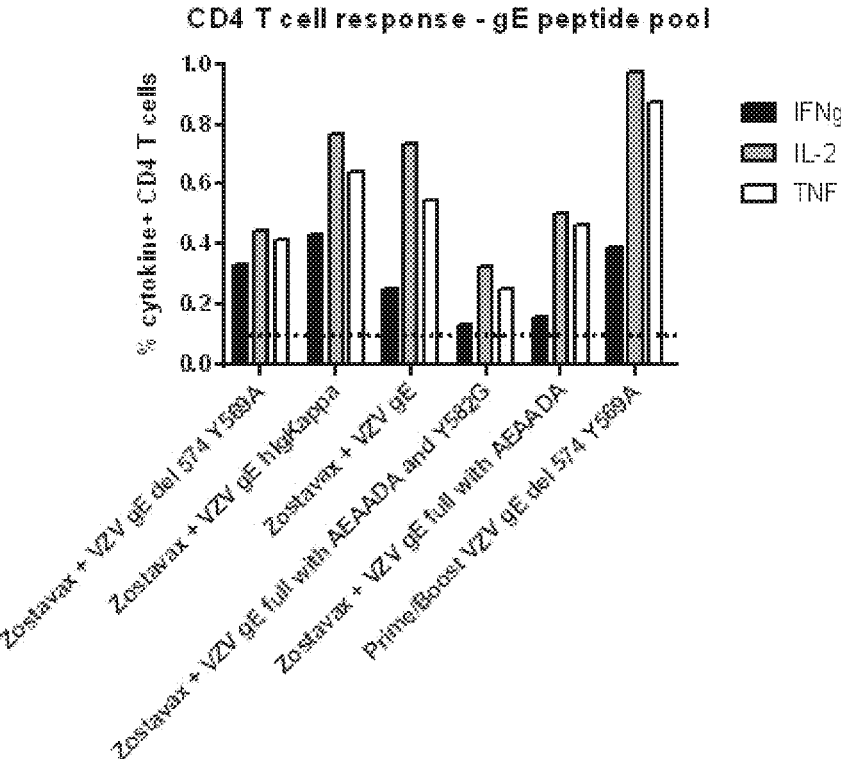
FIGS. 15A and 15B are graphs showing the results of the T cell analysis of mice vaccinated with VZV gE variant mRNAs after primary exposure with ZOSTAVAX® vaccine (groups 1-5) or VZV-gE-del_574_Y569A (group 6). The sequence AEAADA depicted throughout
Figure 15B:
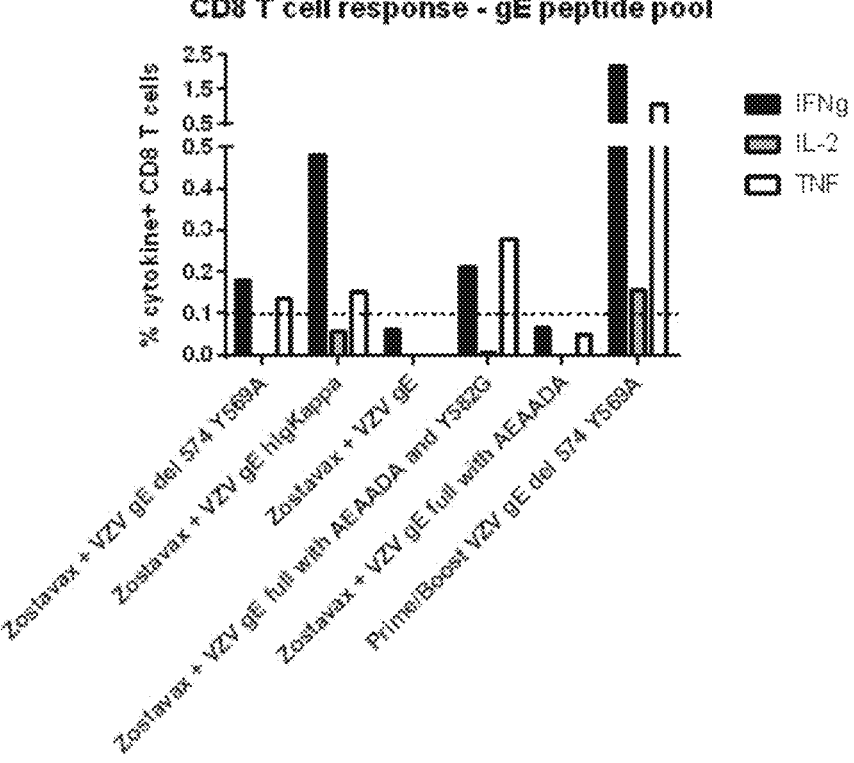

The instant study was defined to test the immunogenicity in BALB/C mice of candidate VZV vaccines comprising a mRNA polynucleotide encoding glycoprotein gE from VZV. Mice were immunized with various VZV mRNA vaccine formulations as set forth below in Table 11. Groups 1 to 5 were primed with ZOSTAVAX® to mimic a primary Varicella exposure and group 6 was primed with mRNA construct VZV-gE-del_574_Y569A. All groups (groups 1-6) were boosted on day 28, as shown in Table 11. The animals were bled on days −3, 21, 38 and 42. Blood and spleens were collected for serological and T cell analysis on days 38 and 42. As shown in FIG. 14A, all groups gave comparable anti-gE antibody responses to mRNA vaccination with the animal receiving mRNA for prime and boost (group 6) trending higher. As shown in FIG. 15A, all groups demonstrated CD4 T-cell responses with mRNA prime and boost (group 6) trending towards a higher response. As shown in FIG. 15B, variable CD8 T-cell responses were noted with the mRNA prime and boost (group 6) demonstrating highest CD8 T-cell frequencies.

TABLE 11

| | | Injection Schedule | | |
| --- | --- | --- | --- | --- |
| G# | Primary Immunization (Day 0) 10 µg | Boost (Day 28) 10 µg | Localization (VERO/ MeWo) of Boost Construct | Number mice per group |
| 1 | ZOSTAVAX ® | VZV-gE-del_574_Y569A | Golgi (high) & cell membrane (high) | 10 |
| 2 | ZOSTAVAX ® | VZV-gE-Oka-hIgKappa | Golgi (low) & cytoplasmic | 10 |
| 3 | ZOSTAVAX ® | VZV-gE-Oka | Golgi/Golgi | 10 |
| 4 | ZOSTAVAX ® | VZV-gE full_with_AEAADA (SEQ ID NO: 58)_and_Y582G | Organelles & cytoplasmic/cell membrane | 10 |
| 5 | ZOSTAVAX ® | VZV-gE-full with AEAADA (SEQ ID NO: 58) | Golgi & diffuse perinuclear/cell membrane | 10 |

TABLE 11-continued

| Injection Schedule | | | |
|---|---|---|---|
| G# | Primary Immunization (Day 0) 10 μg | Boost (Day 28) 10 μg | Localization (VERO/ MeWo) of Boost Construct | Number mice per group |
| 6 | VZV-gE-del_574_Y569A | VZV-gE-del_574_Y569A | Golgi (high) & cell membrane (high) | 10 |

Example 21: Immunogenicity in Non-Human Primates

Figure 16A:
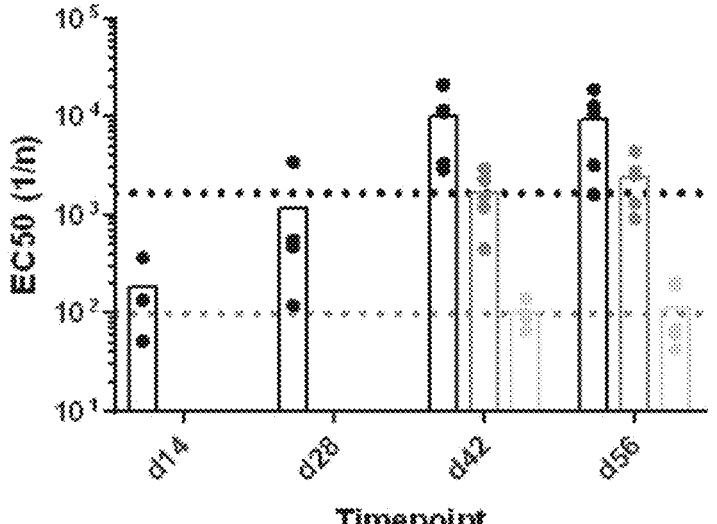
FIGS. 16A and 16B are graphs showing the results of an ELISA assay, which shows the levels of anti-VZV gE IgG in serum of rhesus monkeys vaccinated with either VZV-gE-del_574_Y569A or ZOSTAVAX® after primary exposure with VZV-gE-del_574_Y569A or ZOSTAVAX.
Figure 16B:
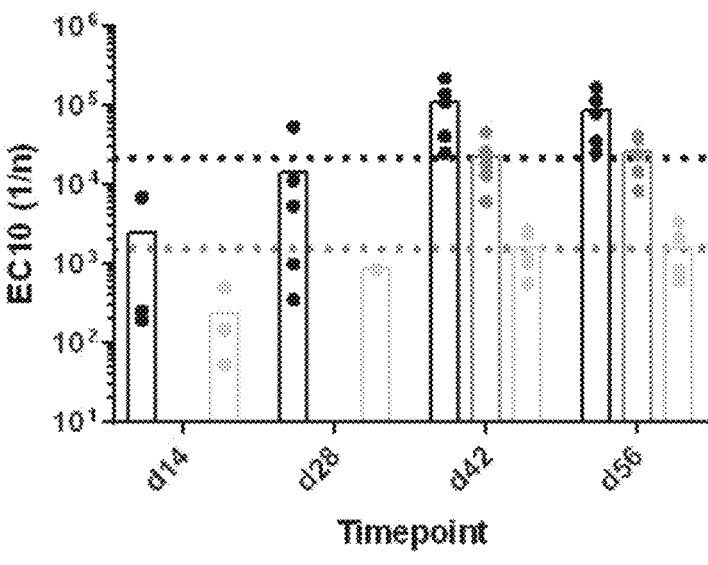
Figure 16C:
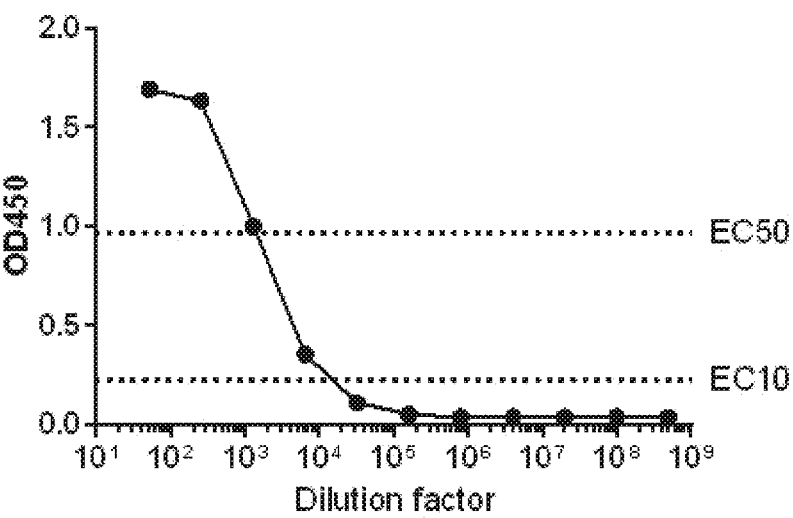
FIG. 16C is a graph showing the determination of EC50 and EC10.
Figure 16D:
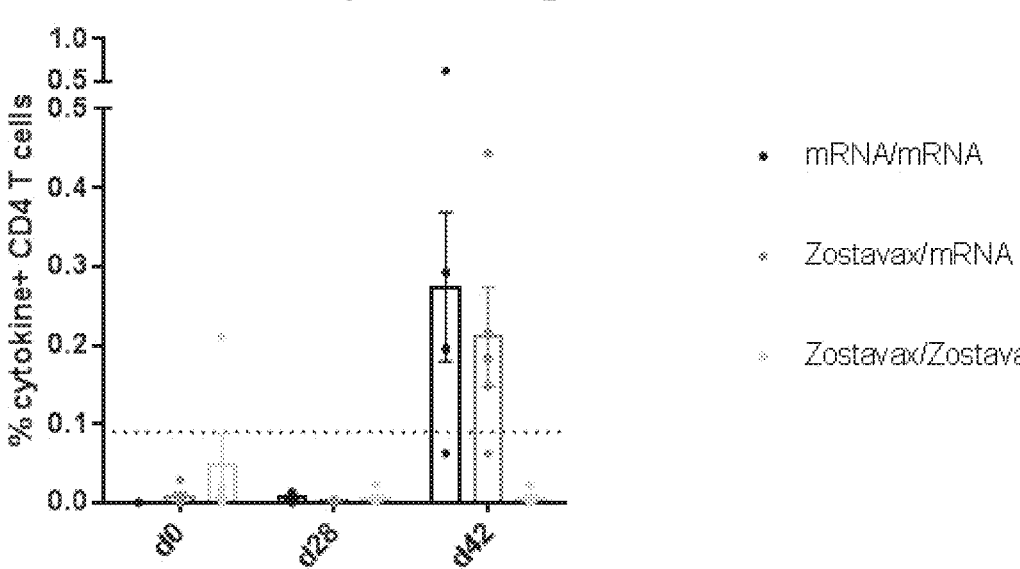
FIGS. 16D, 16E, and 16F are graphs showing the results of the T cell analysis of rhesus monkeys vaccinated with either VZV-gE-del_574_Y569A or ZOSTAVAX® after primary exposure with VZV-gE-del_574_Y569A or ZOSTAVAX®.
Figure 16E:
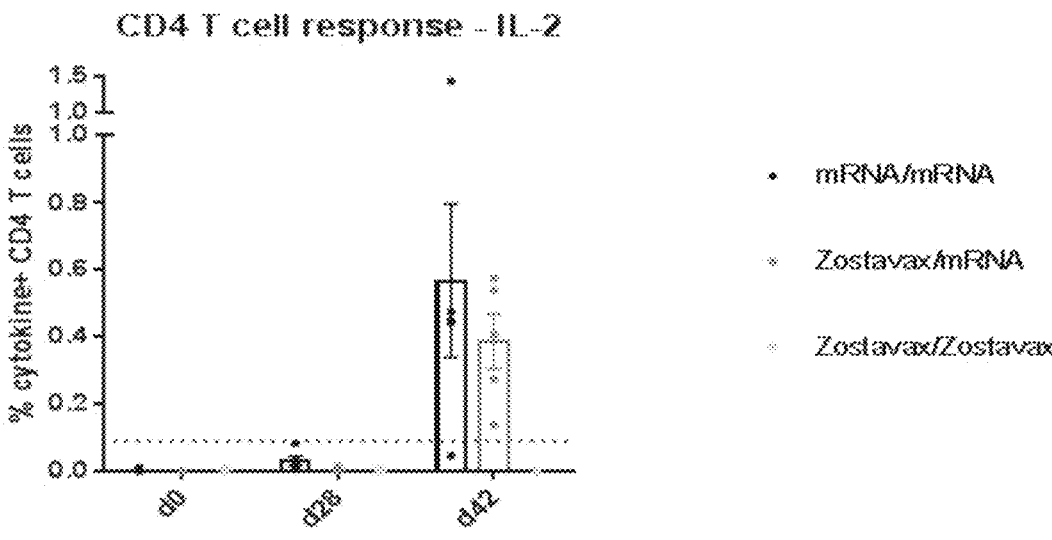
Figure 16F:
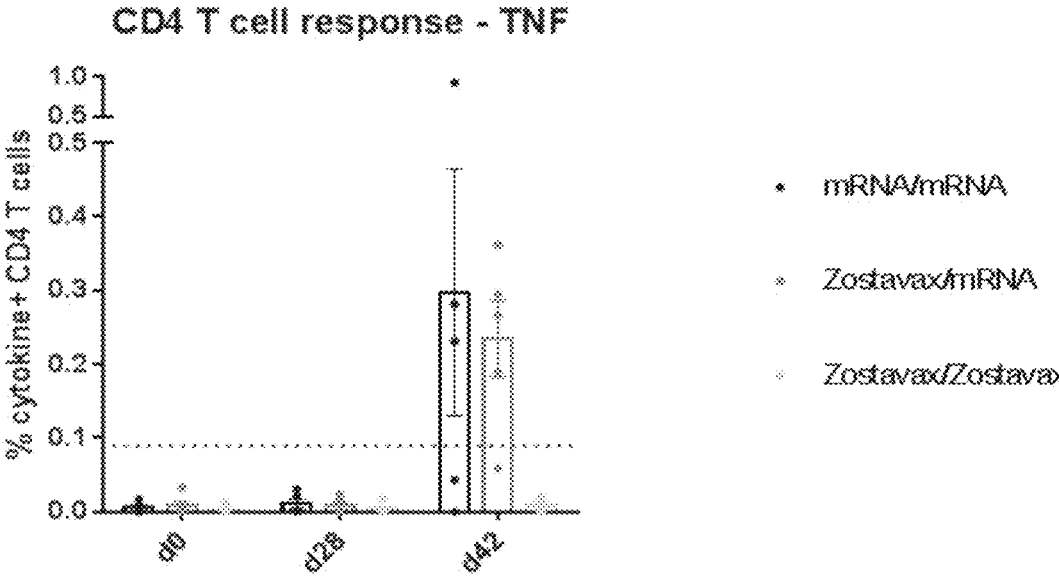

Based on the data in Example 20, the mRNA construct VZV-gE-del_574_Y569A was further evaluated for immunogenicity in non-human primates. Three groups of Rhesus monkeys were primed with mRNA (VZV-gE-del_574_Y569A) or ZOSTAVAX® and boosted as set forth below in Table 12. The animals were bled at days 0, 14, 28, and 42 for serological and T-cell analysis. T-cell analysis was performed on days 0, 28, and 42. As shown in FIGS. 16A and 16B, the mRNA prime and boost (group 1) gave the highest anti-gE titers which were followed by ZOSTAVAX® prime, mRNA boost (group 2). The latter group (group 2) anti-gE titers were approximately 10× better than the ZOSTAVAX® prime, ZOSTAVAX® boost (group 3). As shown in FIGS. 16C and 16D, no CD4-T cells producing IFNγ, IL-2 or TNFα were detected in the ZOSTAVAX® prime, ZOSTAVAX® boost group (group 3). In contrast, as shown in FIGS. 16C and 16D, reasonable frequency of CD4 T-cells producing IFNγ, IL-2 or TNFα were detected in the mRNA prime, mRNA boost group (group 1) and the ZOSTAVAX® prime, mRNA boost group (group 2) and were statistically undifferentiated. These data indicate that one dose of mRNA vaccination after ZOSTAVAX® exposure was equivalent to two doses of mRNA vaccination in inducing comparable T-cell responses.

TABLE 12

| Injection Schedule | | | |
|---|---|---|---|
| G# | Primary Immunization (Day 0) 10 μg | Boost (Day 28) 10 μg | Number Rhesus macaques (male and female) per group |
| 1 | VZV-gE-del_574_Y569A | VZV-gE-del_574_Y569A | 5 |
| 2 | ZOSTAVAX ® | VZV-gE-del_574_Y569A | 5 |
| 3 | ZOSTAVAX ® | ZOSTAVAX ® | 5 |

Figure 17:
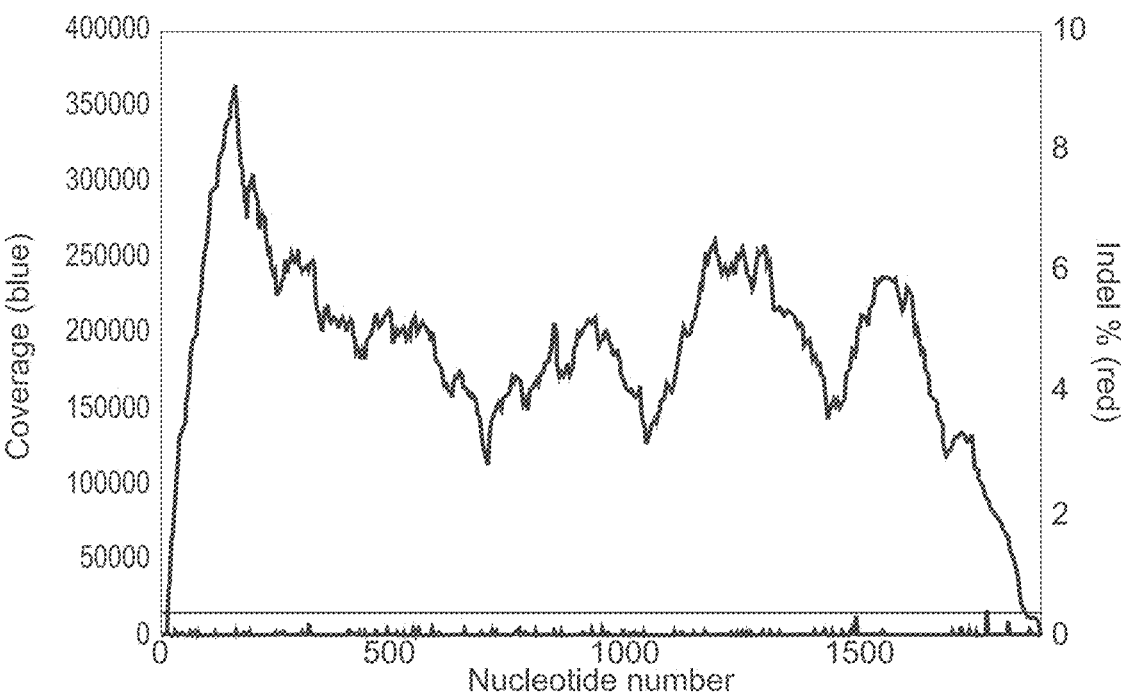
FIG. 17 shows next generation sequencing (NGS) data of VZV mRNA vaccine construct encoding a modified VZV-gE-del_574_Y569A antigen (VZV-gE-del_574_Y569A-v7). Compared to the VZV-gE-del_574_Y569A mRNA vaccine construct, which encodes the gE antigen (e.g., described in FIGS. 13-16), VZV-gE-del_574_Y569A-v7 was modified (6 nucleotide changes were introduced) to reduce the occurrence of indel-causing homopolymeric stretches (stretches of 6 As, 5 As, or 4 As). The data shows that VZV-gE-del_574_Y569A-v7 does not contain significant indels.

Example 22: Expression and In Vivo Localization of VZV-gE-Del_574_Y569A Variants Variants of mRNAs encoding the VZV-gE-del_574_Y569A (variant 7, SEQ ID NO: 107, ORF sequence: SEQ ID NO: 86) or VZV-gE-full length (SEQ ID NO: 135) were constructed, where the nucleotide sequence of the homopolymeric stretches (e.g., 6, 5, or 4 consecutive As) were altered (without altering the amino acid sequence) to reduce the frequency of potential indel formation. Next generation sequencing showed the absence of significant indels in VZV-gE-del_574_Y569A variant 7 (VZV-gE-del_574_Y569A-v7) (FIG. 17). Mass spectrometry detected very low levels of indels in a 4A stretch in nucleotides 760-771 of the ORF.

Figure 18A:
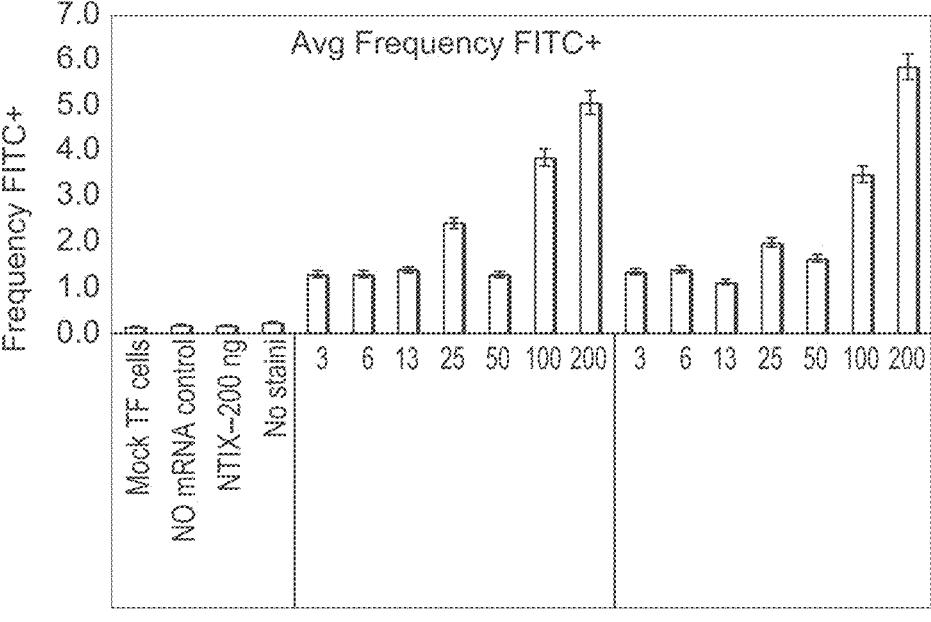
FIG. 18A shows the average frequency of FITC⁺ MeWo cells six hours post transfection with VZV-gE-del_574_Y569A or VZV-gE-del_574_Y569A-v7, measured by fluorescence-activated cell sorting (FACS).
Figure 18B:
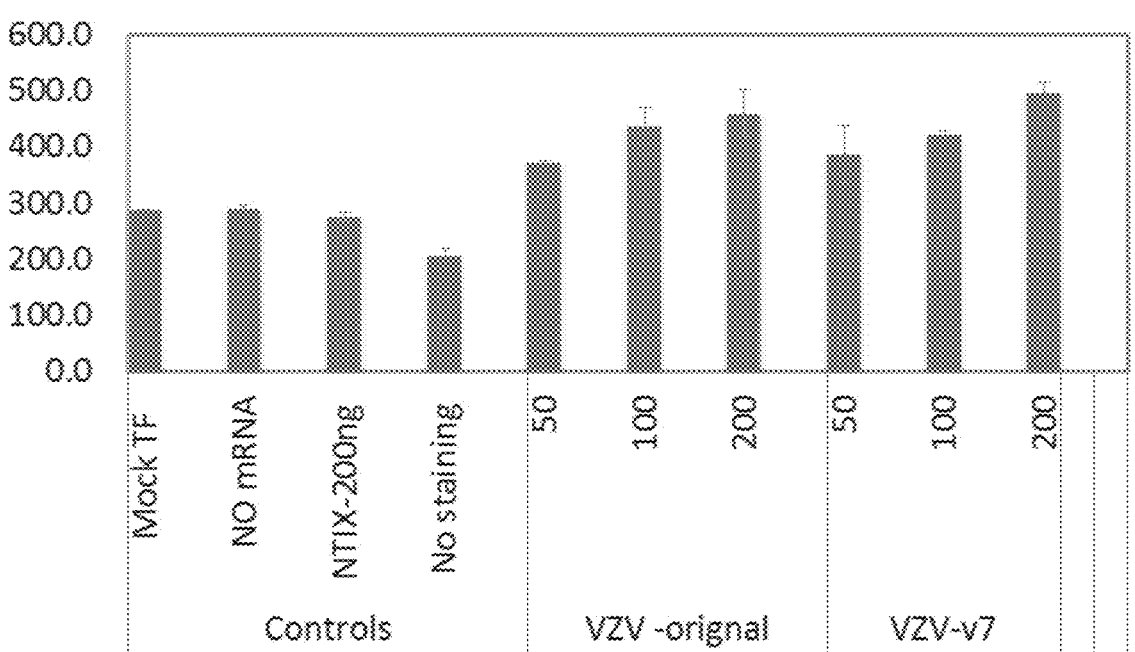
FIG. 18B shows the FITC geometric mean.

Next, the expression levels of VZV-gE-del_574_Y569A-v7 were tested in Mewo and HeLa cells and compared to the VZV-gE-del_574_Y569A mRNA construct. The mRNA constructs (200 ng) were transfected into Mewo or HeLa cells, using the Mirus TF transfection reagent in 96-well plates. NTIX control mRNA and PBS control were used in 30 K of MeWo cells. All cells were serially diluted (2 fold) 6 hours post transfection, permeabilized, stained, and analyzed by flow cytometry for FITC+ cells (cells with antigen expression). Results show that the VZV-gE-del_574_Y569A-v7 mRNA construct was expressed at a level comparable to the VZV-gE-del_574_Y569A mRNA construct in both Mewo cells (FIG. 18A) and HeLa cells (FIG. 18B).

Figure 19A:
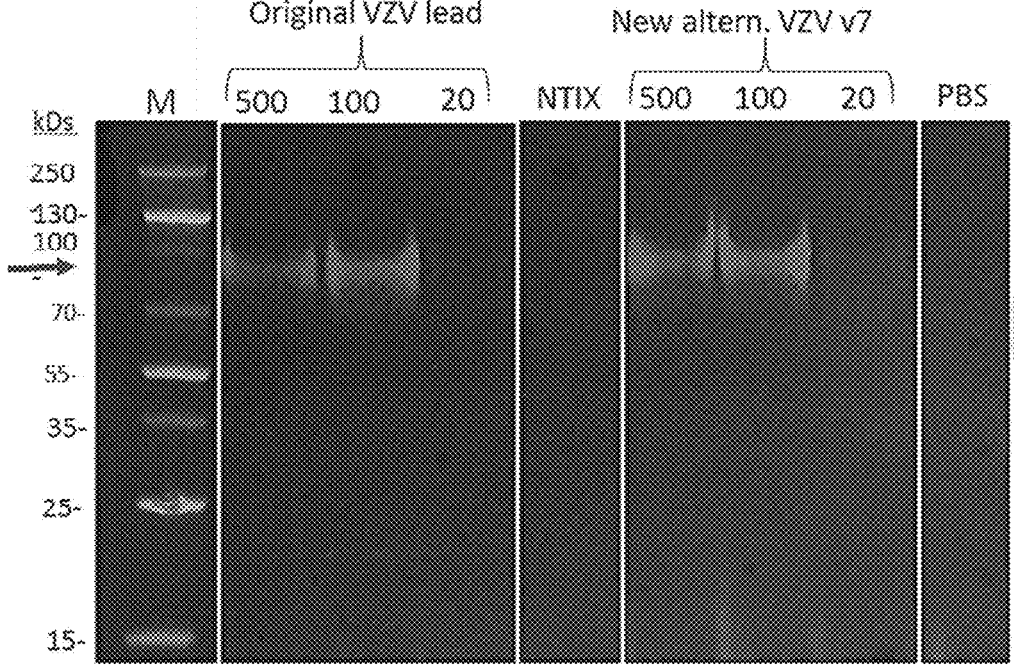

Protein was then detected in cell lysates of HeLa cells transfected (lipoplexed with 3 μl LF2000 per well in a 24-well plate) with either the VZV-gE-del_574_Y569A mRNA construct (500 ng) or the VZV-gE-del_574_Y569A-v7 mRNA construct (500 ng), serially diluted to 100 μg or 20 μg. Western blots for the VZV-gE antigen 16 hours post transfection showed that the VZV-gE-del_574_Y569A-v7 mRNA construct was expressed at a level comparable to the VZV-gE-del_574_Y569A mRNA construct in HeLa cells (FIGS. 19A and 19B).

Next, the in vivo trafficking and localization of different VZV gE antigens were assessed. HeLa or MeWo cells were plated on 96 well plates and transfected with mRNA constructs encoding NTFIX control, full length VZV-gE, VZV-gE-del_574_Y569A, or VZV-gE-del_574_Y569A-v7 with Lipofectamine 2000 (100 ng mRNA/0.4 μl LF per well). Twenty-four hours after transfection, the cells were fixed in 4% PFA, permeabilized with 0.5% TX-100, and co-stained with rabbit anti-GM130 (CST D6B1—Golgi marker) and mouse anti-gE (Abcam 52549) antibodies at room temperature for 1 h in blocking buffer (1% BSA in PBS). The samples were then washed to remove the primary antibody and were incubated with anti-rabbit Alexa 647 and anti-mouse Alexa 488 conjugated antibodies for 30 minutes at room temperature, followed by counterstaining with DAPI for nuclear localization and HCS blue mask for cell segmentation. Cells were imaged with the Opera Phenix high throughput spinning disk confocal.

Figure 21A:
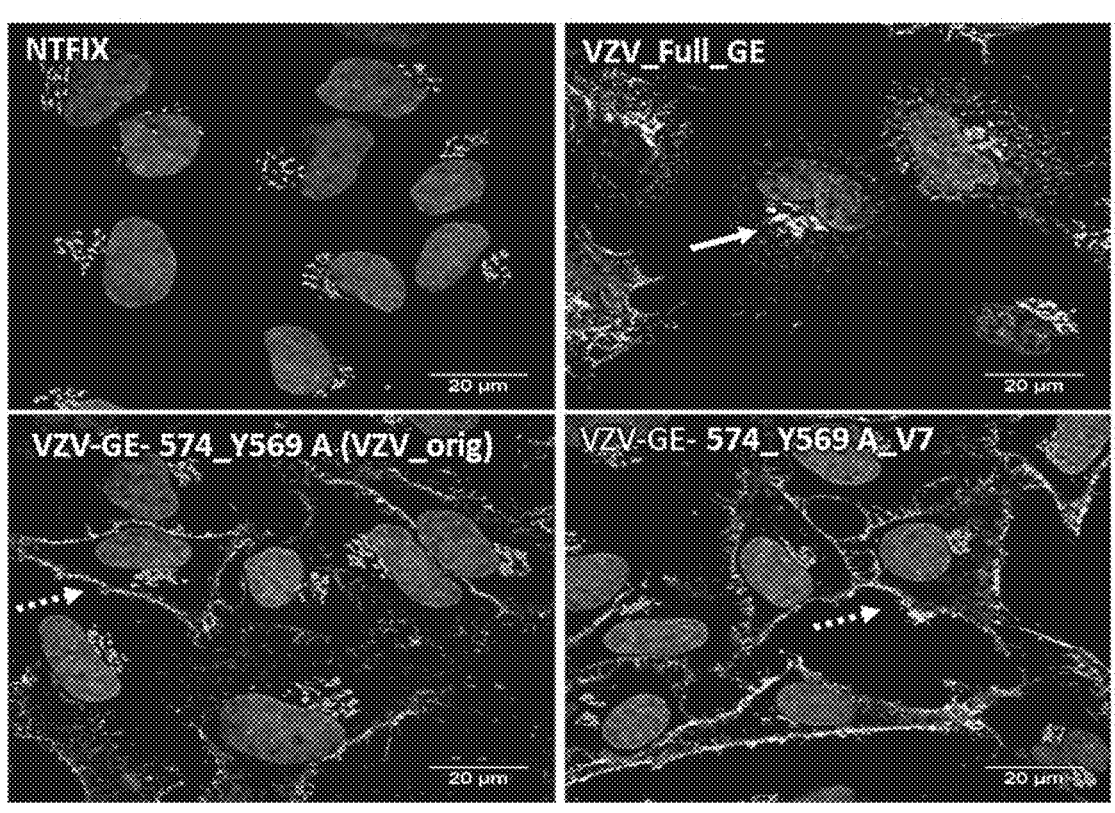
FIGS. 21A-21C are microscopy images showing the localization in HeLa cells (FIG. 21) or MeWo cells (FIGS. 21B and 21C) of full length VZV-gE and VZV-gE-del_574_Y569A antigens encoded by the VZV-gE-del_574_Y569A mRNA construct or the VZV-gE-del_574_Y569A-v7 mRNA construct. The full length VZV gE antigen localized to the golgi, and VZV-gE-del_574_Y569A antigen localized to the cell membrane.
Figure 21B:
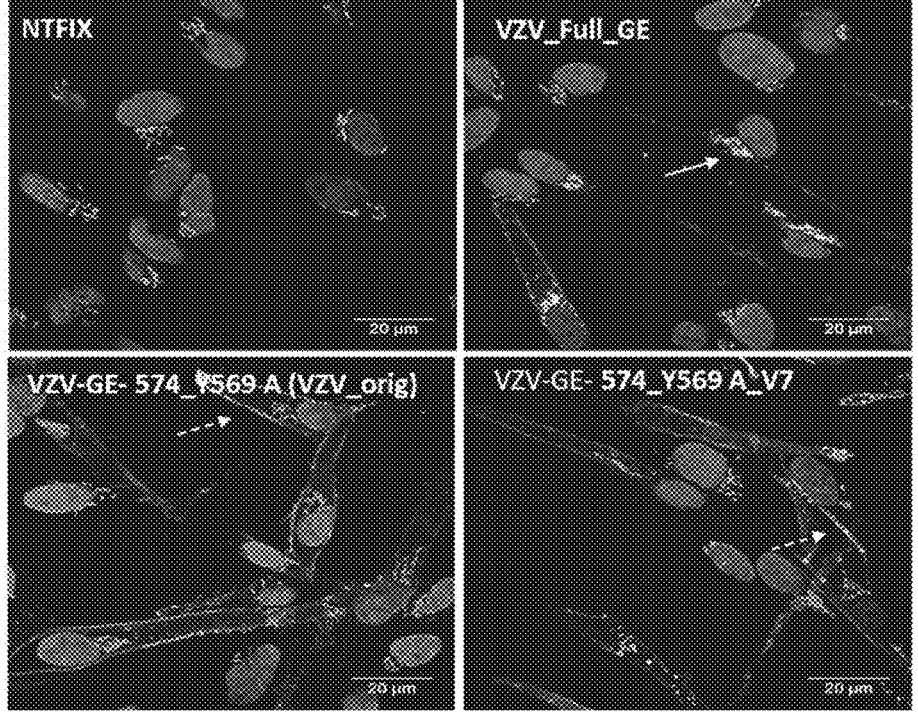
Figure 21C:
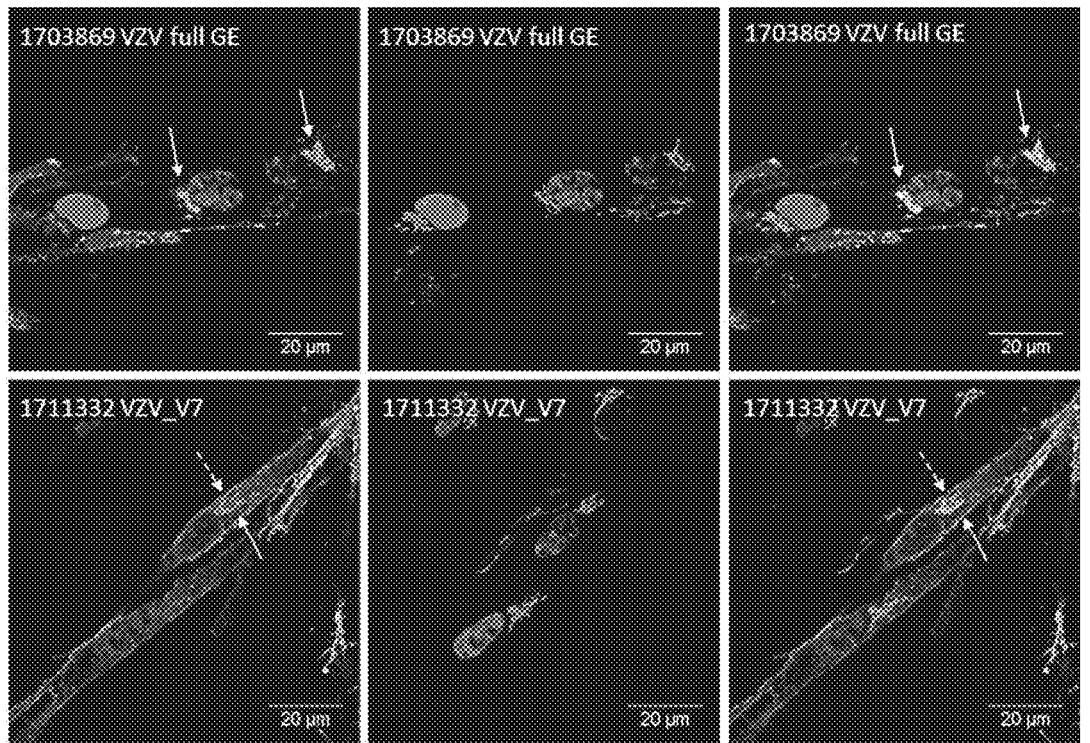
Figure 22A:
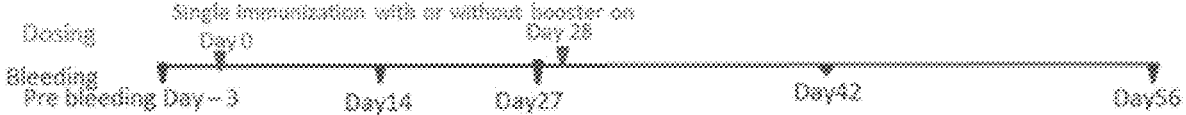
FIGS. 22A-22B show injection schedules.
Figure 22B:
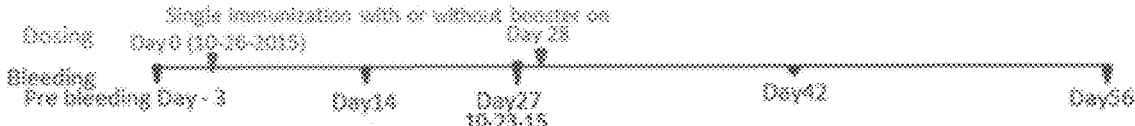

The expression level and the localization of each antigen were quantified. The antigens expressed at comparable levels (FIG. 20A) but VZV-gE-del_574_Y569A encoded by the VZV-gE-del_574_Y569A mRNA construct or the VZV-gE-del_574_Y569A-v7 mRNA construct showed lower golgi localization compared to the full-length VZV-gE (FIG. 20B). A shift in the localization of VZV-gE-del_574_Y569A (encoded by either the VZV-gE-del_574_Y569A mRNA construct or the VZV-gE-del_574_Y569A-v7 mRNA construct) from golgi to the cell membrane, compared to the full-length VZV gE, was observed in HeLA cells (FIG. 21A) and in MeWo cells (FIGS. 21B and 21C).

TABLE 13

Exemplary VZV gE mRNA constructs

| mRNA Construct | ORF of mRNA Construct (excluding the stop codon) |
| --- | --- |
| SE_VZV_gE_full_indel_fixed | AUGGGGACAGUUAAUAAACCUGUGGUGGGGGUAUUGAUGGGGUU<br>CGGAAUUAUCACGGGAACGUUGCGUAUAACGAAUCCGGUCAGAGC<br>AUCCGUCUUGCGAUACGAUGAUUUUCACAUCGAUGAAGACAAACU<br>GGAUACAAACUCCGUAUAUGAGCCUUACUACCAUUCAGAUCAUGC<br>GGAGUCUUCAUGGGUAAAUCGGGGAGAGUCUUCGCGAAAAGCGUA<br>CGAUCAUAACUCACCUUAUAUAUGGCCACGUAAUGAUUAUGAUGG<br>AUUUUUAGAGAACGCACACGAACACCAUGGGGUGUAUAAUCAGGG<br>CCGUGGUAUCGAUAGCGGGGAACGGUUAAUGCAACCCACACAAAU<br>GUCUGCACAGGAGGAUCUUGGGGACGAUACGGGCAUCCACGUUAU<br>CCCUACGUUAAACGGCGAUGACAGACAUAAAAAUUGUAAAUGUGGA<br>CCAACGUCAAUACGGUGACGUGUUUAAAGGAGAUCUUAAUCCAAA<br>ACCCCAAGGCCAAAGACUCAUUGAGGUGUCAGUGGAAGAAAAUCA<br>CCCGUUUACUUUACGCGCACCGAUUCAGCGGAUUUAUGGAGUCCG<br>GUACACCGAGACUUGGAGCUUUUUGCCGUCAUUAACCUGUACGGG<br>AGACGCAGCGCCCGCCAUCCAGCAUAUAUGUUUAAAGCAUACAAC<br>AUGCUUUCAAGACGUGGUGGUGGAUGUGGAUUGCGCGGAAAAUA<br>CUAAAGAGGAUCAGUUGGCCGAAAUCAGUUACCGUUUUCAAGGUA<br>AGAAGGAAGCGGACCAACCGUGGAUUGUUGUAAACACGAGCACAC<br>UGUUUGAUGAACUCGAAUUAGACCCACCCGAGAUUGAACCGGGUG<br>UCUUGAAAGUACUUCGGACAGAGAAACAAUACUUGGGGUGUGUACA<br>UUUGGAACAUGCGCGGCUCCGAUGGUACGUCUACCUACGCCACGU<br>UUUUGGUCACCUGGAAAGGGGAUGAGAAGACAAGAAACCCUACGC<br>CCGCAGUAACUCCUCAACCAAGAGGGGCUGAGUUUCAUAUGUGGA<br>AUUACCACUCGCAUGUAUUUUCAGUUGGUGAUACGUUUAGCUUGG<br>CAAUGCAUCUUCAGUAUAAGAUACAUGAAGCGCCAUUUGAUUUGC<br>UGUUAGAGUGGUUGUAUGUCCCCAUCGAUCCUACAUGUCAACCAA<br>UGCGGUUAUAUUCUACGUGUUUGUAUCAUCCCAACGCACCCCAUU<br>GCCUCUCUCAUAUGAAUUCCGGUUGUACAUUUACCUCGCCACAUU<br>UAGCCCAGCGUGUUGCAAGCACAGUGUAUCAGAAUUGUGAACAUG<br>CAGAUAACUACACCGCAUAUUGUCUGGGAAUAUCUCAUAUGGAGC<br>CUAGCUUUGGUCUAAUCUUACACGACGGGGGCACCACGUUAAAGU<br>UUGUAGAUACACCCGAGAGUUUGUCGGGAUUAUACGUUUUUGUG<br>GUGUAUUUUAACGGGCAUGUUGAAGCCGUAGCAUACACUGUUGUA<br>UCCACAGUAGAUCAUUUUGUAAACGCAAUUGAAGAGCGUGGAUUU<br>CCGCCAACGGCCGGUCAGCCACCGGCGACUACUAAACCCAAGGAA<br>AUUACCCCCGUAAACCCCGGAACGUCACCACUUCUACGAUAUGCC<br>GCAUGGACCGGAGGGCUUGCAGCAGUAGUACUUUUAUGUCUCGUA<br>AUAUUUUUAAUCUGUACGGCUAAACGAAUGAGGGUUAAAGCCUAC<br>AGGGUAGACAAGUCUCCUUACAAUCAGUCAAUGUACUAUGCAGGA<br>CUCCCUGUUGACGAUUUCGAAGACUCAGAGAGUACAGACACAGAA<br>GAAGAAUUCGGAAACGCUAUAGGUGGCUCUCACGGAGGUAGCUCG<br>UAUACAGUGUACAUCGAUAAAACCAGA (SEQ ID NO: 142) |
| SE-VZV-GE-574-Y569A-v2 | AUGGGGACAGUUAAUAAACCUGUGGUGGGGGUAUUGAUGGGGUU<br>CGGAAUUAUCACGGGAACGUUGCGUAUAACGAAUCCGGUCAGAGC<br>AUCCGUCUUGCGAUACGAUGAUUUUCACAUCGAUGAAGACAAACU<br>GGAUACAAACUCCGUAUAUGAGCCUUACUACCAUUCAGAUCAUGC<br>GGAGUCUUCAUGGGUAAAUCGGGGAGAGUCUUCGCGAAAAGCGUA<br>CGAUCAUAACUCACCUUAUAUAUGGCCACGUAAUGAUUAUGAUGG<br>AUUUUUAGAGAACGCACACGAACACCAUGGGGUGUAUAAUCAGGG<br>CCGUGGUAUCGAUAGCGGGGAACGGUUAAUGCAACCCACACAAAU<br>GUCUGCACAGGAGGAUCUUGGGGACGAUACGGGCAUCCACGUUAU<br>CCCUACGUUAAACGGCGAUGACAGACAUAAAAAUUGUAAAUGUGGA<br>CCAACGUCAAUACGGUGACGUGUUUAAAGGAGAUCUUAAUCCAAA<br>ACCCCAAGGCCAAAGACUCAUUGAGGUGUCAGUGGAAGAAAAUCA<br>CCCGUUUACUUUACGCGCACCGAUUCAGCGGAUUUAUGGAGUCCG<br>GUACACCGAGACUUGGAGCUUUUUGCCGUCAUUAACCUGUACGGG<br>AGACGCAGCGCCCGCCAUCCAGCAUAUAUGUUUAAAACAUACAAC<br>AUGCUUUCAAGACGUGGUGGUGGAUGUGGAUUGCGCGGAAAAUA<br>CUAAAGAGGAUCAGUUGGCCGAAAUCAGUUACCGUUUUCAAGGUA<br>AGAAGGAAGCGGACCAACCGUGGAUUGUUGUAAACACGAGCACAC<br>UGUUUGAUGAACUCGAAUUAGACCCCCCCGAGAUUGAACCGGGUG<br>UCUUGAAAGUACUUCGGACAGAGAAACAAUACUUGGGGUGUGUACA<br>UUUGGAACAUGCGCGGCUCCGAUGGUACGUCUACCUACGCCACGU<br>UUUUGGUCACCUGGAAAGGGGAUGAGAAGACAAGAAACCCUACGC<br>CCGCAGUAACUCCUCAACCAAGAGGGGCUGAGUUUCAUAUGUGGA<br>AUUACCACUCGCAUGUAUUUUCAGUUGGUGAUACGUUUAGCUUGG<br>CAAUGCAUCUUCAGUAUAAGAUACAUGAAGCGCCAUUUGAUUUGC<br>UGUUAGAGUGGUUGUAUGUCCCCAUCGAUCCUACAUGUCAACCAA<br>UGCGGUUAUAUUCUACGUGUUUGUAUCAUCCCAACGCACCCCAUU<br>GCCUCUCUCAUAUGAAUUCCGGUUGUACAUUUACCUCGCCACAUU<br>UAGCCCAGCGUGUUGCAAGCACAGUGUAUCAAAAUUGUGAACAUG<br>CAGAUAACUACACCGCAUAUUGUCUGGGAAUAUCUCAUAUGGAGC<br>CUAGCUUUGGUCUAAUCUUACACGACGGGGGCACCACGUUAAAGU<br>UUGUAGAUACACCCGAGAGUUUGUCGGGAUUAUACGUUUUUGUG<br>GUGUAUUUUAACGGGCAUGUUGAAGCCGUAGCAUACACUGUUGUA |

TABLE 13-continued

Exemplary VZV gE mRNA constructs

| mRNA Construct | ORF of mRNA Construct (excluding the stop codon) |
|---|---|
| | UCCACAGUAGAUCAUUUUGUAAACGCAAUUGAAGAGCGUGGAUUU<br>CCGCCAACGGCCGGUCAGCCACCGGCGACUACUAAACCCAAGGAA<br>AUUACCCCCGUAAACCCCGGAACGUCACCACUUCUACGAUAUGCC<br>GCAUGGACCGGAGGGCUUGCAGCAGUAGUACUUUUAUGUCUCGUA<br>AUAUUUUUAAUCUGUACGGCUAAACGAAUGAGGGUUAAAGCCGCC<br>AGGGUAGACAAG (SEQ ID NO: 143) |
| SE-VZV-GE-574-Y569A-v3 | AUGGGGACAGUUAAUAAACCUGUGGUGGGGGUAUUGAUGGGGUU<br>CGGAAUUAUCACGGGAACGUUGCGUAUAACGAAUCCGGUCAGAGC<br>AUCCGUCUUGCGAUACGAUGAUUUUCACAUCGAUGAAGACAAACU<br>GGAUACAAACUCCGUAUAUGAGCCUUACUACCAUUCAGAUCAUGC<br>GGAGUCUUCAUGGGUAAAUCGGGGAGAGUCUUCGCGAAAAGCGUA<br>CGAUCAUAACUCACCUUAUAUAUGGCCACGUAAUGAUUAUGAUGG<br>AUUUUUAGAGAACGCACACGAACACCAUGGGGUGUAUAAUCAGGG<br>CCGUGGUAUCGAUAGCGGGGAACGGUUAAUGCAACCCACACAAAU<br>GUCUGCACAGGAGGAUCUUGGGGACGAUACGGGCAUCCACGUUAU<br>CCCUACGUUAAACGGCGAUGACAGACAUAAAAUUGUAAAUGUGGA<br>CCAACGUCAAUACGGUGACGUGUUUAAAGGAGAUCUUAAUCCAAA<br>ACCCCAAGGCCAAAGACUCAUUGAGGUGUCAGUGGAAGAAAUCA<br>CCCGUUUACUUUACGCGCACCGAUUCAGCGGAUUUAUGGAGUCCG<br>GUACACCGAGACUUGGAGCUUUUUGCCGUCAUUAACCUGUACGGG<br>AGACGCAGCGCCCGCCAUCCAGCAUAUAUGUUUAAAACAUACAAC<br>AUGCUUUCAAGACGUGGUGGUGGAUGUGGAUUGCGCGGAAAAUA<br>CUAAAGAGGAUCAGUUGGCCGAAAUCAGUUACCGUUUUCAAGGUA<br>AGAAGGAAGCGGACCAACCGUGGAUUGUUGUAAACACGAGCACAC<br>UGUUUGAUGAACUCGAAUUAGACCCACCCGAGAUUGAACCGGGUG<br>UCUUGAAAGUACUUCGGACAGAGAAACAAUACUUGGGUGUGUACA<br>UUUGGAACAUGCGCGGCUCCGAUGGUACGUCUACCUACGCCACGU<br>UUUUGGUCACCUGGAAAGGGGAUGAGAAGACAAGAAACCCUACGC<br>CCGCAGUAACUCCUCAACCAAGAGGGGCUGAGUUUCAUAUGUGGA<br>AUUACCACUCGCAUGUAUUUUCAGUUGGUGAUACGUUUAGCUUGG<br>CAAUGCAUCUUCAGUAUAAGAUACAUGAAGCGCCAUUUGAUUUGC<br>UGUUAGAGUGGUUGUAUGUCCCCAUCGAUCCUACAUGUCAACCAA<br>UGCGGUUAUAUUCUACGUGUUUGUAUCAUCCCAACGCACCCCAAU<br>GCCUCUCUCAUAUGAAUUCCGGUUGUACAUUUACCUCGCCACAUU<br>UAGCCCAGCGUGUUGCAAGCACAGUGUAUCAAAAUUGUGAACAUG<br>CAGAUAACUACACCGCAUAUUGUCUGGGAAUAUCUCAUAUGGAGC<br>CUAGCUUUGGUCUAAUCUUACACGACGGGGGCACCACGUUAAAGU<br>UUGUAGAUACACCCGAGAGUUUGUCGGGAUUAUACGUUUUUGUG<br>GUGUAUUUUAACGGGCAUGUUGAAGCCGUAGCAUCACACUGUUGUA<br>UCCACAGUAGAUCAUUUUGUAAACGCAAUUGAAGAGCGUGGAUUU<br>CCGCCAACGGCCGGUCAGCCACCGGCGACUACUAAACCCAAGGAA<br>AUUACCCCCGUAAACCCCGGAACGUCACCACUUCUACGAUAUGCC<br>GCAUGGACCGGAGGGCUUGCAGCAGUAGUACUUUUAUGUCUCGUA<br>AUAUUUUUAAUCUGUACGGCUAAACGAAUGAGGGUUAAAGCCGCC<br>AGGGUAGACAAG (SEQ ID NO: 144) |
| SE-VZV-GE-574-Y569A-v4 | AUGGGGACAGUUAAUAAACCUGUGGUGGGGGUAUUGAUGGGGUU<br>CGGAAUUAUCACGGGAACGUUGCGUAUAACGAAUCCGGUCAGAGC<br>AUCCGUCUUGCGAUACGAUGAUUUUCACAUCGAUGAAGACAAACU<br>GGAUACAAACUCCGUAUAUGAGCCUUACUACCAUUCAGAUCAUGC<br>GGAGUCUUCAUGGGUAAAUCGGGGAGAGUCUUCGCGAAAGGCGUA<br>CGAUCAUAACUCACCUUAUAUAUGGCCACGUAAUGAUUAUGAUGG<br>AUUUUUAGAGAACGCACACGAACACCAUGGGGUGUAUAAUCAGGG<br>CCGUGGUAUCGAUAGCGGGGAACGGUUAAUGCAACCCACACAAAU<br>GUCUGCACAGGAGGAUCUUGGGGACGAUACGGGCAUCCACGUUAU<br>CCCUACGUUAAACGGCGAUGACAGACAUAAGAUUGUAAAUGUGGA<br>CCAACGUCAAUACGGUGACGUGUUUAAAGGAGAUCUUAAUCCAAA<br>GCCCCAAGGCCAAAGACUCAUUGAGGUGUCAGUGGAAGAGAAUCA<br>CCCGUUUACUUUACGCGCACCGAUUCAGCGGAUUUAUGGAGUCCG<br>GUACACCGAGACUUGGAGCUUUUUGCCGUCAUUAACCUGUACGGG<br>AGACGCAGCGCCCGCCAUCCAGCAUAUAUGUUUAAAGCAUACAAC<br>AUGCUUUCAAGACGUGGUGGUGGAUGUGGAUUGCGCGGAGAAUA<br>CUAAAGAGGAUCAGUUGGCCGAAAUCAGUUACCGUUUUCAAGGUA<br>AGAAGGAAGCGGACCAACCGUGGAUUGUUGUAAACACGAGCACAC<br>UGUUUGAUGAACUCGAAUUAGACCCCCCCGAGAUUGAACCGGGUG<br>UCUUGAAAGUACUUCGGACAGAGAAACAAUACUUGGGUGUGUACA<br>UUUGGAACAUGCGCGGCUCCGAUGGUACGUCUACCUACGCCACGU<br>UUUUGGUCACCUGGAAAGGGGAUGAGAAGACAAGAAACCCUACGC<br>CCGCAGUAACUCCUCAACCAAGAGGGGCUGAGUUUCAUAUGUGGA<br>AUUACCACUCGCAUGUAUUUUCAGUUGGUGAUACGUUUAGCUUGG<br>CAAUGCAUCUUCAGUAUAAGAUACAUGAAGCGCCAUUUGAUUUGC<br>UGUUAGAGUGGUUGUAUGUCCCCAUCGAUCCUACAUGUCAACCAA<br>UGCGGUUAUAUUCUACGUGUUUGUAUCAUCCCAACGCACCCCAAU<br>GCCUCUCUCAUAUGAAUUCCGGUUGUACAUUUACCUCGCCACAUU<br>UAGCCCAGCGUGUUGCAAGCACAGUGUAUCAGAAUUGUGAACAUG |

TABLE 13-continued

Exemplary VZV gE mRNA constructs

| mRNA Construct | ORF of mRNA Construct (excluding the stop codon) |
|---|---|
|  | CAGAUAACUACACCGCAUAUUGUCUGGGAAUAUCUCAUAUGGAGC<br>CUAGCUUUGGUCUAAUCUUACACGACGGGGGCACCACGUUAAAGU<br>UUGUAGAUACACCCGAGAGUUUGUCGGGAUUAUACGUUUUUGUG<br>GUGUAUUUUAACGGGCAUGUUGAAGCCGUAGCAUACACUGUUGUA<br>UCCACAGUAGAUCAUUUUGUAAACGCAAUUGAAGAGCGUGGAUUU<br>CCGCCAACGGCCGGUCAGCCACCGGCGACUACUAAACCCAAGGAA<br>AUUACCCCCGUAAACCCCGGAACGUCACCACUUCUACGAUAUGCC<br>GCAUGGACCGGAGGGCUUGCAGCAGUAGUACUUUUAUGUCUCGUA<br>AUAUUUUUAAUCUGUACGGCUAAACGAAUGAGGGUUAAAGCCGCC<br>AGGGUAGACAA (SEQ ID NO: 145) |
| SE-VZV-GE-574-Y569A-v5 | AUGGGGACAGUUAAUAAACCUGUGGUGGGGGUAUUGAUGGGGUU<br>CGGAAUUAUCACGGGAACGUUGCGUAUAACGAAUCCGGUCAGAGC<br>AUCCGUCUUGCGAUACGAUGAUUUUCACAUCGAUGAAGACAAACU<br>GGAUACAAACUCCGUAUAUGAGCCUUACUACCAUUCAGAUCAUGC<br>GGAGUCUUCAUGGGUAAAUCGGGGAGAGUCUUCGCGAAAGGCGUA<br>CGAUCAUAACUCACCUUAUAUAUGGCCACGUAAUGAUUAUGAUGG<br>AUUUUUAGAGAACGCACACGAACACCAUGGGGUGUAUAAUCAGGG<br>CCGUGGUAUCGAUAGCGGGGAACGGUUAAUGCAACCCACACAAAU<br>GUCUGCACAGGAGGAUCUUGGGGACGAUACGGGCAUCCACGUUAU<br>CCCUACGUUAAACGGCGAUGACAGACAUAAGAUUGUAAAUGUGGA<br>CCAACGUCAAUACGGUGACGUGUUUAAAGGAGAUCUUAAUCCAAA<br>GCCCCAAGGCCAAAGACUCAUUGAGGUGUCAGUGGAAGAGAAUCA<br>CCCGUUUACUUUACGCGCACCGAUUCAGCGGAUUUAUGGAGUCCG<br>GUACACCGAGACUUGGAGCUUUUUGCCGUCAUUAACCUGUACGGG<br>AGACGCAGCGCCCGCCAUCCAGCAUAUAUGUUUAAAGCAUACAAC<br>AUGCUUUCAAGACGUGGUGGUGGAUGUGGAUUGCGCGGAGAAUA<br>CUAAAGAGGAUCAGUUGGCCGAAAUCAGUUACCGUUUUCAAGGUA<br>AGAAGGAAGCGGACCAACCGUGGAUUGUUGUAAACACGAGCACAC<br>UGUUUGAUGAACUCGAAUUAGACCCACCCGAGAUUGAACCGGGUG<br>UCUUGAAAGUACUUCGGACAGAGAAACAAUACUUGGGUGUGUACA<br>UUUGGAACAUGCGCGGCUCCGAUGGUACGUCUACCUACGCCACGU<br>UUUUGGUCACCUGGAAAGGGGAUGAGAAGACAAGAAACCCUACGC<br>CCGCAGUAACUCCUCAACCAAGAGGGGCUGAGUUUCAUAUGUGGA<br>AUUACCACUCGCAUGUAUUUUCAGUUGGUGAUACGUUUAGCUUGG<br>CAAUGCAUCUUCAGUAUAAGAUACAUGAAGCGCCAUUUGAUUUGC<br>UGUUAGAGUGGUUGUAUGUCCCCAUCGAUCCUACAUGUCAACCAA<br>UGCGGUUAUAUUCUACGUGUUUGUAUCAUCCCAACGCCACCCCAUU<br>GCCUCUCUCAUAUGAAUUCCGGUUGUACAUUUACCUCGCCACAUU<br>UAGCCCAGCGUGUUGCAAGCACAGUGUAUCAGAAUUGUGAACAUG<br>CAGAUAACUACACCGCAUAUUGUCUGGGAAUAUCUCAUAUGGAGC<br>CUAGCUUUGGUCUAAUCUUACACGACGGGGGCACCACGUUAAAGU<br>UUGUAGAUACACCCGAGAGUUUGUCGGGAUUAUACGUUUUUGUG<br>GUGUAUUUUAACGGGCAUGUUGAAGCCGUAGCAUACACUGUUGUA<br>UCCACAGUAGAUCAUUUUGUAAACGCAAUUGAAGAGCGUGGAUUU<br>CCGCCAACGGCCGGUCAGCCACCGGCGACUACUAAACCCAAGGAA<br>AUUACCCCCGUAAACCCCGGAACGUCACCACUUCUACGAUAUGCC<br>GCAUGGACCGGAGGGCUUGCAGCAGUAGUACUUUUAUGUCUCGUA<br>AUAUUUUUAAUCUGUACGGCUAAACGAAUGAGGGUUAAAGCCGCC<br>AGGGUAGACAAG (SEQ ID NO: 146) |
| SE-VZV-GE-574-Y569A-v6 | AUGGGGACAGUUAAUAAACCUGUGGUGGGGGUAUUGAUGGGGUU<br>CGGAAUUAUCACGGGAACGUUGCGUAUAACGAAUCCGGUCAGAGC<br>AUCCGUCUUGCGAUACGAUGAUUUUCACAUCGAUGAAGACAAACU<br>GGAUACAAACUCCGUAUAUGAGCCUUACUACCAUUCAGAUCAUGC<br>GGAGUCUUCAUGGGUAAAUCGGGGAGAGUCUUCGCGAAAGCGUA<br>CGAUCAUAACUCACCUUAUAUAUGGCCACGUAAUGAUUAUGAUGG<br>AUUUUUAGAGAACGCACACGAACACCAUGGGGUGUAUAAUCAGGG<br>CCGUGGUAUCGAUAGCGGGGAACGGUUAAUGCAACCCACACAAAU<br>GUCUGCACAGGAGGAUCUUGGGGACGAUACGGGCAUCCACGUUAU<br>CCCUACGUUAAACGGCGAUGACAGACAUAAAAUUGUAAAUGUGGA<br>CCAACGUCAAUACGGUGACGUGUUUAAAGGAGAUCUUAAUCCAAA<br>ACCCCAAGGCCAAAGACUCAUUGAGGUGUCAGUGGAAGAAAUCA<br>CCCGUUUACUUUACGCGCACCGAUUCAGCGGAUUUAUGGAGUCCG<br>GUACACCGAGACUUGGAGCUUUUUGCCGUCAUUAACCUGUACGGG<br>AGACGCAGCGCCCGCCAUCCAGCAUAUAUGUUUAAAGCAUACAAC<br>AUGCUUUCAAGACGUGGUGGUGGAUGUGGAUUGCGCGGAAAUA<br>CUAAAGAGGAUCAGUUGGCCGAAAUCAGUUACCGUUUUCAAGGUA<br>AGAAGGAAGCGGACCAACCGUGGAUUGUUGUAAACACGAGCACAC<br>UGUUUGAUGAACUCGAAUUAGACCCCCCGAGAUUGAACCGGGUG<br>UCUUGAAAGUACUUCGGACAGAGAAACAAUACUUGGGUGUGUACA<br>UUUGGAACAUGCGCGGCUCCGAUGGUACGUCUACCUACGCCACGU<br>UUUUGGUCACCUGGAAAGGGGAUGAGAAGACAAGAAACCCUACGC<br>CCGCAGUAACUCCUCAACCAAGAGGGGCUGAGUUUCAUAUGUGGA<br>AUUACCACUCGCAUGUAUUUUCAGUUGGUGAUACGUUUAGCUUGG<br>CAAUGCAUCUUCAGUAUAAGAUACAUGAAGCGCCAUUUGAUUUGC |

TABLE 13-continued

Exemplary VZV qE mRNA constructs

| mRNA Construct | ORF of mRNA Construct (excluding the stop codon) |
|---|---|
| | UGUUAGAGUGGUUGUAUGUCCCCAUCGAUCCUACAUGUCAACCAA UGCGGUUAUAUUCUACGUGUUUGUAUCAUCCCAACGCACCCCAAU GCCUCUCUCAUAUGAAUUCCGGUUGUACAUUUACCUCGCCACAUU UAGCCCAGCGUGUUGCAAGCACAGUGUAUCAGAAUUGUGAACAUG CAGAUAACUACACCGCAUAUUGUCUGGGAAUAUCUCAUAUGGAGC CUAGCUUUGGUCUAAUCUUACACGACGGGGGCACCACGUUAAAGU UUGUAGAUACACCCGAGAGUUUGUCGGGAUUAUACGUUUUUGUG GUGUAUUUUAACGGGCAUGUUGAAGCCGUAGCAUACACUGUUGUA UCCACAGUAGAUCAUUUUGUAAACGCAAUUGAAGAGCGUGGAUUU CCGCCAACGGCCGGUCAGCCACCGGCGACUACUAAACCCAAGGAA AUUACCCCCGUAAACCCCGGAACGUCACCACUUCUACGAUAUGCC GCAUGGACCGGAGGGCUUGCAGCAGUAGUACUUUUAUGUCUCGUA AUAUUUUUAAUCUGUACGGCUAAACGAAUGAGGGUUAAAGCCGCC AGGGUAGACAAG (SEQ ID NO: 147) |
| SE-VZV-GE-574-Y569A-v7 | AUGGGGACAGUUAAUAAACCUGUGGUGGGGGUAUUGAUGGGGUU CGGAAUUAUCACGGGAACGUUGCGUAUAACGAAUCCGGUCAGAGC AUCCGUCUUGCGAUACGAUGAUUUUCACAUCGAUGAAGACAAACU GGAUACAAACUCCGUAUAUGAGCCUUACUACCAUUCAGAUCAUGC GGAGUCUUCAUGGGUAAAUCGGGGAGAGUCUUCGCGAAAAGCGUA CGAUCAUAACUCACCUUAUAUAUGGCCACGUAAUGAUUAUGAUGG AUUUUUAGAGAACGCACACGAACACCAUGGGGGUGUAUAAUCAGGG CCGUGGGUAUCGAUAGCGGGGAACGGUUAAUGCAACCCACACAAU GUCUGCACAGGAGGAUCUUGGGGACGAUACGGGCAUCCACGUUAU CCCUACGUUAAACGGCGAUGACAGACAUAAAAUUGUAAAUGUGGA CCAACGUCAAUACGGUGACGUGUUUAAAGGAGAUCUUAAUCCAAA ACCCCAAGGCCAAAGACUCAUUGAGGUGUCAGUGGAAGAAAAUCA CCCGUUUACUUUACGCGCACCGAUUCAGCGGAUUUAUGGAGUCCG GUACACCGAGACUUGGAGCUUUUUGCCGUCAUUAACCUGUACGGG AGACGCAGCGCCCGCCAUCCAGCAUAUAUGUUUAAAGCAUACAAC AUGCUUUCAAGACGUGGUGGUGGAUGUGGAUUGCGCGGAAAAUA CUAAAGAGGAUCAGUUGGCCGAAAUCAGUUACCGUUUUCAAGGUA AGAAGGAAGCGGACCAACCGUGGAUUGUUGUAAACACGAGCACAC UGUUUGAUGAACUCGAAUUAGACCCACCCGAGAUUGAACCGGGUG UCUUGAAAGUACUUCGGACAGAGAAACAAUACUUGGGGUGUGUACA UUUGGAACAUGCGCGGCUCCGAUGGUACGCUCUACCUACGCCACGU UUUUGGUCACCUGGAAAGGGGAUGAGAAGACAAGAAACCCUACGC CCGCAGUAACUCCUCAACCAAGAGGGGCUGAGUUUCAUAUGUGGA AUUACCACUCGCAUGUAUUUUCAGUUGGUGAUACGUUUAGCUUGG CAAUGCAUCUUCAGUAUAAGAUACAUGAAGCGCCAUUUGAUUUGC UGUUAGAGUGGUUGUAUGUCCCCAUCGAUCCUACAUGUCAACCAA UGCGGUUAUAUUCUACGUGUUUGUAUCAUCCCAACGCACCCCAAU GCCUCUCUCAUAUGAAUUCCGGUUGUACAUUUACCUCGCCACAUU UAGCCCAGCGUGUUGCAAGCACAGUGUAUCAGAAUUGUGAACAUG CAGAUAACUACACCGCAUAUUGUCUGGGAAUAUCUCAUAUGGAGC CUAGCUUUGGUCUAAUCUUACACGACGGGGGCACCACGUUAAAGU UUGUAGAUACACCCGAGAGUUUGUCGGGAUUAUACGUUUUUGUG GUGUAUUUUAACGGGCAUGUUGAAGCCGUAGCAUACACUGUUGUA UCCACAGUAGAUCAUUUUGUAAACGCAAUUGAAGAGCGUGGAUUU CCGCCAACGGCCGGUCAGCCACCGGCGACUACUAAACCCAAGGAA AUUACCCCCGUAAACCCCGGAACGUCACCACUUCUACGAUAUGCC GCAUGGACCGGAGGGCUUGCAGCAGUAGUACUUUUAUGUCUCGUA AUAUUUUUAAUCUGUACGGCUAAACGAAUGAGGGUUAAAGCCGCC AGGGUAGACAAG (SEQ ID NO: 148) |
| SE-VZV-GE-574-Y569A-v8 | AUGGGGACAGUUAAUAAACCUGUGGUGGGCGUAUUGAUGGGGUU CGGAAUUAUCACGGGAACGUUGCGUAUAACGAAUCCGGUCAGAGC AUCCGUCUUGCGAUACGAUGAUUUUCACAUCGAUGAAGACAAACU GGAUACAAACUCCGUAUAUGAGCCUUACUACCAUUCAGAUCAUGC GGAGUCUUCAUGGGUAAAUCGGGGAGAGUCUUCGCGAAAGGCGUA CGAUCAUAACUCACCUUAUAUAUGGCCACGUAAUGAUUAUGAUGG AUUCUUAGAGAACGCACACGAACACCAUGGGGGUGUAUAAUCAGGG CCGUGGGUAUCGAUAGCGGGGAACGGUUAAUGCAACCCACACAAU GUCUGCACAGGAGGAUCUUGGGGACGAUACGGGCAUCCACGUUAU CCCUACGUUAAACGGCGAUGACAGACAUAAGAUUGUAAAUGUGGA CCAACGUCAAUACGGUGACGUGUUUAAAGGAGAUCUUAAUCCAAA GCCCCAAGGCCAAAGACUCAUUGAGGUGUCAGUGGAAGAGAAUCA CCCGUUUACUUUACGCGCACCGAUUCAGCGGAUUUAUGGAGUCCG GUACACCGAGACUUGGAGCUUCUUGCCGUCAUUAACCUGUACGGG AGACGCAGCGCCCGCCAUCCAGCAUAUAUGUUUAAAGCAUACAAC AUGCUUUCAAGACGUGGUGGUGGAUGUGGAUUGCGCGGAGAAUA CUAAAGAGGAUCAGUUGGCCGAAAUCAGUUACCGUUUUCAAGGUA AGAAGGAAGCGGACCAACCGUGGAUUGUUGUAAACACGAGCACAC UGUUUGAUGAACUCGAAUUAGACCCACCCGAGAUUGAACCGGGUG UCUUGAAAGUACUUCGGACAGAGAAACAAUACUUGGGGUGUGUACA UUUGGAACAUGCGCGGCUCCGAUGGUACGCUCUACCUACGCCACGU |

TABLE 13-continued

Exemplary VZV gE mRNA constructs

| mRNA Construct | ORF of mRNA Construct (excluding the stop codon) |
|---|---|
| | UCUUGGUCACCUGGAAAGGGGAUGAGAAGACAAGAAACCCUACGC CCGCAGUAACUCCUCAACCAAGAGGGGCUGAGUUUCAUAUGUGGA AUUACCACUCGCAUGUAUUUUCAGUUGGUGAUACGUUUAGCUUGG CAAUGCAUCUUCAGUAUAAGAUACAUGAAGCGCCAUUUGAUUUGC UGUUAGAGUGGUUGUAUGUCCCCAUCGAUCCUACAUGUCAACCAA UGCGGUUAUAUUCUACGUGUUUGUAUCAUCCCAACGCACCCCAUU GCCUCUCUCAUAUGAAUUCCGGUUGUACAUUUACCUCGCCACAUU UAGCCCAGCGUGUUGCAAGCACAGUGUAUCAGAAUUGUGAACAUG CAGAUAACUACACCGCAUAUUGUCUGGGAAUAUCUCAUAUGGAGC CUAGCUUUGGUCUAAUCUUACACGACGGAGGCACCACGUUAAAGU UUGUAGAUACACCCGAGAGUUUGUCGGGAUUAUACGUCUUUGUGG UGUAUUUUAACGGGCAUGUUGAAGCCGUAGCAUACACUGUUGUAU CCACAGUAGAUCAUUUUGUAAACGCAAUUGAAGAGCGUGGAUUUC CGCCAACGGCCGGUCAGCCACCGGCGACUACUAAACCCAAGGAAA UUACGCCCGUAAACCCCGGAACGUCACCACUUCUACGAUAUGCCG CAUGGACCGGAGGGCUUGCAGCAGUAGUACUUUUUAUGUCUCGUAA UAUUCUUAAUCUGUACGGCUAAACGAAUGAGGGUUAAAGCCGCCA GGGUAGACAAG (SEQ ID NO: 149) |
| VZV-GE-Truncated-modified-V9 | AUGGGCACCGUGAACAAGCCUGUUGUGGGCGUGCUGAUGGGCUUC GGCAUCAUCACAGGCACCCUGCGGAUCACCAAUCCUGUGCGGGCU AGCGUGCUGAGAUACGACGACUUCCACAUCGACGAGGACAAGCUG GACACCAACAGCGUGUACGAGCCCUACUACCACAGCGAUCACGCC GAGUCUAGCUGGGUCAACAGAGGCGAGAGCAGCAGAAAGGCCUAC GACCACAACAGCCCUUACAUCUGGCCCAGAAACGACUACGACGGC UUCCUCGAGAAUGCCCACGAACACCACGGCGUGUACAAUCAAGGC AGAGGCAUCGACAGCGGCGAGAGACUGAUGCAGCCUACACAGAUG AGCGCCCAAGAGGACCUGGGAGAUGAUACCGGCAUCCACGUGAUC CCUACACUGAACGGCGACGACCGGCACAAGAUCGUGAACGUGGAC CAGAGACAGUACGGCGACGUGUUCAAGGGCGACCUGAAUCCUAAG CCUCAGGGCCAGCGCCUGAUCGAGGUUUCCGUGGAAGAGAAUCAC CCUUUCACACUGCGGGCUCCCAUCCAGAGAAUCUACGGCGUGCGC UAUACCGAGACAUGGUCCUUUCUGCCCAGCCUGACAUGUACCGGC GACGCCGCUCCUGCCAUCCAGCACAUUUGUCUGAAGCACACCACC UGUUUCCAGGACGUGGUGGUGGAUGUGGACUGCGCCGAGAACACC AAAGAGGAUCAGCUGGCCGAGAUCAGCUACCGGUUCCAGGGAAAG AAAGAGGCCGACCAGCCUUGGAUCGUGGUCAACACCAGCACACUG UUCGACGAGCUGGAACUGGACCCUCCUGAGAUUGAACCCGGCGUC CUGAAGGUGCUGAGAACCGAGAAGCAGUACCUGGGAGUGUACAUC UGGAACAUGAGAGGCAGCGACGGCACCUCUACCUACGCCACCUUU CUGGUCACAUGGAAGGGCGACGAGAAGACCAGAAAUCCCACACCA GCCGUGACACCUCAGCCUAGAGGCGCCGAAUUUCACAUGUGGAAC UACCACUCUCACGUGUUCAGCGUGGGCGAUACCUUCAGCCUGGCC AUGCAUCUGCAGUACAAGAUCCACGAGGCUCCCUUCGACCUGCUG CUGGAAUGGCUGUACGUGCCCAUCGAUCCUACCUGCCAGCCUAUG CGGCUGUACUCCACCUGUCUGUAUCACCCUAACGCUCCUCAGUGC CUGAGCCACAUGAAUAGCGGCUGCACCUUCACAAGCCCUCACCUG GCUCAGCGAGUGGCCAGCACAGUGUACCAGAAUUGCGAGCACGCC GACAAUUACACCGCCUACUGUCUGGGCAUCAGCCACAUGGAACCU AGCUUCGGCCUGAUCCUGCACGAUGGCGGCACCACACUGAAGUUC GUGGACACACCUGAGAGCCUGAGCGGCCUGUAUGUGUUUGUGGUG UACUUCAACGGCCACGUGGAAGCCGUGGCCUACACCGUGGUGUCU ACCGUGGACCACUUCGUGAACGCCAUCGAGGAAAGAGGCUUCCCU CCAACUGCUGGACAGCCUCCUGCCACCACCAAGCCUAAAGAAAUC ACACCCGUGAAUCCCGGCACUAGCCCUCUGCUUAGAUACGCCGCU UGGACAGGCGGACUGGCUGCCGUUGUUCUGCUGUGCCUGGUCAUC UUCCUGAUCUGCACCGCCAAGCGGAUGAGAGUGAAAGCCGCCAGA GUGGACAAG (SEQ ID NO: 150) |
| Corresponding amino acid sequence | MGTVNKPVVGVLMGFGIITGTLRITNPVRASVLRYDDFHIDEDKLDTNS VYEPYYHSDHAESSWVNRGESSRKAYDHNSPYIWPRNDYDGFLENAH EHHGVYNQGRGIDSGERLMQPTQMSAQEDLGDDTGIHVIPTLNGDDRH KIVNVDQRQYGDVFKGDLNPKPQGQRLIEVSVEENHPFTLRAPIQRIYG VRYTETWSFLPSLTCTGDAAPAIQHICLKHTTCFQDVVVDVDCAENTKE DQLAEISYRFQGKKEADQPWIVVNTSTLFDELELDPPEIEPGVLKVLRTE KQYLGVYIWNMRGSDGTSTYATFLVTWKGDEKTRNPTPAVTPQPRGA EFHMWNYHSHVFSVGDTFSLAMHLQYKIHEAPFDLLLEWLYVPIDPTC QPMRLYSTCLYHPNAPQCLSHMNSGCTFTSPHLAQRVASTVYQNCEHA DNYTAYCLGISHMEPSFGLILHDGGTTLKFVDTPESLSGLYVFVVYFNG HVEAVAYTVVSTVDHFVNAIEERGFPPTAGQPPATTKPKEITPVNPGTSP LLRYAAWTGGLAAVVLLCLVIFLICTAKRMRVKAARVDK (SEQ ID NO: 38) |

TABLE 13-continued

| Exemplary VZV gE mRNA constructs | |
|---|---|
| mRNA Construct | ORF of mRNA Construct (excluding the stop codon) |
| 5' UTR | GGGAAAUAAGAGAGAAAAGAAGAGUAAGAAGAAAUAUAAGAGCC ACC (SEQ ID NO: 138) |
| 3' UTR | UGAUAAUAGGCUGGAGCCUCGGUGGCCAUGCUUCUUGCCCCUUGG GCCUCCCCCCAGCCCCUCCUCCCCUUCCUGCACCCGUACCCCGUG GUCUUUGAAUAAAGUCUGAGUGGGCGGC (SEQ ID NO: 139) |
| PolyA Tail | 100 nt (SEQ ID NO: 140) |

TABLE 14

| Varicella zoster virus Amino Acid Sequences | | |
|---|---|---|
| Protein | Name | GenBank Accession |
| glycoprotein B | envelope glycoprotein B [Human herpesvirus 3] | NP_040154.2 |
| glycoprotein B | ORF31 [Human herpesvirus 3] | AKG57704.1 |
| glycoprotein B | ORF 31 [Human herpesvirus 3] | AIT52967.1 |
| glycoprotein B | envelope glycoprotein B [Human herpesvirus 3] | AFJ68532.1 |
| glycoprotein B | ORF31 [Human herpesvirus 3] | AKG57414.1 |
| glycoprotein B | ORF31 [Human herpesvirus 3] | AKG58507.1 |
| glycoprotein B | RecName: Full = Envelope glycoprotein B; Short = gB; AltName: Full = Glycoprotein II; Flags: Precursor [Human herpesvirus 3 strain Oka vaccine] | Q4JR05.2 |
| glycoprotein B | ORF31 [Human herpesvirus 3] | AEL30845.1 |
| glycoprotein B | glycoprotein B [Human herpesvirus 3] | AAK01041.1 |
| glycoprotein B | glycoprotein B [Human herpesvirus 3] | AEW89232.1 |
| glycoprotein B | glycoprotein B [Human herpesvirus 3] | AEW88728.1 |
| glycoprotein B | ORF31 [Human herpesvirus 3] | AAK19938.1 |
| glycoprotein B | glycoprotein B [Human herpesvirus 3] | AAP32845.1 |
| glycoprotein B | ORF 31 [Human herpesvirus 3] | AHJ08729.1 |
| glycoprotein B | ORF31 [Human herpesvirus 3] | AAY57715.1 |
| glycoprotein B | ORF31 [Human herpesvirus 3] | AGY33726.1 |
| glycoprotein B | ORF 31 [Human herpesvirus 3] | AHJ09321.1 |
| glycoprotein B | ORF31 [Human herpesvirus 3] | AAY57644.1 |
| glycoprotein B | ORF 31 [Human herpesvirus 3] | AHJ09025.1 |
| glycoprotein B | glycoprotein B [Human herpesvirus 3] | AEW88584.1 |
| glycoprotein B | ORF 31 [Human herpesvirus 3] | AHJ09099.1 |
| glycoprotein B | ORF31 [Human herpesvirus 3] | AGY33060.1 |
| glycoprotein B | ORF 31 [Human herpesvirus 3] | AHJ09395.1 |
| glycoprotein C | RecName: Full = Envelope glycoprotein C; Short = gC; AltName: Full = Glycoprotein V; Short = gpV | P09256.2 |
| glycoprotein C | envelope glycoprotein gC [Human herpesvirus 3] | ABH08453.1 |
| glycoprotein C | ORF14 [Human herpesvirus 3] | AIH07125.1 |
| glycoprotein C | unknown protein [Human herpesvirus 3] | AAA69563.1 |
| glycoprotein C | ORF14 [Human herpesvirus 3] | AIH07051.1 |
| glycoprotein C | ORF14 [Human herpesvirus 3] | AIJ28607.1 |
| glycoprotein C | ORF14 [Human herpesvirus 3] | AEL30828.1 |
| glycoprotein C | envelope glycoprotein gC [Human herpesvirus 3] | ABE03032.1 |
| glycoprotein C | envelope glycoprotein gC [Human herpesvirus 3] | ABE67122.1 |
| glycoprotein C | envelope glycoprotein C [Human herpesvirus 3] | NP_040137.1 |
| glycoprotein C | membrane glycoprotein C [Human herpesvirus 3] | AEW88351.1 |
| glycoprotein C | envelope glycoprotein C [Human herpesvirus 3] | AFJ68515.1 |
| glycoprotein C | membrane glycoprotein C [Human herpesvirus 3] | AAT07696.1 |
| glycoprotein C | envelope glycoprotein gC [Human herpesvirus 3] | ABF22098.1 |
| glycoprotein C | membrane glycoprotein C [Human herpesvirus 3] | AEW89287.1 |
| glycoprotein C | glycoprotein C [Human herpesvirus 3] | AGC94505.1 |
| glycoprotein C | envelope glycoprotein gC [Human herpesvirus 3] | ABF21514.1 |
| glycoprotein C | envelope glycoprotein gC [Human herpesvirus 3] | ABF21879.1 |
| glycoprotein C | envelope glycoprotein gC [Human herpesvirus 3] | ABF21587.1 |
| glycoprotein C | ORF 14 [Human herpesvirus 3] | AIT53315.1 |
| glycoprotein C | membrane glycoprotein C [Human herpesvirus 3] | AEW89215.1 |
| glycoprotein C | envelope glycoprotein gC [Human herpesvirus 3] | ABF21660.1 |
| glycoprotein C | membrane glycoprotein C [Human herpesvirus 3] | AEW88567.1 |
| glycoprotein C | envelope glycoprotein gC [Human herpesvirus 3] | CAI44857.1 |
| glycoprotein C | envelope glycoprotein C [Human herpesvirus 3] | AHB80244.1 |
| glycoprotein C | ORF14 [Human herpesvirus 3] | AAY57702.1 |
| glycoprotein C | glycoprotein c [Human herpesvirus 3] | AGS32072.1 |
| glycoprotein C | envelope glycoprotein gC [Human herpesvirus 3] | AGL50971.1 |
| glycoprotein C | membrane glycoprotein C [Human herpesvirus 3] | AAT07772.1 |
| glycoprotein C | membrane glycoprotein C [Human herpesvirus 3] | AEW88495.1 |
| glycoprotein C | ORF 14 [Human herpesvirus 3] | AIT53461.1 |

TABLE 14-continued

| Varicella zoster virus Amino Acid Sequences | | |
| --- | --- | --- |
| Protein | Name | GenBank Accession |
| glycoprotein C | ORF 14 [Human herpesvirus 3] | AIT52950.1 |
| glycoprotein C | ORF14 [Human herpesvirus 3] | AAY57631.1 |
| glycoprotein C | envelope glycoprotein gC [Human herpesvirus 3] | ABF21952.1 |
| glycoprotein C | membrane glycoprotein C [Human herpesvirus 3] | AEW89143.1 |
| glycoprotein C | membrane glycoprotein C [Human herpesvirus 3] | AEW88783.1 |
| glycoprotein C | membrane glycoprotein C [Human herpesvirus 3] | AEW88999.1 |
| glycoprotein C | membrane glycoprotein C [Human herpesvirus 3] | AEW88063.1 |
| glycoprotein C | membrane glycoprotein C [Human herpesvirus 3] | AEW89071.1 |
| glycoprotein C | membrane glycoprotein C [Human herpesvirus 3] | AEW88639.1 |
| glycoprotein C | membrane glycoprotein C [Human herpesvirus 3] | AEW87991.1 |
| glycoprotein C | ORF 14 [Human herpesvirus 3] | AIT53753.1 |
| glycoprotein C | ORF 14 [Human herpesvirus 3] | AIT53096.1 |
| glycoprotein C | envelope glycoprotein gC [Human herpesvirus 3] | ABF22025.1 |
| glycoprotein C | envelope glycoprotein gC [Human herpesvirus 3] | AFO85518.1 |
| glycoprotein C | envelope glycoprotein gC [Human herpesvirus 3] | ABF21733.1 |
| glycoprotein C | envelope glycoprotein gC [Human herpesvirus 3] | ABF21806.1 |
| glycoprotein C | membrane glycoprotein C [Human herpesvirus 3] | AEW89359.1 |
| glycoprotein C | membrane glycoprotein C [Human herpesvirus 3] | AEW88855.1 |
| glycoprotein C | envelope glycoprotein gC [Human herpesvirus 3] | AFO85591.1 |
| glycoprotein C | membrane glycoprotein C [Human herpesvirus 3] | AEW89431.1 |
| glycoprotein C | membrane glycoprotein C [Human herpesvirus 3] | AEW88711.1 |
| glycoprotein C | membrane glycoprotein C [Human herpesvirus 3] | AEW88135.1 |
| glycoprotein C | membrane glycoprotein C [Human herpesvirus 3] | AEW88927.1 |
| glycoprotein C | ORF14 [Human herpesvirus 3] | AKG56156.1 |
| glycoprotein C | ORF14 [Human herpesvirus 3] | AKG57178.1 |
| glycoprotein C | ORF14 [Human herpesvirus 3] | AKG58125.1 |
| glycoprotein C | ORF14 [Human herpesvirus 3] | AGY32970.1 |
| glycoprotein C | ORF14 [Human herpesvirus 3] | AKG56229.1 |
| glycoprotein C | ORF14 [Human herpesvirus 3] | AGY32896.1 |
| glycoprotein C | ORF14 [Human herpesvirus 3] | AKG56521.1 |
| glycoprotein C | ORF 14 [Human herpesvirus 3] | AHJ08712.1 |
| glycoprotein E | unknown [Human herpesvirus 3] | ABE03086.1 |
| glycoprotein E | glycoprotein E [Human herpesvirus 3] | AAK01047.1 |
| glycoprotein E | RecName: Full = Envelope glycoprotein E; Short = gE; Flags: Precursor | Q9J3M8.1 |
| glycoprotein E | membrane glycoprotein E [Human herpesvirus 3] | AEW88548.1 |
| glycoprotein E | ORF68 [Human herpesvirus 3] | AGY33616.1 |
| glycoprotein E | membrane glycoprotein E [Human herpesvirus 3] | AEW89124.1 |
| glycoprotein E | ORF 68 [Human herpesvirus 3] | AIT53150.1 |
| glycoprotein E | unnamed protein product [Human herpesvirus 3] | CAA25033.1 |
| glycoprotein E | envelope glycoprotein E [Human herpesvirus 3] | NP_040190.1 |
| glycoprotein E | ORF68 [Human herpesvirus 3] | AKG56356.1 |
| glycoprotein E | membrane glycoprotein E [Human herpesvirus 3] | AEW89412.1 |
| glycoprotein E | membrane glycoprotein gE [Human herpesvirus 3] | ABF21714.1 |
| glycoprotein E | membrane glycoprotein E [Human herpesvirus 3] | AAT07749.1 |
| glycoprotein E | membrane glycoprotein E [Human herpesvirus 3] | AEW88764.1 |
| glycoprotein E | glycoprotein E [Human herpesvirus 3] | AAG48520.1 |
| glycoprotein E | membrane glycoprotein E [Human herpesvirus 3] | AEW88980.1 |
| glycoprotein H | envelope glycoprotein H [Human herpesvirus 3] | NP_040160.1 |
| glycoprotein H | glycoprotein H [Human herpesvirus 3] | AEW89454.1 |
| glycoprotein H | ORF37 [Human herpesvirus 3 VZV-32] | AAK19252.1 |
| glycoprotein H | RecName: Full = Envelope glycoprotein H; Short = gH; AltName: Full = Glycoprotein III; Short = GPIII; Flags: Precursor | Q775J3.1 |
| glycoprotein H | glycoprotein H [Human herpesvirus 3] | AAK01042.1 |
| glycoprotein H | ORF37 [Human herpesvirus 3] | AKG58587.1 |
| glycoprotein H | ORF37 [Human herpesvirus 3] | AGY33215.1 |
| glycoprotein H | glycoprotein H [Human herpesvirus 3] | AAP32857.1 |
| glycoprotein H | envelope glycoprotein gH [Human herpesvirus 3] | ABE03056.1 |
| glycoprotein H | ORF 37 [Human herpesvirus 3] | AHJ09328.1 |
| glycoprotein H | glycoprotein H [Human herpesvirus 3] | AAP32862.1 |
| glycoprotein H | ORF37 [Human herpesvirus 3] | AKG57421.1 |
| glycoprotein H | ORF37 [Human herpesvirus 3] | AKG56618.1 |
| glycoprotein H | ORF37 [Human herpesvirus 3] | AKG56545.1 |
| glycoprotein H | glycoprotein H [Human herpesvirus 3] | AEW89382.1 |
| glycoprotein H | glycoprotein H [Human herpesvirus 3] | AGC94548.1 |
| glycoprotein I | envelope glycoprotein I [Human herpesvirus 3] | NP_040189.1 |
| glycoprotein I | membrane glycoprotein I [Human herpesvirus 3] | AEW89195.1 |
| glycoprotein I | ORF67 [Human herpesvirus 3] | AKG58616.1 |
| glycoprotein I | ORF67 [Human herpesvirus 3] | AGY34059.1 |
| glycoprotein I | membrane glycoprotein I [Human herpesvirus 3] | AEW89051.1 |
| glycoprotein I | ORF67 [Human herpesvirus 3 VZV-32] | AAK19249.1 |
| glycoprotein I | membrane glycoprotein I [Human herpesvirus 3] | AEW89483.1 |
| glycoprotein K | envelope glycoprotein K [Human herpesvirus 3] | NP_040128.1 |
| glycoprotein K | glycoprotein K [Human herpesvirus 3] | AEW88773.1 |

TABLE 14-continued

Varicella zoster virus Amino Acid Sequences

| Protein | Name | GenBank Accession |
|---|---|---|
| glycoprotein K | ORF 5 [Human herpesvirus 3] | AHJ09368.1 |
| glycoprotein K | ORF5 [ Human herpesvirus 3] | AKG58699.1 |
| glycoprotein K | glycoprotein K [Human herpesvirus 3] | AEW88701.1 |
| glycoprotein K | ORF5 [ Human herpesvirus 3] | AKG56803.1 |
| glycoprotein K | glycoprotein K [Human herpesvirus 3] | AEW88053.1 |
| glycoprotein L | RecName: Full = Envelope glycoprotein L; Short = gL; Flags: Precursor | Q9J3N1.1 |
| glycoprotein L | virion glycoprotein gL [Human herpesvirus 3] | ABE03078.1 |
| glycoprotein L | glycoprotein L [Human herpesvirus 3] | AGM33094.1 |
| glycoprotein L | ORF60 [Human herpesvirus 3] | AKG56786.1 |
| glycoprotein L | envelope glycoprotein L [Human herpesvirus 3] | NP_040182.1 |
| glycoprotein L | virion glycoprotein gL [Human herpesvirus 3] | ABF21706.1 |
| glycoprotein M | envelope glycoprotein M [Human herpesvirus 3] | NP_040172.1 |
| glycoprotein M | ORF 50 [Human herpesvirus 3] | AIT53351.1 |
| glycoprotein M | ORF50 [Human herpesvirus 3] | AKG56119.1 |
| glycoprotein M | ORF50 [Human herpesvirus 3] | AGY33080.1 |
| glycoprotein M | envelope glycoprotein gM [Human herpesvirus 3] | ABE03068.1 |
| glycoprotein M | virion membrane glycoprotein M [Human herpesvirus 3] | AEW88530.1 |
| glycoprotein M | virion membrane glycoprotein M [Human herpesvirus 3] | AEW88674.1 |
| glycoprotein N | envelope glycoprotein N [Human herpesvirus 3] | YP_068406.1 |
| glycoprotein N | ORF9a [Human herpesvirus 3] | AGY33038.1 |
| glycoprotein N | membrane protein [Human herpesvirus 3] | AAT07690.1 |
| glycoprotein N | membrane protein [Human herpesvirus 3] | AEW88273.1 |
| glycoprotein N | membrane protein [Human herpesvirus 3] | AEW88489.1 |

TABLE 15

VZV Polypeptide Sequences

| Name | Sequence | SEQ ID NO: |
|---|---|---|
| gi\|443500676\|gb\| AGC94542.1\| glycoprotein E [Human herpesvirus 3] | MGTVNKPVVGVLMGFGIITGTLRITNPVRASVLRYDDFHI DEDKLDTNSVYEPYYHSDHAESSWVNRGESSRKAYDHN SPYIWPRNDYDGFLENAHEHHGVYNQGRGIDSGERLMQP TQMSAQEDLGDDTGIHVIPTLNGDDRHKIVNVDQRQYGD VFKGDLNPKPQGQRLIEVSVEENHPFTLRAPIQRIYGVRY TETWSFLPSLTCTGDAAPAIQHICLKHTTCFQDVVVDVDC AENTKEDQLAEISYRFQGKKEADQPWIVVNTSTLFDELEL DPPEIEPGVLKVLRTEKQYLGVYIWNMRGSDGTSTYATF LVTWKGDEKTRNPTPAVTPQPRGAEFHMWNYHSHVFSV GDTFSLAMHLQYKIHEAPFDLLLEWLYVPIDPTCQPMRL YSTCLYHPNAPQCLSHMNSGCTFTSPHLAQRVASTVYQN CEHADNYTAYCLGISHMEPSFGLILHDGGTTLKFVDTPES LSGLYVFVVYFNGHVEAVAYTVVSTVDHFVNAIEERGFP PTAGQPPATTKPKEITPVNPGTSPLLRYAAWTGGLAAVV LLCLVIFLICTAKRMRVKAYRVDKSPYNQSMYYAGLPVD DFEDSESTDTEEEFGNAIGGSHGGSSYTVYIDKTR | 45 |
| gi\|443500675\|gb\| AGC94541.1\| glycoprotein I [Human herpesvirus 3] | MFLIQCLISAVIFYIQVTNALIFKGDHVSLQVNSSLTSILIP MQNDNYTEIKGQLVFigEQLPTGTNYSGTLELLYADTVAF CFRSVQVIRYDGCPRIRTSAFISCRYKHSWHYGNSTDRIST EPDAGVMLKITKPGINDAGVYVLLVRLDHSRSTDGFILGV NVYTAGSHHNIHGVIYTSPSLQNGYSTRALFQQARLCDLP ATPKGSGTSLFQHMLDLRAGKSLEDNPWLHEDVVTTETK SVVKEGIENHVYPTDMSTLPEKSLNDPPENLLIIIPIVASV MILTAMVIVIVISVKRRRIKKHPIYRPNTKTRRGIQNATPE SDVMLEAAIAQLATIREESPPHSVVNPFVK | 46 |
| VZV-GE-delete-562 | MGTVNKPVVGVLMGFGIITGTLRITNPVRASVLRYDDFHI DEDKLDTNSVYEPYYHSDHAESSWVNRGESSRKAYDHN SPYIWPRNDYDGFLENAHEHHGVYNQGRGIDSGERLMQP TQMSAQEDLGDDTGVIPTLNGDDRHKIVNVDQRQYGDV FKGDLNPKPQGQRLIEVSVEENHPFTLRAPIQRIYGVRYTE TWSFLPSLTCTGDAAPAIQHICLKHTTCFQDVVVDVDCA ENTKEDQLAEISYRFQGKKEADQPWIVVNTTLFDELELDP PEIEPGVLKVLRTEKQYLGVYIWNMRGSDGTSTYATFLV TWKGDEKTRNPTPAVTPQPRGAEFHMWNYHSHVFSVGD TFSLAMHLQYKIHEAPFDLLLEWLYVPIDPTCQPMRLYST | 47 |

TABLE 15-continued

VZV Polypeptide Sequences

| Name | Sequence | SEQ ID NO: |
|---|---|---|
| | CLYHPNAQCLSHMNSGCTFTSPHLAQRVASTVYQNCEH ADNYTAYCLGISHMEPSFGLILHDGGTTLKFVDTPESLSG LYVFVVYFNGHVEAVAYTVVSTVDHFVNAIEERGFPPTA GQPPATTKPKEITPVNPGTSPLLRYAWTGGLAAVVLLCL VIFLICTA | |
| gi\|46981496\|gb\|A AT07772.1\| membrane glycoprotein C [Human herpesvirus 3] | MKRIQINLILTIACIQLSTESQPTPVSITELYTSAATRKPDPA VAPTSAATRKPDPAVAPTSAATRKPDPAVAPTSAATRKP DPAVAPTSAATRKPDPAVAPTSAATRKPDPAVAPTSAAS RKPDPAVAPTSAASRKPDPAVAPTSAASRKPDPAANTQH SQPPFLYENIQCVHGGIQSIPYFHTFIMPCYMRLTTGQQAA FKQQQKTYEQYSLDPEGSNITRWKSLIRPDLHIEVWFTRH LIDPHRQLGNALIRMPDLPVMLYSNSADLNLINNPEIFTH AKENYVIPDVKTTSDFSVTILSMDATTEGTYIWRVVNTKT KNVISEHSITVTTYYRPNITVVGDPVLTGQTYAAYCNVSK YYPPHSVRVRWTSRFGNIGKNFITDAIQEYANGLFSYVSA VRIPQQKQMDYPPPAIQCNVLWIRDGVSNMKYSAVVTPD VYPFPNVSIGIIDGHIVCTAKCVPRGVVHFVWVNDSPIN HENSEITGVCDQNKRFVNMQSSCPTSELDGPITYSCHLDG YPKKFPPFSAVYTYDASTYATTFSVVAVIIGVISILGTLGLI AVIATLCIRCCS | 48 |
| gi\|9625934\|ref\|NP_040182.1\| envelope glycoprotein L [Human herpesvirus 3] | MASHKWLLQIVFLKTITIAYCLHLQDDTPLFFGAKPLSDV SLIITEPCVSSVYEAWDYAAPPVSNLSEALSGIVVKTKCPV PEVILWFKDKQMAYWTNPYVTLKGLAQSVGEEHKSGDI RDALLDALSGVWVDSTPSSTNIPENGCVWGADRLFQRVC Q | 49 |
| gi\|9625925\|ref\|NP_040172.1\| envelope glycoprotein M [Human herpesvirus 3] | MGTQKKGPRSEKVSPYDTTTPEVEALDHQMDTLNWRIW IIQVMMFTLGAVMLLATLIAASSEYTGIPCFYAAVVDYEL FNATLDGGVWSGNRGGYSAPVLFLEPHSVVAFTYYTALT AMAMAVYTLITAAIIHRETKNQRVRQSSGVAWLVVDPTT LFWGLLSLWLLNAVVLLLAYKQIGVAATLYLGHFATSVI FTTYFCGRGKLDETNIKAVANLRQQSVFLYRLAGPTRAV FVNLMAALMAICILFVSLMLELVVANHLHTGLWSSVSVA MSTFSTLSVVYLIVSELILAHYIHVLIGPSLGTLVACATLG TAAHSYMDRLYDPISVQSPRLIPTTRGTLACLAVFSVVML LLRLMRAYVYHRQKRSRFYGAVRRVPERVRGYIRKVKP AHRNSRRTNYPSQGYGYVYENDSTYETDREDELLYERSN SGWE | 50 |
| gi\|9625912\|ref\|NP_040160.1\| envelope glycoprotein H [Human herpesvirus 3] | MFALVLAVVILPLWTTANKSYVTPTPATRSIGHMSALLRE YSDRNMSLKLEAFYPTGFDEELIKSLHWGNDRKHVFLVI VKVNPTTHEGDVGLVIFPKYLLSPYHFKAEHRAPPPAGRF GFLSHPVTPDVSFFDSSFAPYLTTQHLVAFTTFPPNPLVW HLERAETAATAERPFGVSLLPARPTVPKNTILEHKAHFAT WDALARHTFFSAEAIITNSTLRIHVPLFGSVWPIRYWATG SVLLTSDSGRVEVNIGVGFMSSLISLSSGPPIELIVVPHTVK LNAVTSDTTWFQLNPPGPDPGPSYRVYLLGRGLDMNFSK HATVDICAYPEESLDYRYHLSMAHTEALRMTTKADQHDI NEESYYHIAARIATSIFALSEMGRTTEYFLLDEIVDVQYQL KFLNYILMRIGAGAHPNTISGTSDLIFADPSQLHDELSLLF GQVKPANVDYFISYDEARDQLKTAYALSRGQDHVNALS LARRVIMSIYKGLLVKQNLNATERQALFFASMILLNFREG LENSSRVLDGRTTLLLMTSMCTAAHATQAALNIQEGLAY LNPSKHMFTIPNVYSPCMGSLRTDLTEEIHVMNLLSAIPTR PGLNEVLHTQLDESEIFDAAFKTMMIFTTWTAKDLHILHT HVPEVFTCQDAAARNGEYVLILPAVQGHSYVITRNKPQR GLVYSLADVDVYNPISVVYLSRDTCVSEHGVIETVALPHP DNLKECLYCGSVFLRYLTTGAIMDIIIIDSKDTERQLAAM GNSTIPPFNPDMHGDDSKAVLLFPNGTVVTLLGFERRQAI RMSGQYLGASLGGAFLAVVGFGIIGWMLCGNSRLREYN KIPLT | 51 |
| gi\|584403829\|gb\| AHB80298.1\| envelope glycoprotein E [Human herpesvirus 3] | MFYEALKAELVYTRAVHGFRPRANCVVLSDYIPRVACN MGTVNKPVVGVLMGFGIITGTLRITNPVRASVLRYDDFHI DEDKLDTNSVYEPYYHSDHAESSWVNRGESSRKAYDHN SPYIWPRNDYDGFLENAHEHHGVYNQGRGIDSGERLMQP TQMSAQEDLGDDTGIHVIPTLNGDDRHKIVNVDQRQYGD VFKGDLNPKPQGQRLIEVSVEENHPFTLRAPIQRIYGVRY TETWSFLPSLTCTGDAAPAIQHICLKHTTCFQDVVVDVDC AENTKEDQLAEISYRFQGKKEADQPWIVVNTSTLFDELEL DPPEIEPGVLKVLRTEKQYLGVYIWNMRGSDGTSTYATF LVTWKGDEKTRNPTPAVTPQPRGAEFHMWNYHSHVFV GDTFSLAMHLQYKIHEAPFDLLLEWLYVPIDPTCQPMRL YSTCLYHPNAPQCLSHMNSGCTFTSPHLAQRVASTVYQN | 52 |

TABLE 15-continued

| VZV Polypeptide Sequences | | |
| --- | --- | --- |
| Name | Sequence | SEQ ID NO: |
| | CEHADNYTAYCLGISHMEPSFGLILHDGGTTLKFVDTPES<br>LSGLYVFVVYFNGHVEAVAYTVVSTVDHFVNAIEERGFP<br>PTAGQPPATTKPKEITPVNPGTSPLLRYAAWTGGLAAVV<br>LLCLVIFLICTAKRMRVKAYRVDKSPYNQSMYYAGLPVD<br>DFEDSESTDTEEEFGNAIGGSHGGSSYTVYIDKTR | |
| gi\|46981513\|gb\|A<br>AT07789.1\|<br>glycoprotein B<br>[Human<br>herpesvirus 3] | MFVTAVVSVSPSSFYESLQVEPTQSEDITRSAHLGDGDEIR<br>EAIHKSQDAETKPTFYVCPPPTGSTIVRLEPTRTCPDYHLG<br>KNFTEGIAVVYKENIAAYKFKATVYYKDVIVSTAWAGSS<br>YTQITNRYADRVPIPVSEITDTIDKFGKCSSKATYVRNNH<br>KVEAFNEDKNPQDMPLIASKYNSVGSKAWHTTNDTYMV<br>AGTPGTYRTGTSVNCIIEEVEARSIFPYDSFGLSTGDIIYMS<br>PFFGLRDGAYREHSNYAMDRFHQFEGYRQRDLDTRALL<br>EPAARNFLVTPHLTVGWNWKPKRTEVCSLVKWREVEDV<br>VRDEYAHNFRFTMKTLSTTFISETNEFNLNQIHLSQCVKE<br>EARAIINRIYTTRYNSSHVRTGDIQTYLARGGFVVVFQPLL<br>SNSLARLYLQELVRENTNHSPQKHPTRNTRSRRSVPVELR<br>ANRTITTTSSVEFAMLQFTYDHIQEHVNEMLARISSSWCQ<br>LQNRERALWSGLFPINPSALASTILDQRVKARILGDVISVS<br>NCPELGSDTRIILQNSMRVSGSTTRCYSRPLISIVSLNGSGT<br>VEGQLGTDNELIMSRDLLEPCVANHKRYFLFGHHYVYYE<br>DYRYVREIAVHDVGMISTYVDLNLTLLKDREFMPLQVYT<br>RDELRDTGLLDYSEIQRRNQMHSLRFYDIDKVVQYDSGT<br>AIMQGMAQFFQGLGTAGQAVGHVVLGATGALLSTVHGF<br>TTFLSNPFGALAVGLLVLAGLVAAFFAYRYVLKLKTSPM<br>KALYPLTTKGLKQLPEGMDPFAEKPNATDTPIEEIGDSQN<br>TEPSVNSGFDPDKFREAQEMIKYMTLVSAAERQESKARK<br>KNKTSALLTSRLTGLALRNRRGYSRVRTENVTGV | 53 |
| gi\|46981487\|gb\|A<br>AT07763.1\|<br>glycoprotein K<br>[Human<br>herpesvirus 3] | MQALGIKTEHFIIMCLLSGHAVFTLWYTARVKFEHECVY<br>ATTVINGGPVVWGSYNNSLIYVTFVNHSTFLDGLSGYDY<br>SCRENLLSGDTMVKTAISTPLHDKIRIVLGTRNCHAYFWC<br>VQLKMIFFAWFVYGMYLQFRRIRRMFGPFRSSCELISPTS<br>YSLNYVTRVISNILLGYPYTKLARLLCDVSMRRDGMSKV<br>FNADPISFLYMHKGVTLLMLLEVIAHISSGCIVLLTLGVA<br>YTPCALLYPTYIRILAWVVVCTLAIVELISYVRPKPTKDN<br>HLNHINTGGIRGICTTCCATVMSGLAIKCFYIVIFAIAVVIF<br>MHYEQRVQVSLFGESENSQKH | 54 |
| gi\|443500633\|gb\|<br>AGC94499.1\|<br>glycoprotein N<br>[Human<br>herpesvirus 3] | MGSITASFILITMQILFFCEDSSGEPNFAERNFWHASCSAR<br>GVYIDGSMITTLFFYASLLGVCVALISLAYHACFRLFTRSV<br>LRSTW | 55 |
| Ig heavy chain<br>epsilon-1 signal<br>peptide (IgE HC<br>SP) | MDWTWILFLVAAATRVHS | 56 |
| IgGk chain V-III<br>region HAH<br>signal peptide<br>(IgGk SP) | METPAQLLFLLLLWLPDTTG | 57 |
| Japanese<br>encephalitis PRM<br>signal sequence | MLGSNSGQRVVFTILLLLVAPAYS | 109 |
| VSVg protein<br>signal sequence | MKCLLYLAFLFIGVNCA | 110 |
| Japanese<br>encephalitis JEV<br>signal sequence | MWLVSLAIVTACAGA | 111 |

TABLE 16

Flagellin Nucleic Acid Sequences

| Name | Sequence | SEQ ID NO: |
|---|---|---|
| NT (5' UTR, ORF, 3' UTR) | TCAAGCTTTTGGACCCTCGTACAGAAGCTAATACGACTCACTAT AGGGAAATAAGAGAGAAAAGAAGAGTAAGAAGAAATATAAG AGCCACCATGGCACAAGTCATTAATACAAACAGCCTGTCGCTG TTGACCCAGAATAACCTGAACAAATCCCAGTCCGCACTGGGCA CTGCTATCGAGCGTTTGTCTTCCGGTCTGCGTATCAACAGCGCG AAAGACGATGCGGCAGGACAGGCGATTGCTAACCGTTTTACCG CGAACATCAAAGGTCTGACTCAGGCTTCCCGTAACGCTAACGA CGGTATCTCCATTGCGCAGACCACTGAAGGCGCGCTGAACGAA ATCAACAACAACCTGCAGCGTGTGCGTGAACTGGCGGTTCAGT CTGCGAATGGTACTAACTCCCAGTCTGACCTCGACTCCATCCAG GCTGAAATCACCCAGCGCCTGAACGAAATCGACCGTGTATCCG GCCAGACTCAGTTCAACGGCGTGAAAGTCCTGGCGCAGGACAA CACCCTGACCATCCAGGTTGGTGCCAACGACGGTGAAACTATC GATATTGATTTAAAAGAAATCAGCTCTAAAACACTGGGACTTG ATAAGCTTAATGTCCAAGATGCCTACACCCCGAAAGAAACTGC TGTAACCGTTGATAAAACTACCTATAAAAATGGTACAGATCCT ATTACAGCCCAGAGCAATACTGATATCCAAACTGCAATTGGCG GTGGTGCAACGGGGGTTACTGGGGCTGATATCAAATTTAAAGA TGGTCAATACTATTTAGATGTTAAAGGCGGTGCTTCTGCTGGTG TTTATAAAGCCACTTATGATGAAACTACAAAGAAAGTTAATAT TGATACGACTGATAAAACTCCGTTGGCAACTGCGGAAGCTACA GCTATTCGGGGAACGGCCACTATAACCCACAACCAAATTGCTG AAGTAACAAAAGAGGGTGTTGATACGACCACAGTTGCGGCTCA ACTTGCTGCAGCAGGGGTTACTGGCGCCGATAAGGACAATACT AGCCTTGTAAAACTATCGTTTGAGGATAAAAACGGTAAGGTTA TTGATGGTGGCTATGCAGTGAAAATGGGCGACGATTTCTATGC CGCTACATATGATGAGAAAACAGGTGCAATTACTGCTAAAACC ACTACTTATACAGATGGTACTGGCGTTGCTCAAACTGGAGCTGT GAAATTTGGTGGCGCAAATGGTAAATCTGAAGTTGTTACTGCT ACCGATGGTAAGACTTACTTAGCAAGCGACCTTGACAAACATA ACTTCAGAACAGGCGGTGAGCTTAAAGAGGTTAATACAGATAA GACTGAAAACCCACTGCAGAAAATTGATGCTGCCTTGGCACAG GTTGATACACTTCGTTCTGACCTGGGTGCGGTTCAGAACCGTTT CAACTCCGCTATCACCAACCTGGGCAATACCGTAAATAACCTG TCTTCTGCCCGTAGCCGTATCGAAGATTCCGACTACGCAACCGA AGTCTCCAACATGTCTCGCGCGCAGATTCTGCAGCAGGCCGGT ACCTCCGTTCTGGCGCAGGCGAACCAGGTTCCGCAAAACGTCC TCTCTTTACTGCGTTGATAATAGGCTGGAGCCTCGGTGGCCATG CTTCTTGCCCCTTGGGCCTCCCCCCAGCCCCTCCTCCCCTTCCTG CACCCGTACCCCCGTGGTCTTTGAATAAAGTCTGAGTGGGCGG C | 112 |
| ORF Sequence, NT | ATGGCACAAGTCATTAATACAAACAGCCTGTCGCTGTTGACCC AGAATAACCTGAACAAATCCCAGTCCGCACTGGGCACTGCTAT CGAGCGTTTGTCTTCCGGTCTGCGTATCAACAGCGCGAAAGAC GATGCGGCAGGACAGGCGATTGCTAACCGTTTTACCGCGAACA TCAAAGGTCTGACTCAGGCTTCCCGTAACGCTAACGACGGTAT CTCCATTGCGCAGACCACTGAAGGCGCGCTGAACGAAATCAAC AACAACCTGCAGCGTGTGCGTGAACTGGCGGTTCAGTCTGCGA ATGGTACTAACTCCCAGTCTGACCTCGACTCCATCCAGGCTGAA ATCACCCAGCGCCTGAACGAAATCGACCGTGTATCCGGCCAGA CTCAGTTCAACGGCGTGAAAGTCCTGGCGCAGGACAACACCCT GACCATCCAGGTTGGTGCCAACGACGGTGAAACTATCGATATT GATTTAAAAGAAATCAGCTCTAAAACACTGGGACTTGATAAGC TTAATGTCCAAGATGCCTACACCCCGAAAGAAACTGCTGTAAC CGTTGATAAAACTACCTATAAAAATGGTACAGATCCTATTACA GCCCAGAGCAATACTGATATCCAAACTGCAATTGGCGGTGGTG CAACGGGGGTTACTGGGGCTGATATCAAATTTAAAGATGGTCA ATACTATTTAGATGTTAAAGGCGGTGCTTCTGCTGGTGTTTATA AAGCCACTTATGATGAAACTACAAAGAAAGTTAATATTGATAC GACTGATAAAACTCCGTTGGCAACTGCGGAAGCTACAGCTATT CGGGGAACGGCCACTATAACCCACAACCAAATTGCTGAAGTAA CAAAAGAGGGTGTTGATACGACCACAGTTGCGGCTCAACTTGC TGCAGCAGGGGTTACTGGCGCCGATAAGGACAATACTAGCCTT GTAAAACTATCGTTTGAGGATAAAAACGGTAAGGTTATTGATG GTGGCTATGCAGTGAAAATGGGCGACGATTTCTATGCCGCTAC ATATGATGAGAAAACAGGTGCAATTACTGCTAAAACCACTACT TATACAGATGGTACTGGCGTTGCTCAAACTGGAGCTGTGAAAT TTGGTGGCGCAAATGGTAAATCTGAAGTTGTTACTGCTACCGAT GGTAAGACTTACTTAGCAAGCGACCTTGACAAACATAACTTCA GAACAGGCGGTGAGCTTAAAGAGGTTAATACAGATAAGACTG AAAACCCACTGCAGAAAATTGATGCTGCCTTGGCACAGGTTGA TACACTTCGTTCTGACCTGGGTGCGGTTCAGAACCGTTTCAACT CCGCTATCACCAACCTGGGCAATACCGTAAATAACCTGTCTTCT GCCCGTAGCCGTATCGAAGATTCCGACTACGCAACCGAAGTCT | 113 |

TABLE 16-continued

<u>Flagellin Nucleic Acid Sequences</u>

| Name | Sequence | SEQ ID NO: |
|------|----------|-----------|
| | CCAACATGTCTCGCGCGCAGATTCTGCAGCAGGCCGGTACCTC CGTTCTGGCGCAGGCGAACCAGGTTCCGCAAAACGTCCTCTCTT TACTGCGT | |
| mRNA Sequence (assumes T100 tail) | G*GGGAAAUAAGAGAGAAAAGAAGAGUAAGAAGAAAUAUAA GAGCCACCAUGGCACAAGUCAUUAAUACAAACAGCCUGUCGC UGUUGACCCAGAAUAACCUGAACAAAUCCCAGUCCGCACUGG GCACUGCUAUCGAGCGUUUGUCUUCCGGUCUGCGUAUCAACA GCGCGAAAGACGAUGCGGCCAGGACAGGCGAUUGCUAACCGUU UUACCGCGAACAUCAAAGGUCUGACUCAGGCUUCCCGUAACG CUAACGACGGUAUCUCCAUUGCGCAGACCACUGAAGGCGCGC UGAACGAAAUCAACAACAACCUGCAGCGUGUGCGUGAACUGG CGGUUCAGUCUGCGAAUGGUACUAACUCCCAGUCUGACCUCG ACUCCAUCCAGGCUGAAAUCACCCAGCGCCUGAACGAAAUCG ACCGUGUAUCCGGCCAGACUCAGUUCAACGGCGUGAAAGUCC UGGCGCAGGACAACACCCUGACCAUCCAGGUUGGUGCCAACG ACGGUGAAACUAUCGAUAUUGAUUUAAAAGAAAUCAGCUCU AAAACACUGGGCAUUGAUAAGCUUAAUGUCCAAGAUGCCUAC ACCCCGAAAGAAACUGCUGUAACCGUUGAUAAAACUACCUAU AAAAAUGGUACAGAUCCUAUUACAGCCCAGAGCAAUACUGAU AUCCAAACUGCAAUUGGCGGUGGUGCAACGGGGGUUACUGG GGCUGAUAUCAAAUUUAAAGAUGGUCAAUACUAUUUAGAUG UUAAAGGCGGUGCUUCUGCUGGUGUUUAUAAAGCCACUUAU GAUGAAACUACAAAGAAAGUUAAUAUUGAUACGACUGAUAA AACUCCGUUGGCAACUGCGGAAGCUACAGCUAUUCGGGGAAC GGCCACUAUAACCCACAACCAAAUUGCUGAAGUAACAAAAGA GGGUGUUGAUACGACCACAGUUGCGGCUCAACUUGCUGCAGC AGGGGUUACUGGCGCCGAUAAGGACAAUACUAGCCUUGUAA AACUAUCGUUUGAGGAUAAAAACGGUAAGGUUAUUGAUGGU GGCUAUGCAGUGAAAAUGGGCGACGAUUUCUAUGCCGCUACA UAUGAUGAGAAAACAGGUGCAAUUACUGCUAAAACCACUAC UUAUACAGAUGGUACUGGCGUUGCUCAAACUGGAGCUGUGA AAUUUGGUGGCGCAAAUGGUAAAUCUGAAGUUGUUACUGCU ACCGAUGGUAAGACUUACUUAGCAAGCGACCUUGACAAACAU AACUUCAGAACAGGCGGUGAGCUUAAAGAGGUUAAUACAGA UAAGACUGAAAACCCACUGCAGAAAAUUGAUGCUGCCUUGGC ACAGGUUGAUACACUUCGUUCUGACCUGGGUGCGGUUCAGAA CCGUUUCAACUCCGCUAUCACCAACCUGGGCAAUACCGUAAA UAACCUGUCUUCUGCCCGUAGCCGUAUCGAAGAUUCCGACUA CGCAACCGAAGUCUCCAACAUGUCUCGCGCGCAGAUUCUGCA GCAGGCCGGUACCUCCGUUCUGGCGCAGGCGAACCAGGUUCC GCAAAACGUCCUCUCUUUACUGCGUUGAUAAUAGGCUGGAGC CUCGGUGGCCAUGCUUCUUGCCCCUUGGGCCUCCCCCCAGCC CCUCCUCCCCUUCCUGCACCCGUACCCCGUGGUCUUUGAAU AAAGUCUGAGUGGGCGGCAAAAAAAAAAAAAAAAAAAAAAAA AAAAAAAAAAAAAAAAAAAAAAAAAAAAAAAAAAAAAAAAA AAAAAAAAAAAAAAAAAAAAAAAAAAAAAAAAAAAAUCUAG | 114 |

It should be understood that each of the ORF sequences provided herein may be combined with a 5' and/or 3' UTR, such as those described herein. It should also be understood that the 5' and/or 3' UTR for each construct may be omitted, modified or substituted for a different UTR sequences in any one of the vaccines as provided herein.

TABLE 17

<u>Flagellin Amino Acid Sequences</u>

| Name | Sequence | SEQ ID NO: |
|------|----------|-----------|
| ORF Sequence, AA | MAQVINTNSLSLLTQNNLNKSQSALGTAIERLSSGLRINSAKDDAA GQAIANRFTANIKGLTQASRNANDGISIAQTTEGALNEINNNLQRV RELAVQSANGTNSQSDLDSIQAEITQRLNEIDRVSGQTQFNGVKVL AQDNTLTIQVGANDGETIDIDLKEISSKTLGLDKLNVQDAYTPKET AVTVDKTTYKNGTDPITAQSNTDIQTAIGGGATGVTGADIKFKDG QYYLDVKGGASAGVYKATYDETTKKVNIDTTDKTPLATAEATAI RGTATITHNQIAEVTKEGVDTTTVAAQLAAAGVTGADKDNTSLV KLSFEDKNGKVIDGGYAVKMGDDFYAATYDEKTGAITAKTTTYT DGTGVAQTGAVKFGGANGKSEVVTATDGKTYLASDLDKHNFRT GGELKEVNTDKTENPLQKIDAALAQVDTLRSDLGAVQNRFNSAIT NLGNTVNNLSSARSRIEDSDYATEVSNMSRAQILQQAGTSVLAQA NQVPQNVLSLLR | 115 |

TABLE 17-continued

Flagellin Amino Acid Sequences

| Name | Sequence | SEQ ID NO: |
|------|----------|------------|
| Flagellin-<br>GS linker-<br>circumsporozoite<br>protein<br>(CSP) | MAQVINTNSLSLLTQNNLNKSQSALGTAIERLSSGLRINSAKDDAA<br>GQAIANRFTANIKGLTQASRNANDGISIAQTTEGALNEINNNLQRV<br>RELAVQSANSTNSQSDLDSIQAEITQRLNEIDRVSGQTQFNGVKVL<br>AQDNTLTIQVGANDGETIDIDLKQINSQTLGLDTLNVQQKYKVSD<br>TAATVTGYADTTIALDNSTFKASATGLGGTDQKIDGDLKFDDTTG<br>KYYAKVTVTGGTGKDGYYEVSVDKTNGEVTLAGGATSPLTGGLP<br>ATATEDVKNVQVANADLTEAKAALTAAGVTGTASVVKMSYTDN<br>NGKTIDGGLAVKVGDDYYSATQNKDGSISINTTKYTADDGTSKTA<br>LNKLGGADGKTEVVSIGGKTYAASKAEGHNFKAQPDLAEAAATT<br>TENPLQKIDAALAQVDTLRSDLGAVQNRFNSAITNLGNTVNNLTS<br>ARSRIEDSDYATEVSNMSRAQILQQAGTSVLAQANQVPQNVLSLL<br>RGGGGSGGGGSMMAPDPNANPNANPNANPNANPNANPNANPNA<br>NPNANPNANPNANPNANPNANPNANPNANPNANPNANPNANPN<br>ANPNANPNKNNQGNGQGHNMPNDPNRNVDENANANNAVKNNN<br>NEEPSDKHIEQYLKKIKNSISTEWSPCSVTCGNGIQVRIKPGSANKP<br>KDELDYENDIEKKICKMEKCSSVFNVVNS | 116 |
| Flagellin-<br>RPVT<br>linker-<br>circumsporozoite<br>protein<br>(CSP) | MMAPDPNANPNANPNANPNANPNANPNANPNANPNANPNANPN<br>ANPNANPNANPNANPNANPNANPNANPNANPNANPNANPNKNN<br>QGNGQGHNMPNDPNRNVDENANANNAVKNNNNEEPSDKHIEQY<br>LKKIKNSISTEWSPCSVTCGNGIQVRIKPGSANKPKDELDYENDIEK<br>KICKMEKCSSVFNVVNSRPVTMAQVINTNSLSLLTQNNLNKSQSA<br>LGTAIERLSSGLRINSAKDDAAGAIANRFTANIKGLTASRNAND<br>GISIAQTTEGALNEINNNLQRVRELAVQSANSTNSQSDLDSIQAEIT<br>QRLNEIDRVSGQTQFNGVKVLAQDNTLTIQVGANDGETIDIDLKQI<br>NSQTLGLDTLNVQQKYKVSDTAATVTGYADTTIALDNSTFKASAT<br>GLGGTDQKIDGDLKFDDTTGKYYAKVTVTGGTGKDGYYEVSVD<br>KTNGEVTLAGGATSPLTGGLPATATEDVKNVQVANADLTEAKAA<br>LTAAGVTGTASVVKMSYTDNNGKTIDGGLAVKVGDDYYSATQN<br>KDGSISINTTKYTADDGTSKTALNKLGGADGKTEVVSIGGKTYAA<br>SKAEGHNFKAQPDLAEAAATTTENPLQKIDAALAQVDTLRSDLG<br>AVQNRFNSAITNLGNTVNNLTSARSRIEDSDYATEVSNMSRAQILQ<br>QAGTSVLAQANQVPQNVLSLLR | 117 |

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

SEQUENCE LISTING

```
Sequence total quantity: 150
SEQ ID NO: 1          moltype = DNA   length = 2080
FEATURE               Location/Qualifiers
source                1..2080
                      mol_type = genomic DNA
                      organism = Human alphaherpesvirus 3
SEQUENCE: 1
tcaagctttt ggaccctcgt acagaagcta atacgactca ctatagggaa ataagagaga   60
aaagaagagt aagaagaaat ataagagcca ccatggggac agtgaataag ccggttgtgg   120
gcgtgcttat gggctttggg attattaccg gtacattacg aattaccaat ccagtgcgcg   180
ccagtgtgct gcgttacgac gactttcaca ttgacgagga taagctggat actaacagcg   240
tgtacgaacc ttattaccac tcagatcatg ccgaatcaag ctgggttaat agaggagaaa   300
gcagccgaaa agcctacgac cacaactcac cttatatttg gcccagaaac gattatgacg   360
gtttcctgga aaacgcacat gaacaccatg gagtctacaa ccaaggcagg ggaatcgaca   420
gtggcgagcg tcttatgcag ccaacacaga tgtcggcaca ggaggatctc ggtgatgaca   480
ccggcataca cgtgattccc acattaaacg gcgacgacag acataagatc gtcaatgtgg   540
atcagcgtca gtatgggat gtctttaaag gcgatttgaa tccaaagccc caaggacaga   600
gactgatcga ggtctctgta gaagaaaatc accccttcac tttgcgcgct ccaatccaga   660
ggatttacgg ggtgcgttat accgaaactt ggagtttctt gccgtcactg acgtgtacgg   720
gggatgccgc ccccgcaatc cagcacatct gtctgaaaca caccacatgc tttcaggacg   780
tggttgtgga tgtggattgc gcggaaaaca caaaagaaga ccaactcgcc gaaatcagct   840
atcgtttcta gggtaaaaaa gaggccgacc aaccgtggat tgttgtgaat acgagcacgc   900
tcttcgatga gcttgaactc gatccccogg aaatcgagcc tggggttcta aaagtgttga   960
ggaccgagaa gcagtacctc gggglttata tctggaatat gagaggctcc gatggcacct   1020
ctacctacgc aacgtttctg gttacctgga agggagacga gaagacacgg aatccaacgc   1080
ccgctgtgac ccctcagcct aggggagccg aattccacat gtggaactat cactcccatg   1140
tattcagtgt gggtgacact ttcagcctgg ccatgcacct gcagtataag attcacgagg   1200
caccccttcga cctcctgctg gagtggttgt acgtaccctat tgatcccact tgtcagccca   1260
```

-continued

```
tgcgcctgta ctccacttgc ttgtaccacc ccaatgcacc acagtgtcta tcacacatga   1320
actccgggtg tacctttact tcaccccatc ttgcccagcg ggtcgccagc acagtgtatc   1380
agaactgtga gcatgctgac aactatactg cttattgcct cggaatatcc catatggagc   1440
caagcttcgg gctcatactg cacgatggtg gtacgacact caagttcgtg gacacccccg   1500
aaagcctttc tggcttgtac gtgttcgtgg tctacttcaa tggacatgtg gaggcagtgg   1560
cttacacagt ggtttcgaca gttgatcact ttgtaaatgc cattgaggaa cgcggcttcc   1620
cgcctacagc gggccagccc cctgcgacaa caaaaccaaa agagattacg cccgttaatc   1680
ctgggactag tccattgctg aggtatgccg cctggactgg cggtctggcg gccgtggtac   1740
ttctgtgttt agtcatattt ctgatctgta ccgctaaacg tatgcgggtc aaggcttacc   1800
gtgttgacaa gtctccttac aatcagtcaa tgtactatgc aggactccct gttgacgatt   1860
tcgaagactc agagagtaca gacacagaag aagaattcgg aaacgctata ggtggctctc   1920
acggaggtag ctcgtataca gtgtacatcg ataaaaccag atgataatag gctggagcct   1980
cggtggccat gcttcttgcc ccttgggcct ccccccagcc cctcctcccc ttcctgcacc   2040
cgtacccccg tggtctttga ataaagtctg agtgggcggc                         2080
```

```
SEQ ID NO: 2              moltype = RNA   length = 1276
FEATURE                   Location/Qualifiers
source                    1..1276
                          mol_type = genomic RNA
                          organism = Human alphaherpesvirus 3
SEQUENCE: 2
tcaagctttt ggaccctcgt acagaagcta atacgactca ctatagggaa ataagagaga   60
aaagaagagt aagaagaaat ataagagcca ccatgttttt aatccaatgt ttgatatcgg   120
ccgttatatt ttacatacaa gtgaccaacg ctttgatctt caagggcgac cacgtgagct   180
tgcaagttaa cagcagtctc acgtctatcc ttattcccat gcaaaatgat aattatacag   240
agataaaagg acagcttgtc tttattggag agcaactacc taccatagcg aactatagcg   300
gaacactgga actgttatac gcggatacgg tggcgttttg tttccggtca gtacaagtaa   360
taagatacga cggatgtccc cggattagaa cgagcgcttt tatttcgtgt aggtacaaac   420
attcgtggca ttatggtaac tcaacggatc ggatatcaac agagccggat gctggtgtaa   480
tgttgaaaat taccaaaccg ggaataaatg atgctggtgt gtatgtactt cttgttcggt   540
tagaccatag cagatccacc gatggtttca ttcttggtgt aaatgtatat acagcgggct   600
cgcatcacaa cattcacggg gttatctaca cttctccatc tctacagaat ggatattcta   660
caagagccct tttttcaacaa gctcgtttgt gtgatttacc cgcgacaccc aaagggtccg   720
gtacctccct gtttcaacat atgcttgatc ttcgtgcgg taaatcgtta gaggataacc   780
cttggttaca tgaggacgtt gttacgacag aaactaagtc cgttgttaag gaggggatag   840
aaaatcacgt atatccaacg gatatgtcca cgttacccga aaagtccctt aatgatcctc   900
cagaaaatct acttataatt attcctatag tagcgtctgt catgatcctc accgccatgg   960
ttattgttat tgtaataagc gttaagcgac gtagaattaa aaaacatcca atttatcgcc   1020
caaatacaaa aacaagaagg ggcatacaaa atgcgacacc agaatccgat gtgatgttgg   1080
aggccgccat tgcacaacta gcaacgattc gcgaagaatc cccccacat tccgttgtaa   1140
acccgtttgt taaatagtga taataggctg gagcctcggt ggccatgctt cttgcccctt   1200
gggcctcccc ccagccctc ctcccttcc tgcaccgta cccccgtggt ctttgaataa   1260
agtctgagtg ggcggc                                                  1276
```

```
SEQ ID NO: 3              moltype = DNA   length = 1897
FEATURE                   Location/Qualifiers
misc_feature             1..1897
                          note = Synthetic Polynucleotide
source                    1..1897
                          mol_type = other DNA
                          organism = synthetic construct
SEQUENCE: 3
tcaagctttt ggaccctcgt acagaagcta atacgactca ctatagggaa ataagagaga   60
aaagaagagt aagaagaaat ataagagcca ccatggggac agttaataaa cctgtggtgg   120
gggtattgat ggggttcgga attatcacgg gaacgttgcg tataacgaat ccggtcagag   180
catccgtctt gcgatacgat gattttcaca tcgatgaaga caaactggat acaaactccg   240
tatatgagcc ttactaccat tcagatcatg cggagtcttc atgggtaaat cggggagagt   300
cttcgcgaaa agcgtacgat cataactcac cttatatatg gccacgtaat gattatgatg   360
gattttaga gaacgcacac gaacaccatg gggtgtataa tcagggccgt ggtatcgata   420
gcggggaacg gttaatgcaa cccacacaaa tgtctgcaca ggaggatctt ggggacgata   480
cgggcatcca cgttatccct acgttaaacg gcgatgacag acataaaatt gtaaatgtgg   540
accaacgtca atacggtgac gtgtttaaag gagatcttaa tccaaacccc caaggccaaa   600
gactcattga ggtgtcagtg gaagaaaatc acccgtttac tttacgcgca ccgattcagc   660
ggatttatgg agtccggtac accgagactt ggagctttt gccgtcatta acctgtacgg   720
gagacgcagc gcccgccatc cagcatatat gtttaaaaca tacaacatgc tttcaagacg   780
tggtggtgga tgtggattgc gcggaaaata ctaaagagga tcagttggcc gaaatcagtt   840
accgtttttca aggtaagaag gaagcggacc aaccgtggat tgttgtaaac acgagcacac   900
tgtttgatga actcgaatta gaccccccg agattgaacc gggtgtcttg aaagtacttc   960
ggacagaaaa acaatacttg ggtgtgtaca tttggaacat gcgcggctcc gatggtacgt   1020
ctacctacgc cacgtttttg gtcacctgga aaggggatga aaaaacaaga aaccctacgc   1080
ccgcagtaac tcctcaacca agaggggctg agtttcatat gtggaattac cactcgcatg   1140
tattttcagt tggtgatacg tttagcttgg caatgcatct tcagtataag atacatgaag   1200
cgccatttga tttgctgtta gagtggttgt atgtccccat cgatcctaca tgtcaaccaa   1260
tgcggttata ttctacgtgt ttgtatcatc ccaacgcacc caatgcctc tctcatatga   1320
attccggttg tacatttacc tcgccacatt tagcccagcg tgttgcaagc acagtgtatc   1380
aaaattgtga acatgcagat aactacaccg catattgtct gggaatatct catatgagc   1440
ctagctttgt tctaatctta cacgacgggg gcaccacgtt aaagtttgta gatacacccg   1500
agagtttgtc gggattatac gttttgtgg tgtattttaa cgggcatgtt gaagccgtag   1560
catacacgt tgtatccaca gtagatcatt ttgtaaacgc aattgaagag cgtggatttc   1620
```

```
cgccaacggc cggtcagcca ccggcgacta ctaaacccaa ggaaattacc cccgtaaacc   1680
ccggaacgtc accacttcta cgatatgccg catggaccgg agggcttgca gcagtagtac   1740
ttttatgtct cgtaatattt ttaatctgta cggcttgatg ataataggct ggagcctcgg   1800
tggccatgct tcttgcccct tgggcctccc cccagcccct cctcccttc ctgcacccgt   1860
accccgtgg tctttgaata aagtctgagt gggcggc                            1897
```

```
SEQ ID NO: 4              moltype = DNA  length = 1867
FEATURE                   Location/Qualifiers
misc_feature              1..1867
                          note = Synthetic Polynucleotide
source                    1..1867
                          mol_type = other DNA
                          organism = synthetic construct
SEQUENCE: 4
tcaagctttt ggaccctcgt acagaagcta atacgactca ctatagggaa ataagagaga   60
aaagaagagt aagaagaaat ataagagcca ccatggaaac cccggcgcag ctgctgtttc   120
tgctgctgct gtggctgccg gataccaccg gctccgtctt gcgatacgat gatttttcaca   180
tcgatgaaga caaactggat acaaactccg tatatgagcc ttactaccat tcagatcatg   240
cggagtcttc atgggtaaat cggggagagt cttcgcgaaa agcgtacgat cataactcac   300
cttatatatg gccacgtaat gattatgatg gatttttaga gaacgcacac gaacaccatg   360
gggtgtataa tcagggccgt ggtatcgata gcggggaacg gttaatgcaa cccacacaaa   420
tgtctgcaca ggaggatctt ggggacgata cgggcatcca cgttatccct acgttaaacg   480
gcgatgacag acataaaatt gtaaatgtgg accaacgtca atacggtgac gtgtttaaag   540
gagatcttaa tccaaaaccc caaggccaaa gactcattga ggtgtcagtg gaagaaaatc   600
acccgtttac tttacgcgca ccgattcagc ggatttatgg agtccggtac accgagactt   660
ggagctttt gccgtcatta acctgtacgg gagacgcagc gcccgccatc cagcatatat   720
gtttaaaaca tacaacatgc tttcaagacg tggtggtgga tgtggattgc gcggaaaata   780
ctaaagagga tcagttggcc gaaatcagtt accgtttca aggtaagaag gaagcggacc   840
aaccgtggat tgttgtaaac acgagcacac tgtttgatga actcgaatta gacccccccg   900
agattgaacc gggtgtcttg aaagtacttc ggacagaaaa acaatacttg gtgtgtacga   960
tttggaacat gcgcggctcc gatggtacgt ctacctacgc cacgtttttg gtcacctgga   1020
aagggatgga aaaaacaaga aaccctacgc ccgcagtaac tcctcaacca agagggggctg   1080
agtttcatat gtggaattac cactcgcatg tattttcagt tggtgatacg tttagcttgg   1140
caatgcatct tcagtataag atacatgaag cgccatttga tttgctgtta gagtggttgt   1200
atgtccccat cgatcctaca tgtcaaccaa tgcggttata ttctacgtgt ttgtatcatc   1260
ccaacgcacc ccaatgcctc tctcatatga attccggttg tacatttacc tcgccacatt   1320
tagcccagcg tgttgcaagc acagtgtatc aaaattgtga acatgcagat aactacaccg   1380
catattgtct gggaatatct catatggagc ctagctttgg tctaatctta cacgacgggg   1440
gcaccacgtt aaagtttgta gatacacccg agagtttgtac gttttttgtgg   1500
tgtatttttaa cgggcatgtt gaagccgtag catacactgt tgtatccaca gtagatcatt   1560
ttgtaaacgc aattgaagag cgtggatttc cgccaacggc cggtcagcca ccggcgacta   1620
ctaaacccaa ggaaattacc cccgtaaacc ccggaacgtc accacttcta cgatatgccg   1680
catggaccgg agggcttgca gcagtagtac ttttatgtct cgtaatattt ttaatctgta   1740
cggcttgatg ataataggct ggagcctcgg tggccatgct tcttgcccct tgggcctccc   1800
cccagcccct cctcccttc ctgcacccgt accccgtgg tctttgaata aagtctgagt   1860
gggcggc                                                            1867
```

```
SEQ ID NO: 5              moltype = DNA  length = 1933
FEATURE                   Location/Qualifiers
misc_feature              1..1933
                          note = Synthetic Polynucleotide
source                    1..1933
                          mol_type = other DNA
                          organism = synthetic construct
SEQUENCE: 5
tcaagctttt ggaccctcgt acagaagcta atacgactca ctatagggaa ataagagaga   60
aaagaagagt aagaagaaat ataagagcca ccatggggac agttaataaa cctgtggtgg   120
gggtattgat ggggttcgga attatcacgg gaacgttgcg tataacgaat ccggtcagag   180
catccgtctt gcgatacgat gattttttcaca tcgatgaaga caaactggat acaaactccg   240
tatatgagcc ttactaccat tcagatcatg cggagtcttc atgggtaaat cggggagagt   300
cttcgcgaaa agcgtacgat cataactcac cttatatatg gccacgtaat gattatgatg   360
gatttttaga gaacgcacac gaacaccatg gggtgtataa tcagggccgt ggtatcgata   420
gcggggaacg gttaatgcaa cccacacaaa tgtctgcaca ggaggatctt ggggacgata   480
cgggcatcca cgttatccct acgttaaacg gcgatgacag acataaaatt gtaaatgtgg   540
accaacgtca atacggtgac gtgtttaaag gagatcttaa tccaaaaccc caaggccaaa   600
gactcattga ggtgtcagtg gaagaaaatc acccgtttac tttacgcgca ccgattcagc   660
ggatttatgg agtccggtac accgagactt ggagcttttt gccgtcatta acctgtacgg   720
gagacgcagc gcccgccatc cagcatatat gtttaaaaca tacaacatgc tttcaagacg   780
tggtggtgga tgtggattgc gcggaaaata ctaaagagga tcagttggcc gaaatcagtt   840
accgttttca aggtaagaag gaagcggacc aaccgtggat tgttgtaaac acgagcacac   900
tgtttgatga actcgaatta gacccccccg agattgaacc gggtgtcttg aaagtacttc   960
ggacagaaaa acaatacttg gtgtgtaca tttggaacat gcgcggctcc gatggtacgt   1020
ctacctacgc cacgtttttg gtcacctgga aagggatgga aaaaacaaga aaccctacgc   1080
ccgcagtaac tcctcaacca agagggggctg agtttcatat gtggaattac cactcgcatg   1140
tattttcagt tggtgatacg tttagcttgg caatgcatct tcagtataag atacatgaag   1200
cgccatttga tttgctgtta gagtggttgt atgtccccat cgatcctaca tgtcaaccaa   1260
tgcggttata ttctacgtgt ttgtatcatc ccaacgcacc ccaatgcctc tctcatatga   1320
attccggttg tacatttacc tcgccacatt tagcccagcg tgttgcaagc acagtgtatc   1380
aaaattgtga acatgcagat aactacaccg catattgtct gggaatatct catatggagc   1440
```

-continued

```
ctagctttgg tctaatctta cacgacgggg gcaccacgtt aaagtttgta gatacacccg   1500
agagtttgtc gggattatac gttttttgtgg tgtattttaa cgggcatgtt gaagccgtag   1560
catacactgt tgtatccaca gtagatcatt ttgtaaacgc aattgaagag cgtggatttc   1620
cgccaacggc cggtcagcca ccggcgacta ctaaacccaa ggaaattacc cccgtaaacc   1680
ccggaacgtc accacttcta cgatatgccg catggaccgg agggcttgca gcagtagtac   1740
ttttatgtct cgtaatattt ttaatctgta cggctaaacg aatgagggt aaagcctata   1800
gggtagacaa gtgatgataa taggctggag cctcggtggc catgcttctt gcccttggg    1860
cctcccccca gccctcctc cccttcctgc acccgtaccc ccgtggtctt tgaataaagt    1920
ctgagtgggc ggc                                                      1933
```

SEQ ID NO: 6    moltype = DNA length = 1933
FEATURE      Location/Qualifiers
misc_feature     1..1933
          note = Synthetic Polynucleotide
source       1..1933
          mol_type = other DNA
          organism = synthetic construct
SEQUENCE: 6

```
tcaagctttt ggaccctcgt acagaagcta atacgactca ctatagggaa ataagagaga   60
aaagaagagt aagaagaaat ataagagcca ccatggggga cagttaataaa cctgtggtgg   120
gggtattgat ggggttcgga attatcacgg gaacgttgcg tataacgaat ccggtcagag   180
catccgtctt gcgatacgat gattttcaca tcgatgaaga caaactggat acaaactccg   240
tatatgagcc ttactaccat tcagatcatg cggagtcttc atgggtaaat cggggagagt   300
cttcgcgaaa agcgtacgat cataactcac cttatatatg gccacgtaat gattatgatg   360
gattttttaga gaacgcacac gaacaccatg gggtgtataa tcagggccgt ggtatcgata   420
gcggggaacg gttaatgcaa cccacacaaa tgtctgcaca ggaggatctt ggggacgata   480
cgggcatcca cgttatccct acgttaaacg gcgatgacag acataaaatt gtaaatgtgg   540
accaacgtca atacggtgac gtgtttaaag gagatcttaa tccaaaaccc caaggccaaa   600
gactcattga ggtgtcagtg gaagaaaatc acccgtttac tttacgcgca ccgattcagc   660
ggatttatgg agtccggtac accgagactt ggagctttt gccgtcatta acctgtacgg   720
gagacgcagc gcccgccatc cagcatatat gtttaaaaca tacaacatgc tttcaagacg   780
tggtggtgga tgtggattgc gcggaaaata ctaaagagga tcagttggcc gaaatcagtt   840
accgtttttca aggtaagaag gaagcggacc aaccgtggat tgttgtaaac acgagcacac   900
tgtttgatga actcgaatta gacccccccg agattgaacc gggtgtcttg aaagtacttc   960
ggacagaaaa acaatacttg ggtgtgtaca tttggaacat gcgcggctcc gatggtacgt   1020
ctacctacgc cacgttttttg gtcacctgga aaggggatga aaaaacaaga aaccctacgc   1080
ccgcagtaac tcctcaacca agaggggctg agtttcatat gtggaattac cactcgcatg   1140
tattttcagt tggtgatacg tttagcttgg caatgcatct tcagtataag atacatgaag   1200
cgccatttga tttgctgtta gagtggttgt atgtcccat cgatcctaca tgtcaaccaa   1260
tgcggttata ttctacgtgt ttgtatcatc ccaacgcacc ccaatgcctc tctcatatga   1320
attccggttg tacatttacc tcgccacatt tagcccagcg tgttgcaagc acagtgtatc   1380
aaaattgtga acatgcagat aactacaccg catattgtct gggaatatct catatggagc   1440
ctagctttgg tctaatctta cacgacgggg gcaccacgtt aaagtttgta gatacacccg   1500
agagtttgtc gggattatac gttttttgtgg tgtattttaa cgggcatgtt gaagccgtag   1560
catacactgt tgtatccaca gtagatcatt ttgtaaacgc aattgaagag cgtggatttc   1620
cgccaacggc cggtcagcca ccggcgacta ctaaacccaa ggaaattacc cccgtaaacc   1680
ccggaacgtc accacttcta cgatatgccg catggaccgg agggcttgca gcagtagtac   1740
ttttatgtct cgtaatattt ttaatctgta cggctaaacg aatgagggt aaagccgcca   1800
gggtagacaa gtgatgataa taggctggag cctcggtggc catgcttctt gcccttggg    1860
cctcccccca gccctcctc cccttcctgc acccgtaccc ccgtggtctt tgaataaagt    1920
ctgagtgggc ggc                                                      1933
```

SEQ ID NO: 7    moltype = DNA length = 2083
FEATURE      Location/Qualifiers
misc_feature     1..2083
          note = Synthetic Polynucleotide
source       1..2083
          mol_type = other DNA
          organism = synthetic construct
SEQUENCE: 7

```
tcaagctttt ggaccctcgt acagaagcta atacgactca ctatagggaa ataagagaga   60
aaagaagagt aagaagaaat ataagagcca ccatggggga cagttaataaa cctgtggtgg   120
gggtattgat ggggttcgga attatcacgg gaacgttgcg tataacgaat ccggtcagag   180
catccgtctt gcgatacgat gattttcaca tcgatgaaga caaactggat acaaactccg   240
tatatgagcc ttactaccat tcagatcatg cggagtcttc atgggtaaat cggggagagt   300
cttcgcgaaa agcgtacgat cataactcac cttatatatg gccacgtaat gattatgatg   360
gattttttaga gaacgcacac gaacaccatg gggtgtataa tcagggccgt ggtatcgata   420
gcggggaacg gttaatgcaa cccacacaaa tgtctgcaca ggaggatctt ggggacgata   480
cgggcatcca cgttatccct acgttaaacg gcgatgacag acataaaatt gtaaatgtgg   540
accaacgtca atacggtgac gtgtttaaag gagatcttaa tccaaaaccc caaggccaaa   600
gactcattga ggtgtcagtg gaagaaaatc acccgtttac tttacgcgca ccgattcagc   660
ggatttatgg agtccggtac accgagactt ggagctttt gccgtcatta acctgtacgg   720
gagacgcagc gcccgccatc cagcatatat gtttaaaaca tacaacatgc tttcaagacg   780
tggtggtgga tgtggattgc gcggaaaata ctaaagagga tcagttggcc gaaatcagtt   840
accgtttttca aggtaagaag gaagcggacc aaccgtggat tgttgtaaac acgagcacac   900
tgtttgatga actcgaatta gacccccccg agattgaacc gggtgtcttg aaagtacttc   960
ggacagaaaa acaatacttg ggtgtgtaca tttggaacat gcgcggctcc gatggtacgt   1020
ctacctacgc cacgttttttg gtcacctgga aaggggatga aaaaacaaga aaccctacgc   1080
ccgcagtaac tcctcaacca agaggggctg agtttcatat gtggaattac cactcgcatg   1140
```

-continued

```
tattttcagt tggtgatacg tttagcttgg caatgcatct tcagtataag atacatgaag   1200
cgccatttga tttgctgtta gagtggttgt atgtccccat cgatcctaca tgtcaaccaa   1260
tgcggttata ttctacgtgt ttgtatcatc ccaacgcacc ccaatgcctc tctcatatga   1320
attccggttg tacatttacc tcgccacatt tagcccagcg tgttgcaagc acagtgtatc   1380
aaaattgtga acatgcagat aactacaccg catattgtct gggaatatct catatggagc   1440
ctagctttgg tctaatctta cacgacgggg gcaccacgtt aaagtttgta gatacacccg   1500
agagtttgtc gggattatac gtttttgtgg tgtattttaa cgggcatgtt gaagccgtag   1560
catacactgt tgtatccaca gtagatcatt ttgtaaacgc aattgaagag cgtggatttc   1620
cgccaacggc cggtcagcca ccggcgacta ctaaacccaa ggaaattacc cccgtaaacc   1680
ccggaacgtc accacttcta cgatatgccg catggaccgg agggcttgca gcagtagtac   1740
ttttatgtct cgtaatattt ttaatctgta cggctaaacg aatgagggtt aaagcctata   1800
gggtagacaa gtccccgtat aaccaaagca tgtattacgc tggccttcca gtggacgatt   1860
tcgaggacgc cgaagccgcc gatgccgaag aagagtttgg taacgcgatt ggagggagtc   1920
acgggggttc gagttacacg gtgtatatag ataagacccg gtgatgataa taggctggag   1980
cctcggtggc catgcttctt gccccttggg cctcccccca gccctcctc ccccttcctgc   2040
acccgtaccc ccgtggtctt tgaataaagt ctgagtgggc ggc                     2083
```

```
SEQ ID NO: 8              moltype = DNA   length = 2083
FEATURE                   Location/Qualifiers
misc_feature              1..2083
                          note = Synthetic Polynucleotide
source                    1..2083
                          mol_type = other DNA
                          organism = synthetic construct
SEQUENCE: 8
tcaagctttt ggaccctcgt acagaagcta atacgactca ctatagggaa ataagagaga   60
aaagaagagt aagaagaaat ataagagcca ccatggggac agttaataaa cctgtggtgg   120
gggtattgat ggggttcgga attatcacgg gaacgttgcg tataacgaat ccggtcagag   180
catccgtctt gcgatacgat gattttcaca tcgatgaaga caaactggat acaaactccg   240
tatatgagcc ttactaccat tcagatcatg cggagtcttc atgggtaaat cggggagagt   300
cttcgcgaaa agcgtacgat cataactcac cttatatatg gccacgtaat gattatgatg   360
gattttaga gaacgcacac gaacaccatg gggtgtataa tcagggccgt ggtatcgata   420
gcggggaacg gttaatgcaa cccacacaaa tgtctgcaca ggaggatctt ggggacgata   480
cgggcatcca cgttatccct acgttaaacg gcgatgacag acataaaatt gtaaatgtgg   540
accaacgtca atacggtgac gtgtttaaag gagatcttaa tccaaaaccc caaggccaaa   600
gactcattga ggtgtcagtg gaagaaaatc acccgtttac tttacgcgca ccgattcagc   660
ggatttatgg agtccggtac accgagactt ggagcttttt gccgtcatta acctgtacgg   720
gagacgcagc gcccgccatc cagcatatat gtttaaaaca tacaacatgc tttcaagacg   780
tggtggtgga tgtggattgc gcggaaaata ctaaagagga tcagttggcc gaaatcagtt   840
accgtttttca aggtaagaag gaagcggacc aaccgtggat tgttgtaaac acgagcacac   900
tgtttgatga actcgaatta gacccccccg agattgaacc gggtgtcttg aaagtacttc   960
ggacagaaaa acaatacttg ggtgtgtaca tttggaacat gcgcggctcc gatggtacgt   1020
ctacctacgc cacgtttttg gtcacctgga aaggggatga aaaaacaaga aaccctacgc   1080
ccgcagtaac tcctcaacca agaggggctg agtttcatat gtggaattac cactcgcatg   1140
tattttcagt tggtgatacg tttagcttgg caatgcatct tcagtataag atacatgaag   1200
cgccatttga tttgctgtta gagtggttgt atgtccccat cgatcctaca tgtcaaccaa   1260
tgcggttata ttctacgtgt ttgtatcatc ccaacgcacc ccaatgcctc tctcatatga   1320
attccggttg tacatttacc tcgccacatt tagcccagcg tgttgcaagc acagtgtatc   1380
aaaattgtga acatgcagat aactacaccg catattgtct gggaatatct catatggagc   1440
ctagctttgg tctaatctta cacgacgggg gcaccacgtt aaagtttgta gatacacccg   1500
agagtttgtc gggattatac gtttttgtgg tgtattttaa cgggcatgtt gaagccgtag   1560
catacactgt tgtatccaca gtagatcatt ttgtaaacgc aattgaagag cgtggatttc   1620
cgccaacggc cggtcagcca ccggcgacta ctaaacccaa ggaaattacc cccgtaaacc   1680
ccggaacgtc accacttcta cgatatgccg catggaccgg agggcttgca gcagtagtac   1740
ttttatgtct cgtaatattt ttaatctgta cggctaaacg aatgagggtt aaagcctata   1800
gggtagacaa gtccccgtat aaccaaagca tgtatggcgc tggccttcca gtggacgatt   1860
tcgaggacgc cgaagccgcc gatgccgaag aagagtttgg taacgcgatt ggagggagtc   1920
acgggggttc gagttacacg gtgtatatag ataagacccg gtgatgataa taggctggag   1980
cctcggtggc catgcttctt gccccttggg cctcccccca gccctcctc ccccttcctgc   2040
acccgtaccc ccgtggtctt tgaataaagt ctgagtgggc ggc                     2083
```

```
SEQ ID NO: 9              moltype = RNA   length = 2080
FEATURE                   Location/Qualifiers
misc_feature              1..2080
                          note = Synthetic Polynucleotide
source                    1..2080
                          mol_type = other RNA
                          organism = synthetic construct
SEQUENCE: 9
tcaagctttt ggaccctcgt acagaagcta atacgactca ctatagggaa ataagagaga   60
aaagaagagt aagaagaaat ataagagcca ccatggggac agtgaataag ccggttgtgg   120
gcgtgcttat gggctttggg attattaccg gtacattacg aattaccaat ccagtgcgcg   180
ccagtgtgct gcgttacgac gactttcaca ttgacgagga taagctggat actaacagcg   240
tgtacgaacc ttattaccac tcagatcatg ccgaatcagc ctggtttaat agaggagaaa   300
gcagccgaaa agcctacgac cacaactcac cttatatttg gcccagaaac gattatgacg   360
gtttcctgga aaacgcacat gaacaccatg agtctacaa ccaaggcagg ggaatcgaca   420
gtggcgagcg tcttatgcag ccaacacaga tgtcggcaca ggaggatctc ggtgatgaca   480
ccggcataca cgtgattccc acattaaacg gcgacgacac acataagatc gtcaatgtgg   540
atcagcgtca gtatggggat gtctttaaag gcgatttgaa tccaaagccc caaggacaga   600
```

```
gactgatcga ggtctctgta gaagaaaatc accccttcac tttgcgcgct ccaatccaga  660
ggatttacgg ggtgcgttat accgaaactt ggagtttctt gccgtcactg acgtgtacgg  720
gggatgccgc ccccgcaatc cagcacatct gtctgaaaca caccacatgc tttcaggacg  780
tggttgtgga tgtggattgc gcggaaaaca caaaagaaga ccaactcgcc gaaatcagct  840
atcgttttca gggtaaaaaa gaggccgacc aaccgtggat tgttgtgaat acgagcacgc  900
tcttcgatga gcttgaactc gatccccgg aaatcgagcc tggggttcta aaagtgttga  960
ggaccgagaa gcagtacctc ggggtttata tctggaatat gagaggctcc gatggcacct 1020
ctacctacgg aacgtttctg gttacctgga agggagacga gaagcacgg aatccaacgc 1080
ccgctgtgac ccctcagcct aggggagccg aattccacat gtggaactat cactcccatg 1140
tattcagtgt gggtgacact ttcagcctgg ccatgcacct gcagtataag attcacgagg 1200
caccccttcga cctcctgctg gagtggttgt acgtacctat tgatcccact tgtcagccca 1260
tgcgcctgta ctccacttgc ttgtaccacc ccaatgcacc acagtgtcta tcacacatga 1320
actccgggtg tacctttact tcaccccatc ttgcccagcg ggtcgccagc acagtgtatc 1380
agaactgtga gcatgctgac aactatactg cttattgcct cggaatatcc catatggagc 1440
caagcttcgg gctcatactg cacgatggtg gtacgacact caagttcgtg gacaccccg 1500
aaagcctttc tggcttgtac gtgttcgtgg tctacttcaa tggacatgtg gaggcagtgg 1560
cttacacagt ggtttcgaca gttgatcact ttgtaaatgc cattgaggaa cgcggcttcc 1620
cgcctacagc gggccagccc cctgcgacaa caaaaccaaa agagattacg cccgttaatc 1680
ctgggactag tccattgctg aggtatgccg cctggactgg cggtctgcg gccgtggtac 1740
ttctgtgttt agtcatattt ctgatctgta ccgctaaacg tatgcgggtc aaggcttacc 1800
gtgttgacaa gtctccttac aatcagtcaa tgtactatgc aggactccct gttgacgatt 1860
tcgaagactc agagagtaca gacacagaag aagaattcgg aaacgctata ggtggctctc 1920
acggaggtag ctcgtataca gtgtacatcg ataaaaccag atgataatag gctggagcct 1980
cggtggccat gcttcttgcc ccttgggcct cccccagcc cctcctcccc ttcctgcacc 2040
cgtacccccg tggtctttga ataaagtctg agtgggcggc                        2080
```

SEQ ID NO: 10          moltype = AA  length = 623
FEATURE                Location/Qualifiers
REGION                 1..623
                       note = Synthetic Polypeptide
source                 1..623
                       mol_type = protein
                       organism = synthetic construct
SEQUENCE: 10
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM 120
SAQEDLGDDT GIHVIPTLNG DDRHKIVNVD QRQYGDVFKG DLNPKPQGQR LIEVSVEENH 180
PFTLRAPIQR IYGVRYTETW SFLPSLTCTG DAAPAIQHIC LKHTTCFQDV VVDVDCAENT 240
KEDQLAEISY RFQGKKEADQ PWIVVNTSTL FDELELDPPE IEPGVLKVLR TEKQYLGVYI 300
WNMRGSDGTS TYATFLVTWK GDEKTRNPTP AVTPQPRGAE FHMWNYHSHV FSVGDTFSLA 360
MHLQYKIHEA PFDLLLEWLY VPIDPTCQPM RLYSTCLYHP NAPQCLSHMN SGCTFTSPHL 420
AQRVASTVYQ NCEHADNYTA YCLGISHMEP SFGLILHDGG TTLKFVDTPE SLSGLYVFVV 480
YFNGHVEAVA YTVVSTVDHF VNAIEERGFP PTAGQPPATT KPKEITPVNP GTSPLLRYAA 540
WTGGLAAVVL LCLVIFLICT AKRMRVKAYR VDKSPYNQSM YYAGLPVDDF EDSESTDTEE 600
EFGNAIGGSH GGSSYTVYID KTR                                          623

SEQ ID NO: 11          moltype = RNA  length = 1869
FEATURE                Location/Qualifiers
misc_feature           1..1869
                       note = Synthetic Polynucleotide
source                 1..1869
                       mol_type = other RNA
                       organism = synthetic construct
SEQUENCE: 11
atggggacag tgaataagcc ggttgtgggc gtgcttatgg gctttgggat tattaccggt  60
acattacgaa ttaccaatcc agtgcgcgcc agtgtgctgc gttacgacga ctttcacatt 120
gacgaggata agctggatac taacagcgtg tacgaacctt attaccactc agatcatgcc 180
gaatcaagct gggttaatag aggagaaagc agccgaaaag cctacgacca caactcacct 240
tatatttggc ccagaaacga ttatgacggt ttcctggaaa acgcacatga acaccatgga 300
gtctacaacc aaggcagggg aatcgacagt ggcgagcgtc ttatgcagcc aacacagatg 360
tcggcacagg aggatctcgg tgatgacacc ggcatacacg tgattcccac attaaacggc 420
gacgacgac ataagatcgt caatgtggat cagcgtcagt atggggatgt ctttaaaggc 480
gatttgaatc caaagcccca aggacagaga ctgatcgagg tctctgtaga agaaaatcac 540
ccccttcactt tgcgcgctcc aatccagagg atttacggg gtgcgttatc cgaaacttga 600
agttycttgc cgtcactgac gtgtacgggg gatgccgccc ccgcaatcca gcacatctgt 660
ctgaaacaca ccacatgctt tcaggacgtg gttgtggatg tggattgcgc ggaaaacaca 720
aaagaagacc aactcgccga aatcagctat cgttttcagg gtaaaaaaga ggccgaccaa 780
ccgtggattg ttgtgaatac gagcacgctc ttcgatgagc ttgaactcga tccccggaa 840
atcgagcctg gggttctaaa agtgttgagg accgagaaga gtacctcgg ggtttatatc 900
tggaatatga gaggctccga tggcacctct acctacgcaa cgtttctggt tacctggaag 960
ggagacgaga agcacggaa tccaacgccc gctgtgaccc ctcagcctag gggagccgaa 1020
ttccacatgt ggaactatca ctcccatgta ttcagtgtgg gtgacacttt cagcctggcc 1080
atgcacctgc agtataagat tcacgaggca cccttcgacc tcctgctgga gtggttgtac 1140
gtacctattg atcccacttg tcagcccatg cgcctgtact ccacttgctt gtaccaccc 1200
aatgcaccac agtgtctatc acacatgaac tccgggtgta cctttacttc accccatctt 1260
gcccagcggg tcgccagcac agtgtatcag aactgtgagc atgctgacaa ctatactgct 1320
tattgcctcg gaatatccca tatggagcca agcttcgggc tcatactgca cgatggtggt 1380
acgacactca gttcgtgga caccccgaa agcctttctg gcttgtacgt gttcgtggtc 1440
tacttcaatg gacatgtgga ggcagtggct tacacagtgg tttcgacagt tgatcacttt 1500
```

-continued

```
gtaaatgcca ttgaggaacg cggcttcccg cctacagcgg gccagccccc tgcgacaaca  1560
aaaccaaaag agattacgcc cgttaatcct gggactagtc cattgctgag gtatgccgcc  1620
tggactggcg gtctggcggc cgtggtactt ctgtgtttag tcatatttct gatctgtacc  1680
gctaaacgta tgcgggtcaa ggcttaccgt gttgacaagt ctccttacaa tcagtcaatg  1740
tactatgcag gactccctgt tgacgatttc gaagactcag agagtacaga cacagaagaa  1800
gaattcggaa acgctatagg tggctctcac ggaggtagct cgtatacagt gtacatcgat  1860
aaaaccaga                                                         1869

SEQ ID NO: 12           moltype = RNA   length = 2141
FEATURE                 Location/Qualifiers
misc_feature            1..2141
                        note = Synthetic Polynucleotide
source                  1..2141
                        mol_type = other RNA
                        organism = synthetic construct
SEQUENCE: 12
ggggaaataa gagagaaaag aagagtaaga agaaatataa gagccaccat ggggacagtg  60
aataagccgg ttgtgggcgt gcttatgggc tttgggatta ttaccggtac attacgaatt  120
accaatccag tgcgcgccag tgtgctgcgt tacgacgact ttcacattga cgaggataag  180
ctggatacta acagcgtgta cgaaccttat taccactcag atcatgccga atcaagctgg  240
gttaatagag gagaaagcag ccgaaaagcc tacgaccaca actcacctta tatttggccc  300
agaaacgatt atgacggttt cctggaaaac gcacatgaac accatggagt ctacaaccaa  360
ggcaggggaa tcgacagtgg cgagcgtctt atgcagccaa cacagatgtc ggcacaggag  420
gatctcggtg atgacaccgg catacacgtg attcccacat aaacggcga cgacagacat   480
aagatcgtca atgtggatca gcgtcagtat ggggatgtct ttaaaggcga tttgaatcca  540
aagccccaag gacagagact gatcgaggtc tctgtagaag aaaatcaccc cttcactttg  600
cgcgctccaa tccagaggat ttacggggtg cgttataccg aaacttggag tttcttgccg  660
tcactgacgt gtacggggga tgccgcccccc gcaatccagc acatctgtct gaaacacacc  720
acatgctttc aggacgtggt tgtggatgtg gattgcgcgg aaaacacaaa agaagaccaa  780
ctcgccgaaa tcagctatcg tttttcaggggt aaaaaagagg cgaccaacc gtggattgtt  840
gtgaatacga gcacgctctt cgatgagctt gaactcgatc ccccggaaat cgagcctggg  900
gttctaaaag tgttgaggac cgagaagcag tacctcgggg tttatatctg gaatatgaga  960
ggctccgatg gcacctctac ctacgcaacg tttctggtta cctggaaggg agacgagaag  1020
acacggaatc caacgcccgc tgtgacccct cagcctaggg gagccgaatt ccacatgtgg  1080
aactatcact cccatgtatt cagtgtgggt gacactttca gcctggccat gcacctgcag  1140
tataagattc acgaggcacc cttcgacctc ctgctggagt ggttgtacgt acctattgat  1200
cccacttgtc agcccatgcg cctgtactcc acttgcttgt accaccccaa tgcaccacag  1260
tgtctatcac acatgaactc cgggtgtacc tttacttcac cccatcttgc ccagcgggtc  1320
gccagcacag tgtatcagaa ctgtgagcat gctgacaact atactgctta ttgcctcgga  1380
atatcccata tggagccaag cttcgggctc atactgcacg atggtggtac gacactcaag  1440
ttcgtggaca cccccgaaag cctttctggc ttgtacgtgt cgtggtctca cttcaatgga  1500
catgtggagg cagtggctta cacagtggtt tcgacagttg atcactttgt aaatgccatt  1560
gaggaacgcg gcttcccgcc tacagcgggc cagcccccg cgacaacaa accaaaagag  1620
attacgcccg ttaatcctgg gactagtcca ttgctgaggt atgccgcctg gactggcggt  1680
ctggcggccg tggtacttct gtgtttagtc atatttctga tctgtaccgc taaacgtatg  1740
cgggtcaagg cttaccgtgt tgacaagtct ccttacaatc agtcaatgta ctatgcagga  1800
ctccctgttg acgatttcga agactcagag agtacagaca cagaagaaga attcggaaac  1860
gctataggtg gctctcacgg aggtagctcg tatacagtga catcgataaa accagatga   1920
taataggctg gagcctcggt ggccatgctt cttgccccct gggcctcccc ccagcccctc  1980
ctccccttcc tgcacccgta cccccgtggt ctttgaataa agtctgagtg ggcggcaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaaaa aaaaaatcta g                     2141

SEQ ID NO: 13           moltype = RNA   length = 2050
FEATURE                 Location/Qualifiers
misc_feature            1..2050
                        note = Synthetic Polynucleotide
source                  1..2050
                        mol_type = other RNA
                        organism = synthetic construct
SEQUENCE: 13
tcaagctttt ggaccctcgt acagaagcta atacgactca ctatagggaa ataagagaga  60
aaagaagagt aagaagaaat ataagagcca ccatggggac tccgctcag ctactgttcc  120
tcctgctcct ttggctgcct gatactacag gctctgtttt gcggtacgac gactttcaca  180
tcgatgagga caagctcgac actaatagcg tgtatgagcc ctactaccat tcagatcacg  240
ccgagtcctc ttgggtgaac aggggtgaaa gttctaggaa agcctatgat cacaacagcc  300
cttatatttg gccacggaat gattacgacg gatttctcga aaatgcccac gagcatcacg  360
gagtgtacaa ccagggccgt ggaatcgact ctggggagag attgatgcaa cctacacaga  420
tgagcgccca ggaagatctc gggatgata caggaattca cgttatccct acattaaacg  480
gagatgaccg ccacaaaatc gtcaatgtcg atcaaagaca gtatggagat gtgttcaaag  540
gcgatctcaa ccctaagccg cagggccaga gactcattga ggtgtctgtc gaagagaacc  600
accctttcac tctgcgcgct cccattcaga gaatctatgg agttcgctat acggagactt  660
ggtcattcct tccttcccctg acatgcaccg gagacgcgc cctgccatt cagcacatat  720
gcctgaaaca taccacctgt ttccaggatg tggtggttga tgttgattgt gctgaaaata  780
ccaaggaaga ccaactggcc gagattagtt accggttcca agggaaaaag gaagccgacc  840
agccatggat tgtggttaat acaagcactc tgttcgatga gctcgagctg gatcccccg   900
agatagaacc cggagttctg aaagtgctcc ggacagaaaa acaatatctg ggagtctaca  960
tatggaacat gcgcggttcc gatgggacct ccacttatgc aaccttctc gtcacgtgga   1020
agggagatga gaaaactagg aatcccacac cgctgtcac accacagcca agaggggctg   1080
```

```
agttccatat gtggaactat catagtcacg tgtttagtgt cggagatacg ttttcattgg   1140
ctatgcatct ccagtacaag attcatgagg ctcccttcga tctgttgctt gagtggttgt   1200
acgtcccgat tgacccgacc tgccagccca tgcgactgta cagcacctgt ctctaccatc   1260
caaacgctcc gcaatgtctg agccacatga actctgggtg tactttcacc agtccccacc   1320
tcgcccagcg ggtggcctct actgtttacc agaactgtga gcacgccgac aactacaccg   1380
catactgcct cggtgatttct cacatggaac cctccttcgg actcatcctg cacgatgggg   1440
gcactaccct gaagttcgtt gatacgccag aatctctgtc tgggctctat gttttcgtgg   1500
tctacttcaa tggccatgtc gaggccgtgg cctatactgt cgtttctacc gtggatcatt   1560
ttgtgaacgc catcgaagaa cggggattcc ccctacggc aggccagccg cctgcaacca   1620
ccaagcccaa ggaaataaca ccagtgaacc ctggcacctc acctctccta agatatgccg   1680
cgtggacagg gggactggcg gcagtggtgc tcctctgtct cgtgatcttt ctgatctgta   1740
cagccaagag gatgagggtc aaggcttata gagtggacaa gtccccctac aatcagtcaa   1800
tgtactacgc cggccttccc gttgatgatt ttgaggattc cgagtccaca gatactgagg   1860
aagagttcgg taacgctata ggcggctctc acggggttc aagctacacg gtttacattg   1920
acaagacacg ctgataatag gctggagcct cggtggccat gcttcttgcc ccttgggcct   1980
cccccagcc cctcctcccc ttcctgcacc cgtaccccg tggtctttga ataaagtctg   2040
agtgggcggc                                                          2050

SEQ ID NO: 14          moltype = AA  length = 613
FEATURE                Location/Qualifiers
REGION                 1..613
                       note = Synthetic Polypeptide
source                 1..613
                       mol_type = protein
                       organism = synthetic construct
SEQUENCE: 14
METPAQLLFL LLLWLPDTTG SVLRYDDFHI DEDKLDTNSV YEPYYHSDHA ESSWVNRGES   60
SRKAYDHNSP YIWPRNDYDG FLENAHEHHG VYNQGRGIDS GERLMQPTQM SAQEDLGDDT   120
GIHVIPTLNG DDRHKIVNVD QRQYGDVFKG DLNPKPQGQR LIEVSVEENH PFTLRAPIQR   180
IYGVRYTETW SFLPSLTCTG DAAPAIQHIC LKHTTCFQDV VVDVDCAENT KEDQLAEISY   240
RFQGKKEADQ PWIVVNTSTL FDELELDPPE IEPGVLKVLR TEKQYLGVYI WNMRGSDGTS   300
TYATFLVTWK GDEKTRNPTP AVTPQPRGAE FHMWNYHSHV FSVGDTFSLA MHLQYKIHEA   360
PFDLLLEWLY VPIDPTCQPM RLYSTCLYHP NAPQCLSHMN SGCTFTSPHL AQRVASTVYQ   420
NCEHADNYTA YCLGISHMEP SFGLILHDGG TTLKFVDTPE SLSGLYVFVV YFNGHVEAVA   480
YTVVSTVDHF VNAIEERGFP PTAGQPPATT KPKEITPVNP GTSPLLRYAA WTGGLAAVVL   540
LCLVIFLICT AKRMRVKAYR VDKSPYNQSM YYAGLPVDDF EDSESTDTEE EFGNAIGGSH   600
GGSSYTVYID KTR                                                      613

SEQ ID NO: 15          moltype = RNA  length = 1839
FEATURE                Location/Qualifiers
misc_feature           1..1839
                       note = Synthetic Polynucleotide
source                 1..1839
                       mol_type = other RNA
                       organism = synthetic construct
SEQUENCE: 15
atggagactc ccgctcagct actgttcctc ctgctccttt ggctgcctga tactacaggc   60
tctgtttttgc ggtacgacga ctttcacatc gatgaggaca agctcgacac taatagcgtg   120
tatgagccct actaccattc agatcacgcc gagtcctctt gggtgaacag gggtgaaagt   180
tctaggaaag cctatgatca caacagccct tatatttggc cacggaatga ttacgacgga   240
tttctcgaaa atgcccacga gcatcacgga gtgtacaacc agggccgtgg aatcgactct   300
ggggagagat tgatgcaacc tacacagatg agcgcccagg aagatctcgg ggatgataca   360
ggaattcacg ttatccctac attaaacgga gatgaccgcc acaaaatcgt caatgtcgat   420
caaagacagt atggagatgt gttcaaaggc gatctcaacc ctaagccgca gggccagaga   480
ctcattgagg tgtctgtcga agagaaccac cctttcactc tgcgcgctcc cattcagaga   540
atctatggag ttcgctatac ggagacttgg tcattccttc cttccctgac atgcaccgga   600
gacgccgccc ctgccattca gcacatatgc ctgaaacata ccacctgttt ccaggatgtg   660
gtggttgatg ttgattgtgc tgaaaatacc aaggaagacc aactggccga gattagttac   720
cggttccaag ggaaaaagga agccgaccag ccatggattg tggttaatac aagcactctg   780
ttcgatgagc tcgagctgga tccccccgag atagaacccg gagttctgaa agtgctccga   840
acagaaaaac aatatctggg agtctacata tggaacatgc gcggtccga tgggacctcc   900
acttatgcaa cctttctcgt cacgtggaag ggagatgaga aaactaggaa tcccacaccc   960
gctgtcacac cacagccaag aggggctgag ttccatatgt ggaactatca tagtcacgtg   1020
tttagtgtcg gagatacgtt ttcattggct atgcatctcc agtacaagat tcatgaggct   1080
cccttcgatc tgttgcttga gtggttgtac gtcccgattg acccgacctg ccagcccatg   1140
cgactgtaca gcacctgtct ctaccatcca aacgctccgc aatgtctgag ccacatgaac   1200
tctgggtgta ctttcaccag tccccacctc gcccagcggg tggcctctac tgtttaccag   1260
aactgtgagc acgccgacaa ctacaccgca tactgcctcg gtgatttctca catggaaccc   1320
tccttcggac tcatcctgca cgatgggggc actaccctga agttcgttga tacgccagaa   1380
tctctgtctg ggctctatgt tttcgtggtc tacttcaatg gccatgtcga ggccgtggcc   1440
tatactgtcg tttctaccgt ggatcatttt gtgaacgcca tcgaagaacg gggattcccc   1500
cctacggcag ccagccgcc tgcaaccacc aagcccaagg aaataacacc agtgaaccct   1560
ggcacctcac tctcctaag atatgccgcg tggacagggg gactggcggc agtggtgctc   1620
ctctgtctcg tgatctttct gatctgtaca gccaagagga tgagggtcaa ggcttataga   1680
gtggacaagt cccccctacaa tcagtcaatg tactacgccg ccttcccgt tgatgatttt   1740
gaggattccg agtccacaga tactgaggaa gagttcggta acgctatagg cggctctcac   1800
gggggttcaa gctacacggt ttacattgac aagacacgc                          1839

SEQ ID NO: 16          moltype = RNA  length = 2111
```

-continued

```
FEATURE                 Location/Qualifiers
misc_feature            1..2111
                        note = Synthetic Polynucleotide
source                  1..2111
                        mol_type = other RNA
                        organism = synthetic construct
SEQUENCE: 16
ggggaaataa gagagaaaag aagagtaaga agaaatataa gagccaccat ggagactccc    60
gctcagctac tgttcctcct gctcctttgg ctgcctgata ctacaggctc tgttttgcgg   120
tacgacgact ttcacatcga tgaggacaag ctcgacacta atagcgtgta tgagccctac   180
taccattcag atcacgccga gtcctcttgg gtgaacaggg gtgaaagttc taggaaagcc   240
tatgatcaca acagccctta tatttggcca cggaatgatt acgacggatt tctcgaaaat   300
gcccacgagc atcacggagt gtacaaccag ggccgtggaa tcgactctgg ggagagattg   360
atgcaaccta cacagatgag cgcccaggaa gatctcgggg atgatacagg aattcacgtt   420
atccctacat taaacggaga tgaccgccac aaaatcgtca atgtcgatca aagacagtat   480
ggagatgtgt tcaaaggcga tctcaaccct aagccgcagg gccagagact cattgaggtg   540
tctgtcgaag agaaccaccc tttcactctg cgcgctccca ttcagagaat ctatggagtt   600
cgctatacgg agacttggtc attccttcct tccctgacat gcaccggaga cgccgccct    660
gccattcagc acatatgcct gaaacatacc acctgtttcc aggatgtggt ggttgatgtt   720
gattgtgctg aaaataccaa ggaagaccaa ctggccgaga ttagttaccg gttccaaggg   780
aaaaaggaag ccgaccagcc atggattgtg gttaatacaa gcactctgtt cgatgagctc   840
gagctggatc cccccgagat agaacccgga gttctgaaag tgctccggac agaaaaacaa   900
tatctgggag tctacatatg gaacatgcgc ggttccgatg ggacctccac ttatgcaacc   960
tttctcgtca cgtggaaggg agatgagaaa actaggaatc ccacaccgc tgtcacacca   1020
cagccaagag gggctgagtt ccatatgtgg aactatcata gtcacgtgtt tagtgtcgga   1080
gatacgtttt cattggctat gcatctccag tacaagattc atgaggctcc cttcgatctg   1140
ttgcttgagt ggttgtacgt cccgattgac ccgacctgcc agcccatgcg actgtacagc   1200
acctgtctct accatccaaa cgctccgcaa tgtctgagcc acatgaactc tgggtgtact   1260
ttcaccagtc cccacctcgc ccagcgggtg gcctctactg tttaccagaa ctgtgagcac   1320
gccgacaact acaccgcata ctgcctcggt atttctcaca tggaaccctc cttcggactc   1380
atcctgcacg atgggggcac taccctgaag ttcgttgata cgccagaatc tctgtctggg   1440
ctctatgttt tcgtggtcta cttcaatggc catgtcgagg ccgtggccta tactgtcgtt   1500
tctaccgtgg atcattttgt gaacgccatc gaagaacggg gattcccccc tacggcaggc   1560
cagccgcctg caaccaccaa gcccaaggaa ataacaccag tgaaccctgg cacctcacct   1620
ctcctaagat atgccgcgtg gacagggga ctggcggcag tggtgctcct ctgtctcgtg   1680
atctttctga tctgtacagc caagaggatg agggtcaagg cttatagagt ggacaagtcc   1740
ccctacaatc agtcaatgta ctacgccggc cttcccgttg atgattttga ggattccgag   1800
tccacagata ctgaggaaga gttcggtaac gctataggcg gctctcacgg gggttcaagc   1860
tacacggttt acattgacaa gacacgctga taataggctg gagcctcggt ggccatgctt   1920
cttgcccctt gggcctcccc ccagcccctc ctccccttcc tgcacccgta cccccgtggt   1980
ctttgaataa agtctgagtg ggcggcaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaatcta g                                                        2111

SEQ ID NO: 17        moltype = RNA   length = 1897
FEATURE                 Location/Qualifiers
misc_feature            1..1897
                        note = Synthetic Polynucleotide
source                  1..1897
                        mol_type = other RNA
                        organism = synthetic construct
SEQUENCE: 17
tcaagctttt ggaccctcgt acagaagcta atacgactca ctatagggaa ataagagaga    60
aaagaagagt aagaagaaat ataagagcca ccatggggga cagttaataa cctgtggtgg   120
gggtattgat ggggttcgga attatcacgg gaacgttcg tataacgaat ccggtcagag   180
catccgtctt gcgatacgat gattttcaca tcgatgaaga caaactggat acaaactccg   240
tatatgagcc ttactaccat tcagatcatg cggagtcttc atgggtaaat cggggagagt   300
cttcgcgaaa agcgtacgat cataactcac cttatatatg gccacgtaat gattatgatg   360
gatttttaga gaacgcacac gaacaccatg gggtgtataa cggggccgat ggtatcgata   420
gcgggggaacg gttaatgcaa cccacacaaa tgtctgcaca ggaggatctt ggggacgata   480
cgggcatcca cgttatccct acgttaaacg gcgatgacag acataaaatt gtaaatgtgg   540
accaacgtca atacggtgac gtgtttaaag gagatcttaa tccaaaaccc caaggccaaa   600
gactcattga ggtgtcagtg gaagaaaatc acccgtttac tttacgcgca ccgattcagc   660
ggatttatgg agtccggtac accggagactt ggagcttttc gccgtcatta acctgtacgg   720
gagacgcagc gccgccatc cagcatatat gtttaaaaca tacaacatgc tttcaagacg   780
tggtggtgga tgtgcgattgc gcggaaaata ctaaagagga tcagttggcc gaaatcagtt   840
accgttttca aggtaagaag gaagcggacc aaccgtggat tgttgtaaac acgagcacac   900
tgtttgatga actcgaatta gacccccccg agattgaac gggtgtcttg aaagtacttc   960
ggacagaaaa acaatacttg ggtgtgtaca tttggaacat gcgcggctcc gatgggtacgt  1020
ctacctacgc cacgtttttg gtcacctgga aaggggatga aaaaacaaga aaccctacgc  1080
ccgcagtaac tcctcaacca agagggggctg agtttcatat gtggaattac cactcgcatg  1140
tattttcagt tggtgtatacg tttagcttgg caatgcatct tcagtataag atacatgaag  1200
cgccatttga tttgctgtta gagtggttgt atgtccccat cgatcctaca tgtcaaccaa  1260
tgcggtata ttctacgtgt ttgtatcatc ccaacgcacc ttatattgca cgttaacag   1320
attccggttg tacatttacc tcgccacatt tagcccagcg tgttgcaagc acagtgtatc  1380
aaaattgtga acatgcagat aactacaccg catattgtct gggaatatct catatggagc  1440
ctagcttttgg tctaatcta cacgacgggg gcaccacgtt aaagtttgta gatacacccg   1500
agagtttgtc gggattatac gttttgtggg tgtattttaa cgggcatgtt gaagccgtag  1560
catacactgt tgtatccaca gtagatcatt ttgtaaacgc aattgaagag cgtggatttc  1620
```

-continued

```
cgccaacggc cggtcagcca ccggcgacta ctaaacccaa ggaaattacc cccgtaaacc  1680
ccggaacgtc accacttcta cgatatgccg catggaccgg agggcttgca gcagtagtac  1740
ttttatgtct cgtaatattt ttaatctgta cggcttgatg ataataggct ggagcctcgg  1800
tggccatgct tcttgcccct tgggcctccc cccagcccct cctcccttc ctgcaccgt   1860
accccgtgg tctttgaata aagtctgagt gggcggc                          1897
```

```
SEQ ID NO: 18          moltype = AA   length = 561
FEATURE                Location/Qualifiers
REGION                 1..561
                       note = Synthetic Polypeptide
source                 1..561
                       mol_type = protein
                       organism = synthetic construct
SEQUENCE: 18
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT A                                           561
```

```
SEQ ID NO: 19          moltype = RNA   length = 1686
FEATURE                Location/Qualifiers
misc_feature           1..1686
                       note = Synthetic Polynucleotide
source                 1..1686
                       mol_type = other RNA
                       organism = synthetic construct
SEQUENCE: 19
atggggacag ttaataaacc tgtggtgggg gtattgatgg ggttcggaat tatcacggga  60
acgttgcgta taacgaatcc ggtcagagca tccgtcttgc gatacgatga ttttcacatc  120
gatgaagaca aactggatac aaactccgta tatgagcctt actaccattc agatcatgcg  180
gagtcttcat gggtaaatcg gggagagtct tcgcgaaaag cgtacgatca taactccacct  240
tatatatggc cacgtaatga ttatgatgga ttttagaga acgcacacga acaccatggg  300
gtgtataatc agggccgtgg tatcgatagc ggggaacggt taatgcaacc cacacaaatg  360
tctgcacagg aggatcttgg ggacgatacg ggcatccacg ttatccctac gttaaacggc  420
gatgacagac ataaaattgt aaatgtggac caacgtcaat acggtgacgt gtttaaagga  480
gatcttaatc caaaacccca aggccaaaga ctcattgagg tgtcagtgga agaaaatcac  540
ccgtttactt tacgcgcacc gattcagcgg atttatggag tccggtacac cggcgacttgg  600
agcttttttgc cgtcattaac ctgtacggga gacgcagcgc ccgccatcca gcatatatgt  660
ttaaaacata caacatgctt tcaagacgtg gtggtggatg tggattgcgc ggaaaatact  720
aaagaggatc agttggccga aatcagttac cgttttcaag gtaagaagga agcggaccaa  780
ccgtggattg ttgtaaacac gagcacactg tttgatgaac tcgaattaga cccccccgaa  840
attgaaccgg gtgtcttgaa agtacttcgg acagaaaaac aatacttggg tgtgtacatt  900
tggaacatgc gcggctccga tggtacgtct acctacgcca cgttttttggt cacctggaaa  960
ggggatgaaa aaacaagaaa ccctacgccc gcagtaactc ctcaaccaag aggggctgag  1020
tttcatatgt ggaattacca ctcgcatgta ttttcagttg gtgatacgtt tagcttggca  1080
atgcatcttc agtataagat acatgaagcg ccatttgatt tgctgttaga gtggttgtat  1140
gtccccatcg atcctacatg tcaaccaatg cggttatatt ctacgtgttt gtatcatccc  1200
aacgcacccc aatgcctctc tcatatgaat tccggttgta catttaccctc gccacattta  1260
gcccagcgtg ttgcaagcac agtgtatcaa aattgtgaac atgcagataa ctacaccgca  1320
tattgtctgg gaatatctca tatggagcct agctttggtc taatcttaca cgacgggggc  1380
accacgttaa agtttgtaga tacacccgag agttgtcggg attatacgt ttttgtggtg  1440
tattttaacg gcatgttga agccgtagca tacactgttg tatccacagt agatcatttt  1500
gtaaacgcaa ttgaagagcg tggatttccg ccaacggccg gtcagccacc ggcgactact  1560
aaacccaagg aaattacccc cgtaaacccc ggaacgtcac cacttctacg atatgccgca  1620
tggaccggag ggcttgcagc agtagtactt ttatgtctcg taatatttttt aatctgtacg  1680
gcttga                                                           1686
```

```
SEQ ID NO: 20          moltype = RNA   length = 1958
FEATURE                Location/Qualifiers
misc_feature           1..1958
                       note = Synthetic Polynucleotide
source                 1..1958
                       mol_type = other RNA
                       organism = synthetic construct
SEQUENCE: 20
ggggaaataa gagagaaaag aagagtaaga agaaatataa gagccaccat ggggacagtt  60
aataaacctg tggtggggt attgatgggg ttcggaatta tcacgggaac gttgcgtata  120
acgaatccgg tcagagcatc cgtcttgcga tacgatgatt tcacatcga tgaagacaaa  180
ctggatacaa actccgtata tgagccttac taccattcga atcatgcgga gtcttcatgg  240
gtaaatcggg gagagtcttc gcgaaaagcg tacgatcata actcaccta tatggccca  300
cgtaatgatt atgatggatt tttagagaac gcacacgaac accatggggt gtataatcag  360
ggccgtggta tcgatagcgg ggaacggtta atgcaaccca cacaaatgtc tgcacaggag  420
gatcttgggg acgatacggg catccacgtt atccctacgt taaacggcga tgacagacat  480
```

-continued

```
aaaattgtaa atgtggacca acgtcaatac ggtgacgtgt ttaaaggaga tcttaatcca    540
aaacccaag gccaaagact cattgaggtg tcagtggaag aaaatcaccc gtttacttta    600
cgcgcaccga ttcagcggat ttatggagtc cggtacaccg agacttggag cttttttgccg    660
tcattaacct gtacgggaga cgcagcgccc gccatccagc atatatgttt aaaacataca    720
acatgctttc aagacgtggt ggtggatgtg gattgcgcgg aaaatactaa agaggatcag    780
ttggccgaaa tcagttaccg tttttcaaggt aagaaggaag cggaccaacc gtggattgtt    840
gtaaacacga gcacactgtt tgatgaactc gaattagacc cccccgagat tgaaccgggt    900
gtcttgaaag tacttcggac agaaaaacaa tacttgggtg tgtacatttg gaacatgcgc    960
ggctccgatg gtacgtctac ctacgccacg tttttggtca cctggaaagg ggatgaaaaa   1020
acaagaaacc ctacgcccgc agtaactcct caaccaagag gggctgagtt tcatatgtgg   1080
aattaccact cgcatgtatt ttcagttggt gatacgttta gcttggcaat gcatcttcag   1140
tataagatac atgaagcgcc atttgatttg ctgttagagt ggttgtatgt ccccatcgat   1200
cctacatgtc aaccaatgcg gttatattct acgtgtttgt atcatcccaa cgcaccccaa   1260
tgcctctctc atatgaattc cggttgtaca tttacctcgc cacatttagc ccagcgtgtt   1320
gcaagcacag tgtatcaaaa ttgtgaacat gcagataact acaccgcata ttgtctggga   1380
atatctcata tggagcctag cttttggtcta atcttacacg acgggggcac cacgttaaag   1440
tttgtagata cacccgagag tttgtcggga ttatacgttt ttgtggtgta tttaacggg   1500
catgttgaag ccgtagcata cactgttgta tccacagtag atcatttgt aaacgcaatt   1560
gaagagcgtg gatttccgcc aacggccggt cagccaccgg cgactactaa acccaaggaa   1620
attacccccg taaaccccgg aacgtcacca cttctacgat atgccgcatg gaccggaggg   1680
cttgcagcag tagtactttt atgtctcgta atattttttaa tctgtacggc ttgatgataa   1740
taggctggag cctcggtggc catgcttctt gcccctttggg cctcccccca gcccctcctc   1800
cccttcctgc accgtaccc ccgtggtctt tgaataaagt ctgagtgggc ggcaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaatctag                           1958

SEQ ID NO: 21            moltype = RNA   length = 1867
FEATURE                  Location/Qualifiers
misc_feature             1..1867
                         note = Synthetic Polynucleotide
source                   1..1867
                         mol_type = other RNA
                         organism = synthetic construct
SEQUENCE: 21
tcaagcttt ggaccctcgt acagaagcta atacgactca ctatagggaa ataagagaga     60
aaagaagagt aagaagaaat ataagagcca ccatggaaac cccggcgcag ctgctgtttc    120
tgctgctgct gtggctgccg gataccaccg gctccgtctt gcgatacgat gattttcaca    180
tcgatgaaga caaactggat acaaactccg tatatgagcc ttactaccat tcagatcatg    240
cggagtcttc atgggtaaat cggggagagt cttcgcagaa agcgtacgat cataactcac    300
cttatatatg gccacgtaat gattatgatg gattttaga gaacgcacac gaacaccatg    360
gggtgtataa tcagggccgt ggtatcgata gcggggaacg gttaatgcaa cccacacaaa    420
tgtctgcaca ggaggatctt gggacgata cgggcatcca cgttatccct acgttaaacg    480
gcgatgacag acataaaatt gtaaatgtgg accaacgtca atacggtgtt taaag          540
gagatcttaa tccaaaaccc caaggccaaa gactcattga ggtgtcagtg gaagaaaatc    600
acccgtttac tttacgcgca ccgattcagc ggatttatgg agtccggtac accgagactt    660
ggagcttttt gccgtcatta acctgtacgg gagacgcagc gcccgccatc cagcatatat    720
gtttaaaaca tacaacatgc tttcaagacg tggtggtgga tgtggattgc gcggaaaata    780
ctaaagagga tcagttggcc gaaatcagtt accgttttca aggtaagaag gaagcggacc    840
aaccgtggat tgttgtaaac acgagcacac tgtttgatga actcgaatta gaccccccg     900
agattgaacc gggtgtcttg aaagtacttc ggacagaaaa acaatacttg ggtgtgtaca    960
tttggaacat gcgcggctcc gatggtacgt ctacctacgt cacgtttttg gtcacctgga   1020
aaggggatga aaaacaaga aaccctacgc ccgcagtaac tcctcaacca agaggggctg   1080
agtttcatat gtggaattac cactcgcatg tattttcagt tggtgatacg tttagcttgg   1140
caatgcatct tcagtataag atacatgaag cgccatttga tttgctgtta gagtggttgt   1200
atgtccccat cgatcctaca tgtcaaccaa tgcggttata ttctacgtgt ttgtatcatc   1260
ccaacgcacc ccaatgcctc tctcatatga attccggttg tacatttacc tcgccacatt   1320
tagcccagcg tgttgcaagc acagtgtatc aaaattgtga acatgcagat aactacaccg   1380
catattgtct gggaatatct catatggagc ctagctttgg tctaatctta cacgacgggg   1440
gcaccacgtt aaagtttgta gatacacccg agagtttgtc gggattatac gttttgtgg   1500
tgtattttaa cgggcatgtt gaagccgtag catacactgt tgtatccaca gtagatcatc   1560
ttgtaaacgc aattgaagag cgtggatttc cgccaacggc cggtcagcca ccggcgacta   1620
ctaaacccaa ggaaattacc cccgtaaacc ccggaacgtc accacttcta cgatatgccg   1680
catggaccgg agggcttgca gcagtagtac ttttatgtct cgtaatattt ttaatctgta   1740
cggcttgatg ataataggct ggagcctcgg tggccatgct tcttgcccct tgggcctccc   1800
cccagcccct cctcccccttc ctgcaccgt accccgtggt ctttgaata aagtctgagt   1860
gggcggc                                                             1867

SEQ ID NO: 22            moltype = AA   length = 551
FEATURE                  Location/Qualifiers
REGION                   1..551
                         note = Synthetic Polypeptide
source                   1..551
                         mol_type = protein
                         organism = synthetic construct
SEQUENCE: 22
METPAQLLFL LLLWLPDTTG SVLRYDDFHI DEDKLDTNSV YEPYYHSDHA ESSWVNRGES     60
SRKAYDHNSP YIWPRNDYDG FLENAHEHHG VYNQGRGIDS GERLMQPTQM SAQEDLGDDT    120
GIHVIPTLNG DDRHKIVNVD QRQYGDVFKG DLNPKPQGQR LIEVSVEENH PFTLRAPIQR    180
IYGVRYTETW SFLPSLTCTG DAAPAIQHIC LKHTTCFQDV VVDVDCAENT KEDQLAEISY    240
```

-continued

```
RFQGKKEADQ  PWIVVNTSTL  FDELELDPPE  IEPGVLKVLR  TEKQYLGVYI  WNMRGSDGTS  300
TYATFLVTWK  GDEKTRNPTP  AVTPQPRGAE  FHMWNYHSHV  FSVGDTFSLA  MHLQYKIHEA  360
PFDLLLEWLY  VPIDPTCQPM  RLYSTCLYHP  NAPQCLSHMN  SGCTFTSPHL  AQRVASTVYQ  420
NCEHADNYTA  YCLGISHMEP  SFGLILHDGG  TTLKFVDTPE  SLSGLYVFVV  YFNGHVEAVA  480
YTVVSTVDHF  VNAIEERGFP  PTAGQPPATT  KPKEITPVNP  GTSPLLRYAA  WTGGLAAVVL  540
LCLVIFLICT  A                                                           551

SEQ ID NO: 23          moltype = RNA  length = 1656
FEATURE                Location/Qualifiers
misc_feature           1..1656
                       note = Synthetic Polynucleotide
source                 1..1656
                       mol_type = other RNA
                       organism = synthetic construct
SEQUENCE: 23
atggaaaccc cggcgcagct gctgtttctg ctgctgctgt ggctgccgga taccaccggc  60
tccgtcttgc gatacgatga ttttcacatc gatgaagaca aactggatac aaactccgta  120
tatgagcctt actaccattc agatcatgcg gagtcttcat gggtaaatcg gggagagtct  180
tcgcgaaaag cgtacgatca taactcacct tatatatggc cacgtaatga ttatgatgga  240
tttttagaga acgcacacga acaccatggg gtgtataatc agggccgtgg tatcgatagc  300
ggggaacggt taatgcaacc cacacaaatg tctgcacagg aggatcttgg ggacgatacg  360
ggcatccacg ttatccctac gttaaacggc gatgacagac ataaaattgt aaatgtggac  420
caacgtcaat acggtgacgt gtttaaagga gatcttaatc caaaacccca aggccaaaga  480
ctcattgagg tgtcagtgga agaaaatcac ccgtttactt tacgcgcacc gattcagcgg  540
atttatggag tccggtacac cgagacttgg agctttttgc cgtcattaac ctgtacggga  600
gacgcagcgc ccgccatcca gcatatatgt ttaaaacata caacatgctt tcaagacgtg  660
gtggtggatg tggattgcgc ggaaaatact aaagaggatc agttggccga aatcagttac  720
cgtttttcaag gtaagaagga agcggaccaa ccgtggattg ttgtaaacac gagcacactg  780
tttgatgaac tcgaattaga cccccccgag attgaaccgg gtgtcttgaa agtacttcgg  840
acagaaaaac aatacttggg tgtgtacatt tggaacatgc gcggctccga tggtacgtct  900
acctacgcca cgtttttggt cacctggaaa ggggatgaaa aaacaagaaa ccctacgccc  960
gcagtaactc ctcaaccaag aggggctgag tttcatatgt ggaattacca ctcgcatgta  1020
tttttcagttg gtgatacgtt tagcttggca atgcatcttc agtataagat acatgaagcg  1080
ccatttgatt tgctgttaga gtggttgtat gtcccccatcg atcctacatg tcaaccaatg  1140
cggttatatt ctacgtgttt gtatcatccc aacgcaccccc aatgcctctc tcatatgaat  1200
tccggttgta catttacctc gccacattta gcccagcgtg ttgcaagcac agtgtatcaa  1260
aattgtgaac atgcagataa ctacaccgca tattgtctgg gaatatctca tatggagcct  1320
agctttggtc taatcttaca cgacgggggc accacgttaa agtttgtaga tacacccgag  1380
agtttgtcgg gattatacgt ttttgtggtg tattttaacg ggcatgttga agccgtagca  1440
tacactgttg tatccacagt agatcatttt gtaaacgcaa ttgaagagcg tggatttccg  1500
ccaacggccg gtcagccacc ggcgactact aaacccaagg aaattacccc cgtaaacccc  1560
ggaacgtcac cacttctacg atatgccgca tggaccggag ggcttgcagc agtagtactt  1620
ttatgtctcg taatattttt aatctgtacg gcttga                             1656

SEQ ID NO: 24          moltype = RNA  length = 1928
FEATURE                Location/Qualifiers
misc_feature           1..1928
                       note = Synthetic Polynucleotide
source                 1..1928
                       mol_type = other RNA
                       organism = synthetic construct
SEQUENCE: 24
ggggaaataa gagagaaaag aagagtaaga agaaatataa gagccaccat ggaaaccccg  60
gcgcagctgc tgtttctgct gctgctgtgg ctgccggata ccaccggctc cgtcttgcga  120
tacgatgatt ttcacatcga tgaagacaaa ctggatacaa actccgtata tgagccttac  180
taccattcag atcatgcgga gtcttcatgg gtaaatcggg gagagtcttc gcgaaaagcg  240
tacgatcata actcacctta tatatggcca cgtaatgatt atgatggatt tttagagaac  300
gcacacgaac accatggggt gtataatcag ggccgtggta tcgatagcgg ggaacggtta  360
atgcaaccca cacaaatgtc tgcacaggag gatcttgggg acgatacggg catccacgtt  420
atccctacgt taaacggcga tgacagacat aaaattgtaa atgtggacca acgtcaatac  480
ggtgacgtgt ttaaaggaga tcttaatcca aaaccccaag gccaaagact cattgaggtg  540
tcagtggaag aaaatcaccc gtttacttta cgcgcaccga ttcagcggat ttatggagtc  600
cggtacaccg agacttggag cttttttgccg tcattaacct gtacgggaga cgcagcgccc  660
gccatccagc atatatgttt aaaacataca acatgctttc aagacgtggt ggtggatgtg  720
gattgcgcgg aaaatactaa agaggatcag ttggccgaaa tcagttaccg ttttcaaggt  780
aagaaggaag cggaccaacc gtggattgtt gtaaacacga gcacactgtt tgatgaactc  840
gaattagacc cccccgagat tgaaccgggt gtcttgaaag tacttcggac agaaaaacaa  900
tacttgggtg tgtacatttg gaacatgcgc ggctccgatg gtacgtctac ctacgccacg  960
tttttggtca cctggaaagg ggatgaaaaa acaagaaacc ctacgcccgc agtaactcct  1020
caaccaagag gggctgagtt tcatatgtgg aattaccact cgcatgtatt tttcagttggt  1080
gatacgttta gcttggcaat gcatcttcag tataagatac atgaagcgcc atttgatttg  1140
ctgttagagt ggttgtatgt ccccatcgat cctacatgtc aaccaatgcg gttatattct  1200
acgtgtttgt atcatcccaa cgcaccccaa tgcctctctc atatgaattc cggttgtaca  1260
tttacctcgc cacatttagc cagcgtgtt gcaagcacag tgtatcaaaa ttgtgaacat  1320
gcagataact acaccgcata ttgtctggga atatctcata tggagcctag ctttggtcta  1380
atcttacacg acgggggcac cacgttaaag tttgtagata cacccgagag tttgtcggga  1440
ttatacgttt ttgtggtgta ttttaacggg catgttgaag ccgtagcata cactgttgta  1500
tccacagtag atcattttgt aaacgcaatt gaagagcgtg gatttccgcc aacggccggt  1560
cagccaccgg cgactactaa acccaaggaa attacccccg taaaccccgg aacgtcacca  1620
```

-continued

```
cttctacgat atgccgcatg gaccggaggg cttgcagcag tagtactttt atgtctcgta   1680
atatttttaa tctgtacggc ttgatgataa taggctggag cctcggtggc catgcttctt   1740
gccccttggg cctcccccca gccctcctc cccttcctgc accgtaccc cgtggtctt    1800
tgaataaagt ctgagtgggc ggcaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaatctag                                                          1928
```

```
SEQ ID NO: 25          moltype = RNA  length = 2083
FEATURE                Location/Qualifiers
misc_feature           1..2083
                       note = Synthetic Polynucleotide
source                 1..2083
                       mol_type = other RNA
                       organism = synthetic construct
SEQUENCE: 25
tcaagctttt ggaccctcgt acagaagcta atacgactca ctatagggaa ataagagaga   60
aaagaagagt aagaagaaat ataagagcca ccatggggac agttaataaa cctgtggtgg   120
gggtattgat ggggttcgga attatcacgg gaacgttgcg tataacgaat ccggtcagag   180
catccgtctt gcgatacgat gattttcaca tcgatgaaga caaactggat acaaactccg   240
tatatgagcc ttactaccat tcagatcatg cggagtcttc atgggtaaat cggggagagt   300
cttcgcgaaa agcgtacgat cataactcac cttatatatg gccacgtaat gattatgatg   360
gattttaga gaacgcacac gaacaccatg gggtgtataa cggggccgt ggtatcgtaa   420
gcggggaacg gttaatgcaa cccacacaaa tgtctgcaca ggaggatctt ggggacgata   480
cgggcatcca cgttatccct acgttaaacg gcgatgacag acataaaatt gtaaatgtgg   540
accaacgtca atacggtgac gtgtttaaag gagatcttaa tccaaaaccc caaggccaaa   600
gactcattga ggtgtcagtg gaagaaaatc acccgtttac tttacgcgca cgattcagc   660
ggatttatgg agtccggtac accgagactt ggagctttt gccgtcatta acctgtacgg   720
gagacgcagc gcccgccatc cagcatatat gtttaaaaca tacaacatgc tttcaagacg   780
tggtggtgga tgtggattgc gcggaaaata ctaaagagga tcagttggcc gaaatcagtt   840
accgttttca aggtaagaag gaagcggacc aaccgtggat tgttgtaaac acgagcacac   900
tgtttgatga actcgaatta gaccccccg agattgaacc gggtgtcttg aaagtacttc   960
ggacagaaaa acaatacttg ggtgtgtaca tttggaacat gcgcggctcc gatggtacgt   1020
ctacctacgc cacgtttttg gtcacctgga aggggatga aaaaacaaga aaccctacgc   1080
ccgcagtaac tcctcaacca agaggggctg agtttcatat gtggaattac cactcgcatg   1140
tattttcagt tggtgatacg tttagcttgg caatgcatct tcagtataag atacatgaag   1200
cgccatttga tttgctgtta gagtggttgt atgtccccat cgatcctaca tgtcaaccaa   1260
tgcggttata ttctacgtgt ttgtatcatc ccaacgcacc ccaatgcctc tctcatatga   1320
attccggttg tacatttacc tcgccacatt tagcccagcg tgttgcaagc acagtgtatc   1380
aaaattgtga acattgcagat aactacaccg catattgtgt gggaatatct catatggagc   1440
ctagctttgg tctaatctta cacgacgggg gcaccacgtt aaagtttgta gatacacccg   1500
agagtttgtc gggattatac gtttttgtgg tgtattttaa cgggcatgtt gaagccgtag   1560
catacactgt tgtatccaca gtagatcatt ttgtaaacgc aattgaagag cgtggatttc   1620
cgccaacggc cggtcaagcca ccggcgacta ctaaacccaa ggaaattacc cccgtaaacc   1680
ccggaacgtc accacttcta cgatatgccg catggaccgg agggcttgca gcagtagtac   1740
ttttatgtct cgtaatattt ttaatctgta cggctaaacg aatgagggtt aaagcctata   1800
gggtagacaa gtccccgtat aaccaaagca tgtattacgc tggccttcca gtggacgatt   1860
tcgaggacgc cgaagccgcc gatgccgaag aagagtttgg taacgcgatt ggagggagtc   1920
acggggggttc gagttacacg gtgtatatag ataagacccg gtgatgataa taggctggag   1980
cctcggtggc catgcttctt gccccttggg cctcccccca gccctcctc cccttcctgc   2040
acccgtaccc ccgtggtctt tgaataaagt ctgagtgggc ggc                    2083
```

```
SEQ ID NO: 26          moltype = AA  length = 623
FEATURE                Location/Qualifiers
REGION                 1..623
                       note = Synthetic Polypeptide
source                 1..623
                       mol_type = protein
                       organism = synthetic construct
SEQUENCE: 26
MGTVNKPVVG VLMGFGIITG TLRITNPVRA SVLRYDDFHI DEDKLDTNSV YEPYYHSDHA   60
ESSWVNRGES SRKAYDHNSP YIWPRNDYDG FLENAHEHHG VYNQGRGIDS GERLMQPTQM   120
SAQEDLGDDT GIHVIPTLNG DDRHKIVNVD QRQYGDVFKG DLNPKPQGQR LIEVSVEENH   180
PPTLRAPIQR IYGVRYTETW SFLPSLTCTG DAAPAIQHIC LKHTTCFQDV VVDVDCAENT   240
KEDQLAEISY RFQGKKEADQ PWIVVNTSTL FDELELDPPE IEPGVLKVLR TEKQYLGVYI   300
WNMRGSDGTS TYATFLVTWK GDEKTRNPTP AVTPQPRGAE FHMWNYHSHV FSVGDTFSLA   360
MHLQYKIHEA PFDLLLEWLY VPIDPTCQPM RLYSTCLYHP NAPQCLSHMN SGCTFTSPHL   420
AQRVASTVYQ NCEHADNYTA YCLGISHMEP SFGLILHDGG TTLKFVDTPE SLSGLYFVV   480
YFNGHVEAVA YTVVSTVDHF VNAIEERGPP PTAGQPPATT KPKEITPVNP GTSPLLRYAA   540
WTGGLAAVVL LCLVIFLICT AKRMRVKAYR VDKSPYNQSM YYAGLPVDDF EDAEAADAEE   600
EFGNAIGGSH GGSSYTVYID KTR                                          623
```

```
SEQ ID NO: 27          moltype = RNA  length = 1872
FEATURE                Location/Qualifiers
misc_feature           1..1872
                       note = Synthetic Polynucleotide
source                 1..1872
                       mol_type = other RNA
                       organism = synthetic construct
SEQUENCE: 27
```

-continued

```
atggggacag ttaataaacc tgtggtgggg gtattgatgg ggttcggaat tatcacggga  60
acgttgcgta taacgaatcc ggtcagagca tccgtcttgc gatacgatga ttttcacatc  120
gatgaagaca aactggatac aaactccgta tatgagcctt actaccattc agatcatgcg  180
gagtcttcat gggtaaatcg gggagagtct tcgcgaaaag cgtacgatca taactcacct  240
tatatatggc cacgtaatga ttatgatgga tttttagaga acgcacacga acaccatggg  300
gtgtataatc agggccgtgg tatcgatagc ggggaacggt taatgcaacc cacacaaatg  360
tctgcacagg aggatcttgg ggacgatacg ggcatccacg ttatccctac gttaaacggc  420
gatgacagac ataaaattgt aaatgtggac caacgtcaat acggtgacgt gtttaaagga  480
gatcttaatc caaaacccca aggccaaaga ctcattgagg tgtcagtgga agaaaatcac  540
ccgtttactt tacgcgcacc gattcagcgg atttatggag tccggtacac cgagacttgg  600
agcttttttgc cgtcattaac ctgtacggga gacgcagcgc ccgccatcca gcatatatgt  660
ttaaaacata caacatgctt tcaagacgtg gtggtggatg tggattgcgc ggaaaatact  720
aaagaggatc agttggccga aatcagttac cgttttcaag gtaagaagga agcggaccaa  780
ccgtggattg ttgtaaacac gagcacactg tttgatgaac tcgaattaga cccccccgag  840
attgaaccgg gtgtcttgaa agtacttcgg acagaaaaac aatacttggg tgtgtacatt  900
tggaacatgc gcggctccga tggtacgtct acctacgcca cgttttttggt cacctggaaa  960
ggggatgaaa aaacaagaaa ccctacgccc gcagtaactc ctcaaccaag aggggctgag  1020
tttcatatgt ggaattacca ctcgcatgta ttttcagttg gtgatacgtt tagcttggca  1080
atgcatcttc agtataagat acatgaagcg ccatttgatt tgctgttaga gtggttgtat  1140
gtccccatcg atcctacatg tcaaccaatg cggttatatt ctacgtgttt gtatcatccc  1200
aacgcacccc aatgcctctc tcatatgaat tccggttgta catttacctc gccacattta  1260
gcccagcgtg ttgcaagcac agtgtatcaa aattgtgaac atgcagataa ctacaccgca  1320
tattgtctgg aatatctca tatggagcct agctttggtc taatcttaca cgacgggggc  1380
accacgttaa agtttgtaga tacacccgag agtttgtcgg gattatacgt ttttgtggtg  1440
tattttaacg gcatgttga agccgtagca tacactgttg tatccacagt agatcatttt  1500
gtaaacgcaa ttgaagagcg tggatttccg ccaacgccacc gtcagccacc ggcgactact  1560
aaacccaagg aaattacccc cgtaaacccc ggaacgtcac cacttctacg atatgccgca  1620
tggaccggag ggcttgcagc agtagtactt ttatgtctcg taatattttt aatctgtacg  1680
gctaaacgaa tgagggttaa agcctatagg gtagacaagt ccccgtataa ccaaagcatg  1740
tattacgctg gccttccagt ggacgatttc gaggacgccg aagccgccga tgccgaagaa  1800
gagtttggta acgcgattgg agggagtcac gggggttcga gttacacggt gtatatagat  1860
aagacccggt ga                                                      1872
```

```
SEQ ID NO: 28            moltype = RNA   length = 2144
FEATURE                  Location/Qualifiers
misc_feature             1..2144
                         note = Synthetic Polynucleotide
source                   1..2144
                         mol_type = other RNA
                         organism = synthetic construct
```

```
SEQUENCE: 28
ggggaaataa gagagaaaag aagagtaaga agaaatataa gagccaccat ggggacagtt  60
aataaacctg tggtgggggt attgatgggg ttcggaatta tcacgggaac gttgcgtata  120
acgaatccgg tcagagcatc cgtcttgcga tacgatgatt ttcacatcga tgaagacaaa  180
ctggatacaa actccgtata tgagccttac taccattcag atcatgcgga gtcttcatgg  240
gtaaatcggg agagtcttc gcgaaaagcg tacgatcata actcacctta tatatggcca  300
cgtaatgatt atgatggatt tttagagaac gcacacgaac accatgggg gtataatcag  360
ggccgtggta tcgatagcgg ggaacggtta atgcaaccca cacaaatgtc tgcacaggag  420
gatcttgggg acgatacggg catccacgtt atccctacgt taaacggcga tgacagacat  480
aaaattgtaa atgtggacca acgtcaatac ggtgacgtgt ttaaaggaga tcttaatcca  540
aaaccccaag gccaaagact cattgaggtg tcagtggaag aaaatcaccc gtttactttta  600
cgcgcaccga ttcagcggat ttatggagtc cggtacaccg agacttggag ctttttgccg  660
tcattaacct gtacgggaga cgcagcgccc gccatccagc atatatgttt aaaacataca  720
acatgctttc aagacgtggt ggtggatgtg gattgcgcgg aaaatactaa agaggatcag  780
ttggccgaaa tcagttaccg ttttcaaggt aagaaggaag cggaccaacc gtggattgtt  840
gtaaacacga gcacactgtt tgatgaactc gaattagacc ccccgagat tgaaccgggt  900
gtcttgaaag tacttcggac agaaaaacaa tacttgggtg tgtacatttg gaacatgcgc  960
ggctccgatg gtacgtctac ctacgccacg ttttttggtca cctggaaagg ggatgaaaaa  1020
acaagaaacc ctacgcccgc agtaactcct caaccaagag gggctgagtt tcatatgtg  1080
aattaccact cgcatgtatt ttcagttggt gatacgttta gcttggcaat gcatcttcag  1140
tataagatac atgaagcgcc atttgatttg ctgttagagt ggttgtatgt ccccatcgat  1200
cctacatgtc aaccaatgcg gttatattct acgtgtttgt atcatcccaa cgcacccaa  1260
tgcctctctc atatgaattc cggttgtaca tttacctcgc cacatttagc ccagcgtgtt  1320
gcaagcacag tgtatcaaaa ttgtgaacat gcagataact acaccgcata ttgtctgtta  1380
atatctcata tggagcctag ctttggtcta atcttacacg acgggggcac acgttaaag  1440
tttgtagata cacccgagag tttgtcggga ttatacgttt tgtggtgta ttttaacggg  1500
catgttgaag ccgtagcata cactgttgta tccacagtag atcattttgt aaacgcaatt  1560
gaagagcgtg atttccgcc aacggccggt cagccaccgg cgactactaa acccaaggaa  1620
attaccccg taaacccgg aacgtcacca cttctacgat atgccgcatg gaccggagg  1680
cttgcagcag tagtactttt atgtctcgta atatttttaa tctgtacggc taaacgaatg  1740
agggttaaag cctatagggt agacaagtcc cgtataacc aaagcatgta ttacgctggc  1800
cttccagtgg acgatttcga ggacgccgaa gccgccgatg ccgaagaaga gtttggtaac  1860
gcgattggag ggagtcacgg gggttcgagt tacacggtgt atatagataa gacccggtga  1920
tgataatagg ctggagcctc ggtggccatg cttcttgccc cttgggcctc ccccagccc  1980
ctcctcccct tcctgcaccc gtacccccgt ggtctttgaa taaagtctga gtgggcggca  2040
aaaaaaaaa aaaaaaaaa aaaaaaaaa aaaaaaaaa aaaaaaaaa aaaaaaaaa  2100
aaaaaaaaa aaaaaaaaa aaaaaaaaa aaaaaaaat ctag                      2144
```

```
SEQ ID NO: 29            moltype = RNA   length = 2083
```

-continued

```
FEATURE              Location/Qualifiers
misc_feature         1..2083
                     note = Synthetic Polynucleotide
source               1..2083
                     mol_type = other RNA
                     organism = synthetic construct
SEQUENCE: 29
tcaagctttt ggaccctcgt acagaagcta atacgactca ctatagggaa ataagagaga   60
aaagaagagt aagaagaaat ataagagcca ccatggggac agttaataaa cctgtggtgg  120
gggtattgat ggggttcgga attatcacgg gaacgttgcg tataacgaat ccggtcagag  180
catccgtctt gcgatacgat gattttcaca tcgatgaaga caaactggat acaaactccg  240
tatatgagcc ttactaccat tcagatcatg cggagtcttc atgggtaaat cggggagagt  300
cttcgcgaaa agcgtacgat cataactcac cttatatatg gccacgtaat gattatgatg  360
gatttttaga gaacgcacac gaacaccatg gggtgtataa tcagggccgt ggtatcgata  420
gcggggaacg gttaatgcaa cccacacaaa tgtctgcaca ggaggatctt ggggacgata  480
cgggcatcca cgttatccct acgttaaacg gcgatgacag acataaaatt gtaaatgtgg  540
accaacgtca atacggtgac gtgtttaaag gagatcttaa tccaaaaccc caaggccaaa  600
gactcattga ggtgtcagtg gaagaaaatc acccgttcac tttacgcgca ccgattcagc  660
ggatttatgg agtccggtac accgagactt ggagcttttt gccgtcatta acctgtacgg  720
gagacgcagc gcccgccatc cagcatatat gtttaaaaca tacaacatgc tttcaagacg  780
tggtggtgga tgtggattgc gcggaaaata ctaaagagga tcagttggcc gaaatcagtt  840
accgttttca aggtaagaag gaagcggacc aaccgtggat tgttgtaaac acgagcacac  900
tgtttgatga actcgaatta gacccccccg agattgaacc gggtgtcttg aaagtacttc  960
ggacagaaaa acaatacttg ggtgtgtaca tttggaacat gcgcggctcc gatggtacgt 1020
ctacctacgc cacgttttg gtcacctgga aaggggatga aaaaacaaga aaccctacgc 1080
ccgcagtaac tcctcaacca agaggggctg agtttcatat gtggaattac cactcgcatg 1140
tattttcagt tggtgatacg tttagcttgg caatgcatct tcagtataag atacatgaag 1200
cgccatttga tttgctgtta gagtggttgt atgtccccat cgatcctaca tgtcaaccaa 1260
tgcggttata ttctacgtgt ttgtatcatc ccaacgcacc ccaatgcctc tctcatatga 1320
attccggttg tacatttacc tcgccacatt tagcccagcg tgttgcaagc acagtgtatc 1380
aaaattgtga acatgcagat aactacaccg catattgtct gggaatatct catatggagc 1440
ctagctttgg tctaatctta cacgacgggg gcaccacgtt aaagtttgta gatacacccg 1500
agagtttgtc gggattatac gttttgtgg tgtattttaa cgggcatgtt gaagccgtag 1560
catacactgt tgtatccaca gtagatcatt ttgtaaacga aattgaagag cgtggatttc 1620
cgccaacggc cggtcagcca ccggcgacta ctaaacccaa ggaaattacc cccgtaaacc 1680
ccggaacgtc accacttcta cgatatgccg catggaccgg agggcttgca gcagtagtac 1740
ttttatgtct cgtaatattt ttaatctgta cggctaaacg aatgagggtt aaagcctata 1800
gggtagacaa gtccccgtat aaccaaagca tgtatgcgc tggccttcca gtggacgatt 1860
tcgaggacgc cgaagccgcc gatgccgaag aagagtttgg taacgcgatt ggagggagtc 1920
acggggttc gagttacacg gtgtatatag ataagacccg gtgatgataa taggctggag 1980
cctcggtggc catgcttctt gcccttggg cctcccccca gccctcctc cccttcctgc 2040
acccgtaccc ccgtggtctt tgaataaagt ctgagtgggc ggc               2083
```

```
SEQ ID NO: 30          moltype = AA  length = 623
FEATURE                Location/Qualifiers
REGION                 1..623
                       note = Synthetic Polypeptide
source                 1..623
                       mol_type = protein
                       organism = synthetic construct
SEQUENCE: 30
MGTVNKPVVG VLMGFGIITG TLRITNPVRA SVLRYDDFHI DEDKLDTNSV YEPYYHSDHA   60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAYR VDKSPYNQSM YGAGLPVDDF EDAEAADAEE  600
EFGNAIGGSH GGSSYTVYID KTR                                          623
```

```
SEQ ID NO: 31          moltype = RNA  length = 1872
FEATURE                Location/Qualifiers
misc_feature           1..1872
                       note = Synthetic Polynucleotide
source                 1..1872
                       mol_type = other RNA
                       organism = synthetic construct
SEQUENCE: 31
atggggacag ttaataaacc tgtggtgggg gtattgatgg ggttcggaat tatcacggga   60
acgttgcgta taacgaatcc ggtcagagca tccgtcttgc gatacgatga ttttcacatc  120
gatgaagaca aactggatac aaactccgta tatgagcct tactaccatt cagatcatgg  180
gagtcttcat gggtaaatcg gggagagtct tcgcgaaaag cgtacgatca taactcacct  240
tatatatggc cacgtaatga ttatgatgga ttttagaga cgcacacga acaccatggg  300
gtgtataatc agggccgtgg tatcgatagc ggggaacggt taatgcaacc cacacaaatg  360
tctgcacagg aggatcttgg ggacgatacg ggcatccacg ttatccctac gttaaacggc  420
gatgacgac ataaaattgt aaatgtggac caacgtcaat acggtgacgt gtttaaagga  480
```

```
gatcttaatc caaaacccca aggccaaaga ctcattgagg tgtcagtgga agaaaatcac   540
ccgtttactt tacgcgcacc gattcagcgg atttatggag tccggtacac cgagacttgg   600
agcttttttgc cgtcattaac ctgtacggga gacgcagcgc ccgccatcca gcatatatgt   660
ttaaaacata caacatgctt tcaagacgtg gtggtggatg tggattgcgc ggaaaatact   720
aaagaggatc agttggccga aatcagttac cgtttttcaa gtaagaagga agcggaccaa   780
ccgtggattg ttgtaaacac gagcacactg tttgatgaac tcgaattaga ccccccccgag   840
attgaaccgg gtgtcttgaa agtacttcgg acagaaaaac aatacttggg tgtgtacatt   900
tggaacatgc gcggctccga tggtacgtct acctacgcca cgtttttggt cacctggaaa   960
ggggatgaaa aaacaagaaa ccctacgccc gcagtaactc ctcaaccaag aggggctgaa  1020
tttcatatgt ggaattacca ctcgcatgta ttttcagttg gtgatacgtt tagcttggca  1080
atgcatcttc agtataagat acatgaagcg ccatttgatt tgctgttaga gtggttgtat  1140
gtccccatcg atcctacatg tcaaccaatg cggttatatt ctacgtgttt gtatcatccc  1200
aacgcacccc aatgcctctc tcatatgaat tccggttgta catttacctc gccacattta  1260
gcccagcgtg ttgcaagcac agtgtatcaa aattgtgaac atgcagataa ctacaccgca  1320
tattgtctgg gaatatctca tatggagcct agctttggtc taatcttaca cgacgggggc  1380
accacgttaa agtttgtaga tacacccgag agtttgtcgg gattatacgt ttttgtggtg  1440
tatttttaacg gcatgttga agccgtagca tacactgttg tatccacagt agatcatttt  1500
gtaaacgcaa ttgaagagcg tggatttccg ccaacggccg gtcagccacc ggcgactact  1560
aaacccaagg aaattacccc cgtaaacccc ggaacgtcac cacttctacg atatgccgca  1620
tggaccggag ggcttgcagc agtagtactt ttatgtctcg taatattttt aatctgtacg  1680
gctaaacgaa tgagggttaa agcctatagg gtagacaagt ccccgtataa ccaaagcatg  1740
tatggcgctg gccttccagt ggacgatttc gaggacgccg aagccgccga tgccgaagaa  1800
gagtttggta acgcgattgg agggagtcac gggggttcga gttacacggt gtatatagat  1860
aagacccggt ga                                                      1872
```

```
SEQ ID NO: 32          moltype = RNA  length = 2144
FEATURE                Location/Qualifiers
misc_feature           1..2144
                       note = Synthetic Polynucleotide
source                 1..2144
                       mol_type = other RNA
                       organism = synthetic construct
SEQUENCE: 32
gggggaaataa gagagaaaag aagagtaaga agaaatataa gagccaccat ggggacagtt   60
aataaacctg tggtgggggt attgatgggg ttcggaatta tcacgggaac gttgcgtata  120
acgaatccgg tcagagcatc cgtcttgcga tacgatgatt ttcacatcga tgaagacaaa  180
ctggatacaa actccgtata tgagccttac taccattcag atcatgcgga gtcttcatgg  240
gtaaatcggg gagagtcttc gcgaaaagcg tacgatcata actcacctta tatatggcca  300
cgtaatgatt atgatggatt tttagagaac gcacacgaac accatgggt gtataatcag  360
ggccgtggta tcgatagcgg ggaacggtta atgcaaccca cacaaatgtc tgcacaggag  420
gatcttgggg acgatacggg catccacgtt atccctacgt taaacggcga tgacagacat  480
aaaattgtaa atgtggacca acgtcaatac ggtgacgtgt ttaaaggaga tcttaatcca  540
aaacccaag gccaaagact cattgaggtg tcagtggaa aaatcaccc gtttacttta  600
cgcgcaccga ttcagcggat ttatggagtc cggtacaccg agacttggag cttttttgccc  660
tcattaacct gtacgggaga cgcagcgccc gccatccagc atatatgttt aaaacataca  720
acatgctttc aagacgtggt ggtggatgtg gattgcgcgg aaaatactaa agaggatcag  780
ttggccgaaa tcagttaccg tttttcaaggt aagaaggaa gcggaccaac gtggattgtt  840
gtaaacacga gcacactgtt tgatgaactc gaattagacc ccccgagat tgaacccggg  900
gtcttgaaag tacttcggac agaaaaacaa tacttgggtg tgtacatttg gaacatgcgc  960
ggctccgatg gtacgtctac ctacgccacg ttttttggtca cctggaaagg ggatgaaaaa 1020
acaagaaacc ctacgcccgc agtaactcct caaccaagag gggctgagtt tcatatgtgg 1080
aattaccact cgcatgtatt ttcagttggt gatacgttta gcttggcaat gcatcttcag 1140
tataagatac atgaagcgcc atttgatttg ctgttagagt ggttgtatgt ccccatcgat 1200
cctacatgtc aaccaatgcg gttatattct acgtgtttgt atcatcccaa cgcacccaa  1260
tgcctctctc atatgaattc cggttgtaca tttacctcgc cacatttagc ccagcgtgtt  1320
gcaagcacag tgtatcaaaa ttgtgaacat gcagataact acaccgcata ttgtctggga  1380
atatctcata tggagcctag ctttggtcta atcttacacg acgggggcac cacgttaaag  1440
tttgtagata cacccgagag tttgtcggga ttatacgttt tgtggtgta ttttaacggg  1500
catgttgaag ccgtagcata cactgttgta tccacagtag atcattttgt aaacgcaatt  1560
gaagagcgtg gatttccgcc aacggccggt cagccaccgg cgactactaa acccaaggaa  1620
attacccccg taaaccccgg aacgtcacca cttctacgat atgccgcatg gaccggaggg  1680
cttgcagcag tagtactttt atgtctcgta tatttttaa tctgtacggc taaacgaatg  1740
agggttaaag cctatagggt agacaagtcc cgtataacc aaagcatgta tggcgctggc  1800
cttccagtgg acgatttcga ggacgccgaa gccgccgatg ccgaagaaga gtttggtaac  1860
gcgattggag gggagtcacgg gggttcgagt tacacggtgt atatagataa gacccggtga  1920
tgataatagg ctggagcctc ggtggccatg cttcttgccc cttgggcctc ccccagccc  1980
ctcctcccct tcctgcaccc gtaccccgt ggtctttgaa taaagtctga gtgggcggca  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaat ctag                   2144
```

```
SEQ ID NO: 33          moltype = RNA  length = 1933
FEATURE                Location/Qualifiers
misc_feature           1..1933
                       note = Synthetic Polynucleotide
source                 1..1933
                       mol_type = other RNA
                       organism = synthetic construct
SEQUENCE: 33
tcaagctttt ggaccctcgt acagaagcta atacgactca ctatagggaa ataagagaga   60
```

```
aaagaagagt aagaagaaat ataagagcca ccatggggac agttaataaa cctgtggtgg    120
gggtattgat ggggttcgga attatcacgg gaacgttgcg tataacgaat ccggtcagag    180
catccgtctt gcgatacgat gattttcaca tcgatgaaga caaactggat acaaactccg    240
tatatgagcc ttactaccat tcagatcatg cggagtcttc atgggtaaat cggggagagt    300
cttcgcgaaa agcgtacgat cataactcac cttatatatg gccacgtaat gattatgatg    360
gattttttaga gaacgcacac gaacaccatg gggtgtataa tcagggccgt ggtatcgata    420
gcggggaacg gttaatgcaa cccacacaaa tgtctgcaca ggaggatctt ggggacgata    480
cgggcatcca cgttatccct acgttaaacg gcgatgacag acataaaatt gtaaatgtgg    540
accaacgtca atacggtgac gtgtttaaag gagatctcaa tccaaaaccc caaggccaaa    600
gactcattga ggtgtcagtg gaagaaaatc acccgtttac tttacgcgca ccgattcagc    660
ggatttatgg agtccggtac accgagactt ggagcttttt gccgtcatta acctgtacgg    720
gagacgcagc gcccgccatc cagcatatat gtttaaaaca tacaacatgc tttcaagacg    780
tggtggtgga tgtggattgc gcggaaaata ctaaagagga tcagttggcc gaaatcagtt    840
accgttttca aggtaagaag gaagcggacc aaccgtttac tgttgtaaac acgagcacac    900
tgtttgatga actcgaatta gacccccccg agattgaacc gggtgtcttg aaagtacttc    960
ggacagaaaa acaatacttg ggtgtgtaca tttggaacat gcgcggctcc gatggtacgt   1020
ctacctacgc cacgttttgg gtcacctgga aaggggatga aaaaacaaga aaccctacgc   1080
ccgcagtaac tcctcaacca agagggggctg agtttcatat ggtggaattac cactcgcatg   1140
tattttcagt tggtgatacg tttagcttgg caatgcatct tcagtataag atacatgaag   1200
cgccatttga tttgctgtta gagtggttgt atgtccccat cgatcctaca tgtcaaccaa   1260
tgcggttata ttctacgtgt ttgtatcatc ccaacgcacc ccaatgcctc tctcatatga   1320
attccggttg tacatttacc tcgccacatt tagcccagcg tgttgcaagc acagtgtatc   1380
aaaattgtga acatgcagat aactacaccg catattgtct gggaatatct catatggagc   1440
ctagctttgg tctaatctta cacgacgggg gcaccacgtt aaagtttgta gatacacccg   1500
agagtttgtc gggattatac gttttttgtgg tgtattttaa cgggcatgtt gaagccgtag   1560
catacactgt tgtatccaca gtagatcatt ttgtaaacgc aattgaagag cgtggatttc   1620
cgccaacggc cggtcagcca ccggcgacta ctaaacccaa ggaaattacc cccgtaaacc   1680
ccggaacgtc accacttcta cgatatgccg catggaccgg agggcttgca gcagtagtac   1740
ttttatgtct cgtaatattt ttaatctgta cggctaaacg aatgagggtt aaagcctata   1800
gggtagacaa gtgatgataa taggctggag cctcggtggc catgcttctt gcccccttggg   1860
cctcccccca gcccctcctc cccttcctgc acccgtaccc ccgtggtctt tgaataaagt   1920
ctgagtgggc ggc                                                        1933
```

```
SEQ ID NO: 34              moltype = AA  length = 573
FEATURE                    Location/Qualifiers
REGION                     1..573
                           note = Synthetic Polypeptide
source                     1..573
                           mol_type = protein
                           organism = synthetic construct
SEQUENCE: 34
MGTVNKPVVG VLMGFGIITG TLRITNPVRA SVLRYDDFHI DEDKLDTNSV YEPYYHSDHA    60
ESSWVNRGES SRKAYDHNSP YIWPRNDYDG FLENAHEHHG VYNQGRGIDS GERLMQPTQM   120
SAQEDLGDDT GIHVIPTLNG DDRHKIVNVD QRQYGDVFKG DLNPKPQGQR LIEVSVEENH   180
PPTLRAPIQR IYGVRYTETW SFLPSLTCTG DAAPAIQHIC LKHTTCFQDV VVDVDCAENT   240
KEDQLAEISY RFQGKKEADQ PWIVVNTSTL FDELELDPPE IEPGVLKVLR TEKQYLGVYI   300
WNMRGSDGTS TYATFLVTWK GDEKTRNPTP AVTPQPRGAE FHMWNYHSHV FSVGDTFSLA   360
MHLQYKIHEA PFDLLLEWLY VPIDPTCQPM RLYSTCLYHP NAPQCLSHMN SGCTFTSPHL   420
AQRVASTVYQ NCEHADNYTA YCLGISHMEP SFGLILHDGG TTLKFVDTPE SLSGLYVFVV   480
YFNGHVEAVA YTVVSTVDHF VNAIEERGFP PTAGQPPATT KPKEITPVNP GTSPLLRYAA   540
WTGGLAAVVL LCLVIFLICT AKRMRVKAYR VDK                                 573
```

```
SEQ ID NO: 35              moltype = RNA  length = 1722
FEATURE                    Location/Qualifiers
misc_feature               1..1722
                           note = Synthetic Polynucleotide
source                     1..1722
                           mol_type = other RNA
                           organism = synthetic construct
SEQUENCE: 35
atggggacag ttaataaacc tgtggtgggg gtattgatgg ggttcggaat tatcacggga    60
acgttgcgta taacgaatcc ggtcagagca tccgtcttgc gatacgatga ttttcacatc   120
gatgaagaca aactggatac aaactccgta tatgagcctt actaccattc agatcatgcg   180
gagtcttcat gggtaaatcg gggagagtct tcgcgaaaag cgtacgatca taactcacct   240
tatatatggc cacgtaatga ttatgatgga ttttttagaga acgcacacga acaccatggg   300
gtgtataatc agggccgtgg tatcgatagc ggggaacggt taatgcaacc cacacaaatg   360
tctgcacagg aggatcttgg ggacgatacg gcatccacg ttatccctac gttaaacggc   420
gatgacagac ataaaattgt aaatgtggac caacgtcaat acggtgacgt gtttaaagga   480
gatcttaatc caaaacccca aggccaaaga ctcattgagg tgtcagtgga agaaaatcac   540
ccgtttactt tacgcgcacc gattcagcgg atttatgg agtccggtacac cgagacttgg   600
agcttttgc cgtcattaac ctgtacggga cgcagcgc cgccatcca gcatatatgt   660
ttaaaacata acatgctt tcaagacgtg gtggtggatg tggattgcgc ggaaaatact   720
aaagaggatc agttggccga aatcagttac cgttttcaag gtaagaagga gcggaccaa   780
ccgtttgattg ttgtaaacac gagcacactg tttgatgaac tcgaattaga cccccccgag   840
attgaaccgg gtgtcttgaa agtacttcgg acagaaaaac aatacttggg tgtgtacatt   900
tggaacatgc gcggctccga tggtacgtct acctacgcca cgttttggt cacctggaaa   960
ggggatgaaa aaacaagaaa ccctacgccc gcagtaactc ctcaaccaag aggggctgag  1020
tttcatatgg gaattacca ctcgcatgta ttttcagttg gtgatacgtt tagcttggca  1080
atgcatcttc agtataagat acatgaagcg ccatttgatt tgctgttaga gtggttgtat  1140
```

```
gtccccatcg atcctacatg tcaaccaatg cggttatatt ctacgtgttt gtatcatccc   1200
aacgcacccc aatgcctctc tcatatgaat tccggttgta catttacctc gccacattta   1260
gcccagcgtg ttgcaagcac agtgtatcaa aattgtgaac atgcagataa ctacaccgca   1320
tattgtctgg gaatatctca tatggagcct agctttggtc taatcttaca cgacgggggc   1380
accagcgttaa agtttgtaga tacacccgag agtttgtcgg gattatacgt ttttgtggtg   1440
tattttaacg ggcatgttga agccgtagca tacactgttg tatccacagt agatcatttt   1500
gtaaacgcaa ttgaagagcg tggatttccg ccaacggccg gtcagccacc ggcgactact   1560
aaacccaagg aaaattacccc cgtaaacccc ggaacgtcac cacttctacg atatgccgca   1620
tggaccggag ggcttgcagc agtagtactt ttatgtctcg taatattttt aatctgtacg   1680
gctaaacgaa tgagggttaa agcctatagg gtagacaagt ga                      1722
```

```
SEQ ID NO: 36           moltype = RNA   length = 1994
FEATURE                 Location/Qualifiers
misc_feature            1..1994
                        note = Synthetic Polynucleotide
source                  1..1994
                        mol_type = other RNA
                        organism = synthetic construct
SEQUENCE: 36
ggggaaataa gagagaaaag aagagtaaga agaaatataa gagccaccat ggggacagtt   60
aataaacctg tggtgggggt attgatgggg ttcggaatta tcacgggaac gttgcgtata   120
acgaatccgg tcagagcatc cgtcttgcga tacgatgatt ttcacatcga tgaagacaaa   180
ctggatacaa actccgtata tgagccttac taccattcag atcatgcgga gtcttcatgg   240
gtaaatcggg gagagtcttc gcgaaaagcg tacgatcata actcacctta tatatggcca   300
cgtaatgatt atgatggatt tttagagaac gcacacgaac accatggggt gtataatcag   360
ggccgtggta tcgatagcgg ggaacggtta atgcaaccca cacaaatgtc tgcacaggag   420
gatcttgggg acgatacggg catccacgtt atccctacgt taaacggcga tgacagacat   480
aaaattgtaa atgtggacca acgtcaatac ggtgacgtgt ttaaaggaga tcttaatcca   540
aaaccccaag gccaaagact cattgaggtg tcagtggaag aaaatcaccc gtttacttta   600
cgcgcaccga ttcagcggat ttatggagtc cggtacaccg agacttggag cttttttgccg   660
tcattaacct gtacgggaga cgcagcgccc gccatccagc atatatgttt aaaacataca   720
acatgctttc aagacgtggt ggtggatgtg gattgcgcgg aaaatactaa agaggatcag   780
ttggccgaaa tcagttaccg ttttcaaggt aagaaggaag cggaccaacc gtggattgtt   840
gtaaacacga gcacactgtt tgatgaactc gaattagacc ccccgagat tgaaccgggt   900
gtcttgaaag tacttcggac agaaaaacaa tacttgggtg tgtacatttg gaacatgcgc   960
ggctccgatg gtacgtctac ctacgccacg ttttttggtca cctggaaagg ggatgaaaaa   1020
acaagaaacc ctacgcccgc agtaactcct caaccaagag gggctgagtt tcatatgtgg   1080
aattaccact cgcatgtatt ttcagttggt gatacgttta gcttggcaat gcatcttcag   1140
tataagatac atgaagcgcc atttgatttg ctgttagagt ggttgtatgt ccccatcgat   1200
cctacatgtc aaccaatgcg gttatattct acgtgtttgt atcatcccaa cgcaccccaa   1260
tgcctctctc atatgaattc cggttgtaca tttacctcgc cacatttagc ccagcgtgtt   1320
gcaagcacag tgtatcaaaa ttgtgaacat gcagataact acaccgcata ttgtctggga   1380
atatctcata tggagcctag ctttggtcta atcttacacg acgggggcac cagcgttaaag   1440
tttgtagata cacccgagag tttgtcggga ttatacgttt ttgtggtgta ttttaacggg   1500
catgttgaag ccgtagcata cactgttgta tccacagtag atcattttgt aaacgcaatt   1560
gaagagcgtg gatttccgcc aacggccggt cagccaccgg cgactactaa acccaaggaa   1620
attaccccg taaaccccgg aacgtcacca cttctacgat atgccgcatg gaccggaggg   1680
cttgcagcag tagtactttt atgtctcgta atatttttaa tctgtacggc taaacgaatg   1740
agggttaaag cctatagggt agacaagtga tgataatagg ctggagcctc ggtggccatg   1800
cttcttgccc cttgggcctc cccccagccc ctcctcccct tcctgcaccc gtaccccgt    1860
ggtctttgaa taaagtctga gtgggcggca aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaat ctag                                                     1994
```

```
SEQ ID NO: 37           moltype = RNA   length = 1933
FEATURE                 Location/Qualifiers
misc_feature            1..1933
                        note = Synthetic Polynucleotide
source                  1..1933
                        mol_type = other RNA
                        organism = synthetic construct
SEQUENCE: 37
tcaagctttt ggaccctcgt acagaagcta atacgactca ctatagggaa ataagagaga   60
aaagaagagt aagaagaaat ataagagcca ccatgggggac agttaataaa cctgtggtgg   120
gggtattgat ggggttcgga attatcacgg gaacgttgcg tataacgaat ccggtcagag   180
catccgtctt gcgatacgat gattttcaca tcgatgaaga caaactggat acaaactccg   240
tatatgagcc ttactaccat tcagatcatg cggagtcttc atgggtaaat cggggagagt   300
cttcgcgaaa agcgtacgat cataactcac cttatatatg gccacgtaat gattatgatg   360
gatttttaga gaacgcacac gaacaccatg gggtgtataa tcagggccgt ggtatcgata   420
gcggggaacg gttaatgcaa cccacacaaa tgtctgcaca ggaggatctt ggggacgata   480
cgggcatcca cgttatccct acgttaaacg gcgatgacag acataaaatt gtaaatgtgg   540
accaacgtca atacggtgac gtgtttaaag gagatcttaa tccaaaaccc caaggccaaa   600
gactcattga ggtgtcagtg gaagaaaatc accgtttac tttacgcgca ccgattcagc   660
ggatttatgg agtccggtac accgagactt ggagcttttt gccgtcatta acctgtacgg   720
gagacgcagc gcccgccatc cagcatatat gtttaaaaca tacaacatgc tttcaagacg   780
tggtggtgga tgtggattgc gcggaaaata ctaaagagga tcagttggcc gaaatcagtt   840
accgttttca aggtaagaag gaagcggacc aaccgtggat tgttgtaaac acgagcacac   900
tgtttgatga actcgaatta gacccccccg agattgaacc gggtgtcttg aaagtacttc   960
ggacagaaaa acaatacttg ggtgtgtaca tttggaacat gcgcggctcc gatggtacgt   1020
```

-continued

```
ctacctacgc cacgttttg gtcacctgga aagggggatga aaaaacaaga aaccctacgc   1080
ccgcagtaac tcctcaacca agagggggctg agtttcatat gtggaattac cactcgcatg   1140
tatttcagt tggtgatacg tttagcttgg caatgcatct tcagtataag atacatgaag   1200
cgccatttga tttgctgtta gagtggttgt atgtccccat cgatcctaca tgtcaaccaa   1260
tgcggttata ttctacgtgt ttgtatcatc ccaacgcacc ccaatgcctc tctcatatga   1320
attccggttg tacatttacc tcgccacatt tagcccagcg tgttgcaagc acagtgtatc   1380
aaaattgtga acatgcagat aactacaccg catattgtct gggaatatct catatggagc   1440
ctagctttgg tctaatctta cacgacgggg gcaccacgtt aaagtttgta gatacacccg   1500
agagtttgtc gggattatac gttttgtgg tgtattttaa cgggcatgtt gaagccgtag   1560
catacactgt tgtatccaca gtagatcatt ttgtaaacgc aattgaagag cgtggatttc   1620
cgccaacggc cggtcagcca ccggcgacta ctaaacccaa ggaaattacc cccgtaaacc   1680
ccggaacgtc accacttcta cgatatgccg catggaccgg agggcttgca gcagtagtac   1740
ttttatgtct cgtaatattt ttaatctgta cggctaaacg aatgagggtt aaagccgcca   1800
gggtagacaa gtgatgataa taggctggag cctcggtggc catgcttctt gcccctttggg   1860
cctcccccca gcccctcctc cccttcctgc acccgtaccc ccgtggtctt tgaataaagt   1920
ctgagtgggc ggc                                                      1933
```

```
SEQ ID NO: 38            moltype = AA   length = 573
FEATURE                  Location/Qualifiers
REGION                   1..573
                         note = Synthetic Polypeptide
source                   1..573
                         mol_type = protein
                         organism = synthetic construct
SEQUENCE: 38
MGTVNKPVVG VLMGFGIITG TLRITNPVRA SVLRYDDFHI DEDKLDTNSV YEPYYHSDHA   60
ESSWVNRGES SRKAYDHNSP YIWPRNDYDG FLENAHEHHG VYNQGRGIDS GERLMQPTQM   120
SAQEDLGDDT GIHVIPTLNG DDRHKIVNVD QRQYGDVFKG DLNPKPQGQR LIEVSVEENH   180
PFTLRAPIQR IYGVRYTETW SFLPSLTCTG DAAPAIQHIC LKHTTCFQDV VVDVDCAENT   240
KEDQLAEISY RFQGKKEADQ PWIVVNTSTL FDELELDPPE IEPGVLKVLR TEKQYLGVYI   300
WNMRGSDGTS TYATFLVTWK GDEKTRNPTP AVTPQPRGAE FHMWNYHSHV FSVGDTFSLA   360
MHLQYKIHEA PFDLLLEWLY VPIDPTCQPM RLYSTCLYHP NAPQCLSHMN SGCTFTSPHL   420
AQRVASTVYQ NCEHADNYTA YCLGISHMEP SFGLILHDGG TTLKFVDTPE SLSGLYVFVV   480
YFNGHVEAVA YTVVSTVDHF VNAIEERGFP PTAGQPPATT KPKEITPVNP GTSPLLRYAA   540
WTGGLAAVVL LCLVIFLICT AKRMRVKAAR VDK                                573
```

```
SEQ ID NO: 39            moltype = RNA   length = 1722
FEATURE                  Location/Qualifiers
misc_feature             1..1722
                         note = Synthetic Polynucleotide
source                   1..1722
                         mol_type = other RNA
                         organism = synthetic construct
SEQUENCE: 39
atggggacag ttaataaacc tgtggtgggg gtattgatgg ggttcggaat tatcacggga   60
acgttgcgta taacgaatcc ggtcagagca tccgtcttgc gatacgatga ttttcacatc   120
gatgaagaca aactggatac aaactccgta tatgagcctt actaccattc agatcatgcg   180
gagtcttcat gggtaaatcg gggagagtct tcgcgaaaag cgtacgatca taactcacct   240
tatatatggc cacgtaatga ttatgatgga tttttagaga cgcacacga acaccatggg   300
gtgtataatc agggccgtgg tatcgatagc ggggaacggt taatgcaacc cacacaaatg   360
tctgcacagg aggatcttgg ggacgatacg ggcatccacg ttatccctac gttaaacgga   420
gatgacagac ataaaattgt aaatgtggac caacgtcaat acggtgacgt gtttaaagga   480
gatcttaatc caaaacccca aggccaaaga ctcattgagg tgtcagtgga agaaaatcac   540
ccgtttactt tacgcgcacc gattcagcgg atttatggag tccggtacac cgagacttgg   600
agcttttgc cgtcattaac ctgtacggga gacgcagcgc ccgccatcca gcatatatgt   660
ttaaaacata caacatgctt tcaagacgtg gtggtggatg tggattgcgc ggaaaatact   720
aaagaggatc agttggccga aatcagttac cgttttcaag gtaagaagga agcggaccaa   780
ccgtggattg ttgtaaacac gagcacactg tttgatgaac tcgaattaga cccccccgag   840
attgaaccgg gtgtcttgaa agtacttcgg acagaaaaac aatacttggg tgtgtacatt   900
tggaacatgc gcggctccga tggtacgtct acctacgcca cgtttttggt cacctggaaa   960
ggggatgaaa aaacaagaaa ccctacgccc gcagtaactc ctcaaccaag aggggctgag   1020
tttcatatgt ggaattacca ctcgcatgta ttttcagttg gtgatacgtt tagcttggca   1080
atgcatcttc agtataagat acatgaagcg ccatttgatt tgctgttaga gtggttgtat   1140
gtccccatcg atcctacatg tcaaccaatg cggttatatt ctacgtgttt tgtatcatcc   1200
aacgcacccc aatgcctctc tcatatgaat tccggttgta catttacctc gccacattta   1260
gcccagcgtg ttgcaagcac agtgtatcaa aattgtgaac atgcagataa ctacaccgca   1320
tattgtctgg gaatatctca tatggagcct agctttggtc taatcttaca cgacggggggc   1380
accacgttaa agtttgtaga tacacccgag agtttgtcgg gattatacgt ttttgtggtg   1440
tatttttaacg ggcatgttga agccgtagca tacactgttg tatccacagt agatcatttt   1500
gtaaacgcaa ttgaagagcg tggatttccg ccaacggccg tcagccacc ggcgactact   1560
aaacccaagg aaattacccc cgtaaacccc ggaacgtcac cacttctacg atatgccgca   1620
tggaccggag ggcttgcagc agtagtactt ttatgtctcg taatattttt aatctgtacg   1680
gctaaacgaa tgagggttaa agccgccagg gtagacaagt ga                      1722
```

```
SEQ ID NO: 40            moltype = RNA   length = 1994
FEATURE                  Location/Qualifiers
misc_feature             1..1994
                         note = Synthetic Polynucleotide
source                   1..1994
```

-continued

```
                              mol_type = other RNA
                              organism = synthetic construct
SEQUENCE: 40
ggggaaataa gagagaaaag aagagtaaga agaaatataa gagccaccat ggggacagtt    60
aataaacctg tggtgggggt attgatgggg ttcggaatta tcacgggaac gttgcgtata   120
acgaatccgg tcagagcatc cgtcttgcga tacgatgatt ttcacatcga tgaagacaaa   180
ctggatacaa actccgtata tgagccttac taccattcag atcatgcgga gtcttcatgg   240
gtaaatcggg gagagtcttc gcgaaaagcg tacgatcata actcacctta tatatggcca   300
cgtaatgatt atgatggatt tttagagaac gcacacgaac accatgggg gtataatcag    360
ggccgtggta tcgatagcgg ggaacggtta atgcaaccca cacaaatgtc tgcacaggag   420
gatcttgggg acgatacggg catccacgtt atccctacgt taaacggcga tgacagacat   480
aaaattgtaa atgtggacca acgtcaatac ggtgacgtgt ttaaaggaga tcttaatcca   540
aaaccccaag gccaaagact cattgaggtg tcagtggaag aaaatcaccc gtttacttta   600
cgcgcaccga ttcagcggat ttatggagtc cggtacaccg agacttggag ctttttgccg   660
tcattaacct gtacgggaga cgcagcgccc gccatccagc atatatgttt aaaacataca   720
acatgctttc aagacgtggt ggtggatgtg gattgcgcgg aaaatactaa agaggatcag   780
ttggccgaaa tcagttaccg tttttcaaggt aagaaggaag cggaccaacc gtggattgtt   840
gtaaacacga gcacactgtt tgatgaactc gaattagacc cccccgagat tgaaccgggt   900
gtcttgaaag tacttcggac agaaaaacaa tacttgggtg tgtacatttg gaacatgcgc   960
ggctccgatg gtacgtctac ctacgccacg ttttttggtca cctggaaagg ggatgaaaaa  1020
acaagaaacc ctacgcccgc agtaactcct caaccaagag gggctgagtt tcatatgtgg  1080
aattaccact cgcatgtatt ttcagttggt gatacgttta gcttggcaat gcatcttcag  1140
tataagatac atgaagcgcc atttgatttg ctgttagagt ggttgtatgt ccccatcgat  1200
cctacatgtc aaccaatgcg gttatattct acgtgtttgt atcatcccaa cgcaccccaa  1260
tgcctctctc atatgaattc cggttgtaca tttacctcgc cacatttagc ccagcgtgtt  1320
gcaagcacag tgtatcaaaa ttgtgaacat gcagataact acaccgcata ttgtctggga  1380
atatctcata tggagcctag ctttggtcta atcttacacg acggggggcac cacgttaaag  1440
tttgtagata cacccgagag tttgtcggga ttatacgttt ttgtggtgta ttttaacggg  1500
catgttgaag ccgtagcata cactgttgta tccacagtag atcatttgt aaacgcaatt   1560
gaagagcgtg gatttccgcc aacggccggt cagccaccgg cgactactaa acccaaggaa  1620
attacccccg taaaccccgg aacgtcacca cttctacgat atgccgcatg gaccggaggg  1680
cttgcagcag tagtacttttt atgtctcgta atattttaa tctgtacggc taaacgaatg   1740
agggttaaag ccgccagggt agacaagtga tgataatagg ctggagcctc ggtggccatg  1800
cttcttgccc cttgggcctc cccccagccc ctcctcccct tcctgcaccc gtaccccgt   1860
ggtctttgaa taaagtctga gtgggcggca aaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaat ctag                                                     1994

SEQ ID NO: 41            moltype = DNA   length = 2050
FEATURE                  Location/Qualifiers
misc_feature             1..2050
                         note = Synthetic Polynucleotide
source                   1..2050
                         mol_type = other DNA
                         organism = synthetic construct
SEQUENCE: 41
tcaagctttt ggaccctcgt acagaagcta atacgactca ctataggaa ataagagaga     60
aaagaagagt aagaagaaat ataagagcca ccatggagac tcccgctcag ctactgttcc   120
tcctgctcct ttggctgcct gatactacag gctctgtttt gcggtacgac gactttcaca   180
tcgatgagga caagctcgac actaatagcg tgtatgagcc ctactaccat tcagatcacg   240
ccgagtcctc ttgggtgaac aggggtgaaa gttctaggaa agcctatgat cacaacagcc   300
cttatatttg gccacggaat gattacgacg gatttctcga aaatgcccac gagcatcacg   360
gagtgtacaa ccagggccgt ggaatcgact ctggggagag attgatgcaa cctacacaga   420
tgagcgccca ggaagatctc ggggatgata caggaattca cgttatccct acattaaacg   480
gagatgaccg ccacaaaatc gtcaatgtcg atcaaagaca gtatgggagt gtgttcaaag   540
gcgatctcaa ccctaagccg cagggccaga gactcattga ggtgtctgtc gaagagaacc   600
accctttcac tctgcgcgct cccattcaga gaatctatgg agttcgctat acggagactt   660
ggtcattcct tccttccctg acatgcaccg gagacgccgc ccctgccatt cagcacatat   720
gcctgaaaca taccacctgt ttccaggatg tggtggttga tgttgattgt gctgaaaata   780
ccaaggaaga ccaactggcc gagattagtt accggttcca agggaaaaag gaagccgacc   840
agccatggat tgtggttaat acaagcactc tgttcgatga gctcgagctg gatcccccg    900
agatagaacc cggagttctg aaagtgctcc ggacagaaaa acaatatctg ggagtctaca   960
tatggaacat gcgcggttcc gatgggacct ccacttatgc aacctttctc gtcacgtgga  1020
agggagatga gaaactagg aatcccacac cgctgtcacc accacagcca agggggctg    1080
agttccatat gtggaactat catagtcacg tgtttagtgg cggagatacg tttttcattgg  1140
ctatgcatct ccagtacaag attcatgagg ctcccttcga tctgttgctt gagtggttgt  1200
acgtcccgat tgacccgacc tgccagccca tgcgactgta cagcacctgt ctctaccatc  1260
caaacgctcc gcaatgtctg agccacatga actctgggtg tactttcacc agtccccacc  1320
tcgcccagcg ggtggcctct actgtttacc agaactgga gcacgccgac aactacaccg  1380
catactgcct cggtatttct cacatggaac cctccttcgg actcatcctg cacgatgggg  1440
gcactaccct gaagttcgtt gatacgccag aatctctgtc tgggctctat gtttttcgtgg  1500
tctacttcaa tggccatgtc gaggccgtgg cctatactgt cgtttctacc gtggatcatt   1560
ttgtgaacgc catcgaagaa cggggattcc ccctacggc aggccagccg cctgcaacca  1620
ccaagcccaa ggaaataaca ccagtgaacc ctggcacctc acctcccta agatatgccg  1680
cgtggacagg gggactggcg gcagtggtgc tcctctgtct cgtgatcttt ctgatcgtta  1740
cagccaagag gatgagggtc aaggcttata gagtggacaa gtcccctac aatcagtcaa   1800
tgtactacgc cggccttccc gttgatgatt ttgaggattc cgagtccaca gatactgagg   1860
aagagttcgg taacgctata ggcggctctc acggggttc aagctacacg gtttacattg    1920
acaagacacg ctgataatag gctggagcct cggtggccat gcttcttgcc ccttgggcct  1980
```

-continued

```
cccccagcc cctcctcccc ttcctgcacc cgtaccccg tggtctttga ataaagtctg   2040
agtgggcggc                                                        2050

SEQ ID NO: 42          moltype = AA  length = 354
FEATURE                Location/Qualifiers
REGION                 1..354
                       note = Synthetic Polypeptide
source                 1..354
                       mol_type = protein
                       organism = synthetic construct
SEQUENCE: 42
MFLIQCLISA VIFYIQVTNA LIFKGDHVSL QVNSSLTSIL IPMQNDNYTE IKGQLVFIGE   60
QLPTGTNYSG TLELLYADTV AFCFRSVQVI RYDGCPRIRT SAFISCRYKH SWHYGNSTDR   120
ISTEPDAGVM LKITKPGIND AGVYVLLVRL DHSRSTDGFI LGVNVYTAGS HHNIHGVIYT   180
SPSLQNGYST RALFQQARLC DLPATPKGSG TSLFQHMLDL RAGKSLEDNP WLHEDVVTTE   240
TKSVVKEGIE NHVYPTDMST LPEKSLNDPP ENLLIIIPIV ASVMILTAMV IVIVISVKRR   300
RIKKHPIYRP NTKTRRGIQN ATPESDVMLE AAIAQLATIR EESPPHSVVN PFVK          354

SEQ ID NO: 43          moltype = RNA  length = 1065
FEATURE                Location/Qualifiers
misc_feature           1..1065
                       note = Synthetic Polynucleotide
source                 1..1065
                       mol_type = other RNA
                       organism = synthetic construct
SEQUENCE: 43
atgtttttaa tccaatgttt gatatcggcc gttatatttt acatacaagt gaccaacgct   60
ttgatcttca agggcgacca cgtgagcttg caagttaaca gcagtctcac gtctatcctt   120
attcccatgc aaaatgataa ttatacagag ataaaaggac agcttgtctt tattggagag   180
caactaccta ccgggacaaa ctatagcgga acactggtac tgttatacgc ggatacggtg   240
gcgtttttgtt tccggtcagt acaagtaata agatacgacg gatgtccccg gattagaacg   300
agcgctttta tttcgtgtag gtacaaacat tcgtggcatt atggtaactc aacggatcgg   360
atatcaacag agccggatgc tggtgtaatg ttgaaaatta ccaaaccggg aataaatgat   420
gctggtgtgt atgtacttct tgttcggtta gaccatagca gatccaccga tggtttcatt   480
cttggtgtaa atgtatatac agcgggctcg catcacaaca ttcacggggt tatctacact   540
tctccatctc tacagaatgg atattctaca agagcccttt ttcaacaagc tcgtttgtgt   600
gatttacccg cgacacccaa agggtccggt acctccctgt ttcaacatat gcttgatctt   660
cgtgccggta aatcgttaga ggataaccct tggttacatg aggacgttgt tacgacagaa   720
actaagtccg ttgttaagga ggggatagaa aatcacgtat atccaacgga tatgtccacg   780
ttacccgaaa agtcccttaa tgatcctcca gaaaatctac ttataattat tcctatagta   840
gcgtctgtca tgatcctcac cgccatggtt attgttattg taataagcgt taagcgacgt   900
agaattaaaa aacatccaat ttatcgccca aatacaaaaa caagaagggg catacaaaat   960
gcgacaccag aatccgatgt gatgttggag gccgccattg cacaactagc aacgattcgc   1020
gaagaatccc cccacattc cgttgtaaac ccgtttgtta aatag             1065

SEQ ID NO: 44          moltype = RNA  length = 1337
FEATURE                Location/Qualifiers
misc_feature           1..1337
                       note = Synthetic Polynucleotide
source                 1..1337
                       mol_type = other RNA
                       organism = synthetic construct
SEQUENCE: 44
ggggaaataa gagagaaaag aagagtaaga agaaatataa gagccaccat gttttttaatc   60
caatgtttga tatcggccgt tatattttac atacaagtga ccaacgcttt gatcttcaag   120
ggcgaccacg tgagcttgca agttaacagc agtctcacgt ctatccttat tcccatgcaa   180
aatgataatt atacagagat aaaaggacag cttgtcttta ttggagagca actacctacc   240
gggacaaact atagcggaac actggaactg ttatacgcgg atacggtggc gtttttgtttc   300
cggtcagtac aagtaataag atacgacgga tgtccccgga ttagaacgag cgctttttatt   360
tcgtgtaggt acaaacattc gtggcattat ggtaactcaa cggatcggat atcaacagag   420
ccggatgctg gtgtaatgtt gaaaattacc aaaccgggaa taaatgatgc tggtgtgtat   480
gtacttcttg ttcggttaga ccatagcaga tccaccgatg gtttcattct tggtgtaaat   540
gtatatacag cgggctcgca tcacaacatt cacggggtta tctacacttc catctctca   600
cagaatggat attctacaag agcctttttt caacaagctt gttgtgtgat ttacccgcg   660
acacccaaag gtccggtac ctccctgttt caacatatgc ttgatcttcg tgccggtaaa   720
tcgttagagg ataaccctg gttacatgag gacgttgtta cgacagaaac taagtccgtt   780
gttaaggagg ggatagaaaa tcacgtatat ccaacggata tgtccacgtt acccgaaaag   840
tcccttaatg atcctccaga aaatctactt ataattattc ctatagtagc gtctgtcatg   900
atcctcaccg ccatggttat tgttattgta ataagcgtag aattaaaaaa   960
catccaattt atcgcccaaa tacaaaaaca agaaggggca tacaaaatgc gacaccagaa   1020
tccgatgtga tgttggaggc cgccattgca caactagcaa cgattcgcga agaatccccc   1080
ccacattccg ttgtaaaccc gtttgttaaa tagtgataat aggctggagc ctcggtggc   1140
atgcttcttc cccttgggc ctcccccag ccctcctcc ccttcctgca cccgtacccc   1200
cgtggtcttt gaataaagtc tgagtgggcg gcaaaaaaaa aaaaaaaaa aaaaaaaaa   1260
aaaaaaaaaa aaaaaaaaaa aaaaaaaaa aaaaaaaaa aaaaaaaaa aaaaaaaaa   1320
aaaaaaaaaa aatctag                                               1337

SEQ ID NO: 45          moltype = AA  length = 623
FEATURE                Location/Qualifiers
```

```
source                   1..623
                         mol_type = protein
                         organism = Homo sapiens
SEQUENCE: 45
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAYR VDKSPYNQSM YYAGLPVDDF EDSESTDTEE  600
EFGNAIGGSH GGSSYTVYID KTR                                          623

SEQ ID NO: 46          moltype = AA   length = 354
FEATURE                Location/Qualifiers
source                 1..354
                       mol_type = protein
                       organism = Homo sapiens
SEQUENCE: 46
MFLIQCLISA VIFYIQVTNA LIFKGDHVSL QVNSSLTSIL IPMQNDNYTE IKGQLVFIGE  60
QLPTGTNYSG TLELLYADTV AFCFRSVQVI RYDGCPRIRT SAFISCRYKH SWHYGNSTDR  120
ISTEPDAGVM LKITKPGIND AGVYVLLVRL DHSRSTDGFI LGVNVYTAGS HHNIHGVIYT  180
SPSLQNGYST RALFQQARLC DLPATPKGSG TSLFQHMLDL RAGKSLEDNP WLHEDVVTTE  240
TKSVVKEGIE NHVYPTDMST LPEKSLNDPP ENLLIIIPIV ASVMILTAMV IVIVISVKRR  300
RIKKHPIYRP NTKTRRGIQN ATPESDVMLE AAIAQLATIR EESPPHSVVN PFVK         354

SEQ ID NO: 47          moltype = AA   length = 556
FEATURE                Location/Qualifiers
REGION                 1..556
                       note = Synthetic Polypeptide
source                 1..556
                       mol_type = protein
                       organism = synthetic construct
SEQUENCE: 47
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GVIPTLNGDD RHKIVNVDQR QYGDVFKGDL NPKPQGQRLI EVSVEENHPF  180
TLRAPIQRIY GVRYTETWSF LPSLTCTGDA APAIQHICLK HTTCFQDVVV DVDCAENTKE  240
DQLAEISYRF QGKKEADQPW IVVNTTLFDE LELDPPEIEP GVLKVLRTEK QYLGVYIWNM  300
RGSDGTSTYA TFLVTWKGDE KTRNPTPAVT PQPRGAEFHM WNYHSHVFSV GDTFSLAMHL  360
QYKIHEAPFD LLLEWLYVPI DPTCQPMRLY STCLYHPNAQ CLSHMNSGCT FTSPHLAQRV  420
ASTVYQNCEH ADNYTAYCLG ISHMEPSFGL ILHDGGTTLK FVDTPESLSG LYVFVVYFNG  480
HVEAVAYTVV STVDHFVNAI EERGFPPTAG QPPATTKPKE ITPVNPGTSP LLRYAWTGGL  540
AAVVLLCLVI FLICTA                                                  556

SEQ ID NO: 48          moltype = AA   length = 574
FEATURE                Location/Qualifiers
source                 1..574
                       mol_type = protein
                       organism = Homo sapiens
SEQUENCE: 48
MKRIQINLIL TIACIQLSTE SQPTPVSITE LYTSAATRKP DPAVAPTSAA TRKPDPAVAP  60
TSAATRKPDP AVAPTSAATR KPDPAVAPTS AATRKPDPAV APTSAATRKP DPAVAPTSAA  120
SRKPDPAVAP TSAASRKPDP AVAPTSAASR KPDPAANTQH SQPPFLYENI QCVHGGIQSI  180
PYFHTFIMPC YMRLTTGQQA AFKQQQKTYE QYSLDPEGSN ITRWKSLIRP DLHIEVWFTR  240
HLIDPHRQLG NALIRMPDLP VMLYSNSADL NLINNPEIFT HAKENYVIPD VKTTSDFSVT  300
ILSMDATTEG TYIWRVVNTK TKNVISEHSI TVTTYYRPNI TVVGDPVLTG QTYAAYCNVS  360
KYYPPHSVRV RWTSRFGNIG KNFITDAIQE YANGLFSYVS AVRIPQQKQM DYPPPAIQCN  420
VLWIRDGVSN MKYSAVVTPD VYPFPNVSIG IIDGHIVCTA KCVPRGVVHF VWWVNDSPIN  480
HENSEITGVC DQNKRFVNMQ SSCPTSELDG PITYSCHLDG YPKKFPPFSA VYTYDASTYA  540
TTFSVVAVII GVISILGTLG LIAVIATLCI RCCS                              574

SEQ ID NO: 49          moltype = AA   length = 159
FEATURE                Location/Qualifiers
source                 1..159
                       mol_type = protein
                       organism = Homo sapiens
SEQUENCE: 49
MASHKWLLQI VFLKTITIAY CLHLQDDTPL FFGAKPLSDV SLIITEPCVS SVYEAWDYAA  60
PPVSNLSEAL SGIVVKTKCP VPEVILWFKD KQMAYWTNPY VTLKGLAQSV GEEHKSGDIR  120
DALLDALSGV WVDSTPSSTN IPENGCVWGA DRLFQRVCQ                         159

SEQ ID NO: 50          moltype = AA   length = 435
FEATURE                Location/Qualifiers
source                 1..435
                       mol_type = protein
```

```
                                  organism = Homo sapiens
SEQUENCE: 50
MGTQKKGPRS EKVSPYDTTT PEVEALDHQM DTLNWRIWII QVMMFTLGAV MLLATLIAAS   60
SEYTGIPCFY AAVVDYELFN ATLDGGVWSG NRGGYSAPVL FLEPHSVVAF TYYTALTAMA  120
MAVYTLITAA IIHRETKNQR VRQSSGVAWL VVDPTTLFWG LLSLWLLNAV VLLLAYKQIG  180
VAATLYLGHF ATSVIFTTYF CGRGKLDETN IKAVANLRQQ SVFLYRLAGP TRAVFVNLMA  240
ALMAICILFV SLMLELVVAN HLHTGLWSSV SVAMSTFSTL SVVYLIVSEL ILAHYIHVLI  300
GPSLGTLVAC ATLGTAAHSY MDRLYDPISV QSPRLIPTTR GTLACLAVFS VVMLLLRLMR  360
AYVYHRQKRS RFYGAVRRVP ERVRGYIRKV KPAHRNSRRT NYPSQGYGYV YENDSTYETD  420
REDELLYERS NSGWE                                                   435

SEQ ID NO: 51              moltype = AA  length = 841
FEATURE                    Location/Qualifiers
source                     1..841
                           mol_type = protein
                           organism = Homo sapiens
SEQUENCE: 51
MFALVLAVVI LPLWTTANKS YVTPTPATRS IGHMSALLRE YSDRNMSLKL EAFYPTGFDE   60
ELIKSLHWGN DRKHVFLVIV KVNPTTHEGD VGLVIFPKYL LSPYHFKAEH RAPFPAGRFG  120
FLSHPVTPDV SFFDSSFAPY LTTQHLVAFT TFPPNPLVWH LERAETAATA ERPFGVSLLP  180
ARPTVPKNTI LEHKAHFATW DALARHTFFS AEAIITNSTL RIHVPLFGSV WPIRYWATGS  240
VLLTSDSGRV EVNIGVGFMS SLISLSSGPP IELIVVPHTV KLNAVTSDTT WFQLNPPGPD  300
PGPSYRVYLL GRGLDMNFSK HATVDICAYP EESLDYRYHL SMAHTEALRM TTKADQHDIN  360
EESYYHIAAR IATSIFALSE MGRTTEYFLL DEIVDVQYQL KFLNYILMRI GAGAHPNTIS  420
GTSDLIFADP SQLHDELSLL FGQVKPANVD YFISYDEARD QLKTAYALSR GQDHVNALSL  480
ARRVIMSIYK GLLVKQNLNA TERQALFFAS MILLNFREGL ENSSRVLDGR TTLLLMTSMC  540
TAAHATQAAL NIQEGLAYLN PSKHMFTIPN VYSPCMGSLR TDLTEEIHVM NLLSAIPTRP  600
GLNEVLHTQL DESEIFDAAF KTMMIFTTWT AKDLHILHTH VPEVFTCQDA AARNGEYVLI  660
LPAVQGHSYV ITRNKPQRGL VYSLADVDVY NPISVVYLSR DTCVSEHGVI ETVALPHPDN  720
LKECLYCGSV FLRYLTTGAI MDIIIIDSKD TERQLAAMGN STIPPFNPDM HGDDSKAVLL  780
FPNGTVVTLL GFERRQAIRM SGQYLGASLG GAFLAVVGFG IIGWMLCGNS RLREYNKIPL  840
T                                                                  841

SEQ ID NO: 52              moltype = AA  length = 661
FEATURE                    Location/Qualifiers
source                     1..661
                           mol_type = protein
                           organism = Homo sapiens
SEQUENCE: 52
MFYEALKAEL VYTRAVHGFR PRANCVVLSD YIPRVACNMG TVNKPVVGVL MGFGIITGTL   60
RITNPVRASV LRYDDFHIDE DKLDTNSVYE PYYHSDHAES SWVNRGESSR KAYDHNSPYI  120
WPRNDYDGFL ENAHEHHGVY NQGRGIDSGE RLMQPTQMSA QEDLGDDTGI HVIPTLNGDD  180
RHKIVNVDQR QYGDVFKGDL NPKPQGQRLI EVSVEENHPF TLRAPIQRIY GVRYTETWSF  240
LPSLTCTGDA APAIQHICLK HTTCFQDVVV DVDCAENTKE DQLAEISYRF QGKKEADQPW  300
IVVNTSTLFD ELELDPPEIE PGVLKVLRTE KQYLGVYIWN MRGSDGTSTY ATFLVTWKGD  360
EKTRNPTPAV TPQPRGAEFH MWNYHSHVFS VGDTFSLAMH LQYKIHEAPF DLLLEWLYVP  420
IDPTCQPMRL YSTCLYHPNA PQCLSHMNSG CTFTSPHLAQ RVASTVYQNC EHADNYTAYC  480
LGISHMEPSF GLILHDGGTT LKFVDTPESL SGLYVFVVYF NGHVEAVAYT VVSTVDHFVN  540
AIEERGFPPT AGQPPATTKP KEITPVNPGT SPLLRYAAWT GGLAAVVLLC LVIFLICTAK  600
RMRVKAYRVD KSPYNQSMYY AGLPVDDFED SESTDTEEEF GNAIGGSHGG SSYTVYIDKT  660
R                                                                  661

SEQ ID NO: 53              moltype = AA  length = 868
FEATURE                    Location/Qualifiers
source                     1..868
                           mol_type = protein
                           organism = Homo sapiens
SEQUENCE: 53
MFVTAVVSVS PSSFYESLQV EPTQSEDITR SAHLGDGDEI REAIHKSQDA ETKPTFYVCP   60
PPTGSTIVRL EPTRTCPDYH LGKNFTEGIA VVYKENIAAY KFKATVYYKD VIVSTAWAGS  120
SYTQITNRYA DRVPIPVSEI TDTIDKFGKC SSKATYVRNN HKVEAFNEDK NPQDMPLIAS  180
KYNSVGSKAW HTTNDTYMVA GTPGTYRTGT SVNCIIEEVE ARSIFPYDSF GLSTGDIIYM  240
SPFFGLRDGA YREHSNYAMD RFHQPEGYRQ RDLDTRALLE PAARNFLVTP HLTVGWNWKP  300
KRTEVCSLVK WREVEDVVRD EYAHNFRFTM KTLSTTFISE TNEFNLNQIH LSQCVKEEAR  360
AIINRIYTTR YNSSHVRTGD IQTYLARGGF VVVFQPLLSN SLARLYLQEL VRENTNHSPQ  420
KHPTRNTRSR RSVPVELRAN RTITTTSSVE FAMLQFTYDH IQEHVNEMLA RISSSWCQLQ  480
NRERALWSGL FPINPSALAS TILDQRVKAR ILGDVISVSN CPELGSDTRI ILQNSMRVSG  540
STTRCYSRPL ISIVSLNGSG TVEGQLGTDN ELIMSRDLLE PCVANHKRYF LPGHHYVYYE  600
DYRYVREIAV HDVGMISTYV DLNLTLLKDR EFMPLQVYTR DELRDTGLLD YSEIQRRNQM  660
HSLRFYDIDK VVQYDSGTAI MQGMAQFFQG LGTAGQAVGH VVLGATGALL STVHGFTTFL  720
SNPFGALAVG LLVLAGLVAA FFAYRYVLKL KTSPMKALYP LTTKGLKQLP EGMDPFAEKP  780
NATDTPIEEI GDSQNTEPSV NSGFDPDKFR EAQEMIKYMT LVSAAERQES KARKKNKTSA  840
LLTSRLTGLA LRNRRGYSRV RTENVTGV                                     868

SEQ ID NO: 54              moltype = AA  length = 340
FEATURE                    Location/Qualifiers
source                     1..340
                           mol_type = protein
                           organism = Homo sapiens
```

```
SEQUENCE: 54
MQALGIKTEH FIIMCLLSGH AVFTLWYTAR VKFEHECVYA TTVINGGPVV WGSYNNSLIY   60
VTFVNHSTFL DGLSGYDYSC RENLLSGDTM VKTAISTPLH DKIRIVLGTR NCHAYFWCVQ   120
LKMIFFAWFV YGMYLQFRRI RRMFGPFRSS CELISPTSYS LNYVTRVISN ILLGYPYTKL   180
ARLLCDVSMR RDGMSKVFNA DPISFLYMHK GVTLLMLLEV IAHISSGCIV LLTLGVAYTP   240
CALLYPTYIR ILAWVVVCTL AIVELISYVR PKPTKDNHLN HINTGGIRGI CTTCCATVMS   300
GLAIKCFYIV IFAIAVVIFM HYEQRVQVSL FGESENSQKH                        340

SEQ ID NO: 55         moltype = AA  length = 87
FEATURE               Location/Qualifiers
source                1..87
                      mol_type = protein
                      organism = Homo sapiens
SEQUENCE: 55
MGSITASFIL ITMQILFFCE DSSGEPNFAE RNFWHASCSA RGVYIDGSMI TTLFFYASLL   60
GVCVALISLA YHACFRLFTR SVLRSTW                                      87

SEQ ID NO: 56         moltype = AA  length = 18
FEATURE               Location/Qualifiers
REGION                1..18
                      note = Synthetic Polypeptide
source                1..18
                      mol_type = protein
                      organism = synthetic construct
SEQUENCE: 56
MDWTWILFLV AAATRVHS                                                18

SEQ ID NO: 57         moltype = AA  length = 20
FEATURE               Location/Qualifiers
REGION                1..20
                      note = Synthetic Polypeptide
source                1..20
                      mol_type = protein
                      organism = synthetic construct
SEQUENCE: 57
METPAQLLFL LLLWLPDTTG                                              20

SEQ ID NO: 58         moltype = AA  length = 6
FEATURE               Location/Qualifiers
REGION                1..6
                      note = Synthetic Polypeptide
source                1..6
                      mol_type = protein
                      organism = synthetic construct
SEQUENCE: 58
AEAADA                                                            6

SEQ ID NO: 59         moltype = AA  length = 6
FEATURE               Location/Qualifiers
REGION                1..6
                      note = Synthetic Polypeptide
source                1..6
                      mol_type = protein
                      organism = synthetic construct
SEQUENCE: 59
SESTDT                                                            6

SEQ ID NO: 60         moltype = RNA  length = 1885
FEATURE               Location/Qualifiers
misc_feature          1..1885
                      note = Synthetic Polynucleotide
source                1..1885
                      mol_type = other RNA
                      organism = synthetic construct
SEQUENCE: 60
gggaaataag agagaaaaga agagtaagaa gaaatataag agccaccatg ggcaccgtga   60
acaagcccgt cgtgggcgtg ctgatgggct tcggcatcat caccggcacc ctgcggatca   120
ccaatcctgt gcgggccagc gtgctgagat acgacgactt ccacatcgac gaggacaagc   180
tggacaccaa cagcgtgtac gagccctact accacagcga ccacgccgag agcagctggg   240
tcaacagagg cgagtccagc cggaaggcct acgaccacaa cagcccctac atctggcccc   300
ggaacgacta cgacggcttc ctggaaaatg cccacgagca ccacgccgtg tacaaccagg   360
gcagaggcat cgacagcggc gagagactga tgcagcccac ccagatgagc gcccaggaag   420
atctgggcga cgacaccggc atccacgtga tccctaccct gaacggcgac gaccggcaca   480
agatcgtgaa cgtggaccag cggcagtacg gcgacgtgtt caagggcgac ctgaacccca   540
agccccaggg acagcggctg attgaggtgc ccgtggaaga gaaccacccc ttcaccctga   600
gagcccctat ccagcggatc tacggcgtgc gctataccga gacttggagc ttcctgccca   660
gcctgacctg tactggcgac gccgctcctg ccatccagca catctgcctg aagcacacca   720
cctgtttcca ggacgtggtg gtggacgtgg actgcgccga gaacaccaaa gaggaccagc   780
tggccgagat cagctaccgg ttccagggca agaaagaggc cgaccagccc tggatcgtcg   840
```

```
tgaacaccag caccctgttc gacgagctgg aactggaccc tcccgagatc gaacccgggg   900
tgctgaaggt gctgcggacc gagaagcagt acctgggagt gtacatctgg aacatgcggg   960
gcagcgacgg cacctctacc tacgccacct tcctcgtgac ctggaagggc gacgagaaaa  1020
cccggaaccc tacccctgcc gtgacccctc agcctagagg cgccgagttt cacatgtgga  1080
attaccacag ccacgtgttc agcgtgggcg acaccttctc cctggccatg catctgcagt  1140
acaagatcca cgaggcccct ttcgacctgc tgctggaatg gctgtacgtg cccatcgacc  1200
ctacctgcca gcccatgcgg ctgtactcca cctgtctgta ccaccccaac gcccctcagt  1260
gcctgagcca catgaatagc ggctgcacct tcaccagccc tcacctggct cagagggtgg  1320
ccagcaccgt gtaccagaat tgcgagcacg ccgacaacta caccctgggca  1380
tcagccacat ggaacccagc ttcggcctga tcctgcacga tggcggcacc accctgaagt  1440
tcgtggacac ccctgagtcc ctgagcggcc tgtacgtgtt cgtggtgtac ttcaacggcc  1500
acgtggaagc cgtggcctac accgtggtgt ccaccgtgga ccacttcgtg aacgccatcg  1560
aggaacgggg cttccctcca actgctggac agcctcctgc caccaccaag cccaaagaaa  1620
tcacccctgt gaaccccggc accagcccac tgctgcttgg acaggcggac  1680
tggctgctgt ggtgctgctg tgcctcgtga ttttcctgat ctgcaccgcc aagcggatga  1740
gagtgaaggc cgcagagtg gacaagtgat aataggctgg agcctcggtg gccatgcttc  1800
ttgccccttg ggcctccccc cagccctcc tccccttcct gcaccgtac ccccgtggtc  1860
tttgaataaa gtctgagtgg gcggc                                        1885
```

SEQ ID NO: 61                     moltype = AA   length = 573
FEATURE                           Location/Qualifiers
REGION                            1..573
                                  note = Synthetic Polypeptide
source                            1..573
                                  mol_type = protein
                                  organism = synthetic construct
SEQUENCE: 61
```
MGTVNKPVVG VLMGFGIITG TLRITNPVRA SVLRYDDFHI DEDKLDTNSV YEPYYHSDHA   60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAAR VDK                               573
```

SEQ ID NO: 62                     moltype = RNA   length = 1719
FEATURE                           Location/Qualifiers
misc_feature                      1..1719
                                  note = Synthetic Polynucleotide
source                            1..1719
                                  mol_type = other RNA
                                  organism = synthetic construct
SEQUENCE: 62
```
atgggcaccg tgaacaagcc cgtcgtgggc gtgctgatgg gcttcggcat catcaccggc   60
accctgcgga tcaccaatcc tgtgcgggcc agcgtgctga gatacgacga cttccacatc  120
gacgaggaca agctggacac caacagcgtg tacgagccct actaccacag cgaccacgcc  180
gagagcagct gggtcaacag aggcgagtcc agccggaagg cctacgacca caacagcccc  240
tacatctggc cccggaacga ctacgacggc ttcctggaaa atgcccacga gcaccacggc  300
gtgtacaacc agggcagagg catcgacagc ggcgagagac tgatgcagcc cacccagatg  360
agcgcccagg aagatctggg cgacgacacc ggcatccacg tgatccctac cctgaacggc  420
gacgaccggc acaagatcgt gaacgtggac cagcggcagt acggcgacgt gttcaagggc  480
gacctgaacc ccaagcccca gggacagcgg ctgattgagg tgtccgtgga agagaaccac  540
cccttcaccc tgagagcccc tatccagcgg atctacggcg tgcgctatac cgagacttgg  600
agcttcctgc ccagcctgac ctgtactggc gacgccgctc ctgccatcca gcacatctgc  660
ctgaagcaca ccacctgttt ccaggacgtg gtggtggacg tggactgcgc cgagaacacc  720
aaagaggacc agctggccga gatcagctac cggttccagg gcaagaaaga ggccgaccag  780
ccctggatcg tcgtgaacac cagcaccctg ttcgacgagc tggaactgga ccctccccag  840
atcgaacccg gggtgctgaa ggtgctgcgc accgagaagc agtacctggg agtgtacatc  900
tggaacatgc ggggcagcga cggcacctct acctacgcca ccttcctcgt gacctggaag  960
ggcgacgaga aaacccggaa ccctacccct gccgtgaccc ctcagcctag aggcgccgag 1020
tttcacatgt ggaattacca cagccacgtg ttcagcgtgg gcgacacctt ctccctggcc 1080
atgcatctgc agtacaagat ccacgaggcc cctttcgacc tgctgctgga atggctgtac 1140
gtgcccatcg accctacctg ccagcccatg cggctgtact ccacctgtct gtaccacccc 1200
aacgcccctc agtgcctgag ccacatgaat agcggctgca ccttcaccag ccctcacctg 1260
gctcagaggg tggccagcac cgtgtaccag aattgcgagc acgccgacaa ctacaccgcc 1320
tactgcctgg gcatcagcca catggaaccc agcttcggcc tgatcctgca cgatggcggc 1380
accaccctga gttcgtggaa cacccctgag tccctgagcg gcctgtacgt gttcgtggtg 1440
tacttcaacg gccacgtgga agccgtggcc tacaccgtgg tgtccaccgt ggaccacttc 1500
gtgaacgcca tcgaggaacg gggcttccct ccaactgctg gacagcctcc tgccaccacc 1560
aagcccaaag aaatcacccc tgtgaacccc ggcaccagcc cactgctgcg ctatgctgct 1620
tggacaggcg gactggctgc tgtggtgctg ctgtgcctcg tgattttcct gatctgcacc 1680
gccaagcgga tgagagtgaa ggccgccaga gtggacaag                        1719
```

SEQ ID NO: 63                     moltype = RNA   length = 1990
FEATURE                           Location/Qualifiers
misc_feature                      1..1990

-continued

```
                              note = Synthetic Polynucleotide
source                        1..1990
                              mol_type = other RNA
                              organism = synthetic construct
SEQUENCE: 63
gggaaataag agagaaaaga agagtaagaa gaaatataag agccaccatg ggcaccgtga   60
acaagcccgt cgtgggcgtg ctgatgggct tcggcatcat caccggcacc ctgcggatca  120
ccaatcctgt gcgggccagc gtgctgagat acgacgactt ccacatcgac gaggacaagc  180
tggacaccaa cagcgtgtac gagccctact accacagcga ccacgccgag agcagctggg  240
tcaacagagg cgagtccagc cggaaggcct acgaccacaa cagcccctac atctggcccc  300
ggaacgacta cgacggcttc ctggaaaatg cccacgagca ccacggcgtg tacaaccagg  360
gcagaggcat cgacagcggc gagagactga tgcagcccac ccagatgagc gcccaggaag  420
atctgggcga cgacaccggc atccacgtga tccctaccct gaacggcgac gaccggcaca  480
agatcgtgaa cgtggaccag cggcagtacg gcgacgtgtt caaggcgac ctgaacccca  540
agccccaggg acagcggctg attgaggtgt ccgtggaaga gaaccacccc ttcaccctga  600
gagcccctat ccagcggatc tacggcgtgc gctataccga gacttggagc ttcctgccca  660
gcctgacctg tactggcgac gccgctcctg ccatccagca catctgcctg aagcacacca  720
cctgtttcca ggacgtggtg gtggacgtgg actgcgccga gaacaccaaa gaggaccagc  780
tggccgagat cagctaccgg ttccagggca agaaagaggc cgaccagccc tggatcgtcg  840
tgaacaccag cacctgttc gacgagctgg aactggaccc tcccgagatc gaacccgggg  900
tgctgaaggt gctgcggacc gagaagcagt acctgggagt gtacatctgg aacatgcggg  960
gcagcgacgg cacctctacc tacgccacct tcctcgtgac ctggaagggc gacgagaaaa 1020
cccggaaccc taccctgcc gtgacccctc agcctagagg cgccgagttt cacatgtgga 1080
attaccacag ccacgtgttc agcgtgggcg acacctttctc cctggccatg catctgcagt 1140
acaagatcca cgaggcccct ttcgacctgc tgctggaatg gctgtacgtg cccatcgacc 1200
ctacctgcca gcccatgcgg ctgtactcca cctgtctgta ccaccccaac gcccctcagt 1260
gcctgagcca catgaatagc ggctgcacct tcaccagcc tcacctggct cagagggtgg 1320
ccagcaccgt gtaccagaat tgcgagcacg ccgacaacta caccgcctac tgcctgggca 1380
tcagccacat ggaacccagc ttcggcctga tcctgcacga tggcggcacc accctgaagt 1440
tcgtggacac ccctgagtcc ctgagcggcc tgtacgtgtt cgtggtgtac ttcaacggcc 1500
acgtggaagc cgtggcctac accgtggtgt ccaccgtgga ccacttcgtg aacgccatcg 1560
aggaacgggg cttccctcca actgctggac agcctcctgc caccaccaag cccaaagaaa 1620
tcacccctgt gaaccccggc accagcccac tgctgcgcta tgctgcttgg acaggcggac 1680
tggctgctgt ggtgctgctg tgcctcgtga ttttcctgat ctgcaccgcc aagcggatga 1740
gagtgaaggc cgccagagtg gacaagtgat aataggctgg agcctcggtg gccatgcttc 1800
ttgccccttg ggcctccccc cagccctcc tccccttcct gcaccgtac ccccgtggtc 1860
tttgaataaa gtctgagtgg gcggcaaaaa aaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaatctag                                                        1990

SEQ ID NO: 64        moltype = RNA  length = 1885
FEATURE              Location/Qualifiers
misc_feature        1..1885
                    note = Synthetic Polynucleotide
source              1..1885
                    mol_type = other RNA
                    organism = synthetic construct
SEQUENCE: 64
gggaaataag agagaaaaga agagtaagaa gaaatataag agccaccatg gggacagtta   60
ataaacctgt ggtgggggta ttgatggggt tcggaattat cacgggaacg ttgcgtataa  120
cgaatccggt cagagcatcc gtcttgcgat acgatgattt tcacatcgat gaagacaaac  180
tggatacaaa ctccgtatat gagccttact accattcaga tcatgcggag tcttcatggg  240
taaatcgggg agagtcttcg cgaaaagcgt acgatcataa ctcaccttat atatggccac  300
gtaatgatta tgatggattt ttagagaacg cacacgaaca ccatgggtg tataatcagg  360
gccgtggtat cgatagcggg gaacggttaa tgcaacccac acaaatgtct gcacaggagg  420
atcttgggga cgatacgggc atccacgtta tccctacgtt aaacggcgat gacagacata  480
aaattgtaaa tgtggaccaa cgtcaatacg gtgacgtgtt taaaggagat cttaatccaa  540
aacccccaagg ccaaagactc attgaggtgt cagtggaaga aaatcacccg tttactttac  600
gcgcaccgat tcagcggatt tatggagtcc ggtacaccga gacttggagc tttttgccgt  660
cattaacctg tacgggagac gcagcgcccg ccatccagca tatatgttta aaacatacaa  720
catgctttca agacgtggtg gtggatgtgg attgcgcgga aaatactaaa gaggatcagt  780
tggccgaaat cagttaccgt tttcaaggta agaaggaagc ggaccaaccg tggattgttg  840
taaacacgag cacactgttt gatgaactcg aattagaccc ccccgagatt gaaccggggtg  900
tcttgaaagt acttcggaca gagaaacaat acttgggtgt gtacatttgg aacatgcgcg  960
gctccgatgg tacgtctacc tacgccacgt tttttggtcac ctggaaaggg gatgagaaga 1020
caagaaaccc tacgcccgca gtaactcctc aaccaagagg ggctgagttt catatgtgga 1080
attaccactc gcatgtattt tcagttggtg atacgtttag cttggcaatg catcttcagt 1140
ataagataca tgaagcgcca tttgatttgc tgttagagtg gttgtatgtc cccatcgatc 1200
ctacatgtca accaatgcgg ttatattcta cgtgtttgta tcatcccaac gcaccccaat 1260
gcctctctca tatgaattcc ggttgtacat ttacctcgcc acatttagcc cagcgtgttg 1320
caagcacagt gtatcaaaat tgtgaacatg cagataacta caccgcatat tgtctgggaa 1380
tatctcatat ggagcctagc tttggtctaa tcttacacga cggggggcacc acgttaaagt 1440
ttgtagatac acccgagagt ttgtcgggat tatacgtttt tgtggtgtat tttaacgggc 1500
atgttgaagc cgtagcatac actgttgtat ccacagtaga tcattttgta aacgcaattg 1560
aagagcgtgg atttccgcca acggccggtc agccaccggc gactactaaa cccaaggaaa 1620
ttaccccgt aaaccccgga acgtcaccac ttctacgata tgccgcatgg accggagggc 1680
ttgcagcagt agtactttta tgtctcgtaa tatttttaat ctgtacggct aaacgaatga 1740
gggttaaagc cgcagggta gacaagtgat aataggctgg agcctcggtg gccatgcttc 1800
ttgccccttg ggcctccccc cagccctcc tcccttcct gcaccgtac ccccgtggtc 1860
```

```
tttgaataaa gtctgagtgg gcggc                                               1885

SEQ ID NO: 65              moltype = AA   length = 573
FEATURE                    Location/Qualifiers
REGION                     1..573
                           note = Synthetic Polypeptide
source                     1..573
                           mol_type = protein
                           organism = synthetic construct
SEQUENCE: 65
MGTVNKPVVG VLMGFGIITG TLRITNPVRA SVLRYDDFHI DEDKLDTNSV YEPYYHSDHA   60
ESSWVNRGES SRKAYDHNSP YIWPRNDYDG FLENAHEHHG VYNQGRGIDS GERLMQPTQM   120
SAQEDLGDDT GIHVIPTLNG DDRHKIVNVD QRQYGDVFKG DLNPKPQGQR LIEVSVEENH   180
PFTLRAPIQR IYGVRYTETW SFLPSLTCTG DAAPAIQHIC LKHTTCFQDV VVDVDCAENT   240
KEDQLAEISY RFQGKKEADQ PWIVVNTSTL FDELELDPPE IEPGVLKVLR TEKQYLGVYI   300
WNMRGSDGTS TYATFLVTWK GDEKTRNPTP AVTPQPRGAE FHMWNYHSHV FSVGDTFSLA   360
MHLQYKIHEA PFDLLLEWLY VPIDPTCQPM RLYSTCLYHP NAPQCLSHMN SGCTFTSPHL   420
AQRVASTVYQ NCEHADNYTA YCLGISHMEP SFGLILHDGG TTLKFVDTPE SLSGLYVFVV   480
YFNGHVEAVA YTVVSTVDHF VNAIEERGFP PTAGQPPATT KPKEITPVNP GTSPLLRYAA   540
WTGGLAAVVL LCLVIFLICT AKRMRVKAAR VDK                               573

SEQ ID NO: 66              moltype = RNA   length = 1719
FEATURE                    Location/Qualifiers
misc_feature               1..1719
                           note = Synthetic Polynucleotide
source                     1..1719
                           mol_type = other RNA
                           organism = synthetic construct
SEQUENCE: 66
atggggacag ttaataaacc tgtggtgggg gtattgatgg ggttcggaat tatcacggga   60
acgttgcgta taacgaatcc ggtcagagca tccgtcttgc gatacgatga ttttcacatc   120
gatgaagaca aactggatac aaactccgta tatgagcctt actaccattc agatcatgcg   180
gagtcttcat gggtaaatcg gggagagtct tcgcgaaaag cgtacgatca taactcacct   240
tatatatggc cacgtaatga ttatgatgga tttttagaga acgcacacgg acaccatggg   300
gtgtataatc agggccgtgg tatcgatagc ggggaacggt taatgcaacc cacacaaatg   360
tctgcacagg aggatcttgg ggacgatacg ggcatccacg ttatccctac gttaaacggc   420
gatgacagac ataaaaattgt aaatgtggac caacgtcaat acggtgacgt gtttaaagga   480
gatcttaatc caaaacccca aggccaaaga ctcattgagg tgtcagtgga agaaaatcac   540
ccgtttactt tacgcgcacc gattcagcgg atttatggag tccggtacac ggacgacttgg   600
agctttttgc cgtcattaac ctgtacggga gacgcagcgc ccgccatcca gcatatatgt   660
ttaaaacata caacatgctt tcaagacgtg gtggtggatg tggattgcgc ggaaaaatact   720
aaagaggatc agttggccga aatcagttac cgttttcaag gtaagaagga agcggaccaa   780
ccgtggattg ttgtaaacac gagcacactg tttgatgaac tcgaattaga ccccccccgaa   840
attgaaccgg gtgtcttgaa agtacttcgg acagagaaac aatacttggg tgtgtacatt   900
tggaacatgc gcggctccga tggtacgtct acctacgcca cgtttttggt cacctggaaa   960
ggggatgaga agacaagaaa ccctacgccc gcagtaactc ctcaaccaag aggggctgag   1020
tttcatatgt ggaattacca ctcgcatgta ttttcagttg gtgatacgtt tagcttggca   1080
atgcatcttc agtataagat acatgaagcg ccatttgatt tgctgttaga gtggttgtat   1140
gtccccatcg atcctacatg tcaaccaatg cggttatatt ctacgtgttt gtatcatccc   1200
aacgcacccc aatgcctctc tcatatgaat tccggttgta catttacctc gccacattta   1260
gcccagcgtg ttgcaagcac agtgtatcaa aattgtgaac atgcagataa ctacaccgca   1320
tattgtctgg gaatatctca tatggagcct agctttggtc taatcttaca cgacgggggc   1380
accacgttaa agtttgtaga tacacccgag agtttgtcgg gattatacgt ttttgtggtg   1440
tattttaacg ggcatgttga agccgtagca tacactgttg tatccacagt agatcatttt   1500
gtaaacgcaa ttgaagagcg tggatttccg ccaacggccc gtcagccacc ggcgactact   1560
aaacccaagg aaattacccc cgtaaacccc ggaacgtcac cacttctacg atatgccgca   1620
tggaccggag ggcttgcagc agtagtactt ttatgtctcg taatatttt aatctgtacg   1680
gctaaacgaa tgagggttaa agccgccagg gtagacaag                         1719

SEQ ID NO: 67              moltype = RNA   length = 1990
FEATURE                    Location/Qualifiers
misc_feature               1..1990
                           note = Synthetic Polynucleotide
source                     1..1990
                           mol_type = other RNA
                           organism = synthetic construct
SEQUENCE: 67
gggaaataag agagaaaaga agagtaagaa gaaatataag agccaccatg gggacagtta   60
ataaacctgt ggtgggggta ttgatggggt tcggaattat cacgggaacg ttgcgtataa   120
cgaatccggt cagagcatcc gtcttgcgat acgatgattt tcacatcgat gaagacaaac   180
tggatacaaa ctccgtatat gagccttact accattcaga tcatgcggag tcttcatggg   240
taaatcgggg agagtcttcg cgaaaagcgt acgatcaata ctcaccttat atatggccac   300
gtaatgatta tgatggattt ttagagaacg cacacgaaca ccatggggtg tataatcagg   360
gccgtggtat cgatagcggg gaacggttaa tgcaacccac acaaatgtct gcacaggagg   420
atcttgggga cgatacgggc atccacgtta ccctacgtt aaacggcgat gacagacata   480
aaattgtaaa tgtggaccaa cgtcaatacg gtgacgtgtt taaaggagat cttaatccaa   540
aaccccaagg ccaaagactc attgaggtgt cagtggaaga aaatcacccg tttacttac   600
gcgcaccgat tcagcggatt tatggagtcc ggtacaccga cttggagc tttttgccgt   660
cattaacctg tacgggagac gcagcgcccg ccatccagca tatatgttta aaacatacaa   720
```

```
catgctttca agacgtggtg gtggatgtgg attgcgcgga aaatactaaa gaggatcagt    780
tggccgaaat cagttaccgt tttcaaggta agaaggaagc ggaccaaccg tggattgttg    840
taaacacgag cacactgttt gatgaactcg aattagaccc ccccgagatt gaaccgggtg    900
tcttgaaagt acttcggaca gagaaacaat acttgggtgt gtacatttgg aacatgcgcg    960
gctccgatgg tacgtctacc tacgccacgt ttttggtcac ctggaaaggg gatgagaaga   1020
caagaaaccc tacgcccgca gtaactcctc aaccaagagg ggctgagttt catatgtgga   1080
attaccactc gcatgtattt tcagttggtg atacgtttag cttggcaatg catcttcagt   1140
ataagataca tgaagcgcca tttgatttgc tgttagagtg gttgtatgtc cccatcgatc   1200
ctacatgtca accaatgcgg ttatattcta cgtgtttgta tcatcccaac gcaccccaat   1260
gcctctctca tatgaattcc ggttgtacat ttacctcgcc acatttagcc cagcgtgttg   1320
caagcacagt gtatcaaaat tgtgaacatg cagataacta caccgcatat tgtctgggaa   1380
tatctcatat ggagcctagc tttggtctaa tcttacacga cggggggcacc acgttaaagt   1440
ttgtagatac acccgagagt ttgtcgggat tatacgtttt tgtggtgtat tttaacgggc   1500
atgttgaagc cgtagcatac actgttgtat ccacagtaga tcattttgta aacgcaattg   1560
aagagcgtgg atttccgcca acggccggtc agccaccggc gactactaaa cccaaggaaa   1620
ttaccccgt aaaccccgga acgtcaccac ttctacgata tgccgcatgg accggagggc   1680
ttgcagcagt agtactttta tgtctcgtaa tattttttaat ctgtacggct aaacgaatga   1740
gggttaaagc cgccagggta gacaagtgat aataggctgg agcctcggtg gccatgcttc   1800
ttgcccttg ggcctcccc cagcccctcc tccccttcct gcaccgtac cccgtggtc    1860
tttgaataaa gtctgagtgg gcggcaaaaa aaaaaaaaa aaaaaaaaa aaaaaaaaa    1920
aaaaaaaaa aaaaaaaaa aaaaaaaaa aaaaaaaaa aaaaaaaaa aaaaaaaaa    1980
aaaaatctag                                                       1990
```

```
SEQ ID NO: 68          moltype = RNA  length = 1885
FEATURE                Location/Qualifiers
misc_feature           1..1885
                       note = Synthetic Polynucleotide
source                 1..1885
                       mol_type = other RNA
                       organism = synthetic construct
SEQUENCE: 68
gggaaataag agagaaaaga agagtaagaa gaaatataag agccaccatg gggacagtta    60
ataaacctgt ggtgggggta ttgatggggt tcggaattat cacgggaacg ttgcgtataa   120
cgaatccggt cagagcatcc gtcttgcgat acgatgattt tcacatcggat gaagacaaac   180
tggatacaaa ctccgtatat gagccttact accattcaga tcatcgggag tcttcatggg   240
taaatcgggg agagtcttcg cgaaaagcgt acgatcataa ctcaccttat atatggccac   300
gtaatgatta tgatggattt ttagagaacg cacacgaaca ccatgggtgt gtataatcagg   360
gccgtggtat cgatagcggg gaacggttaa tgcaacccac acaaatgtct gcacaggagg   420
atcttgggga cgatacgggc atccacgtta tccctacgtt aaacggcgat gacagacata   480
aaattgtaaa tgtggaccaa cgtcaatacg gtgacgtgtt taaaggagat cttaatccaa   540
aaccccaagg ccaaagactc attgaggtgt cagtggaaga aaatcacccg tttactttac   600
gcgcaccgat tcagcggatt tatggagtcc ggtacaccga acttggagc tttttgccgt   660
cattaacctg tacgggagac gcagcgcccg ccatccagca tatatgttta aaacatacaa   720
catgctttca agacgtggtg gtggatgtgg attgcgcgga aaatactaaa gaggatcagt    780
tggccgaaat cagttaccgt tttcaaggta agaaggaagc ggaccaaccg tggattgttg    840
taaacacgag cacactgttt gatgaactcg aattagaccc acccgagatt gaaccgggtg    900
tcttgaaagt acttcggaca gagaaacaat acttgggtgt gtacatttgg aacatgcgcg    960
gctccgatgg tacgtctacc tacgccacgt ttttggtcac ctggaaaggg gatgagaaga   1020
caagaaaccc tacgcccgca gtaactcctc aaccaagagg ggctgagttt catatgtgga   1080
attaccactc gcatgtattt tcagttggtg atacgtttag cttggcaatg catcttcagt   1140
ataagataca tgaagcgcca tttgatttgc tgttagagtg gttgtatgtc cccatcgatc   1200
ctacatgtca accaatgcgg ttatattcta cgtgtttgta tcatcccaac gcaccccaat   1260
gcctctctca tatgaattcc ggttgtacat ttacctcgcc acatttagcc cagcgtgttg   1320
caagcacagt gtatcaaaat tgtgaacatg cagataacta caccgcatat tgtctgggaa   1380
tatctcatat ggagcctagc tttggtctaa tcttacacga cggggggcacc acgttaaagt   1440
ttgtagatac acccgagagt ttgtcgggat tatacgtttt tgtggtgtat tttaacgggc   1500
atgttgaagc cgtagcatac actgttgtat ccacagtaga tcattttgta aacgcaattg   1560
aagagcgtgg atttccgcca acggccggtc agccaccggc gactactaaa cccaaggaaa   1620
ttaccccgt aaaccccgga acgtcaccac ttctacgata tgccgcatgg accggagggc   1680
ttgcagcagt agtactttta tgtctcgtaa tattttttaat ctgtacggct aaacgaatga   1740
gggttaaagc cgccagggta gacaagtgat aataggctgg agcctcggtg gccatgcttc   1800
ttgcccttg ggcctcccc cagcccctcc tccccttcct gcaccgtac cccgtggtc    1860
tttgaataaa gtctgagtgg gcggc                                      1885
```

```
SEQ ID NO: 69          moltype = AA  length = 573
FEATURE                Location/Qualifiers
REGION                 1..573
                       note = Synthetic Polypeptide
source                 1..573
                       mol_type = protein
                       organism = synthetic construct
SEQUENCE: 69
MGTVNKPVVG VLMGFGIITG TLRITNPVRA SVLRYDDFHI DEDKLDTNSV YEPYYHSDHA    60
ESSWVNRGES SRKAYDHNSP YIWPRNDYDG FLENAHEHHG VYNQGRGIDS GERLMQPTQM   120
SAQEDLGDDT GIHVIPTLNG DDRHKIVNVD QRQYGDVFKG DLNPKPQGQR LIEVSVEENH   180
PFTLRAPIQR IYGVRYTETW SFLPSLTCTG DAAPAIQHIC LKHTTCFQDV VVDVDCAENT   240
KEDQLAEISY RFQGKKEADQ PWIVVNTSTL FDELELDPPE IEPGVLKVLR TEKQYLGVYI   300
WNMRGSDGTS TYATFLVTWK GDEKTRNPTP AVTPQPRGAE FHMWNYHSHV FSVGDTFSLA   360
MHLQYKIHEA PFDLLLEWLY VPIDPTCQPM RLYSTCLYHP NAPQCLSHMN SGCTFTSPHL   420
```

```
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAAR VDK                               573

SEQ ID NO: 70           moltype = RNA  length = 1719
FEATURE                 Location/Qualifiers
misc_feature            1..1719
                        note = Synthetic Polynucleotide
source                  1..1719
                        mol_type = other RNA
                        organism = synthetic construct
SEQUENCE: 70
atggggacag ttaataaacc tgtggtgggg gtattgatgg ggttcggaat tatcacggga  60
acgttgcgta taacgaatcc ggtcagagca tccgtcttgc gatacgatga ttttcacatc  120
gatgaagaca aactggatac aaaactccgta tatgagcctt actaccattc agatcatgcg  180
gagtcttcat gggtaaatcg gggagagtct tcgcgaaaag cgtacgatca taactcacct  240
tatatatggc cacgtaatga ttatgatgga ttttttagaga acgcacacga acaccatggg  300
gtgtataatc agggccgtgg tatcgatagc ggggaacggt taatgcaacc cacacaaatg  360
tctgcacagg aggatcttgg ggacgatacg ggcatccacg ttatccctac gttaaacggc  420
gatgacagac ataaaattgt aaatgtggac caacgtcaat acggtgacgt gtttaaagga  480
gatcttaatc caaaacccca aggccaaaga ctcattgagg tgtcagtgga agaaaatcac  540
ccgtttactt tacgcgcacc gattcagcgg atttatggag tccggtacgac cgagacttgg  600
agcttttttgc cgtcattaac ctgtacggga gacgcagcgc ccgccatcca gcatatatgt  660
ttaaaacata caacatgctt tcaagacgtg gtggtggatg tggattgcgc ggaaaatact  720
aaagaggatc agttggccga aatcagttac cgttttcaag gtaagaagga agcggaccaa  780
ccgtggattg ttgtaaacac gagcacactg tttgatgaac tcgaattaga cccacaccgaa  840
attgaaccgg gtgtcttgaa agtacttcgg acagagaaac aatacttggg tgtgtacatt  900
tggaacatgc gcggctccga tggtacgtct acctacgcca cgttttttggt cacctggaaa  960
ggggatgaga agacaagaaa ccctacgccc gcagtaactc ctcaaccaag aggggctgag  1020
tttcatatgt ggaattacca ctcgcatgta ttttcagttg gtgatacgtt tagcttggca  1080
atgcatcttc agtataagat acatgaagcg ccatttgatt tgctgttaga gtggttgtat  1140
gtccccatcg atcctacatg tcaaccaatg cggttatatt ctacgtgttt gtatcatccc  1200
aacgcacccc aatgcctctc tcatatgaat tccggttgta catttacctc gccacattta  1260
gcccagcgtg ttgcaagcac agtgtatcaa aattgtgaac atgcagataa ctacaccgca  1320
tattgtctgg gaatatctca tatggagcct agctttggtc taatcttaca cgacgggggc  1380
accacgttaa agtttgtaga tacacccgag agtttgtcgg gattatacgt ttttgtggtg  1440
tattttaacg gcatgttga agccgtagca tacactgttg tatccacagt agatcatttt  1500
gtaaacgcaa ttgaagagcg tggatttccg ccaacggccg tcagccacc ggcgactact  1560
aaacccaagg aaattacccc cgtaaacccc ggaacgtcac cacttctacg atatgccgca  1620
tggaccggag ggcttgcagc agtagtactt ttatgtctcg taatattttt aatctgtacg  1680
gctaaacgaa tgagggttaa agccgccagg gtagacaag                        1719

SEQ ID NO: 71           moltype = RNA  length = 1990
FEATURE                 Location/Qualifiers
misc_feature            1..1990
                        note = Synthetic Polynucleotide
source                  1..1990
                        mol_type = other RNA
                        organism = synthetic construct
SEQUENCE: 71
gggaaataag agagaaaaga agagtaagaa gaaatataag agccaccatg gggacagtta  60
ataaacctgt ggtgggggta ttgatggggt tcggaattat cacgggaacg ttgcgtataa  120
cgaatccggt cagagcatcc gtcttgcgat acgatgattt tcacatcgat gaagacaaac  180
tggatacaaa ctccgtatat gagccttact accattcaga tcatgcggag tcttcatggg  240
taaatcgggg agagtcttcg cgaaaagcgt acgatcataa ctcaccttat atatggccac  300
gtaatgatta tgatggattt ttagagaacg cacacgaaca ccatgggtg tataatcagg  360
gccgtggtat cgatagcggg gaacggttaa tgcaacccac acaaatgtct gcacaggagg  420
atcttgggga cgatacgggc atccacgtta tccctacgtt aaacggcgat gacagacata  480
aaattgtaaa tgtggaccaa cgtcaatacg gtgacgtgtt taaaggagat cttaatccaa  540
aaccccaagg ccaaagactc attgaggtgt cagtggaaga aaatcaccg tttacttttac  600
gcgcaccgat tcagcggatt tatggagtcc ggtacaccga cttggagc tttttgccgt  660
cattaacctg tacgggagac gcagcgcccg ccatccagca tatatgttta aaacatacaa  720
catgctttca agacgtggtg gtggatgtgg attgcgcgga aaatactaaa gaggatcagt  780
tggccgaaat cagttaccgt tttcaaggta gaaggaaccg gaccaaccg tggattgttg  840
taaacacgag cacactgttt gatgaactcg aattagaccc acccgagatt gaaccgggtg  900
tcttgaaagt acttcggaca gagaacaat acttgggtgt gtacatttgg aacatgcgcg  960
gctccgatgt acgtctacc tacgccacgt ttttggtcac ctggaaaggg gatgagaaga  1020
caagaaaccc tacgcccgca gtaactcctc aaccaagagg ggctgagttt catatgtgga  1080
attaccactc gcatgtattt cagttggtg atacgttttag cttggcaatg catcttcagt  1140
ataagataca tgaagcgcca tttgatttgc tgttagagtg gttgtatgtc cccatcgatc  1200
ctacatgtca accaatgcgg ttatattcta cgtgtttgta tcatcccaac gcaccccaat  1260
gcctctctca tatgaattcc ggttgtacat ttacctcgcc acatttagcc cagcgtgttg  1320
caagcacagt gtatcaaaat tgtgaacatg cagataacta caccgcatat tgtctgggaa  1380
tatctcatgg ggagcctagc tttggtctaa tcttacacg cgggggccac acgttaaagt  1440
ttgtagatac acccgagagt ttgtcggat tatacgtttt tgtggtgtat tttaacggc  1500
atgttgaagc gtagcatac actgttgtat ccacagtaga tcattttgta aacgcaattg  1560
aagagcgtga atttccgcca acggccggtc agccaccggc gactactaaa cccaaggaaa  1620
ttaccccccgt aaaccccgga acgtcaccac ttctacgata tgccgcatgg accggagggc  1680
ttgcagcagt agtactttta tgtctcgtaa tatttttaat ctgtacggct aaacgaatga  1740
```

```
gggttaaagc cgccagggta gacaagtgat aataggctgg agcctcggtg gccatgcttc  1800
ttgccccttg ggcctccccc cagcccctcc tccccttcct gcacccgtac ccccgtggtc  1860
tttgaataaa gtctgagtgg gcggcaaaaa aaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaatctag                                                        1990

SEQ ID NO: 72              moltype = RNA   length = 1885
FEATURE                    Location/Qualifiers
misc_feature               1..1885
                           note = Synthetic Polynucleotide
source                     1..1885
                           mol_type = other RNA
                           organism = synthetic construct
SEQUENCE: 72
gggaaataag agagaaaaga agagtaagaa gaaatataag agccaccatg gggacagtta  60
ataaacctgt ggtgggggta ttgatggggt tcggaattat cacgggaacg ttgcgtataa  120
cgaatccggt cagagcatcc gtcttgcgat acgatgattt tcacatcgat gaagacaaac  180
tggatacaaa ctccgtatat gagccttact accattcaga tcatcggaag tcttcatggg  240
taaatcgggg agagtcttcg cgaaaggcgt acgatcataa ctcaccttat atatggccac  300
gtaatgatta tgatggattt ttagagaacg cacacgaaca ccatggggtg tataatcagg  360
gccgtggtat cgatagcggg gaacggttaa tgcaacccac acaaatgtct gcacaggagg  420
atcttgggga cgatacgggc atccacgtta tccctacgtt aaacggcgat gacagacata  480
agattgtaaa tgtggaccaa cgtcaatacg gtgacgtgtt taaaggagat cttaatccaa  540
agccccaagg ccaaagactc attgaggtgt cagtggaaga gaatcacccg tttactttac  600
gcgcaccgat tcagcggatt tatggagtcc ggtacaccga gacttggagc tttttgccgt  660
cattaacctg tacgggagac gcagcgcccg ccatccgacg tatatgttta aagcatacaa  720
catgctttca agacgtggtg gtggatgtgg attgcgcgga gaatactaaa gaggatcagt  780
tggccgaaat cagttaccgt tttcaaggta agaaggaagc ggaccaaccg tggattgttg  840
taaacacgag cacactgttt gatgaactcg aattagaccc ccccgagatt gaaccggggtg  900
tcttgaaagt acttcggaca gagaaacaat acttgggtgt gtacatttgg aacatgcgcg  960
gctccgatgg tacgtctacc tacgccacgt tttttggtcac ctggaaaggg gatgagaaga  1020
caagaaaccc tacgcccgca gtaactcctc aaccaagagg ggctgagttt catatgtgga  1080
attaccactc gcatgtattt tcagttggtg atacgtttag cttggcaatg catcttcagt  1140
ataagataca tgaagcgcca tttgatttgc tgttagagtg gttgtatgtc cccatcgatc  1200
ctacatgtca accaatgcgg ttatattcta cgtgtttgta tcatcccaac gcaccccaat  1260
gcctctctca tatgaattcc ggttgtacat ttacctcgcc acatttagcc cagcgtgttg  1320
caagcacagt gtatcagaat tgtgaacatg cagataacta caccgcatat tgtctgggaa  1380
tatctcatat ggagcctagc tttggtctaa tcttacacga cggggggcacc acgttaaagt  1440
ttgtagatac acccgagagt ttgtcgggat atacgttttt tgtggtgtat tttaacgggc  1500
atgttgaagc cgtagcatac actgttgtat ccacagtaga tcattttgta aacgcaattg  1560
aagagcgtgg atttccgcca acggccggtc agccaccggc gactactaaa cccaaggaaa  1620
ttaccccgt aaacccggga acgtcaccac ttctacgata tgccgcatgg accggaggggc  1680
ttgcagcagt agtactttta tgtctcgtaa tattttaat ctgtacggct aaacgaatga  1740
gggttaaagc cgccagggta gacaagtgat aataggctgg agcctcggtg gccatgcttc  1800
ttgcccccttg ggcctccccc cagcccctcc tccccttcct gcacccgtac ccccgtggtc  1860
tttgaataaa gtctgagtgg gcggc                                        1885

SEQ ID NO: 73              moltype = AA   length = 573
FEATURE                    Location/Qualifiers
REGION                     1..573
                           note = Synthetic Polypeptide
source                     1..573
                           mol_type = protein
                           organism = synthetic construct
SEQUENCE: 73
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAAR VDK                               573

SEQ ID NO: 74              moltype = RNA   length = 1719
FEATURE                    Location/Qualifiers
misc_feature               1..1719
                           note = Synthetic Polynucleotide
source                     1..1719
                           mol_type = other RNA
                           organism = synthetic construct
SEQUENCE: 74
atggggacag ttaataaacc tgtggtgggg gtattgatgg ggttcggaat tatcacggga  60
acgttgcgta taacgaatcc ggtcagagca tccgtcttgc gatacgatga ttttcacatc  120
gatgaagaca aactggatac aaactccgta tatgagcctt actaccattc agatcatgcg  180
gagtcttcat gggtaaatcg gggagagtct tcgcgaaagg cgtacgatca taactcacct  240
tatatatggc cacgtaatga ttatgatgga ttttagaga acgcacacga acaccatggg  300
```

-continued

```
gtgtataatc agggccgtgg tatcgatagc ggggaacggt taatgcaacc cacacaaatg   360
tctgcacagg aggatcttgg ggacgatacg ggcatccacg ttatccctac gttaaacggc   420
gatgacagac ataagattgt aaatgtggac caacgtcaat acggtgacgt gtttaaagga   480
gatcttaatc caaagcccca aggccaaaga ctcattgagg tgtcagtgga agagaatcac   540
ccgtttactt tacgcgcacc gattcagcgg atttatggag tccggtacac cgagacttgg   600
agcttttttgc cgtcattaac ctgtacggga gacgcagcgc ccgccatcca gcatatatgt   660
ttaaagcata caacatgctt tcaagacgtg gtggtggatg tggattgcgc ggagaatact   720
aaagaggatc agttggccga aatcagttac cgttttcaag gtaagaagga agcggaccaa   780
ccgtggattg ttgtaaacac gagcacactg tttgatgaac tcgaattaga cccccccagg   840
attgaaccgg gtgtcttgaa agtacttcgg acagagaaac aatacttggg tgtgtacatt   900
tggaacatgc gcggctccga tggtacgtct acctacgcca cgttttttggt cacctggaaa   960
ggggatgaga agacaagaaa ccctacgccc gcagtaactc ctcaaccaag aggggctgag  1020
tttcatatgt ggaattacca ctcgcatgta ttttcagttg gtgatacgtt tagcttggca  1080
atgcatcttc agtataagat acatgaagcg ccatttgatt tgctgttaga gtggttgtat  1140
gtccccatcg atcctacatg tcaaccaatg cggttatatt ctacgtgttt gtatcatccc  1200
aacgcacccc aatgcctctc tcatatgaat tccggttgta catttacctc gccacattta  1260
gcccagcgtg ttgcaagcac agtgtatcag aattgtgaac atgcagataa ctacaccgca  1320
tattgtctgg gaatatctca tatggagcct agctttggtc taatcttaca cgacgggggc  1380
accacgttaa agtttgtaga tacacccgag agtttgtcgg gattatacgt ttttgtggtg  1440
tattttaacg ggcatgttga agccgtagca tacactgttg tatccacagt agatcatttt  1500
gtaaacgcaa ttgaagagcg tggatttccg ccaacggccg gtcagccacc ggcgactact  1560
aaacccaagg aaattacccc cgtaaacccc ggaacgtcac cacttctacg atatgccgca  1620
tggaccggag ggcttgcagc agtagtactt ttatgtctcg taatattttt aatctgtacg  1680
gctaaacgaa tgagggttaa agccgccagg gtagacaag                         1719

SEQ ID NO: 75          moltype = RNA  length = 1990
FEATURE                Location/Qualifiers
misc_feature           1..1990
                       note = Synthetic Polynucleotide
source                 1..1990
                       mol_type = other RNA
                       organism = synthetic construct
SEQUENCE: 75
gggaaataag agagaaaaga agagtaagaa gaaatataag agccaccatg gggacagtta   60
ataaacctgt ggtgggggta ttgatggggt tcggaattat cacgggaacg ttgcgtataa  120
cgaatccggt cagagcatcc gtcttgcgat acgatgattt tcacatcgat gaagacaaac  180
tggatacaaa ctccgtatat gagccttact accattcaga tcatgcggag tcttcatggg  240
taaatcgggg agagtcttcg cgaaaggcgt acgatcataa ctcaccttat atatggccac  300
gtaatgatta tgatggattt ttagagaacg cacacgaaca catcgggggtg tataatcagg  360
gccgtggtat cgatagcggg gaacggttaa tgcaacccac acaaatgtct gcacaggagg  420
atcttgggga cgatacgggc atccacgtta tccctacgtt aaacggcgat gacagacata  480
agattgtaaa tgtggaccaa cgtcaatacg gtgacgtgtt taaaggagat cttaatccaa  540
agccccaagg ccaaagactc attgaggtgt cagtggaaga gaatcacccg tttactttac  600
gcgcaccgat tcagcggatt tatggagtcc ggtacaccga cttggagc tttttgccgt     660
cattaacctg tacgggagac gcagcgcccg ccatccagca tatatgttta aagcatacaa  720
catgctttca gacgtggtg gtggatgtgg attgcgcgga gaatactaaa gaggatcagt    780
tggccgaaat cagttaccgt tttcaaggta agaaggaagc ggaccaaccg tggattgttg  840
taaacacgag cacactgttt gatgaactcg aattagaccc ccccgagatt gaaccgggtg  900
tcttgaaagt acttcggaca gagaacaat acttgggtgt gtacatttgg aacatgcgcg     960
gctccgatgt tacgtctacc tacgccacgt ttttggtcac ctggaaaggg gatgagaaga  1020
caagaaaccc tacgcccgca gtaactcctc aaccaaggg ggctgagttt catatgtcagt    1080
attaccactc gcatgtattt tcagttggtg atacgtttag cttggcaatg catcttcagt  1140
ataagataca tgaagcgcca tttgatttgc tgttagagtg gttgtatgtc cccatcgatc  1200
ctacatgtca accaatgcgg ttatattcta cgtgtttgta tcatcccaac gcaccccaat  1260
gcctctctca tatgaattcc ggttgtacat ttacctcgcc acatttagcg cagcgtgttg  1320
caagcacagt gtatcagaat tgtgaacatg cagataacta caccgcatat tgtctgggga  1380
tatctcatat ggagcctagc tttggtctaa tcttacacga cgggggcacc acgttaaagt  1440
ttgtagatac acccgagagt ttgtcgggat tatacgtttt tgtggtgtat tttaacgggc  1500
atgttgaagc cgtagcatac actgttgtat ccacagtaga tcattttgta aacgcaattg  1560
aagagcgtgg atttccgcca acggccggtc agccaccggc gactactaaa cccaaggaaa  1620
ttaccccgt aaaccccgga acgtcaccac ttctacgata tgccgcatgg accggaggggc   1680
ttgcagcagt actttta tgtctcgtaa tattttttaat ctgtacggct aaacgaatga     1740
gggttaaagc cgcagggta gacaagtgat aataggctgg agccttcggtg gccatgcttc   1800
ttgccccttg ggcctccccc cagcccctcc tccccttcct gcaccccgtac cccgtggtc    1860
tttgaataaa gtctgagtgg gcggcaaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaatctag                                                        1990

SEQ ID NO: 76          moltype = RNA  length = 1885
FEATURE                Location/Qualifiers
misc_feature           1..1885
                       note = Synthetic Polynucleotide
source                 1..1885
                       mol_type = other RNA
                       organism = synthetic construct
SEQUENCE: 76
gggaaataag agagaaaaga agagtaagaa gaaatataag agccaccatg gggacagtta   60
ataaacctgt ggtgggggta ttgatggggt tcggaattat cacgggaacg ttgcgtataa  120
cgaatccggt cagagcatcc gtcttgcgat acgatgattt tcacatcgat gaagacaaac  180
```

-continued

```
tggatacaaa ctccgtatat gagccttact accattcaga tcatgcggag tcttcatggg   240
taaatcgggg agagtcttcg cgaaaggcgt acgatcataa ctcaccttat atatggccac   300
gtaatgatta tgatggattt ttagagaacg cacacgaaca ccatgggtg tataatcagg    360
gccgtggtat cgatagcggg gaacggttaa tgcaacccac acaaatgtct gcacaggagg   420
atcttgggga cgatacgggc atccacgtta tccctacgtt aaacggcgat gacagacata   480
agattgtaaa tgtggaccaa cgtcaatacg gtgacgtgtt taaaggagat cttaatccaa   540
agccccaagg ccaaagactc attgaggtgt cagtggaaga gaatcacccg tttactttac   600
gcgcaccgat tcagcggatt tatggagtcc ggtacaccga gacttggagc tttttgccgt   660
cattaacctg tacgggagac gcagcgcccg ccatccagca tatatgttta aagcatacaa   720
catgctttca agacgtggtg gtggatgtgg attgcgcgga gaatactaaa gaggatcagt   780
tggccgaaat cagttaccgt tttcaaggta agaaggaagc ggaccaaccg tggattgttg   840
taaacacgag cacactgttt gatgaactcg aattagaccc acccgagatt gaaccgggtg   900
tcttgaaagt acttcggaca gagaaacaat acttgggtgt gtacatttgg aacatgcgcg   960
gctccgatgg tacgtctacc tacgccacgt ttttggtcac ctggaaaggg gatgagaaga  1020
caagaaaccc tacgcccgca gtaactcctc aaccaagagg ggctgagttt catatgtgga  1080
attaccactc gcatgtattt tcagttggtg atacgtttag cttggcaatg catcttcagt  1140
ataagataca tgaagcgcca tttgatttgc tgttagagtg gttgtatgtc cccatcgatc  1200
ctacatgtca accaatgcgg ttatattcta cgtgtttgta tcatcccaac gcaccccaat  1260
gcctctctca tatgaattcc ggttgtacat ttacctcgcc acatttagcc cagcgtgttg  1320
caagcacagt gtatcagaat tgtgaacatg cagataacta caccgcatat tgtctgggaa  1380
tatctctat ggagcctagc tttggtctaa tcttacacga cggggggcacc acgttaaagt  1440
ttgtagatac acccgagagt ttgtcgggat tatacgtttt tgtggtgtat tttaacgggc  1500
atgttgaagc cgtagcatac actgttgtat ccacagtaga tcattttgta aacgcaattg  1560
aagagcgtgg atttccgcca acggccggtc agccaccggc gactactaaa cccaaggaaa  1620
ttaccccgt aaaccccgga acgtcaccac ttctacgata tgccgcatgg accggagggc   1680
ttgcagcagt agtactttta tgtctcgtaa tatttttaat ctgtacggct aaacgaatga  1740
gggttaaagc cgccagggta gacaagtgat aataggctgg agcctcggtg gccatgcttc  1800
ttgccccttg ggcctcccc cagcccctcc tccccttcct gcacccgtac ccccgtggtc   1860
tttgaataaa gtctgagtgg gcggc                                        1885
```

SEQ ID NO: 77          moltype = AA   length = 573
FEATURE                Location/Qualifiers
REGION                 1..573
                       note = Synthetic Polypeptide
source                 1..573
                       mol_type = protein
                       organism = synthetic construct
SEQUENCE: 77

```
MGTVNKPVVG VLMGFGIITG TLRITNPVRA SVLRYDDFHI DEDKLDTNSV YEPYYHSDHA   60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAAR VDK                               573
```

SEQ ID NO: 78          moltype = RNA   length = 1719
FEATURE                Location/Qualifiers
misc_feature          1..1719
                       note = Synthetic Polynucleotide
source                 1..1719
                       mol_type = other RNA
                       organism = synthetic construct
SEQUENCE: 78

```
atggggacag ttaataaacc tgtggtgggg gtattgatgg ggttcggaat tatcacggga   60
acgttgcgta taacgaatcc ggtcagagca tccgtcttgc gatacgatga ttttccacatc  120
gatgaagaca aactggatac aaactccgta tatgagcctt actaccattc agatcatgcg   180
gagtcttcat gggtaaatcg gggagagtct tcgcgaaagg cgtacgatca taactcacct   240
tatatatggc cacgtaatga ttatgatgga ttttttagaga acgcacacga acaccatggg  300
gtgtataatc agggccgtgg tatcgatagc ggggaacggt taatgcaacc cacacaaatg  360
tctgcacagg aggatcttgg ggacgatacg ggcatccacg ttatccctac gttaaacgga  420
gatgacagac ataagattgt aaatgtggac caacgtcaat acggtgacgt gtttaaagga  480
gatcttaatc caaagcccca aggccaaaga ctcattgagg tgtcagtgga gagaatcac   540
ccgtttactt tacgcgcacc gattcagcgg atttatggag tccggtacac cgagacttgg  600
agctttttgc cgtcattaac ctgtacggga gacgcagcgc ccgccatcca gcatatatgt  660
ttaaagcata caacatgctt tcaagacgtg gtggtggatg tggattgcgc ggagaatact  720
aaagaggatc agttggccga aatcagttac cgttttcaag gtaagaagga agcggaccaa  780
ccgtggattg ttgtaaacac gagcacactg tttgatgaac tcgaattaga cccacccgag  840
attgaaccgg gtgtcttgaa agtacttcgg acagagaaac aatacttggg tgtgtacatt  900
tggaacatgc gcggctccga tggtacgtct acctacgcca cgttttttggt cacctggaaa  960
ggggatgaga agacaagaaa ccctacgccc gcagtaactc ctcaaccaag aggggctgag 1020
tttcatatgt ggaattacca ctcgcatgta ttttcagttg gtgatacgtt tagcttggca 1080
atgcatcttc agtataagat acatgaagcg ccatttgatt tgctgttaga gtggttgtat 1140
gtccccatcg atcctacatg tcaaccaatg cggttatatt ctacgtgttt gtatcatccc 1200
aacgcacccc aatgcctctc tcatatgaat tccggttgta catttacctc gccacattta 1260
gcccagcgtg ttgcaagcac agtgtatcag aattgtgaac atgcagataa ctacaccgca 1320
```

-continued

```
tattgtctgg gaatatctca tatggagcct agctttggtc taatcttaca cgacggggc    1380
accacgttaa agtttgtaga tacacccgag agtttgtcgg gattatacgt ttttgtggtg    1440
tattttaacg ggcatgttga agccgtagca tacactgttg tatccacagt agatcatttt    1500
gtaaacgcaa ttgaagagcg tggatttccg ccaacggccg gtcagccacc ggcgactact    1560
aaacccaagg aaattacccc cgtaaacccc ggaacgtcac cacttctacg atatgccgca    1620
tggaccggag ggcttgcagc agtagtactt ttatgtctcg taatattttt aatctgtacg    1680
gctaaacgaa tgagggttaa agccgccagg gtagacaag                          1719
```

```
SEQ ID NO: 79          moltype = RNA  length = 1990
FEATURE                Location/Qualifiers
misc_feature           1..1990
                       note = Synthetic Polynucleotide
source                 1..1990
                       mol_type = other RNA
                       organism = synthetic construct
SEQUENCE: 79
gggaaataag agagaaaaga agagtaagaa gaaatataag agccaccatg gggacagtta    60
ataaacctgt ggtgggggta ttgatggggt tcggaattat cacgggaacg ttgcgtataa    120
cgaatccggt cagagcatcc gtcttgcgat acgatgattt tcacatcgat gaagacaaac    180
tggatacaaa ctccgtatat gagccttact accattcaga tcatgcggag tcttcatggg    240
taaatcgggg agagtcttcg cgaaaggcgt acgatcataa ctcaccttat atatggccac    300
gtaatgatta tgatggattt ttagagaacg cacacgaaca ccatggggtg tataatcagg    360
gccgtggtat cgatagcggg gaacggttaa tgcaacccac acaaatgtct gcacaggagg    420
atcttgggga cgatacgggc atccacgtta tccctacgtt aaacggcgat gacagacata    480
agattgtaaa tgtggaccaa cgtcaatacg gtgacgtgtt taaaggagat cttaatccaa    540
agccccaagg ccaaagactc attgaggtgt cagtggaaga gaatcacccg tttactttac    600
gcgcaccgat tcagcggatt tatggagtcc ggtacaccga acttggagc ttttgccgt     660
cattaacctg tacgggagac gcagcgcccg ccatccagca tatatgttta aagcatacaa    720
catgctttca agacgtggtg gtggatgtgg attgcgcgga gaatactaaa gaggatcagt    780
tggccgaaat cagttaccgt tttcaaggta agaaggaagc ggaccaaccg tggattgttg    840
taaacacgag cacactgttt gatgaactcg aattagaccc acccgagatt gaaccgggtg    900
tcttgaaagt acttcggaca gagaaacaat acttgggtgt gtacatttgg aacatgcgcg    960
gctccgatgg tacgtctacc tacgccacgt ttttggtcac ctggaaaggg gatgagaaga   1020
caagaaaccc tacgcccgca gtaactcctc aaccaagagg ggctgagttt catatgtgga   1080
attaccactc gcatgtattt tcagttggtg atacgtttag cttggcaatg catcttcagt   1140
ataagataca tgaagcgcca tttgatttgc tgttagagtg gttgtatgtc cccatcgatc   1200
ctacatgtca accaatgcgg ttatattcta cgtgtttgta tcatcccaac gcaccccaat   1260
gcctctctca tatgaattcc ggttgtacat ttacctcgcc acatttagcc cagcgtgttg   1320
caagcacagt gtatcagaat tgtgaacatg cagataacta caccgcatat tgtctgggaa   1380
tatctcatat ggagcctagc tttggtctaa tcttacacga cggggcacc acgttaaagt    1440
ttgtagatac acccgagagt ttgtcggat tatacgtttt tgtggtgtat tttaacgggc    1500
atgttgaagc cgtagcatac actgttgtat ccacagtaga tcattttgta aacgcaattg    1560
aagagcgtgg atttccgcca acggccggtc agccaccggc gactactaaa cccaaggaaa   1620
ttaccccgt aaaccccgga acgtcaccac ttctacgata tgccgcatgg accgggggc     1680
ttgcagcagt agtactttta tgtctcgtaa tatttttaat ctgtacggct aaacgaatga   1740
gggttaaagc cgccagggta gacaagtgat aataggctgg agcctcggtg gccatgcttc   1800
ttgcccccttg ggcctcccccc cagccccctcc tccccttcct gcacccgtac ccccgtggtc   1860
tttgaataaa gtctgagtgg gcggcaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaatctag                                                         1990
```

```
SEQ ID NO: 80          moltype = RNA  length = 1885
FEATURE                Location/Qualifiers
misc_feature           1..1885
                       note = Synthetic Polynucleotide
source                 1..1885
                       mol_type = other RNA
                       organism = synthetic construct
SEQUENCE: 80
gggaaataag agagaaaaga agagtaagaa gaaatataag agccaccatg gggacagtta    60
ataaacctgt ggtgggggta ttgatggggt tcggaattat cacgggaacg ttgcgtataa    120
cgaatccggt cagagcatcc gtcttgcgat acgatgattt tcacatcgat gaagacaaac    180
tggatacaaa ctccgtatat gagccttact accattcaga tcatgcggag tcttcatggg    240
taaatcgggg agagtcttcg cgaaaagcgt acgatcataa ctcaccttat atatggccac    300
gtaatgatta tgatggattt ttagagaacg cacacgaaca ccatggggtg tataatcagg    360
gccgtggtat cgatagcggg gaacggttaa tgcaacccac acaaatgtct gcacaggagg    420
atcttgggga cgatacgggc atccacgtta tccctacgtt aaacggcgat gacagacata    480
aaattgtaaa tgtggaccaa cgtcaatacg gtgacgtgtt taaaggagat cttaatccaa    540
aaccccaagg ccaaagactc attgaggtgt cagtggaaga aaatcacccg tttactttac    600
gcgcaccgat tcagcggatt tatggagtcc ggtacaccga acttggagc ttttgccgt     660
cattaacctg tacgggagac gcagcgcccg ccatccagca tatatgttta aagcatacaa    720
catgctttca agacgtggtg gtggatgtgg attgcgcgga aaatactaaa gaggatcagt    780
tggccgaaat cagttaccgt tttcaaggta agaaggaagc ggaccaaccg tggattgttg    840
taaacgag cacactgttt gatgaactcg aattagaccc acccgagatt gaaccgggtg      900
tcttgaaagt acttcggaca gagaaacaat acttgggtgt gtacatttgg aacatgcgcg    960
gctccgatgg tacgtctacc tacgccacgt ttttggtcac ctggaaaggg gatgagaaga   1020
caagaaaccc tacgcccgca gtaactcctc aaccaagagg ggctgagttt catatgtgga   1080
attaccactc gcatgtattt tcagttggtg atacgtttag cttggcaatg catcttcagt   1140
ataagataca tgaagcgcca tttgatttgc tgttagagtg gttgtatgtc cccatcgatc   1200
```

```
ctacatgtca accaatgcgg ttatattcta cgtgtttgta tcatcccaac gcacccaat  1260
gcctctctca tatgaattcc ggttgtacat ttacctcgcc acatttagcc cagccgtgttg  1320
caagcacagt gtatcagaat tgtgaacatg cagataacta caccgcatat tgtctgggaa  1380
tatctcatat ggagcctagc tttggtctaa tcttacacga cggggggcacc acgttaaagt  1440
ttgtagatac acccgagagt ttgtcgggat tatacgtttt tgtggtgtat tttaacgggc  1500
atgttgaagc cgtagcatac actgttgtat ccacagtaga tcattttgta aacgcaattg  1560
aagagcgtgg atttccgcca acggccggtc agccaccggc gactactaaa cccaaggaaa  1620
ttaccccgt aaaccccgga acgtcaccac ttctacgata tgccgcatgg accggagggc  1680
ttgcagcagt agtactttta tgtctcgtaa tatttttaat ctgtacggct aaacgaatga  1740
gggttaaagc cgccagggta gacaagtgat aataggctgg agcctcggtg gccatgcttc  1800
ttgccccttg ggcctccccc cagccctcc tccccttcct gcaccagtac ccccgtggtc  1860
tttgaataaa gtctgagtgg gcggc                                     1885
```

```
SEQ ID NO: 81              moltype = AA  length = 573
FEATURE                    Location/Qualifiers
REGION                     1..573
                           note = Synthetic Polypeptide
source                     1..573
                           mol_type = protein
                           organism = synthetic construct
SEQUENCE: 81
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAAR VDK                             573
```

```
SEQ ID NO: 82              moltype = RNA  length = 1719
FEATURE                    Location/Qualifiers
misc_feature               1..1719
                           note = Synthetic Polynucleotide
source                     1..1719
                           mol_type = other RNA
                           organism = synthetic construct
SEQUENCE: 82
atggggacag ttaataaacc tgtggtgggg gtattgatgg ggttcggaat tatcacggga  60
acgttgcgta taacgaatcc ggtcagagca tccgtcttgc gatacgatga tttttcacatc  120
gatgaagaca aactggatac aaactccgta tatgagcctt actaccattc agatcatgcg  180
gagtcttcat gggtaaatcg gggagagtct tcgcgaaaag cgtacgatca taactcacct  240
tatatatggc cacgtaatga ttatgatgga ttttttagaga acgcacacga acaccatggg  300
gtgtataatc agggccgtgg tatcgatagc ggggaacggt taatgcaacc cacacaaatg  360
tctgcacagg aggatcttgg ggacgatacg ggcatccacg ttatccctac gttaaacggc  420
gatgacagac ataaaattgt aaatgtggac caacgtcaat acggtgacgt gtttaaagga  480
gatcttaatc caaaacccca aggccaaaga ctcattgagg tgtcagtgga agaaaatcac  540
ccgtttactt tacgcgcacc gattcagcgg atttatggag tccggtacac cgagacttgg  600
agctttttgc cgtcattaac ctgtacggga gacgcagcgc ccgccatcca gcatatatgt  660
ttaaagcata caacatgctt tcaagacgtg gtggtggatg tggattgcgc ggaaaatact  720
aaagaggatc agttggccga aatcagttac cgttttcaag gtaagaagga agcggaccaa  780
ccgtggattg ttgtaaacac gagcacactg tttgatgaac tcgaattaga ccccccggag  840
attgaaaccgg gtgtcttgaa agtacttcgg acagagaaac aatacttggg tgtgtacatt  900
tggaacatgc gcggctccga tggtacgtct acctacgcca cgttttttggt cacctggaaa  960
ggggatgaga agacaagaaa ccctacgccc gcagtaactc ctcaaccaag aggggctgag  1020
tttcatatgt ggaattacca ctcgcatgta ttttcagttg gtgatacgtt tagcttggca  1080
atgcatcttc agtataagat acatgaagcg ccatttgatt tgctgttaga gtggttgtat  1140
gtccccatcg atcctacatg tcaaccaatg cggttatatt ctacgtgttt gtatcatccc  1200
aacgcacccc aatgcctctc tcatatgaat tccggttgta catttacctc gccacattta  1260
gcccagcgtg ttgcaagcac agtgtatcag aattgtgaac atgcagataa ctacaccgca  1320
tattgtctgg gaatatctca tatggagcct agctttggtc taatcttaca cgacggggggc  1380
accacgttaa agtttgtaga tacacccgag agtttgtcgg gattatacgt ttttgtggtg  1440
tattttaacg ggcatgttga agccgtagca tacactgttg tatccacagt agatcatttt  1500
gtaaacgcaa ttgaagagcg tggatttccg ccaacggccg gtcagccacc ggcgactact  1560
aaacccaagg aaattacccc cgtaaacccc ggaacgtcac cacttctacg atatgccgca  1620
tggaccggag ggcttgcagc agtagtactt ttatgtctcg taatattttt aatctgtacg  1680
gctaaacgaa tgagggttaa agccgccagg gtagacaag                       1719
```

```
SEQ ID NO: 83              moltype = RNA  length = 1990
FEATURE                    Location/Qualifiers
misc_feature               1..1990
                           note = Synthetic Polynucleotide
source                     1..1990
                           mol_type = other RNA
                           organism = synthetic construct
SEQUENCE: 83
gggaaataag agagaaaaga agagtaagaa gaaatataag agccaccatg gggacagtta  60
```

-continued

```
ataaacctgt ggtgggggta ttgatggggt tcggaattat cacgggaacg ttgcgtataa   120
cgaatccggt cagagcatcc gtcttgcgat acgatgattt tcacatcgat gaagacaaac   180
tggatacaaa ctccgtatat gagccttact accattcaga tcatgcggag tcttcatggg   240
taaatcgggg agagtcttcg cgaaaagcgt acgatcataa ctcaccttat atatggccac   300
gtaatgatta tgatggattt ttagagaacg cacacgaaca ccatggggtg tataatcagg   360
gccgtggtat cgatagcggg gaacggttaa tgcaacccac acaaatgtct gcacaggagg   420
atcttgggga cgatacgggc atccacgtta tccctacgtt aaacggcgat gacagacata   480
aaattgtaaa tgtggaccaa cgtcaatacg gtgacgtgtt taaaggagat cttaatccaa   540
aaccccaagg ccaaagactc attgaggtgt cagtggaaga aaatcacccg tttactttac   600
gcgcaccgat tcagcggatt tatggagtcc ggtacaccga gacttggagc tttttgccgt   660
cattaacctg tacgggagac gcagcgcccg ccatccagca tatatgttta aagcatacaa   720
catgctttca agacgtggtg gtggatgtgg attgcgcgga aaatactaaa gaggatcagt   780
tggccgaaat cagttaccgt tttcaaggta agaaggaagc ggaccaaccg tggattgttg   840
taaacacgag cacactgttt gatgaactcg aattagaccc ccccgagatt gaaccgggtg   900
tcttgaaagt acttcggaca gagaaacaat acttgggtgt gtacatttgg aacatgcgcg   960
gctccgatgg tacgtctacc tacgccacgt ttttggtcac ctggaaaggg gatgagaaga  1020
caagaaaccc tacgcccgca gtaactcctc aaccaagagg ggctgagttt catatgtgga  1080
attaccactc gcatgtattt tcagttggtg atacgtttag cttggcaatg catcttcagt  1140
ataagataca tgaagcgcca tttgatttgc tgttagagtg gttgtatgtc cccatcgatc  1200
ctacatgtca accaatgcgg ttatattcta cgtgtttgta tcatcccaac gcaccccaat  1260
gcctctctca tatgaattcc ggttgtacat ttacctcgcc acatttagcc cagcgtgttg  1320
caagcacagt gtatcagaat tgtgaacatg cagataacta caccgcatat tgtctgggaa  1380
tatctcatat ggagcctagc tttggtctaa tcttacacga cggggggcacc acgttaaagt  1440
ttgtagatac acccgagagt ttgtcgggat tatacgtttt tgtggtgtat tttaacgggc  1500
atgttgaagc cgtagcatac actgttgtat ccacagtaga tcattttgta aacgcaattg  1560
aagagcgtgg atttccgcca acggccggtc agccaccggc gactactaaa cccaaggaaa  1620
ttaccccgt aaaccccgga acgtcaccac ttctacgata tgccgcatgg accggagggc  1680
ttgcagcagt agtactttta tgtctcgtaa tatttttaat ctgtacggct aaacgaatga  1740
gggttaaagc cgccagggta gacaagtgat aataggctgg agcctcggtg gccatgcttc  1800
ttgcccccttg ggcctccccc cagccccctcc tcccccttcct gcaccccgtac ccccgtggtc  1860
tttgaataaa gtctgagtgg gcggcaaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaatctag                                                         1990

SEQ ID NO: 84            moltype = RNA   length = 1885
FEATURE                  Location/Qualifiers
misc_feature            1..1885
                        note = Synthetic Polynucleotide
source                  1..1885
                        mol_type = other RNA
                        organism = synthetic construct SEQUENCE: 84
gggaaataag agagaaaaga agagtaagaa gaaatataag agccaccatg gggacagtta   60
ataaacctgt ggtgggggta ttgatggggt tcggaattat cacgggaacg ttgcgtataa   120
cgaatccggt cagagcatcc gtcttgcgat acgatgattt tcacatcgat gaagacaaac   180
tggatacaaa ctccgtatat gagccttact accattcaga tcatgcggag tcttcatggg   240
taaatcgggg agagtcttcg cgaaaagcgt acgatcataa ctcaccttat atatggccac   300
gtaatgatta tgatggattt ttagagaacg cacacgaaca ccatggggtg tataatcagg   360
gccgtggtat cgatagcggg gaacggttaa tgcaacccac acaaatgtct gcacaggagg   420
atcttgggga cgatacgggc atccacgtta tccctacgtt aaacggcgat gacagacata   480
aaattgtaaa tgtggaccaa cgtcaatacg gtgacgtgtt taaaggagat cttaatccaa   540
aaccccaagg ccaaagactc attgaggtgt cagtggaaga aaatcacccg tttactttac   600
gcgcaccgat tcagcggatt tatggagtcc ggtacaccga gacttggagc tttttgccgt   660
cattaacctg tacgggagac gcagcgcccg ccatccagca tatatgttta aagcatacaa   720
catgctttca agacgtggtg gtggatgtgg attgcgcgga aaatactaaa gaggatcagt   780
tggccgaaat cagttaccgt tttcaaggta agaaggaagc ggaccaaccg tggattgttg   840
taaacacgag cacactgttt gatgaactcg aattagaccc acccgagatt gaaccgggtg   900
tcttgaaagt acttcggaca gagaaacaat acttgggtgt gtacatttgg aacatgcgcg   960
gctccgatgg tacgtctacc tacgccacgt ttttggtcac ctggaaaggg gatgagaaga  1020
caagaaaccc tacgcccgca gtaactcctc aaccaagagg ggctgagttt catatgtgga  1080
attaccactc gcatgtattt tcagttggtg atacgtttag cttggcaatg catcttcagt  1140
ataagataca tgaagcgcca tttgatttgc tgttagagtg gttgtatgtc cccatcgatc  1200
ctacatgtca accaatgcgg ttatattcta cgtgtttgta tcatcccaac gcaccccaat  1260
gcctctctca tatgaattcc ggttgtacat ttacctcgcc acatttagcc cagcgtgttg  1320
caagcacagt gtatcagaat tgtgaacatg cagataacta caccgcatat tgtctgggaa  1380
tatctcatat ggagcctagc tttggtctaa tcttacacga cggggggcacc acgttaaagt  1440
ttgtagatac acccgagagt ttgtcgggat tatacgtttt tgtggtgtat tttaacgggc  1500
atgttgaagc cgtagcatac actgttgtat ccacagtaga tcattttgta aacgcaattg  1560
aagagcgtgg atttccgcca acggccggtc agccaccggc gactactaaa cccaaggaaa  1620
ttaccccgt aaaccccgga acgtcaccac ttctacgata tgccgcatgg accggagggc  1680
ttgcagcagt agtactttta tgtctcgtaa tatttttaat ctgtacggct aaacgaatga  1740
gggttaaagc cgccagggta gacaagtgat aataggctgg agcctcggtg gccatgcttc  1800
ttgcccccttg ggcctccccc cagccccctcc tcccccttcct gcaccccgtac ccccgtggtc  1860
tttgaataaa gtctgagtgg gcggc                                        1885

SEQ ID NO: 85            moltype = AA   length = 573
FEATURE                  Location/Qualifiers
REGION                  1..573
                        note = Synthetic Polypeptide
```

```
source                  1..573
                        mol_type = protein
                        organism = synthetic construct
SEQUENCE: 85
MGTVNKPVVG VLMGFGIITG TLRITNPVRA SVLRYDDFHI DEDKLDTNSV YEPYYHSDHA   60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAAR VDK                               573

SEQ ID NO: 86          moltype = RNA   length = 1719
FEATURE                Location/Qualifiers
misc_feature           1..1719
                       note = Synthetic Polynucleotide
source                 1..1719
                       mol_type = other RNA
                       organism = synthetic construct
SEQUENCE: 86
atggggacag ttaataaacc tgtggtgggg gtattgatgg ggttcggaat tatcacggga   60
acgttgcgta taacgaatcc ggtcagagca tccgtcttgc gatacgatga tttttcacatc  120
gatgaagaca aactggatac aaactccgta tatgagcctt actaccattc agatcatgcg  180
gagtcttcat gggtaaatcg gggagagtct tcgcgaaaag cgtacgatca taactcacct  240
tatatatggc cacgtaatga ttatgatgga ttttagaga acgcacacga acaccatggg   300
gtgtataatc agggccgtgg tatcgatagc ggggaacggt taatgcaacc cacacaaatg  360
tctgcacagg aggatcttgg ggacgatacg ggcatccacg ttatccctac gttaaacggc  420
gatgacagac ataaaattgt aaatgtggac caacgtcaat acggtgacgt gtttaaagga  480
gatcttaatc caaaacccca aggccaaaga ctcattgagg tgtcagtgga agaaaatcac  540
ccgtttactt tacgcgcacc gattcagcgg atttatggag tccggtacac cgagacttgg  600
agctttttgc cgtcattaac ctgtacggga gacgcagcgc ccgccatcca gcatatatgt  660
ttaaagcata caacatgctt tcaagacgtg gtggtgatg tggattgcgc ggaaaatact  720
aaagaggatc agttggccga aatcagttac cgtgttttcaag gtaagaagga agcggaccaa  780
ccgtggattg ttgtaaacac gagcacactg tttgatgaac tcgaattaga cccacccgag  840
attgaaccgg gtgtgtcttgaa agtacttcgg acagagaaac aatacttggg tgtgtacatt  900
tggaacatgc gcggctccga tggtacgtct acctacgcca cgtttttggt cacctggaaa  960
ggggatgaga agacaagaaa ccctacgccc gcagtaactc ctcaaccaag aggggctgag  1020
tttcatatgt ggaattacca ctcgcatgta ttttcagttg gtgatacgtt tagcttggca  1080
atgcatcttc agtataagat acatgaagcg ccatttgatt tgctgttaga gtggttgtat  1140
gtcccatcg atcctacatg tcaaccaatg cggttatatt ctacgtgttt gtatcatccc  1200
aacgcacccc aatgcctctc tcatatgaat tccggttgta catttacctc gccacatta  1260
gcccagcgtg ttgcaagcac agtgtatcag aattgtgaac atgcagataa ctacaccgca  1320
tattgtctgg gaatatctca tatggagcct agctttggtc taatcttaca cgacgggggc  1380
accacgttaa agtttgtaga tacacccgag agtttgtcgg agttatacgt ttttgtggtg  1440
tattttaacg ggcatgttga agccgtagca tacactgttg tatccacagt agatcatttt  1500
gtaaacgcaa ttgaagagcg tggatttccg ccaacggccg tcagccacc ggcgactact  1560
aaacccaagg aaattacccc cgtaaacccc ggaacgtcac cacttctacg atatgccgca  1620
tggaccggag ggcttgcagc agtagtactt ttatgtctcg taatattttt aatctgtacg  1680
gctaaacgaa tgagggttaa agccgccagg gtagacaag              1719

SEQ ID NO: 87          moltype = RNA   length = 1990
FEATURE                Location/Qualifiers
misc_feature           1..1990
                       note = Synthetic Polynucleotide
source                 1..1990
                       mol_type = other RNA
                       organism = synthetic construct
SEQUENCE: 87
gggaaataag agagaaaaga agagtaagaa gaaatataag agccaccatg gggacagtta   60
ataaacctgt ggtggggggta ttgatggggt tcggaattat cacgggaacg ttgcgtataa  120
cgaatccggt cagagcatcc gtcttgcgat acgatgattt tcacatcgag gaagacaaac  180
tggatacaaa ctccgtatat gagccttact accattcaga tcatgcggag tcttcatggg  240
taaatcgggg agagtcttcg cgaaaagcgt acgatcataa ctcaccttat atatggccac  300
gtaatgatta tgatggattt ttagagaacg cacacgaaca ccatggggtg tataatcagg  360
gccgtggtat cgatagcggg gaacggttaa tgcaacccac acaaatgtct gcacaggagg  420
atcttggggg cgatacgggc atccacgtta tccctacgtt aaacggcgat gacagacata  480
aaattgtaaa tgtggaccaa cgtcaatacg gtgacgtgtt taaaggagat cttaatccaa  540
aaccccaagg ccaaagactc attgaggtgt cagtggaaga aaatcacccg tttactttac  600
gcgcaccgat tcagcggatt tatggagtcc ggtacaccga gacttggagc ttttttgccgt  660
cattaacctg tacgggagac gcagcgcccg ccatccagca tatatgttta aagcatacaa  720
catgctttca agacgtggtg gtgatgtcg attgcgcgga aaatactaaa gaggatcagt  780
tggccgaaat cagttaccgt tttcaaggta gaaggaagc ggaccaaccg tggattgttg  840
taaacacgag cacactgttt gatgaactcg aattagaccc acccgagatt gaaccggggtg  900
tcttgaaagt acttcggaca gagaaacaat acttgggtgt gtacatttgg aacatgcgcg  960
gctccgatgg tacgtctacc tacgccacgt tttttggtcac ctggaaaggg gatgagaaga  1020
caagaaaccc tacgcccgca gtaactcctc aaccaagagg ggctgagttt catatgtgga  1080
```

```
attaccactc gcatgtattt tcagttggtg atacgtttag cttggcaatg catcttcagt   1140
ataagataca tgaagcgcca tttgatttgc tgttagagtg gttgtatgtc cccatcgatc   1200
ctacatgtca accaatgcgg ttatattcta cgtgtttgta tcatcccaac gcaccccaat   1260
gcctctctca tatgaattcc ggttgtacat ttacctcgcc acatttagcc cagcgtgttg   1320
caagcacagt gtatcagaat tgtgaacatg cagataacta caccgcatat tgtctgggaa   1380
tatctcatat ggagcctagc tttggtctaa tcttacacga cggggggcacc acgttaaagt   1440
ttgtagatac acccgagagt ttgtcgggat tatacgtttt tgtggtgtat tttaacgggc   1500
atgttgaagc cgtagcatac actgttgtat ccacagtaga tcattttgta aacgcaattg   1560
aagagcgtgg atttccgcca acggccggtc agccaccggc gactactaaa cccaaggaaa   1620
ttaccccgt aaaccccgga acgtcaccac ttctacgata tgccgcatgg accggagggc   1680
ttgcagcagt agtacttta tgtctcgtaa tattttaat ctgtacggct aaacgaatga   1740
gggttaaagc cgccagggta gacaagtgat aataggctgg agcctcggtg gccatgcttc   1800
ttgcccttg ggcctccccc cagccctcc tccccttcct gcaccgtac cccgtggtc    1860
tttgaataaa gtctgagtgg gcggcaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaatctag                                                        1990

SEQ ID NO: 88           moltype = RNA  length = 1885
FEATURE                 Location/Qualifiers
misc_feature            1..1885
                        note = Synthetic Polynucleotide
source                  1..1885
                        mol_type = other RNA
                        organism = synthetic construct SEQUENCE: 88
gggaaataag agagaaaaga agagtaagaa gaaatataag agccaccatg gggacagtta   60
ataaacctgt ggtgggcgta ttgatggggt tcggaattat cacgggaacg ttgcgtataa   120
cgaatccggt cagagcatcc gtcttgcgat acgatgattt tcacatcgat gaagacaaac   180
tggatacaaa ctccgtatat gagccttact accattcaga tcatgcggag tcttcatggg   240
taaatcgggg agagtcttcg cgaaaggcgt acgatcataa ctcaccttat atatggccac   300
gtaatgatta tgatggattc ttagagaacg cacacgaaca ccatgggatg tataatcagg   360
gccgtggtat cgatagcggg gaacggttaa tgcaacccac acaaatgtct gcacaggagg   420
atcttgggga cgatacgggc atccacgtta tccctacgtt aaacggcgat gacagacata   480
agattgtaaa tgtggaccaa cgtcaatacg gtgacgtgtt taaaggagat cttaatccaa   540
agccccaagg ccaaagactc attgaggtgt cagtggaaga gaatcacccg tttactttac   600
gcgcaccgat tcagcggatt tatggagtcc ggtacaccga gacttggagc ttcttgccgt   660
cattaacctg tacgggagac gcagcgcccg ccatccagca tatatgttta aagcatacaa   720
catgctttca agacgtggtg gtggatgtgg attgcgcgga gaatactaaa gaggatcagt   780
tggccgaaat cagttaccgt tttcaaggta agaaggaagc ggaccaaccg ttggattgttg   840
taaacacgag cacactgttt gatgaactcg aattagaccc acccgagatt gaaccgggtg   900
tcttgaaagt acttcggaca gagaaacaat acttgggtgt gtacatttgg aacatgcgcg   960
gctccgatgg tacgtctacc tacgccacgt tcttggtcac ctggaaaggg gatgagaaga   1020
caagaaaccc tacgcccgca gtaactcctc aaccaagagg ggctgagttt catatgtgga   1080
attaccactc gcatgtattt tcagttggtg atacgtttag cttggcaatg catcttcagt   1140
ataagataca tgaagcgcca tttgatttgc tgttagagtg gttgtatgtc cccatcgatc   1200
ctacatgtca accaatgcgg ttatattcta cgtgtttgta tcatcccaac gcaccccaat   1260
gcctctctca tatgaattcc ggttgtacat ttacctcgcc acatttagcc cagcgtgttg   1320
caagcacagt gtatcagaat tgtgaacatg cagataacta caccgcatat tgtctgggaa   1380
tatctcatat ggagcctagc tttggtctaa tcttacacga cggaggcacc acgttaaagt   1440
ttgtagatac acccgagagt ttgtcgggat tatacgtctt tgtggtgtat tttaacgggc   1500
atgttgaagc cgtagcatac actgttgtat ccacagtaga tcattttgta aacgcaattg   1560
aagagcgtgg atttccgcca acggccggtc agccaccggc gactactaaa cccaaggaaa   1620
ttacgcccgt aaaccccgga acgtcaccac ttctacgata tgccgcatgg accggagggc   1680
ttgcagcagt agtacttta tgtctcgtaa tattcttaat ctgtacggct aaacgaatga   1740
gggttaaagc cgccagggta gacaagtgat aataggctgg agcctcggtg gccatgcttc   1800
ttgcccttg ggcctccccc cagccctcc tccccttcct gcaccgtac cccgtggtc    1860
tttgaataaa gtctgagtgg gcggc                                       1885

SEQ ID NO: 89           moltype = AA  length = 573
FEATURE                 Location/Qualifiers
REGION                  1..573
                        note = Synthetic Polypeptide
source                  1..573
                        mol_type = protein
                        organism = synthetic construct SEQUENCE: 89
MGTVNKPVVG VLMGFGIITG TLRITNPVRA SVLRYDDFHI DEDKLDTNSV YEPYYHSDHA   60
ESSWVNRGES SRKAYDHNSP YIWPRNDYDG FLENAHEHHG VYNQGRGIDS GERLMQPTQM   120
SAQEDLGDDT GIHVIPTLNG DDRHKIVNVD QRQYGDVFKG DLNPKPQGQR LIEVSVEENH   180
PFTLRAPIQR IYGVRYTETW SFLPSLTCTG DAAPAIQHIC LKHTTCFQDV VVDVDCAENT   240
KEDQLAEISY RFQGKKEADQ PWIVVNTSTL FDELELDPPE IEPGVLKVLR TEKQYLGVYI   300
WNMRGSDGTS TYATFLVTWK GDEKTRNPTP AVTPQPRGAE FHMWNYHSHV FSVGDTFSLA   360
MHLQYKIHEA PFDLLLEWLY VPIDPTCQPM RLYSTCLYHP NAPQCLSHMN SGCTFTSPHL   420
AQRVASTVYQ NCEHADNYTA YCLGISHMEP SFGLILHDGG TTLKFVDTPE SLSGLYVFVV   480
YFNGHVEAVA YTVVSTVDHF VNAIEERGFP PTAGQPPATT KPKEITPVNP GTSPLLRYAA   540
WTGGLAAVVL LCLVIFLICT AKRMRVKAAR VDK                               573

SEQ ID NO: 90           moltype = RNA  length = 1719
FEATURE                 Location/Qualifiers
```

-continued

```
misc_feature          1..1719
                      note = Synthetic Polynucleotide
source                1..1719
                      mol_type = other RNA
                      organism = synthetic construct
SEQUENCE: 90
atggggacag ttaataaacc tgtggtgggc gtattgatgg ggttcggaat tatcacggga    60
acgttgcgta taacgaatcc ggtcagagca tccgtcttgc gatacgatga ttttcacatc   120
gatgaagaca aactggatac aaactccgta tatgagcctt actaccattc agatcatgcg   180
gagtcttcat gggtaaatcg gggagagtct tcgcgaaagg cgtacgatca taactcacct   240
tatatatggc cacgtaatga ttatgatgga ttcttagaga acgcacacga acaccatggg   300
gtgtataatc agggccgtgg tatcgatagc ggggaacggt taatgcaacc cacacaaatg   360
tctgcacagg aggatcttgg ggacgatacg ggcatccacg ttatccctac gttaaacggc   420
gatgacagac ataagattgt aaatgtggac caacgtcaat acggtgacgt gtttaaagga   480
gatcttaatc caaagcccca aggccaaaga ctcattgagg tgtcagtgga agagaatcac   540
ccgtttactt tacgcgcacc gattcagcgg atttatggag tccggtacac cgagacttgg   600
agcttcttgc cgtcattaac ctgtacggga gacgcagcgc ccgccatcca gcatatatgt   660
ttaaagcata caacatgctt tcaagacgtg gtggtggatg tggattgcgc ggagaatact   720
aaagaggatc agttggccga aatcagttac cgttttcaag gtaagaagga agcggaccaa   780
ccgtggattg ttgtaaacac gagcacactg tttgatgaac tcgaattaga cccacccgag   840
attgaaccgg gtgtcttgaa agtacttcgg acagagaaac aatacttggg tgtgtacatt   900
tggaacatgac gcggctccga tggtacgtct acctacgcca cgttcttggt cacctggaaa   960
ggggatgaga agacaagaaa ccctacgccc gcagtaactc ctcaaccaag aggggctgag  1020
tttcatatgt ggaattacca ctcgcatgta ttttcagttg gtgatacgtt tagcttggca  1080
atgcatcttc agtataagat acatgaagcg ccatttgatt tgctgttaga gtggttgtat  1140
gtccccatcg atcctacatg tcaaccaatg cggttatatt ctacgtgttt gtatcatccc  1200
aacgcacccc aatgcctctc tcatatgaat tccggttgta catttacctc gccacattta  1260
gcccagcgtg ttgcaagcac agtgtatcag aattgtgaac atgcagataa ctacaccgca  1320
tattgtctgg gaatatctca tatggagcct agctttggtc taatcttaca cgacggaggc  1380
accacgttaa agtttgtaga tacacccgag agtttgtcgt gatatacgt ctttgtggtg  1440
tattttaacg ggcatgttga agccgtagca tacactgttg tatccacagt agatcatttt  1500
gtaaacgcaa ttgaagagcg tggatttccg ccaacggccg gtcagccacc ggcgactact  1560
aaacccaagg aaattacgcc cgtaaacccc ggaacgtcac cacttctacg atatgccgca  1620
tggaccggag ggcttgcagc agtagtactt ttatgtctcg taatattctt aatctgtacg  1680
gctaaacgaa tgagggttaa agccgccagg gtagacaag                         1719

SEQ ID NO: 91           moltype = RNA   length = 1990
FEATURE                 Location/Qualifiers
misc_feature            1..1990
                        note = Synthetic Polynucleotide
source                  1..1990
                        mol_type = other RNA
                        organism = synthetic construct
SEQUENCE: 91
gggaaataag agagaaaaga agagtaagaa gaaatataag agccaccatg gggacagtta    60
ataaacctgt ggtgggcgta ttgatggggt tcggaattat cacgggaacg ttgcgtataa   120
cgaatccggt cagagcatcc gtcttgcgat acgatgattt tcacatcgat gaagacaaac   180
tggatacaaa ctccgtatat gagccttact accattcaga tcatgcggag tcttcatggg   240
taaatcgggg agagtcttcg cgaaaggcgt acgatcataa ctcaccttat atatggccac   300
gtaatgatta tgatggattc ttagagaacg cacacgaaca ccatgggtg tataatcagg   360
gccgtggtat cgatagcggg gaacggttaa tgcaacccac aaaatgtct gcacaggtat   420
atcttgggga cgatacgggc atccacgtta tccctacgtt aaacggcgat gacagacata   480
agattgtaaa tgtggaccaa cgtcaatacg gtgacgtgtt taaaggagat cttaatccaa   540
agccccaagg ccaaagactc attgaggtgt cagtggaaga gaatcacccg tttactttac   600
gcgcaccgat tcagcggatt tatggagtcc ggtacacgac cttggagc ttcttgccgt   660
cattaacctg tacgggagac gcagcgcccg ccatccagca tatatgttta aagcatacaa   720
catgctttca agacgtggtg gtggatgtgg attgcgcgga gaatactaaa gaggatcagt   780
tggccgaaat cagttaccgt tttcaaggta agaaggaagc ggaccaaccg tggattgttg   840
taaacacgag cacactgttt gatgaactcg aattagaccc gagattgaa ccgggtgtt   900
tcttgaaagt acttcggaca gagaaacaat acttgggtgt gtacatttgg aacatgcgcg   960
gctccgatgg tacgtctacc tacgccacgt tcttggtcac ctggaaaggg gatgagaaga  1020
caagaaaccc tacgcccgca gtaactcctc aaccaagagg ggctgagttt catatgtgga  1080
attaccactc gcatgtattt tcagttggtg atacgtttag cttggcaatg catcttcagt  1140
ataagataca tgaagcgcca tttgatttgc tgttagagtg gttgtatgtc cccatcgatc  1200
ctacatgtca accaatgcgg ttatattcta cgtgtttgta tcatcccaac gcacccaat  1260
gcctctctca tatgaattcc ggttgtacat tacctcgcc acatttagcc cagcgtgttg  1320
caagcacagt gtatcagaat tgtgaacatg cagataacta caccgcatat tgtctgggaa  1380
tatctcatat ggagcctagc tttggtctaa tcttacacga cggaggcacc acgttaaagt  1440
ttgtagatac acccgagagt ttgtcgggat tatacgtct tgtggtgtat tttaacggc  1500
atgttgaagc cgtagcatac actgttgtat ccacagtaga tcattttgta aacgcaattg  1560
aagagcgtgg atttccgcca acggccggtc agccaccggc gactactaaa cccaaggaaa  1620
ttacgcccgt aaaccccgga acgtcaccac ttctacgata tgccgcatgg accggagggc  1680
ttgcagcagt agtactttta tgtctcgtaa tattcttaat ctgtacggct aaacgaatga  1740
gggttaaagc cgccagggta gacaagtgat aataggctgg agcctcggtg gccatgcttc  1800
ttgccccttg ggcctccccc agccctcc tcccctcct gcaccgtac ccccgtggtc  1860
tttgaataaa gtctgagtgg gcggcaaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaatctag                                                         1990
```

```
SEQ ID NO: 92           moltype = RNA   length = 2141
FEATURE                 Location/Qualifiers
source                  1..2141
                        mol_type = genomic RNA
                        organism = Human alphaherpesvirus 3
SEQUENCE: 92
ggggaaataa gagagaaaag aagagtaaga agaaatataa gagccaccat ggggacagtg   60
aataagccgg ttgtgggcgt gcttatgggc tttgggatta ttaccggtac attacgaatt  120
accaatccag tgcgcgccag tgtgctgcgt tacgacgact ttcacattga cgaggataag  180
ctggatacta acagcgtgta cgaaccttat taccactcag atcatgccga atcaagctgg  240
gttaatagag gagaaagcag ccgaaaagcc tacgaccaca actcacctta tatttggccc  300
agaaacgatt atgacggttt cctggaaaac gcacatgaac accatggagt ctacaaccaa  360
ggcagggaa tcgacagtgg cgagcgtctt atgcagccaa cacagatgtc ggcacaggag  420
gatctcggtg atgacaccgg catacacgtg attcccacat taaacggcga cgacagacat  480
aagatcgtca atgtggatca gcgtcagtat ggggatgtct ttaaaggcga tttgaatcca  540
aagccccaag gacagagact gatcgaggtc tctgtagaag aaaatcaccc cttcactttg  600
cgcgctccaa tccagaggat ttacggggtg cgttataccg aaacttggag tttcttgccg  660
tcactgacgt gtacgggga tgccgcccc gcaatccagc acatctgtct gaaacacacc  720
acatgctttc aggacgtggt tgtggatgtg gattgcgcgg aaaacacaaa agaagaccaa  780
ctcgccgaaa tcagctatcg tttttcagggt aaaaaagagg ccgaccaacc gtggattgtt  840
gtgaatacga gcacgctctt cgatgagctt gaactcgatc ccccggaaat cgagcctggg  900
gttctaaaag tgttgaggac cgagaagcag tacctcgggt tttatatctg gaatatgaga  960
ggctccgatg gcacctctac ctacgcaacg tttctggtta cctggaaggg agacgagaag 1020
acacggaatc caacgcccgc tgtgacccct cagcctaggg gagccgaatt ccacatgtgg 1080
aactatcact cccatgtatt cagtgtgggg gacactttca gcctggccat gcacctgcag 1140
tataagattc acgaggcacc cttcgacctc ctgctgacgt ggttgtacgt acctattgat 1200
cccacttgtc agcccatgcg cctgtactcc acttgcttgt accacccaa tgcaccacag 1260
tgtctatcac acatgaactc cgggtgtacc tttacttcac cccatcttgc ccagcgggtc 1320
gccagcacag tgtatcagaa ctgtgagcat gctgacaact atactgctta ttgcctcgga 1380
atatcccata tggagccaag cttcgggctc atactgcacg atggtggtac gacactcaag 1440
ttcgtggaca cccccgaaag cctttctggc ttgtacgtgt tcgtggtcta cttcaatgga 1500
catgtggagg cagtggctta cacagtggtt tcgacagttg atcactttgt aaatgccatt 1560
gaggaacgcg gcttcccgcc tacagcgggc cagcccctg cgacaacaaa accaaaagag 1620
attacgcccg ttaatcctgg gactagtcca ttgctgaggt atgccgcctg gactggcggt 1680
ctggcggccg tggtacttct gtgtttagtc atatttctga tctgtaccgc taaacgtatg 1740
cgggtcaagg cttaccgtgt tgacaagtct ccttacaatc agtcaatgta ctatgcagga 1800
ctccctgttg acgatttcga agactcagag agtacagaca cagaagaaga attcggaaac 1860
gctataggt gctctcacgg aggtagctcg tatacagtgt acatcgataa aaccagatga 1920
taataggctg gagcctcggt ggccatgctt cttgcccctt gggcctcccc ccagcccctc 1980
ctcccttcc tgcacccgta cccccgtggt cttttgaataa agtctgagtg ggcggcaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaatcta g                     2141

SEQ ID NO: 93           moltype = RNA   length = 2111
FEATURE                 Location/Qualifiers
misc_feature            1..2111
                        note = Synthetic Polynucleotide
source                  1..2111
                        mol_type = other RNA
                        organism = synthetic construct
SEQUENCE: 93
ggggaaataa gagagaaaag aagagtaaga agaaatataa gagccaccat ggagactccc   60
gctcagctac tgttcctcct gctcctttgg ctgcctgata ctacaggctc tgttttgcgg  120
tacgacgact ttcacatcga tgaggacaag ctcgacacta atagcgtgta tgagccctac  180
taccattcag atcacgccga gtcctcttgg gtgaacaggg gtgaaagttc taggaaagcc  240
tatgatcaca acagcccta tatttggcca cggaatgatt acgacggatt tctcgaaaat  300
gcccacgagc atcacggagt gtacaaccag ggccgtggaa tcgactctgg ggagagattg  360
atgcaaccta cacagatgag cgcccaggaa gatctcgggg atgatacagg aattcacgtt  420
atccctacat taaacggaga tgaccgccac aaaatcgtca atgtcgatca aagacagtat  480
ggagatgtgt tcaaaggcga tctcaaccct aagccgcagg gccagagact cattgaggtg  540
tctgtcgaag agaaccaccc tttcactctg cgcgctccca ttcagagaat ctatggagtt  600
cgctatacgg agacttggtc attccttcct tccctgacat gcaccggaga gcgcgcccct  660
gccattcagc acatatgcct gaaacatacc acctgtttcc aggatgtggt ggttgatgtt  720
gattgtgctg aaaataccaa ggaagaccaa ctggccgaga ttagttaccg gttccaaagg  780
aaaaaggaag ccgaccagcc atggattgtg gttaatacaa gcactctgtt cgatgagctc  840
gagctggatc ccccgagat agaacccgga gttctgaaag tgctccggac agaaaaacaa  900
tatctgggag tctacatatg gaacatgcgc ggttccgatg ggacctccac ttatgcaacc  960
tttctcgtca cgtggaaggg agatgagaaa actaggacca ccacacccgc tgtcacacca 1020
cagccaagag gggctgagtt ccatatgtgg aactatcata tcacgtcgtt tagtgtcgga 1080
gatacgtttt cattggctat gcatctccag tacaagattc atgaggctcc cttcgatctg 1140
ttgcttgagt ggttgtacgt cccgattgac ccgacctgcc agcccatgcg actgtacagc 1200
acctgtctct accatccaaa cgctccgcaa tgtctgagcc acatgaactc tgggtgtact 1260
ttcaccagtc cccacctcgc ccagcgggtg gcctctactg tttaccagaa ctgtgagcac 1320
gccgacaact acaccgcata ctgcctcggt atttctcaca tggagccaag cttcgggctc 1380
atcctgcacg atgggggcac taccctgaag ttcgttgata cgccagaatc tctgtctggg 1440
ctctatgttt tcgtggtcta cttcaatggc catgtcgagg ccgtggccta tactgtcgtt 1500
tctaccgtgg atcattttgt gaacgccatc gaagaacggg gattccccc tacggcaggc 1560
cagccgcctc aaccaccaa gcccaaggaa ataacaccag tgaaccctgg cacctcacct 1620
ctcctaagat atgccgcgtg gacaggggga ctggcggcag tggtgctcct ctgtctcgtg 1680
```

-continued

```
atctttctga tctgtacagc caagaggatg agggtcaagg cttatagagt ggacaagtcc    1740
ccctacaatc agtcaatgta ctacgccggc cttcccgttg atgattttga ggattccgag    1800
tccacagata ctgaggaaga gttcggtaac gctataggcg gctctcacgg gggttcaagc    1860
tacacggttt acattgacaa gacacgctga taataggctg gagcctcggt ggccatgctt    1920
cttgcccctt gggcctcccc ccagcccctc ctccccttcc tgcacccgta cccccgtggt    1980
ctttgaataa agtctgagtg ggcggcaaaa aaaaaaaaa aaaaaaaaaa aaaaaaaaaa    2040
aaaaaaaaaa aaaaaaaaaa aaaaaaaaaa aaaaaaaaaa aaaaaaaaaa aaaaaaaaaa    2100
aaaaaatcta g                                                        2111

SEQ ID NO: 94          moltype = RNA   length = 1958
FEATURE                Location/Qualifiers
misc_feature           1..1958
                       note = Synthetic Polynucleotide
source                 1..1958
                       mol_type = other RNA
                       organism = synthetic construct
SEQUENCE: 94
gggggaaataa gagagaaaag aagagtaaga agaaatataa gagccaccat ggggacagtt    60
aataaacctg tggtgggggt attgatgggg ttcggaatta tcacgggaac gttgcgtata    120
acgaatccgg tcagagcatc cgtcttgcga tacgatgatt ttcacatcga tgaagacaaa    180
ctggatacaa actccgtata tgagccttac taccattcag atcatgcgga gtcttcatgg    240
gtaaatcggg gagagtcttc gcgaaaagcg tacgatcata actcacctta tatatggcca    300
cgtaatgatt atgatggatt tttagagaac gcacacgaac accatggggt gtataatcag    360
ggccgtggta tcgatagcgg ggaacggtta atgcaaccca cacaaatgtc tgcacaggag    420
gatcttgggg acgatacggg catccacgtt atccctacgt taaacggcga tgacagacat    480
aaaattgtaa atgtggacca acgtcaatac ggtgacgtgt ttaaaggaga tcttaatcca    540
aaaccccaag gccaaagact cattgaggtg tcagtggaag aaaatcaccc gtttacttta    600
cgcgcaccga ttcagcggat ttatggagtc cggtacaccg agacttggag cttttttgccg    660
tcattaacct gtacgggaga cgcagcgccc gccatccagc atatatgttt aaaacataca    720
acatgctttc aagacgtggt ggtggatgtg gattgcgcg aaaatactaa agaggatcag    780
ttggccgaaa tcagttaccg ttttcaaggt aagaaggaag cggaccaacc gtggattgtt    840
gtaaacacga gcacactgtt tgatgaactc gaattagacc cccccgagat tgaaccgggt    900
gtcttgaaag tacttcggac agaaaaacaa tacttgggtg tgtacatttg gaacatgcgc    960
ggctccgatg gtacgtctac ctacgccacg tttttggtca cctggaaagg ggatgaaaaa    1020
acaagaaacc ctacgcccgc agtaactcct caaccaagag gggctgagtt tcatatgtgg    1080
aattaccact cgcatgtatt ttcagttggt gatacgttta gcttggcaat gcatcttcag    1140
tataagatac atgaagcgcc atttgatttg ctgttagagt ggttgtatgt ccccatcgat    1200
cctacatgtc aaccaatgcg gttatattct acgtgtttgt atcatcccaa cgcaccccaa    1260
tgcctctctc atatgaattc cggttgtaca tttacctcgc cacatttagc ccagcgtgtt    1320
gcaagcacag tgtatcaaaa ttgtgaacat gcagataact acaccgcata ttgtctggga    1380
atatctcata tggagcctag ctttggtcta atcttacacg acgggggcac cacgttaaag    1440
tttgtagata cacccgagag tttgtcggga ttatacgttt ttgtggtgta ttttaacggg    1500
catgttgaag cctagcata cactgttgta tccacagtag atcattttgt aaacgcaatt    1560
gaagagcgtg gatttccgcc aacggccggt cagccaccgg cgactactaa acccaaggaa    1620
attaccccg taaaccccgg aacgtcacca cttctacgat atgccgcatg gaccggaggg    1680
cttgcagcag tagtacttttt atgtctcgta atatttttaa tctgtacggc ttgatgataa    1740
taggctggag cctcggtggc catgcttctt gccccttggg cctcccccca gcccctcctc    1800
cccttcctgc accgtaccc ccgtggtctt tgaataaagt ctgagtgggc ggcaaaaaaa    1860
aaaaaaaaaa aaaaaaaaaa aaaaaaaaaa aaaaaaaaaa aaaaaaaaaa aaaaaaaaaa    1920
aaaaaaaaaa aaaaaaaaaa aaaaaaaaaa aaatctag                           1958

SEQ ID NO: 95          moltype = RNA   length = 1928
FEATURE                Location/Qualifiers
misc_feature           1..1928
                       note = Synthetic Polynucleotide
source                 1..1928
                       mol_type = other RNA
                       organism = synthetic construct
SEQUENCE: 95
gggggaaataa gagagaaaag aagagtaaga agaaatataa gagccaccat ggaaaccccg    60
gcgcagctgc tgtttctgct gctgctgtgg ctgccggata ccaccggctc cgtcttgcga    120
tacgatgatt ttcacatcga tgaagacaaa ctggatacaa actccgtata tgagccttac    180
taccattcag atcatgcgga gtcttcatgg gtaaatcggg gagagtcttc gcgaaaagcg    240
tacgatcata actcacctta tatatggcca cgtaatgatt atgatggatt tttagagaac    300
gcacacgaac accatggggt gtataatcag ggccgtggta tcgatagcgg ggaacggtta    360
atgcaaccca cacaaatgtc tgcacaggag gatcttgggg acgatacggg catccacgtt    420
atccctacgt taaacggcga tgacagacat aaaattgtaa atgtggacca acgtcaatac    480
ggtgacgtgt ttaaaggaga tcttaatcca aaaccccaag gccaaagact cattgaggtg    540
tcagtggaag aaaatcaccc gtttacttta cgcgcaccga ttcagcggat ttatggagtc    600
cggtacaccg agacttggag cttttttgccg tcattaacct gtacgggaga cgcagcgccc    660
gccatccagc atatatgttt aaaacataca acatgctttc aagacgtggt ggtggatgtg    720
gattgcgcgg aaaatactaa agaggatcag ttggccgaaa tcagttaccg ttttcaaggt    780
aagaaggaag cggaccaacc gtggattgtt gtaaacacga gcacactgtt tgatgaactc    840
gaattagacc cccccgagat tgaaccgggt gtcttgaaag tacttcggac agaaaaacaa    900
tacttgggtg tgtacatttg gaacatgcgc ggctccgatg gtacgtctac ctacgccacg    960
tttttggtca cctggaaagg ggatgaaaaa acaagaaacc ctacgcccgc agtaactcct    1020
caaccaagag gggctgagtt tcatatgtgg aattaccact cgcatgtatt ttcagttggt    1080
gatacgttta gcttggcaat gcatcttcag tataagatac atgaagcgcc atttgatttg    1140
ctgttagagt ggttgtatgt ccccatcgat cctacatgtc aaccaatgcg gttatattct    1200
```

```
acgtgtttgt atcatcccaa cgcaccccaa tgcctctctc atatgaattc cggttgtaca    1260
tttacctcgc cacatttagc ccagcgtgtt gcaagcacag tgtatcaaaa ttgtgaacat    1320
gcagataact acaccgcata ttgtctggga atatctcata tggagcctag ctttggtcta    1380
atcttacacg acgggggcac cacgttaaag tttgtagata cacccgagag tttgtcggga    1440
ttatacgttt ttgtggtgta ttttaacggg catgttgaag ccgtagcata cactgttgta    1500
tccacagtag atcattttgt aaacgcaatt gaagagcgtg gatttccgcc aacggccggt    1560
cagccaccgg cgactactaa acccaaggaa attaccccg taaaccccgg aacgtcacca    1620
cttctacgat atgccgcatg gaccggaggg cttgcagcag tagtactttt atgtctcgta    1680
atattttaa tctgtacggc ttgatgataa taggctggag cctcggtggc catgcttctt    1740
gcccttggg cctcccccca gcccctcctc ccttcctgc acccgtaccc ccgtggtctt    1800
tgaataaagt ctgagtgggc ggcaaaaaaa aaaaaaaaaa aaaaaaaaaa aaaaaaaaaa    1860
aaaaaaaaaa aaaaaaaaaa aaaaaaaaaa aaaaaaaaaa aaaaaaaaaa aaaaaaaaaa    1920
aaatctag                                                              1928
```

```
SEQ ID NO: 96          moltype = RNA  length = 2144
FEATURE                Location/Qualifiers
misc_feature           1..2144
                       note = Synthetic Polynucleotide
source                 1..2144
                       mol_type = other RNA
                       organism = synthetic construct
SEQUENCE: 96
ggggaaataa gagagaaaag aagagtaaga agaaatataa gagccaccat ggggacagtt    60
aataaacctg tggtgggggt attgatgggg ttcggaatta tcacgggaac gttgcgtata    120
acgaatccgt tcagagcatc cgtcttgcga tacgatgatt ttcacatcga tgaagacaaa    180
ctggatacaa actccgtata tgagccttac taccattcag atcatgcgga gtcttcatgg    240
gtaaatcggg gagagtcttc gcgaaaagcg tacgatcata actcaccttc tatatggcca    300
cgtaatgatt atgatggatt tttagagaac gcacacgaac accatggggt gtataatcag    360
ggccgtggta tcgatagcgg ggaacggtta atgcaaccca cacaaatgtc tgcacaggag    420
gatcttgggg acgatacggg catccacgtt atccctacgt taaacggcga tgacagacat    480
aaaattgtaa atgtggacca acgtcaatac ggtgacgtgt ttaaaggaga tcttaatcca    540
aaaccccaag gccaaagact cattgaggtg tcagtggaag aaaatcaccc gtttacttta    600
cgcgcaccga ttcagcggat ttatggagtc cggtacaccg agacttggag cttttttgccg    660
tcattaacct gtacgggaga cgcagcgccc gccatccagc atatatgttt aaaacataca    720
acatgctttc aagacgtggt ggtggatgtg gattgcgcgg aaaatactaa agaggatcag    780
ttggccgaaa tcagttaccg ttttcaaggt aagaaggaag cggaccaacc gtggattgtt    840
gtaaacacga gcacactgtt tgatgaactc gaattagacc cccccgagat tgaaccgggt    900
gtcttgaaag tacttcggac agaaaaacaa tacttgggtg tgtacatttg gaacatgcgc    960
ggctccgatg gtacgtctac ctacgccacg ttttggtca cctggaaagg ggatgaaaaa    1020
acaagaaacc ctacgcccgc agtaactcct caaccaagag gggctgagtt tcatatgtgg    1080
aattaccact cgcatgtatt ttcagttggt gatacgttta gcttggcaat gcatcttcag    1140
tataagatac atgaagcgcc atttgatttg ctgttagagt ggttgtatgt ccccatcgat    1200
cctacatgtc aaccaatgcg gttatattct acgtgtttgt atcatcccaa cgcaccccaa    1260
tgcctctctc atatgaattc cggttgtaca tttacctcgc cacatttagc ccagcgtgtt    1320
gcaagcacag tgtatcaaaa ttgtgaacat gcagataact acaccgcata ttgtctggga    1380
atatctcata tggagcctag ctttggtcta atcttacacg acgggggcac cacgttaaag    1440
tttgtagata cacccgagag tttgtcggga ttatacgttt ttgtggtgta ttttaacggg    1500
catgttgaag ccgtagcata cactgttgta tccacagtag atcattttgt aaacgcaatt    1560
gaagagcgtg gatttccgcc aacggccggt cagccaccgg cgactactaa acccaaggaa    1620
attaccccg taaaccccgg aacgtcacca cttctacgat atgccgcatg gaccggaggg    1680
cttgcagcag tagtactttt atgtctcgta atattttaa tctgtacggc taaacgaatg    1740
agggttaaag cctataggt agacaagtcc ccgtataacc aaagcatgta ttacgctggc    1800
cttccagtgg acgatttcga ggacgccgaa gccgccgatg ccgaagaaga gtttggtaac    1860
gcgattggag ggagtcacgg gggttcgagt tacacggtgt atatagataa gacccggtga    1920
tgataatagg ctggagcctc ggtggccatg cttcttgccc cttgggcctc ccccagccc    1980
ctcctcccct tcctgcaccc gtacccccgt ggtctttgaa taaagtctga gtgggcggca    2040
aaaaaaaaaa aaaaaaaaaa aaaaaaaaaa aaaaaaaaaa aaaaaaaaaa aaaaaaaaaa    2100
aaaaaaaaaa aaaaaaaaaa aaaaaaaaaa aaaaaaaat ctag                      2144
```

```
SEQ ID NO: 97          moltype = RNA  length = 2144
FEATURE                Location/Qualifiers
misc_feature           1..2144
                       note = Synthetic Polynucleotide
source                 1..2144
                       mol_type = other RNA
                       organism = synthetic construct
SEQUENCE: 97
ggggaaataa gagagaaaag aagagtaaga agaaatataa gagccaccat ggggacagtt    60
aataaacctg tggtgggggt attgatgggg ttcggaatta tcacgggaac gttgcgtata    120
acgaatccgg tcagagcatc cgtcttgcga tacgatgatt ttcacatcga tgaagacaaa    180
ctggatacaa actccgtata tgagccttac taccattcag atcatgcgga gtcttcatgg    240
gtaaatcggg gagagtcttc gcgaaaagcg tacgatcata actcaccttc tatatggcca    300
cgtaatgatt atgatggatt tttagagaac gcacacgaac accatggggt gtataatcag    360
ggccgtggta tcgatagcgg ggaacggtta atgcaaccca cacaaatgtc tgcacaggag    420
gatcttgggg acgatacggg catccacgtt atccctacgt taaacggcga tgacagacat    480
aaaattgtaa atgtggacca acgtcaatac ggtgacgtgt ttaaaggaga tcttaatcca    540
aaaccccaag gccaaagact cattgaggtg tcagtggaag aaaatcaccc gtttacttta    600
cgcgcaccga ttcagcggat ttatggagtc cggtacaccg agacttggag cttttttgccg    660
tcattaacct gtacgggaga cgcagcgccc gccatccagc atatatgttt aaaacataca    720
```

-continued

```
acatgctttc aagacgtggt ggtggatgtg gattgcgcgg aaaatactaa agaggatcag    780
ttggccgaaa tcagttaccg ttttcaaggt aagaaggaag cggaccaacc gtggattgtt    840
gtaaacacga gcacactgtt tgatgaactc gaattagacc cccccgagat tgaaccgggt    900
gtcttgaaag tacttcggac agaaaaacaa tacttgggtg tgtacatttg gaacatgcgc    960
ggctccgatg gtacgtctac ctacgccacg tttttggtca cctggaaagg ggatgaaaaa   1020
acaagaaacc ctacgcccgc agtaactcct caaccaagag gggctgagtt tcatatgtgg   1080
aattaccact cgcatgtatt ttcagttggt gatacgttta gcttggcaat gcatcttcag   1140
tataagatac atgaagcgcc atttgatttg ctgttagagt ggttgtatgt ccccatcgat   1200
cctacatgtc aaccaatgcg gttatattct acgtgtttgt atcatcccaa cgcacccaa   1260
tgcctctctc atatgaattc cggttgtaca tttacctcgc cacatttagc ccagcgtgtt   1320
gcaagcacag tgtatcaaaa ttgtgaacat gcagataact acaccgcata ttgtctggga   1380
atatctcata tggagcctag ctttggtcta atcttacacg acgggggcac cacgttaaag   1440
tttgtagata cacccgagag tttgtcggga ttatacgttt ttgtggtgta ttttaacggg   1500
catgttgaag ccgtagcata cactgttgta tccacagtag atcattttgt aaacgcaatt   1560
gaagagcgtg gatttccgcc aacggccggt cagccaccgg cgactactaa acccaaggaa   1620
attaccccccg taaaccccgg aacgtcacca cttctacgat atgccgcatg gaccggaggg   1680
cttgcagcag tagtacttttt atgtctcgta atatttttaa tctgtacggc taaacgaatg   1740
agggttaaag cctatagggt agacaagtcc ccgtataacc aaagcatgta tggcgctggc   1800
cttccagtgg acgatttcga ggacgccgaa gccgccgatg ccgaagaaga gtttggtaac   1860
gcgattggag ggagtcacgg gggttcgagt tacacggtgt atatagataa gacccggtga   1920
tgataatagg ctggagcctc ggtggccatg cttcttgccc cttgggcctc cccccagccc   1980
ctcctcccct tcctgcaccc gtacccccgt ggtctttgaa taaagtctga gtgggcggca   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaat ctag                    2144
```

```
SEQ ID NO: 98          moltype = RNA  length = 1994
FEATURE                Location/Qualifiers
misc_feature           1..1994
                       note = Synthetic Polynucleotide
source                 1..1994
                       mol_type = other RNA
                       organism = synthetic construct
```

```
SEQUENCE: 98
gggggaaataa gagagaaaag aagagtaaga agaaatataa gagccaccat ggggacagtt     60
aataaacctg tggtgggggt attgatgggg ttcggaatta tcacgggaac gttgcgtata    120
acgaatccgg tcagagcatc cgtcttgcga tacgatgatt ttcacatcga tgaagacaaa    180
ctggatacaa actccgtata tgagccttac taccattcag atcatgcgga gtcttcatgg    240
gtaaatcggg gagagtcttc gcgaaaagcg tacgatcata actcacctta tatatggcca    300
cgtaatgatt atgatggatt tttagagaac gcacacgaac accatgggt gtataatcag    360
ggccgtggta tcgatagcgg ggaacggtta atgcaaccca cacaaatgtc tgcacaggag    420
gatcttgggg acgatacggg catccacgtt atccctacgt taaacggcga tgacagacat    480
aaaattgtaa atgtggacca acgtcaatac ggtgacgtgt ttaaaggaga tcttaatcca    540
aaaccccaag gccaaagact cattgaggtg tcagtggaag aaaatcaccc gtttactttta    600
cgcgcaccga ttcagcggat ttatggagtc cggtacaccg agacttggag cttttttgccg    660
tcattaacct gtacgggaga cgcagcgccc gccatccagc atatatgttt aaaacataca    720
acatgctttc aagacgtggt ggtggatgtg gattgcgcgg aaaatactaa agaggatcag    780
ttggccgaaa tcagttaccg ttttcaaggt aagaaggaag cggaccaacc gtggattgtt    840
gtaaacacga gcacactgtt tgatgaactc gaattagacc cccccgagat tgaaccgggt    900
gtcttgaaag tacttcggac agaaaaacaa tacttgggtg tgtacatttg gaacatgcgc    960
ggctccgatg gtacgtctac ctacgccacg tttttggtca cctggaaagg ggatgaaaaa   1020
acaagaaacc ctacgcccgc agtaactcct caaccaagag gggctgagtt tcatatgtgg   1080
aattaccact cgcatgtatt ttcagttggt gatacgttta gcttggcaat gcatcttcag   1140
tataagatac atgaagcgcc atttgatttg ctgttagagt ggttgtatgt ccccatcgat   1200
cctacatgtc aaccaatgcg gttatattct acgtgtttgt atcatcccaa cgcacccaa   1260
tgcctctctc atatgaattc cggttgtaca tttacctcgc cacatttagc ccagcgtgtt   1320
gcaagcacag tgtatcaaaa ttgtgaacat gcagataact acaccgcata ttgtctggga   1380
atatctcata tggagcctag ctttggtcta atcttacacg acgggggcac cacgttaaag   1440
tttgtagata cacccgagag tttgtcggga ttatacgttt ttgtggtgta ttttaacggg   1500
catgttgaag ccgtagcata cactgttgta tccacagtag atcattttgt aaacgcaatt   1560
gaagagcgtg gatttccgcc aacggccggt cagccaccgg cgactactaa acccaaggaa   1620
attaccccccg taaaccccgg aacgtcacca cttctacgat atgccgcatg gaccggaggg   1680
cttgcagcag tagtacttttt atgtctcgta atatttttaa tctgtacggc taaacgaatg   1740
agggttaaag cctatagggt agacaagtga tgataatagg ctggagcctc ggtggccatg   1800
cttcttgccc cttgggcctc cccccagccc ctcctcccct tcctgcaccc gtacccccgt   1860
ggtctttgaa taaagtctga gtgggcggca aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaat ctag                                                     1994
```

```
SEQ ID NO: 99          moltype = RNA  length = 1994
FEATURE                Location/Qualifiers
misc_feature           1..1994
                       note = Synthetic Polynucleotide
source                 1..1994
                       mol_type = other RNA
                       organism = synthetic construct
SEQUENCE: 99
gggggaaataa gagagaaaag aagagtaaga agaaatataa gagccaccat ggggacagtt     60
aataaacctg tggtgggggt attgatgggg ttcggaatta tcacgggaac gttgcgtata    120
acgaatccgg tcagagcatc cgtcttgcga tacgatgatt ttcacatcga tgaagacaaa    180
```

-continued

```
ctggatacaa actccgtata tgagccttac taccattcag atcatgcgga gtcttcatgg   240
gtaaatcggg gagagtcttc gcgaaaagcg tacgatcata actcacctta tatatggcca   300
cgtaatgatt atgatggatt tttagagaac gcacacgaac accatggggt gtataatcag   360
ggccgtggta tcgatagcgg ggaacggtta atgcaaccca cacaaatgtc tgcacaggag   420
gatcttgggg acgatacggg catccacgtt atccctactg taaacgggca tgacagacat   480
aaaattgtaa atgtggacca acgtcaatac ggtgacgtgt ttaaaggaga tcttaatcca   540
aaaccccaag gccaaagact cattgaggtg tcagtggaag aaaatcaccc gtttacttta   600
cgcgcaccga ttcagcggat ttatggagtc cggtacaccg agacttggag cttttttgccg   660
tcattaacct gtacgggaga cgcagcgccc gccatccagc atatatgttt aaaacataca   720
acatgctttc aagacgtggt ggtggatgtg gattgcgcgg aaaatactaa agaggatcag   780
ttggccgaaa tcagttaccg ttttcaaggt aagaaggaag cggaccaacc gtggattgtt   840
gtaaacacga gcacactgtt tgatgaactc gaattagacc cccccgagat tgaaccgggt   900
gtcttgaaag tacttcggac agaaaaacaa tacttgggtg tgtacatttg gaacatgcgc   960
ggctccgatg gtacgtctac ctacgccacg tttttggtcc cctggaaagg ggatgaaaaa  1020
acaagaaacc ctacgcccgc agtaactcct caaccaagag gggctgagtt tcatatgtgg  1080
aattaccact cgcatgtatt ttcagttggt gatacgttta gcttggcaat gcatcttcag  1140
tataagatac atgaagcgcc atttgatttg ctgttagagt ggttgtatgt ccccatcgat  1200
cctacatgtc aaccaatgcg gttatattct acgtgtttgt atcatcccaa cgcaccccaa  1260
tgcctctctc atatgaattc cggttgtaca tttacctcgc cacatttagc ccagcgtgtt  1320
gcaagcacag tgtatcaaaa ttgtgaacat gcagataact acaccgcata ttgtctggga  1380
atatctcata tggagcctag ctttggtcta atcttacacg acgggggcac cacgttaaag  1440
tttgtagata cacccgagag tttgtcggga ttatacgttt ttgtggtgta ttttaacgag  1500
catgttgaag ccgtagcata cactgttgta tccacagtga atcattttgt aaacgcaatt  1560
gaagagcgtg gatttccgcc aacggccggt cagccaccgg cgactactaa acccaaggaa  1620
attaccccg taaaccccgg aacgtcacca cttctacgat atgccgcatg gaccggaggg  1680
cttgcagcag tagtactttt atgtctcgta atattttaca tctgtacggc taaacgaatg  1740
agggttaaag ccgccagggt agacaagtga tgataatagg ctggagcctc ggtggccatg  1800
cttcttgccc cttgggcctc cccccagccc ctcctcccct tcctgcaccc gtaccccgt   1860
ggtctttgaa taaagtctga gtgggcggca aaaaaaaaa aaaaaaaaa aaaaaaaaa   1920
aaaaaaaaa aaaaaaaaa aaaaaaaaa aaaaaaaaa aaaaaaaaa aaaaaaaaa   1980
aaaaaaaaat ctag                                                     1994
```

```
SEQ ID NO: 100         moltype = RNA  length = 1337
FEATURE                Location/Qualifiers
misc_feature           1..1337
                       note = Synthetic Polynucleotide
source                 1..1337
                       mol_type = other RNA
                       organism = synthetic construct
SEQUENCE: 100
ggggaaataa gagagaaaag aagagtaaga agaaatataa gagccaccat gtttttaatc    60
caatgtttga tatcggccgt tatattttac atacaagtga ccaacgcttt gatcttcaag   120
ggcgaccacg tgagcttgca agttaacagc agtctcacgt ctatccttat tcccatgcaa   180
aatgataatt atacagagat aaaaggacag cttgtcttta ttggagagca actacctacc   240
gggacaaact atagcggaac actggaactg ttatacgcgg atacggtggc gttttgtttc   300
cggtcagtac aagtaataag atacgacgga tgtccccgga ttagaacgag cgcttttatt   360
tcgtgtaggt acaaacattc gtggcattat ggtaactcaa ggatcggat atcaacagag   420
ccggatgctg gtgtaatgtt gaaaattacc aaaccgggaa taaatgatgc tggtgtgtat   480
gtacttcttg ttcggttaga ccatagcaga tccaccgatg gtttcattct tggtgtaaat   540
gtatatacag cgggctcgca tcacaacatt cacgggtta tctacacttc tccatctcta   600
cagaatggat attctacaag agcccttttt caacaagctc gtttgtgtga tttacccgcg   660
acacccaaag ggtccggtac ctcctgttt caacatatgc ttgatcttcg tgccggtaaa   720
tcgttagagg ataaccttg gttacatgag gacgttgtta cgacagaaac taagtccgtt   780
gttaaggagg ggatagaaaa tcacgtatat ccaacggata tgtccacgtt acccgaaag   840
tcccttaatg atcctccaga aaatctactt ataattattc ctatagtagc gtctgtcatg   900
atcctcaccg ccatggttat tgttattgta ataagcgtta agcgacgtag aattaaaaaa   960
catccaattt atcgcccaaa tacaaaaaca agaagggca tacaaatgc gacaccagaa  1020
tccgatgtga tgttggaggc cgccattgca caactagcaa cgattcgcga agaatccccc  1080
ccacattccg ttgtaaaccc gtttgttaaa tagtgataat aggctgagga ctcggtggcc  1140
atgcttcttg cccccttggc ctcccccag ccctcctcc ccttcctgca cccgtacccc  1200
cgtggtcttt gaataaagtc tgagtgggcg gcaaaaaaaa aaaaaaaaa aaaaaaaaa  1260
aaaaaaaaa aaaaaaaaa aaaaaaaaa aaaaaaaaa aaaaaaaaa aaaaaaaaa  1320
aaaaaaaaa aatctag                                                  1337
```

```
SEQ ID NO: 101         moltype = RNA  length = 1991
FEATURE                Location/Qualifiers
misc_feature           1..1991
                       note = Synthetic Polynucleotide
source                 1..1991
                       mol_type = other RNA
                       organism = synthetic construct
SEQUENCE: 101
ggggaaataa gagagaaaag aagagtaaga agaaatataa gagccaccat gggcaccgtg    60
aacaagcccg tcgtgggggt gctgatgggc ttcggcatca tcaccggcac cctgcggatc   120
accaatcctg tgcgggccag cgtgctgaga tacgacgact ccacatcga cgaggacaag   180
ctggacacca acagcgtgta cgagccctac taccacagcg accacgccga gagcagctgg   240
gtcaacagag gcgagtccag ccggaaggcc tacgaccaca acagccccta catctggccc   300
cggaacgact acgacggctt cctggaaaat gcccacgagc accacggcgt gtacaaccag   360
ggcagaggca tcgacagcgg cgagagactg atgcagccca cccagatgag cgcccaggaa   420
```

-continued

```
gatctgggcg acgacaccgg catccacgtg atccctaccc tgaacggcga cgaccggcac    480
aagatcgtga acgtggacca gcggcagtac ggcgacgtgt tcaagggcga cctgaacccc    540
aagccccagg gacagcggct gattgaggtg tccgtggaag agaaccaccc cttcaccctg    600
agagcccta  tccagcggat ctacggcgtg cgctataccg agacttggag cttcctgccc    660
agcctgacct gtactggcga cgccgctcct gccatccagc acatctgcct gaagcacacc    720
acctgtttcc aggacgtggt ggtggacgtg gactgcgccg agaacaccaa agaggaccag    780
ctggccgaga tcagctaccg gttccagggc aagaaagagg ccgaccagcc ctggatcgtc    840
gtgaacacca gcaccctgtt cgacgagctg gaactggacc ctcccgagat cgaacccggg    900
gtgctgaagg tgctgcggac cgagaagcag tacctgggag tgtacatctg gaacatgcgg    960
ggcagcgacg gcacctctac ctacgccacc ttcctcgtga cctggaaggg cgacgagaaa   1020
acccggaacc ctacccctgc cgtgacccct cagcctagag gcgccgagtt tcacatgtgg   1080
aattaccaca gccacgtgtt cagcgtgggc gacaccttct ccctggccat gcatctgcag   1140
tacaagatcc acgaggcccc tttcgacctg ctgctggaat ggctgtacgt gcccatcgac   1200
cctacctgcc agcccatgcg gctgtactcc acctgtctgt accaccccaa cgcccctccag   1260
tgcctgagcc acatgaatag cggctgcacc ttcaccagcc ctcacctggc tcagagggtg   1320
gccagcaccg tgtaccagaa ttgccgagcac gccgacaact acaccgccta ctgcctgggc   1380
atcagccaca tggaacccag cttcggcctg atcctgcacg atggcggcac caccctgaag   1440
ttcgtggaca cccctgagtc cctgagcggc ctgtacgtcg tcgtggtgta cttcaacggc   1500
cacgtggaag ccgtgcccta caccgtggtg tccaccgtgg accacttcgt gaacgccatc   1560
gaggaacggg gcttccctcc aactgctgga cagcctcctg ccaccaccaa gcccaaagaa   1620
atcacccctg tgaaccccgg caccagccca ctgctgcgct atgctgcttg gacaggcgga   1680
ctggctgctg tggtgctgct gtgcctcgtg attttcctga tctgcaccgc caagcggatg   1740
agagtgaagg ccgccagagt ggacaagtga taataggctg gagcctcggt ggccatgctt   1800
cttgcccctt gggcctcccc ccagcccctc ctcccttcc tgcacccgta cccccgtggt   1860
ctttgaataa agtctgagtg ggcggcaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaatcta g                                                       1991
```

```
SEQ ID NO: 102           moltype = RNA  length = 1991
FEATURE                  Location/Qualifiers
misc_feature             1..1991
                         note = Synthetic Polynucleotide
source                   1..1991
                         mol_type = other RNA
                         organism = synthetic construct
SEQUENCE: 102
ggggaaataa gagagaaaag aagagtaaga agaaatataa gagccaccat ggggacagtt    60
aataaacctg tggtgggggt attgatgggg ttcggaatta tcacgggaac gttgcgtata   120
acgaatccgg tcagagcatc cgtcttgcga tacgatgatt ttcacatcga tgaagacaaa   180
ctggatacaa actccgtata tgagccttac taccattcag atcatgcgga gtcttcatgg   240
gtaaatcggg gagagtcttc gcgaaaagcg tacgatcata actcaccttta tatatggcca   300
cgtaatgatt atgatggatt tttagagaac gcacacgaac accatggggt gtataatcag   360
ggccgtggta tcgatagcgg ggaacggtta atgcaaccca cacaaatgtc tgcacaggag   420
gatcttgggg acgatacggg catccacgtt atccctacgt taaacggcga tgacagacat   480
aaaattgtaa atgtggacca acgtcaatac ggtgacgtgt ttaaaggaga tcttaatcca   540
aaaccccaag gccaaagact cattgaggtg tcagtggaag aaaatcaccc gtttacttta   600
cgcgcaccga ttcagcggat ttatggagtc cggtacaccg agacttggag cttttttgccg   660
tcattaacct gtacgggaga cgcagcgccc gccatccagc atatatgttt aaaacataca   720
acatgctttc aagacgtggt ggtggatgtg gattgcgcgg aaaatactaa agaggatcag   780
ttggccgaaa tcagttaccg ttttcaaggt aagaaggaag cggaccaacc gtggattgtt   840
gtaaacacga gcacactgtt tgatgaactc gaattagacc ccccgagat tgaacccggt   900
gtcttgaaag tacttcggac agagaaacaa tacttgggtg tgtacatttg gaacatgcgc   960
ggctccgatg gtacgtctac ctacgccacg ttttttggtca cctggaaagg ggatgagaag  1020
acaagaaacc ctacgcccgc agtaactcct caaccaagag gggctgagtt tcatatgtgg  1080
aattaccact cgcatgtatt ttcagttggt gatacgttta gctggcaat gcatcttcag  1140
tataagatac atgaagcgcc atttgatttg ctgttagagt ggttgtatgt ccccatcgat  1200
cctacatgtc aaccaatgcg gttatattct acgtgtttgt atcatcccaa cgcaccccaa  1260
tgcctctctc atatgaattc cggttgtaca tttacctcgc cacatttagc ccagcgtgtt  1320
gcaagcacag tgtatcaaaa ttgtgaacat gcagataact acaccgcata ttgtctggga  1380
atatctcata tggagcctag ctttggtcta atcttacacg acgggggcac cacgttaaag  1440
tttgtagata cacccgagag tttgtcggga ttatacgttt ttgtggtgta ttttaacggg  1500
catgttgaag ccgtagcata cactgttgta tccacagtag atcattttgt aaacgcaatt  1560
gaagagcgtg gatttccgcc aacggccggt cagccaccgg cgactactaa acccaaggaa  1620
attaccccg taaaccccgg aacgtcacca cttctacgat tctgcaccgc gaccgaggg  1680
cttcagcag tagtactttt atgtctcgta atatttttaa tctgtacggc taaacgaatg  1740
agggttaaag ccgccagggt agacaagtga taataggctg gagcctcggt ggccatgctt  1800
cttgcccctt gggcctcccc ccagcccctc ctcccttcc tgcacccgta cccccgtggt   1860
ctttgaataa agtctgagtg ggcggcaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaatcta g                                                      1991
```

```
SEQ ID NO: 103           moltype = RNA  length = 1991
FEATURE                  Location/Qualifiers
misc_feature             1..1991
                         note = Synthetic Polynucleotide
source                   1..1991
                         mol_type = other RNA
                         organism = synthetic construct
SEQUENCE: 103
```

-continued

```
gggggaaataa gagagaaaag aagagtaaga agaaatataa gagccaccat ggggacagtt   60
aataaacctg tggtgggggt attgatgggg ttcggaatta tcacgggaac gttgcgtata  120
acgaatccgg tcagagcatc cgtcttgcga tacgatgatt ttcacatcga tgaagacaaa  180
ctggatacaa actccgtata tgagccttac taccattcag atcatgcgga gtcttcatgg  240
gtaaatcggg gagagtcttc gcgaaaagcg tacgatcata actcacctta tatatggcca  300
cgtaatgatt atgatggatt tttagagaac gcacacgaac accatggggt gtataatcag  360
ggccgtggta tcgatagcgg ggaacggtta atgcaaccca cacaaatgtc tgcacaggag  420
gatcttgggg acgatacggg catccacgtt atccctacgt taaacggcga tgacagacat  480
aaaattgtaa atgtggacca acgtcaatac ggtgacgtgt ttaaaggaga tcttaatcca  540
aaaccccaag gccaaagact cattgaggtg tcagtggaag aaaatcaccc gtttacttta  600
cgcgcaccga ttcagcggat ttatggagtc cggtacaccg agacttggag cttttttgccg  660
tcattaacct gtacgggaga cgcagcgccc gccatccagc atatatgtttt aaaacataca  720
acatgctttc aagacgtggt ggtggatgtg gattgcgcgg aaaatactaa agaggatcag  780
ttggccgaaa tcagttaccg ttttcaaggt aagaaggaag cggaccaacc gtggattgtt  840
gtaaacacga gcacactgtt tgatgaactc gaattagacc caccccgagat tgaaccgggt  900
gtcttgaaag tacttcggac agagaaacaa tacttgggtg tgtacatttg gaacatgcgc  960
ggctccgatg gtacgtctac ctacgccacg ttttttggtca cctggaaagg ggatgagaag 1020
acaagaaacc ctacgcccgc agtaactcct caaccaagag gggctgagtt tcatatgtgg 1080
aattaccact cgcatgtatt ttcagttggt gatacgttta gcttggcaat gcatcttcag 1140
tataagatac atgaagcgcc atttgatttg ctgttagagt ggttgtatgt ccccatcgat 1200
cctacatgtc aaccaatgcg gttatattct acgtgtttgt atcatcccaa cgcaccccaa 1260
tgcctctctc atatgaattc cggttgtaca tttacctcgc cacatttagc ccagcgtgtt 1320
gcaagcacag tgtatcaaaa ttgtgaacat gcagataact acaccgcata ttgtctggga 1380
atatctcata tggagcctag ctttggtcta atcttacacg acgggggcac cacgttaaag 1440
tttgtagata caccccgagag tttgtcggga ttatacgttt ttgtggtgta ttttaacggg 1500
catgttgaag ccgtagcata cactgttgta tccacagtag atcattttgt aaacgcaatt 1560
gaagagcgtg gatttccgcc aacggccggt cagccaccgg cgactactaa acccaaggaa 1620
attacccccg taaaccccgg aacgtcacca cttctacgat atgccgcatg gaccggaggg 1680
cttgcagcag tagtacttttt atgtctcgta atattttttaa tctgtacggc taaacgaatg 1740
agggttaaag ccgccagggt agacaagtga taataggctg gagcctcggt ggccatgctt 1800
cttgcccctt gggcctcccc ccagcccctc ctcccttcc tgcacccgta cccccgtggt 1860
ctttgaataa agtctgagtg ggcggcaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaatcta g                                                      1991

SEQ ID NO: 104          moltype = RNA  length = 1991
FEATURE                 Location/Qualifiers
misc_feature            1..1991
                        note = Synthetic Polynucleotide
source                  1..1991
                        mol_type = other RNA
                        organism = synthetic construct
SEQUENCE: 104
gggggaaataa gagagaaaag aagagtaaga agaaatataa gagccaccat ggggacagtt   60
aataaacctg tggtgggggt attgatgggg ttcggaatta tcacgggaac gttgcgtata  120
acgaatccgg tcagagcatc cgtcttgcga tacgatgatt ttcacatcga tgaagacaaa  180
ctggatacaa actccgtata tgagccttac taccattcag atcatgcgga gtcttcatgg  240
gtaaatcggg gagagtcttc gcgaaaggcg tacgatcata actcacctta tatatggcca  300
cgtaatgatt atgatggatt tttagagaac gcacacgaac accatggggt gtataatcag  360
ggccgtggta tcgatagcgg ggaacggtta atgcaaccca cacaaatgtc tgcacaggag  420
gatcttgggg acgatacggg catccacgtt atccctacgt taaacggcga tgacagacat  480
aagattgtaa atgtggacca acgtcaatac ggtgacgtgt ttaaaggaga tcttaatcca  540
aagcccaag gccaaagact cattgaggtg tcagtggaag agaatcaccc gtttacttta  600
cgcgcaccga ttcagcggat ttatggagtc cggtacaccg agacttggag cttttttgccg  660
tcattaacct gtacgggaga cgcagcgccc gccatccagc atatatgtttt aaagcataca  720
acatgctttc aagacgtggt ggtggatgtg gattgcgcgg agaatactaa agaggatcag  780
ttggccgaaa tcagttaccg ttttcaaggt aagaaggaag cggaccaacc gtggattgtt  840
gtaaacacga gcacactgtt tgatgaactc gaattagacc ccccccgagat tgaaccgggt  900
gtcttgaaag tacttcggac agagaaacaa tacttgggtg tgtacatttg gaacatgcgc  960
ggctccgatg gtacgtctac ctacgccacg ttttttggtca cctggaaagg ggatgagaag 1020
acaagaaacc ctacgcccgc agtaactcct caaccaagag gggctgagtt tcatatgtgg 1080
aattaccact cgcatgtatt ttcagttggt gatacgttta gcttggcaat gcatcttcag 1140
tataagatac atgaagcgcc atttgatttg ctgttagagt ggttgtatgt ccccatcgat 1200
cctacatgtc aaccaatgcg gttatattct acgtgtttgt atcatcccaa cgcaccccaa 1260
tgcctctctc atatgaattc cggttgtaca tttacctcgc cacatttagc ccagcgtgtt 1320
gcaagcacag tgtatcagaa ttgtgaacat gcagataact acaccgcata ttgtctggga 1380
atatctcata tggagcctag ctttggtcta atcttacacg acgggggcac cacgttaaag 1440
tttgtagata caccccgagag tttgtcggga ttatacgttt ttgtggtgta ttttaacggg 1500
catgttgaag ccgtagcata cactgttgta tccacagtag atcattttgt aaacgcaatt 1560
gaagagcgtg gatttccgcc aacggccggt cagccaccgg cgactactaa acccaaggaa 1620
attacccccg taaaccccgg aacgtcacca cttctacgat atgccgcatg gaccggaggg 1680
cttgcagcag tagtacttttt atgtctcgta atattttttaa tctgtacggc taaacgaatg 1740
agggttaaag ccgccagggt agacaagtga taataggctg gagcctcggt ggccatgctt 1800
cttgcccctt gggcctcccc ccagcccctc ctcccttcc tgcacccgta cccccgtggt 1860
ctttgaataa agtctgagtg ggcggcaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaatcta g                                                      1991

SEQ ID NO: 105          moltype = RNA  length = 1991
```

-continued

```
FEATURE              Location/Qualifiers
misc_feature         1..1991
                     note = Synthetic Polynucleotide
source               1..1991
                     mol_type = other RNA
                     organism = synthetic construct
SEQUENCE: 105
ggggaaataa gagagaaaag aagagtaaga agaaatataa gagccaccat ggggacagtt    60
aataaacctg tggtgggggt attgatgggg ttcggaatta tcacgggaac gttgcgtata   120
acgaatccgg tcagagcatc cgtcttgcga tacgatgatt ttcacatcga tgaagacaaa   180
ctggatacaa actccgtata tgagccttac taccattcag atcatgcgga gtcttcatgg   240
gtaaatcggg gagagtcttc gcgaaaggcg tacgatcata actcaccttta tatatggcca   300
cgtaatgatt atgatggatt tttagagaac gcacacgaac accatggggt gtataatcag   360
ggccgtggta tcgatagcgg ggaacggtta atgcaaccca cacaaatgtc tgcacaggag   420
gatcttgggg acgatacggg catccacgtt atccctacgt taaacggcga tgacagacat   480
aagattgtaa atgtggacca acgtcaatac ggtgacgtgt ttaaaggaga tcttaatcca   540
aagccccaag gccaaagact cattgaggtg tcagtggaag agaatcaccc gtttacttta   600
cgcgcaccga ttcagcggat ttatggagtc cggtacaccg agacttggag cttttttgccg   660
tcattaacct gtacgggaga cgcagcgccc gccatccagc atatatgttt aaagcataca   720
acatgctttc aagacgtggt ggtggatgtg gattgcgcgg agaatactaa agaggatcag   780
ttggccgaaa tcagttaccg tttttcaaggt aagaaggaag cggaccaacc gtggattgtt   840
gtaaacacga gcacactgtt tgatgaactc gaattagacc cacccgagat tgaaccgggt   900
gtcttgaaag tacttcggac agagaaacaa tacttgggtg tgtacatttg gaacatgcgc   960
ggctccgatg gtacgtctac ctacgccacg ttttttggtca cctggaaagg ggatgagaag  1020
acaagaaacc ctacgcccgc agtaactcct caaccaagag gggctgagtt tcatatgtgg  1080
aattaccact cgcatgtatt ttcagttggt gatacgttta gcttggcaat gcatcttcag  1140
tataagatac atgaagcgcc atttgatttg ctgttagagt ggttgtatgt ccccatcgat  1200
cctacatgtc aaccaatgcg gttatattct acgtgtttgt atcatcccaa cgcaccccaa  1260
tgcctctctc atatgaattc cggttgtaca tttacctcgc cacatttagc ccagcgtgtt  1320
gcaagcacag tgtatcagaa ttgtgaacat gcagataact acaccgcata ttgtctggga  1380
atatctcata tggagcctag cttttggtcta atcttacacg acgggggcac cacgttaaag  1440
tttgtagata cacccgagag tttgtcggga ttatacgttt ttgtggtgta ttttaacggg  1500
catgttgaag ccgtagcata cactgttgta tccacagtag atcattttgt aaacgcaatt  1560
gaagagcgtg gatttccgcc aacggccggt cagccaccgg cgactactaa acccaaggaa  1620
attacccccg taaaccccgg aacgtcacca cttctacgat atgccgcatg gaccggaggg  1680
cttgcagcag tagtactttt atgtctcgta atattttttaa tctgtacggc taaacgaatg  1740
agggttaaag ccgccagggt agacaagtga taataggctg gagcctcggt ggccatgctt  1800
cttgcccctt gggcctcccc ccagcccctc ctccccttcc tgcacccgta cccccgtggt  1860
ctttgaataa agtctgagtg ggcggcaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaatcta g                                                        1991

SEQ ID NO: 106     moltype = RNA  length = 1991
FEATURE              Location/Qualifiers
misc_feature         1..1991
                     note = Synthetic Polynucleotide
source               1..1991
                     mol_type = other RNA
                     organism = synthetic construct
SEQUENCE: 106
ggggaaataa gagagaaaag aagagtaaga agaaatataa gagccaccat ggggacagtt    60
aataaacctg tggtgggggt attgatgggg ttcggaatta tcacgggaac gttgcgtata   120
acgaatccgg tcagagcatc cgtcttgcga tacgatgatt ttcacatcga tgaagacaaa   180
ctggatacaa actccgtata tgagccttac taccattcag atcatgcgga gtcttcatgg   240
gtaaatcggg gagagtcttc gcgaaaagcg tacgatcata actcaccttta tatatggcca   300
cgtaatgatt atgatggatt tttagagaac gcacacgaac accatggggt gtataatcag   360
ggccgtggta tcgatagcgg ggaacggtta atgcaaccca cacaaatgtc tgcacaggag   420
gatcttgggg acgatacggg catccacgtt atccctacgt taaacggcga tgacagacat   480
aaaattgtaa atgtggacca acgtcaatac ggtgacgtgt ttaaaggaga tcttaatcca   540
aaaccccaag gccaaagact cattgaggtg tcagtggaag aaaatcaccc gtttacttta   600
cgcgcaccga ttcagcggat ttatggagtc cggtacaccg agacttggag cttttttgccg   660
tcattaacct gtacgggaga cgcagcgccc gccatccagc atatatgttt aaagcataca   720
acatgctttc aagacgtggt ggtggatgtg gattgcgcgg aaaatactaa agaggatcag   780
ttggccgaaa tcagttaccg tttttcaaggt aagaaggaag cggaccaacc gtggattgtt   840
gtaaacacga gcacactgtt tgatgaactc gaattagacc cccccgagat tgaaccgggt   900
gtcttgaaag tacttcggac agagaaacaa tacttgggtg tgtacatttg gaacatgcgc   960
ggctccgatg gtacgtctac ctacgccacg ttttttggtca cctggaaagg ggatgagaag  1020
acaagaaacc ctacgcccgc agtaactcct caaccaagag gggctgagtt tcatatgtgg  1080
aattaccact cgcatgtatt ttcagttggt gatacgttta gcttggcaat gcatcttcag  1140
tataagatac atgaagcgcc atttgatttg ctgttagagt ggttgtatgt ccccatcgat  1200
cctacatgtc aaccaatgcg gttatattct acgtgtttgt atcatcccaa cgcaccccaa  1260
tgcctctctc atatgaattc cggttgtaca tttacctcgc cacatttagc ccagcgtgtt  1320
gcaagcacag tgtatcagaa ttgtgaacat gcagataact acaccgcata ttgtctggga  1380
atatctcata tggagcctag cttttggtcta atcttacacg acgggggcac cacgttaaag  1440
tttgtagata cacccgagag tttgtcggga ttatacgttt ttgtggtgta ttttaacggg  1500
catgttgaag ccgtagcata cactgttgta tccacagtag atcattttgt aaacgcaatt  1560
gaagagcgtg gatttccgcc aacggccggt cagccaccgg cgactactaa acccaaggaa  1620
attacccccg taaaccccgg aacgtcacca cttctacgat atgccgcatg gaccggaggg  1680
cttgcagcag tagtactttt atgtctcgta atattttttaa tctgtacggc taaacgaatg  1740
```

```
agggttaaag ccgccagggt agacaagtga taataggctg gagcctcggt ggccatgctt    1800
cttgcccctt gggcctcccc ccagcccctc ctccccttcc tgcacccgta cccccgtggt    1860
ctttgaataa agtctgagtg ggcggcaaaa aaaaaaaaaa aaaaaaaaaa aaaaaaaaaa    1920
aaaaaaaaaa aaaaaaaaaa aaaaaaaaaa aaaaaaaaaa aaaaaaaaaa aaaaaaaaaa    1980
aaaaaatcta g                                                         1991
```

```
SEQ ID NO: 107          moltype = RNA  length = 1991
FEATURE                 Location/Qualifiers
misc_feature            1..1991
                        note = Synthetic Polynucleotide
source                  1..1991
                        mol_type = other RNA
                        organism = synthetic construct
SEQUENCE: 107
ggggaaataa gagagaaaag aagagtaaga agaaatataa gagccaccat ggggacagtt    60
aataaacctg tggtggggggt attgatgggg ttcggaatta tcacgggaac gttgcgtata    120
acgaatccgg tcagagcatc cgtcttgcga tacgatgatt ttcacatcga tgaagacaaa    180
ctggatacaa actccgtata tgagccttac taccattcag atcatgcgga gtcttcatgg    240
gtaaatcggg gagagtcttc gcgaaaagcg tacgatcata actcacctta tatatggcca    300
cgtaatgatt atgatggatt tttagagaac gcacacgaac accatggggt gtataatcag    360
ggccgtggta tcgatagcgg ggaacggtta atgcaaccca cacaaatgtc tgcacaggag    420
gatcttgggg acgatacggg catccacgtt atccctacgt taaacggcga tgacagacat    480
aaaattgtaa atgtggacca acgtcaatac ggtgacgtgt ttaaaggaga tcttaatcca    540
aaaccccaag gccaaagact cattgaggtg tcagtggaag aaaatcaccc gtttactttta   600
cgcgcaccga ttcagcggat ttatggagtc cggtacaccg agacttggag cttttttgccg   660
tcattaacct gtacgggaga cgcagcgccc gccatccagc atatatgttt aaagcataca    720
acatgctttc aagacgtggt ggtggatgtg gattgcgcgg aaaatactaa agaggatcag    780
ttggccgaaa tcagttaccg ttttcaaggt aagaaggaag cggaccaacc gtggattgtt    840
gtaaacacga gcacactgtt tgatgaactc gaattagacc cacccgagat tgaaccgggt    900
gtcttgaaag tacttcggac agagaaacaa tacttgggtg tgtacatttg gaacatgccgc    960
ggctccgatg gtacgtctac ctacgccacg ttttttggtca cctggaaagg ggatgagaag    1020
acaagaaacc ctacgcccgc agtaactcct caaccaagag gggctgagtt tcatatgtgg    1080
aattaccact cgcatgtatt ttcagttggt gatacgttta gcttggcaat gcatcttcag    1140
tataagatac atgaagcgcc atttgatttg ctgttagagt ggttgtatgt ccccatcgat    1200
cctacatgtc aaccaatgcg gttatattct acgtgtttgt atcatcccaa cgcacacccaa   1260
tgcctctctc atatgaattc cggttgtaca tttacctcgc cacatttagc ccagcgtgtt    1320
gcaagcacag tgtatcagaa ttgtgaacat gcagataact acaccgcata ttgtctggga    1380
atatctcata tggagcctag cttttggtcta atcttcacg acgggggcac cacgttaaag     1440
tttgtagata caccgagag tttgtcggga ttatacgttt ttgtggtgta ttttaacggg     1500
catgttgaag ccgtagcata cactgttgta tccacagtag atcattttgt aaacgcaatt    1560
gaagagcgtg gatttccgcc aacggccggt cagccaccgg cgactactaa acccaaggaa    1620
attacccccg taaaccccgg aacgtcacca cttctacgat atgccgcatg gaccggaggg    1680
cttgcacgag tagtacttttt atgtctcgta atatttttaa tctgtacggc taaacgaatg    1740
agggttaaag ccgccagggt agacaagtga taataggctg gagcctcggt ggccatgctt    1800
cttgcccctt gggcctcccc ccagcccctc ctccccttcc tgcacccgta cccccgtggt    1860
ctttgaataa agtctgagtg ggcggcaaaa aaaaaaaaaa aaaaaaaaaa aaaaaaaaaa    1920
aaaaaaaaaa aaaaaaaaaa aaaaaaaaaa aaaaaaaaaa aaaaaaaaaa aaaaaaaaaa    1980
aaaaaatcta g                                                         1991
```

```
SEQ ID NO: 108          moltype = RNA  length = 1965
FEATURE                 Location/Qualifiers
misc_feature            1..1965
                        note = Synthetic Polynucleotide
source                  1..1965
                        mol_type = other RNA
                        organism = synthetic construct
SEQUENCE: 108
gagaagaaat ataagagcca ccatggggac agttaataaa cctgtggtgg gcgtattgat    60
ggggttcgga attatcacgg gaacgttgcg tataacgaat ccggtcagag catccgtctt    120
gcgatacgat gattttcaca tcgatgaaga caaactggat acaaactccg tatatgagcc    180
ttactaccat tcagatcatg cggagtcttc atgggtaaat cggggagagt cttcgcgaaa    240
ggcgtacgat cataactcac cttatatatg gccacgtaat gattatgatg gattcttaga    300
gaacgcacac gaacaccatg gggtgtataa tcagggccgt ggtatcgata gcggggaacg    360
gttaatgcaa cccacacaaa tgtctgcaca ggaggatctt ggggacgatac ggggcatcca    420
cgttatccct acgttaaacg gcgatgacag acataagatt gtaaatgtgg accaacgtca    480
atacggtgac gtgtttaaag gagatcttaa tccaaagccc caaggccaaa gactcattga    540
ggtgtcagtg gaagagaatc acccgtttac tttacgcgca ccgattcagc ggatttatgg    600
agtccggtac accgagactt ggagcttctt gccgtcatta acctgtacgg gagacgcagc    660
gcccgccatc cagcatatat gtttaaagca tacaacatgc tttcaagacg tggtggttgc    720
tgtggattgc gcggagaata ctaaagagga tcagttggcc gaaatcagtt accgttttca    780
aggtaagaag gaagcggacc aaccgtggat tgttgtaaac acgagcacac tgtttgatga    840
actcgaatta gacccacccg agattgaacc gggtgtcttg aaagtacttc ggacagagaa    900
acaatacttg ggtgtgtaca tttggaacat gcgcggctcc gatggtacgt ctacctacgc    960
cacgttcttg gtcacctgga aaggggatga gaagacgaga acccctacgc ccgcagtaac    1020
tcctcaacca agaggggctg agtttcatat gtggaattac cactcgcatg tattttcagt    1080
tggtgatacg tttagcttgg caatgcatct tcagtataag atacatgaag cgccatttga    1140
tttgctgtta gagtggttgt atgtccccat cgatcctaca tgtcaaccaa tgcggttata    1200
ttctacgtgt ttgtatcatc ccaacgcacc ccaatgcctc tctcatatga attccggttg    1260
tacatttacc tcgccacatt tagcccagcg tgttgcaagc acagtgtatc agaattgtga    1320
```

```
acatgcagat aactacaccg catattgtct gggaatatct catatggagc ctagctttgg   1380
tctaatctta cacgacggag gcaccacgtt aaagtttgta gatacacccg agagtttgtc   1440
gggattatac gtctttgtgg tgtattttaa cgggcatgtt gaagccgtag catacactgt   1500
tgtatccaca gtagatcatt ttgtaaacgc aattgaagag cgtggatttc cgccaacggc   1560
cggtcagcca ccggcgacta ctaaacccaa ggaaattacg cccgtaaacc ccggaacgtc   1620
accacttcta cgatatgccg catggaccgg agggcttgca gcagtagtac ttttatgtct   1680
cgtaatattc ttaatctgta cggctaaacg aatgagggtt aaagccgcca gggtagacaa   1740
gtgataatag gctggagcct cggtggccat gcttcttgcc ccttgggcct cccccagcc    1800
cctcctcccc ttcctgcacc cgtacccccg tggtctttga ataaagtctg agtgggcggc   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa tctag                   1965

SEQ ID NO: 109          moltype = AA   length = 24
FEATURE                 Location/Qualifiers
REGION                  1..24
                        note = Synthetic Polypeptide
source                  1..24
                        mol_type = protein
                        organism = synthetic construct
SEQUENCE: 109
MLGSNSGQRV VFTILLLLVA PAYS                                           24

SEQ ID NO: 110          moltype = AA   length = 17
FEATURE                 Location/Qualifiers
REGION                  1..17
                        note = Synthetic Polypeptide
source                  1..17
                        mol_type = protein
                        organism = synthetic construct
SEQUENCE: 110
MKCLLYLAFL FIGVNCA                                                   17

SEQ ID NO: 111          moltype = AA   length = 15
FEATURE                 Location/Qualifiers
REGION                  1..15
                        note = Synthetic Polypeptide
source                  1..15
                        mol_type = protein
                        organism = synthetic construct
SEQUENCE: 111
MWLVSLAIVT ACAGA                                                     15

SEQ ID NO: 112          moltype = DNA   length = 1729
FEATURE                 Location/Qualifiers
misc_feature            1..1729
                        note = Synthetic Polynucleotide
source                  1..1729
                        mol_type = other DNA
                        organism = synthetic construct
SEQUENCE: 112
tcaagctttt ggaccctcgt acagaagcta atacgactca ctatagggaa ataagagaga   60
aaagaagagt aagaagaaat ataagagcca ccatggcaca agtcattaat acaaacagcc   120
tgtcgctgtt gacccagaat aacctgaaca aatcccagtc cgcactgggc actgctatcg   180
agcgtttgtc ttccggtctg cgtatcaaca gcgcgaaaga cgatgcggca ggacaggcga   240
ttgctaaccg ttttaccgcg aacatcaaag gtctgactca ggcttcccgt aacgctaacg   300
acggtatctc cattgcgcag accactgaag gcgcgctgaa cgaaatcaac aacaacctgc   360
agcgtgtgcg tgaactggcg gttcagtctg cgaatggtac taactcccag tctgacctcg   420
actccatcca ggctgaaatc acccagcgcc tgaacgaaat cgaccgtgta tccggccaga   480
ctcagttcaa cggcgtgaaa gtcctggcgc aggacaacac cctgaccatc caggttggtg   540
ccaacgacgg tgaaactatc gatattgatt taaagagaaat cagctctaaa acactgggac   600
ttgataagct taatgtccaa gatgcctaca ccccgaaaga aactgctgta accgttgata   660
aaactaccta taaaaatggt acagatccta ttacagccca gagcaatact gatatccaaa   720
ctgcaattgg cggtggtgca acggggggtta ctggggctga tatcaaattt aaagatggtc   780
aatactattt agatgttaaa ggcggtgctt ctgctggtga ttataagcc acttatgatg   840
aaactacaaa gaaagttaat attgatacga ctgataaaac tccgttggca actgcggaag   900
ctacagctat tcggggaacg gccactataa cccacaacca aattgctgaa gtaacaaaag   960
agggtgttga tacgaccaca gttgcggctc aacttgctgc agcagggggtt actggcgccg   1020
ataaggacaa tactagcctt gtaaaactat cgtttgagga taaaaacggt aaggttattg   1080
atggtggcta tgcagtgaaa atgggcgacg atttctatgc cgctacatat gatgagaaaa   1140
caggtgcaat tactgctaaa accactactt atacagatgg tactggcgtt gctcaaactg   1200
gagctgtgaa atttggtggc gcaaatggta aatctgaagt tgttactgct accgatggta   1260
agacttactt agcaagcgac cttgacaaac ataacttcag aacaggcggt gagcttaaag   1320
aggttaatac agataagact gaaaacccac tgcagaaaat tgatgctgcc ttggcacagg   1380
ttgatacact tcgttctgac ctgggtgcgg ttcagaaccg tttcaactcc gctatcacca   1440
acctgggcaa taccgtaaat aacctgtctt ctgcccgtag ccgtatcgaa gattccgact   1500
acgcaaccga agtctccaac atgtctcgcg cgcagattct gcagcaggcc ggtacctccg   1560
ttctggcgca ggcgaaccag gttccgcaaa acgtcctctc tttactgcgt tgataatagg   1620
ctggagcctg ggtggccatg cttcttgccc cttgggcctc cccccagccc ctcctccct    1680
tcctgcaccc gtacccccgt ggtctttgaa taaagtctga gtgggcggc                1729
```

```
SEQ ID NO: 113          moltype = DNA  length = 1518
FEATURE                 Location/Qualifiers
misc_feature            1..1518
                        note = Synthetic Polynucleotide
source                  1..1518
                        mol_type = other DNA
                        organism = synthetic construct
SEQUENCE: 113
atggcacaag tcattaatac aaacagcctg tcgctgttga cccagaataa cctgaacaaa   60
tcccagtccg cactgggcac tgctatcgag cgtttgtctt ccggtctgcg tatcaacagc  120
gcgaaagacg atgcggcagg acaggcgatt gctaaccgtt ttaccgcgaa catcaaaggt  180
ctgactcagg cttcccgtaa cgctaacgac ggtatctcca ttgcgcagac cactgaaggc  240
gcgctgaacg aaatcaacaa caacctgcag cgtgtgcgtg aactggcggt tcagtctgcg  300
aatggtacta actcccagtc tgacctcgac tccatccagg ctgaaatcac ccagcgcctg  360
aacgaaatcg accgtgtatc cggccagact cagttcaacg gcgtgaaagt cctggcgcag  420
gacaacaccc tgaccatcca ggttggtgcc aacgacggtg aaactatcga tattgattta  480
aaagaaatca gctctaaaac actgggactt gataagctta atgtccaaga tgcctacacc  540
ccgaaagaaa ctgctgtaac cgttgataaa actacctata aaaatggtac agatcctatt  600
acagcccaga gcaatactga tatccaaact gcaattggcg gtggtgcaac ggggggttact  660
ggggctgata tcaaatttaa agatggtcaa tactatttag atgttaaagg cggtgcttct  720
gctggtgttt ataaagccac ttatgatgaa actacaaaga aagttaatat tgatacgact  780
gataaaactc cgttggcaac tgcggaagct cagcgtattc ggggaacggc cactataacc  840
cacaaccaaa ttgctgaagt aacaaaagag ggtgttgata cgaccacagt tgcggctcaa  900
cttgctgcag caggggttac tggcgccgat aaggacaata ctagccttgt aaaactatcg  960
tttgaggata aaaacggtaa ggttattgat ggtggctatg cagtgaaaat gggcgacgat 1020
ttctatgccg ctacatatga tgagaaaaca ggtgcaatta ctgctaaaac cactacttat 1080
acagatggta ctgcgcttgc tcaaactgga gctgtgaaat ttggtggcgc aaatggtaaa 1140
tctgaagttg ttactgctac cgatggtaag acttacttag caagcgacct tgacaaacat 1200
aacttcagaa caggcggtga gcttaaagag gttaatacag ataagactga aaacccactg 1260
cagaaaattg atgctgcctt ggcacaggtt gatacacttc gttctgacct gggtgcggtt 1320
cagaaccgtt tcaactccgc tatcaccaac ctgggcaata ccgtaaataa cctgtcttct 1380
gcccgtagcc gtatcgaaga ttccgactac gcaaccgaag tctccaacat gtctcgcgcg 1440
cagattctgc agcaggccgg tacctccgtt ctggcgcagg cgaaccaggt tccgcaaaac 1500
gtcctctctt tactgcgt                                                1518

SEQ ID NO: 114          moltype = RNA  length = 1790
FEATURE                 Location/Qualifiers
misc_feature            1..1790
                        note = Synthetic Polynucleotide
source                  1..1790
                        mol_type = other RNA
                        organism = synthetic construct
SEQUENCE: 114
ggggaaataa gagagaaaag aagagtaaga agaaatataa gagccaccat ggcacaagtc   60
attaatacaa acagcctgtc gctgttgacc cagaataacc tgaacaaatc ccagtccgca  120
ctgggcactg ctatcgagcg tttgtcttcc ggtctgcgta tcaacagcga aaagacgat  180
gcggcaggac aggcgattgc taaccgtttt accgcgaaca tcaaaggtct gactcaggct  240
tcccgtaacg ctaacgacgg tatctccatt gcgcagacca ctgaaggcgc gctgaacgaa  300
atcaacaaca acctgcagcg tgtgcgtgaa ctggcggttc agtctgcgaa tggtactaac  360
tcccagtctg acctcgactc catccaggct gaaatcaccc agcgcctgaa cgaaatcagc  420
cgtgtatccg gccagactca gttcaacggc gtgaaagtcc tggcgcagga caacaccctg  480
accatccagg ttggtgccaa cgacggtgaa actatcgata ttgatttaaa agaaatcagc  540
tctaaaacac tgggacttga taagcttaat gtccaagatg cctacacccc gaaagaaact  600
gctgtaaccg ttgataaaac tacctataaa aatggtacag atcctattac agcccagagc  660
aatactgata tccaaactgc aattggcggt ggtgcaacgg gggttactgg ggctgatatc  720
aaatttaaag atggtcaata ctatttagat gttaaaggcg gtgcttctgc tggtgtttat  780
aaagccactt atgatgaaac tacaaagaaa gttaatattg atacgactga taaaactccg  840
ttggcaactg cggaagctac agctattcgg ggaacggcca ctataaccca caaccaaatt  900
gctgaagtaa caaaagaggg tgttgatacg accacagttg cggctcaact tgctgcagca  960
ggggttactg gcgccgataa ggacaatact agccttgtaa aactatcgtt tgaggataaa 1020
aacggtaagg ttattgatgg tggctatgca gtgaaaatgg gcgacgattt ctatgccgct 1080
acatatgatg agaaaacagg tgcaattact gctaaaacca ctacttatac agatggtact 1140
gcgcttgctc aaactggagc tgtgaaattt ggtggcgcaa atggtaaatc tgaagttgtt 1200
actgctaccg atggtaagac ttacttagca agcgaccttg acaaacataa cttcagaaca 1260
ggcggtgagc ttaaagaggt taatacagat aagactgaaa cccactgcag aaaattgat 1320
gctgccttgg cacaggttga tacacttcgt tctgacctgg gtgcggttca gaaccgtttc 1380
aactccgcta tcaccaacct gggcaatacc gtaaataacc tgtcttctgc ccgtagccgt 1440
atcgaagatt ccgactacgc aaccgaagtc tccaacatgt ctcgcgcgca gattctgcag 1500
caggccggta cctccgttct ggcgcaggcg aaccaggttc cgcaaaacgt cctctcttta 1560
ctgcgttgat aataggctgg agcctcggtg gccatgcttc ttgcccccttg ggcctccccc 1620
cagcccctcc tcccccttcct gcaccgtac ccccgtggtc tttgaataaa gtctgagtgg 1680
gcggcaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaatctag             1790

SEQ ID NO: 115          moltype = AA  length = 506
FEATURE                 Location/Qualifiers
REGION                  1..506
                        note = Synthetic Polypeptide
```

```
source                1..506
                      mol_type = protein
                      organism = synthetic construct
SEQUENCE: 115
MAQVINTNSL SLLTQNNLNK SQSALGTAIE RLSSGLRINS AKDDAAGQAI ANRFTANIKG  60
LTQASRNAND GISIAQTTEG ALNEINNNLQ RVRELAVQSA NGTNSQSDLD SIQAEITQRL 120
NEIDRVSGQT QFNGVKVLAQ DNTLTIQVGA NDGETIDIDL KEISSKTLGL DKLNVQDAYT 180
PKETAVTVDK TTYKNGTDPI TAQSNTDIQT AIGGGATGVT GADIKFKDGQ YYLDVKGGAS 240
AGVYKATYDE TTKKVNIDTT DKTPLATAEA TAIRGTATIT HNQIAEVTKE GVDTTTVAAQ 300
LAAAGVTGAD KDNTSLVKLS FEDKNGKVID GGYAVKMGDD FYAATYDEKT GAITAKTTTY 360
TDGTGVAQTG AVKFGGANGK SEVVTATDGK TYLASDLDKH NFRTGGELKE VNTDKTENPL 420
QKIDAALAQV DTLRSDLGAV QNRFNSAITN LGNTVNNLSS ARSRIEDSDY ATEVSNMSRA 480
QILQQAGTSV LAQANQVPQN VLSLLR                                      506

SEQ ID NO: 116        moltype = AA   length = 698
FEATURE               Location/Qualifiers
REGION                1..698
                      note = Synthetic Polypeptide
source                1..698
                      mol_type = protein
                      organism = synthetic construct
SEQUENCE: 116
MAQVINTNSL SLLTQNNLNK SQSALGTAIE RLSSGLRINS AKDDAAGQAI ANRFTANIKG  60
LTQASRNAND GISIAQTTEG ALNEINNNLQ RVRELAVQSA NSTNSQSDLD SIQAEITQRL 120
NEIDRVSGQT QFNGVKVLAQ DNTLTIQVGA NDGETIDIDL KQINSQTLGL DTLNVQQKYK 180
VSDTAATVTG YADTTIALDN STFKASATGL GGTDQKIDGD LKFDDTTGKY YAKVTVTGGT 240
GKDGYYEVSV DKTNGEVTLA GGATSPLTGG LPATATEDVK NVQVANADLT EAKAALTAAG 300
VTGTASVVKM SYTDNNGKTI DGGLAVKVGD DYYSATQNKD GSISINTTKY TADDGTSKTA 360
LNKLGGADGK TEVVSIGGKT YAASKAEGHN FKAQPDLAEA AATTTENPLQ KIDAALAQVD 420
TLRSDLGAVQ NRFNSAITNL GNTVNNLTSA RSRIEDSDYA TEVSNMSRAQ ILQQAGTSVL 480
AQANQVPQNV LSLLRGGGGS GGGGSMMAPD PNANPNANPN ANPNANPNAN PNANPNANPN 540
ANPNANPNAN PNANPNANPN ANPNANPNAN PNANPNANPN ANPNANPKN NQGNGQGHNM 600
PNDPNRNVDE NANANNAVKN NNNEEPSDKH IEQYLKKIKN SISTEWSPCS VTCGNGIQVR 660
IKPGSANKPK DELDYENDIE KKICKMEKCS SVFNVVNS                        698

SEQ ID NO: 117        moltype = AA   length = 692
FEATURE               Location/Qualifiers
REGION                1..692
                      note = Synthetic Polypeptide
source                1..692
                      mol_type = protein
                      organism = synthetic construct
SEQUENCE: 117
MMAPDPNANP NANPNANPNA NPNANPNANP NANPNANPNA NPNANPNANP NANPNANPNA  60
NPNANPNANP NANPNANPNA NPNKNNQGNG QGHNMPNDPN RNVDENANAN NAVKNNNNEE 120
PSDKHIEQYL KKIKNSISTE WSPCSVTCGN GIQVRIKPGS ANKPKDELDY ENDIEKKICK 180
MEKCSSVFNV VNSRPVTMAQ VINTNSLSLL TQNNLNKSQS ALGTAIERLS SGLRINSAKD 240
DAAGQAIANR FTANIKGLTQ ASRNANDGIS IAQTTEGALN EINNNLQRVR ELAVQSANST 300
NSQSDLDSIQ AEITQRLNEI DRVSGQTQFN GVKVLAQDNT LTIQVGANDG ETIDIDLKQI 360
NSQTLGLDTL NVQQKYKVSD TAATVTGYAD TTIALDNSTF KASATGLGGT DQKIDGDLKF 420
DDTTGKYYAK VTVTGGTGKD GYYEVSVDKT NGEVTLAGGA TSPLTGGLPA TATEDVKNVQ 480
VANADLTEAK AALTAAGVTG TASVVKMSYT DNNGKTIDGG LAVKVGDDYY SATQNKDGSI 540
SINTTKYTAD DGTSKTALNK LGGADGKTEV VSIGGKTYAA SKAEGHNFKA QPDLAEAAAT 600
TTENPLQKID AALAQVDTLR SDLGAVQNRF NSAITNLGNT VNNLTSARSR IEDSDYATEV 660
SNMSRAQILQ QAGTSVLAQA NQVPQNVLSL LR                              692

SEQ ID NO: 118        moltype = AA   length = 13
FEATURE               Location/Qualifiers
source                1..13
                      mol_type = protein
                      organism = Salmonella enterica
SEQUENCE: 118
LQRVRELAVQ SAN                                                    13

SEQ ID NO: 119        moltype = AA   length = 4
FEATURE               Location/Qualifiers
REGION                1..4
                      note = Synthetic Polypeptide
source                1..4
                      mol_type = protein
                      organism = synthetic construct
SEQUENCE: 119
AYRV                                                              4

SEQ ID NO: 120        moltype = AA   length = 4
FEATURE               Location/Qualifiers
REGION                1..4
                      note = Synthetic Polypeptide
source                1..4
```

```
                        mol_type = protein
                        organism = synthetic construct
SEQUENCE: 120
AARV                                                                    4

SEQ ID NO: 121          moltype = AA  length = 4
FEATURE                 Location/Qualifiers
REGION                  1..4
                        note = Synthetic Polypeptide
source                  1..4
                        mol_type = protein
                        organism = synthetic construct
SEQUENCE: 121
YAGL                                                                    4

SEQ ID NO: 122          moltype = AA  length = 4
FEATURE                 Location/Qualifiers
REGION                  1..4
                        note = Synthetic Polypeptide
source                  1..4
                        mol_type = protein
                        organism = synthetic construct
SEQUENCE: 122
SSTT                                                                    4

SEQ ID NO: 123          moltype = RNA  length = 2080
FEATURE                 Location/Qualifiers
source                  1..2080
                        mol_type = genomic RNA
                        organism = Human alphaherpesvirus 3
SEQUENCE: 123
tcaagctttt ggaccctcgt acagaagcta atacgactca ctatagggaa ataagagaga   60
aaagaagagt aagaagaaat ataagagcca ccatggggac agtgaataag ccggttgtgg   120
gcgtgcttat gggctttggg attattaccg gtacattacg aattaccaat ccagtgcgcg   180
ccagtgtgct gcgttacgac gactttcaca ttgacgagga taagctggat actaacagcg   240
tgtacgaacc ttattaccac tcagatcatg ccgaatcaag ctgggttaat agaggagaaa   300
gcagccgaaa agcctacgac cacaactcac cttatatttg gcccagaaac gattatgacg   360
gtttcctgga aaacgcacat gaacaccatg gagtctacaa ccaaggcagg ggaatcgaca   420
gtggcgagcg tcttatgcag ccaacacaga tgtcggcaca gaggatctcc ggtgatgaca   480
ccggcataca cgtgattccc acattaaacg gcgacgacag acataagatc gtcaatgtgg   540
atcagccgtca gtatggggat gtctttaaag gcgatttgaa tccaaagccc caaggacaga   600
gactgatcga ggtctctgta gaagaaaatc accccttcac tttgcgcgct ccaatccaga   660
ggatttacgg ggtgcgttat accgaaactt ggagtttctt gccgtcactg acgtgtacgg   720
gggatgccgc ccccgcaatc cagcacatct gtctgaaaca caccacatgc tttcaggacg   780
tggttgtgga tgtggattgc gcggaaaaca caaaagaaga ccaactcgcc gaaatcagct   840
atcgttttca gggtaaaaaa gaggccgacc aaccgtggat tgttgtgaat acgagcacgc   900
tcttcgatga gcttgaactc gatcccccgg aaatcgacgc tggggttcta aaagtgttga   960
ggaccgagaa gcagtacctc ggggtttata tctggaatat gagaggctcc gatggcacct   1020
ctacctacgc aacgtttctg gttacctgga agggagacga gaagacacgg aatccaacgc   1080
ccgctgtgac ccctcagcct aggggagccg aattccacat gtggaactat cactccatg   1140
tattcagtgt gggtgacact ttcagcctgg ccatgcacct gcagtataag attcacgagg   1200
cacccttcga cctcctgctg gagtggttgt acgtacctat tgatcccact tgtcagccca   1260
tgcgcctgta ctccacttgc ttgtaccacc ccaatgcacc acagtgtcta tcacacatga   1320
actccgggtg tacctttact tcaccccatc ttgcccagcg ggtcgccagc acagtgtatc   1380
agaactgtga gcatgctgac aactatactg cttattgcct cggaatatcc catatggagc   1440
caagcttcgg gctcatactg cacgatggtg gtacgacact caagttcgtg gacaccccg   1500
aaaagccttc tggcttgtac gtgttcgtgg tctacttcaa tggacatgtg gaggcagtgg   1560
cttacacagt ggtttcgaca gttgatcact ttgtaaatgc cattgaggaa cgcgcgcttcc   1620
cgcctacagc gggccagccc cctgcgacaa caaaaccaaa agagattacg cccgttaatc   1680
ctgggactag tccattgctg aggtatgccg cctggactgg cggtctggcg gccgtgtac   1740
ttctgtgttt agtcatattt ctgatctgta ccgctaaacg tatgcgggtc aaggcttacc   1800
gtgttgacaa gtctccttac aatcagtcaa tgtactatgc aggactccct gttgacgatt   1860
tcgaagactc agagagtaca gacacagaag aagaattcgg aaacgctata ggtggctctc   1920
acggagggtag ctcgtataca gtgtacatcg ataaaccgag atgataatag gctggagcct   1980
cggtggccat gcttcttgcc ccttgggcct ccccccagcc cctcctcccc ttcctgcacc   2040
cgtaccccg tggtctttga ataaagtctg agtgggcggc   2080

SEQ ID NO: 124          moltype = RNA  length = 1276
FEATURE                 Location/Qualifiers
source                  1..1276
                        mol_type = genomic RNA
                        organism = Human alphaherpesvirus 3
SEQUENCE: 124
tcaagctttt ggaccctcgt acagaagcta atacgactca ctatagggaa ataagagaga   60
aaagaagagt aagaagaaat ataagagcca ccatgttttt aatccaatgt ttgatatcgg   120
ccgtttatat ttacatacaa gtgaccaacg ctttgatctt caaggcgac cacgtgagct   180
tgcaagttaa cagcagtctc acgtctatcc ttattcccat gcaaaatgat aattatacag   240
agataaaagg acagcttgtc tttattggag agcaactacc taccgggaca aactatacgc   300
gaacactgga actgttatac gcggatacgg tggcgttttg tttccggtca gtacaagtaa   360
```

```
taagatacga cggatgtccc cggattagaa cgagcgcttt tatttcgtgt aggtacaaac    420
attcgtggca ttatggtaac tcaacggatc ggatatcaac agagccggat gctggtgtaa    480
tgttgaaaat taccaaaccg ggaataaatg atgctggtgt gtatgtactt cttgttcggt    540
tagaccatag cagatccacc gatggtttca ttcttggtgt aaatgtatat acagcgggct    600
cgcatacaaa cattcacggg gttatctaca cttctccatc tctacagaat ggatattcta    660
caagagccct tttcaacaa gctcgtttgt gtgatttacc cgcgacaccc aaagggtccg    720
gtacctccct gtttcaacat atgcttgatc ttcgtgccgg taaatcgtta gaggataacc    780
cttggttaca tgaggacgtt gttacgacag aaactaagtc cgttgttaag gaggggatag    840
aaaatcacgt atatccaacg gatatgtcca cgttacccga aaagtccctt aatgatcctc    900
cagaaaatct acttataatt attcctatag tagcgtctgt catgatcctc accgccatgg    960
ttattgttat tgtaataagc gttaagcgac gtagaattaa aaaacatcca atttatcgcc   1020
caaatacaaa aacaagaagg ggcatacaaa atgcgacacc agaatccgat gtgatgttgg   1080
aggccgccat tgcacaacta gcaacgattc gcgaagaatc cccccacat tccgttgtaa    1140
acccgtttgt taaatagtga taataggctg gagcctcggc ggccatgctt ctttgcccctt   1200
gggcctcccc ccagccccte ctcccctccc tgcacccgta cccccgtggt ctttgaataa   1260
agtctgagtg ggcggc                                                  1276

SEQ ID NO: 125          moltype = RNA  length = 1897
FEATURE                 Location/Qualifiers
misc_feature           1..1897
                        note = Synthetic Polynucleotide
source                 1..1897
                        mol_type = other RNA
                        organism = synthetic construct
SEQUENCE: 125
tcaagctttt ggaccctcgt acagaagcta atacgactca ctatagggaa ataagagaga    60
aaagaagagt aagaagaaat ataagagcca ccatggggac agttaatata cctgtggtgg    120
gggtattgat ggggttcgga attatcacgg gaacgttgcg tataacgaat ccggtcagag    180
catccgtctt gcgatacgat gattttcaca tcgatgaaga caaactggat acaaactccg    240
tatatgagcc ttactaccat tcagatcatg cggagtcttc atgggtaaat cggggagagt    300
cttcgcgaaa agcgtacgat cataactcac cttatatatg gccacgtaat gattatgatg    360
gatttttaga gaacgcacac gaacaccatg gggtgtataa tcagggccgt ggtatcgata    420
gcggggaacg gttaatgcaa cccacacaaa tgtctgcaca ggaggatctt ggggacgata    480
cgggcatcca cgttatccct acgttaaacg gcgatgacag acataaaatt gtaaatgtgg    540
accaacgtca atacggtgac gtgtttaaag gagatcttaa tccaaaaccc caaggccaaa    600
gactcattga ggtgtcagtg gaagaaaatc acccgtttac tttacgcgca ccgattcagc    660
ggatttatgg agtccggtac accgagactt ggagcttttt gccgtcatta acctgtacgg    720
gagacgcagc gcccgccatc cagcatatat gtttaaaaca tacaacatgc tttcaagacg    780
tggtggtgga tgtggattgc gcggaaaata ctaaagagga tcagttggcc gaaatcagtt    840
accgtttttca aggtaagaag gaagcggacc aaccgtggat tgttgtaaac acgagcacac    900
tgtttgatga actcgaatta gaccccccg agattgaacc gggtgtcttg aaagtacttc    960
ggacagaaaa acaatacttg ggtgtgtaca tttggaacat gcgcggctcc gatggtacgt   1020
ctacctacgc cacgtttttg gtcacctgga aagggatga aaaacaaga aaccctacgc   1080
ccgcagtaac tcctcaacca agaggggctg agtttcatat gtggaattac cactcgcatg   1140
tattttcagt tggtgatacg tttagcttgg caatgcatct tcagtataag atacatgaag   1200
cgccatttga tttgctgtta gagtggttgt atgtccccat cgatcctaca tgtcaaccaa   1260
tgcggttata ttctacgtgt ttgtatcatc ccaacgcacc ccaatgcctc tctcatatga   1320
attccggttg tacatttacc tcgccacatt tagcccagcg tgttgcaagc acagtgtatc   1380
aaaattgtga acatgcagat aactacaccg catattgtct gggaatatct catatggagc   1440
ctagctttgg tctaatctta cacgacgggg gcaccacgtt aaagtttgta gatacacccg   1500
agagtttgtc gggattatac gtttttgtgg tgtattttaa cgggcatgtt gaagccgtaa   1560
catacactgt tgtatccaca gtagatcatt ttgtaaacgc aattgaagag cgtgggatttc   1620
cgccaacggc cggtcagcca ccggcgacta ctaaacccaa ggaaattacc cccgtaaacc   1680
ccggaacgtc accacttcta cgatatgccg catggaccgg agggcttgca gcagtagtac   1740
ttttatgtct cgtaatattt ttaatctgta cggcttgatg ataataggct ggagcctcgg   1800
tggccatgct tcttgcccct tgggcctccc cccagccccct cctcccttc ctgcaccgt   1860
accccgtgg tctttgaata aagtctgagt gggcggc                             1897

SEQ ID NO: 126          moltype = RNA  length = 1867
FEATURE                 Location/Qualifiers
misc_feature           1..1867
                        note = Synthetic Polynucleotide
source                 1..1867
                        mol_type = other RNA
                        organism = synthetic construct
SEQUENCE: 126
tcaagctttt ggaccctcgt acagaagcta atacgactca ctatagggaa ataagagaga    60
aaagaagagt aagaagaaat ataagagcca ccatggggac cccggcgcag ctgctgtttc    120
tgctgctgct gtggctgccg gataccaccg gctccgtctt gcgatacgat gattttcaca    180
tcgatgaaga caaactggat acaaactccg tatatgagcc ttactaccat tcagatcatg    240
cggagtcttc atgggtaaat cggggagagt cttcgcgaaa agcgtacgat cataactcac    300
cttatatatg gccacgtaat gattatgatg gattttaga gaacgcacac gaacaccatg    360
gggtgtataa tcagggccgt ggtatcgata gcggggaacg gttaatgcaa cccacacaaa    420
tgtctgcaca ggaggatctt ggggacgata cgggcatcca cgttatccct acgttaaacg    480
gcgatgacag acataaaatt gtaaatgtgg accaacgtca atacggtgac gtgtttaaag    540
gagatcttaa tccaaaaccc caaggccaaa gactcattga ggtgtcagtg gaagaaaatc    600
acccgtttac tttacgcgca ccgattcagc ggatttatgg agtccggtac accgagactt    660
ggagcttttt gccgtcatta acctgtacgg gagacgcagc gcccgccatc cagcatatat    720
gtttaaaaca tacaacatgc tttcaagacg tggtggtgga tgtggattgc gcggaaaata    780
```

-continued

```
ctaaagagga tcagttggcc gaaatcagtt accgttttca aggtaagaag gaagcggacc   840
aaccgtggat tgttgtaaac acgagcacac tgtttgatga actcgaatta gacccccccg   900
agattgaacc gggtgtcttg aaagtacttc ggacagaaaa acaatacttg ggtgtgtaca   960
tttggaacat gcgcggctcc gatggtacgt ctacctacgc cacgtttttg gtcacctgga  1020
aagggggatga aaaaacaaga aaccctacgc ccgcagtaac tcctcaacca aaggggctg  1080
agtttcatat gtggaattac cactcgcatg tattttcagt tggtgatacg tttagcttgg  1140
caatgcatct tcagtataag atacatgaag cgccatttga tttgctgtta gagtggttgt  1200
atgtccccat cgatcctaca tgtcaaccaa tgcggttata ttctacgtgt ttgtatcatc  1260
ccaacgcacc ccaatgcctc tctcatatga attccggttg tacatttacc tcgccacatt  1320
tagcccagcg tgttgcaagc acagtgtatc aaaattgtga acatgcagat aactacaccg  1380
catattgtct gggaatatct catatggagc ctagctttgg tctaatctta cacgacgggg  1440
gcaccacgtt aaagtttgta gatacacccg agagtttgtc gggattatac gttttgtgg   1500
tgtattttaa cgggcatgtt gaagccgtag catacactgt tgtatccaca gtagatcatt  1560
ttgtaaacgc aattgaagag cgtggatttc cgccaacggc cggtcagcca ccggcgacta  1620
ctaaacccaa ggaaattacc cccgtaaacc ccggaacgtc accacttcta cgatatgccg  1680
catggaccgg agggcttgca gcagtagtac ttttatgtct cgtaatattt ttaatctgta  1740
cggcttgatg ataataggct ggagcctcgg tggccatgct tcttgcccct tgggcctccc  1800
cccagcccct cctccccttc ctgcacccgt accccgtgtg tctttgaata aagtctgagt  1860
gggcggc                                                            1867
```

```
SEQ ID NO: 127           moltype = RNA  length = 1933
FEATURE                  Location/Qualifiers
misc_feature             1..1933
                         note = Synthetic Polynucleotide
source                   1..1933
                         mol_type = other RNA
                         organism = synthetic construct
SEQUENCE: 127
tcaagctttt ggaccctcgt acagaagcta atacgactca ctatagggaa ataagagaga   60
aaagaagagt aagaagaaat ataagagcca ccatggggac agttaataaa cctgtggtgg  120
gggtattgat ggggttcgga attatcacgg gaacgttgcg tataacgaat ccggtcagag  180
catccgtctt gcgatacgat gattttcaca tcgatgaaga caaactggat acaaactccg  240
tatatgagcc ttactaccat tcagatcatg cggagtcttc atgggtaaat cggggagagt  300
cttcgcgaaa agcgtacgat cataactcac cttatatatg gccacgtaat gattatgatg  360
gatttttaga gaacgcacac gaacaccatg gggtgtataa tcagggccgt ggtatcgata  420
gcggggaacg gttaatgcaa cccacacaaa tgtctgcaca ggaggatctt ggggacgata  480
cgggcatcca cgttatccct acgttaaacg gcgatgacag acataaaatt gtaaatgtgg  540
accaacgtca atacggtgac gtgtttaaag gagatcttaa tccaaaaccc caaggccaaa  600
gactcattga ggtgtcagtg gaagaaaatc accgttttac tttacgcgca ccgattcagc  660
ggatttatgg agtccggtac accgagactc ggagcttttt gccgtcatta acctgtacgg  720
gagacgcagc gcccgccatc cagcatatat gtttaaaaca tacaacatgc tttcaagacg  780
tggtggtgga tgtggattgc gcggaaaata ctaaagagga tcagttggcc gaaatcagtt  840
accgttttca aggtaagaag gaagcggacc aaccgtggat tgttgtaaac acgagcacac  900
tgtttgatga actcgaatta gacccccccg agattgaacc gggtgtcttg aaagtacttc  960
ggacagaaaa acaatacttg ggtgtgtaca tttggaacat gcgcggctcc gatggtacgt  1020
ctacctacgc cacgtttttg gtcacctgga aagggggatga aaaaacaaga aaccctacgc  1080
ccgcagtaac tcctcaacca agagggggctg agtttcatat gtggaattac cactcgcatg  1140
tattttcagt tggtgatacg tttagcttgg caatgcatct tcagtataag atacatgaag  1200
cgccatttga tttgctgtta gagtggttgt atgtccccat cgatcctaca tgtcaaccaa  1260
tgcggttata ttctacgtgt ttgtatcatc ccaacgcacc ccaatgcctc tctcatatga  1320
attccggttg tacatttacc tcgccacatt tagcccagcg tgttgcaagc acagtgtatc  1380
aaaattgtga acatgcagat aactacaccg catattgtct gggaatatct catatggagc  1440
ctagctttgg tctaatctta cacgacgggg gcaccacgtt aaagtttgta gatacacccg  1500
agagtttgtc gggattatac gttttgtgg tgtattttaa cgggcatgtt gaagccgtag  1560
catacactgt tgtatccaca gtagatcatt ttgtaaacgc aattgaagag cgtggatttc  1620
cgccaacggc cggtcagcca ccggcgacta ctaaacccaa ggaaattacc cccgtaaacc  1680
ccggaacgtc accacttcta cgatatgccg catggaccgg agggcttgca gcagtagtac  1740
ttttatgtct cgtaatattt ttaatctgta cggctaaacg aatgagggt aaagcctata  1800
gggtagacaa gtgatgataa taggctggag cctcggtggc catgcttctt gccccttggg  1860
cctcccccca gccctcctc cccttcctgc accccgtaccc cgtggtctt tgaataaagt  1920
ctgagtgggc ggc                                                     1933
```

```
SEQ ID NO: 128           moltype = RNA  length = 1933
FEATURE                  Location/Qualifiers
misc_feature             1..1933
                         note = Synthetic Polynucleotide
source                   1..1933
                         mol_type = other RNA
                         organism = synthetic construct
SEQUENCE: 128
tcaagctttt ggaccctcgt acagaagcta atacgactca ctatagggaa ataagagaga   60
aaagaagagt aagaagaaat ataagagcca ccatggggac agttaataaa cctgtggtgg  120
gggtattgat ggggttcgga attatcacgg gaacgttgcg tataacgaat ccggtcagag  180
catccgtctt gcgatacgat gattttcaca tcgatgaaga caaactggat acaaactccg  240
tatatgagcc ttactaccat tcagatcatg cggagtcttc atgggtaaat cggggagagt  300
cttcgcgaaa agcgtacgat cataactcac cttatatatg gccacgtaat gattatgatg  360
gatttttaga gaacgcacac gaacaccatg gggtgtataa tcagggccgt ggtatcgata  420
gcggggaacg gttaatgcaa cccacacaaa tgtctgcaca ggaggatctt ggggacgata  480
cgggcatcca cgttatccct acgttaaacg gcgatgacag acataaaatt gtaaatgtgg  540
```

-continued

```
accaacgtca atacggtgac gtgtttaaag gagatcttaa tccaaaaccc caaggccaaa    600
gactcattga ggtgtcagtg gaagaaaatc acccgtttac tttacgcgca ccgattcagc    660
ggatttatgg agtccggtac accgagactt ggagcttttt gccgtcatta acctgtacgg    720
gagacgcagc gcccgccatc cagcatatat gtttaaaaca tacaacatgc tttcaagacg    780
tggtggtgga tgtggattgc gcggaaaata ctaaagagga tcagttggcc gaaatcagtt    840
accgttttca aggtaagaag gaagcggacc aaccgtggat tgttgtaaac acgagcacac    900
tgtttgatga actcgaatta gaccccccg agattgaacc gggtgtcttg aaagtacttc     960
ggacagaaaa acaatacttg ggtgtgtaca tttggaacat gcgcggctcc gatggtacgt   1020
ctacctacgc cacgtttttg gtcacctgga aaggggatga aaaaacaaga aaccctacgc   1080
ccgcagtaac tcctcaacca agaggggctg agtttcatat gtggaattac cactcgcatg   1140
tattttcagt tggtgatacg tttagcttgg caatgcatct tcagtataag atacatgaag   1200
cgccatttga tttgctgtta gagtggttgt atgtccccat cgatcctaca tgtcaaccaa   1260
tgcggttata ttctacgtgt ttgtatcatc ccaacgcacc ccaatgcctc tctcatatga   1320
attccggttg tacatttacc tcgccacatt tagcccagcg tgttgcaagc acagtgtatc   1380
aaaattgtga acatgcagat aactacaccg catattgtct gggaatatct catatggagc   1440
ctagctttgg tctaatctta cacgacgggg gcaccacgtt aaagtttgta gatacacccg   1500
agagtttgtc gggattatac gttttttgtgg tgtattttaa cgggcatgtt gaagccgtag   1560
catacactgt tgtatccaca gtagatcatt ttgtaaacgc aattgaagag cgtggatttc   1620
cgccaacggc cggtcagcca ccggcgacta ctaaacccaa ggaaattacc cccgtaaacc   1680
ccggaacgtc accacttcta cgatatgccg catggaccgg agggcttgca gcagtagtac   1740
ttttatgtct cgtaatattt ttaatctgta cggctaaacg aatgagggtt aaagccgcca   1800
gggtagacaa gtgatgataa taggctggag cctcggtggc catgcttctt gccccttggg   1860
cctcccccca gcccctcctc cccttcctgc acccgtaccc ccgtggtctt tgaataaagt   1920
ctgagtgggc ggc                                                      1933
```

```
SEQ ID NO: 129        moltype = RNA  length = 2083
FEATURE               Location/Qualifiers
misc_feature          1..2083
                      note = Synthetic Polynucleotide
source                1..2083
                      mol_type = other RNA
                      organism = synthetic construct
SEQUENCE: 129
tcaagctttt ggaccctcgt acagaagcta atacgactca ctatagggaa ataagagaga    60
aaagaagagt aagaagaaat ataagagcca ccatggggac agttaataaa cctgtggtgg    120
gggtattgat ggggttcgga attatcacgg gaacgttgcg tataacgaat ccggtcagag    180
catccgtctt gcgatacgat gattttcaca tcgatgaaga caaactggat acaaactccg    240
tatatgagcc ttactaccat tcagatcatg cggagtcttc atgggtaaat cggggagagt    300
cttcgccgaaa agcgtacgat cataactcac cttatatatg cgcacgtaat gattatgatg    360
gattttaga gaacgcacac gaacaccatg gggtgtataa tcagggccgt ggtatcgata    420
gcggggaacg gttaatgcaa cccacacaaa tgtctgcaca ggaggatctt ggggacgata    480
cgggcatcca cgttatccct acgttaaacg gcgatgacag acataaaatt gtaaatgtgg    540
accaacgtca atacggtgac gtgtttaaag gagatcttaa tccaaaaccc caaggccaaa    600
gactcattga ggtgtcagtg gaagaaaatc acccgtttac tttacgcgca ccgattcagc    660
ggatttatgg agtccggtac accgagactt ggagcttttt gccgtcatta acctgtacgg    720
gagacgcagc gcccgccatc cagcatatat gtttaaaaca tacaacatgc tttcaagacg    780
tggtggtgga tgtggattgc gcggaaaata ctaaagagga tcagttggcc gaaatcagtt    840
accgttttca aggtaagaag gaagcggacc aaccgtggat tgttgtaaac acgagcacac    900
tgtttgatga actcgaatta gaccccccg agattgaacc gggtgtcttg aaagtacttc     960
ggacagaaaa acaatacttg ggtgtgtaca tttggaacat gcgcggctcc gatggtacgt   1020
ctacctacgc cacgtttttg gtcacctgga aaggggatga aaaaacaaga aaccctacgc   1080
ccgcagtaac tcctcaacca agaggggctg agtttcatat gtggaattac cactcgcatg   1140
tattttcagt tggtgatacg tttagcttgg caatgcatct tcagtataag atacatgaag   1200
cgccatttga tttgctgtta gagtggttgt atgtccccat cgatcctaca tgtcaaccaa   1260
tgcggttata ttctacgtgt ttgtatcatc ccaacgcacc ccaatgcctc tctcatatga   1320
attccggttg tacatttacc tcgccacatt tagcccagcg tgttgcaagc acagtgtatc   1380
aaaattgtga acatgcagat aactacaccg catattgtct gggaatatct catatggagc   1440
ctagctttgg tctaatctta cacgacgggg gcaccacgtt aaagtttgta gatacacccg   1500
agagtttgtc gggattatac gttttttgtgg tgtattttaa cgggcatgtt gaagccgtag   1560
catacactgt tgtatccaca gtagatcatt ttgtaaacgc aattgaagag cgtggatttc   1620
cgccaacggc cggtcagcca ccggcgacta ctaaacccaa ggaaattacc cccgtaaacc   1680
ccggaacgtc accacttcta cgatatgccg catggaccgg agggcttgca gcagtagtac   1740
ttttatgtct cgtaatattt ttaatctgta cggctaaacg aatgagggtt aaagcctata   1800
gggtagacaa gtccccgtat aaccaaagca tgtattacgc tggccttcca gtggacgatt   1860
tcgaggacgc cgaagccgcc gatgccgaag aagagtttgg taacgcgatt ggagggagtc   1920
acggggttc gagttacacg gtgtatatag ataagacccg gtgatgataa taggctggag   1980
cctcggtggc catgcttctt gccccttggg cctcccccca gcccctcctc cccttcctgc   2040
acccgtaccc ccgtggtctt tgaataaagt ctgagtgggc ggc                     2083
```

```
SEQ ID NO: 130        moltype = RNA  length = 2083
FEATURE               Location/Qualifiers
misc_feature          1..2083
                      note = Synthetic Polynucleotide
source                1..2083
                      mol_type = other RNA
                      organism = synthetic construct
SEQUENCE: 130
tcaagctttt ggaccctcgt acagaagcta atacgactca ctatagggaa ataagagaga    60
aaagaagagt aagaagaaat ataagagcca ccatggggac agttaataaa cctgtggtgg    120
```

-continued

```
gggtattgat ggggttcgga attatcacgg gaacgttgcg tataacgaat ccggtcagag   180
catccgtctt gcgatacgat gattttcaca tcgatgaaga caaactggat acaaactccg   240
tatatgagcc ttactaccat tcagatcatg cggagtcttc atgggtaaat cggggagagt   300
cttcgcgaaa agcgtacgat cataactcac cttatatatg gccacgtaat gattatgatg   360
gatttttaga gaacgcacac gaacaccatg gggtgtataa tcagggccgt ggtatcgata   420
gcggggaacg gttaatgcaa cccacacaaa tgtctgcaca ggaggatctt ggggacgata   480
cgggcatcca cgttatccct acgttaaacg gcgatgacag acataaaatt gtaaatgtgg   540
accaacgtca atacggtgac gtgtttaaag gagatcttaa tccaaaaccc caaggccaaa   600
gactcattga ggtgtcagtg gaagaaaatc acccgtttac tttacgcgca ccgattcagc   660
ggatttattg agtccggtac accgagactt ggagcttttt gccgtcatta acctgtacgg   720
gagacgcagc gcccgccatc cagcatatat gtttaaaaca tacaacatgc tttcaagacg   780
tggtggtgga tgtggattgc gcggaaaata ctaaagagga tcagttggcc gaaatcagtt   840
accgtttca aggtaagaag gaagcggacc aaccgtggat tgttgtaaac acgagcacac   900
tgtttgatga actcgaatta gacccccccg agattgaacc gggtgtcttg aaagtacttc   960
ggacagaaaa acaatacttg ggtgtgtaca tttggaacat gcgcggctcc gatggtacgt  1020
ctacctacgc cacgtttttg gtcacctgga aaggggatga aaaaacaaga aaccctacgc  1080
ccgcagtaac tcctcaacca agaggggctg agtttcatat gtggaattac cactcgcatg  1140
tattttcagt tggtgatacg tttagcttgg caatgcatct tcagtataag atacatgaag  1200
cgccatttga tttgctgtta gagtggttgt atgtccccat cgatcctaca tgtcaaccaa  1260
tgcggttata ttctacgtgt ttgtatcatc ccaacgcacc ccaatgcctc tctcatatga  1320
attccggttg tacatttacc tcgccacatt tagcccagcg tgttgcaagc acagtgtatc  1380
aaaattgtga acatggcagat aactacaccg catattgtct gggaatatct catatggagc  1440
ctagctttgg tctaatctta cacgacgggg gcaccacgtt aaagtttgta gatacacccg  1500
agagtttgtc gggattatac gttttgtgg tgtattttaa cgggcatgtt gaagccgtag  1560
catacactgt tgtatccaca gtagatcatt ttgtaaacgc aattgaagag cgtggatttc  1620
cgccaacggc cggtcagcca ccggcgacta ctaaacccaa ggaaattacc cccgtaaacc  1680
ccggaacgtc accacttcta cgatatgccg catggaccgg agggcttgca gcagtagtac  1740
ttttatgtct cgtaatattt ttaatctgta cggctaaacg aatgagggtt aaagcctata  1800
gggtagacaa gtccccgtat aaccaaagca tgtatggcgc tggccttcca gtggacgatt  1860
tcgaggaccg cgaagccgcc gatgccgaag aagagtttga taacgcgatt ggagggagtc  1920
acggggttc gagttacacg gtgtatatag ataagacccg gtgatgataa taggctggag  1980
cctcggtggc catgcttctt gccccttggg cctcccccca gccctcctc cccttcctgc  2040
acccgtaccc ccgtggtctt tgaataaagt ctgagtgggc ggc                    2083
```

SEQ ID NO: 131              moltype = RNA   length = 2050
FEATURE                     Location/Qualifiers
misc_feature               1..2050
                            note = Synthetic Polynucleotide
source                     1..2050
                            mol_type = other RNA
                            organism = synthetic construct
SEQUENCE: 131

```
tcaagctttt ggaccctcgt acagaagcta atacgactca ctatagggaa ataagagaga   60
aaagaagagt aagaagaaat ataagagcca ccatggagac tcccgctcag ctactgttcc  120
tcctgctcct ttggctgcct gatactacag gctctgtttt gcggtacgac gactttcaca  180
tcgatgagga caagctcgac actaatagcg tgtatgagcc ctactaccat tcagatcacg  240
ccgagtcctc ttgggtgaac aggggtgaaa gttctaggaa agcctatgat cacaacagcc  300
cttatatttg gccacggaat gattacgacg gatttctcga aaatgcccac gagcatcacg  360
gagtgtacaa ccagggccgt ggaatcgact ctggggagag attgatgcaa cctacacaga  420
tgagcgccca ggaagatctc ggggatgata caggaattca cgttatccct acattaaacg  480
gagatgaccg ccacaaaatc gtcaatgtcg atcaaagaca gtatggagat gtgttcaaag  540
gcgatctcaa ccctaagccg cagggccaga gactcattga ggtgtctgtc gaagagaacc  600
accctttcac tctgcgcgct cccattcaga gaatctatgg agttcgctat acggagactt  660
ggtcattcct tccttccctg acatgcaccg gagacgccgc ccctgccatt cagcacatat  720
gcctgaaaca taccacctgt ttccaggatg tggtggttga tgttgattgt gctgaaaata  780
ccaaggaaga ccaactggcc gagattagtt accggttcca agggaaaaag gaagccgacc  840
agccatggat tgtggttaat acaagcactc tgttcgatga gctcgagctg gatcccccg  900
agatagaacc cggagttctg aaagtgctcc ggacagaaaa acaatatctg ggagtctaca  960
tatggaacat gcgcggttcc gatggggacct ccacttatgc aacctttctc gtcacgtgga  1020
agggagatga gaaaactagg aatcccacac ccgctgtcac accacagcca gagggggctg  1080
agttccatat gtggaactat catagtcacg tgtttagtgt cggagatacg tttttcattgg  1140
ctatgcatct ccagtacaag attcatgagg ctcccttcga tctgttgctt gagtggttgt  1200
acgtcccgat tgacccgacc tgccagccca tgcgactgta cagcacctgt ctctaccatc  1260
caaacgctcc gcaatgtctg agccacatga actctgtcg tacttcacc agtccccacc  1320
tcgcccagcg ggtggcctct actgtttacc agaactgtga gcacggcgac aactacaccc  1380
catactgcct cggtatttct cacatggaac cctccttcgg actcatcctg cacgatgggg  1440
gcactaccct gaagttcgtt gatacgccag aatctctgtc tgggctctat gttttcgtgg  1500
tctacttcaa tggccatgtc gaggccgtgg cctatactgt cgtttctacc gtggatcatt  1560
ttgtgaacgc catcgaagaa cggggattcc ccctacggc aggccagccg cctgcaacca  1620
ccaagcccaa ggaaataaca ccagtgaacc ctggcacctc acctctccta agatatgccg  1680
cgtggacagg gggactggcg gcagtggtgc tcctctgtct cgtgatcttt ctgatcgtta  1740
cagccaagag gatgagggtc aaggcttata gagtggacaa gtcccctac aatcagtcaa  1800
tgtactacgc cggccttccc gttgatgatt ttgaggattc cgagtccaca gatactgagg  1860
aagagttcgg taacgctata ggcggctctc acggggggtc aagctacacg gtttacattg  1920
acaagacacg ctgataatag gctggagcct cggtggccat gcttcttgcc ccttgggcct  1980
ccccccagcc cctcctcccc ttcctgcacc cgtaccccccg tggtctttga ataaagtctg  2040
agtgggcggc                                                        2050
```

SEQ ID NO: 132              moltype = AA   length = 4

```
FEATURE             Location/Qualifiers
REGION              1..4
                    note = Synthetic Polypeptide
source              1..4
                    mol_type = protein
                    organism = synthetic construct
SEQUENCE: 132
GAGL                                                                          4

SEQ ID NO: 133      moltype = RNA  length = 1844
FEATURE             Location/Qualifiers
misc_feature        1..1844
                    note = Synthetic Polynucleotide
source              1..1844
                    mol_type = other RNA
                    organism = synthetic construct
SEQUENCE: 133
atggggacag ttaataaacc tgtggtgggg gtattgatgg ggttcggaat tatcacggga   60
acgttgcgta taacgaatcc ggtcagagca tccgtcttgc gatacgatga ttttcacatc  120
gatgaagaca aactggatac aaactccgta tatgagcctt actaccattc agatcatgcg  180
gagtcttcat gggtaaatcg gggagagtct tcgcgaaaag cgtacgataa tcataactca  240
cctatatat ggccacgtaa tgattatgat ggattttag agaacgcaca cgaacaccat  300
ggggtgtata atcagggccg tggtatcgat agcggggaac ggttaatgca acccacacaa  360
atgtctgcac aggaggatct tggggacgat acgggcatcc acgttatccc tacgttaaac  420
ggcgatgaca gacataaaat tgtaaatgtg gaccaacgtc aatacggtga cgtgtttaaa  480
ggagatctta atccaaaacc ccaaggccaa agactcattg aggtgtcagt ggaagaaaat  540
caccgtttta ctttacgcgc accgattcag cggatttatg gagtccggta caccgagact  600
tggagctttt tgccgtcatt aacctgtacg ggagacgcag cgcccgccat ccagcatata  660
tgtttaaaac atacaacatg ctttcaagac gtggtggtgg atgtggattg cgcggaaaat  720
actaaagagg atcagttggc cgaaatcagt taccgtttc aaggtaagaa ggaagcggac  780
caaccgtgga ttgttgtaaa cacgagcaca ctgtttgatg aactcgaatt agacccccc  840
gagattgaac cgggtgtctt gaaagtactt cggacagaaa aacaatactt gggtgtgtac  900
atttggaaca tgcgcggctc cgatggtacg tctacctacg ccacgttttt ggtcacctgg  960
aaaggggatg aaaaaacaag aaacccctacg cccgcagtaa ctcctcaacc aagaggggct 1020
gagtttcata tgtggaatta ccactcgcat gtattttcag ttggtgatac gtttagcttg 1080
gcaatgcatc ttcagtataa gatacatgaa gcgccatttg atttgctgtt agagtggttg 1140
tatgtcccca tcgatcctac atgtcaacca atgcggttat attctacgtg tttgtatcat 1200
cccaacgcac cccaatgcct ctctcatatg aattccggtt gtacatttac ctcgccacat 1260
ttagcccagc gtgttgcaag cacagtgtat caaaattgca aacatgcaga taactacacc 1320
gcatattgtc tgggaatatc tcatatggag cctagctttg gtctaatctt acacgacggg 1380
ggcaccacgt taaagtttgt agatacaccc gagagtttgt cgggattata cgttttttgtg 1440
gtgtatttta acgggcatgt tgaagccgta gcatacactg ttgtatccac agtagatcat 1500
tttgtaaacg caattgaaga gcgtggattt ccgccaacgg ccggtaactc accggcgact 1560
actaaaccca aggaaattac ccccgtaaac cccggaacgt caccacttct acgatatgcc 1620
gcatggaccg gagggcttgc agcagtagta cttttatgtc tcgtaatatt tttaatctgt 1680
acggctaaac gaatgagggt taaagccgcc agggtagaca agtgatgata ataggctgga 1740
gcctcggtgg ccatgcttct tgcccccttgg gcctccccc agcccctcct ccccttcctg 1800
caccccgtacc cccgtggtct ttgaataaag tctgagtggg cggc                1844

SEQ ID NO: 134      moltype = RNA  length = 1838
FEATURE             Location/Qualifiers
misc_feature        1..1838
                    note = Synthetic Polynucleotide
source              1..1838
                    mol_type = other RNA
                    organism = synthetic construct
SEQUENCE: 134
atggggacag ttaataaacc tgtggtgggg gtattgatgg ggttcggaat tatcacggga   60
acgttgcgta taacgaatcc ggtcagagca tccgtcttgc gatacgatga ttttcacatc  120
gatgaagaca aactggatac aaactccgta tatgagcctt actaccattc agatcatgcg  180
gagtcttcat gggtaaatcg gggagagtct tcgcgaaaag cgtacgatca taactcacct  240
tatatatggc cacgtaatga ttatgatgga tttttagaga cgcacacga acaccatggg  300
gtgtataatc agggccgtgg tatcgatagc ggggaacggt taatgcaacc cacacaaatg  360
tctgcacagg aggatcttgg ggacgatacg gcatccacg ttatccctac gttaaacgga  420
gatgacagac ataaaattgt aaatgtggac caacgtcaat acggtgacgt gtttaaagga  480
gatcttaatc caaaacccca aggccaaaga ctcattgagg tgtcagtgga agaaaatcac  540
ccgtttactt tacgcgcacc gattcagcgg atttatggag tccggtacac cgagacttgg  600
agctttttgc cgtcattaac ctgtacggga cgcagcgc ccgccatcca gcatatatgt  660
ttaaagcata caacatgctt tcaagacgtg gtggtggatg tggattgcgc ggaaaatact  720
aaagaggatc agttggccga aatcagttac cgttttcaag gtaagaagga agcggaccaa  780
ccgtggattg ttgtaaacac gagcacactg tttgatgaac tcgaattaga cccacccgag  840
attgaaccgg gtgtcttgaa agtacttcgg acagagaaac aatacttggg tgtgtacatt  900
tggaacatgc gcggctccga tggtacgtct acctacgcca cgttttttggt cacctggaaa  960
ggggatgaga acaagaaaa ccctacgccc gcagtaactc ctcaaccaag aggggctgag 1020
tttcatatgt ggaattacca ctcgcatgta ttttcagttg gtgatacgtt tagcttggca 1080
atgcatcttc agtataagat acatgaagcg ccatttgatt tgctgttaga gtggttgtat 1140
gtccccatcg atcctacatg tcaaccaatg cggttatatt ctacgtgttt gtatcatccc 1200
aacgcacccc aatgcctctc tcatgaat ccggttgta catttaccte gccacattta 1260
gcccagcgtg ttgcaagcac agtgtatcag aattgtgaac atgcagataa ctacaccgca 1320
```

```
tattgtctgg gaatatctca tatggagcct agctttggtc taatcttaca cgacggggge   1380
accacgttaa agtttgtaga tacacccgag agtttgtcgg gattatacgt ttttgtggtg   1440
tattttaacg ggcatgttga agccgtagca tacactgttg tatccacagt agatcatttt   1500
gtaaacgcaa ttgaagagcg tggatttccg ccaacggccg gtcagccacc ggcgactact   1560
aaaccaagg aaattacccc cgtaaacccc ggaacgtcac cacttctacg atatgccgca   1620
tggaccggag ggcttgcagc agtagtactt ttatgtctcg taatattttt aatctgtacg   1680
gctaaacgaa tgagggttaa agccgccagg gtagacaagt gataataggc tggagcctcg   1740
gtggccatgc ttcttgcccc ttgggcctcc ccccagcccc tcctcccctt cctgcacccg   1800
tacccccgtg gtctttgaat aaagtctgag tgggcggc                          1838
```

SEQ ID NO: 135          moltype = RNA   length = 2036
FEATURE                 Location/Qualifiers
misc_feature            1..2036
                        note = Synthetic Polynucleotide
source                  1..2036
                        mol_type = other RNA
                        organism = synthetic construct
SEQUENCE: 135

```
ggggaaataa gagagaaaag aagagtaaga agaaatataa gagccaccat ggggacagtt   60
aataaacctg tggtgggggt attgatgggg ttcggaatta tcacgggaac gttgcgtata   120
acgaatccgc tcagagcatc cgtcttgcga tacgatgatt ttcacatcga tgaagacaaa   180
ctggatacaa actccgtata tgagccttac taccattcag atcatgcgga gtcttcatgg   240
gtaaatcggg gagagtcttc gcgaaaagcg tacgatcata actcaccta tatatggcca   300
cgtaatgatt atgatggatt tttagagaac gcacacgaac accatggggt gtataatcag   360
ggccgtggta tcgatagcgg ggaacggtta atgcaaccca cacaaatgtc tgcacaggag   420
gatcttgggg acgatacggg catccacgtt atccctacgt taaacggcga tgacagacat   480
aaaattgtaa atgtggacca acgtcaatac ggtgacgtgt ttaaaggaga tcttaatcca   540
aaaccccaag gccaaagact cattgaggtg tcagtggaag aaaatcaccc gtttacttta   600
cgcgcaccga ttcagcggat ttatggagtc cggtacaccg agacttggag cttttttgccg   660
tcattaacct gtacgggaga cgcagcgccc gccatccagc atatatgttt aaagcataca   720
acatgctttc aagacgtggt ggtggatgtg gattgcgcgg aaaatactaa agaggatcag   780
ttggccgaaa tcagttaccg ttttcaaggt aagaaggaag cggaccaacc gtggattgtt   840
gtaaacacga gcacactgtt tgatgaactc gaattagacc cacccgagat tgaaccgggt   900
gtcttgaaag tacttcggac agagaaacaa tacttgggtg tgtacatttg gaacatgcgc   960
ggctccgatg gtacgtctac ctacgccacg ttttttggtca cctggaaagg ggatgagaag   1020
acaagaaacc ctacgcccgc agtaactcct caaccaagag gggctgagtt tcatatgtgg   1080
aattaccact cgcatgtatt ttcagttggt gatacgttta gcttggcaat gcatcttcag   1140
tataagatac atgaagcgcc atttgatttg ctgttagagt ggttgtatgt ccccatcgat   1200
cctacatgtc aaccaatgcg gttatattct acgtgtttgt atcatcccaa cgcaccccaa   1260
tgcctctctc atatgaattc cggttgtaca tttacctcgc cacatttagc ccagcgtgtt   1320
gcaagcacag tgtatcagaa ttgtgaacat gcagataact acaccgcata ttgtctggga   1380
atatctcata tggagcctag ctttggtcta atcttacacg acgggggcac cacgttaaag   1440
tttgtagata cacccgagag tttgtcggga ttatacgtta ttgtggtgtta ttttaacggg   1500
catgttgaag ccgtagcata cactgttgta tccacagtag atcattttgt aaacgcaatt   1560
gaagagcgtg gatttccgcc aacggccggt cagccaccgg cgactactaa acccaaggaa   1620
attacccccg taaaccccgg aacgtcacca cttctacgat atgccgcatg gaccggaggg   1680
cttgcagcag tagtactttt atgtctcgta atattttaa atctgtacgg ctaaacgaatg   1740
agggttaaag cctacagggt agacaagtct ccttacaatc agtcaatgta ctatgcagga   1800
ctccctgttg acgatttcga agactcagag agtacagaca cagaagaaga attcggaaac   1860
gctataggtg gctctcacgg aggtagctcg tatacagtgt acatcgataa aaccagatga   1920
taataggctg gagcctcggt ggccatgctt cttgcccctt gggcctcccc ccagcccctc   1980
ctcccttcc tgcacccgta ccccgtggt ctttgaataa agtctgagtg gcggc          2036
```

SEQ ID NO: 136          moltype = RNA   length = 1991
FEATURE                 Location/Qualifiers
misc_feature            1..1991
                        note = Synthetic Polynucleotide
source                  1..1991
                        mol_type = other RNA
                        organism = synthetic construct
SEQUENCE: 136

```
ggggaaataa gagagaaaag aagagtaaga agaaatataa gagccaccat ggggacagtt   60
aataaacctg tggtgggggt attgatgggg ttcggaatta tcacgggaac gttgcgtata   120
acgaatccgc tcagagcatc cgtcttgcga tacgatgatt ttcacatcga tgaagacaaa   180
ctggatacaa actccgtata tgagccttac taccattcag atcatgcgga gtcttcatgg   240
gtaaatcggg gagagtcttc gcgaaaagcg tacgatcata actcaccta tatatggcca   300
cgtaatgatt atgatggatt tttagagaac gcacacgaac accatggggt gtataatcag   360
ggccgtggta tcgatagcgg ggaacggtta atgcaaccca cacaaatgtc tgcacaggag   420
gatcttgggg acgatacggg catccacgtt atccctacgt taaacggcga tgacagacat   480
aaaattgtaa atgtggacca acgtcaatac ggtgacgtgt ttaaaggaga tcttaatcca   540
aaaccccaag gccaaagact cattgaggtg tcagtggaag aaaatcaccc gtttacttta   600
cgcgcaccga ttcagcggat ttatggagtc cggtacaccg agacttggag cttttttgccg   660
tcattaacct gtacgggaga cgcagcgccc gccatccagc atatatgttt aaagcataca   720
acatgctttc aagacgtggt ggtggatgtg gattgcgcgg aaaatactaa agaggatcag   780
ttggccgaaa tcagttaccg ttttcaaggt aagaaggaag cggaccaacc gtggattgtt   840
gtaaacacga gcacactgtt tgatgaactc gaattagacc cccccgagat tgaaccgggt   900
gtcttgaaag tacttcggac agagaaacaa tacttgggtg tgtacatttg gaacatgcgc   960
ggctccgatg gtacgtctac ctacgccacg ttttttggtca cctggaaagg ggatgagaag   1020
acaagaaacc ctacgcccgc agtaactcct caaccaagag gggctgagtt tcatatgtgg   1080
```

```
aattaccact cgcatgtatt ttcagttggt gatacgttta gcttggcaat gcatcttcag      1140
tataagatac atgaagcgcc atttgatttg ctgttagagt ggttgtatgt ccccatcgat      1200
cctacatgtc aaccaatgcg gttatattct acgtgtttgt atcatcccaa cgcaccccaa      1260
tgcctctctc atatgaattc cggttgtaca tttacctcgc cacatttagc ccagcgtgtt      1320
gcaagcacag tgtatcagaa ttgtgaacat gcagataact acaccgcata ttgtctggga      1380
atatctcata tggagcctag ctttggtcta atcttacacg acgggggcac cacgttaaag      1440
tttgtagata cacccgagag tttgtcggga ttatacgttt ttgtggtgta ttttaacggg      1500
catgttgaag ccgtagcata cactgttgta tccacagtag atcattttgt aaacgcaatt      1560
gaagagcgtg gatttccgcc aacggccggt cagccaccgg cgactactaa acccaaggaa      1620
attaccccg taaaccccgg aacgtcacca cttctacgat atgccgcatg gaccggaggg      1680
cttgcagcag tagtactttt atgtctcgta atatttttaa tctgctacggc taaacgaatg      1740
agggttaaag ccgccagggt agacaagtga taataggctg gagcctcggt ggccatgctt      1800
cttgcccctt gggcctcccc ccagcccctc ctcccccttcc tgcacccgta cccccgtggt      1860
ctttgaataa agtctgagtg ggcggcaaaa aaaaaaaaaa aaaaaaaaaa aaaaaaaaaa      1920
aaaaaaaaaa aaaaaaaaaa aaaaaaaaaa aaaaaaaaaa aaaaaaaaaa aaaaaaaaaa      1980
aaaaaatcta g                                                           1991
```

```
SEQ ID NO: 137          moltype = RNA  length = 1991
FEATURE                 Location/Qualifiers
misc_feature            1..1991
                        note = Synthetic Polynucleotide
source                  1..1991
                        mol_type = other RNA
                        organism = synthetic construct
SEQUENCE: 137
gggggaaataa gagagaaaag aagagtaaga agaaatataa gagccaccat gggcaccgtg      60
aacaagcctg ttgtgggccgt gctgatgggc ttcggcatca tcacaggcac cctgcgggatc      120
accaatcctg tgcgggctag cgtgctgaga tacgacgact tccacatcga cgaggacaag      180
ctggacacca acagcgtgta cgagccctac taccacagcg atcacgccga gtctagctgg      240
gtcaacagag gcgagagcag cagaaaggcc tacgaccaca cagcccctta catctggctg      300
agaaacgact acgacggctt cctcgagaat gcccacgaac accacggccgt gtacaatcaa      360
ggcagaggca tcgacagcgg cgagagactg atgcagccta cacagatgag cgcccaagag      420
gacctgggag atgataccgg catccacgtg atccctacac tgaacggcga cgaccggcac      480
aagatcgtga acgtggacca gagacagtac ggcgacgtgt tcaagggcga cctgaatcct      540
aagcctcagg gccagcgcct gatcgaggtt tccgtggaag agaatcaccc tttcacactg      600
cgggctccca tccagagaat ctacggccgtg cgctataccg agacatggtc ctttctgccc      660
agcctgacat gtaccggcga cgccgctcct gccatccagc acatttgtct gaagcacacc      720
acctgtttcc aggacgtggt ggtggatgtg gactgcgccg agaacaccaa agaggatcag      780
ctggccgaga tcagctaccg gttccaggga aagaaagagg ccgaccagcc ttggatcgtg      840
gtcaacacca gcacactgtt cgacgagctg gaactggacc ctcctgagat tgaacccggc      900
gtcctgaagg tgctgagaac cgagaagcag tacctgggag tgtacatctg gaacatgaga      960
ggcagcgacg gcacctctac ctacgccacc tttctggtca catggaaggg cgacgagaag     1020
accagaaatc ccacaccagc cgtgacacct cagcctagag gcgccgaatt tcacatgtgg     1080
aactaccact ctcacgtgtt cagcgtgggc gataccttca gcctggccat gcatctgcag     1140
tacaagatcc acgaggctcc cttcgacctg ctgctggaat ggctgtacgt gcccatcgat     1200
cctacctgcc agcctatgcg gctgtactcc acctgtctgt atcaccctaa cgctcctcag     1260
tgcctgagcc acatgaatag cggctgcacc ttcacaagcc ctcacctggc tcagcgagtg     1320
gccagcacag tgtaccagaa ttgcgagcac gccgacaatt acaccgccta ctgtctgggc     1380
atcagccaca tggaacctag cttcggcctg atcctgcacg atggcggcac cacactgaag     1440
ttcgtggaca cacctgagag cctgagcggc ctgtatgtgt ttgtggtgta cttcaacggc     1500
cacgtggaag ccgtggccta caccgtggtg tctaccgtgg accacttcgt gaacgccatc     1560
gaggaaagag gcttccctcc aactgctgga cagcctcctg ccaccaccaa gcctaaagaa     1620
atcacacccg tgaatcccgg cactagccct ctgcttagat acgccgcttg gacaggcgga     1680
ctggctgctg ttgttctgct gtgcctggtc atcttcctga tctgcaccgc caagcggatg     1740
agagtgaaag ccgccagagt ggacaagtga taataggctg gagcctcggt ggccatgctt     1800
cttgcccctt gggcctcccc ccagcccctc ctcccccttcc tgcacccgta cccccgtggt     1860
ctttgaataa agtctgagtg ggcggcaaaa aaaaaaaaaa aaaaaaaaaa aaaaaaaaaa     1920
aaaaaaaaaa aaaaaaaaaa aaaaaaaaaa aaaaaaaaaa aaaaaaaaaa aaaaaaaaaa     1980
aaaaaatcta g                                                          1991
```

```
SEQ ID NO: 138          moltype = RNA  length = 47
FEATURE                 Location/Qualifiers
misc_feature            1..47
                        note = Synthetic Polynucleotide
source                  1..47
                        mol_type = other RNA
                        organism = synthetic construct
SEQUENCE: 138
gggaaataag agagaaaaga agagtaagaa gaaatataag agccacc                    47
```

```
SEQ ID NO: 139          moltype = RNA  length = 119
FEATURE                 Location/Qualifiers
misc_feature            1..119
                        note = Synthetic Polynucleotide
source                  1..119
                        mol_type = other RNA
                        organism = synthetic construct
SEQUENCE: 139
tgataatagg ctggagcctc ggtggccatg cttcttgccc cttgggcctc cccccagccc      60
```

```
ctcctcccct tcctgcaccc gtaccccgt ggtctttgaa taaagtctga gtgggcggc    119

SEQ ID NO: 140          moltype = RNA  length = 105
FEATURE                 Location/Qualifiers
misc_feature            1..105
                        note = Synthetic Polynucleotide
source                  1..105
                        mol_type = other RNA
                        organism = synthetic construct
SEQUENCE: 140
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa tctag                   105

SEQ ID NO: 141          moltype = RNA  length = 1991
FEATURE                 Location/Qualifiers
misc_feature            1..1991
                        note = Synthetic Polynucleotide
source                  1..1991
                        mol_type = other RNA
                        organism = synthetic construct
SEQUENCE: 141
ggggaaataa gagagaaaag aagagtaaga agaaatataa gagccaccat ggggacagtt    60
aataaacctg tggtgggcgt attgatgggg ttcggaatta tcacgggaac gttgcgtata   120
acgaatccgg tcagagcatc cgtcttgcga tacgatgatt ttcacatcga tgaagacaaa   180
ctggatacaa actccgtata tgagccttac taccattcag atcatgcgga gtcttcatgg   240
gtaaatcggg gagagtcttc gcgaaaggcg tacgatcata actcaccta tatatggcca    300
cgtaatgatt atgatggatt cttagagaac gcacacgaac accatggggt gtataatcag   360
ggccgtggta tcgatagcgg ggaacggtta atgcaaccca cacaaatgtc tgcacaggag   420
gatcttgggg acgatacggg catccacgtt atccctacgt taaacggcga tgacagacat   480
aagattgtaa atgtggacca acgtcaatac ggtgacgtgt ttaaaggaga tcttaatcca   540
aagcccaag gccaaagact cattgaggtg tcagtggaag agaatcaccc gtttacttta    600
cgcgcaccga ttcagcggat ttatggagtc cggtacaccg agacttggag cttcttgccg   660
tcattaacct gtacgggaga cgcagcgccc gccatccagc atatatgttt aaagcataca   720
acatgctttc aagacgtggt ggtggatgtg gattgcgcgg agaatactaa agaggatcag   780
ttggccgaaa tcagttaccg tttcaaggt aagaaggaag cggaccaacc gtggattgtt    840
gtaaacacga gcacactgtt tgatgaactc gaattagacc cacccgagat tgaaccgggt   900
gtcttgaaag tacttcggac agagaaacaa tacttgggtg tgtacatttg gaacatgcgc   960
ggctccgatg gtacgtctac ctacgccacg ttcttggtca cctggaaagg ggatgagaag  1020
acaagaaacc ctacgcccgc agtaactcct caaccaagag gggctgagtt tcatatgtgg  1080
aattaccact cgcatgtatt ttcagttggt gatacgttta gcttggcaat gcatcttcag  1140
tataagatac atgaagcgcc atttgatttg ctgttagagt ggttgtatgt ccccatcgat  1200
cctacatgtc aaccaatgcg gttatattct acgtgtttgt atcatcccaa cgcaccccaa  1260
tgcctctctc atatgaattc cggttgtaca tttacctcgc cacatttagc ccagcgtgtt  1320
gcaagcacag tgtatcagaa ttgtgaacat gcagataact acaccgcata ttgtctggga  1380
atatctcata tggagcctag ctttggtcta atcttacacg acggaggcac cacgttaaag  1440
tttgtagata cacccgagag tttgtcggga ttatacgtct ttgtggtgta ttttaacggg  1500
catgttgaag ccgtagcata cactgttgta tccacagtag atcattttgt aaacgcaatt  1560
gaagagcgtg gatttccgcc aacggccggt cagccaccgg cgactactaa acccaaggaa  1620
attacgcccg taaaccccgg aacgtcacca cttctacgat atgccgcatg gaccggaggg  1680
cttgcagcag tagtacttt atgtctcgta atattcttaa tctgtacggc taaacgaatg   1740
agggttaaag ccgccagggt agacaagtga taataggctg gagcctcggt ggccatgctt  1800
cttgcccctt gggcctcccc ccagcccctc ctcccttcc tgcacccgta ccccgtggt    1860
ctttgaataa agtctgagtg ggcggcaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaatcta g                                                      1991

SEQ ID NO: 142          moltype = RNA  length = 1869
FEATURE                 Location/Qualifiers
misc_feature            1..1869
                        note = Synthetic Polynucleotide
source                  1..1869
                        mol_type = other RNA
                        organism = synthetic construct
SEQUENCE: 142
atggggacag ttaataaacc tgtggtgggg gtattgatgg ggttcggaat tatcacggga    60
acgttgcgta taacgaatcc ggtcagagca tccgtcttgc gatacgatga ttttcacatc   120
gatgaagaca aactggatac aaactccgta tatgagcctt actaccattc agatcatgcg   180
gagtcttcat gggtaaatcg gggagagtct tcgcgaaaag cgtacgatca taactcacct   240
tatatatggc cacgtaatga ttatgatgga ttttagaga acgcacacga acaccatggg   300
gtgtataatc agggccgtgg tatcgatagc ggggaacggt taatgcaacc cacacaaatg   360
tctgcacagg aggatcttgg ggacgatacg ggcatccacg ttatccctac gttaaacggc   420
gatgacagac ataaaattgt aaatgtggac caacgtcaat acggtgacgt gtttaaagga   480
gatcttaatc caaaacccca aggccaaaga ctcattgagg tgtcagtgga agaaaatcac   540
ccgtttactt tacgcgcacc gattcagcgg atttatggag tccggtacac cgagacttgg   600
agctttttgc cgtcattaac ctgtacggga gacgcagcgc cgccatcca gcatatatgt   660
ttaaagcata acacatgctt tcaagacgtg gtggtggatg tggattgcgc ggaaaatact   720
aaagaggatc agttggccga aatcagttac cgttttcaag gtaagaagga gcggaccaa    780
ccgtggattg ttgtaaacac gagcacactg tttgatgaac tcgaattaga cccacccgag   840
attgaaccgg gtgtgcttgaa agtacttcgg acagagaaac aatactgggg tgtgtacatt   900
```

-continued

```
tggaacatgc gcggctccga tggtacgtct acctacgcca cgttttttggt cacctggaaa    960
ggggatgaga agacaagaaa ccctacgccc gcagtaactc ctcaaccaag aggggctgag   1020
tttcatatgt ggaattacca ctcgcatgta ttttcagttg gtgatacgtt tagcttggca   1080
atgcatcttc agtataagat acatgaagcg ccatttgatt tgctgttaga gtggttgtat   1140
gtccccatcg atcctacatg tcaaccaatg cggttatatt ctacgtgttt gtatcatccc   1200
aacgcacccc aatgcctctc tcatatgaat tccggttgta catttacctc gccacattta   1260
gcccagcgtg ttgcaagcac agtgtatcag aattgtgaac atgcagataa ctacaccgca   1320
tattgtctgg gaatatctca tatggagcct agctttggtc taatcttaca cgacgggggc   1380
accacgttaa agtttgtaga tacacccgag agtttgtcgg gattatacgt ttttgtggtg   1440
tattttaacg ggcatgttga agccgtagca tacactgttg tatccacagt agatcatttt   1500
gtaaacgcaa ttgaagagcg tggatttccg ccaacggccg gtcagccacc ggcgactact   1560
aaacccaagg aaaattacccc cgtaaacccc ggaacgtcac cacttctacg atatgccgca   1620
tggaccggag ggcttgcagc agtagtactt ttatgtctcg taatattttt aatctgtacg   1680
gctaaacgaa tgagggttaa agcctacagg gtagacaagt ctccttacaa tcagtcaatg   1740
tactatgcag gactccctgt tgacgatttc gaagactcag agagtacaga cacagaagaa   1800
gaattcggaa acgctatagg tggctctcac ggaggtagct cgtatacagt gtacatcgat   1860
aaaaccaga                                                          1869
```

```
SEQ ID NO: 143        moltype = RNA  length = 1719
FEATURE               Location/Qualifiers
misc_feature          1..1719
                      note = Synthetic Polynucleotide
source                1..1719
                      mol_type = other RNA
                      organism = synthetic construct
SEQUENCE: 143
atggggacag ttaataaacc tgtggtgggg gtattgatgg ggttcggaat tatcacggga    60
acgttgcgta taacgaatcc ggtcagagca tccgtcttgc gatacgatga ttttcacatc   120
gatgaagaca aactggatac aaaactccgta tatgagcctt actaccattc agatcatgcg   180
gagtcttcat gggtaaatcg gggagagtct tcgcgaaaag cgtacgatca taactcacct   240
tatatatggc cacgtaatga ttatgatgga ttttttagaga acgcacacga acaccatggg   300
gtgtataatc agggccgtgg tatcgatagc ggggaacggt taatgcaacc cacacaaatg   360
tctgcacagg aggatcttgg ggacgatacg ggcatccacg ttatccctac gttaaacggc   420
gatgacagac ataaaattgt aaatgtggac caacgtcaat acggtgacgt gtttaaagga   480
gatcttaatc caaaacccca aggccaaaga ctcattgagg tgtcagtgga agaaaatcac   540
ccgtttactt tacgcgcacc gattcagcgg atttatggag tccggtacac cgagacttgg   600
agctttttgc cgtcattaac ctgtacggga gacgcagcgc ccgccatcca gcatatatgt   660
ttaaaacata caacatgctt tcaagacgtg gtggtggatg tggattgcgc ggaaaatact   720
aaagaggatc agttggccga aatcagttac cgttttcaag gtaagaagga agcggaccaa   780
ccgtggattg ttgtaaacac gagcacactg tttgatgaac tcgaattaga cccccccgag   840
attgaaccgg gtgtcttgaa agtacttcgg acagagaaac aatacttggg tgtgtacatt   900
tggaacatgc gcggctccga tggtacgtct acctacgcca cgttttttggt cacctggaaa   960
ggggatgaga agacaagaaa ccctacgccc gcagtaactc ctcaaccaag aggggctgag  1020
tttcatatgt ggaattacca ctcgcatgta ttttcagttg gtgatacgtt tagcttggca  1080
atgcatcttc agtataagat acatgaagcg ccatttgatt tgctgttaga gtggttgtat  1140
gtccccatcg atcctacatg tcaaccaatg cggttatatt ctacgtgttt gtatcatccc  1200
aacgcacccc aatgcctctc tcatatgaat tccggttgta catttacctc gccacattta  1260
gcccagcgtg ttgcaagcac agtgtatcaa aattgtgaac atgcagataa ctacaccgca  1320
tattgtctgg gaatatctca tatggagcct agctttggtc taatcttaca cgacgggggc  1380
accacgttaa agtttgtaga tacacccgag agtttgtcgg gattatacgt ttttgtggtg  1440
tattttaacg ggcatgttga agccgtagca tacactgttg tatccacagt agatcatttt  1500
gtaaacgcaa ttgaagagcg tggatttccg ccaacggccg gtcagccacc ggcgactact  1560
aaacccaagg aaaattacccc cgtaaacccc ggaacgtcac cacttctacg atatgccgca  1620
tggaccggag ggcttgcagc agtagtactt ttatgtctcg taatattttt aatctgtacg  1680
gctaaacgaa tgagggttaa agccgccagg gtagacaag                         1719
```

```
SEQ ID NO: 144        moltype = RNA  length = 1719
FEATURE               Location/Qualifiers
misc_feature          1..1719
                      note = Synthetic Polynucleotide
source                1..1719
                      mol_type = other RNA
                      organism = synthetic construct
SEQUENCE: 144
atggggacag ttaataaacc tgtggtgggg gtattgatgg ggttcggaat tatcacggga    60
acgttgcgta taacgaatcc ggtcagagca tccgtcttgc gatacgatga ttttcacatc   120
gatgaagaca aactggatac aaaactccgta tatgagcctt actaccattc agatcatgcg   180
gagtcttcat gggtaaatcg gggagagtct tcgcgaaaag cgtacgatca taactcacct   240
tatatatggc cacgtaatga ttatgatgga ttttttagaga acgcacacga acaccatggg   300
gtgtataatc agggccgtgg tatcgatagc ggggaacggt taatgcaacc cacacaaatg   360
tctgcacagg aggatcttgg ggacgatacg ggcatccacg ttatccctac gttaaacggc   420
gatgacagac ataaaattgt aaatgtggac caacgtcaat acggtgacgt gtttaaagga   480
gatcttaatc caaaacccca aggccaaaga ctcattgagg tgtcagtgga agaaaatcac   540
ccgtttactt tacgcgcacc gattcagcgg atttatggag tccggtacac cgagacttgg   600
agctttttgc cgtcattaac ctgtacggga gacgcagcgc ccgccatcca gcatatatgt   660
ttaaaacata caacatgctt tcaagacgtg gtggtggatg tggattgcgc ggaaaatact   720
aaagaggatc agttggccga aatcagttac cgttttcaag gtaagaagga agcggaccaa   780
ccgtggattg ttgtaaacac gagcacactg tttgatgaac tcgaattaga cccacccgag   840
attgaaccgg gtgtcttgaa agtacttcgg acagagaaac aatacttggg tgtgtacatt   900
```

-continued

```
tggaacatgc gcggctccga tggtacgtct acctacgcca cgtttttggt cacctggaaa    960
ggggatgaga agacaagaaa ccctacgccc gcagtaactc ctcaaccaag aggggctgag   1020
tttcatatgt ggaattacca ctcgcatgta ttttcagttg gtgatacgtt tagcttggca   1080
atgcatcttc agtataagat acatgaagcg ccatttgatt tgctgttaga gtggttgtat   1140
gtccccatcg atcctacatg tcaaccaatg cggttatatt ctacgtgttt gtatcatccc   1200
aacgcacccc aatgcctctc tcatatgaat tccggttgta catttacctc gccacattta   1260
gcccagcgtg ttgcaagcac agtgtatcaa aattgtgaac atgcagataa ctacaccgca   1320
tattgtctgg gaatatctca tatggagcct agctttggtc taatcttaca cgacgggggc   1380
accacgttaa agtttgtaga tacacccgag agtttgtcgg gattatacgt ttttgtggtg   1440
tattttaacg ggcatgttga agccgtagca tacactgttg tatccacagt agatcatttt   1500
gtaaacgcaa ttgaagagcg tggatttccg ccaacggccg gtcagccacc ggcgactact   1560
aaacccaagg aaattacccc cgtaaacccc ggaacgtcac cacttctacg atatgccgca   1620
tggaccggag ggcttgcagc agtagtactt ttatgtctcg taatattttt aatctgtacg   1680
gctaaacgaa tgagggttaa agccgccagg gtagacaag              1719
```

```
SEQ ID NO: 145          moltype = RNA   length = 1718
FEATURE                 Location/Qualifiers
misc_feature            1..1718
                        note = Synthetic Polynucleotide
source                  1..1718
                        mol_type = other RNA
                        organism = synthetic construct
SEQUENCE: 145
atggggacag ttaataaacc tgtggtgggg gtattgatgg ggttcggaat tatcacggga    60
acgttgcgta taacgaatcc ggtcagagca tccgtcttgc gatacgatga ttttcacatc   120
gatgaagaca aactggatac aaactccgta tatgagcctt actaccattc agatcatgcg   180
gagtcttcat gggtaaatcg gggagagtct tcgcgaaagg cgtacgatca taactcacct   240
tatatatggc cacgtaatga ttatgatgga ttttttagaga acgcacacga acaccatggg   300
gtgtataatc agggccgtgg tatcgatagc ggggaacggt taatgcaacc cacacaaatg   360
tctgcacagg aggatcttgg ggacgatacg ggcatccacg ttatccctac gttaaacggc   420
gatgacagac ataagattgt aaatgtggac caacgtcaat acggtgacgt gtttaaagga   480
gatcttaatc caaagcccca aggccaaaga ctcattgagg tgtcagtgga agagaatcac   540
ccgtttactt tacgcgcacc gattcagcgg atttatggag tccggtacac cgagacttgg   600
agcttttgc cgtcattaac ctgtacggga gacgcagcgc ccgccatcca gcatatatgt   660
ttaaagcata caacatgctt tcaagacgtg gtggtggatg tggattgcgc ggagaatact   720
aaagaggatc agttggccga aatcagttac cgttttcaag gtaagaagga agcggaccaa   780
ccgtggattg ttgtaaacac gagcacactg tttgatgaac tcgaattaga ccccccccgag   840
attgaaccgg gtgtcttgaa agtacttcgg acagagaaac aatacttggg tgtgtacatt   900
tggaacatgc gcggctccga tggtacgtct acctacgcca cgtttttggt cacctggaaa   960
ggggatgaga agacaagaaa ccctacgccc gcagtaactc ctcaaccaag aggggctgag  1020
tttcatatgt ggaattacca ctcgcatgta ttttcagttg gtgatacgtt tagcttggca  1080
atgcatcttc agtataagat acatgaagcg ccatttgatt tgctgttaga gtggttgtat  1140
gtccccatcg atcctacatg tcaaccaatg cggttatatt ctacgtgttt gtatcatccc  1200
aacgcacccc aatgcctctc tcatatgaat tccggttgta catttacctc gccacattta  1260
gcccagcgtg ttgcaagcac agtgtatcag aattgtgaac atgcagataa ctacaccgca  1320
tattgtctgg gaatatctca tatggagcct agctttggtc taatcttaca cgacgggggc  1380
accacgttaa agtttgtaga tacacccgag agtttgtcgg gattatacgt ttttgtggtg  1440
tattttaacg ggcatgttga agccgtagca tacactgttg tatccacagt agatcatttt  1500
gtaaacgcaa ttgaagagcg tggatttccg ccaacggccg gtcagccacc ggcgactact  1560
aaacccaagg aaattacccc cgtaaacccc ggaacgtcac cacttctacg atatgccgca  1620
tggaccggag ggcttgcagc agtagtactt ttatgtctcg taatattttt aatctgtacg  1680
gctaaacgaa tgagggttaa agccgccagg gtagacaa               1718
```

```
SEQ ID NO: 146          moltype = RNA   length = 1719
FEATURE                 Location/Qualifiers
misc_feature            1..1719
                        note = Synthetic Polynucleotide
source                  1..1719
                        mol_type = other RNA
                        organism = synthetic construct
SEQUENCE: 146
atggggacag ttaataaacc tgtggtgggg gtattgatgg ggttcggaat tatcacggga    60
acgttgcgta taacgaatcc ggtcagagca tccgtcttgc gatacgatga ttttcacatc   120
gatgaagaca aactggatac aaactccgta tatgagcctt actaccattc agatcatgcg   180
gagtcttcat gggtaaatcg gggagagtct tcgcgaaagg cgtacgatca taactcacct   240
tatatatggc cacgtaatga ttatgatgga ttttttagaga acgcacacga acaccatggg   300
gtgtataatc agggccgtgg tatcgatagc ggggaacggt taatgcaacc cacacaaatg   360
tctgcacagg aggatcttgg ggacgatacg ggcatccacg ttatccctac gttaaacggc   420
gatgacagac ataagattgt aaatgtggac caacgtcaat acggtgacgt gtttaaagga   480
gatcttaatc caaagcccca aggccaaaga ctcattgagg tgtcagtgga agagaatcac   540
ccgtttactt tacgcgcacc gattcagcgg atttatggag tccggtacac cgagacttgg   600
agcttttgc cgtcattaac ctgtacggga gacgcagcgc ccgccatcca gcatatatgt   660
ttaaagcata caacatgctt tcaagacgtg gtggtggatg tggattgcgc ggagaatact   720
aaagaggatc agttggccga aatcagttac cgttttcaag gtaagaagga agcggaccaa   780
ccgtggattg ttgtaaacac gagcacactg tttgatgaac tcgaattaga cccacccgag   840
attgaaccgg gtgtcttgaa agtacttcgg acagagaaac aatacttggg tgtgtacatt   900
tggaacatgc gcggctccga tggtacgtct acctacgcca cgtttttggt cacctggaaa   960
ggggatgaga agacaagaaa ccctacgccc gcagtaactc ctcaaccaag aggggctgag  1020
tttcatatgt ggaattacca ctcgcatgta ttttcagttg gtgatacgtt tagcttggca  1080
```

-continued

```
atgcatcttc agtataagat acatgaagcg ccatttgatt tgctgttaga gtggttgtat    1140
gtccccatcg atcctacatg tcaaccaatg cggttatatt ctacgtgttt gtatcatccc    1200
aacgcacccc aatgcctctc tcatatgaat tccggttgta catttacctc gccacattta    1260
gcccagcgtg ttgcaagcac agtgtatcag aattgtgaac atgcagataa ctacaccgca    1320
tattgtctgg gaatatctca tatggagcct agctttggtc taatcttaca cgacgggggc    1380
accacgttaa agtttgtaga tacacccgag agtttgtcgg gattatacgt ttttgtggtg    1440
tattttaacg ggcatgttga agccgtagca tacactgttg tatccacagt agatcatttt    1500
gtaaacgcaa ttgaagagcg tggatttccg ccaacggccg gtcagccacc ggcgactact    1560
aaacccaagg aaattacccc cgtaaacccc ggaacgtcac cacttctacg atatgccgca    1620
tggaccggag ggcttgcagc agtagtactt ttatgtctcg taatattttt aatctgtacg    1680
gctaaacgaa tgagggttaa agccgccagg gtagacaag                           1719
```

SEQ ID NO: 147          moltype = RNA  length = 1719
FEATURE                 Location/Qualifiers
misc_feature           1..1719
                        note = Synthetic Polynucleotide
source                  1..1719
                        mol_type = other RNA
                        organism = synthetic construct
SEQUENCE: 147

```
atggggacag ttaataaacc tgtggtgggg gtattgatgg ggttcggaat tatcacggga     60
acgttgcgta taacgaatcc ggtcagagca tccgtcttgc gatacgatga ttttcacatc    120
gatgaagaca aactggatac aaactccgta tatgagcctt actaccattc agatcatgcg    180
gagtcttcat gggtaaatcg gggagagtct tcgcgaaaag cgtacgatca taactcacct    240
tatatatggc cacgtaatga ttatgatgga ttttagaga acgcacacga acaccatggg    300
gtgtataatc agggccgtgg tatcgatagc ggggaacggt tatcaacc cacacaaatg    360
tctgcacagg aggatcttgg ggacgatacg ggcatccacg ttatccctac gttaaacggc    420
gatgacagac ataaaattgt aaatgtggac caacgtcaat acggtgacgt gtttaaagga    480
gatcttaatc caaaacccca aggccaaaga ctcattgagg tgtcagtgga agaaaatcac    540
ccgtttactt tacgcgcacc gattcagcgg atttatggag tccggtacac cgagacttgg    600
agcttttttgc cgtcattaac ctgtacggga gacgcagcgc ccgccatcca gcatatatgt    660
ttaaagcata caacatgctt tcaagacgtg gtggtggatg tggattgcgc ggaaaatact    720
aaagaggatc agttggccga aatcagttac cgtttcaag gtaagaagga agcggaccaa    780
ccgtggattg ttgtaaacac gagcacactg tttgatgaac tcgaattaga cccccccgag    840
attgaaccgg gtgtcttgaa agtacttcgg acagagaaac aatacttggg tgtgtacatt    900
tggaacatgc gcggctccga tggtacgtct acctacgcca cgttttttggt cacctggaaa    960
ggggatgaga agacaagaaa ccctacgccc gcagtaactc ctcaaccaag aggggctgag   1020
tttcatatgt ggaattacca ctcgcatgta tttttcagttg gtgatacgtt tagcttggca   1080
atgcatcttc agtataagat acatgaagcg ccatttgatt tgctgttaga gtggttgtat   1140
gtccccatcg atcctacatg tcaaccaatg cggttatatt ctacgtgttt gtatcatccc   1200
aacgcacccc aatgcctctc tcatatgaat tccggttgta catttacctc gccacattta   1260
gcccagcgtg ttgcaagcac agtgtatcag aattgtgaac atgcagataa ctacaccgca   1320
tattgtctgg gaatatctca tatggagcct agctttggtc taatcttaca cgacgggggc   1380
accacgttaa agtttgtaga tacacccgag agtttgtcgg gattatacgt ttttgtggtg   1440
tattttaacg ggcatgttga agccgtagca tacactgttg tatccacagt agatcatttt   1500
gtaaacgcaa ttgaagagcg tggatttccg ccaacggccg gtcagccacc ggcgactact   1560
aaacccaagg aaattacccc cgtaaacccc ggaacgtcac cacttctacg atatgccgca   1620
tggaccggag ggcttgcagc agtagtactt ttatgtctcg taatattttt aatctgtacg   1680
gctaaacgaa tgagggttaa agccgccagg gtagacaag                          1719
```

SEQ ID NO: 148          moltype = RNA  length = 1719
FEATURE                 Location/Qualifiers
misc_feature           1..1719
                        note = Synthetic Polynucleotide
source                  1..1719
                        mol_type = other RNA
                        organism = synthetic construct
SEQUENCE: 148

```
atggggacag ttaataaacc tgtggtgggg gtattgatgg ggttcggaat tatcacggga     60
acgttgcgta taacgaatcc ggtcagagca tccgtcttgc gatacgatga ttttcacatc    120
gatgaagaca aactggatac aaactccgta tatgagcctt actaccattc agatcatgcg    180
gagtcttcat gggtaaatcg gggagagtct tcgcgaaaag cgtacgatca taactcacct    240
tatatatggc cacgtaatga ttatgatgga ttttttagaga acgcacacga acaccatggg    300
gtgtataatc agggccgtgg tatcgatagc ggggaacggt tatcaacc cacacaaatg    360
tctgcacagg aggatcttgg ggacgatacg ggcatccacg ttatccctac gttaaacggc    420
gatgacagac ataaaattgt aaatgtggac caacgtcaat acggtgacgt gtttaaagga    480
gatcttaatc caaaacccca aggccaaaga ctcattgagg tgtcagtgga agaaaatcac    540
ccgtttactt tacgcgcacc gattcagcgg atttatggag tccggtacac cgagacttgg    600
agcttttttgc cgtcattaac ctgtacggga gacgcagcgc ccgccatcca gcatatatgt    660
ttaaagcata caacatgctt tcaagacgtg gtggtggatg tggattgcgc ggaaaatact    720
aaagaggatc agttggccga aatcagttac cgtttcaag gtaagaagga agcggaccaa    780
ccgtggattg ttgtaaacac gagcacactg tttgatgaac tcgaattaga cccacccgag    840
attgaaccgg gtgtcttgaa agtacttcgg acagagaaac aatacttggg tgtgtacatt    900
tggaacatgc gcggctccga tggtacgtct acctacgcca cgttttttggt cacctggaaa    960
ggggatgaga agacaagaaa ccctacgccc gcagtaactc ctcaaccaag aggggctgag   1020
tttcatatgt ggaattacca ctcgcatgta tttttcagttg gtgatacgtt tagcttggca   1080
atgcatcttc agtataagat acatgaagcg ccatttgatt tgctgttaga gtggttgtat   1140
gtccccatcg atcctacatg tcaaccaatg cggttatatt ctacgtgttt gtatcatccc   1200
aacgcacccc aatgcctctc tcatatgaat tccggttgta catttacctc gccacattta   1260
```

```
gcccagcgtg ttgcaagcac agtgtatcag aattgtgaac atgcagataa ctacaccgca    1320
tattgtctgg gaatatctca tatggagcct agctttggtc taatcttaca cgacgggggc    1380
accacgttaa agtttgtaga tacacccgag agtttgtcgg gattatacgt ttttgtggtg    1440
tattttaacg ggcatgttga agccgtagca tacactgttg tatccacagt agatcatttt    1500
gtaaacgcaa ttgaagagcg tggatttccg ccaacggccg gtcagccacc ggcgactact    1560
aaacccaagg aaattacccc cgtaaacccc ggaacgtcac cacttctacg atatgccgca    1620
tggaccggag ggcttgcagc agtagtactt ttatgtctcg taatatttttt aatctgtacg    1680
gctaaacgaa tgagggttaa agccgccagg gtagacaag                            1719
```

```
SEQ ID NO: 149          moltype = RNA   length = 1719
FEATURE                 Location/Qualifiers
misc_feature            1..1719
                        note = Synthetic Polynucleotide
source                  1..1719
                        mol_type = other RNA
                        organism = synthetic construct
SEQUENCE: 149
atggggacag ttaataaacc tgtggtgggc gtattgatgg ggttcggaat tatcacggga    60
acgttgcgta taacgaatcc ggtcagagca tccgtcttgc gatacgatga tttttcacatc   120
gatgaagaca aactggatac aaactccgta tatgagcctt actaccattc agatcatgcg    180
gagtcttcat gggtaaatcg gggagagtct tcgcgaaagg cgtacgatca taactcacct    240
tatatatggc cacgtaatga ttatgatgga ttcttagaga acgcacacga acaccatgga    300
gtgtataatc agggccgtgg tatcgatagc ggggaacggt taatgcaacc cacacaaatg    360
tctgcacagg aggatcttgg ggacgatacg ggcatccacg ttatccctac gttaaacggc    420
gatgacagac ataagattgt aaatgtggac caacgtcaat acggtgacgt gtttaaagga    480
gatcttaatc caaagcccca aggccaaaga ctcattgagg tgtcagtgga agagaatcac    540
ccgtttactt tacgcgcacc gattcagcgg atttattggag tccggtacac cgagacttgg    600
agcttcttgc cgtcattaac ctgtacggga gacgcagcgc ccgccatcca gcatatatgt    660
ttaaagcata caacatgctt tcaagacgtg gtggtggatg tggattgcgc ggagaatact    720
aaagaggatc agttggccga aatcagttac cgtttttcag gtaagaagga agcggaccaa    780
ccgtggattg ttgtaaacac gagcacactg tttgatgaac tcgaattaga cccacccgag    840
attgaaccgg gtgtcttgaa agtacttcgg acagagaaac aatacttggg tgtgtacatt    900
tggaacatgc gcggctccga tggtacgtct acctacgcca cgttcttggt cacctggaaa    960
ggggatgaga agacaagaaa ccctacgccc gcagtaactc ctcaaccaag aggggctgag    1020
tttcatatgt ggaattacca ctcgcatgta ttttcagttg gtgatacgtt tagcttggca    1080
atgcatcttc agtataagat acatgaagcg ccatttgatt tgctgttaga gtggttgtat    1140
gtccccatcg atcctacatg tcaaccaatg cggttatatt ctacgtgttt gtatcatccc    1200
aacgcacccc aatgcctctc tcatatgaat tccggttgta catttacctc gccacattta    1260
gcccagcgtg ttgcaagcac agtgtatcag aattgtgaac atgcagataa ctacaccgca    1320
tattgtctgg gaatatctca tatggagcct agctttggtc taatcttaca cgacggaggc    1380
accacgttaa agtttgtaga tacacccgag agtttgtcgg gattatacgt ctttgtggtg    1440
tattttaacg ggcatgttga agccgtagca tacactgttg tatccacagt agatcatttt    1500
gtaaacgcaa ttgaagagcg tggatttccg ccaacggccg gtcagccacc ggcgactact    1560
aaacccaagg aaattacgcc cgtaaacccc ggaacgtcac cacttctacg atatgccgca    1620
tggaccggag ggcttgcagc agtagtactt ttatgtctcg taatatttctt aatctgtacg    1680
gctaaacgaa tgagggttaa agccgccagg gtagacaag                            1719
```

```
SEQ ID NO: 150          moltype = RNA   length = 1719
FEATURE                 Location/Qualifiers
misc_feature            1..1719
                        note = Synthetic Polynucleotide
source                  1..1719
                        mol_type = other RNA
                        organism = synthetic construct
SEQUENCE: 150
atgggcaccg tgaacaagcc tgttgtgggc gtgctgatgg gcttcggcat catcacaggc    60
accctgcgga tcaccaatcc tgtgcgggct agcgtgctga gatacgacga cttccacatc    120
gacgaggaca agctggacac caacagcgtg tacgagccct actaccacag cgatcacgcc    180
gagtctagct gggtcaacag aggcgagagc agcagaaagg cctacgacca caacagccct    240
tacatctggc ccagaaacga ctacgacggc ttcctcgaga atgccaacga acaccacggc    300
gtgtacaatc aaggcagagg catcgacagc ggcgagagac tgatgcagcc tacacagatg    360
agcgcccaag aggacctggg agatgatacc ggcatccacg tgatccctac actgaacggc    420
gacgaccggc acaagatcgt gaacgtggac cagagacagt acggcgacgt gttcaagggc    480
gacctgaatc ctaagcctca gggccagcgc ctgatcgagg tttcctggaa gagaatccac    540
cctttcacac tgcgggctcc catccagaga atctacggcg tgcgctatac cgagacatgg    600
tcctttctgc ccagcctgac atgtaccggc gacgccgctc ctgccatcca gcacatttgt    660
ctgaagcaca ccacctgttt ccaggacgtg gtggtggatg tggactgcgc cgagaacacc    720
aaagaggatc agctggccga gatcagctac cggttccagg gaaagaaaga ggccgaccag    780
ccttggatcg tggtcaacac cagcacactg ttcgacgagc tggaactgga ccctcctgag    840
attgaacccg gcgtcctgaa ggtgctgaga accgagaagc agtacctggg agtgtacatc    900
tggaacatga gaggcagcga cggcacctct acctacgcca cctttctggt cacatggaag    960
ggcgacgaga agaccagaaa tcccacacca gccgtgacac tcagcctag aggcgccgaa    1020
tttcacatgt ggaactacca ctctcacgtg ttcagcgtgg gcgatacctt cagcctggcc    1080
atgcatctgc agtacaagat ccacgaggct cccttcgacc tgctgctgga atggctgtac    1140
gtgcccatcg atcctacctg ccagcctatg cggctgtact ccacctgtct gtatcaccct    1200
aacgctcctc agtgcctgag ccacatgaat agcggctgca ccttcacaag ccctcacctg    1260
gctcagcgag tggccagcac agtgtaccag aattgcgagc acgccgacaa ttacaccgcc    1320
tactgtctgg gcatcagcca catggaacct agcttcggcc tgatcctgca cgatggcggc    1380
accacactga agttcgtgga cacacctgag agcctgagcg gcctgtatgt gtttgtggtg    1440
```

-continued

```
tacttcaacg gccacgtgga agccgtggcc tacaccgtgg tgtctaccgt ggaccacttc   1500
gtgaacgcca tcgaggaaag aggcttccct ccaactgctg gacagcctcc tgccaccacc   1560
aagcctaaag aaatcacacc cgtgaatccc ggcactagcc ctctgcttag atacgccgct   1620
tggacaggcg gactggctgc tgttgttctg ctgtgcctgg tcatcttcct gatctgcacc   1680
gccaagcgga tgagagtgaa agccgccaga gtggacaag                          1719
```

What is claimed is:

1. A messenger ribonucleic acid (mRNA) vaccine comprising;

(a) an mRNA polynucleotide comprising from 5' to 3' a 5'untranslated region UTR, an open reading frame (ORF) encoding a varicella zoster virus (VZV) glycoprotein E(gE) protein, the protein comprising an amino acid sequence of SEQ ID NO: 38, a protein comprising a Y569A or a Y582G mutation, relative to the amino acid sequence of SEQ ID NO: 10, a protein comprising a truncated polypeptide lacking the cytoplasmic tail domain shown in amino acids 574-623 of SEQ ID NO: 10, or a truncated polypeptide lacking the transmembrane anchor domain shown in amino acids 562-573 of SEQ ID NO: 10 and a 3' UTR, wherein 100% of uracil nucleosides in the ORF of the mRNA polynucleotide are N1-methylpseudouridine; and (b) a lipid nanoparticle comprising 1,2-distearoyl-sn-glycero-3-phosphocholine (DSPC), PEG-distearoyl glycerol (PEG DMG) and a compound of Formula (I):

$$
\begin{array}{c}
R_4\diagdown N \diagup R_1 \\
R_2 \\
\left(\begin{array}{c} R_5 \\ R_6 \end{array}\right)_m \diagup M \diagup R_3 \diagup R_7,
\end{array}
\tag{I}
$$

or a salt thereof, wherein:

$R_1$ is selected from the group consisting of $C_{5-30}$ alkyl, $C_{5-20}$ alkenyl, and —R"M'R';

$R_2$ and $R_3$ are independently selected from the group consisting of $C_{1-14}$ alkyl and $C_{2-14}$ alkenyl;

$R_4$ is —$(CH_2)_nQ$, wherein Q is-OR, and n is selected from 1, 2, 3, 4, and 5;

each $R_5$ is H;

each $R_6$ is H;

M and M' are independently selected from —C(O)O— and —OC(O)—;

$R_7$ is H;

R is H;

R' is selected from the group consisting of $C_{1-18}$ alkyl and $C_{2-18}$ alkenyl;

R" is selected from the group consisting of $C_{3-14}$ alkyl and $C_{3-14}$ alkenyl; and m is selected from 5, 6, 7, 8, 9, 10, 11, 12, and 13.

2. The mRNA vaccine of claim 1, wherein the VZV gE protein comprises the amino acid sequence of SEQ ID NO: 38.

3. The mRNA vaccine of claim 1, wherein the ORF comprises a nucleotide sequence comprising at least 90% sequence identity to the mRNA sequence corresponding to SEQ ID NO: 62.

4. The mRNA vaccine of claim 1, wherein the ORF comprises the nucleotide sequence of SEQ ID NO: 62.

5. The mRNA vaccine of claim 2, wherein the ORF comprises a nucleotide sequence comprising at least 90% sequence identity to a mRNA sequence corresponding to SEQ ID NO: 62.

6. The mRNA vaccine of claim 1, wherein the ORF comprises a nucleotide sequence comprising at least 90% sequence identity to nucleotides 49-1767 of SEQ ID NO: 101.

7. The mRNA vaccine of claim 1, wherein the ORF comprises a nucleotide sequence comprising nucleotides 49-1767 of SEQ ID NO: 101.

8. The mRNA vaccine of claim 2, wherein the ORF comprises a nucleotide sequence comprising at least 90% sequence identity to nucleotides 49-1767 of SEQ ID NO: 101.

9. The mRNA vaccine of claim 1, wherein the VZV gE protein comprises a Y569A mutation, relative to the amino acid sequence of SEQ ID NO: 10.

10. The mRNA vaccine of claim 1, wherein the VZV gE protein comprises a Y582G mutation, relative to the amino acid sequence of SEQ ID NO: 10.

11. The mRNA vaccine of claim 1, wherein the VZV gE protein is a truncated polypeptide lacking the cytoplasmic tail domain shown in amino acids 574-623 of SEQ ID NO: 10.

12. The mRNA vaccine of claim 1, wherein the VZV gE protein is a truncated polypeptide lacking the transmembrane anchor domain shown in amino acids 562-573 of SEQ ID NO: 10.

13. The mRNA vaccine of claim 1, wherein the mRNA vaccine comprises a second mRNA polynucleotide comprising a second ORF encoding a VZV antigen selected from the group consisting of gB, gI, gM, and gH.

14. A method of inducing an antigen specific immune response in a subject, comprising:

administering to the subject the mRNA vaccine of claim 1.

15. The method of claim 14, wherein the mRNA vaccine is administered in a total dose of 25 μg-100 μg of the mRNA polynucleotide.

* * * * *